United States Patent
Eckelman et al.

(10) Patent No.: US 12,195,533 B2
(45) Date of Patent: Jan. 14, 2025

(54) MULTISPECIFIC POLYPEPTIDE CONSTRUCTS CONTAINING A CONSTRAINED CD3 BINDING DOMAIN AND A RECEPTOR BINDING REGION AND METHODS OF USING THE SAME

(71) Applicant: Inhibrx Biosciences, Inc., La Jolla, CA (US)

(72) Inventors: Brendan P. Eckelman, Encinitas, CA (US); Michael D. Kaplan, San Diego, CA (US); Katelyn M. Willis, Encinitas, CA (US); Quinn Deveraux, La Jolla, CA (US); Kyle S. Jones, San Marcos, CA (US); Rajay A. Pandit, San Diego, CA (US); John C. Timmer, La Jolla, CA (US)

(73) Assignee: Inhibrx Biosciences, Inc., La Jolla, CA (US)

( * ) Notice: Subject to any disclaimer, the term of this patent is extended or adjusted under 35 U.S.C. 154(b) by 408 days.

(21) Appl. No.: 16/520,293

(22) Filed: Jul. 23, 2019

(65) Prior Publication Data
US 2020/0048350 A1 Feb. 13, 2020

Related U.S. Application Data

(60) Provisional application No. 62/832,268, filed on Apr. 10, 2019, provisional application No. 62/744,641, filed on Oct. 11, 2018, provisional application No. 62/702,888, filed on Jul. 24, 2018.

(51) Int. Cl.
*C07K 16/28* (2006.01)

(52) U.S. Cl.
CPC ...... *C07K 16/2809* (2013.01); *C07K 16/2818* (2013.01); *C07K 16/2827* (2013.01); *C07K 16/2878* (2013.01); *C07K 2317/24* (2013.01); *C07K 2317/31* (2013.01); *C07K 2317/56* (2013.01); *C07K 2317/624* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,522,811 A | 6/1985 | Eppstein et al. | |
| 5,258,498 A | 11/1993 | Huston et al. | |
| 5,500,362 A | 3/1996 | Robinson et al. | |
| 5,525,491 A | 6/1996 | Huston et al. | |
| 5,731,168 A | 3/1998 | Carter et al. | |
| 5,821,337 A | 10/1998 | Carter et al. | |
| 6,132,992 A | 10/2000 | Ledbetter et al. | |
| 7,183,076 B2 | 2/2007 | Arathoon et al. | |
| 7,959,925 B2 | 6/2011 | Weinberg et al. | |
| 8,044,178 B2 | 10/2011 | Boghaert et al. | |
| 9,006,399 B2 | 4/2015 | Liu et al. | |
| 9,346,884 B2 | 5/2016 | Beste et al. | |
| 9,605,084 B2 | 3/2017 | Moore et al. | |
| 9,644,016 B2 | 5/2017 | Stagliano et al. | |
| 9,650,446 B2 | 5/2017 | Moore et al. | |
| 9,701,759 B2 | 7/2017 | Desjarlais et al. | |
| 10,010,626 B2 * | 7/2018 | Chang | A61P 35/00 |
| 10,066,015 B2 * | 9/2018 | Zhukovsky | A61P 35/00 |
| 10,087,250 B2 | 10/2018 | Bruenker et al. | |
| 10,093,742 B2 | 10/2018 | Timmer et al. | |
| 10,131,710 B2 | 11/2018 | Moore et al. | |
| 10,858,417 B2 * | 12/2020 | Moore | C07K 16/2803 |
| 11,866,507 B2 | 1/2024 | Eckelman et al. | |
| 2005/0123546 A1 | 6/2005 | Umana et al. | |
| 2011/0097339 A1 | 4/2011 | Holmes et al. | |
| 2011/0274685 A1 | 11/2011 | Keler et al. | |
| 2012/0149876 A1 | 6/2012 | Von Kreudenstein et al. | |
| 2012/0237498 A1 | 9/2012 | Ahrens et al. | |

(Continued)

FOREIGN PATENT DOCUMENTS

| | | |
|---|---|---|
| CN | 108084265 | 5/2018 |
| EP | 1378 520 | 1/2004 |

(Continued)

OTHER PUBLICATIONS

Driessens et al., Immunological Reviews (2009), vol. 229: 126-144. (Year: 2009).*
Malia et al., Proteins, 2016; 84:427-434. (Year: 2016).*
Barthelemy et al., Journal of Biological Chemistry, 2008, 283:3639-3654. (Year: 2008).*

(Continued)

*Primary Examiner* — Meera Natarajan
*Assistant Examiner* — Cheom-Gil Cheong
(74) *Attorney, Agent, or Firm* — Morrison & Foerster LLP

(57) ABSTRACT

The invention relates generally to multispecific polypeptides that bind at least CD3, a second antigen, and a receptor of a T cell, such as a costimulatory receptor or an inhibitory receptor, in which the multispecific polypeptide constructs are able to engage CD3. In some embodiments, the multispecific polypeptide constructs bind a costimulatory receptor and provide costimulatory binding activity. In some embodiments, the multispecific polypeptide constructs bind an inhibitory receptor and block inhibitory activity. In some aspects, the multispecific polypeptides have constrained CD3 binding and bind to or engage CD3 only upon binding to the second antigen, such as a tumor associated antigen. In some embodiments, the multispecific polypeptides contain cleavable linkers that, when cleaved, result in dual effector functions. Also provided are methods of making and using these multispecific polypeptides in a variety of therapeutic, diagnostic and prophylactic indications.

27 Claims, 53 Drawing Sheets

Specification includes a Sequence Listing.

(56) References Cited

U.S. PATENT DOCUMENTS

| | | |
|---|---|---|
| 2013/0183321 A1 | 7/2013 | Smith et al. |
| 2013/0273054 A1 | 10/2013 | Bossenmaier et al. |
| 2014/0072581 A1 | 3/2014 | Dixit et al. |
| 2014/0140989 A1 | 5/2014 | Eckelman et al. |
| 2014/0154253 A1 | 6/2014 | Ng et al. |
| 2014/0288275 A1 | 9/2014 | Moore et al. |
| 2014/0294823 A1 | 10/2014 | Moore et al. |
| 2014/0348841 A1 | 11/2014 | Schebye et al. |
| 2014/0363426 A1 | 12/2014 | Moore et al. |
| 2015/0064204 A1 | 3/2015 | Beers et al. |
| 2015/0079088 A1 | 3/2015 | Lowman et al. |
| 2015/0087810 A1 | 3/2015 | Moore et al. |
| 2015/0239991 A1 | 8/2015 | Blein et al. |
| 2015/0307617 A1 | 10/2015 | Du et al. |
| 2015/0307628 A1 | 10/2015 | Kim et al. |
| 2016/0039942 A1 | 2/2016 | Cobbold et al. |
| 2016/0122425 A1 | 5/2016 | Daugherty et al. |
| 2016/0194399 A1 | 7/2016 | Irving et al. |
| 2016/0289324 A1 | 10/2016 | Moore et al. |
| 2017/0022284 A1 | 1/2017 | Timmer et al. |
| 2017/0037130 A1 | 2/2017 | Raum et al. |
| 2017/0081397 A1 | 3/2017 | Stagliano et al. |
| 2017/0114141 A1 | 4/2017 | Amann et al. |
| 2017/0137517 A1 | 5/2017 | Bowman |
| 2017/0198050 A1 | 7/2017 | Eckelman et al. |
| 2017/0198051 A1 | 7/2017 | Eckelman et al. |
| 2017/0204139 A1 | 7/2017 | Moore et al. |
| 2017/0209492 A1 | 7/2017 | June |
| 2017/0226215 A1 | 8/2017 | Gray et al. |
| 2017/0320958 A1 | 11/2017 | Timmer et al. |
| 2018/0011883 A1 | 1/2018 | Goldbrenner et al. |
| 2018/0016354 A1 | 1/2018 | Wozniak-Knopp et al. |
| 2018/0230225 A1* | 8/2018 | Fan .................. C07K 14/70517 |
| 2019/0010242 A1 | 1/2019 | Eckelman et al. |
| 2019/0100594 A1 | 4/2019 | Timmer et al. |
| 2019/0218515 A1 | 7/2019 | Ballesteros Nobell et al. |
| 2019/0330366 A1 | 10/2019 | Eckelman et al. |
| 2020/0190193 A1 | 6/2020 | Pandit et al. |
| 2021/0340273 A1* | 11/2021 | Timmer .................. C07K 16/30 |
| 2021/0380679 A1* | 12/2021 | Eckelman .......... C07K 16/2809 |
| 2023/0124851 A1 | 4/2023 | Eckelman et al. |
| 2023/0295336 A1 | 9/2023 | Eckelman et al. |
| 2023/0348600 A1 | 11/2023 | Timmer et al. |
| 2024/0101704 A1 | 3/2024 | Eckelman et al. |

FOREIGN PATENT DOCUMENTS

| | | |
|---|---|---|
| EP | 1736 484 | 12/2006 |
| EP | 3502140 | 6/2019 |
| JP | 2010-535032 | 11/2010 |
| JP | 2013-538204 | 10/2013 |
| WO | WO-1998/050431 | 11/1998 |
| WO | WO-2000/024884 | 5/2000 |
| WO | WO-2005/035584 | 4/2005 |
| WO | WO-2005-063816 | 7/2005 |
| WO | WO-2005/100402 | 10/2005 |
| WO | WO-2006/029879 | 3/2006 |
| WO | WO 2009/018386 | 2/2009 |
| WO | WO-2009/089004 | 7/2009 |
| WO | WO-2009/124931 | 10/2009 |
| WO | WO 2010/009391 | 1/2010 |
| WO | WO 2010/037836 | 4/2010 |
| WO | WO-2010/151792 | 12/2010 |
| WO | WO-2011/028683 | 3/2011 |
| WO | WO-2011/143545 | 11/2011 |
| WO | WO 2012/025525 | 3/2012 |
| WO | WO-2012/058768 | 5/2012 |
| WO | WO-2012/162067 | 11/2012 |
| WO | WO 2013/041687 | 3/2013 |
| WO | WO-2013/101909 | 7/2013 |
| WO | WO 2013/128194 | 9/2013 |
| WO | WO-2014/067011 | 5/2014 |
| WO | WO-2014/099997 | 6/2014 |
| WO | WO-2014/125273 | 8/2014 |
| WO | WO-2014/145806 | 9/2014 |
| WO | WO-2015/026894 | 2/2015 |
| WO | WO 2015/168469 | 11/2015 |
| WO | WO-2015/197598 | 12/2015 |
| WO | WO-2015/197789 | 12/2015 |
| WO | WO-2016/020309 | 2/2016 |
| WO | WO-2016/033225 | 3/2016 |
| WO | WO-2016/034666 | 3/2016 |
| WO | WO 2016/046778 | 3/2016 |
| WO | WO-2016/055593 | 4/2016 |
| WO | WO-2016/086189 | 6/2016 |
| WO | WO-2016/087416 | 6/2016 |
| WO | WO-2016/097408 | 6/2016 |
| WO | WO-2016/105450 | 6/2016 |
| WO | WO-2016/138038 | 9/2016 |
| WO | WO-2016/177762 | 11/2016 |
| WO | WO-2016/179517 | 11/2016 |
| WO | WO 2016/180982 | 11/2016 |
| WO | WO-2016/192613 | 12/2016 |
| WO | WO-2017/015623 | 1/2017 |
| WO | WO-2017/021349 | 2/2017 |
| WO | WO-2017/030926 | 2/2017 |
| WO | WO-2017/055398 | 4/2017 |
| WO | WO-2017/060144 | 4/2017 |
| WO | WO-2017/068186 | 4/2017 |
| WO | WO-2017/123650 | 7/2017 |
| WO | WO-2017/123673 | 7/2017 |
| WO | WO-2017/134140 | 8/2017 |
| WO | WO-2017/134440 | 8/2017 |
| WO | WO-2017/167672 | 10/2017 |
| WO | WO-2017/172981 | 10/2017 |
| WO | WO-2017/182672 | 10/2017 |
| WO | WO-2018/014260 | 1/2018 |
| WO | WO-2018/027025 | 2/2018 |
| WO | WO-2018/068201 | 4/2018 |
| WO | WO-2018/068695 | 4/2018 |
| WO | WO-2018/127473 | 7/2018 |
| WO | WO-2018/167486 | 9/2018 |
| WO | WO-2018/185045 | 10/2018 |
| WO | WO-2018/191438 | 10/2018 |
| WO | WO-2019/200022 | 10/2019 |
| WO | WO 2019/201866 | 10/2019 |
| WO | WO 2020/023553 | 1/2020 |
| WO | WO 2020/076970 | 4/2020 |
| WO | WO 2020/076977 | 4/2020 |
| WO | WO 2020/076992 | 4/2020 |
| WO | WO 2020/077257 | 4/2020 |
| WO | WO-2021/155071 | 8/2021 |

OTHER PUBLICATIONS

Beiboer et al., Journal of Molecular Biology, 2000, 296:833-849. (Year: 2000).*

Choi et al., 2011, Molecular BioSystems, 2011, 7:3327-334. (Year: 2011).*

De Genst et al., Developmental and Comparative Immunology, 2006, 30:187-98. (Year: 2006).*

Griffiths et al., The EMBO Journal, 1993, 12:725-734. (Year: 1993).*

Klimka et al., British Journal of Cancer, 2000, 83:252-260. (Year: 2000).*

Ward et al, Nature, 1989, 341:544-546. (Year: 1989).*

Kumar et al., "Molecular cloning and expression of the Fabs of human autoantibodies in *Escherichia coli*," J. Biol. Chem. (2000) 275(45):35129-36.

Smith-Gill et al., "Contributions of immunoglobulin heavy and light chains to antibody specificity for lysozyme and two haptens," J. Immunol. (1987) 139(12):4135-44.

Song et al., "Light chain of natural antibody plays a dominant role in protein antigen binding," Biochem. Biophys. Res. Comm. (2000) 268(2):390-94.

Taylor et al., "Nanocell targeting using engineered bispecific antibodies," Mabs (2015) 7(1):53-65.

Ward et al., "Binding activities of a repertoire of single immunoglobulin variable domains secreted from *Escherichia coli*," Nature (1989) 341:544-56.

(56) References Cited

OTHER PUBLICATIONS

Huet et al., "Multivalent nanobodies targeting death receptor 5 elicit superior tumor killing through efficient caspase induction," MABS (2014) 6(6):1560-70.
Husain et al., "Expanding the boundaries of biotherapeutics with bispecific antibodies," Biodrugs (2018) 32(5):441-64.
Cheng et al., "Construction and expression of a reshaped VH domain against human CD28 molecules," Preparative Biochemistry and Biotechnology (2002) 32(3):239-251.
Ohannesian et al., "Carcinoembryonic antigen and other glycoconjugates act as ligands for galectin-3 in human colon carcinoma cells," Cancer Res. (1995) 55(10): 2191-2199.
Henry et al., "Stability-Diversity tradeoffs impose fundamental constraints on selection of synthetic human VH/VL single-domain antibodies from in vitro display libraries," Frontiers in Immunology (2017) 8:1-15.
Kim et al., "Mutational approaches to improve the biophysical properties of human single-domain antibodies," Biochimica et Biophysica Acta (2014) 1844:1983-2001.
Alegre et al., "Effect of a single amino acid mutation on the activating and immunosuppressive properties of a "humanized" OKT3 monoclonal antibody," J Immunol (1992) 148(11):3461-3468.
Bacac et al., "CD20 Tcb (RG6026), a Novel "2:1" T Cell Bispecific Antibody for the Treatment of B Cell Malignancies," Blood (2016) 128:1836.
Baldrick, "Pharmaceutical Excipient Development: The Need for Preclinical Guidance," Regul Toxicol Pharm (2000) 32(2):210-218.
Beliveau et al., "Probing the substrate specificities of matriptase, matriptase-2, hepsin and DESC1 with internally quenched fluorescent peptides," FEBS J (2009) 276(8):2213-2226.
Brinkmann et al., "The making of bispecific antibodies," MABS (2017) 9(2):182-212.
Bruggemann et al., "Comparison of the effector functions of human immunoglobulins using a matched set of chimeric antibodies," J Exp Med (1987) 166(5):1351-1361.
Carter et al., "Bispecific human IgG by design," J Immunol Methods (2001) 248(1-2):7-15.
Charman, "Lipids, lipophilic drugs, and oral drug delivery-some emerging concepts," J Pharm Sci (2000) 89(8):967-978.
Chen et al., "Fusion protein linkers: property, design and functionality," Adv Drug Deliv Rev (2013) 65(10):1357-1369.
Clynes et al., "Fc receptors are required in passive and active immunity to melanoma," Proc Natl Acad Sci USA (1998) 95(2):652-656.
Cragg et al., "Antibody specificity controls in vivo effector mechanisms of anti-CD20 reagents," Blood (2004) 103:2738-2743.
Cragg et al., "Complement-mediated lysis by anti-CD20 mAb correlates with segregation into lipid rafts," Blood (2003) 101(3):1045-1052.
Dall'Acqua et al., "Properties of Human IgG1s Engineered for Enhanced Binding to the Neonatal Fc Receptor (FcRn)*," J Biol Chem (2006) 281(33):23514-23524.
Davies et al., "Antibody-Antigen Complexes," Annu Rev Biochem (1990) 59:439-473.
Davis et al., "SEEDbodies: fusion proteins based on strand-exchange engineered domain (SEED) CH3 heterodimers in an Fc analogue platform for asymmetric binders or immunofusions and bispecific antibodies," Protein Eng Des Sel (2010) 23(4):195-202.
Deisenhofer, "Crystallographic refinement and atomic models of a human Fc fragment and its complex with fragment B of protein A from *Staphylococcus aureus* at 2.9- and 2.8-.ANG. resolution," Biochemistry (1981) 20(9):2361-2370.
Gazzano-Santoro et al., "A non-radioactive complement-dependent cytotoxicity assay for anti-CD20 monoclonal antibody," J Immunol Methods (1997) 202(2):163-171.
Gunasekaran et al., "Enhancing antibody Fc heterodimer formation through electrostatic steering effects: applications to bispecific molecules and monovalent IgG," J Biol Chem (2010) 285(25):19637-19646.

Ha et al., "Immunoglobulin Fc Heterodimer Platform Technology: From Design to Applications in Therapeutic Antibodies and Proteins," Front Immunol (2016) 7:394.
Harwood et al., "ATTACK, a novel bispecific T cell-recruiting antibody with trivalent EGFR binding and monovalent CD3 binding for cancer immunotherapy," Oncoimmunology (2018) 7(1):e1377874.
Hellstrom et al., "Antitumor effects of L6, an IgG2a antibody that reacts with most human carcinomas," Proc Natl Acad Sci USA (1986) 83(18):7059-7063.
Hellstrom et al., "Strong antitumor activities of IgG3 antibodies to a human melanoma-associated ganglioside," Proc Natl Acad Sci USA (1985) 82(5):1499-1502.
Hernandez-Hoyos et al., "MOR209/ES414, a Novel Bispecific Antibody Targeting PSMA for the Treatment of Metastatic Castration-Resistant Prostate Cancer," Mol Cancer Ther (2016) 15(9):2155-2165.
Idusogie et al., "Engineered antibodies with increased activity to recruit complement," J Immunol (2001) 166(4):2571-2575.
Jendeberg et al., "Engineering of Fc(1) and Fc(3) from human immunoglobulin G to analyse subclass specificity for staphylococcal protein A," J Immnuol Methods (1997) 201(1):25-34.
Kaneko et al., "Optimizing Therapeutic Antibody Function," Biodrugs (2011) 25(1):1-11.
La Rocca et al., "Zymographic detection and clinical correlations of MMP-2 and MMP-9 in breast cancer sera," British Journal of Cancer (2004) 90:1414-1421.
Lazar et al., "Engineered antibody Fc variants with enhanced effector function," Proc Natl Acad Sci USA (2006) 103(11):4005-4010.
Leaver-Fay et al., "Computationally Designed Bispecific Antibodies using Negative State Repertoires," Structure (2016) 24(4):641-651.
Malmqvist, "Biospecific interaction analysis using biosensor technology," Nature (1993) 361:186-187.
Marasco et al., "Design, intracellular expression, and activity of a human antihuman immunodeficiency virus type 1 gp120 single-chain antibody," Proc Natl Acad Sci USA (1993) 90(16):7889-7893.
Merchant et al., "An efficient route to human bispecific IgG," Nat Biotechnol (1998) 16(7):677-681.
Miller, "Protein-protein recognition and the association of immunoglobulin constant domains," JMB (1990) 216(4):965-973.
Moore et al., "A novel bispecific antibody format enables simultaneous bivalent and monovalent co-engagement of distinct target antigens," MAbs (2011) 3(6):546-557.
Moore et al., "Engineered Fc variant antibodies with enhanced ability to recruit complement and mediate effector functions," MAbs (2010) 2(2):181-189.
Natsume et al., "Engineered Antibodies of IgG1/IgG3 Mixed Isotype with Enhanced Cytotoxic Activities," Cancer Res (2008) 68(10):3863-3872.
Petkova et al., "Enhanced half-life of genetically engineered human IgG1 antibodies in a humanized FcRn mouse model: potential application in humorally mediated autoimmune disease," Int Immunol (2006) 18(12):1759-1769.
Powell et al., "Compendium of excipients for parenteral formulations," PDA J Pharm Sci Technol (1998) 52(5):238-311.
Ridgway et al., "'Knobs-into-holes' engineering of antibody CH3 domains for heavy chain heterodimerization," Protein engineering (1996) 9(7):617-621.
Shields et al., "High Resolution Mapping of the Binding Site on Human IgG1 for FcγRI, FcγRII, FcγRIII, and FcRn and Design of IgG1 Variants with Improved Binding to the FcγR*," JBC (2001) 276(9):6591-6604.
Stavenhagen et al., "Enhancing the potency of therapeutic monoclonal antibodies via Fc optimization," Adv Enzyme Regul (2008) 48:152-164.
Stavenhagen et al., "Fc Optimization of Therapeutic Antibodies Enhances Their Ability to Kill Tumor Cells In vitro and Controls Tumor Expansion In vivo via Low-Affinity Activating Fcγ Receptors," Cancer Res (2007) 67(18):8882-8890.
Von Kreudenstein et al., "Improving biophysical properties of a bispecific antibody scaffold to aid developability: quality by molecular design," MAbs (2013) 5(5):646-654.

(56) References Cited

OTHER PUBLICATIONS

Wang, "Lyophilization and development of solid protein pharmaceuticals," Int J Pharm (2000) 203(1-2):1-60.

Xing et al., "BiHC, a T-Cell-Engaging Bispecific Recombinant Antibody, Has Potent Cytotoxic Activity Against Her2 Tumor Cells," Transl Oncol (2017) 10(5):780-785.

Zalevsky et al., "Enhanced antibody half-life improves in vivo activity," Nat Biotechnol (2010) 28(2):157-159.

U.S. Appl. No. 17/283,902, filed Apr. 8, 2021, by Eckelman et al. (Copy not provided). Copy not submitted herewith pursuant to the waiver of 37 C.F.R. § 1.98(a)(2)(iii) issued by the Office on Sep. 21, 2004).

Asano et al. "Domain order of a bispecific diabody dramatically enhances its antitumor activity beyond structural format conversion: the case of the hEx3 diabody." *Protein Engineering, Design & Selection* 26.5 (2013): 359-367.

Kuo et al., "Engineering a CD123xCD3 bispecific scFv immunofusion for the treatment of leukemia and elimination of leukemia stem cells," Protein Eng Des Sel. (2012) 25(10): 561-9.

Stavenhagen et al., "Fc Optimization of Therapeutic Antibodies Enhances Their Ability to Kill Tumor Cells In vitro and Controls Tumor Expansion In vivo via Low-Affinity Activating Fcγ Receptors," Cancer Res (2007) 67(18):8882-8890.

Weidle et al. "The intriguing options of multispecific antibody formats for treatment of cancer." *Cancer genomics & proteomics* 10.1 (2013): 1-18.

Schmiedel e tal. "Expression of a bispecific dsFv-dsFv' antibody fragment in *Escherichia coli*." Protein Engineering 13.10 (2000): 725-734.

Ma et al., "Targeting immunotherapy for bladder cancer using anti-CD3x B7-H3 bispecific antibody," Cancer Med (2018) 7(10):5167-5177.

Maeda et al., "Engineering of functional chimeric protein G-Vargula luciferase," Anal Biochem. (1997) 249(2):147-52.

Miyazaki, "Studies on Alpaca VHH antibodies for industrial applications," Kagoshima University Repository, Jun. 1, 2015, 102 pages. https://ir.kagoshima-u.ac.jp/records/9025 (Machine translation provided).

Zhang et al., "Amplification Ex Vivo and Cytocidal Activity of Leukemia Tumor-Associated Antigen-Specific Cytotoic T Lympohcytes," Chinese Journal of Experimental Hematology, (2015) 23(3); 814-820; (Article in Chinese; English abstract provided).

* cited by examiner

FIG. 3
cx3546, cx3547, cx5951
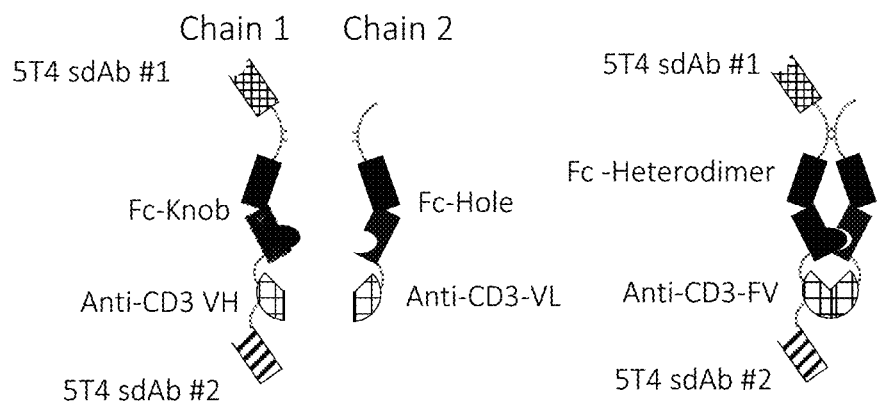
cx3499, cx3497, cx5185
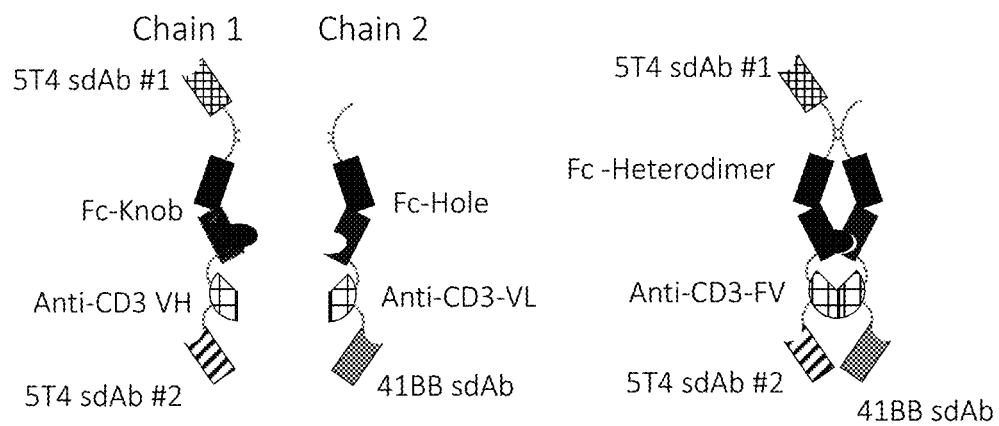

B7H3 Positive

B7H3 Knock-down

B7H3 Positive

B7H3 Knock-down

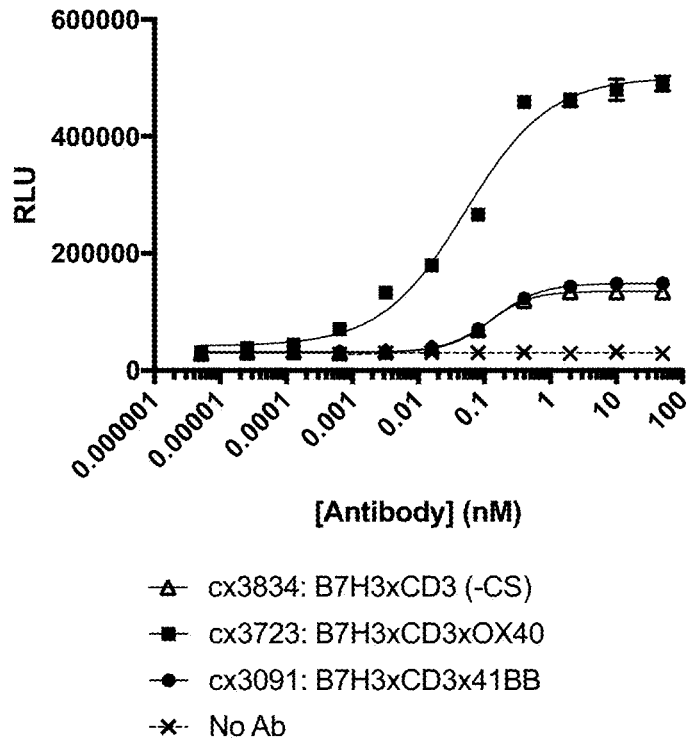
FIG. 14A ox40 Jurkat Repoter / A375 copy
- cx3834: B7H3xCD3 (-CS)
- cx3723: B7H3xCD3xOX40
- cx3091: B7H3xCD3x41BB
- No Ab
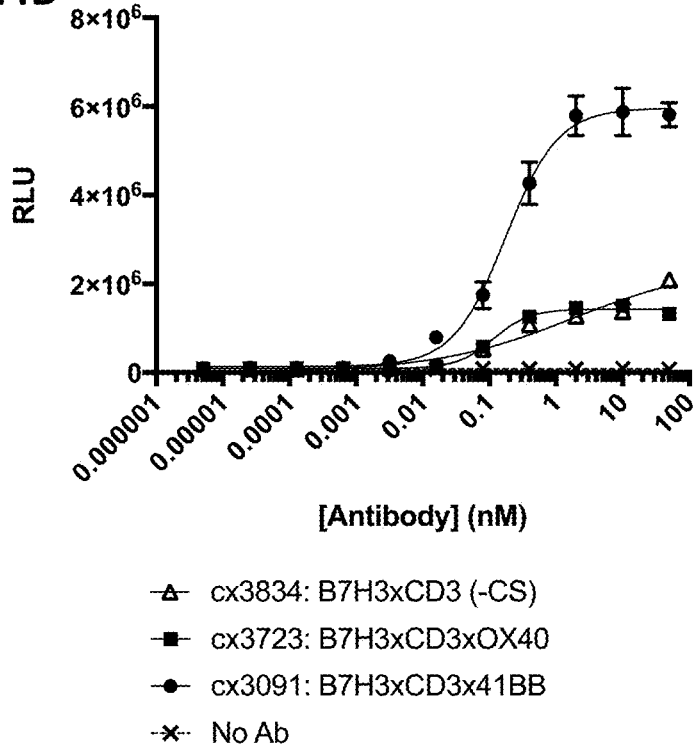
FIG. 14B 41BB Jurkat Repoter / A375
- cx3834: B7H3xCD3 (-CS)
- cx3723: B7H3xCD3xOX40
- cx3091: B7H3xCD3x41BB
- No Ab

FIG. 19A
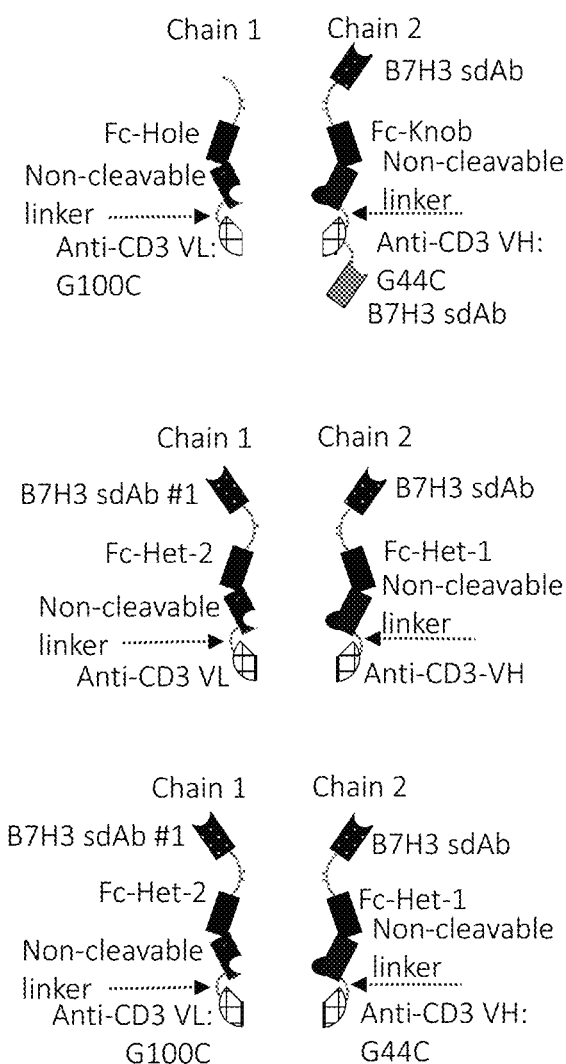
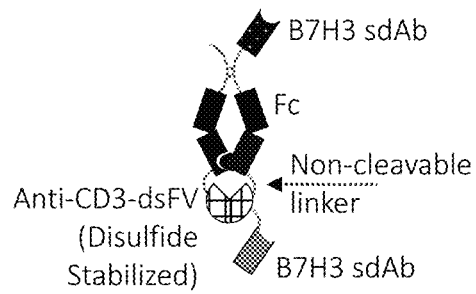
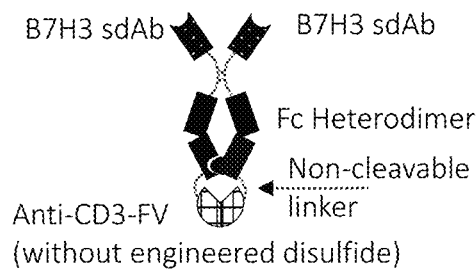
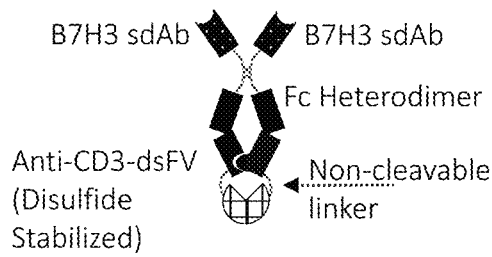

FIG. 19C
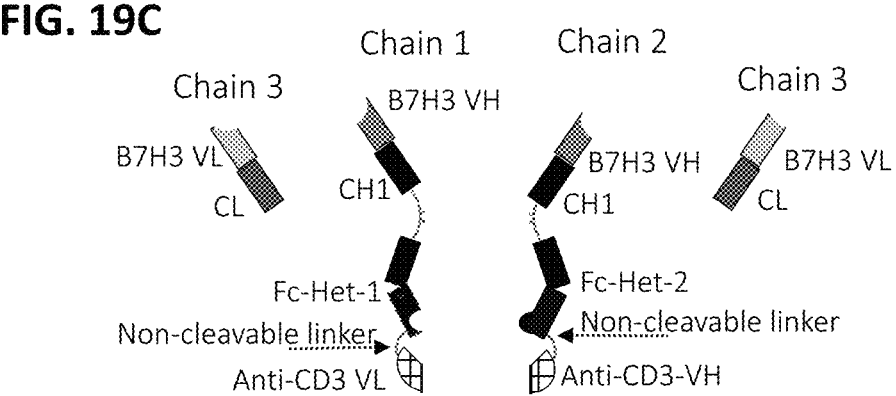
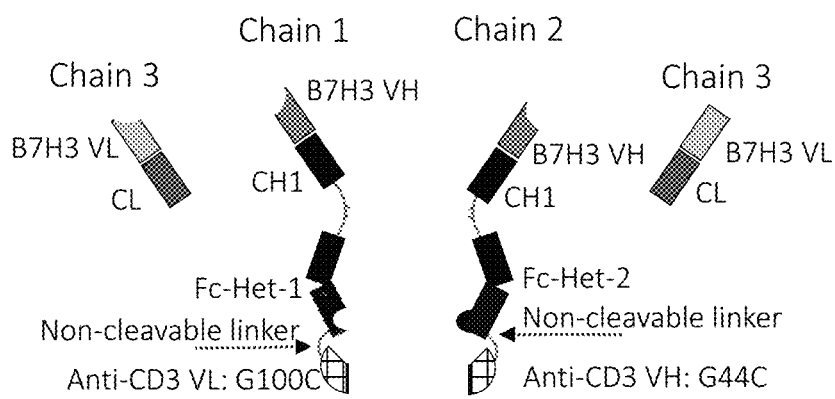
MAB-Fv: cx5067
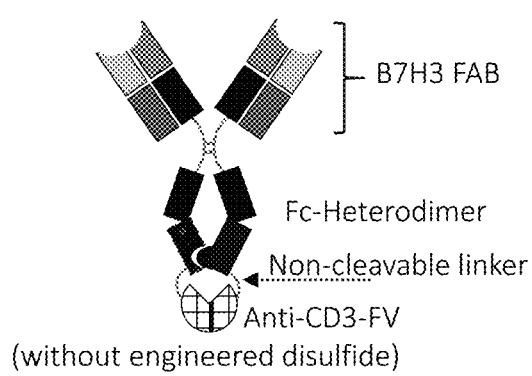
MAB-dsFV: cx6083, cx6084
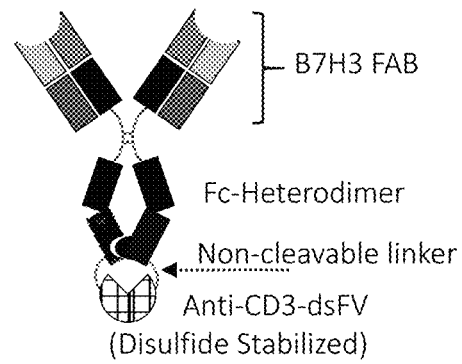

FIG. 20
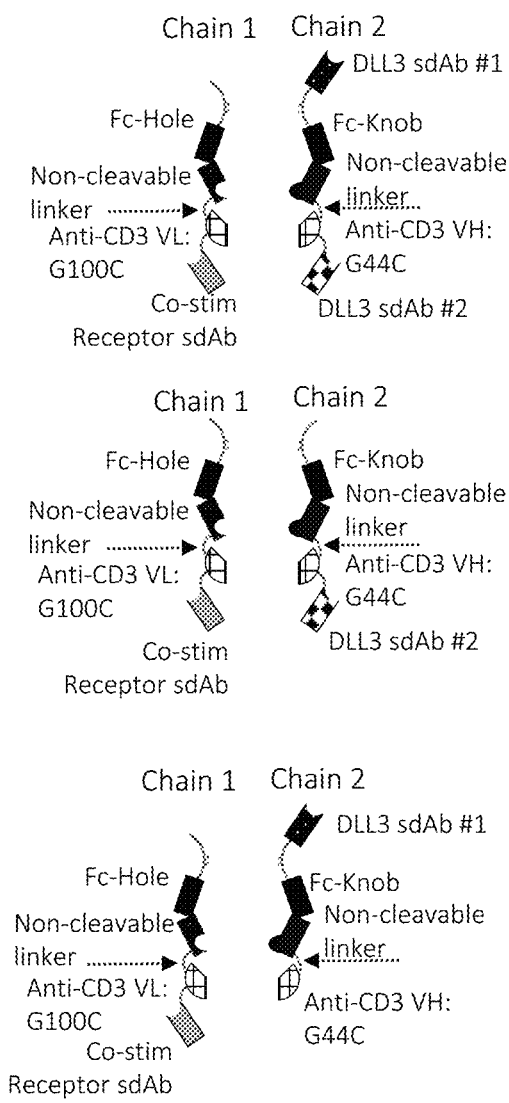
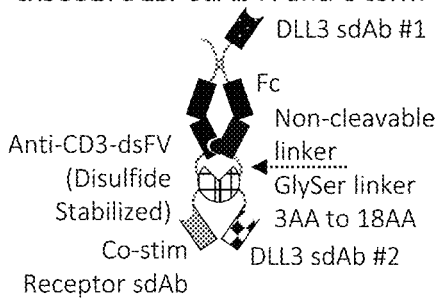
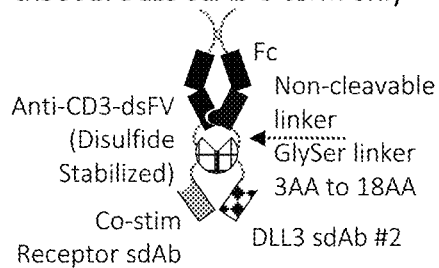
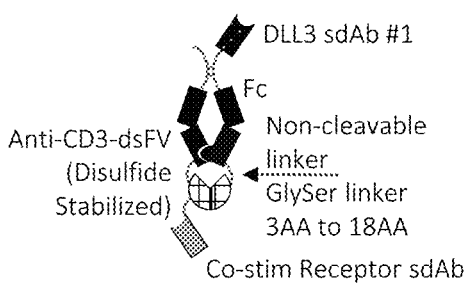

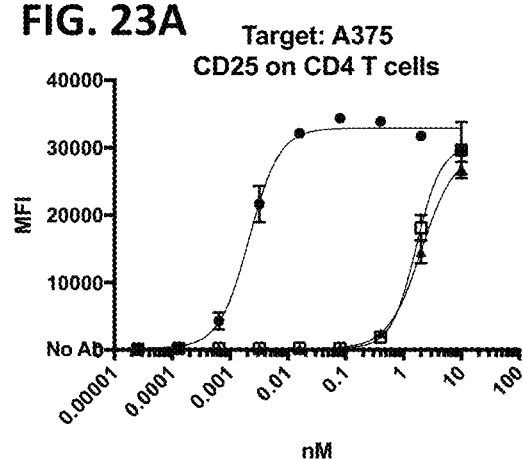
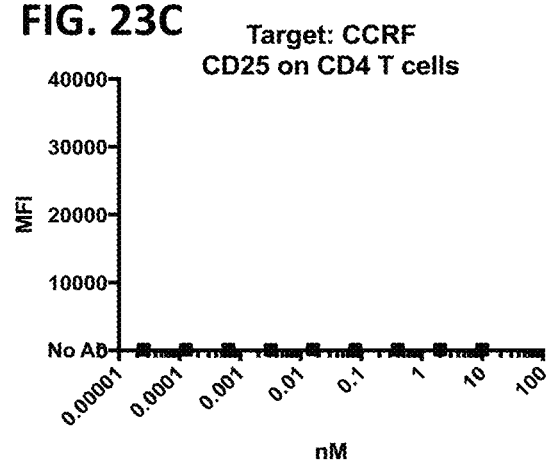
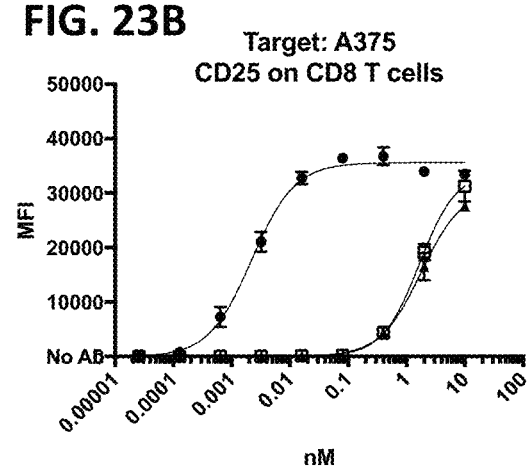
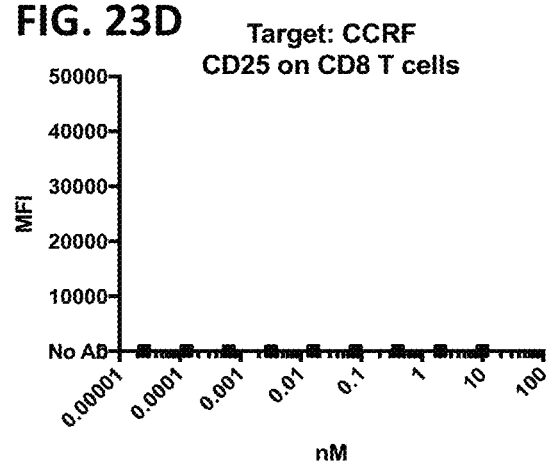

FIG. 31A
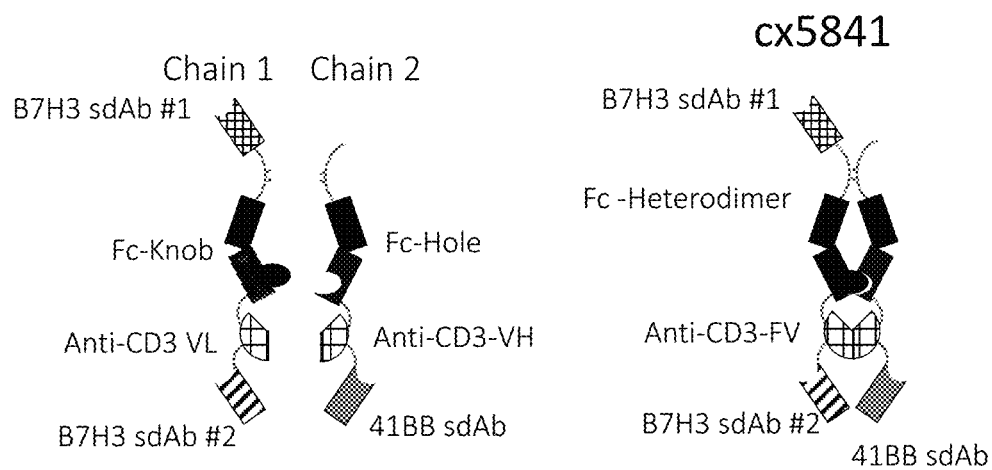
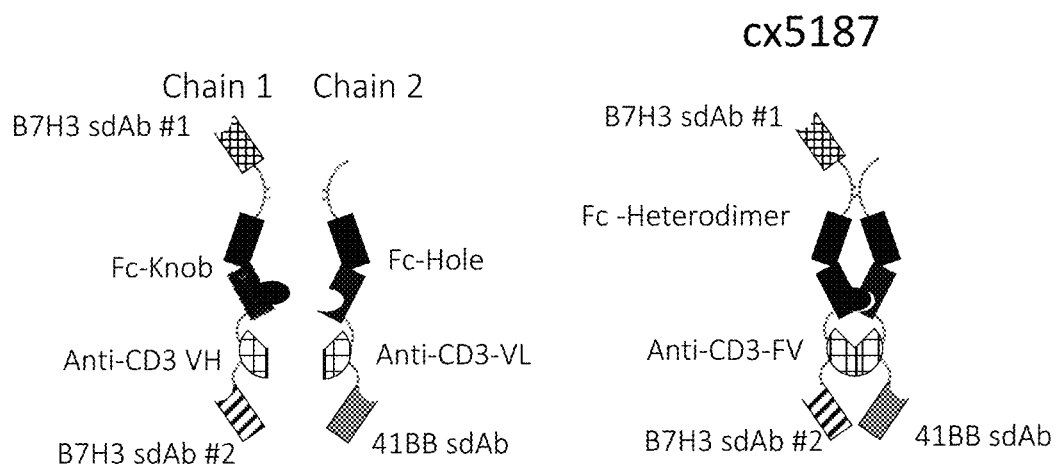

SEQUENCE LISTING

<160> NUMBER OF SEQ ID NOS: 326

<210> SEQ ID NO 1
<211> LENGTH: 218

```
<212> TYPE: PRT
<213> ORGANISM: Artificial Sequence
<220> FEATURE:
<223> OTHER INFORMATION: IgG1 Fc

<400> SEQUENCE: 1

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 2
<211> LENGTH: 215
<212> TYPE: PRT
<213> ORGANISM: Artificial Sequence
<220> FEATURE:
<223> OTHER INFORMATION: xELL Fc

<400> SEQUENCE: 2

Pro Ala Pro Gly Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser His Glu Asp Pro Glu Val Lys Phe Asn Trp Tyr Val Asp
        35                  40                  45

Gly Val Glu Val His Asn Ala Lys Thr Lys Pro Arg Glu Glu Gln Tyr
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Ala Leu
                85                  90                  95

Pro Ala Pro Ile Glu Lys Thr Ile Ser Lys Ala Lys Gly Gln Pro Arg
            100                 105                 110
```

```
Glu Pro Gln Val Tyr Thr Leu Pro Pro Ser Arg Asp Glu Leu Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
            165                 170                 175

Lys Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
            195                 200                 205

Leu Ser Leu Ser Pro Gly Lys
    210                 215
```

<210> SEQ ID NO 3
<211> LENGTH: 217
<212> TYPE: PRT
<213> ORGANISM: Artificial Sequence
<220> FEATURE:
<223> OTHER INFORMATION: IgG2 Fc

<400> SEQUENCE: 3

```
Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Lys Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 4
<211> LENGTH: 218
<212> TYPE: PRT
<213> ORGANISM: Artificial Sequence
<220> FEATURE:
<223> OTHER INFORMATION: IgG3 Fc

<400> SEQUENCE: 4

```
Pro Ala Pro Glu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
                35                  40                  45

Tyr Val Asp Gly Val Glu Val His Asn Ala Lys Thr Lys Pro Arg Glu
            50                  55                  60

Glu Gln Tyr Asn Ser Thr Phe Arg Val Val Ser Val Leu Thr Val Leu
65              70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
            115                 120                 125

Met Thr Lys Asn Gln Val Ser Leu Thr Cys Leu Val Lys Gly Phe Tyr
            130                 135                 140

Pro Ser Asp Ile Ala Val Glu Trp Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
            195                 200                 205

Gln Lys Ser Leu Ser Leu Ser Pro Gly Lys
        210                 215
```

<210> SEQ ID NO 5
<211> LENGTH: 218
<212> TYPE: PRT
<213> ORGANISM: Artificial Sequence
<220> FEATURE:
<223> OTHER INFORMATION: IgG4 Fc

<400> SEQUENCE: 5

```
Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
                35                  40                  45

Tyr Val Asp Gly Val Glu Val His Asn Ala Lys Thr Lys Pro Arg Glu
            50                  55                  60

Glu Gln Phe Asn Ser Thr Tyr Arg Val Val Ser Val Leu Thr Val Leu
65              70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
```

```
                 115                 120                 125
Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
                180                 185                 190

Val Phe Ser Cys Ser Val Met His Glu Ala Leu His Asn His Tyr Thr
                195                 200                 205

Gln Lys Ser Leu Ser Leu Ser Leu Gly Lys
    210                 215

<210> SEQ ID NO 6
<211> LENGTH: 218
<212> TYPE: PRT
<213> ORGANISM: Artificial Sequence
<220> FEATURE:
<223> OTHER INFORMATION: IgG4 Fc

<400> SEQUENCE: 6

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
                20                  25                  30

Val Val Val Asp Val Ser Gln Glu Asp Pro Glu Val Gln Phe Asn Trp
            35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
                100                 105                 110

Gln Pro Arg Glu Pro Gln Val Tyr Thr Leu Pro Pro Ser Gln Glu Glu
            115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
                180                 185                 190

Val Phe Ser Cys Ser Val Met His Glu Ala Leu His Asn His Tyr Thr
                195                 200                 205

Gln Lys Ser Leu Ser Leu Ser Leu Gly Lys
    210                 215

<210> SEQ ID NO 7
<211> LENGTH: 14
<212> TYPE: PRT
<213> ORGANISM: Artificial Sequence
<220> FEATURE:
<223> OTHER INFORMATION: Hinge
```

```
<400> SEQUENCE: 7

Glu Pro Lys Ser Ser Asp Lys Thr His Thr Cys Pro Pro Cys
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Hinge

<400> SEQUENCE: 8

Asp Lys Thr His Thr Cys Pro Pro Cys
1               5

<210> SEQ ID NO 9
<211> LENGTH: 11
<212> TYPE: PRT
<213> ORGANISM: Artificial Sequence
<220> FEATURE:
<223> OTHER INFORMATION: Hinge

<400> SEQUENCE: 9

Glu Ser Lys Tyr Gly Pro Pro Cys Pro Pro Cys
1               5                   10

<210> SEQ ID NO 10
<211> LENGTH: 6
<212> TYPE: PRT
<213> ORGANISM: Artificial Sequence
<220> FEATURE:
<223> OTHER INFORMATION: (GGS)2 Linker

<400> SEQUENCE: 10

Gly Gly Ser Gly Gly Ser
1               5

<210> SEQ ID NO 11
<211> LENGTH: 9
<212> TYPE: PRT
<213> ORGANISM: Artificial Sequence
<220> FEATURE:
<223> OTHER INFORMATION: (GGS)3 Linker

<400> SEQUENCE: 11

Gly Gly Ser Gly Gly Ser Gly Gly Ser
1               5

<210> SEQ ID NO 12
<211> LENGTH: 12
<212> TYPE: PRT
<213> ORGANISM: Artificial Sequence
<220> FEATURE:
<223> OTHER INFORMATION: (GGS)4 Linker

<400> SEQUENCE: 12

Gly Gly Ser Gly Gly Ser Gly Gly Ser Gly Gly Ser
1               5                   10

<210> SEQ ID NO 13
<211> LENGTH: 15
<212> TYPE: PRT
<213> ORGANISM: Artificial Sequence
<220> FEATURE:
<223> OTHER INFORMATION: (GGS)5 Linker
```

<400> SEQUENCE: 13

Gly Gly Ser Gly Gly Ser Gly Gly Ser Gly Gly Ser
1               5                   10                  15

<210> SEQ ID NO 14
<211> LENGTH: 125
<212> TYPE: PRT
<213> ORGANISM: Artificial Sequence
<220> FEATURE:
<223> OTHER INFORMATION: anti-CD3 Hv

<400> SEQUENCE: 14

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 15
<211> LENGTH: 109
<212> TYPE: PRT
<213> ORGANISM: Artificial Sequence
<220> FEATURE:
<223> OTHER INFORMATION: anti-CD3 Lv

<400> SEQUENCE: 15

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 16
<211> LENGTH: 5
<212> TYPE: PRT
<213> ORGANISM: Artificial Sequence
<220> FEATURE:
<223> OTHER INFORMATION: anti-CD3 VH CDR1

<400> SEQUENCE: 16

```
Thr Tyr Ala Met Asn
1               5

<210> SEQ ID NO 17
<211> LENGTH: 19
<212> TYPE: PRT
<213> ORGANISM: Artificial Sequence
<220> FEATURE:
<223> OTHER INFORMATION: anti-CD3 VH CDR2

<400> SEQUENCE: 17

Arg Ile Arg Ser Lys Tyr Asn Asn Tyr Ala Thr Tyr Tyr Ala Asp Ser
1               5                   10                  15

Val Lys Asp

<210> SEQ ID NO 18
<211> LENGTH: 14
<212> TYPE: PRT
<213> ORGANISM: Artificial Sequence
<220> FEATURE:
<223> OTHER INFORMATION: anti-CD3 VH CDR3

<400> SEQUENCE: 18

His Gly Asn Phe Gly Asn Ser Tyr Val Ser Trp Phe Ala Tyr
1               5                   10

<210> SEQ ID NO 19
<211> LENGTH: 14
<212> TYPE: PRT
<213> ORGANISM: Artificial Sequence
<220> FEATURE:
<223> OTHER INFORMATION: anti-CD3 VL CDR1

<400> SEQUENCE: 19

Arg Ser Ser Thr Gly Ala Val Thr Thr Ser Asn Tyr Ala Asn
1               5                   10

<210> SEQ ID NO 20
<211> LENGTH: 7
<212> TYPE: PRT
<213> ORGANISM: Artificial Sequence
<220> FEATURE:
<223> OTHER INFORMATION: anti-CD3 VL CDR2

<400> SEQUENCE: 20

Gly Thr Asn Lys Arg Ala Pro
1               5

<210> SEQ ID NO 21
<211> LENGTH: 9
<212> TYPE: PRT
<213> ORGANISM: Artificial Sequence
<220> FEATURE:
<223> OTHER INFORMATION: anti-CD3 VL CDR3

<400> SEQUENCE: 21

Ala Leu Trp Tyr Ser Asn Leu Trp Val
1               5

<210> SEQ ID NO 22
<211> LENGTH: 4
<212> TYPE: PRT
<213> ORGANISM: Artificial Sequence
<220> FEATURE:
<223> OTHER INFORMATION: Granzyme B substrate
```

```
<400> SEQUENCE: 22

Leu Glu Ala Asp
1

<210> SEQ ID NO 23
<211> LENGTH: 4
<212> TYPE: PRT
<213> ORGANISM: Artificial Sequence
<220> FEATURE:
<223> OTHER INFORMATION: Granzyme B substrate

<400> SEQUENCE: 23

Arg Gln Ala Arg
1

<210> SEQ ID NO 24
<211> LENGTH: 4
<212> TYPE: PRT
<213> ORGANISM: Artificial Sequence
<220> FEATURE:
<223> OTHER INFORMATION: MMP substrate

<400> SEQUENCE: 24

Pro Ala Gly Leu
1

<210> SEQ ID NO 25
<211> LENGTH: 19
<212> TYPE: PRT
<213> ORGANISM: Artificial Sequence
<220> FEATURE:
<223> OTHER INFORMATION: Linker

<400> SEQUENCE: 25

Thr Gly Leu Glu Ala Asp Gly Ser Pro Ala Gly Leu Gly Arg Gln Ala
1               5                   10                  15

Arg Val Gly

<210> SEQ ID NO 26
<211> LENGTH: 19
<212> TYPE: PRT
<213> ORGANISM: Artificial Sequence
<220> FEATURE:
<223> OTHER INFORMATION: Linker

<400> SEQUENCE: 26

Thr Gly Leu Glu Ala Asp Gly Ser Arg Gln Ala Arg Val Gly Pro Ala
1               5                   10                  15

Gly Leu Gly

<210> SEQ ID NO 27
<211> LENGTH: 19
<212> TYPE: PRT
<213> ORGANISM: Artificial Sequence
<220> FEATURE:
<223> OTHER INFORMATION: Linker

<400> SEQUENCE: 27

Thr Gly Ser Pro Ala Gly Leu Glu Ala Asp Gly Ser Arg Gln Ala Arg
1               5                   10                  15

Val Gly Ser

<210> SEQ ID NO 28
<211> LENGTH: 19
```

```
<212> TYPE: PRT
<213> ORGANISM: Artificial Sequence
<220> FEATURE:
<223> OTHER INFORMATION: Linker

<400> SEQUENCE: 28

Thr Gly Pro Ala Gly Leu Gly Leu Glu Ala Asp Gly Ser Arg Gln Ala
1               5                   10                  15

Arg Val Gly

<210> SEQ ID NO 29
<211> LENGTH: 19
<212> TYPE: PRT
<213> ORGANISM: Artificial Sequence
<220> FEATURE:
<223> OTHER INFORMATION: Linker

<400> SEQUENCE: 29

Thr Gly Arg Gln Ala Arg Val Gly Leu Glu Ala Asp Gly Ser Pro Ala
1               5                   10                  15

Gly Leu Gly

<210> SEQ ID NO 30
<211> LENGTH: 18
<212> TYPE: PRT
<213> ORGANISM: Artificial Sequence
<220> FEATURE:
<223> OTHER INFORMATION: Linker

<400> SEQUENCE: 30

Thr Gly Ser Arg Gln Ala Arg Val Gly Pro Ala Gly Leu Glu Ala Asp
1               5                   10                  15

Gly Ser

<210> SEQ ID NO 31
<211> LENGTH: 20
<212> TYPE: PRT
<213> ORGANISM: Artificial Sequence
<220> FEATURE:
<223> OTHER INFORMATION: Linker

<400> SEQUENCE: 31

Thr Gly Pro Ala Gly Leu Gly Ser Arg Gln Ala Arg Val Gly Leu Glu
1               5                   10                  15

Ala Asp Gly Ser
            20

<210> SEQ ID NO 32
<211> LENGTH: 125
<212> TYPE: PRT
<213> ORGANISM: Artificial Sequence
<220> FEATURE:
<223> OTHER INFORMATION: anti-CD3 VH1

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60
```

Ser Val Lys Asp Arg Phe Thr Ile Ser Arg Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 33
<211> LENGTH: 125
<212> TYPE: PRT
<213> ORGANISM: Artificial Sequence
<220> FEATURE:
<223> OTHER INFORMATION: anti-CD3 VH2

<400> SEQUENCE: 33

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
            85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 34
<211> LENGTH: 125
<212> TYPE: PRT
<213> ORGANISM: Artificial Sequence
<220> FEATURE:
<223> OTHER INFORMATION: anti-CD3 VH3

<400> SEQUENCE: 34

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Asn Leu Lys Thr Glu Asp Thr Ala Met Tyr
            85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser

-continued

```
            115                 120                 125

<210> SEQ ID NO 35
<211> LENGTH: 125
<212> TYPE: PRT
<213> ORGANISM: Artificial Sequence
<220> FEATURE:
<223> OTHER INFORMATION: anti-CD3 VH4

<400> SEQUENCE: 35

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 36
<211> LENGTH: 125
<212> TYPE: PRT
<213> ORGANISM: Artificial Sequence
<220> FEATURE:
<223> OTHER INFORMATION: anti-CD3 VH5

<400> SEQUENCE: 36

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 37
<211> LENGTH: 125
<212> TYPE: PRT
<213> ORGANISM: Artificial Sequence
<220> FEATURE:
<223> OTHER INFORMATION: anti-CD3 VH6

<400> SEQUENCE: 37
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 38
<211> LENGTH: 125
<212> TYPE: PRT
<213> ORGANISM: Artificial Sequence
<220> FEATURE:
<223> OTHER INFORMATION: anti-CD3 VH7

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
            115                 120                 125

<210> SEQ ID NO 39
<211> LENGTH: 124
<212> TYPE: PRT
<213> ORGANISM: Artificial Sequence
<220> FEATURE:
<223> OTHER INFORMATION: anti-CD3 VH8

<400> SEQUENCE: 39

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp

```
              50                  55                  60
Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser
                115                 120
```

<210> SEQ ID NO 40
<211> LENGTH: 125
<212> TYPE: PRT
<213> ORGANISM: Artificial Sequence
<220> FEATURE:
<223> OTHER INFORMATION: anti-CD3 VH9

<400> SEQUENCE: 40

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                 20                  25                  30

Ala Met Asn Trp Val Arg Gln Ala Pro Gly Lys Gly Leu Glu Trp Val
                 35                  40                  45

Ala Arg Ile Arg Ser Lys Tyr Asn Asn Tyr Ala Thr Tyr Tyr Ala Asp
             50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Thr Val Thr Val Ser Ser
                115                 120                 125
```

<210> SEQ ID NO 41
<211> LENGTH: 125
<212> TYPE: PRT
<213> ORGANISM: Artificial Sequence
<220> FEATURE:
<223> OTHER INFORMATION: anti-CD3 VH10

<400> SEQUENCE: 41

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                 20                  25                  30

Ala Met Asn Trp Val Arg Gln Ala Pro Gly Lys Gly Leu Glu Trp Val
                 35                  40                  45

Ala Arg Ile Arg Ser Lys Tyr Asn Asn Tyr Ala Thr Tyr Tyr Ala Asp
             50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Tyr Phe
                100                 105                 110
```

```
Ala Tyr Trp Gly Gln Gly Thr Thr Val Thr Val Ser Ser
            115                 120                 125
```

<210> SEQ ID NO 42
<211> LENGTH: 125
<212> TYPE: PRT
<213> ORGANISM: Artificial Sequence
<220> FEATURE:
<223> OTHER INFORMATION: anti-CD3 VH11

<400> SEQUENCE: 42

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125
```

<210> SEQ ID NO 43
<211> LENGTH: 125
<212> TYPE: PRT
<213> ORGANISM: Artificial Sequence
<220> FEATURE:
<223> OTHER INFORMATION: anti-CD3 VH12

<400> SEQUENCE: 43

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Lys Pro
            115                 120                 125
```

<210> SEQ ID NO 44
<211> LENGTH: 125
<212> TYPE: PRT
<213> ORGANISM: Artificial Sequence
<220> FEATURE:
<223> OTHER INFORMATION: anti-CD3 VH13

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
            85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Lys Pro
        115                 120                 125

<210> SEQ ID NO 45
<211> LENGTH: 125
<212> TYPE: PRT
<213> ORGANISM: Artificial Sequence
<220> FEATURE:
<223> OTHER INFORMATION: anti-CD3 VH14

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
            85                  90                  95

Tyr Cys Val Arg His Gly Asn Phe Gly Asn Ser Tyr Val Ser Trp Phe
            100                 105                 110

Ala Tyr Trp Gly Cys Gly Thr Leu Val Thr Val Lys Pro
        115                 120                 125

<210> SEQ ID NO 46
<211> LENGTH: 125
<212> TYPE: PRT
<213> ORGANISM: Artificial Sequence
<220> FEATURE:
<223> OTHER INFORMATION: anti-CD3 VH15

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

```
Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
                115                 120                 125
```

<210> SEQ ID NO 47
<211> LENGTH: 125
<212> TYPE: PRT
<213> ORGANISM: Artificial Sequence
<220> FEATURE:
<223> OTHER INFORMATION: anti-CD3 VH16

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
                35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
                115                 120                 125
```

<210> SEQ ID NO 48
<211> LENGTH: 125
<212> TYPE: PRT
<213> ORGANISM: Artificial Sequence
<220> FEATURE:
<223> OTHER INFORMATION: anti-CD3 VH17

<400> SEQUENCE: 48

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
                35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110
```

Ala Tyr Trp Gly Gln Gly Thr Leu Val Thr Val Ser Ser
        115                 120                 125

<210> SEQ ID NO 49
<211> LENGTH: 125
<212> TYPE: PRT
<213> ORGANISM: Artificial Sequence
<220> FEATURE:
<223> OTHER INFORMATION: anti-CD3 VH18

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 50
<211> LENGTH: 125
<212> TYPE: PRT
<213> ORGANISM: Artificial Sequence
<220> FEATURE:
<223> OTHER INFORMATION: anti-CD3 VH19

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 51
<211> LENGTH: 125
<212> TYPE: PRT
<213> ORGANISM: Artificial Sequence
<220> FEATURE:
<223> OTHER INFORMATION: anti-CD3 VH20

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 52
<211> LENGTH: 125
<212> TYPE: PRT
<213> ORGANISM: Artificial Sequence
<220> FEATURE:
<223> OTHER INFORMATION: anti-CD3 VH21

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 53
<211> LENGTH: 125
<212> TYPE: PRT
<213> ORGANISM: Artificial Sequence
<220> FEATURE:
<223> OTHER INFORMATION: anti-CD3 VH22

<400> SEQUENCE: 53

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Ser Ser
 65                  70                  75                  80

Leu Tyr Leu Gln Met Asn Asn Leu Lys Thr Glu Asp Thr Ala Met Tyr
                    85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 54
<211> LENGTH: 125
<212> TYPE: PRT
<213> ORGANISM: Artificial Sequence
<220> FEATURE:
<223> OTHER INFORMATION: anti-CD3 VH23

<400> SEQUENCE: 54

Glu Val Lys Leu Val Glu Ser Gly Gly Gly Leu Val Lys Pro Gly Arg
 1               5                  10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Cys Leu Glu Trp Val
            35                  40                  45

Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Ser Ile
 65                  70                  75                  80

Leu Tyr Leu Gln Met Asn Asn Leu Lys Thr Glu Asp Thr Ala Met Tyr
                    85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 55
<211> LENGTH: 125
<212> TYPE: PRT
<213> ORGANISM: Artificial Sequence
<220> FEATURE:
<223> OTHER INFORMATION: anti-CD3 VH24

<400> SEQUENCE: 55

Glu Val Lys Leu Val Glu Ser Gly Gly Gly Leu Val Lys Pro Gly Arg
 1               5                  10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Cys Leu Glu Trp Val
            35                  40                  45

Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Ser Ile
 65                  70                  75                  80

Leu Tyr Leu Gln Met Asn Ser Leu Lys Thr Glu Asp Thr Ala Met Tyr
                    85                  90                  95

Tyr Cys Val Arg His Gly Asn Phe Gly Asn Ser Tyr Val Ser Trp Phe

```
                100              105              110
Ala Tyr Trp Gly Gln Gly Thr Leu Val Thr Val Ser Ser
        115              120              125

<210> SEQ ID NO 56
<211> LENGTH: 125
<212> TYPE: PRT
<213> ORGANISM: Artificial Sequence
<220> FEATURE:
<223> OTHER INFORMATION: anti-CD3 VH25

<400> SEQUENCE: 56

Glu Val Lys Leu Val Glu Ser Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 57
<211> LENGTH: 125
<212> TYPE: PRT
<213> ORGANISM: Artificial Sequence
<220> FEATURE:
<223> OTHER INFORMATION: anti-CD3 VH26

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 58
<211> LENGTH: 125
<212> TYPE: PRT
<213> ORGANISM: Artificial Sequence
<220> FEATURE:
```

<223> OTHER INFORMATION: anti-CD3 VH27

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 59
<211> LENGTH: 124
<212> TYPE: PRT
<213> ORGANISM: Artificial Sequence
<220> FEATURE:
<223> OTHER INFORMATION: anti-CD3 VH28

<400> SEQUENCE: 59

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser
        115                 120

<210> SEQ ID NO 60
<211> LENGTH: 125
<212> TYPE: PRT
<213> ORGANISM: Artificial Sequence
<220> FEATURE:
<223> OTHER INFORMATION: anti-CD3 VH29

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val

```
                35                  40                  45
Ala Arg Ile Arg Ser Lys Tyr Asn Asn Tyr Ala Thr Tyr Tyr Ala Asp
            50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Val Arg His Gly Asn Phe Gly Asn Ser Tyr Val Ser Trp Phe
            100                 105                 110
Ala Tyr Trp Gly Gln Gly Thr Thr Val Thr Val Ser Ser
            115                 120                 125

<210> SEQ ID NO 61
<211> LENGTH: 125
<212> TYPE: PRT
<213> ORGANISM: Artificial Sequence
<220> FEATURE:
<223> OTHER INFORMATION: anti-CD3 VH30

<400> SEQUENCE: 61

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asn Thr Tyr
            20                  25                  30
Ala Met Asn Trp Val Arg Gln Ala Pro Gly Lys Cys Leu Glu Trp Val
            35                  40                  45
Ala Arg Ile Arg Ser Lys Tyr Asn Asn Tyr Ala Thr Tyr Tyr Ala Asp
            50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Val Arg His Gly Asn Phe Gly Asn Ser Tyr Val Ser Tyr Phe
            100                 105                 110
Ala Tyr Trp Gly Gln Gly Thr Thr Val Thr Val Ser Ser
            115                 120                 125

<210> SEQ ID NO 62
<211> LENGTH: 125
<212> TYPE: PRT
<213> ORGANISM: Artificial Sequence
<220> FEATURE:
<223> OTHER INFORMATION: anti-CD3 VH31

<400> SEQUENCE: 62

Glu Val Gln Leu Val Glu Ser Gly Gly Gly Leu Val Gln Pro Lys Gly
1               5                   10                  15
Ser Leu Lys Leu Ser Cys Ala Ala Ser Gly Phe Thr Phe Asn Thr Tyr
            20                  25                  30
Ala Met Asn Trp Val Arg Gln Ala Pro Gly Lys Cys Leu Glu Trp Val
            35                  40                  45
Ala Arg Ile Arg Ser Lys Tyr Asn Asn Tyr Ala Thr Tyr Tyr Ala Asp
            50                  55                  60
Ser Val Lys Asp Arg Phe Thr Ile Ser Arg Asp Asp Ser Gln Ser Ile
65                  70                  75                  80
Leu Tyr Leu Gln Met Asn Asn Leu Lys Thr Glu Asp Thr Ala Met Tyr
                85                  90                  95
```

```
Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 63
<211> LENGTH: 109
<212> TYPE: PRT
<213> ORGANISM: Artificial Sequence
<220> FEATURE:
<223> OTHER INFORMATION: anti-CD3 VL1

<400> SEQUENCE: 63

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 64
<211> LENGTH: 109
<212> TYPE: PRT
<213> ORGANISM: Artificial Sequence
<220> FEATURE:
<223> OTHER INFORMATION: anti-CD3 VL2

<400> SEQUENCE: 64

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Glu Ile Lys
            100                 105

<210> SEQ ID NO 65
<211> LENGTH: 109
<212> TYPE: PRT
<213> ORGANISM: Artificial Sequence
<220> FEATURE:
<223> OTHER INFORMATION: anti-CD3 VL3

<400> SEQUENCE: 65

Gln Ala Val Val Thr Gln Glu Pro Ser Leu Thr Val Ser Pro Gly Gly
```

```
1               5                   10                  15
Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu
                100                 105

<210> SEQ ID NO 66
<211> LENGTH: 109
<212> TYPE: PRT
<213> ORGANISM: Artificial Sequence
<220> FEATURE:
<223> OTHER INFORMATION: anti-CD3 VL4

<400> SEQUENCE: 66

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Thr Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
                100                 105

<210> SEQ ID NO 67
<211> LENGTH: 109
<212> TYPE: PRT
<213> ORGANISM: Artificial Sequence
<220> FEATURE:
<223> OTHER INFORMATION: anti-CD3 VL5

<400> SEQUENCE: 67

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Thr Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95
```

Leu Trp Val Phe Gly Gly Gly Thr Lys Leu Thr Val Leu
            100                 105

<210> SEQ ID NO 68
<211> LENGTH: 109
<212> TYPE: PRT
<213> ORGANISM: Artificial Sequence
<220> FEATURE:
<223> OTHER INFORMATION: anti-CD3 VL6

<400> SEQUENCE: 68

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 69
<211> LENGTH: 109
<212> TYPE: PRT
<213> ORGANISM: Artificial Sequence
<220> FEATURE:
<223> OTHER INFORMATION: anti-CD3 VL7

<400> SEQUENCE: 69

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 70
<211> LENGTH: 109
<212> TYPE: PRT
<213> ORGANISM: Artificial Sequence
<220> FEATURE:
<223> OTHER INFORMATION: anti-CD3 VL8

<400> SEQUENCE: 70

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly

```
            20                  25                  30
Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
     50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Val Leu Trp Tyr Ser Asn
                 85                  90                  95

Arg Trp Val Phe Gly Gly Gly Thr Lys Leu Thr Val Leu
            100                 105

<210> SEQ ID NO 71
<211> LENGTH: 109
<212> TYPE: PRT
<213> ORGANISM: Artificial Sequence
<220> FEATURE:
<223> OTHER INFORMATION: anti-CD3 VL9

<400> SEQUENCE: 71

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Thr Ser
             20                  25                  30

Asn Tyr Ala Asn Trp Val Gln Gln Lys Pro Gly Gln Ala Phe Arg Gly
         35                  40                  45

Leu Ile Gly Gly Thr Asn Lys Arg Ala Pro Gly Val Pro Ala Arg Phe
     50                  55                  60

Ser Gly Ser Leu Leu Gly Gly Lys Ala Ala Leu Thr Ile Ser Gly Ala
 65                  70                  75                  80

Gln Pro Glu Asp Glu Ala Asp Tyr Tyr Cys Ala Leu Trp Tyr Ser Asn
                 85                  90                  95

His Trp Val Phe Gly Gly Gly Thr Lys Leu Glu Ile Lys
            100                 105

<210> SEQ ID NO 72
<211> LENGTH: 109
<212> TYPE: PRT
<213> ORGANISM: Artificial Sequence
<220> FEATURE:
<223> OTHER INFORMATION: anti-CD3 VL10

<400> SEQUENCE: 72

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Thr Ser
             20                  25                  30

Asn Tyr Ala Asn Trp Val Gln Gln Lys Pro Gly Gln Ala Phe Arg Gly
         35                  40                  45

Leu Ile Gly Gly Thr Asn Lys Arg Ala Pro Gly Val Pro Ala Arg Phe
     50                  55                  60

Ser Gly Ser Leu Leu Gly Gly Lys Ala Ala Leu Thr Ile Ser Gly Ala
 65                  70                  75                  80

Gln Pro Glu Asp Glu Ala Asp Tyr Tyr Cys Ala Leu Trp Tyr Ser Asn
                 85                  90                  95

His Trp Val Phe Gly Cys Gly Thr Lys Leu Glu Ile Lys
            100                 105
```

<210> SEQ ID NO 73
<211> LENGTH: 109
<212> TYPE: PRT
<213> ORGANISM: Artificial Sequence
<220> FEATURE:
<223> OTHER INFORMATION: anti-CD3 VL11

<400> SEQUENCE: 73

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Cys Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Glu Gly Thr Lys Leu Glu Ile Lys
            100                 105

<210> SEQ ID NO 74
<211> LENGTH: 109
<212> TYPE: PRT
<213> ORGANISM: Artificial Sequence
<220> FEATURE:
<223> OTHER INFORMATION: anti-CD3 VL12

<400> SEQUENCE: 74

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Cys Gly Thr Lys Leu Thr Val Leu
            100                 105

<210> SEQ ID NO 75
<211> LENGTH: 109
<212> TYPE: PRT
<213> ORGANISM: Artificial Sequence
<220> FEATURE:
<223> OTHER INFORMATION: anti-CD3 VL13

<400> SEQUENCE: 75

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly

```
                    35                  40                  45
Leu Ile Gly Gly Thr Asn Lys Arg Ala Pro Gly Val Pro Ala Arg Phe
        50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Glu Ile Lys
                100                 105
```

<210> SEQ ID NO 76
<211> LENGTH: 109
<212> TYPE: PRT
<213> ORGANISM: Artificial Sequence
<220> FEATURE:
<223> OTHER INFORMATION: anti-CD3 VL14

<400> SEQUENCE: 76

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Cys Gly Thr Lys Leu Thr Val Leu
                100                 105
```

<210> SEQ ID NO 77
<211> LENGTH: 109
<212> TYPE: PRT
<213> ORGANISM: Artificial Sequence
<220> FEATURE:
<223> OTHER INFORMATION: anti-CD3 VL15

<400> SEQUENCE: 77

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Thr Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
                100                 105
```

<210> SEQ ID NO 78
<211> LENGTH: 109

```
<212> TYPE: PRT
<213> ORGANISM: Artificial Sequence
<220> FEATURE:
<223> OTHER INFORMATION: anti-CD3 VL16

<400> SEQUENCE: 78

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Cys Gly Thr Lys Leu Thr Val Leu
            100                 105

<210> SEQ ID NO 79
<211> LENGTH: 109
<212> TYPE: PRT
<213> ORGANISM: Artificial Sequence
<220> FEATURE:
<223> OTHER INFORMATION: anti-CD3 VL17

<400> SEQUENCE: 79

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Cys Gly Thr Lys Leu Thr Val Leu
            100                 105

<210> SEQ ID NO 80
<211> LENGTH: 109
<212> TYPE: PRT
<213> ORGANISM: Artificial Sequence
<220> FEATURE:
<223> OTHER INFORMATION: anti-CD3 VL18

<400> SEQUENCE: 80

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
```

```
                    50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Cys Gly Thr Lys Leu Thr Val Leu
                100                 105

<210> SEQ ID NO 81
<211> LENGTH: 109
<212> TYPE: PRT
<213> ORGANISM: Artificial Sequence
<220> FEATURE:
<223> OTHER INFORMATION: anti-CD3 VL19

<400> SEQUENCE: 81

Gln Thr Val Val Thr Gln Glu Pro Ser Leu Thr Val Ser Pro Gly Gly
  1               5                  10                  15

Thr Val Thr Leu Thr Cys Gly Ser Ser Thr Gly Ala Val Thr Ser Gly
                 20                  25                  30

Asn Tyr Pro Asn Trp Val Gln Gln Lys Pro Gly Gln Ala Pro Arg Gly
             35                  40                  45

Leu Ile Gly Gly Thr Lys Phe Leu Ala Pro Gly Thr Pro Ala Arg Phe
         50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Val Leu Trp Tyr Ser Asn
                 85                  90                  95

Arg Trp Val Phe Gly Cys Gly Thr Lys Leu Thr Val Leu
                100                 105

<210> SEQ ID NO 82
<211> LENGTH: 226
<212> TYPE: PRT
<213> ORGANISM: Artificial Sequence
<220> FEATURE:
<223> OTHER INFORMATION: Knob Fc

<400> SEQUENCE: 82

Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
         50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
        130                 135                 140
```

```
Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Thr
225

<210> SEQ ID NO 83
<211> LENGTH: 226
<212> TYPE: PRT
<213> ORGANISM: Artificial Sequence
<220> FEATURE:
<223> OTHER INFORMATION: Hole Fc

<400> SEQUENCE: 83

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
        100                 105                 110

Glu Lys Thr Ile Ser Lys Ala Lys Gly Gln Pro Arg Glu Pro Gln Val
    115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Thr
225

<210> SEQ ID NO 84
<211> LENGTH: 223
<212> TYPE: PRT
<213> ORGANISM: Artificial Sequence
<220> FEATURE:
```

<223> OTHER INFORMATION: Knob Fc

<400> SEQUENCE: 84

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Thr
    210                 215                 220
```

<210> SEQ ID NO 85
<211> LENGTH: 223
<212> TYPE: PRT
<213> ORGANISM: Artificial Sequence
<220> FEATURE:
<223> OTHER INFORMATION: Hole Fc

<400> SEQUENCE: 85

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125
```

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Thr
    210                 215                 220

<210> SEQ ID NO 86
<211> LENGTH: 226
<212> TYPE: PRT
<213> ORGANISM: Artificial Sequence
<220> FEATURE:
<223> OTHER INFORMATION: Knob Fc

<400> SEQUENCE: 86

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 87
<211> LENGTH: 226
<212> TYPE: PRT
<213> ORGANISM: Artificial Sequence
<220> FEATURE:
<223> OTHER INFORMATION: Hole Fc

<400> SEQUENCE: 87

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 88
<211> LENGTH: 223
<212> TYPE: PRT
<213> ORGANISM: Artificial Sequence
<220> FEATURE:
<223> OTHER INFORMATION: Knob Fc

<400> SEQUENCE: 88

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr

```
            100                 105                 110
Ile Ser Lys Ala Lys Gly Gln Pro Arg Glu Pro Gln Val Tyr Thr Leu
            115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
            195                 200                 205

Leu His Asn His Tyr Thr Gln Lys Ser Leu Ser Leu Ser Pro Gly
            210                 215                 220

<210> SEQ ID NO 89
<211> LENGTH: 223
<212> TYPE: PRT
<213> ORGANISM: Artificial Sequence
<220> FEATURE:
<223> OTHER INFORMATION: Hole Fc

<400> SEQUENCE: 89

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
            195                 200                 205

Leu His Asn His Tyr Thr Gln Lys Ser Leu Ser Leu Ser Pro Gly
            210                 215                 220

<210> SEQ ID NO 90
<211> LENGTH: 226
<212> TYPE: PRT
```

<213> ORGANISM: Artificial Sequence
<220> FEATURE:
<223> OTHER INFORMATION: Hole Fc

<400> SEQUENCE: 90

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Thr
225
```

<210> SEQ ID NO 91
<211> LENGTH: 223
<212> TYPE: PRT
<213> ORGANISM: Artificial Sequence
<220> FEATURE:
<223> OTHER INFORMATION: Hole Fc

<400> SEQUENCE: 91

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95
```

```
Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
        130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro Thr
    210                 215                 220
```

<210> SEQ ID NO 92
<211> LENGTH: 226
<212> TYPE: PRT
<213> ORGANISM: Artificial Sequence
<220> FEATURE:
<223> OTHER INFORMATION: Hole Fc

<400> SEQUENCE: 92

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly
225
```

<210> SEQ ID NO 93
<211> LENGTH: 223
<212> TYPE: PRT
<213> ORGANISM: Artificial Sequence
<220> FEATURE:
<223> OTHER INFORMATION: Hole Fc

<400> SEQUENCE: 93

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro Gly
    210                 215                 220
```

<210> SEQ ID NO 94
<211> LENGTH: 226
<212> TYPE: PRT
<213> ORGANISM: Artificial Sequence
<220> FEATURE:
<223> OTHER INFORMATION: Knob Fc

<400> SEQUENCE: 94

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn His Tyr Thr Gln Lys Ser Leu Ser Leu Ser
    210                 215                 220

Pro Thr
225

<210> SEQ ID NO 95
<211> LENGTH: 223
<212> TYPE: PRT
<213> ORGANISM: Artificial Sequence
<220> FEATURE:
<223> OTHER INFORMATION: Knob Fc

<400> SEQUENCE: 95

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn His Tyr Thr Gln Lys Ser Leu Ser Leu Ser Pro Thr
    210                 215                 220

<210> SEQ ID NO 96
<211> LENGTH: 226
<212> TYPE: PRT
<213> ORGANISM: Artificial Sequence
<220> FEATURE:
<223> OTHER INFORMATION: Knob Fc

<400> SEQUENCE: 96

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn His Tyr Thr Gln Lys Ser Leu Ser Leu Ser
    210                 215                 220

Pro Gly
225

<210> SEQ ID NO 97
<211> LENGTH: 223
<212> TYPE: PRT
<213> ORGANISM: Artificial Sequence
<220> FEATURE:
<223> OTHER INFORMATION: Knob Fc

<400> SEQUENCE: 97

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val

```
                65                  70                  75                  80
Ser Val Leu Thr Val Leu His Gln Asp Trp Leu Asn Gly Lys Glu Tyr
                    85                  90                  95

Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Tyr Thr Leu
                115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Val Leu Asp
                165                 170                 175

Ser Asp Gly Ser Phe Phe Leu Tyr Ser Lys Leu Thr Val Asp Lys Ser
                180                 185                 190

Arg Trp Gln Gln Gly Asn Val Phe Ser Cys Ser Val Val His Glu Ala
                195                 200                 205

Leu His Asn His Tyr Thr Gln Lys Ser Leu Ser Leu Ser Pro Gly
210                 215                 220

<210> SEQ ID NO 98
<211> LENGTH: 226
<212> TYPE: PRT
<213> ORGANISM: Artificial Sequence
<220> FEATURE:
<223> OTHER INFORMATION: Hole Fc

<400> SEQUENCE: 98

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Val
                195                 200                 205

His Glu Ala Leu His Asn Arg Tyr Thr Gln Lys Ser Leu Ser Leu Ser
```

Pro Thr
225

<210> SEQ ID NO 99
<211> LENGTH: 223
<212> TYPE: PRT
<213> ORGANISM: Artificial Sequence
<220> FEATURE:
<223> OTHER INFORMATION: Hole Fc

<400> SEQUENCE: 99

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn Arg Tyr Thr Gln Lys Ser Leu Ser Leu Ser Pro Thr
    210                 215                 220

<210> SEQ ID NO 100
<211> LENGTH: 226
<212> TYPE: PRT
<213> ORGANISM: Artificial Sequence
<220> FEATURE:
<223> OTHER INFORMATION: Hole Fc

<400> SEQUENCE: 100

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
            195                 200                 205

His Glu Ala Leu His Asn Arg Tyr Thr Gln Lys Ser Leu Ser Leu Ser
210                 215                 220

Pro Gly
225

<210> SEQ ID NO 101
<211> LENGTH: 223
<212> TYPE: PRT
<213> ORGANISM: Artificial Sequence
<220> FEATURE:
<223> OTHER INFORMATION: Hole Fc

<400> SEQUENCE: 101

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
            85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val His Glu Ala
            195                 200                 205

Leu His Asn Arg Tyr Thr Gln Lys Ser Leu Ser Leu Ser Pro Gly
    210                 215                 220

<210> SEQ ID NO 102
<211> LENGTH: 5
<212> TYPE: PRT
<213> ORGANISM: Artificial Sequence
<220> FEATURE:
<223> OTHER INFORMATION: Peptide Linker

<400> SEQUENCE: 102

Pro Gly Gly Gly Gly
1               5

<210> SEQ ID NO 103
<211> LENGTH: 4
<212> TYPE: PRT
<213> ORGANISM: Artificial Sequence
<220> FEATURE:
<223> OTHER INFORMATION: Peptide Linker

<400> SEQUENCE: 103

Gly Gly Gly Gly
1

<210> SEQ ID NO 104
<211> LENGTH: 18
<212> TYPE: PRT
<213> ORGANISM: Artificial Sequence
<220> FEATURE:
<223> OTHER INFORMATION: Linker

<400> SEQUENCE: 104

Gly Pro Ala Gly Leu Gly Leu Glu Pro Asp Gly Ser Arg Gln Ala Arg
1               5                   10                  15

Val Gly

<210> SEQ ID NO 105
<211> LENGTH: 18
<212> TYPE: PRT
<213> ORGANISM: Artificial Sequence
<220> FEATURE:
<223> OTHER INFORMATION: Linker

<400> SEQUENCE: 105

Gly Gly Ser Gly Gly Gly Gly Ile Glu Pro Asp Ile Gly Gly Ser Gly
1               5                   10                  15

Gly Ser

<210> SEQ ID NO 106
<211> LENGTH: 18
<212> TYPE: PRT
<213> ORGANISM: Artificial Sequence
<220> FEATURE:
<223> OTHER INFORMATION: Linker

<400> SEQUENCE: 106

Gly Gly Ser Gly Gly Gly Gly Leu Glu Ala Asp Thr Gly Gly Ser Gly
1               5                   10                  15

Gly Ser

<210> SEQ ID NO 107

```
<211> LENGTH: 9
<212> TYPE: PRT
<213> ORGANISM: Artificial Sequence
<220> FEATURE:
<223> OTHER INFORMATION: Linker

<400> SEQUENCE: 107

Gly Ser Ile Glu Pro Asp Ile Gly Ser
1               5

<210> SEQ ID NO 108
<211> LENGTH: 9
<212> TYPE: PRT
<213> ORGANISM: Artificial Sequence
<220> FEATURE:
<223> OTHER INFORMATION: Linker

<400> SEQUENCE: 108

Gly Ser Leu Glu Ala Asp Thr Gly Ser
1               5

<210> SEQ ID NO 109
<211> LENGTH: 18
<212> TYPE: PRT
<213> ORGANISM: Artificial Sequence
<220> FEATURE:
<223> OTHER INFORMATION: Linker

<400> SEQUENCE: 109

Gly Gly Ser Gly Gly Gly Gly Ile Glu Pro Asp Gly Gly Ser Gly
1               5                   10                  15

Gly Ser

<210> SEQ ID NO 110
<211> LENGTH: 18
<212> TYPE: PRT
<213> ORGANISM: Artificial Sequence
<220> FEATURE:
<223> OTHER INFORMATION: Linker

<400> SEQUENCE: 110

Gly Gly Ser Gly Gly Gly Gly Ile Glu Pro Asp Val Gly Gly Ser Gly
1               5                   10                  15

Gly Ser

<210> SEQ ID NO 111
<211> LENGTH: 18
<212> TYPE: PRT
<213> ORGANISM: Artificial Sequence
<220> FEATURE:
<223> OTHER INFORMATION: Linker

<400> SEQUENCE: 111

Gly Gly Ser Gly Gly Gly Gly Ile Glu Pro Asp Ser Gly Gly Ser Gly
1               5                   10                  15

Gly Ser

<210> SEQ ID NO 112
<211> LENGTH: 18
<212> TYPE: PRT
<213> ORGANISM: Artificial Sequence
<220> FEATURE:
<223> OTHER INFORMATION: Linker

<400> SEQUENCE: 112
```

Gly Gly Ser Gly Gly Gly Gly Ile Glu Pro Asp Thr Gly Gly Ser Gly
1               5                   10                  15

Gly Ser

<210> SEQ ID NO 113
<211> LENGTH: 12
<212> TYPE: PRT
<213> ORGANISM: Artificial Sequence
<220> FEATURE:
<223> OTHER INFORMATION: Linker

<400> SEQUENCE: 113

Gly Gly Gly Ser Leu Glu Pro Asp Gly Ser Gly Ser
1               5                   10

<210> SEQ ID NO 114
<211> LENGTH: 18
<212> TYPE: PRT
<213> ORGANISM: Artificial Sequence
<220> FEATURE:
<223> OTHER INFORMATION: Linker

<400> SEQUENCE: 114

Gly Pro Ala Gly Leu Gly Leu Glu Ala Asp Gly Ser Arg Gln Ala Arg
1               5                   10                  15

Val Gly

<210> SEQ ID NO 115
<211> LENGTH: 15
<212> TYPE: PRT
<213> ORGANISM: Artificial Sequence
<220> FEATURE:
<223> OTHER INFORMATION: Linker

<400> SEQUENCE: 115

Gly Gly Glu Gly Gly Gly Gly Ser Gly Gly Ser Gly Gly Gly Ser
1               5                   10                  15

<210> SEQ ID NO 116
<211> LENGTH: 18
<212> TYPE: PRT
<213> ORGANISM: Artificial Sequence
<220> FEATURE:
<223> OTHER INFORMATION: Linker

<400> SEQUENCE: 116

Gly Ser Ser Ala Gly Ser Glu Ala Gly Gly Ser Gly Gln Ala Gly Val
1               5                   10                  15

Gly Ser

<210> SEQ ID NO 117
<211> LENGTH: 18
<212> TYPE: PRT
<213> ORGANISM: Artificial Sequence
<220> FEATURE:
<223> OTHER INFORMATION: Linker

<400> SEQUENCE: 117

Gly Gly Ser Gly Gly Gly Gly Leu Glu Ala Glu Gly Ser Gly Gly Gly
1               5                   10                  15

Gly Ser

<210> SEQ ID NO 118
<211> LENGTH: 18

```
<212> TYPE: PRT
<213> ORGANISM: Artificial Sequence
<220> FEATURE:
<223> OTHER INFORMATION: Linker

<400> SEQUENCE: 118

Gly Gly Ser Gly Gly Gly Gly Ile Glu Pro Asp Pro Gly Gly Ser Gly
1               5                   10                  15

Gly Ser

<210> SEQ ID NO 119
<211> LENGTH: 18
<212> TYPE: PRT
<213> ORGANISM: Artificial Sequence
<220> FEATURE:
<223> OTHER INFORMATION: Linker

<400> SEQUENCE: 119

Gly Gly Gly Gly Gly Ser Gly Gly Gly Gly Ser Gly Gly Gly Gly
1               5                   10                  15

Gly Ser

<210> SEQ ID NO 120
<211> LENGTH: 129
<212> TYPE: PRT
<213> ORGANISM: Artificial Sequence
<220> FEATURE:
<223> OTHER INFORMATION: FR alpha sdAb

<400> SEQUENCE: 120

Gln Leu Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Asn Tyr
            20                  25                  30

Ala Ile Gly Trp Phe Arg Gln Ala Pro Gly Lys Glu Arg Glu Gly Val
        35                  40                  45

Ser Cys Ile Ser Ser Asp Gly Ser Thr Tyr Tyr Ala Asp Ser Val
    50                  55                  60

Lys Gly Arg Phe Thr Ile Ser Arg Asn Asn Ala Lys Gly Thr Val Tyr
65                  70                  75                  80

Leu Leu Met Asn Ser Leu Lys Pro Glu Asp Thr Ala Val Tyr Tyr Cys
                85                  90                  95

Ala Thr Glu Leu Val Pro Ala Cys Thr Tyr Ser Asn Gly Arg Gly Pro
            100                 105                 110

Leu Asp Gly Met Asp Tyr Trp Gly Lys Gly Thr Gln Val Thr Val Lys
        115                 120                 125

Pro

<210> SEQ ID NO 121
<211> LENGTH: 119
<212> TYPE: PRT
<213> ORGANISM: Artificial Sequence
<220> FEATURE:
<223> OTHER INFORMATION: FR alpha sdAb

<400> SEQUENCE: 121

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asp
            20                  25                  30
```

Ala Thr Ala Trp Tyr Arg Gln Ala Pro Gly Lys Gln Arg Glu Leu Val
         35                  40                  45

Ala Ile Ile Thr Ser Ser Gly Ser Thr Asn Tyr Pro Glu Ser Val Lys
 50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Asn
                 85                  90                  95

Ala Ile Thr Arg Tyr Gly Gly Ser Tyr Asp Phe Trp Gly Gln Gly
                 100                 105                 110

Thr Leu Val Thr Val Lys Pro
            115

<210> SEQ ID NO 122
<211> LENGTH: 101
<212> TYPE: PRT
<213> ORGANISM: Artificial Sequence
<220> FEATURE:
<223> OTHER INFORMATION: FR alpha sdAb

<400> SEQUENCE: 122

Glu Val Gln Pro Gly Gly Ser Leu Arg Leu Ser Cys Ala Ala Ser Glu
1               5                   10                  15

Thr Phe Gly Val Val Phe Thr Leu Gly Trp Tyr Arg Gln Ala Pro Gly
            20                  25                  30

Lys Gly Arg Glu Phe Val Ala Arg Val Thr Gly Thr Asp Thr Val Asp
         35                  40                  45

Tyr Ala Glu Ser Val Lys Gly Arg Phe Thr Ile Ser Ser Asp Phe Ala
 50                  55                  60

Arg Asn Thr Val Tyr Leu Gln Met Asn Ser Leu Arg Ala Glu Asp Thr
 65                  70                  75                  80

Ala Val Tyr Tyr Cys Asn Thr Gly Ala Tyr Trp Gly Gln Gly Thr Leu
                 85                  90                  95

Val Thr Val Lys Pro
            100

<210> SEQ ID NO 123
<211> LENGTH: 125
<212> TYPE: PRT
<213> ORGANISM: Artificial Sequence
<220> FEATURE:
<223> OTHER INFORMATION: cMET sdAb

<400> SEQUENCE: 123

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
         35                  40                  45

Leu Cys Ile Asp Ala Ser Asp Asp Ile Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Gly Val Tyr Tyr Cys
                 85                  90                  95

Ala Thr Pro Ile Gly Leu Ser Ser Cys Leu Leu Glu Tyr Asp Tyr
                 100                 105                 110

Asp Tyr Trp Gly Gln Gly Thr Leu Val Thr Val Lys Pro
         115                 120                 125

<210> SEQ ID NO 124
<211> LENGTH: 245
<212> TYPE: PRT
<213> ORGANISM: Artificial Sequence
<220> FEATURE:
<223> OTHER INFORMATION: B7H3 scFv

<400> SEQUENCE: 124

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser Gly Gly Gly Gly Ser
        115                 120                 125

Gly Gly Gly Gly Ser Gly Gly Gly Ser Asp Ile Gln Leu Thr Gln
    130                 135                 140

Ser Pro Ser Phe Leu Ser Ala Ser Val Gly Asp Arg Val Thr Ile Thr
145                 150                 155                 160

Cys Lys Ala Ser Gln Asn Val Asp Thr Asn Val Ala Trp Tyr Gln Gln
                165                 170                 175

Lys Pro Gly Lys Ala Pro Lys Ala Leu Ile Tyr Ser Ala Ser Tyr Arg
            180                 185                 190

Tyr Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Tyr Asn Asn Tyr Pro Phe Thr Phe Gly Gln Gly Thr
225                 230                 235                 240

Lys Leu Glu Ile Lys
            245

<210> SEQ ID NO 125
<211> LENGTH: 247
<212> TYPE: PRT
<213> ORGANISM: Artificial Sequence
<220> FEATURE:
<223> OTHER INFORMATION: CD20 scFv

<400> SEQUENCE: 125

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met

```
                35                  40                  45
Gly Arg Ile Phe Pro Gly Asp Gly Asp Thr Asp Tyr Asn Gly Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
                100                 105                 110

Thr Leu Val Thr Val Ser Gly Ser Gly Gly Gly Ser Gly Gly Gly
            115                 120                 125

Gly Thr Gly Gly Gly Ser Asp Ile Val Met Thr Gln Thr Pro Leu
    130                 135                 140

Ser Leu Pro Val Thr Pro Gly Glu Pro Ala Ser Ile Ser Cys Arg Ser
145                 150                 155                 160

Ser Lys Ser Leu Leu His Ser Asn Gly Ile Thr Tyr Leu Tyr Trp Tyr
                165                 170                 175

Leu Gln Lys Pro Gly Gln Ser Pro Gln Leu Leu Ile Tyr Gln Met Ser
                180                 185                 190

Asn Leu Val Ser Gly Val Pro Asp Arg Phe Ser Gly Ser Gly Ser Gly
            195                 200                 205

Thr Asp Phe Thr Leu Lys Ile Ser Arg Val Glu Ala Glu Asp Val Gly
210                 215                 220

Val Tyr Tyr Cys Ala Gln Asn Leu Glu Leu Pro Tyr Thr Phe Gly Gly
225                 230                 235                 240

Gly Thr Lys Val Glu Ile Lys
                245

<210> SEQ ID NO 126
<211> LENGTH: 241
<212> TYPE: PRT
<213> ORGANISM: Artificial Sequence
<220> FEATURE:
<223> OTHER INFORMATION: DLL3 scFv

<400> SEQUENCE: 126

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
                 20                  25                  30

Tyr Trp Ser Trp Ile Arg Gln Pro Pro Gly Lys Gly Leu Glu Trp Ile
             35                  40                  45

Gly Tyr Val Tyr Tyr Ser Gly Thr Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Ser Ile Ala Val Thr Gly Phe Tyr Phe Asp Tyr Trp Gly Gln Gly Thr
                100                 105                 110

Leu Val Thr Val Ser Ser Gly Gly Gly Gly Ser Gly Gly Gly Gly Ser
            115                 120                 125

Gly Gly Gly Gly Ser Glu Ile Val Leu Thr Gln Ser Pro Gly Thr Leu
    130                 135                 140

Ser Leu Ser Pro Gly Glu Arg Val Thr Leu Ser Cys Arg Ala Ser Gln
```

145                 150                 155                 160
Arg Val Asn Asn Tyr Leu Ala Trp Tyr Gln Gln Arg Pro Gly Gln
                    165                 170                 175

Ala Pro Arg Leu Leu Ile Tyr Gly Ala Ser Ser Arg Ala Thr Gly Ile
                180                 185                 190

Pro Asp Arg Phe Ser Gly Ser Gly Ser Gly Thr Asp Phe Thr Leu Thr
                195                 200                 205

Ile Ser Arg Leu Glu Pro Glu Asp Phe Ala Val Tyr Tyr Cys Gln Gln
210                 215                 220

Tyr Asp Arg Ser Pro Leu Thr Phe Gly Gly Gly Thr Lys Leu Glu Ile
225                 230                 235                 240

Lys

<210> SEQ ID NO 127
<211> LENGTH: 225
<212> TYPE: PRT
<213> ORGANISM: Artificial Sequence
<220> FEATURE:
<223> OTHER INFORMATION: B7H3 Fd

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Ser Ser Phe
            20                  25                  30

Gly Met His Trp Val Arg Gln Ala Pro Gly Lys Gly Leu Glu Trp Val
            35                  40                  45

Ala Tyr Ile Ser Ser Asp Ser Ser Ala Ile Tyr Tyr Ala Asp Thr Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 128
<211> LENGTH: 214
<212> TYPE: PRT
<213> ORGANISM: Artificial Sequence

<220> FEATURE:
<223> OTHER INFORMATION: B7H3 LC

<400> SEQUENCE: 128

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 129
<211> LENGTH: 225
<212> TYPE: PRT
<213> ORGANISM: Artificial Sequence
<220> FEATURE:
<223> OTHER INFORMATION: 5T4 Fd

<400> SEQUENCE: 129

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gln Trp Asp Tyr Asp Val Arg Ala Met Asn Tyr Trp
            100                 105                 110

Gly Gln Gly Thr Ser Val Thr Val Ser Ser Ala Ser Thr Lys Gly Pro

-continued

```
              115                 120                 125
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225
```

<210> SEQ ID NO 130
<211> LENGTH: 214
<212> TYPE: PRT
<213> ORGANISM: Artificial Sequence
<220> FEATURE:
<223> OTHER INFORMATION: 5T4 LC

<400> SEQUENCE: 130

```
Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg Leu Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 131
<211> LENGTH: 222
<212> TYPE: PRT

```
<213> ORGANISM: Artificial Sequence
<220> FEATURE:
<223> OTHER INFORMATION: gpNMB Fd

<400> SEQUENCE: 131
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Phe
            20                  25                  30

Asn Tyr Tyr Trp Ser Trp Ile Arg His His Pro Gly Lys Gly Leu Glu
        35                  40                  45

Trp Ile Gly Tyr Ile Tyr Tyr Ser Gly Ser Thr Tyr Ser Asn Pro Ser
    50                  55                  60

Leu Lys Ser Arg Val Thr Ile Ser Val Asp Thr Ser Lys Asn Gln Phe
65                  70                  75                  80

Ser Leu Thr Leu Ser Ser Val Thr Ala Ala Asp Thr Ala Val Tyr Tyr
                85                  90                  95

Cys Ala Arg Gly Tyr Asn Trp Asn Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

```
<210> SEQ ID NO 132
<211> LENGTH: 215
<212> TYPE: PRT
<213> ORGANISM: Artificial Sequence
<220> FEATURE:
<223> OTHER INFORMATION: gpNMB LC

<400> SEQUENCE: 132
```

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Asn Asn
            20                  25                  30

Leu Val Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys Arg Thr Val Ala
            100                 105                 110

-continued

```
Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 133
<211> LENGTH: 223
<212> TYPE: PRT
<213> ORGANISM: Artificial Sequence
<220> FEATURE:
<223> OTHER INFORMATION: DLL3 Fd

<400> SEQUENCE: 133

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Ala Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Ser
65                  70                  75                  80

Leu Gln Ile Ile Asn Leu Lys Asn Glu Asp Thr Ala Thr Tyr Phe Cys
                85                  90                  95

Ala Arg Ile Gly Asp Ser Ser Pro Ser Asp Tyr Trp Gly Gln Gly Thr
            100                 105                 110

Thr Leu Thr Val Ser Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 134
<211> LENGTH: 214
<212> TYPE: PRT
<213> ORGANISM: Artificial Sequence
<220> FEATURE:
```

<223> OTHER INFORMATION: DLL3 LC

<400> SEQUENCE: 134

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Val Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ala Gly
    50                  55                  60

Ser Gly Tyr Gly Thr Asp Phe Ser Phe Thr Ile Ser Thr Val Gln Ala
65                  70                  75                  80

Glu Asp Leu Ala Val Tyr Phe Cys Gln Gln Asp Tyr Thr Ser Pro Trp
                85                  90                  95

Thr Phe Gly Gly Gly Thr Lys Leu Glu Ile Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 135
<211> LENGTH: 6
<212> TYPE: PRT
<213> ORGANISM: Artificial Sequence
<220> FEATURE:
<223> OTHER INFORMATION: Linker

<400> SEQUENCE: 135

Gly Gly Gly Gly Gly Ser
1               5

<210> SEQ ID NO 136
<211> LENGTH: 5
<212> TYPE: PRT
<213> ORGANISM: Artificial Sequence
<220> FEATURE:
<223> OTHER INFORMATION: Linker

<400> SEQUENCE: 136

Ile Glu Pro Asp Ile
1               5

<210> SEQ ID NO 137
<211> LENGTH: 5
<212> TYPE: PRT
<213> ORGANISM: Artificial Sequence
<220> FEATURE:
<223> OTHER INFORMATION: Linker

<400> SEQUENCE: 137

Leu Glu Ala Asp Thr
1               5

<210> SEQ ID NO 138
<211> LENGTH: 5
<212> TYPE: PRT
<213> ORGANISM: Artificial Sequence
<220> FEATURE:
<223> OTHER INFORMATION: Linker

<400> SEQUENCE: 138

Ile Glu Pro Asp Gly
1               5

<210> SEQ ID NO 139
<211> LENGTH: 5
<212> TYPE: PRT
<213> ORGANISM: Artificial Sequence
<220> FEATURE:
<223> OTHER INFORMATION: Linker

<400> SEQUENCE: 139

Ile Glu Pro Asp Val
1               5

<210> SEQ ID NO 140
<211> LENGTH: 5
<212> TYPE: PRT
<213> ORGANISM: Artificial Sequence
<220> FEATURE:
<223> OTHER INFORMATION: Linker

<400> SEQUENCE: 140

Ile Glu Pro Asp Ser
1               5

<210> SEQ ID NO 141
<211> LENGTH: 5
<212> TYPE: PRT
<213> ORGANISM: Artificial Sequence
<220> FEATURE:
<223> OTHER INFORMATION: Linker

<400> SEQUENCE: 141

Ile Glu Pro Asp Thr
1               5

<210> SEQ ID NO 142
<211> LENGTH: 4
<212> TYPE: PRT
<213> ORGANISM: Artificial Sequence
<220> FEATURE:
<223> OTHER INFORMATION: Linker

<400> SEQUENCE: 142

Leu Glu Pro Asp
1

<210> SEQ ID NO 143
<211> LENGTH: 4
<212> TYPE: PRT
<213> ORGANISM: Artificial Sequence
<220> FEATURE:
<223> OTHER INFORMATION: Linker

<400> SEQUENCE: 143

Leu Glu Ala Glu
1

<210> SEQ ID NO 144
<211> LENGTH: 5
<212> TYPE: PRT
<213> ORGANISM: Artificial Sequence
<220> FEATURE:
<223> OTHER INFORMATION: Linker

<400> SEQUENCE: 144

Ile Glu Pro Asp Pro
1               5

<210> SEQ ID NO 145
<211> LENGTH: 274
<212> TYPE: PRT
<213> ORGANISM: Artificial Sequence
<220> FEATURE:
<223> OTHER INFORMATION: Second Polypeptide Chain of B7-H3 x CD3
      Bispecific DART-A Diabody

<400> SEQUENCE: 145

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Ser Phe Gly Met His Trp Val Arg Gln Ala Pro Gly
145                 150                 155                 160

Lys Gly Leu Glu Trp Val Ala Tyr Ile Ser Ser Asp Ser Ser Ala Ile
                165                 170                 175

Tyr Tyr Ala Asp Thr Val Lys Gly Arg Phe Thr Ile Ser Arg Asp Asn
            180                 185                 190

Ala Lys Asn Ser Leu Tyr Leu Gln Met Asn Ser Leu Arg Asp Glu Asp
        195                 200                 205

Thr Ala Val Tyr Tyr Cys Gly Arg Gly Arg Glu Asn Ile Tyr Tyr Gly
    210                 215                 220

Ser Arg Leu Asp Tyr Trp Gly Gln Gly Thr Thr Val Thr Val Ser Ser
225                 230                 235                 240

Gly Gly Cys Gly Gly Gly Lys Val Ala Ala Leu Lys Glu Lys Val Ala
                245                 250                 255

Ala Leu Lys Glu Lys Val Ala Ala Leu Lys Glu Lys Val Ala Ala Leu
            260                 265                 270

Lys Glu

<210> SEQ ID NO 146
<211> LENGTH: 227
<212> TYPE: PRT
<213> ORGANISM: Artificial Sequence
<220> FEATURE:
<223> OTHER INFORMATION: Third Polypeptide Chain of B7-H3 x CD3
      Bispecific DART-A Diabody

<400> SEQUENCE: 146

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Lys
225

<210> SEQ ID NO 147
<211> LENGTH: 18
<212> TYPE: PRT
<213> ORGANISM: Artificial Sequence
<220> FEATURE:
<223> OTHER INFORMATION: Linker

<400> SEQUENCE: 147

Gly Gly Ser Gly Gly Gly Gly Ser Gly Gly Gly Gly Ser Gly Gly Gly
1               5                   10                  15

Gly Ser

<210> SEQ ID NO 148
<211> LENGTH: 19
<212> TYPE: PRT
<213> ORGANISM: Artificial Sequence

```
<220> FEATURE:
<223> OTHER INFORMATION: Linker

<400> SEQUENCE: 148

Thr Gly Gly Ser Gly Gly Gly Ile Glu Pro Asp Ile Gly Gly Ser
1               5                   10                  15

Gly Gly Ser

<210> SEQ ID NO 149
<211> LENGTH: 5
<212> TYPE: PRT
<213> ORGANISM: Artificial Sequence
<220> FEATURE:
<223> OTHER INFORMATION: Linker

<400> SEQUENCE: 149

Gly Gly Gly Gly Ser
1               5

<210> SEQ ID NO 150
<211> LENGTH: 5
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (1)..(1)
<223> OTHER INFORMATION: X1= I, L, Y, M, F, V, or A
<220> FEATURE:
<221> NAME/KEY: VARIANT
<222> LOCATION: (2)..(2)
<223> OTHER INFORMATION: X2 = A, G, S, V, E, D, Q, N, or Y
<220> FEATURE:
<221> NAME/KEY: VARIANT
<222> LOCATION: (3)..(3)
<223> OTHER INFORMATION: X3 = H, P, A, V, G, S, or T
<220> FEATURE:
<221> NAME/KEY: VARIANT
<222> LOCATION: (4)..(4)
<223> OTHER INFORMATION: X4 = D or E
<220> FEATURE:
<221> NAME/KEY: VARIANT
<222> LOCATION: (5)..(5)
<223> OTHER INFORMATION: X5 = I, L, Y, M, F, V, T, S, G or A

<400> SEQUENCE: 150

Xaa Xaa Xaa Xaa Xaa
1               5

<210> SEQ ID NO 151
<211> LENGTH: 5
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (1)..(1)
<223> OTHER INFORMATION: X1 = I or L
<220> FEATURE:
<221> NAME/KEY: VARIANT
<222> LOCATION: (3)..(3)
<223> OTHER INFORMATION: X3 = P or A
<220> FEATURE:
<221> NAME/KEY: VARIANT
<222> LOCATION: (5)..(5)
<223> OTHER INFORMATION: X5 = I, V, T, S, or G

<400> SEQUENCE: 151

Xaa Glu Xaa Asp Xaa
```

```
1               5

<210> SEQ ID NO 152
<211> LENGTH: 5
<212> TYPE: PRT
<213> ORGANISM: Artificial Sequence
<220> FEATURE:
<223> OTHER INFORMATION: Linker

<400> SEQUENCE: 152

Leu Glu Pro Asp Gly
1               5

<210> SEQ ID NO 153
<211> LENGTH: 5
<212> TYPE: PRT
<213> ORGANISM: Artificial Sequence
<220> FEATURE:
<223> OTHER INFORMATION: Linker

<400> SEQUENCE: 153

Leu Glu Ala Asp Gly
1               5

<210> SEQ ID NO 154
<211> LENGTH: 5
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (1)..(1)
<223> OTHER INFORMATION: X1 = any amino acid
<220> FEATURE:
<221> NAME/KEY: VARIANT
<222> LOCATION: (5)..(5)
<223> OTHER INFORMATION: X5 = A or V

<400> SEQUENCE: 154

Xaa Gln Ala Arg Xaa
1               5

<210> SEQ ID NO 155
<211> LENGTH: 5
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (5)..(5)
<223> OTHER INFORMATION: X5 = A or V

<400> SEQUENCE: 155

Arg Gln Ala Arg Xaa
1               5

<210> SEQ ID NO 156
<211> LENGTH: 5
<212> TYPE: PRT
<213> ORGANISM: Artificial Sequence
<220> FEATURE:
<223> OTHER INFORMATION: Linker

<400> SEQUENCE: 156

Arg Gln Ala Arg Val
1               5
```

```
<210> SEQ ID NO 157
<211> LENGTH: 4
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (1)..(1)
<223> OTHER INFORMATION: X1 = P, V or A
<220> FEATURE:
<221> NAME/KEY: VARIANT
<222> LOCATION: (2)..(2)
<223> OTHER INFORMATION: X2 = Q or D
<220> FEATURE:
<221> NAME/KEY: VARIANT
<222> LOCATION: (3)..(3)
<223> OTHER INFORMATION: X3 = A or N
<220> FEATURE:
<221> NAME/KEY: VARIANT
<222> LOCATION: (4)..(4)
<223> OTHER INFORMATION: X4 = L, I or M

<400> SEQUENCE: 157

Xaa Xaa Xaa Xaa
1

<210> SEQ ID NO 158
<211> LENGTH: 4
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (2)..(2)
<223> OTHER INFORMATION: X2 = Q or D
<220> FEATURE:
<221> NAME/KEY: VARIANT
<222> LOCATION: (3)..(3)
<223> OTHER INFORMATION: X3 = A or N
<220> FEATURE:
<221> NAME/KEY: VARIANT
<222> LOCATION: (4)..(4)
<223> OTHER INFORMATION: X4 = L or I

<400> SEQUENCE: 158

Pro Xaa Xaa Xaa
1

<210> SEQ ID NO 159
<211> LENGTH: 22
<212> TYPE: PRT
<213> ORGANISM: Artificial Sequence
<220> FEATURE:
<223> OTHER INFORMATION: P2A

<400> SEQUENCE: 159

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 160
<211> LENGTH: 19
<212> TYPE: PRT
<213> ORGANISM: Artificial Sequence
<220> FEATURE:
<223> OTHER INFORMATION: P2A

<400> SEQUENCE: 160
```

-continued

Ala Thr Asn Phe Ser Leu Leu Lys Gln Ala Gly Asp Val Glu Glu Asn
1               5                   10                  15

Pro Gly Pro

<210> SEQ ID NO 161
<211> LENGTH: 20
<212> TYPE: PRT
<213> ORGANISM: Artificial Sequence
<220> FEATURE:
<223> OTHER INFORMATION: E2A

<400> SEQUENCE: 161

Gln Cys Thr Asn Tyr Ala Leu Leu Lys Leu Ala Gly Asp Val Glu Ser
1               5                   10                  15

Asn Pro Gly Pro
            20

<210> SEQ ID NO 162
<211> LENGTH: 22
<212> TYPE: PRT
<213> ORGANISM: Artificial Sequence
<220> FEATURE:
<223> OTHER INFORMATION: F2A

<400> SEQUENCE: 162

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 163
<211> LENGTH: 18
<212> TYPE: PRT
<213> ORGANISM: Artificial Sequence
<220> FEATURE:
<223> OTHER INFORMATION: T2A

<400> SEQUENCE: 163

Glu Gly Arg Gly Ser Leu Leu Thr Cys Gly Asp Val Glu Glu Asn Pro
1               5                   10                  15

Gly Pro

<210> SEQ ID NO 164
<211> LENGTH: 24
<212> TYPE: PRT
<213> ORGANISM: Artificial Sequence
<220> FEATURE:
<223> OTHER INFORMATION: T2A

<400> SEQUENCE: 164

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 165
<211> LENGTH: 66
<212> TYPE: DNA
<213> ORGANISM: Artificial Sequence
<220> FEATURE:
<223> OTHER INFORMATION: P2A

<400> SEQUENCE: 165

```
ggatctggag caacaaactt ctcactactc aaacaagcag gtgacgtgga ggagaatccc    60
ggaccc                                                               66
```

<210> SEQ ID NO 166
<211> LENGTH: 18
<212> TYPE: PRT
<213> ORGANISM: Artificial Sequence
<220> FEATURE:
<223> OTHER INFORMATION: Linker

<400> SEQUENCE: 166

```
Gly Ser Pro Ala Gly Leu Glu Ala Asp Gly Ser Arg Gln Ala Arg Val
1               5                   10                  15

Gly Ser
```

<210> SEQ ID NO 167
<211> LENGTH: 122
<212> TYPE: PRT
<213> ORGANISM: Mus musculus
<220> FEATURE:
<221> NAME/KEY: MISC_FEATURE
<223> OTHER INFORMATION: anti-5T4 VH
<220> FEATURE:
<221> NAME/KEY: misc_feature
<222> LOCATION: (97)..(97)
<223> OTHER INFORMATION: Xaa can be any naturally occurring amino acid

<400> SEQUENCE: 167

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Xaa Cys Val Arg Gln Trp Asp Tyr Asp Val Arg Ala Met Asn Tyr Trp
            100                 105                 110

Gly Gln Gly Thr Ser Val Thr Val Ser Ser
        115                 120
```

<210> SEQ ID NO 168
<211> LENGTH: 107
<212> TYPE: PRT
<213> ORGANISM: Mus musculus
<220> FEATURE:
<221> NAME/KEY: MISC_FEATURE
<223> OTHER INFORMATION: anti-5T4 VL

<400> SEQUENCE: 168

```
Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg Leu Thr Gly Val Pro Asp Arg Phe Thr Gly
```

```
                50                  55                  60
Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr Pro Tyr
                 85                  90                  95

Thr Phe Gly Gly Gly Thr Lys Leu Glu Ile Lys
                100                 105

<210> SEQ ID NO 169
<211> LENGTH: 504
<212> TYPE: PRT
<213> ORGANISM: Artificial Sequence
<220> FEATURE:
<223> OTHER INFORMATION: First Polypeptide Chain of B7-H3 x CD3
      Bispecific DART-A Diabody

<400> SEQUENCE: 169

Asp Ile Gln Leu Thr Gln Ser Pro Ser Phe Leu Ser Ala Ser Val Gly
 1               5                  10                  15

Asp Arg Val Thr Ile Thr Cys Lys Ala Ser Gln Asn Val Asp Thr Asn
                 20                  25                  30

Val Ala Trp Tyr Gln Gln Lys Pro Gly Lys Ala Pro Lys Ala Leu Ile
             35                  40                  45

Tyr Ser Ala Ser Tyr Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Phe
                 85                  90                  95

Thr Phe Gly Gln Gly Thr Lys Leu Glu Ile Lys Gly Gly Gly Ser Gly
                100                 105                 110

Gly Gly Gly Glu Val Gln Leu Val Glu Ser Gly Gly Gly Leu Val Gln
             115                 120                 125

Pro Gly Gly Ser Leu Arg Leu Ser Cys Ala Ala Ser Gly Phe Thr Phe
130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Asp Arg Phe Thr Ile Ser Arg Asp Asp Ser
                180                 185                 190

Lys Asn Ser Leu Tyr Leu Gln Met Asn Ser Leu Lys Thr Glu Asp Thr
            195                 200                 205

Ala Val Tyr Tyr Cys Val Arg His Gly Asn Phe Gly Asn Ser Tyr Val
210                 215                 220

Ser Trp Phe Ala Tyr Trp Gly Gln Gly Thr Leu Val Thr Val Ser Ser
225                 230                 235                 240

Gly Gly Cys Gly Gly Gly Glu Val Ala Ala Leu Glu Lys Glu Val Ala
                245                 250                 255

Ala Leu Glu Lys Glu Val Ala Ala Leu Glu Lys Glu Val Ala Ala Leu
            260                 265                 270

Glu Lys Gly Gly Gly Asp Lys Thr His Thr Cys Pro Pro Cys Pro Ala
        275                 280                 285

Pro Glu Ala Ala Gly Gly Pro Ser Val Phe Leu Phe Pro Pro Lys Pro
    290                 295                 300
```

```
Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
    370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415

Lys Asn Gln Val Ser Leu Trp Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
    450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500

<210> SEQ ID NO 170
<211> LENGTH: 15
<212> TYPE: PRT
<213> ORGANISM: Artificial Sequence
<220> FEATURE:
<223> OTHER INFORMATION: Linker

<400> SEQUENCE: 170

Gly Gly Gly Gly Ser Gly Gly Gly Gly Ser Gly Gly Gly Gly Ser
1               5                   10                  15

<210> SEQ ID NO 171
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (4)..(6)
<223> OTHER INFORMATION: repeated 0 to 10 times

<400> SEQUENCE: 171

Gly Gly Ser Gly Gly Ser
1               5

<210> SEQ ID NO 172
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(6)
```

```
<223> OTHER INFORMATION: repeated 1 to 4 times

<400> SEQUENCE: 172

Gly Gly Gly Gly Gly Ser
1               5

<210> SEQ ID NO 173
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 1 to 5 times

<400> SEQUENCE: 173

Gly Gly Gly Gly Ser
1               5

<210> SEQ ID NO 174
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(1)
<223> OTHER INFORMATION: Repeated 1 to 5 times
<220> FEATURE:
<221> NAME/KEY: VARIANT
<222> LOCATION: (2)..(2)
<223> OTHER INFORMATION: X2= A, V, L, I, M,F, W, P, G, S, T, C, Y, N,Q,
      K, R, H, D, or E
<220> FEATURE:
<221> NAME/KEY: REPEAT
<222> LOCATION: (3)..(3)
<223> OTHER INFORMATION: Repeated 1 to 5 times
<220> FEATURE:
<221> NAME/KEY: VARIANT
<222> LOCATION: (4)..(4)
<223> OTHER INFORMATION: X4 = A, V, L, I, M,F, W, P, G, S, T, C, Y, N,Q,
      K, R, H, D, or E
<220> FEATURE:
<221> NAME/KEY: REPEAT
<222> LOCATION: (5)..(5)
<223> OTHER INFORMATION: Repeated 1 to 5 times

<400> SEQUENCE: 174

Gly Xaa Gly Xaa Gly
1               5

<210> SEQ ID NO 175
<211> LENGTH: 11
<212> TYPE: PRT
<213> ORGANISM: Artificial Sequence
<220> FEATURE:
<223> OTHER INFORMATION: Linker
<220> FEATURE:
<221> NAME/KEY: VARIANT
<222> LOCATION: (4)..(4)
<223> OTHER INFORMATION: X4 = A, V, L, I, M,F, W, P, G, S, T, C, Y, N,Q,
      K, R, H, D, or E
<220> FEATURE:
<221> NAME/KEY: VARIANT
<222> LOCATION: (8)..(8)
<223> OTHER INFORMATION: X8 = A, V, L, I, M,F, W, P, G, S, T, C, Y, N,Q,
      K, R, H, D, or E

<400> SEQUENCE: 175
```

```
Gly Gly Gly Xaa Gly Gly Gly Xaa Gly Gly Gly
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Linker

<400> SEQUENCE: 176

Ala Thr Thr Thr Gly Ser Ser Pro Gly Pro Thr
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Linker

<400> SEQUENCE: 177

Gly Gly Gly Gly Gly Cys Gly Gly Gly Gly Gly
1               5                   10

<210> SEQ ID NO 178
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 178

Glu Ala Ala Ala Lys
1               5

<210> SEQ ID NO 179
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (3)..(4)
<223> OTHER INFORMATION: Repeated 2 to 20 times

<400> SEQUENCE: 179

Ala Ser Ala Pro Gly Thr
1               5

<210> SEQ ID NO 180
<211> LENGTH: 9
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (3)..(7)
<223> OTHER INFORMATION: Repeated 2 to 20 times

<400> SEQUENCE: 180

Ala Ser Glu Ala Ala Ala Lys Gly Thr
1               5
```

```
<210> SEQ ID NO 181
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 181

Gly Gly Gly Gly Ala
1               5

<210> SEQ ID NO 182
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 182

Pro Gly Gly Gly Ser
1               5

<210> SEQ ID NO 183
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 183

Ala Gly Gly Gly Ser
1               5

<210> SEQ ID NO 184
<211> LENGTH: 20
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (4)..(17)
<223> OTHER INFORMATION: Repeated 2 to 20 times

<400> SEQUENCE: 184

Gly Gly Ser Glu Gly Lys Ser Ser Gly Ser Gly Ser Glu Ser Lys Ser
1               5                   10                  15

Thr Gly Gly Ser
            20

<210> SEQ ID NO 185
<211> LENGTH: 5
<212> TYPE: PRT
<213> ORGANISM: Artificial Sequence
<220> FEATURE:
<223> OTHER INFORMATION: Linker
```

```
<220> FEATURE:
<221> NAME/KEY: REPEAT
<222> LOCATION: (1)..(5)
<223> OTHER INFORMATION: Repeated 1 to 9 times

<400> SEQUENCE: 185

Ser Ser Ser Ser Gly
1               5

<210> SEQ ID NO 186
<211> LENGTH: 9
<212> TYPE: PRT
<213> ORGANISM: Artificial Sequence
<220> FEATURE:
<223> OTHER INFORMATION: Linker

<400> SEQUENCE: 186

Ser Ser Ser Ala Ser Ala Ser Ser Ala
1               5

<210> SEQ ID NO 187
<211> LENGTH: 7
<212> TYPE: PRT
<213> ORGANISM: Artificial Sequence
<220> FEATURE:
<223> OTHER INFORMATION: Linker

<400> SEQUENCE: 187

Gly Ser Pro Gly Ser Pro Gly
1               5

<210> SEQ ID NO 188
<211> LENGTH: 241
<212> TYPE: PRT
<213> ORGANISM: Artificial Sequence
<220> FEATURE:
<223> OTHER INFORMATION: DLL3 scFv

<400> SEQUENCE: 188

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
                165                 170                 175
```

```
Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln Gln
    210                 215                 220

Tyr Asp Arg Ser Pro Leu Thr Phe Gly Gly Gly Thr Lys Leu Glu Ile
225                 230                 235                 240

Lys

<210> SEQ ID NO 189
<211> LENGTH: 119
<212> TYPE: PRT
<213> ORGANISM: Artificial Sequence
<220> FEATURE:
<223> OTHER INFORMATION: CD20 VH

<400> SEQUENCE: 189

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 190
<211> LENGTH: 115
<212> TYPE: PRT
<213> ORGANISM: Artificial Sequence
<220> FEATURE:
<223> OTHER INFORMATION: CD20 VL

<400> SEQUENCE: 190

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110
```

Arg Thr Val
        115

<210> SEQ ID NO 191
<211> LENGTH: 204
<212> TYPE: PRT
<213> ORGANISM: Artificial Sequence
<220> FEATURE:
<223> OTHER INFORMATION: 41BBL

<400> SEQUENCE: 191

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Asn
    130                 135                 140

Ser Ala Phe Gly Phe Gln Gly Arg Leu Leu His Leu Ser Ala Gly Gln
145                 150                 155                 160

Arg Leu Gly Val His Leu His Thr Glu Ala Arg Ala Arg His Ala Trp
                165                 170                 175

Gln Leu Thr Gln Gly Ala Thr Val Leu Gly Leu Phe Arg Val Thr Pro
            180                 185                 190

Glu Ile Pro Ala Gly Leu Pro Ser Pro Arg Ser Glu
        195                 200

<210> SEQ ID NO 192
<211> LENGTH: 116
<212> TYPE: PRT
<213> ORGANISM: Artificial Sequence
<220> FEATURE:
<223> OTHER INFORMATION: 41BB VH

<400> SEQUENCE: 192

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 193
<211> LENGTH: 108
<212> TYPE: PRT
<213> ORGANISM: Artificial Sequence
<220> FEATURE:
<223> OTHER INFORMATION: 41BB VL

<400> SEQUENCE: 193

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

<210> SEQ ID NO 194
<211> LENGTH: 121
<212> TYPE: PRT
<213> ORGANISM: Artificial Sequence
<220> FEATURE:
<223> OTHER INFORMATION: 41BB VH

<400> SEQUENCE: 194

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
        115                 120

<210> SEQ ID NO 195
<211> LENGTH: 109
<212> TYPE: PRT
<213> ORGANISM: Artificial Sequence
<220> FEATURE:
<223> OTHER INFORMATION: 41BB VL

<400> SEQUENCE: 195

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105

<210> SEQ ID NO 196
<211> LENGTH: 120
<212> TYPE: PRT
<213> ORGANISM: Artificial Sequence
<220> FEATURE:
<223> OTHER INFORMATION: 41BB VH

<400> SEQUENCE: 196

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30

Tyr Met His Trp Val Arg Gln Ala Pro Gly Gln Gly Leu Glu Trp Met
        35                  40                  45

Gly Trp Val Asn Pro Met Ser Gly Gly Thr Asn Tyr Ala Gln Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Met Ala Met Arg Leu Glu Leu Asp Lys Trp Gly Gln
            100                 105                 110

Gly Thr Leu Val Thr Val Ser Ser
        115                 120

<210> SEQ ID NO 197
<211> LENGTH: 106
<212> TYPE: PRT
<213> ORGANISM: Artificial Sequence
<220> FEATURE:
<223> OTHER INFORMATION: 41BB VL

<400> SEQUENCE: 197

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Val Val
            85                  90                  95

Phe Gly Gly Gly Thr Gln Leu Thr Val Leu
            100                 105

<210> SEQ ID NO 198
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 198

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
        35                  40                  45

Asn Lys Met Met Ala Thr Ile Tyr Glu Leu Lys Glu Asp Lys Ser Tyr
50                  55                  60

Asn Val Thr Gly Val Thr Phe Asp Asp Lys Lys Cys Thr Tyr Ala Ile
65                  70                  75                  80

Ser Thr Phe Val Pro Gly Ser Gln Pro Gly Glu Phe Thr Leu Gly Lys
            85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 199
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 199

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
            35                  40                  45

Ile Lys Met Met Ala Thr Ile Tyr Glu Leu Lys Glu Asp Lys Ser Tyr
50                  55                  60

Asp Val Thr Met Val Lys Phe Asp Lys Lys Cys Met Tyr Asp Ile
65                  70                  75                  80

Trp Thr Phe Val Pro Gly Ser Gln Pro Gly Glu Phe Thr Leu Gly Lys
            85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 200
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 200

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45

Asn Lys Met Met Ala Thr Ile Tyr Glu Leu Lys Glu Asp Lys Ser Tyr
50                  55                  60

Asp Val Thr Ala Val Ala Phe Asp Lys Lys Cys Thr Tyr Asp Ile
65                  70                  75                  80

Trp Thr Phe Val Pro Gly Ser Gln Pro Gly Glu Phe Thr Leu Gly Lys
            85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 201
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 201

Gln Asp Ser Thr Ser Asp Leu Ile Pro Ala Pro Pro Leu Ser Lys Val
1               5                   10                  15

```
Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
            35                  40                  45

Asn Lys Met Met Ala Thr Ile Tyr Glu Leu Lys Glu Asp Lys Ser Tyr
 50                      55                  60

Asp Val Thr Ala Val Ala Phe Asp Asp Lys Lys Cys Thr Tyr Asp Ile
 65                      70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
                100                 105                 110

Thr Asn Tyr Asn Gln His Ala Met Val Phe Phe Lys Phe Val Phe Gln
                115                 120                 125

Asn Arg Glu Glu Phe Tyr Ile Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 202
<211> LENGTH: 175
<212> TYPE: PRT
<213> ORGANISM: Artificial Sequence
<220> FEATURE:
<223> OTHER INFORMATION: 41BB Anticalin

<400> SEQUENCE: 202

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Ser Lys Met
            35                  40                  45

Met Ala Thr Ile Tyr Glu Leu Lys Glu Asp Lys Ser Tyr Asp Val Thr
 50                      55                  60

Gly Val Ser Phe Asp Asp Lys Lys Cys Thr Tyr Ala Ile Met Thr Phe
 65                      70                  75                  80

Val Pro Gly Ser Gln Pro Gly Glu Phe Thr Leu Gly Lys Ile Lys Ser
                85                  90                  95

Phe Pro Gly His Thr Ser Ser Leu Val Arg Val Val Ser Thr Asn Tyr
                100                 105                 110

Asn Gln His Ala Met Val Phe Phe Lys Phe Val Phe Gln Asn Arg Glu
            115                 120                 125

Glu Phe Tyr Ile Thr Leu Tyr Gly Arg Thr Lys Glu Leu Thr Ser Glu
            130                 135                 140

Leu Lys Glu Asn Phe Ile Arg Phe Ser Lys Ser Leu Gly Leu Pro Glu
145                 150                 155                 160

Asn His Ile Val Phe Pro Val Pro Ile Asp Gln Cys Ile Asp Gly
                165                 170                 175

<210> SEQ ID NO 203
<211> LENGTH: 178
<212> TYPE: PRT
```

<213> ORGANISM: Artificial Sequence
<220> FEATURE:
<223> OTHER INFORMATION: 41BB Anticalin

<400> SEQUENCE: 203

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Ile Lys Leu Arg Glu Asp Lys Asp Pro
            35                  40                  45

Val Lys Met Met Ala Thr Ile Tyr Glu Leu Lys Glu Asp Lys Ser Tyr
50                  55                  60

Asp Val Thr Gly Val Thr Phe Asp Asp Lys Lys Cys Arg Tyr Asp Ile
65                  70                  75                  80

Ser Thr Phe Val Pro Gly Ser Gln Pro Gly Glu Phe Thr Phe Gly Lys
                85                  90                  95

Ile Lys Ser Phe Pro Gly His Thr Ser Ser Leu Val Arg Val Val Ser
                100                 105                 110

Thr Asn Tyr Asn Gln His Ala Met Val Phe Phe Lys Phe Val Phe Gln
                115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 204
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 204

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Ile Arg Leu Arg Glu Asp Lys Asp Pro
            35                  40                  45

His Lys Met Met Ala Thr Ile Tyr Glu Leu Lys Glu Asp Lys Ser Tyr
50                  55                  60

Asp Val Thr Gly Val Thr Phe Asp Asp Lys Lys Cys Thr Tyr Ala Ile
65                  70                  75                  80

Ser Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
                100                 105                 110

Thr Asn Tyr Asn Gln His Ala Met Val Phe Phe Lys Phe Val Phe Gln
                115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly

```
                145                 150                 155                 160
Leu Pro Glu Asn His Ile Val Phe Pro Val Pro Ile Asp Gln Cys Ile
                165                 170                 175
Asp Gly

<210> SEQ ID NO 205
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 205

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Ile Lys Leu Arg Glu Asp Lys Asp Pro
            35                  40                  45

Asn Lys Met Met Ala Thr Ile Tyr Glu Leu Lys Glu Asp Lys Ser Tyr
    50                  55                  60

Asp Val Thr Gly Val Thr Phe Asp Asp Lys Lys Cys Thr Tyr Ala Ile
65                  70                  75                  80

Ser Thr Leu Val Pro Gly Ser Gln Pro Gly Glu Phe Thr Phe Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
    115                 120                 125

Asn Arg Glu Glu Phe Tyr Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 206
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 206

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Ile Arg Leu Arg Glu Asp Lys Asp Pro
            35                  40                  45

Ser Lys Met Met Ala Thr Ile Tyr Glu Leu Lys Glu Asp Lys Ser Tyr
    50                  55                  60

Asp Val Thr Ala Val Thr Phe Asp Asp Lys Lys Cys Asn Tyr Ala Ile
65                  70                  75                  80

Ser Thr Phe Val Pro Gly Ser Gln Pro Gly Glu Phe Thr Leu Gly Lys
                85                  90                  95
```

```
Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 207
<211> LENGTH: 184
<212> TYPE: PRT
<213> ORGANISM: Artificial Sequence
<220> FEATURE:
<223> OTHER INFORMATION: 71-254 of human 41BBL

<400> SEQUENCE: 207

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
            35                  40                  45

Ser Leu Thr Gly Gly Leu Ser Tyr Lys Glu Asp Thr Lys Glu Leu Val
50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
            130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180

<210> SEQ ID NO 208
<211> LENGTH: 170
<212> TYPE: PRT
<213> ORGANISM: Artificial Sequence
<220> FEATURE:
<223> OTHER INFORMATION: 85-254 of human 41BBL

<400> SEQUENCE: 208

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30
```

```
Gly Val Ser Leu Thr Gly Gly Leu Ser Tyr Lys Glu Asp Thr Lys Glu
            35                  40                  45

Leu Val Val Ala Lys Ala Gly Val Tyr Tyr Val Phe Phe Gln Leu Glu
 50                  55                  60

Leu Arg Arg Val Val Ala Gly Glu Gly Ser Gly Ser Val Ser Leu Ala
 65                  70                  75                  80

Leu His Leu Gln Pro Leu Arg Ser Ala Ala Gly Ala Ala Ala Leu Ala
                85                  90                  95

Leu Thr Val Asp Leu Pro Pro Ala Ser Ser Glu Ala Arg Asn Ser Ala
                100                 105                 110

Phe Gly Phe Gln Gly Arg Leu Leu His Leu Ser Ala Gly Gln Arg Leu
                115                 120                 125

Gly Val His Leu His Thr Glu Ala Arg Ala Arg His Ala Trp Gln Leu
                130                 135                 140

Thr Gln Gly Ala Thr Val Leu Gly Leu Phe Arg Val Thr Pro Glu Ile
145                 150                 155                 160

Pro Ala Gly Leu Pro Ser Pro Arg Ser Glu
                165                 170
```

<210> SEQ ID NO 209
<211> LENGTH: 175
<212> TYPE: PRT
<213> ORGANISM: Artificial Sequence
<220> FEATURE:
<223> OTHER INFORMATION: 80-254 of human 41BBL

<400> SEQUENCE: 209

```
Asp Pro Ala Gly Leu Leu Asp Leu Arg Gln Gly Met Phe Ala Gln Leu
 1               5                  10                  15

Val Ala Gln Asn Val Leu Leu Ile Asp Gly Pro Leu Ser Trp Tyr Ser
                20                  25                  30

Asp Pro Gly Leu Ala Gly Val Ser Leu Thr Gly Gly Leu Ser Tyr Lys
                35                  40                  45

Glu Asp Thr Lys Glu Leu Val Val Ala Lys Ala Gly Val Tyr Tyr Val
 50                  55                  60

Phe Phe Gln Leu Glu Leu Arg Arg Val Val Ala Gly Glu Gly Ser Gly
 65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
                100                 105                 110

Ala Arg Asn Ser Ala Phe Gly Phe Gln Gly Arg Leu Leu His Leu Ser
                115                 120                 125

Ala Gly Gln Arg Leu Gly Val His Leu His Thr Glu Ala Arg Ala Arg
                130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175
```

<210> SEQ ID NO 210
<211> LENGTH: 203
<212> TYPE: PRT
<213> ORGANISM: Artificial Sequence
<220> FEATURE:
<223> OTHER INFORMATION: 52-254 of human 41BBL -continued

```
<400> SEQUENCE: 210

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu Pro Ser Pro Arg Ser Glu
        195                 200

<210> SEQ ID NO 211
<211> LENGTH: 178
<212> TYPE: PRT
<213> ORGANISM: Artificial Sequence
<220> FEATURE:
<223> OTHER INFORMATION: 71-248 of human 41BBL

<400> SEQUENCE: 211

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
        130                 135                 140

His Leu His Thr Glu Ala Arg Ala Arg His Ala Trp Gln Leu Thr Gln
```

```
                    145                 150                 155                 160
Gly Ala Thr Val Leu Gly Leu Phe Arg Val Thr Pro Glu Ile Pro Ala
                165                 170                 175

Gly Leu

<210> SEQ ID NO 212
<211> LENGTH: 164
<212> TYPE: PRT
<213> ORGANISM: Artificial Sequence
<220> FEATURE:
<223> OTHER INFORMATION: 85-248 of human 41BBL

<400> SEQUENCE: 212

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
                20                  25                  30

Gly Val Ser Leu Thr Gly Gly Leu Ser Tyr Lys Glu Asp Thr Lys Glu
            35                  40                  45

Leu Val Val Ala Lys Ala Gly Val Tyr Tyr Val Phe Phe Gln Leu Glu
        50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
        115                 120                 125

Gly Val His Leu His Thr Glu Ala Arg Ala Arg His Ala Trp Gln Leu
    130                 135                 140

Thr Gln Gly Ala Thr Val Leu Gly Leu Phe Arg Val Thr Pro Glu Ile
145                 150                 155                 160

Pro Ala Gly Leu

<210> SEQ ID NO 213
<211> LENGTH: 169
<212> TYPE: PRT
<213> ORGANISM: Artificial Sequence
<220> FEATURE:
<223> OTHER INFORMATION: 80-248 of human 41BBL

<400> SEQUENCE: 213

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
                20                  25                  30

Asp Pro Gly Leu Ala Gly Val Ser Leu Thr Gly Gly Leu Ser Tyr Lys
            35                  40                  45

Glu Asp Thr Lys Glu Leu Val Val Ala Lys Ala Gly Val Tyr Tyr Val
        50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110
```

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu
                165

<210> SEQ ID NO 214
<211> LENGTH: 197
<212> TYPE: PRT
<213> ORGANISM: Artificial Sequence
<220> FEATURE:
<223> OTHER INFORMATION: 52-248 of human 41BBL

<400> SEQUENCE: 214

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
    130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu
        195

<210> SEQ ID NO 215
<211> LENGTH: 121
<212> TYPE: PRT
<213> ORGANISM: Artificial Sequence
<220> FEATURE:
<223> OTHER INFORMATION: 41BB sdAb

<400> SEQUENCE: 215

Glu Val Gln Leu Leu Glu Ser Gly Gly Gly Val Gln Pro Gly Gly
1               5                   10                  15

Ser Leu Arg Leu Ser Cys Ala Ala Ser Gly Phe Ser Phe Ser Ile Asn
            20                  25                  30

Ala Met Gly Trp Tyr Arg Gln Ala Pro Gly Lys Arg Arg Glu Phe Val

```
                35                  40                  45
Ala Ala Ile Glu Ser Gly Arg Asn Thr Val Tyr Ala Glu Ser Val Lys
 50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Gly
                 85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120

<210> SEQ ID NO 216
<211> LENGTH: 133
<212> TYPE: PRT
<213> ORGANISM: Artificial Sequence
<220> FEATURE:
<223> OTHER INFORMATION: OX40 ligand

<400> SEQUENCE: 216

Gln Val Ser His Arg Tyr Pro Arg Ile Gln Ser Ile Lys Val Gln Phe
 1               5                  10                  15

Thr Glu Tyr Lys Lys Glu Lys Gly Phe Ile Leu Thr Ser Gln Lys Glu
                20                  25                  30

Asp Glu Ile Met Lys Val Gln Asn Asn Ser Val Ile Ile Asn Cys Asp
             35                  40                  45

Gly Phe Tyr Leu Ile Ser Leu Lys Gly Tyr Phe Ser Gln Glu Val Asn
 50                  55                  60

Ile Ser Leu His Tyr Gln Lys Asp Glu Glu Pro Leu Phe Gln Leu Lys
 65                  70                  75                  80

Lys Val Arg Ser Val Asn Ser Leu Met Val Ala Ser Leu Thr Tyr Lys
                 85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 217
<211> LENGTH: 133
<212> TYPE: PRT
<213> ORGANISM: Artificial Sequence
<220> FEATURE:
<223> OTHER INFORMATION: OX40 ligand

<400> SEQUENCE: 217

Gln Val Ser His Arg Tyr Pro Arg Phe Gln Ser Ile Lys Val Gln Phe
 1               5                  10                  15

Thr Glu Tyr Lys Lys Glu Lys Gly Phe Ile Leu Thr Ser Gln Lys Glu
                20                  25                  30

Asp Glu Ile Met Lys Val Gln Asn Asn Ser Val Ile Ile Asn Cys Asp
             35                  40                  45

Gly Phe Tyr Leu Ile Ser Leu Lys Gly Tyr Phe Ser Gln Glu Val Asn
 50                  55                  60

Ile Ser Leu His Tyr Gln Lys Asp Glu Glu Pro Leu Phe Gln Leu Lys
 65                  70                  75                  80
```

```
Lys Val Arg Ser Val Asn Ser Leu Met Val Ala Ser Leu Thr Tyr Lys
                85                  90                  95
Asp Lys Val Tyr Leu Asn Val Thr Thr Asp Asn Thr Ser Leu Asp Asp
            100                 105                 110
Phe His Val Asn Gly Gly Glu Leu Ile Leu Ile His Gln Asn Pro Gly
        115                 120                 125
Glu Phe Cys Val Leu
    130

<210> SEQ ID NO 218
<211> LENGTH: 133
<212> TYPE: PRT
<213> ORGANISM: Artificial Sequence
<220> FEATURE:
<223> OTHER INFORMATION: OX40 ligand

<400> SEQUENCE: 218

Gln Val Ser His Arg Tyr Pro Arg Ile Gln Ser Ile Lys Val Gln Phe
1               5                   10                  15
Thr Glu Tyr Lys Lys Glu Lys Gly Phe Ile Leu Thr Ser Gln Lys Glu
            20                  25                  30
Asp Glu Ile Met Lys Val Gln Asn Asn Ser Val Ile Ile Asn Cys Asp
        35                  40                  45
Gly Phe Tyr Leu Ile Ser Leu Lys Gly Tyr Phe Ser Gln Glu Val Asn
    50                  55                  60
Ile Ser Leu His Tyr Gln Lys Asp Glu Glu Pro Leu Phe Gln Leu Lys
65                  70                  75                  80
Lys Val Arg Ser Val Asn Ser Leu Met Val Ala Ser Leu Thr Tyr Lys
                85                  90                  95
Asp Lys Val Tyr Leu Asn Val Thr Thr Asp Asn Thr Ser Leu Asp Asp
            100                 105                 110
Phe His Val Asn Gly Gly Glu Leu Ile Leu Ile His Gln Asn Pro Gly
        115                 120                 125
Glu Phe Cys Val Leu
    130

<210> SEQ ID NO 219
<211> LENGTH: 133
<212> TYPE: PRT
<213> ORGANISM: Artificial Sequence
<220> FEATURE:
<223> OTHER INFORMATION: OX40 ligand

<400> SEQUENCE: 219

Gln Val Ser His Arg Tyr Pro Arg Ile Gln Ser Ile Lys Val Gln Phe
1               5                   10                  15
Thr Glu Tyr Lys Lys Glu Lys Gly Phe Ile Leu Thr Ser Gln Lys Glu
            20                  25                  30
Asp Glu Ile Met Lys Val Gln Asp Asn Ser Val Ile Ile Asn Cys Asp
        35                  40                  45
Gly Phe Tyr Leu Ile Ser Leu Lys Gly Tyr Phe Ser Gln Glu Val Asp
    50                  55                  60
Ile Ser Leu His Tyr Gln Lys Asp Glu Glu Pro Leu Phe Gln Leu Lys
65                  70                  75                  80
Lys Val Arg Ser Val Asn Ser Leu Met Val Ala Ser Leu Thr Tyr Lys
                85                  90                  95
Asp Lys Val Tyr Leu Asn Val Thr Thr Asp Asn Thr Ser Leu Asp Asp
            100                 105                 110
```

Phe His Val Asn Gly Gly Glu Leu Ile Leu Ile His Gln Asn Pro Gly
        115                 120                 125

Glu Phe Cys Val Leu
    130

<210> SEQ ID NO 220
<211> LENGTH: 132
<212> TYPE: PRT
<213> ORGANISM: Artificial Sequence
<220> FEATURE:
<223> OTHER INFORMATION: OX40 ligand

<400> SEQUENCE: 220

Val Ser His Arg Tyr Pro Arg Ile Gln Ser Ile Lys Val Gln Phe Thr
1               5                   10                  15

Glu Tyr Lys Lys Glu Lys Gly Phe Ile Leu Thr Ser Gln Lys Glu Asp
            20                  25                  30

Glu Ile Met Lys Val Gln Asn Asn Ser Val Ile Ile Asn Cys Asp Gly
        35                  40                  45

Phe Tyr Leu Ile Ser Leu Lys Gly Tyr Phe Ser Gln Glu Val Asn Ile
    50                  55                  60

Ser Leu His Tyr Gln Lys Asp Glu Glu Pro Leu Phe Gln Leu Lys Lys
65                  70                  75                  80

Val Arg Ser Val Asn Ser Leu Met Val Ala Ser Leu Thr Tyr Lys Asp
                85                  90                  95

Lys Val Tyr Leu Asn Val Thr Thr Asp Asn Thr Ser Leu Asp Asp Phe
            100                 105                 110

His Val Asn Gly Gly Glu Leu Ile Leu Ile His Gln Asn Pro Gly Glu
        115                 120                 125

Phe Cys Val Leu
    130

<210> SEQ ID NO 221
<211> LENGTH: 117
<212> TYPE: PRT
<213> ORGANISM: Artificial Sequence
<220> FEATURE:
<223> OTHER INFORMATION: OX40 VH

<400> SEQUENCE: 221

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

-continued

```
<210> SEQ ID NO 222
<211> LENGTH: 109
<212> TYPE: PRT
<213> ORGANISM: Artificial Sequence
<220> FEATURE:
<223> OTHER INFORMATION: OX40 VL

<400> SEQUENCE: 222

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg Thr
            100                 105

<210> SEQ ID NO 223
<211> LENGTH: 121
<212> TYPE: PRT
<213> ORGANISM: Artificial Sequence
<220> FEATURE:
<223> OTHER INFORMATION: OX40 VH

<400> SEQUENCE: 223

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser
        115                 120

<210> SEQ ID NO 224
<211> LENGTH: 112
<212> TYPE: PRT
<213> ORGANISM: Artificial Sequence
<220> FEATURE:
<223> OTHER INFORMATION: OX40 VL

<400> SEQUENCE: 224

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 225
<211> LENGTH: 115
<212> TYPE: PRT
<213> ORGANISM: Artificial Sequence
<220> FEATURE:
<223> OTHER INFORMATION: OX40 sdAb

<400> SEQUENCE: 225

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Asp Ala
            20                  25                  30

Phe Met Tyr Trp Val Arg Gln Ala Pro Gly Lys Gly Leu Glu Trp Val
        35                  40                  45

Ser Ser Ile Ser Asn Arg Gly Leu Lys Thr Ala Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ser Arg Asp Val Asp Gly Asp Phe Arg Gly Gln Gly Thr Leu Val Thr
            100                 105                 110

Val Lys Pro
        115

<210> SEQ ID NO 226
<211> LENGTH: 128
<212> TYPE: PRT
<213> ORGANISM: Artificial Sequence
<220> FEATURE:
<223> OTHER INFORMATION: GITR ligand

<400> SEQUENCE: 226

Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
            20                  25                  30

Val Ser Asp Trp Lys Leu Glu Ile Leu Gln Asn Gly Leu Tyr Leu Ile
        35                  40                  45

Tyr Gly Gln Val Ala Pro Asn Ala Asn Tyr Asn Asp Val Ala Pro Phe
    50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                85                  90                  95

Asp Thr Ile Asp Leu Ile Phe Asn Ser Glu His Gln Val Leu Lys Asn
```

```
                100                 105                 110
Asn Thr Tyr Trp Gly Ile Ile Leu Leu Ala Asn Pro Gln Phe Ile Ser
            115                 120                 125

<210> SEQ ID NO 227
<211> LENGTH: 118
<212> TYPE: PRT
<213> ORGANISM: Artificial Sequence
<220> FEATURE:
<223> OTHER INFORMATION: GITR VH

<400> SEQUENCE: 227

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Thr Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Gly Gly Tyr Tyr Asp Ser Met Asp Tyr Trp Gly Gln Gly Thr
            100                 105                 110

Leu Val Thr Val Ser Ser
            115

<210> SEQ ID NO 228
<211> LENGTH: 111
<212> TYPE: PRT
<213> ORGANISM: Artificial Sequence
<220> FEATURE:
<223> OTHER INFORMATION: GITR VL

<400> SEQUENCE: 228

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Val Ser Phe Met Asn Trp Tyr Gln Gln Lys Pro Gly Gln Ala Pro
        35                  40                  45

Arg Leu Leu Ile Tyr Ala Ala Ser Asn Gln Gly Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Thr Lys
                85                  90                  95

Glu Val Thr Trp Thr Phe Gly Gln Gly Thr Lys Val Glu Ile Lys
            100                 105                 110

<210> SEQ ID NO 229
<211> LENGTH: 119
<212> TYPE: PRT
<213> ORGANISM: Artificial Sequence
<220> FEATURE:
<223> OTHER INFORMATION: GITR VH

<400> SEQUENCE: 229
```

-continued

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Gln Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Arg Arg Tyr Phe Pro Phe Ala Tyr Trp Gly Gln Gly
                100                 105                 110

Thr Leu Val Thr Val Ser Ser
            115
```

<210> SEQ ID NO 230
<211> LENGTH: 107
<212> TYPE: PRT
<213> ORGANISM: Artificial Sequence
<220> FEATURE:
<223> OTHER INFORMATION: GITR VL

<400> SEQUENCE: 230

```
Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Thr Asn
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Thr Asp Pro Leu
                85                  90                  95

Thr Phe Gly Gly Gly Thr Lys Val Glu Ile Lys
                100                 105
```

<210> SEQ ID NO 231
<211> LENGTH: 125
<212> TYPE: PRT
<213> ORGANISM: Artificial Sequence
<220> FEATURE:
<223> OTHER INFORMATION: GITR VH

<400> SEQUENCE: 231

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Gly Tyr Phe Trp Ser Trp Ile Arg Gln Pro Pro Gly Lys Gly Leu Glu
        35                  40                  45

Trp Ile Gly Tyr Ile Tyr Tyr Ser Gly Thr Thr Tyr Tyr Asn Pro Ser
    50                  55                  60

Leu Lys Ser Arg Val Thr Ile Ser Ile Asp Thr Ser Lys Asn Gln Phe
```

```
                65                  70                  75                  80
Ser Leu Lys Leu Ser Ser Val Thr Ala Ala Asp Thr Ala Val Tyr Tyr
                    85                  90                  95

Cys Ala Arg Asp Leu Phe Tyr Tyr Asp Thr Ser Gly Pro Arg Gly Phe
            100                 105                 110

Asp Pro Trp Gly Gln Gly Thr Leu Val Thr Val Ser Ser
        115                 120                 125

<210> SEQ ID NO 232
<211> LENGTH: 108
<212> TYPE: PRT
<213> ORGANISM: Artificial Sequence
<220> FEATURE:
<223> OTHER INFORMATION: GITR VL

<400> SEQUENCE: 232

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ser Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Ser Pro
                85                  90                  95

Trp Thr Phe Gly Gln Gly Thr Lys Val Glu Ile Lys
            100                 105

<210> SEQ ID NO 233
<211> LENGTH: 123
<212> TYPE: PRT
<213> ORGANISM: Artificial Sequence
<220> FEATURE:
<223> OTHER INFORMATION: GITR VH

<400> SEQUENCE: 233

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Pro Gly Ser Asn Lys Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Leu Gly Tyr Tyr Tyr Tyr Gly Met Asp Val
            100                 105                 110

Trp Gly Gln Gly Thr Thr Val Thr Val Ser Ser
        115                 120

<210> SEQ ID NO 234
<211> LENGTH: 107
```

<212> TYPE: PRT
<213> ORGANISM: Artificial Sequence
<220> FEATURE:
<223> OTHER INFORMATION: GITR VL

<400> SEQUENCE: 234

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Trp
                85                  90                  95

Thr Phe Gly Gln Gly Thr Lys Val Asp Ile Lys
            100                 105

<210> SEQ ID NO 235
<211> LENGTH: 119
<212> TYPE: PRT
<213> ORGANISM: Artificial Sequence
<220> FEATURE:
<223> OTHER INFORMATION: GITR sdAb

<400> SEQUENCE: 235

Glu Val Gln Leu Leu Glu Ser Gly Gly Gly Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Ala Ser Ala Pro
50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 236
<211> LENGTH: 193
<212> TYPE: PRT
<213> ORGANISM: Artificial Sequence
<220> FEATURE:
<223> OTHER INFORMATION: CD70-ECD residues 39-193 UniProt No. P32970

<400> SEQUENCE: 236

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu

```
                35                  40                  45
Pro Leu Glu Ser Leu Gly Trp Asp Val Ala Glu Leu Gln Leu Asn His
 50                  55                  60

Thr Gly Pro Gln Gln Asp Pro Arg Leu Tyr Trp Gln Gly Gly Pro Ala
 65                  70                  75                  80

Leu Gly Arg Ser Phe Leu His Gly Pro Glu Leu Asp Lys Gly Gln Leu
                 85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 237
<211> LENGTH: 119
<212> TYPE: PRT
<213> ORGANISM: Artificial Sequence
<220> FEATURE:
<223> OTHER INFORMATION: CD70 VH

<400> SEQUENCE: 237

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Asp Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Ser Gly Asn Trp Gly Phe Phe Asp Tyr Trp Gly Gln Gly
            100                 105                 110

Thr Leu Val Thr Val Ser Ser
        115

<210> SEQ ID NO 238
<211> LENGTH: 107
<212> TYPE: PRT
<213> ORGANISM: Artificial Sequence
<220> FEATURE:
<223> OTHER INFORMATION: CD70 VL

<400> SEQUENCE: 238

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Arg Trp
```

```
                20                  25                  30
Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Arg
                85                  90                  95

Thr Phe Gly Gln Gly Thr Lys Val Glu Ile Lys
            100                 105

<210> SEQ ID NO 239
<211> LENGTH: 124
<212> TYPE: PRT
<213> ORGANISM: Artificial Sequence
<220> FEATURE:
<223> OTHER INFORMATION: ICOS sdAb

<400> SEQUENCE: 239

Gln Val Gln Leu Gln Gln Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Gly Met Gly Trp Tyr Arg Gln Ala Pro Gly Lys Glu Arg Glu Leu Val
        35                  40                  45

Ala Gly Leu Thr Ser Gly Gly Ser Val Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Arg Ala Glu Ile Phe Thr Arg Thr Gly Glu Asn Tyr Tyr Gly Met Asp
            100                 105                 110

Tyr Trp Gly Lys Gly Thr Gln Val Thr Val Lys Pro
        115                 120

<210> SEQ ID NO 240
<211> LENGTH: 124
<212> TYPE: PRT
<213> ORGANISM: Artificial Sequence
<220> FEATURE:
<223> OTHER INFORMATION: CD28 sdAb

<400> SEQUENCE: 240

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ala Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95
```

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120

<210> SEQ ID NO 241
<211> LENGTH: 109
<212> TYPE: PRT
<213> ORGANISM: artificial sequence
<220> FEATURE:
<223> OTHER INFORMATION: anti-CD3 VL (CON)

<400> SEQUENCE: 241

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Thr Val Leu
            100                 105

<210> SEQ ID NO 242
<211> LENGTH: 288
<212> TYPE: PRT
<213> ORGANISM: artificial sequence
<220> FEATURE:
<223> OTHER INFORMATION: PD-1

<400> SEQUENCE: 242

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Val Trp Val Leu Ala Val Ile Cys
            180                 185                 190

Ser Arg Ala Ala Arg Gly Thr Ile Gly Ala Arg Thr Gly Gln Pro
            195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 243
<211> LENGTH: 115
<212> TYPE: PRT
<213> ORGANISM: artificial sequence
<220> FEATURE:
<223> OTHER INFORMATION: 18H10

<400> SEQUENCE: 243

Gln Val Gln Leu Val Gln Ser Gly Gly Gly Leu Val Gln Pro Gly Gly
1               5                   10                  15

Ser Leu Arg Leu Ser Cys Val Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr His Tyr Ala Asp Ser Val Lys Gly Arg Phe
    50                  55                  60

Thr Ile Ser Arg Glu Asn Ala Lys Asn Thr Val Ile Leu Gln Met Asn
65                  70                  75                  80

Ser Leu Asn Pro Glu Asp Thr Ala Val Tyr Tyr Cys Tyr Leu Tyr Thr
                85                  90                  95

Asp Asn Leu Gly Thr Ser Trp Gly Gln Gly Thr Leu Val Thr Val Lys
            100                 105                 110

Pro Gly Gly
        115

<210> SEQ ID NO 244
<211> LENGTH: 6
<212> TYPE: PRT
<213> ORGANISM: artificial sequence
<220> FEATURE:
<223> OTHER INFORMATION: (GGS)2 linker

<400> SEQUENCE: 244

Gly Gly Ser Gly Gly Ser
1               5

<210> SEQ ID NO 245
<211> LENGTH: 6
<212> TYPE: PRT
<213> ORGANISM: artificial sequence
<220> FEATURE:
<223> OTHER INFORMATION: (GGS)2 linker

<400> SEQUENCE: 245

Gly Gly Ser Gly Gly Ser
1               5

<210> SEQ ID NO 246
<211> LENGTH: 9
<212> TYPE: PRT
<213> ORGANISM: artificial sequence
<220> FEATURE:
<223> OTHER INFORMATION: (GGS)3 linker

<400> SEQUENCE: 246

Gly Gly Ser Gly Gly Ser Gly Gly Ser
1               5

<210> SEQ ID NO 247
<211> LENGTH: 12
<212> TYPE: PRT
<213> ORGANISM: artificial sequence
<220> FEATURE:
<223> OTHER INFORMATION: (GGS)4 linker

<400> SEQUENCE: 247

Gly Gly Ser Gly Gly Ser Gly Gly Ser Gly Gly Ser
1               5                   10

<210> SEQ ID NO 248
<211> LENGTH: 15
<212> TYPE: PRT
<213> ORGANISM: artificial sequence
<220> FEATURE:
<223> OTHER INFORMATION: (GGS)5 linker

<400> SEQUENCE: 248

Gly Gly Ser Gly Gly Ser Gly Gly Ser Gly Gly Ser Gly Gly Ser
1               5                   10                  15

<210> SEQ ID NO 249
<211> LENGTH: 4
<212> TYPE: PRT
<213> ORGANISM: artificial sequence
<220> FEATURE:
<223> OTHER INFORMATION: glycine linker

<400> SEQUENCE: 249

Gly Gly Gly Gly
1

<210> SEQ ID NO 250
<211> LENGTH: 5
<212> TYPE: PRT
<213> ORGANISM: artificial sequence
<220> FEATURE:
<223> OTHER INFORMATION: glycine linker

<400> SEQUENCE: 250

Gly Gly Gly Gly Gly
1               5

<210> SEQ ID NO 251
<211> LENGTH: 117
<212> TYPE: PRT
<213> ORGANISM: artificial sequence
<220> FEATURE:
<223> OTHER INFORMATION: hz18H10v1

<400> SEQUENCE: 251

Glu Val Gln Leu Val Glu Ser Gly Gly Gly Glu Val Gln Pro Gly Gly

```
               1               5                  10                 15
            Ser Leu Arg Leu Ser Cys Ala Ala Ser Gly Ser Met Thr Gly Ala Asn
                           20                  25                 30

Thr Met Gly Trp Tyr Arg Gln Ala Pro Gly Lys Gly Arg Asp Leu Val
                       35                  40                 45

Ser Leu Ile Gly Asn Tyr Val Thr His Tyr Ala Glu Ser Val Lys Gly
                   50                  55                 60

Arg Phe Thr Ile Ser Arg Asp Asn Ala Lys Asn Thr Leu Tyr Leu Gln
             65                  70                  75                 80

Met Ser Ser Leu Arg Ala Glu Asp Thr Ala Val Tyr Tyr Cys Tyr Leu
                           85                  90                 95

Tyr Thr Asp Asn Leu Gly Thr Ser Trp Gly Gln Gly Thr Leu Val Thr
                           100                 105                110

Val Lys Pro Gly Gly
                       115

<210> SEQ ID NO 252
<211> LENGTH: 117
<212> TYPE: PRT
<213> ORGANISM: artificial sequence
<220> FEATURE:
<223> OTHER INFORMATION: hz18H10v2

<400> SEQUENCE: 252

Glu Val Gln Leu Val Glu Ser Gly Gly Gly Val Gln Pro Gly Gly
             1               5                  10                 15

Ser Leu Arg Leu Ser Cys Ala Ala Ser Gly Ser Met Thr Gly Ala Asn
                           20                  25                 30

Thr Met Gly Trp Tyr Arg Gln Ala Pro Gly Lys Gln Arg Asp Leu Val
                       35                  40                 45

Ser Leu Ile Gly Asn Tyr Val Thr His Tyr Ala Glu Ser Val Lys Gly
                   50                  55                 60

Arg Phe Thr Ile Ser Arg Asp Asn Ala Lys Asn Thr Leu Tyr Leu Gln
             65                  70                  75                 80

Met Ser Ser Leu Arg Ala Glu Asp Thr Ala Val Tyr Tyr Cys Tyr Leu
                           85                  90                 95

Tyr Thr Asp Asn Leu Gly Thr Ser Trp Gly Gln Gly Thr Leu Val Thr
                           100                 105                110

Val Lys Pro Gly Gly
                       115

<210> SEQ ID NO 253
<211> LENGTH: 117
<212> TYPE: PRT
<213> ORGANISM: artificial sequence
<220> FEATURE:
<223> OTHER INFORMATION: hz18H10v3

<400> SEQUENCE: 253

Glu Val Gln Leu Val Glu Ser Gly Gly Gly Val Gln Pro Gly Gly
             1               5                  10                 15

Ser Leu Arg Leu Ser Cys Ala Ala Ser Gly Ser Met Thr Gly Ala Asn
                           20                  25                 30

Thr Met Gly Trp Tyr Arg Gln Ala Pro Gly Lys Gln Arg Asp Leu Val
                       35                  40                 45

Ser Leu Ile Gly Asn Tyr Val Thr His Tyr Ala Glu Ser Val Lys Gly
                   50                  55                 60
```

```
Arg Phe Thr Ile Ser Arg Asp Asn Ala Lys Asn Thr Val Tyr Leu Gln
 65                  70                  75                  80

Met Ser Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 254
<211> LENGTH: 117
<212> TYPE: PRT
<213> ORGANISM: artificial sequence
<220> FEATURE:
<223> OTHER INFORMATION: hz18H10v4

<400> SEQUENCE: 254

Glu Val Gln Leu Val Glu Ser Gly Gly Gly Glu Val Gln Pro Gly Gly
  1               5                  10                  15

Ser Leu Arg Leu Ser Cys Ala Ala Ser Gly Ser Met Thr Gly Ala Asn
             20                  25                  30

Thr Met Gly Trp Tyr Arg Gln Ala Pro Gly Lys Gln Arg Asp Leu Val
         35                  40                  45

Ala Leu Ile Gly Asn Tyr Val Thr His Tyr Ala Glu Ser Val Lys Gly
     50                  55                  60

Arg Phe Thr Ile Ser Arg Asp Asn Ala Lys Asn Thr Val Tyr Leu Gln
 65                  70                  75                  80

Met Ser Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 255
<211> LENGTH: 117
<212> TYPE: PRT
<213> ORGANISM: artificial sequence
<220> FEATURE:
<223> OTHER INFORMATION: z18H10v5

<400> SEQUENCE: 255

Glu Val Gln Leu Val Glu Ser Gly Gly Gly Glu Val Gln Pro Gly Gly
  1               5                  10                  15

Ser Leu Arg Leu Ser Cys Ala Ala Ser Gly Ser Met Thr Gly Ala Asn
             20                  25                  30

Thr Met Gly Trp Tyr Arg Gln Ala Pro Gly Lys Gln Arg Asp Leu Val
         35                  40                  45

Ala Leu Ile Gly Asn Tyr Val Thr His Tyr Ala Glu Ser Val Lys Gly
     50                  55                  60

Arg Phe Thr Ile Ser Arg Glu Asn Ala Lys Asn Thr Val Tyr Leu Gln
 65                  70                  75                  80

Met Ser Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
            100                 105                 110

Val Lys Pro Gly Gly
        115
```

<210> SEQ ID NO 256
<211> LENGTH: 117
<212> TYPE: PRT
<213> ORGANISM: artificial sequence
<220> FEATURE:
<223> OTHER INFORMATION: hz18H10v6

<400> SEQUENCE: 256

Glu Val Gln Leu Val Glu Ser Gly Gly Gly Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 257
<211> LENGTH: 117
<212> TYPE: PRT
<213> ORGANISM: artificial sequence
<220> FEATURE:
<223> OTHER INFORMATION: hz18H10v7

<400> SEQUENCE: 257

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 258
<211> LENGTH: 117
<212> TYPE: PRT
<213> ORGANISM: artificial sequence
<220> FEATURE:
<223> OTHER INFORMATION: hz18H10v8

<400> SEQUENCE: 258

Glu Val Gln Leu Val Glu Ser Gly Gly Gly Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 259
<211> LENGTH: 117
<212> TYPE: PRT
<213> ORGANISM: artificial sequence
<220> FEATURE:
<223> OTHER INFORMATION: hz18H10v9

<400> SEQUENCE: 259

Glu Val Gln Leu Val Glu Ser Gly Gly Gly Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 260
<211> LENGTH: 117
<212> TYPE: PRT
<213> ORGANISM: artificial sequence
<220> FEATURE:
<223> OTHER INFORMATION: hz18H10v10

<400> SEQUENCE: 260

Glu Val Gln Leu Val Glu Ser Gly Gly Gly Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 261
<211> LENGTH: 117
<212> TYPE: PRT
<213> ORGANISM: artificial sequence
<220> FEATURE:
<223> OTHER INFORMATION: hz18H10v11

<400> SEQUENCE: 261

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 262
<211> LENGTH: 117
<212> TYPE: PRT
<213> ORGANISM: artificial sequence
<220> FEATURE:
<223> OTHER INFORMATION: hz18H10v12

<400> SEQUENCE: 262

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly

115

<210> SEQ ID NO 263
<211> LENGTH: 117
<212> TYPE: PRT
<213> ORGANISM: artificial sequence
<220> FEATURE:
<223> OTHER INFORMATION: hz18H10v13

<400> SEQUENCE: 263

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Glu Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 264
<211> LENGTH: 117
<212> TYPE: PRT
<213> ORGANISM: artificial sequence
<220> FEATURE:
<223> OTHER INFORMATION: hz18H10v14

<400> SEQUENCE: 264

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 265
<211> LENGTH: 117
<212> TYPE: PRT
<213> ORGANISM: artificial sequence
<220> FEATURE:
<223> OTHER INFORMATION: hz18H10v15

<400> SEQUENCE: 265

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 266
<211> LENGTH: 117
<212> TYPE: PRT
<213> ORGANISM: artificial sequence
<220> FEATURE:
<223> OTHER INFORMATION: hz18H10v16

<400> SEQUENCE: 266

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 267
<211> LENGTH: 117
<212> TYPE: PRT
<213> ORGANISM: artificial sequence
<220> FEATURE:
<223> OTHER INFORMATION: hz18H10v17

<400> SEQUENCE: 267

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
```

```
                 50                  55                  60

Arg Phe Thr Ile Ser Arg Asp Asn Ala Lys Asn Thr Val Tyr Leu Gln
 65                  70                  75                  80

Met Asn Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 268
<211> LENGTH: 10
<212> TYPE: PRT
<213> ORGANISM: artificial sequence
<220> FEATURE:
<223> OTHER INFORMATION: CDR1

<400> SEQUENCE: 268

Gly Ser Met Thr Gly Ala Asn Thr Met Gly
1               5                   10

<210> SEQ ID NO 269
<211> LENGTH: 9
<212> TYPE: PRT
<213> ORGANISM: artificial sequence
<220> FEATURE:
<223> OTHER INFORMATION: (GGS)3 linker

<400> SEQUENCE: 269

Gly Gly Ser Gly Gly Ser Gly Gly Ser
1               5

<210> SEQ ID NO 270
<211> LENGTH: 12
<212> TYPE: PRT
<213> ORGANISM: artificial sequence
<220> FEATURE:
<223> OTHER INFORMATION: (GGS)4 linker

<400> SEQUENCE: 270

Gly Gly Ser Gly Gly Ser Gly Gly Ser Gly Gly Ser
1               5                   10

<210> SEQ ID NO 271
<211> LENGTH: 15
<212> TYPE: PRT
<213> ORGANISM: artificial sequence
<220> FEATURE:
<223> OTHER INFORMATION: (GGS)5 linker

<400> SEQUENCE: 271

Gly Gly Ser Gly Gly Ser Gly Gly Ser Gly Gly Ser Gly Gly Ser
1               5                   10                  15

<210> SEQ ID NO 272
<211> LENGTH: 10
<212> TYPE: PRT
<213> ORGANISM: artificial sequence
<220> FEATURE:
<223> OTHER INFORMATION: CDR1

<400> SEQUENCE: 272

Gly Ser Val Thr Gly Ala Asn Thr Met Gly
1               5                   10
```

```
<210> SEQ ID NO 273
<211> LENGTH: 10
<212> TYPE: PRT
<213> ORGANISM: artificial sequence
<220> FEATURE:
<223> OTHER INFORMATION: CDR1

<400> SEQUENCE: 273

Gly Ser Ile Thr Gly Ala Asn Thr Met Gly
1               5                   10

<210> SEQ ID NO 274
<211> LENGTH: 6
<212> TYPE: PRT
<213> ORGANISM: artificial sequence
<220> FEATURE:
<223> OTHER INFORMATION: (GGS)2 linker

<400> SEQUENCE: 274

Gly Gly Ser Gly Gly Ser
1               5

<210> SEQ ID NO 275
<211> LENGTH: 9
<212> TYPE: PRT
<213> ORGANISM: artificial sequence
<220> FEATURE:
<223> OTHER INFORMATION: (GGS)3 linker

<400> SEQUENCE: 275

Gly Gly Ser Gly Gly Ser Gly Gly Ser
1               5

<210> SEQ ID NO 276
<211> LENGTH: 12
<212> TYPE: PRT
<213> ORGANISM: artificial sequence
<220> FEATURE:
<223> OTHER INFORMATION: (GGS)4 linker

<400> SEQUENCE: 276

Gly Gly Ser Gly Gly Ser Gly Gly Ser Gly Gly Ser
1               5                   10

<210> SEQ ID NO 277
<211> LENGTH: 15
<212> TYPE: PRT
<213> ORGANISM: artificial sequence
<220> FEATURE:
<223> OTHER INFORMATION: (GGS)5 linker

<400> SEQUENCE: 277

Gly Gly Ser Gly Gly Ser Gly Gly Ser Gly Gly Ser Gly Gly Ser
1               5                   10                  15

<210> SEQ ID NO 278
<211> LENGTH: 8
<212> TYPE: PRT
<213> ORGANISM: artificial sequence
<220> FEATURE:
<223> OTHER INFORMATION: CDR2

<400> SEQUENCE: 278

Leu Ile Gly Asn Tyr Val Thr His
1               5
```

```
<210> SEQ ID NO 279
<211> LENGTH: 6
<212> TYPE: PRT
<213> ORGANISM: artificial sequence
<220> FEATURE:
<223> OTHER INFORMATION: (GGS)2 linker

<400> SEQUENCE: 279

Gly Gly Ser Gly Gly Ser
1               5

<210> SEQ ID NO 280
<211> LENGTH: 9
<212> TYPE: PRT
<213> ORGANISM: artificial sequence
<220> FEATURE:
<223> OTHER INFORMATION: (GGS)3  linker

<400> SEQUENCE: 280

Gly Gly Ser Gly Gly Ser Gly Gly Ser
1               5

<210> SEQ ID NO 281
<211> LENGTH: 12
<212> TYPE: PRT
<213> ORGANISM: artificial sequence
<220> FEATURE:
<223> OTHER INFORMATION: (GGS)4 linker

<400> SEQUENCE: 281

Gly Gly Ser Gly Gly Ser Gly Gly Ser Gly Gly Ser
1               5                   10

<210> SEQ ID NO 282
<211> LENGTH: 15
<212> TYPE: PRT
<213> ORGANISM: artificial sequence
<220> FEATURE:
<223> OTHER INFORMATION: (GGS)5 linker

<400> SEQUENCE: 282

Gly Gly Ser Gly Gly Ser Gly Gly Ser Gly Gly Ser Gly Gly Ser
1               5                   10                  15

<210> SEQ ID NO 283
<211> LENGTH: 8
<212> TYPE: PRT
<213> ORGANISM: artificial sequence
<220> FEATURE:
<223> OTHER INFORMATION: CDR3

<400> SEQUENCE: 283

Tyr Thr Asp Asn Leu Gly Thr Ser
1               5

<210> SEQ ID NO 284
<211> LENGTH: 215
<212> TYPE: PRT
<213> ORGANISM: artificial sequence
<220> FEATURE:
<223> OTHER INFORMATION: Fc xELL

<400> SEQUENCE: 284

Pro Ala Pro Gly Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
                20                  25                  30
```

```
Asp Val Ser His Glu Asp Pro Glu Val Lys Phe Asn Trp Tyr Val Asp
            35                  40                  45

Gly Val Glu Val His Asn Ala Lys Thr Lys Pro Arg Glu Glu Gln Tyr
        50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Ala Leu
                85                  90                  95

Pro Ala Pro Ile Glu Lys Thr Ile Ser Lys Ala Lys Gly Gln Pro Arg
            100                 105                 110

Glu Pro Gln Val Tyr Thr Leu Pro Pro Ser Arg Asp Glu Leu Thr Lys
        115                 120                 125

Asn Gln Val Ser Leu Thr Cys Leu Val Lys Gly Phe Tyr Pro Ser Asp
130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Lys Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
        195                 200                 205

Leu Ser Leu Ser Pro Gly Lys
210                 215

<210> SEQ ID NO 285
<211> LENGTH: 226
<212> TYPE: PRT
<213> ORGANISM: artificial sequence
<220> FEATURE:
<223> OTHER INFORMATION: Fc-Het-1

<400> SEQUENCE: 285

Asp Lys Thr His Thr Cys Pro Pro Cys Pro Ala Pro Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Lys His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Glu Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Glu Glu Met Thr Lys Asn Gln Val Ser Leu
    130                 135                 140

Thr Cys Asp Val Ser Gly Phe Tyr Pro Ser Asp Ile Ala Val Glu Trp
145                 150                 155                 160

Glu Ser Asp Gly Gln Pro Glu Asn Asn Tyr Lys Thr Thr Pro Pro Val
                165                 170                 175
```

```
Leu Asp Ser Asp Gly Ser Phe Phe Leu Tyr Ser Lys Leu Thr Val Asp
            180                 185                 190

Lys Ser Arg Trp Glu Gln Gly Asp Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 286
<211> LENGTH: 226
<212> TYPE: PRT
<213> ORGANISM: artificial sequence
<220> FEATURE:
<223> OTHER INFORMATION: Fc-Het-2

<400> SEQUENCE: 286

Asp Lys Thr His Thr Cys Pro Pro Cys Pro Ala Pro Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Lys His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Glu Gln Met Thr Lys Asn Gln Val Lys Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 287
<211> LENGTH: 125
<212> TYPE: PRT
<213> ORGANISM: artificial sequence
<220> FEATURE:
<223> OTHER INFORMATION: CD3-VH32

<400> SEQUENCE: 287

Glu Val Gln Leu Val Glu Ser Gly Gly Gly Leu Val Gln Pro Gly Gly
```

```
1               5                  10                 15
Ser Leu Arg Leu Ser Cys Ala Ala Ser Gly Phe Thr Phe Ser Thr Tyr
                20                 25                 30
Ala Met Asn Trp Val Arg Gln Ala Pro Gly Lys Gly Leu Glu Trp Val
                35                 40                 45
Gly Arg Ile Arg Ser Lys Tyr Asn Asn Tyr Ala Thr Tyr Tyr Ala Asp
        50                 55                 60
Ser Val Lys Gly Arg Phe Thr Ile Ser Arg Asp Asp Ser Lys Asn Thr
65                 70                 75                 80
Leu Tyr Leu Gln Met Asn Ser Leu Arg Ala Glu Asp Thr Ala Val Tyr
                85                 90                 95
Tyr Cys Val Arg His Gly Asn Phe Gly Asp Ser Tyr Val Ser Trp Phe
                100                105                110
Ala Tyr Trp Gly Gln Gly Thr Leu Val Thr Val Ser Ser
                115                120                125

<210> SEQ ID NO 288
<211> LENGTH: 109
<212> TYPE: PRT
<213> ORGANISM: artificial sequence
<220> FEATURE:
<223> OTHER INFORMATION: CD3-VL20

<400> SEQUENCE: 288

Gln Ala Val Val Thr Gln Glu Pro Ser Leu Thr Val Ser Pro Gly Gly
1               5                  10                 15

Thr Val Thr Leu Thr Cys Gly Ser Ser Thr Gly Ala Val Thr Thr Ser
                20                 25                 30

Asn Tyr Ala Asn Trp Val Gln Gln Lys Pro Gly Lys Ser Pro Arg Gly
                35                 40                 45

Leu Ile Gly Gly Thr Asn Lys Arg Ala Pro Gly Val Pro Ala Arg Phe
        50                 55                 60

Ser Gly Ser Leu Leu Gly Gly Lys Ala Ala Leu Thr Ile Ser Gly Ala
65                 70                 75                 80

Gln Pro Glu Asp Glu Ala Asp Tyr Tyr Cys Ala Leu Trp Tyr Ser Asn
                85                 90                 95

His Trp Val Phe Gly Gly Gly Thr Lys Leu Thr Val Leu
                100                105

<210> SEQ ID NO 289
<211> LENGTH: 109
<212> TYPE: PRT
<213> ORGANISM: artificial sequence
<220> FEATURE:
<223> OTHER INFORMATION: CD3-VL21

<400> SEQUENCE: 289

Gln Ala Val Val Thr Gln Glu Pro Ser Leu Thr Val Ser Pro Gly Gly
1               5                  10                 15

Thr Val Thr Leu Thr Cys Gly Ser Ser Thr Gly Ala Val Thr Thr Ser
                20                 25                 30

Asn Tyr Ala Asn Trp Val Gln Gln Lys Pro Gly Lys Ser Pro Arg Gly
                35                 40                 45

Leu Ile Gly Gly Thr Asn Lys Arg Ala Pro Gly Val Pro Ala Arg Phe
        50                 55                 60

Ser Gly Ser Leu Leu Gly Gly Lys Ala Ala Leu Thr Ile Ser Gly Ala
65                 70                 75                 80
```

```
Gln Pro Glu Asp Glu Ala Asp Tyr Tyr Cys Ala Leu Trp Tyr Ser Asn
                85                  90                  95

His Trp Val Phe Gly Cys Gly Thr Lys Leu Thr Val Leu
            100                 105

<210> SEQ ID NO 290
<211> LENGTH: 123
<212> TYPE: PRT
<213> ORGANISM: artificial sequence
<220> FEATURE:
<223> OTHER INFORMATION: CD3-VH34

<400> SEQUENCE: 290

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Thr Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val
        115                 120

<210> SEQ ID NO 291
<211> LENGTH: 225
<212> TYPE: PRT
<213> ORGANISM: artificial sequence
<220> FEATURE:
<223> OTHER INFORMATION: Knob Fc

<400> SEQUENCE: 291

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160
```

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro
225

<210> SEQ ID NO 292
<211> LENGTH: 225
<212> TYPE: PRT
<213> ORGANISM: artificial sequence
<220> FEATURE:
<223> OTHER INFORMATION: Hole Fc

<400> SEQUENCE: 292

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro
225

<210> SEQ ID NO 293
<211> LENGTH: 222
<212> TYPE: PRT
<213> ORGANISM: artificial sequence
<220> FEATURE:
<223> OTHER INFORMATION: Knob Fc

<400> SEQUENCE: 293

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro
    210                 215                 220

<210> SEQ ID NO 294
<211> LENGTH: 222
<212> TYPE: PRT
<213> ORGANISM: artificial sequence
<220> FEATURE:
<223> OTHER INFORMATION: Hole Fc

<400> SEQUENCE: 294

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys

```
            130                 135                 140
Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
                195                 200                 205

Leu His Asn His Tyr Thr Gln Lys Ser Leu Ser Leu Ser Pro
            210                 215                 220

<210> SEQ ID NO 295
<211> LENGTH: 225
<212> TYPE: PRT
<213> ORGANISM: artificial sequence
<220> FEATURE:
<223> OTHER INFORMATION: Hole Fc

<400> SEQUENCE: 295

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro
225

<210> SEQ ID NO 296
<211> LENGTH: 222
<212> TYPE: PRT
<213> ORGANISM: artificial sequence
<220> FEATURE:
<223> OTHER INFORMATION: Hole Fc
```

<400> SEQUENCE: 296

```
Asp Lys Thr His Thr Cys Pro Pro Cys Pro Ala Pro Gly Gly Pro Ser
1               5                   10                  15
Val Phe Leu Phe Pro Pro Lys Pro Lys Asp Thr Leu Met Ile Ser Arg
            20                  25                  30
Thr Pro Glu Val Thr Cys Val Val Val Asp Val Ser His Glu Asp Pro
        35                  40                  45
Glu Val Lys Phe Asn Trp Tyr Val Asp Gly Val Glu Val His Asn Ala
    50                  55                  60
Lys Thr Lys Pro Arg Glu Glu Gln Tyr Asn Ser Thr Tyr Arg Val Val
65                  70                  75                  80
Ser Val Leu Thr Val Leu His Gln Asp Trp Leu Asn Gly Lys Glu Tyr
                85                  90                  95
Lys Cys Lys Val Ser Asn Lys Ala Leu Pro Ala Pro Ile Glu Lys Thr
            100                 105                 110
Ile Ser Lys Ala Lys Gly Gln Pro Arg Glu Pro Gln Val Cys Thr Leu
        115                 120                 125
Pro Pro Ser Arg Asp Glu Leu Thr Lys Asn Gln Val Ser Leu Ser Cys
    130                 135                 140
Ala Val Lys Gly Phe Tyr Pro Ser Asp Ile Ala Val Glu Trp Glu Ser
145                 150                 155                 160
Asn Gly Gln Pro Glu Asn Asn Tyr Lys Thr Thr Pro Pro Val Leu Asp
                165                 170                 175
Ser Asp Gly Ser Phe Phe Leu Val Ser Lys Leu Thr Val Asp Lys Ser
            180                 185                 190
Arg Trp Gln Gln Gly Asn Val Phe Ser Cys Ser Val Met His Glu Ala
        195                 200                 205
Leu His Asn Arg Tyr Thr Gln Lys Ser Leu Ser Leu Ser Pro
    210                 215                 220
```

<210> SEQ ID NO 297
<211> LENGTH: 225
<212> TYPE: PRT
<213> ORGANISM: artificial sequence
<220> FEATURE:
<223> OTHER INFORMATION: Knob Fc

<400> SEQUENCE: 297

```
Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Tyr
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
```

```
Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
            195                 200                 205

His Glu Ala Leu His Asn His Tyr Thr Gln Lys Ser Leu Ser Leu Ser
210                 215                 220

Pro
225

<210> SEQ ID NO 298
<211> LENGTH: 222
<212> TYPE: PRT
<213> ORGANISM: artificial sequence
<220> FEATURE:
<223> OTHER INFORMATION: Knob Fc

<400> SEQUENCE: 298

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn His Tyr Thr Gln Lys Ser Leu Ser Leu Ser Pro
210                 215                 220

<210> SEQ ID NO 299
<211> LENGTH: 225
<212> TYPE: PRT
<213> ORGANISM: artificial sequence
<220> FEATURE:
```

<223> OTHER INFORMATION: Hole Fc

<400> SEQUENCE: 299

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn Arg Tyr Thr Gln Lys Ser Leu Ser Leu Ser
    210                 215                 220

Pro
225
```

<210> SEQ ID NO 300
<211> LENGTH: 222
<212> TYPE: PRT
<213> ORGANISM: artificial sequence
<220> FEATURE:
<223> OTHER INFORMATION: Hole Fc

<400> SEQUENCE: 300

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110
```

-continued

```
Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
        130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
                180                 185                 190

Arg Trp Gln Gln Gly Asn Val Phe Ser Cys Ser Val Val His Glu Ala
                195                 200                 205

Leu His Asn Arg Tyr Thr Gln Lys Ser Leu Ser Leu Ser Pro
        210                 215                 220

<210> SEQ ID NO 301
<211> LENGTH: 118
<212> TYPE: PRT
<213> ORGANISM: artificial sequence
<220> FEATURE:
<223> OTHER INFORMATION: B7H3 sdAb B7h3 hz1A5v51

<400> SEQUENCE: 301

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Ser Phe Ser Ser Asn
            20                  25                  30

Val Met Met Trp Val Arg Gln Ala Pro Gly Lys Gly Leu Glu Trp Val
        35                  40                  45

Ser Thr Ile Tyr Ser Ser Gly Thr Gly Thr Phe Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Pro Glu Asp Thr Ala Val Tyr Tyr Cys
                85                  90                  95

Ala Thr Ser Gly Pro Val Arg Gly Trp Gly Pro Arg Ser Gln Gly Thr
            100                 105                 110

Leu Val Thr Val Lys Pro
        115

<210> SEQ ID NO 302
<211> LENGTH: 117
<212> TYPE: PRT
<213> ORGANISM: artificial sequence
<220> FEATURE:
<223> OTHER INFORMATION: sdAb B7H3 hz58E05v27

<400> SEQUENCE: 302

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Thr Phe Ser Ser Tyr
            20                  25                  30

His Met Ser Trp Phe Arg Gln Ala Pro Gly Lys Gln Arg Glu Pro Val
        35                  40                  45

Ala Thr Ser His His Gly Gly Thr Thr Asn Tyr Ala Gly Ser Val Lys
    50                  55                  60

Gly Arg Phe Thr Ile Ser Arg Asp Asn Ala Lys Asn Thr Val Tyr Leu
```

```
                65                  70                  75                  80
Gln Met Asn Thr Leu Arg Ala Glu Asp Thr Ala Val Tyr Tyr Cys Lys
                    85                  90                  95

Ala Asp His Gly Tyr Gln Gly Arg Gly Tyr Trp Gly Gln Gly Thr Leu
            100                 105                 110

Val Thr Val Lys Pro
        115

<210> SEQ ID NO 303
<211> LENGTH: 117
<212> TYPE: PRT
<213> ORGANISM: artificial sequence
<220> FEATURE:
<223> OTHER INFORMATION: sdAb B7H3 hz58E05v55

<400> SEQUENCE: 303

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Ser Tyr
            20                  25                  30

His Met Ser Trp Phe Arg Gln Ala Pro Gly Lys Gln Arg Glu Leu Val
        35                  40                  45

Ala Thr Ser His His Gly Gly Thr Thr Asn Tyr Ala Gly Ser Val Lys
    50                  55                  60

Gly Arg Phe Thr Ile Ser Arg Asp Asn Ala Lys Asn Thr Val Tyr Leu
65                  70                  75                  80

Gln Met Asn Thr Leu Arg Ala Glu Asp Thr Ala Val Tyr Tyr Cys Lys
                    85                  90                  95

Ala Asp His Gly Tyr Gln Gly Arg Gly Tyr Trp Gly Gln Gly Thr Leu
            100                 105                 110

Val Thr Val Lys Pro
        115

<210> SEQ ID NO 304
<211> LENGTH: 117
<212> TYPE: PRT
<213> ORGANISM: artificial sequence
<220> FEATURE:
<223> OTHER INFORMATION: sdAb B7H3 hz58E05v48

<400> SEQUENCE: 304

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Ser Tyr
            20                  25                  30

His Met Ser Trp Phe Arg Gln Ala Pro Gly Lys Gln Arg Glu Pro Val
        35                  40                  45

Ala Thr Ser His His Gly Gly Thr Thr Asn Tyr Ala Gly Ser Val Lys
    50                  55                  60

Gly Arg Phe Thr Ile Ser Arg Asp Asn Ala Lys Asn Thr Val Tyr Leu
65                  70                  75                  80

Gln Met Asn Thr Leu Arg Ala Glu Asp Thr Ala Val Tyr Tyr Cys Lys
                    85                  90                  95

Ala Asp His Gly Tyr Gln Gly Arg Gly Tyr Trp Gly Gln Gly Thr Leu
            100                 105                 110

Val Thr Val Lys Pro
        115
```

<210> SEQ ID NO 305
<211> LENGTH: 127
<212> TYPE: PRT
<213> ORGANISM: artificial sequence
<220> FEATURE:
<223> OTHER INFORMATION: sdAb B7H3 hz57B04v24

<400> SEQUENCE: 305

Glu Val Gln Leu Val Glu Ser Gly Gly Gly Glu Val Gln Pro Gly Gly
1               5                   10                  15

Ser Leu Arg Leu Ser Cys Ala Pro Ser Glu Arg Thr Phe Ser Thr Tyr
            20                  25                  30

Thr Met Gly Trp Phe Arg Gln Ala Pro Gly Lys Glu Arg Glu Phe Val
        35                  40                  45

Ala Val Val Asn Trp Gly Gly Ser Lys Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Gly Gly Ala Tyr Ser Gly Pro Tyr Tyr Asp Thr Arg Gln Tyr
            100                 105                 110

Thr Tyr Trp Gly Gln Gly Thr Leu Val Thr Val Lys Pro Gly Gly
        115                 120                 125

<210> SEQ ID NO 306
<211> LENGTH: 120
<212> TYPE: PRT
<213> ORGANISM: artificial sequence
<220> FEATURE:
<223> OTHER INFORMATION: sdAb DLL3 hz10D9v7

<400> SEQUENCE: 306

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Thr Asn Thr Ile Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Phe Ser Arg Asp Tyr Glu Phe Tyr Trp Gly Gln
            100                 105                 110

Gly Thr Leu Val Thr Val Lys Pro
        115                 120

<210> SEQ ID NO 307
<211> LENGTH: 115
<212> TYPE: PRT
<213> ORGANISM: artificial sequence
<220> FEATURE:
<223> OTHER INFORMATION: sdAb DLL3 hz8E7v16

<400> SEQUENCE: 307

Glu Val Gln Leu Val Glu Ser Gly Gly Gly Glu Val Gln Pro Gly Gly

-continued

```
                1               5              10              15
Ser Leu Arg Leu Ser Cys Gly Pro Ser Glu Ile Ile Thr Ser Asp Lys
            20                  25                  30

Ser Met Gly Trp Val Arg Gln Ala Pro Gly Lys Gln Arg Asn Leu Val
            35                  40                  45

Ala Gly Ile Ser Asn Val Gly Ser Thr Asn Tyr Ala Gln Ser Val Lys
        50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Asn Glu Tyr Trp Gly Gln Gly Thr Leu Val Thr
            100                 105                 110

Val Lys Pro
    115

<210> SEQ ID NO 308
<211> LENGTH: 10
<212> TYPE: PRT
<213> ORGANISM: artificial sequence
<220> FEATURE:
<223> OTHER INFORMATION: 41BB CDR1

<400> SEQUENCE: 308

Gly Phe Ser Phe Ser Ile Asn Ala Met Gly
1               5                  10

<210> SEQ ID NO 309
<211> LENGTH: 9
<212> TYPE: PRT
<213> ORGANISM: artificial sequence
<220> FEATURE:
<223> OTHER INFORMATION: 41BB CDR2

<400> SEQUENCE: 309

Ala Ile Glu Ser Gly Arg Asn Thr Val
1               5

<210> SEQ ID NO 310
<211> LENGTH: 13
<212> TYPE: PRT
<213> ORGANISM: artificial sequence
<220> FEATURE:
<223> OTHER INFORMATION: 41BB CDR3

<400> SEQUENCE: 310

Leu Lys Gly Asn Arg Val Val Ser Pro Ser Val Ala Tyr
1               5                  10

<210> SEQ ID NO 311
<211> LENGTH: 125
<212> TYPE: PRT
<213> ORGANISM: artificial sequence
<220> FEATURE:
<223> OTHER INFORMATION: CD3-VH33

<400> SEQUENCE: 311

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
```

```
                35                  40                  45
Gly Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 312
<211> LENGTH: 10
<212> TYPE: PRT
<213> ORGANISM: artificial sequence
<220> FEATURE:
<223> OTHER INFORMATION: anti-CD3 VH CDR1

<400> SEQUENCE: 312

Gly Phe Thr Phe Asn Thr Tyr Ala Met Asn
1               5                   10

<210> SEQ ID NO 313
<211> LENGTH: 12
<212> TYPE: PRT
<213> ORGANISM: artificial sequence
<220> FEATURE:
<223> OTHER INFORMATION: anti-CD3 VH CDR2

<400> SEQUENCE: 313

Arg Ile Arg Ser Lys Tyr Asn Asn Tyr Ala Thr Tyr
1               5                   10

<210> SEQ ID NO 314
<211> LENGTH: 14
<212> TYPE: PRT
<213> ORGANISM: artificial sequence
<220> FEATURE:
<223> OTHER INFORMATION: CD3-VH7, VH33 CDR3

<400> SEQUENCE: 314

His Gly Asn Phe Gly Asp Ser Tyr Val Ser Trp Phe Ala Tyr
1               5                   10

<210> SEQ ID NO 315
<211> LENGTH: 9
<212> TYPE: PRT
<213> ORGANISM: artificial sequence
<220> FEATURE:
<223> OTHER INFORMATION: CD3-VL2, VL21 CDR3

<400> SEQUENCE: 315

Ala Leu Trp Tyr Ser Asn His Trp Val
1               5

<210> SEQ ID NO 316
<211> LENGTH: 9
<212> TYPE: PRT
<213> ORGANISM: artificial sequence
<220> FEATURE:
<223> OTHER INFORMATION: CD3-VL8 CDR3

<400> SEQUENCE: 316
```

```
Val Leu Trp Tyr Ser Asn Arg Trp Val
1               5
```

<210> SEQ ID NO 317
<211> LENGTH: 10
<212> TYPE: PRT
<213> ORGANISM: artificial sequence
<220> FEATURE:
<223> OTHER INFORMATION: CD3 VH33 CDR1

<400> SEQUENCE: 317

```
Gly Phe Thr Phe Ser Thr Tyr Ala Met Asn
1               5                   10
```

<210> SEQ ID NO 318
<211> LENGTH: 12
<212> TYPE: PRT
<213> ORGANISM: artificial sequence
<220> FEATURE:
<223> OTHER INFORMATION: CD3 VH33 CDR1

<400> SEQUENCE: 318

```
Arg Ile Arg Ser Lys Tyr Asn Asn Tyr Ala Thr Tyr
1               5                   10
```

<210> SEQ ID NO 319
<211> LENGTH: 14
<212> TYPE: PRT
<213> ORGANISM: artificial sequence
<220> FEATURE:
<223> OTHER INFORMATION: CD3 VL21 CDR1

<400> SEQUENCE: 319

```
Gly Ser Ser Thr Gly Ala Val Thr Thr Ser Asn Tyr Ala Asn
1               5                   10
```

<210> SEQ ID NO 320
<211> LENGTH: 7
<212> TYPE: PRT
<213> ORGANISM: artificial sequence
<220> FEATURE:
<223> OTHER INFORMATION: CD3 VL21 CDR2

<400> SEQUENCE: 320

```
Gly Thr Asn Lys Arg Ala Pro
1               5
```

<210> SEQ ID NO 321
<211> LENGTH: 121
<212> TYPE: PRT
<213> ORGANISM: artificial sequence
<220> FEATURE:
<223> OTHER INFORMATION: 41BB sdAb

<400> SEQUENCE: 321

```
Glu Val Gln Leu Val Glu Ser Gly Gly Glu Val Gln Pro Gly Gly
1               5                   10                  15

Ser Leu Arg Leu Ser Cys Ala Ala Ser Gly Phe Ser Phe Ser Ile Asn
                20                  25                  30

Ala Met Gly Trp Tyr Arg Gln Ala Pro Gly Lys Arg Arg Glu Phe Val
            35                  40                  45

Ala Ala Ile Glu Ser Gly Arg Asn Thr Val Tyr Ala Glu Ser Val Lys
        50                  55                  60

Gly Arg Phe Thr Ile Ser Arg Asp Asn Ala Lys Asn Thr Val Tyr Leu
65                  70                  75                  80
```

Gln Met Ser Ser Leu Arg Ala Glu Asp Thr Ala Val Tyr Tyr Cys Gly
                85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120

<210> SEQ ID NO 322
<211> LENGTH: 122
<212> TYPE: PRT
<213> ORGANISM: artificial sequence
<220> FEATURE:
<223> OTHER INFORMATION: sdAb 5T4 hz12E9v9

<400> SEQUENCE: 322

Glu Val Gln Leu Val Glu Ser Gly Gly Gly Val Gln Pro Gly Gly
1               5                   10                  15

Ser Leu Arg Leu Ser Cys Ala Ala Ser Gly Arg Pro Phe Ser Ser Lys
            20                  25                  30

Thr Met Ala Trp Phe Arg Gln Ala Pro Gly Lys Glu Arg Glu Phe Val
        35                  40                  45

Ala Ala Val Arg Trp Ile Gly Gly Ala Thr Arg Tyr Thr Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Gly Gln Ala Trp Gly Thr Lys Phe Thr Asp Tyr Ser Asp Trp
            100                 105                 110

Gly Gln Gly Thr Leu Val Thr Val Lys Pro
        115                 120

<210> SEQ ID NO 323
<211> LENGTH: 129
<212> TYPE: PRT
<213> ORGANISM: artificial sequence
<220> FEATURE:
<223> OTHER INFORMATION: sdAb 5T4 hz16G10v11

<400> SEQUENCE: 323

Glu Val Gln Leu Val Glu Ser Gly Gly Gly Val Gln Pro Gly Gly
1               5                   10                  15

Ser Leu Arg Leu Ser Cys Ala Ala Ser Gly Arg Pro Phe Ser Ser Tyr
            20                  25                  30

Ala Met Gly Trp Phe Arg Gln Ala Pro Gly Lys Glu Arg Glu Thr Val
        35                  40                  45

Ala Ala Val Ser Arg Asn Ala Gly Ser Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Ala Arg Ser Ala Ala Tyr Ser Arg Ser Glu Tyr Thr Glu
            100                 105                 110

Lys His Asp Tyr Thr Tyr Trp Gly Gln Gly Thr Leu Val Thr Val Lys
            115                 120                 125

Pro

<210> SEQ ID NO 324
<211> LENGTH: 618
<212> TYPE: PRT
<213> ORGANISM: artificial sequence
<220> FEATURE:
<223> OTHER INFORMATION: human DLL3

<400> SEQUENCE: 324

```
Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Pro Gly Ala Pro Arg Ser
        35                  40                  45

Pro Cys Ser Ala Arg Leu Pro Cys Arg Leu Phe Phe Arg Val Cys Leu
    50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
    130                 135                 140

Arg Val Ala Gly Arg Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
        355                 360                 365
```

-continued

```
Leu Asp Leu Gly His Ala Leu Arg Cys Arg Cys Arg Ala Gly Phe Ala
        370                 375                 380

Gly Pro Arg Cys Glu His Asp Leu Asp Cys Ala Gly Arg Ala Cys
385                 390                 395                 400

Ala Asn Gly Gly Thr Cys Val Glu Gly Gly Ala His Arg Cys Ser
                405                 410                 415

Cys Ala Leu Gly Phe Gly Gly Arg Asp Cys Arg Glu Arg Ala Asp Pro
            420                 425                 430

Cys Ala Ala Arg Pro Cys Ala His Gly Gly Arg Cys Tyr Ala His Phe
                435                 440                 445

Ser Gly Leu Val Cys Ala Cys Ala Pro Gly Tyr Met Gly Ala Arg Cys
        450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Leu Pro Pro Ala
                485                 490                 495

Leu Gly Leu Leu Val Ala Ala Gly Val Ala Gly Ala Ala Leu Leu Leu
            500                 505                 510

Val His Val Arg Arg Arg Gly His Ser Gln Asp Ala Gly Ser Arg Leu
515                 520                 525

Leu Ala Gly Thr Pro Glu Pro Ser Val His Ala Leu Pro Asp Ala Leu
        530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
                565                 570                 575

Ile Ser Ala Pro Ser Ile Tyr Ala Arg Glu Val Ala Thr Pro Leu Phe
            580                 585                 590

Pro Pro Leu His Thr Gly Arg Ala Gly Gln Arg Gln His Leu Leu Phe
                595                 600                 605

Pro Tyr Pro Ser Ser Ile Leu Ser Val Lys
        610                 615

<210> SEQ ID NO 325
<211> LENGTH: 4
<212> TYPE: PRT
<213> ORGANISM: Artificial Sequence
<220> FEATURE:
<223> OTHER INFORMATION: Linker

<400> SEQUENCE: 325

Gly Gly Gly Ala
1

<210> SEQ ID NO 326
<211> LENGTH: 5
<212> TYPE: PRT
<213> ORGANISM: Artificial Sequence
<220> FEATURE:
<223> OTHER INFORMATION: Linker

<400> SEQUENCE: 326

Gly Gly Gly Gly Ala
1               5
```

MULTISPECIFIC POLYPEPTIDE CONSTRUCTS CONTAINING A CONSTRAINED CD3 BINDING DOMAIN AND A RECEPTOR BINDING REGION AND METHODS OF USING THE SAME

CROSS-REFERENCE TO RELATED APPLICATIONS

This application claims priority to U.S. provisional application 62/702,888, filed Jul. 24, 2018, entitled "MULTISPECIFIC POLYPEPTIDE CONSTRUCTS CONTAINING A CONSTRAINED CD3 BINDING DOMAIN AND A CO-STIMULATORY RECEPTOR BINDING REGION AND METHODS OF USING THE SAME;" U.S. provisional application 62/744,641, filed Oct. 11, 2018, entitled "MULTISPECIFIC POLYPEPTIDE CONSTRUCTS CONTAINING A CONSTRAINED CD3 BINDING DOMAIN AND A CO-STIMULATORY RECEPTOR BINDING REGION AND METHODS OF USING THE SAME;" and U.S. provisional application 62/832,268, filed Apr. 10, 2019, entitled "MULTISPECIFIC POLYPEPTIDE CONSTRUCTS CONTAINING A CONSTRAINED CD3 BINDING DOMAIN AND A RECEPTOR BINDING REGION AND METHODS OF USING THE SAME," the contents of each of which are incorporated by reference in their entirety for all purposes.

INCORPORATION BY REFERENCE OF SEQUENCE LISTING

The present application is being filed along with a Sequence Listing in electronic format. The Sequence Listing is provided as a file entitled 744952000800SubSeqList.TXT, created Jun. 5, 2022, which is 319,445 bytes in size. The information in the electronic format of the Sequence Listing is incorporated by reference in its entirety.

FIELD

The invention relates generally to multispecific polypeptides that bind at least CD3, a second antigen, and a receptor of a T cell, such as a costimulatory receptor or an inhibitory receptor, in which the multispecific polypeptide constructs are able to engage CD3. In some embodiments, the multispecific polypeptide constructs bind a costimulatory receptor and provide costimulatory binding activity. In some embodiments, the multispecific polypeptide constructs bind an inhibitory receptor and block inhibitory activity. In some aspects, the multispecific polypeptides have constrained CD3 binding and bind to or engage CD3 only upon binding to the second antigen, such as a tumor associated antigen. In some embodiments, the multispecific polypeptide constructs contain cleavable linkers that, when cleaved, result in dual effector functions. Also provided are methods of making and using these multispecific polypeptides in a variety of therapeutic, diagnostic and prophylactic indications.

BACKGROUND

Therapeutic antibodies that cause target cell depletion generally rely on effector functions mediated via interaction with Fc-gamma-receptors (FcγRs) and complement proteins. Effector cells expressing FcγRs are predominantly those of the innate immune system. T-cells are not direct effector cells involved in antibody mediated target cell depletion.

CD3 (Cluster of Differentiation 3) T-cell co-receptor is a multimeric protein composed of four distinct polypeptide chains, referred to as the ε, γ, δ, and ζ chains. The CD3 complex serves as the signaling module of the T cell receptor that associates non-covalently with the antigen-binding a/b chains of T cell receptor (TCR).

Because direct engagement of CD3 results in T-cell activation, it is a desirable target for a variety of therapeutic and/or diagnostic indications. Accordingly, there exists a need for antibodies and therapeutics that target the CD3/TCR pathway.

SUMMARY

Provided herein are multispecific polypeptide constructs containing a first component including an immunoglobulin Fc region and a second component including a CD3-binding region, wherein the first and second components are coupled by a linker, wherein the Fc region is positioned N-terminal to the CD3-binding region; one or both of the first and second components contains at least one antigen binding domain that binds a tumor associated antigen (TAA); and one or both of the first and second components includes at least one co-stimulatory receptor binding region (CRBR) that binds a co-stimulatory receptor. In some embodiments, the CD3-binding region binds CD3 (CD3ε). In some aspects, the multispecific polypeptide construct contains at least or about or two antigen binding domains that binds a TAA and a CRBR. Exemplary constructs are described herein.

Also provided herein are multispecific polypeptide constructs containing a first component including an immunoglobulin Fc region and a second component including a CD3-binding region, wherein the first and second components are coupled by a linker, wherein the Fc region is positioned N-terminal to the CD3-binding region; one or both of the first and second components contains at least one antigen binding domain that binds a tumor associated antigen (TAA); and one or both of the first and second components includes at least one inhibitory receptor binding region (IRBR) that binds a inhibitory receptor. In some embodiments, the CD3-binding region binds CD3 (CD3ε). In some aspects, the multispecific polypeptide construct contains at least or about or two antigen binding domains that binds a TAA and a IRBR. Exemplary constructs are described herein.

Also provided herein are multispecific polypeptide constructs containing a first component including an immunoglobulin Fc region and a second component including a CD3-binding region, wherein the first and second components are coupled by a linker, wherein the Fc region is positioned N-terminal to the CD3-binding region; one or both of the first and second components contains at least one antigen binding domain that binds a tumor associated antigen (TAA); one or both of the first and second components includes at least one inhibitory receptor binding region (IRBR) that binds a inhibitory receptor; and one or both of the first and second components includes at least one costimulatory receptor binding region (CRBR) that binds a costimulatory receptor. In some embodiments, the CD3-binding region binds CD3 (CD3ε). In some aspects, the multispecific polypeptide construct contains at least or about or two antigen binding domains that binds a TAA, a CRBR and a IRBR. Exemplary constructs are described herein.

In some embodiments, the at least one antigen binding domain is positioned amino-terminally relative to the Fc region and/or carboxy-terminally relative to the CD3 binding region of the multispecific polypeptide construct. In some embodiments, the at least one co-stimulatory receptor binding region (CRBR) is positioned amino-terminally relative to the Fc region and/or carboxy-terminally relative to the CD3 binding region of the multispecific polypeptide construct.

In some embodiments, the first component includes a first antigen binding domain and the second component includes a second antigen binding domain, wherein each of the antigen binding domains bind a tumor associated antigen (TAA). In some embodiments, the first antigen binding domain is positioned amino-terminally relative to the Fc region of the multispecific construct and the second antigen binding domain is positioned carboxy-terminally relative to the CD3 binding region of the multispecific construct. In some embodiments, the first or the second component further contains the co-stimulatory receptor binding region (CRBR).

Provided herein are multispecific polypeptide constructs containing in order, from N-terminus to C-terminus: a co-stimulatory receptor binding region (CRBR) that binds a co-stimulatory receptor and/or an antigen binding domain that binds a tumor-associated antigen (TAA); an immunoglobulin Fc region; a linker; a CD3 binding region that binds CD3 (CD3ε); and a co-stimulatory receptor binding region (CRBR) that binds a co-stimulatory receptor and/or an antigen binding domain that binds to a tumor-associated antigen (TAA); wherein the multispecific polypeptide construct includes at least one CRBR and at least one antigen binding domain. In some embodiments, the multispecific polypeptide construct contains only one co-stimulatory receptor binding region (CRBR). In some embodiments, the multispecific polypeptide construct contains two antigen binding domains that binds to a TAA. In some embodiments, the antigen binding domains bind to the same tumor-associated antigen (TAA). In some embodiments, one antigen binding domain is positioned amino-terminally relative to the Fc region and one antigen binding domain is positioned carboxy-terminally relative to the CD3 binding region.

Provided herein are multispecific polypeptide constructs containing in order, from N-terminus to C-terminus: an immunoglobulin Fc region; a linker; a CD3 binding region that binds CD3 (CD3ε); and an antigen binding domain that binds a tumor-associated antigen (TAA) and a co-stimulatory receptor binding region (CRBR) that binds a co-stimulatory receptor. Provided herein are multispecific polypeptide constructs, wherein the multispecific construct includes in order, from N-terminus to C-terminus: an antigen binding domain that binds a tumor-associated antigen (TAA) and a co-stimulatory receptor binding region (CRBR) that binds a co-stimulatory receptor; an immunoglobulin Fc region; a linker; and a CD3 binding region that binds CD3 (CD3ε).

In some of any such embodiments, the Fc region is a homodimeric Fc region. In some examples, the Fc region is an Fc region of a human IgG1, a human IgG2, a human IgG3, or a human IgG4, or is an immunologically active fragment thereof. In some cases, the Fc region includes a polypeptide includes the amino acid sequence set forth in SEQ ID NO: 1 or a sequence of amino acids that has at least 90%, 91%, 92%, 93%, 94%, 95%, 96%, 97%, 98%, 99% sequence identity to SEQ ID NO:1. In some embodiments, the Fc region includes a polypeptide includes the amino acid sequence set forth in SEQ ID NO: 2 or a sequence of amino acids that has at least 90%, 91%, 92%, 93%, 94%, 95%, 96%, 97%, 98%, 99% sequence identity to SEQ ID NO:2; the Fc region includes a polypeptide includes the amino acid sequence set forth in SEQ ID NO: 4 or a sequence of amino acids that has at least 90%, 91%, 92%, 93%, 94%, 95%, 96%, 97%, 98%, 99% sequence identity to SEQ ID NO:4; or the Fc region includes a polypeptide includes the amino acid sequence set forth in SEQ ID NO: 5 or a sequence of amino acids that has at least 90%, 91%, 92%, 93%, 94%, 95%, 96%, 97%, 98%, 99% sequence identity to SEQ ID NO:5.

In some embodiments, the Fc region is a heterodimeric Fc region. In some embodiments, one or both Fc polypeptides of the heterodimeric Fc region includes at least one modification to induce heterodimerization compared to a polypeptide of a homodimeric Fc region, optionally compared to the Fc polypeptide set forth in SEQ ID NO:1 or an immunologically active fragment thereof. In some embodiments, each of the Fc polypeptides of the heterodimeric Fc independently contain at least one amino acid modification. In some embodiments, each of the Fc polypeptides of the heterodimeric Fc include a knob-into-hole modification or include a charge mutation to increase electrostatic complementarity of the polypeptides. In some cases, the amino acid modification is a knob-into-hole modification.

In some embodiments, the first Fc polypeptide of the heterodimeric Fc includes the modification selected from among Thr366Ser, Leu368Ala, Tyr407Val, and combinations thereof and the second Fc polypeptide of the heterodimeric Fc includes the modification Thr366Trp. In some embodiments, the first and second Fc polypeptides further includes a modification of a non-cysteine residue to a cysteine residue, wherein the modification of the first polypeptide is at one of the position Ser354 and Tyr349 and the modification of the second Fc polypeptide is at the other of the position Ser354 and Tyr349. In some embodiments, the amino acid modification is a charge mutation to increase electrostatic complementarity of the polypeptides.

In some embodiments, the first and/or second Fc polypeptides or each of the first and second Fc polypeptide include a modification in complementary positions, wherein the modification is replacement with an amino acid having an opposite charge to the complementary amino acid of the other polypeptide. In some embodiments, one of the first or second Fc polypeptide of the heterodimeric Fc further includes a modification at residue Ile253. In some cases, the modification is Ile253Arg. In some instances, one of the first or second Fc polypeptide of the heterodimeric Fc further includes a modification at residue His435. In some examples, the modification is His435Arg. In some embodiments, the Fc region includes a polypeptide that lacks Lys447.

In some embodiments, the Fc region includes a polypeptide containing at least one modification to enhance FcRn binding. In some examples, the modification is at a position selected from the group consisting of Met252, Ser254, Thr256, Met428, Asn434, and combinations thereof. In some embodiments, the modification is at a position selected from the group consisting of Met252Y, Ser254T, Thr256E, Met428L, Met428V, Asn434S, and combinations thereof. In some embodiments, the modification is at position Met252 and at position Met428. In some embodiments, the modification is Met252Y and Met428L. In some embodiments, the modification is Met252Y and Met428V.

In some embodiments, the first polypeptide of the heterodimeric Fc includes the sequence of amino acids set forth in any of SEQ ID NOS:82, 86, 94 or 96, and the second polypeptide of the heterodimeric Fc includes the sequence of amino acids set forth in any of SEQ ID NOS:83, 87, 90, 92, 98 or 100. In some embodiments, the Fc region includes a polypeptide including at least one amino acid modification that reduces effector function and/or reduces binding to an effector molecule selected from an Fc gamma receptor or C1q. In some embodiments, the one or more amino acid modification is deletion of one or more of Glu233, Leu234 or Leu235. In some embodiments, the first polypeptide of the heterodimeric Fc includes the sequence of amino acids set forth in any of SEQ ID NOS: 84, 88, 95 or 97 and the second polypeptide of the heterodimeric Fc includes the sequence of amino acids set forth in any of SEQ ID NOS: 85, 89, 91, 93, 99 or 101. In some embodiments, the Fc region includes a polypeptide including at least one modification to enhance FcγR binding. In some embodiments, the modification is modification at Ser239 or Ile332. In some embodiments, the glycosylation of the Fc region is modified to enhance FcγR binding as compared to an unmodified Fc region. In some embodiments, the Fc region lacks or has reduced fucose content.

In some of any such embodiments, the CD3 binding region is an anti-CD3 antibody or antigen-binding fragment. In some embodiments, the anti-CD3 antibody or antigen binding fragment includes a variable heavy chain region (VH) and a variable light chain region (VL). In some embodiments, the CD3 binding region is monovalent. In some embodiments, the CD3 binding region is an variable fragment (Fv) including a variable heavy chain region (VH) and a variable light chain region (VL). In some embodiments, the anti-CD3 antibody or antigen binding fragment is not a single chain antibody, optionally is not a single chain variable fragment (scFv). In some embodiments, the Fc is a heterodimeric Fc and the VH and VL that contain the anti-CD3 antibody or antigen binding fragment are linked to opposite polypeptides of the heterodimeric Fc.

In some embodiments, the CD3 binding region is not able to, or is not substantially able to, bind or engage CD3 unless at least one of the antigen binding domain is bound to its TAA. In some embodiments, the CD3 binding region is not able to, or is not substantially able to, bind or engage CD3 unless at least two of the antigen binding domain is bound to its TAA.

In some embodiments, the linker is a polypeptide linker. In some examples, the linker is a polypeptide of up to 25 amino acids in length. In some embodiments, the linker is a polypeptide of from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids. In some embodiments, the linker is a polypeptide that is 3, 4, 5, 6, 7, 8, 9, 10, 11, 12, 13, 14, 15, 16, 17, 18, 19 or 20 amino acids in length. In some instances, the linker is a polypeptide that is 3 to 18 amino acids in length. In some embodiments, the linker is a polypeptide that is 12 to 18 amino acids in length. In some embodiments, the linker is a polypeptide that is 15 to 18 amino acids in length.

In some embodiments, the linker is a non-cleavable linker. In some embodiments, the non-cleavable linker does not contain a substrate recognition site that is specifically recognized for cleavage by a protease. In some embodiments, the non-cleavable linker includes GS, GGS, GGGGS (SEQ ID NO:149), GGGGGS (SEQ ID NO:135) and combinations thereof. In some embodiments, the non-cleavable linker includes (GGS)n, wherein n is 1 to 10. In some embodiments, the non-cleavable linker includes (GGGGS)n (SEQ ID NO: 173), wherein n is 1 to 10. In some embodiments, the non-cleavable linker includes (GGGGGS)n (SEQ ID NO:172), wherein n is 1 to 4. In some instances, the non-cleavable linker includes GGS. In some embodiments, the non-cleavable linker includes GGGGS (SEQ ID NO: 149). In some embodiments, the non-cleavable linker includes GGGGGS (SEQ ID NO: 135). In some embodiments, the non-cleavable linker includes (GGS)$_2$ (SEQ ID NO: 10). In some embodiments, the non-cleavable linker includes GGSGGSGGS (SEQ ID NO: 11). In some embodiments, the non-cleavable linker includes GGSGGSGGSGGS (SEQ ID NO: 12). In some cases, the non-cleavable linker includes GGSGGSGGSGGSGGS (SEQ ID NO: 13). In some embodiments, the non-cleavable linker includes GGGGGSGGGGGSGGGGGS (SEQ ID NO: 119). In some embodiments, the non-cleavable linker includes GGSGGGGSGGGGSGGGGS (SEQ ID NO: 147). In some embodiments, the non-cleavable linker includes and GGGGSGGGGSGGGGS (SEQ ID NO:170).

In some embodiments, the linker is a cleavable linker.

Provided herein are multispecific polypeptide constructs containing a first component including a heterodimeric Fc region and a second component including an anti-CD3 antibody or antigen-binding fragment including a variable heavy chain region (VH) and a variable light chain region (VL), wherein the VH and VL that include the anti-CD3 antibody or antigen binding fragment are linked to opposite polypeptides of the heterodimeric Fc; the first and second components are coupled by a cleavable linker, wherein the heterodimeric Fc region is positioned N-terminal to the anti-CD3 antibody; one or both of the first and second components includes at least one antigen binding domain that binds a tumor associated antigen (TAA); and one or both of the first and second components includes at least one co-stimulatory receptor binding region (CRBR) that binds a co-stimulatory receptor. In some embodiments, binding of the CD3-binding region to CD3 is substantially reduced when the multispecific polypeptide construct is in an uncleaved state compared to a cleaved state. In some embodiments, in a cleaved state, the first and second components are not linked.

In some embodiments, the cleavable linker is a polypeptide that functions as a substrate for a protease. In some embodiments, the protease is produced by an immune effector cell, by a tumor, or by cells present in the tumor microenvironment. In some embodiments, the protease is produced by an immune effector cell and the immune effector cell is an activated T cell, a natural killer (NK) cell, or an NK T cell. In some embodiments, the protease is selected from among matriptase, a matrix metalloprotease (MMP), granzyme B, and combinations thereof. In some instances, the protease is granzyme B.

In some embodiments, the cleavable linker includes an amino acid sequence of the general formula P4 P3 P2 P1↓P1' (SEQ ID NO: 150), wherein P4 is amino acid I, L, Y, M, F, V, or A; P3 is amino acid A, G, S, V, E, D, Q, N, or Y; P2 is amino acid H, P, A, V, G, S, or T; P1 is amino acid D or E; and P1' is amino acid I, L, Y, M, F, V, T, S, G or A. In some embodiments, the cleavable linker includes an amino acid sequence of the general formula P4 P3 P2 P1↓P1' (SEQ ID NO: 151), wherein P4 is amino acid I or L;

P3 is amino acid E; P2 is amino acid P or A; P1 is amino acid D; and P1' is amino acid I, V, T, S, or G. In some embodiments, the cleavable linker includes the amino acid sequence IEPDI (SEQ ID NO:136), LEPDG (SEQ ID NO:152, LEADT (SEQ ID NO:137), IEPDG (SEQ ID NO:138), IEPDV (SEQ ID NO:139), IEPDS (SEQ ID NO:140), IEPDT (SEQ ID NO:141) or LEADG (SEQ ID NO:153). In some embodiments, the cleavable linker includes an amino acid sequence selected from the group consisting of SEQ ID NOs:22, 105-112, 136-141, 148, 150-153. In some examples, the cleavable linker includes the amino acid sequence set forth in SEQ ID NO:105.

In some embodiments, the protease is matriptase. In some embodiments, the cleavable linker includes the sequence P1QAR↓(A/V) (SEQ ID NO: 154), wherein P1 is any amino acid; or the cleavable linker includes the sequence RQAR (A/V) (SEQ ID NO: 155). In some examples, the cleavable linker includes the sequence RQARV (SEQ ID NO: 156). In some embodiments, the cleavable linker includes an amino acid sequence selected from the group consisting of SEQ ID NOs: 23, 154-156. In some embodiments, the protease is an MMP. In some embodiments, the MMP is MMP-2. In some examples, the cleavable linker contains the general formula P3 P2 P1↓P1' (SEQ ID NO: 157), wherein P3 is P, V or A; P2 is Q or D; P1 is A or N; and P1' is L, I or M. In some embodiments, the cleavable linker contains the general formula P3 P2 P1↓P1' (SEQ ID NO: 158), wherein P3 is P; P2 is Q or D; P1 is A or N; and P1' is L or I. In some instances, the cleavable linker includes the sequence PAGL (SEQ ID NO:24). In some embodiments, the cleavable linker includes an amino acid sequence selected from the group consisting of SEQ ID NOs:22-31, 104-114, 117-118, 136-144, 148, 150-158.

In some embodiments, the multispecific polypeptide construct includes at least a first polypeptide comprising the first Fc polypeptide of the heterodimeric Fc region, the linker and the VH or VL domain of the anti-CD3 antibody or antigen binding fragment; and a second polypeptide comprising the second Fc polypeptide of the heterodimeric Fc region, the linker, optionally the same linker as present in the first polypeptide, and the other of the VH or VL domain of the anti-CD3 antibody or antigen binding fragment, wherein one or both of the first and second polypeptide comprise at least one antigen-binding domain that binds to a tumor associated antigen (TAA) and one or both of the first and second components comprises at least one co-stimulatory receptor binding region (CRBR) that binds a co-stimulatory receptor, wherein the multispecific polypeptide construct contains at least one CRBR and at least one antigen binding domain.

In some embodiments, only one of the first or second polypeptide includes the at least one antigen-binding domain that binds a TAA. In some embodiments, the at least one antigen binding domain is positioned amino-terminally relative to the Fc region and/or is positioned carboxy-terminally relative to the CD3 binding region of one of the first or second polypeptide of the multispecific polypeptide construct. In some embodiments, the at least one antigen binding domain is positioned amino-terminally relative to the Fc region of the multispecific construct and the second antigen binding domain is positioned carboxy-terminally relative to the CD3 binding region of the multispecific construct. In some embodiments, only one of the first or second polypeptide includes the at least one co-stimulatory receptor binding region (CRBR) that binds a co-stimulatory receptor. In some embodiments, the co-stimulatory receptor binding region (CRBR) is positioned amino-terminally relative to the Fc region or is positioned carboxy-terminally relative to the CD3 binding region of one of the first or second polypeptide of the multispecific polypeptide construct.

In some embodiments, the first polypeptide contains in order of N-terminus to C-terminus: a first antigen binding domain that binds a tumor-associated antigen (TAA), the first Fc polypeptide of the heterodimeric Fc region, the linker, the VL or VH of the anti-CD3 antibody or antigen binding fragment, and a second antigen binding domain that binds a tumor-associated antigen (TAA); and the second polypeptide contains in order of N-terminus to C-terminus: the second Fc polypeptide of the heterodimeric Fc region, the linker, optionally the same linker as present in the first polypeptide, the other of the VH or VL of the anti-CD3 antibody or antigen binding fragment, and the co-stimulatory receptor binding region (CRBR) that binds a co-stimulatory receptor.

In some embodiments, the antigen binding domain, or independently each of the antigen binding domains, contains an extracellular domain or binding fragment thereof of the native cognate binding partner of the TAA, or a variant thereof that exhibits binding activity to the TAA. In some embodiments, the antigen binding domain, or independently each of the antigen binding domains, is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

In some embodiments, the at least one co-stimulatory receptor binding region (CRBR) is or contains the extracellular domain or binding fragment thereof of the native cognate binding partner of the co-stimulatory receptor, or a variant thereof that exhibits binding activity to the co-stimulatory receptor. In some embodiments, the at least one co-stimulatory receptor binding region (CRBR) is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody. In some embodiments, the antibody or antigen-binding fragment thereof is a Fv, a scFv, a Fab, a single domain antibody (sdAb), a VNAR, or a VHH. In some examples, the antibody or antigen-binding fragment is an sdAb. In some embodiments, the sdAb is a human or humanized sdAb. In some embodiments, the sdAb is VHH, VNAR, an engineered VH domain or an engineered VK domain. In some embodiments, the antibody or antigen-binding fragment thereof is an scFv. In some embodiments, the antibody or antigen-binding fragment thereof is a Fab.

In some embodiments, the multispecific polypeptide construct contains a first polypeptide containing the first Fc polypeptide of the heterodimeric Fc region, the linker and the VH domain of the anti-CD3 antibody or antigen binding fragment; a second polypeptide containing the second Fc polypeptide of the heterodimeric Fc region, the linker and the VL domain of the anti-CD3 antibody or antigen binding fragment, a third polypeptide containing a VH-CH1 (Fd) or VL-CL of a Fab antibody fragment that binds to a tumor-associated antigen, a fourth polypeptide containing a VH-CH1 (Fd) or VL-CL of a Fab antibody fragment that binds to a co-stimulatory receptor, wherein the first and/or second polypeptide further contains (1) the other of the VH-CH1 (Fd) or VL-CL of the Fab antibody fragment that binds to the tumor-associated antigen and the (2) other of the VH-CH1 (Fd) or VL-CL of the Fab antibody fragment that binds to the co-stimulatory receptor.

In some embodiments, the multispecific polypeptide construct contains a first polypeptide containing the first Fc polypeptide of the heterodimeric Fc region, the linker and the VH domain of the anti-CD3 antibody or antigen binding fragment; a second polypeptide containing the second Fc polypeptide of the heterodimeric Fc region, the linker and the VL domain of the anti-CD3 antibody or antigen binding fragment; and a third polypeptide containing a VH-CH1 (Fd) or VL-CL of a Fab antibody fragment that binds to a co-stimulatory receptor, wherein the first and/or second polypeptide further contains the other of the VH-CH1 (Fd) or VL-CL of the Fab antibody fragment that binds to the co-stimulatory receptor, and the first and/or second polypeptide further contains at least one antigen binding domain that binds a tumor associated antigen (TAA).

In some embodiments, the multispecific polypeptide construct contains a first polypeptide containing the first Fc polypeptide of the heterodimeric Fc region, the linker and the VH domain of the anti-CD3 antibody or antigen binding fragment; a second polypeptide containing the second Fc polypeptide of the heterodimeric Fc region, the linker and the VL domain of the anti-CD3 antibody or antigen binding fragment, and a third polypeptide containing a VH-CH1 (Fd) or VL-CL of a Fab antibody fragment that binds to a tumor-associated antigen, wherein the first and/or second polypeptide further contains the other of the VH-CH1 (Fd) or VL-CL of the Fab antibody fragment that binds to the tumor-associated antigen, and the first and/or second polypeptide further contains at least one co-stimulatory receptor binding region (CRBR) that binds a co-stimulatory receptor.

In some embodiments, only one of the first or second polypeptide contains the other of the VH-CH1 (Fd) or VL-CL of the Fab antibody fragment. In some embodiments, both the first or second polypeptide contains the other of the VH-CH1 (Fd) or VL-CL of the Fab antibody fragment. In some embodiments, the other of the VH-CH1 (Fd) or VL-CL of the Fab antibody fragment is positioned amino-terminally relative to the Fc region and/or at the carboxy-terminally relative to the CD3 binding region of one of the first or second polypeptide of the multispecific polypeptide construct. In some embodiments, the other of the VH-CH1 (Fd) or VL-CL of the Fab antibody fragment is positioned amino-terminally relative to the Fc region of the first polypeptide or second polypeptide and at the carboxy-terminally relative to the CD3 binding region of the other of the first or second polypeptide.

In some of any such embodiments, the antigen binding domain, or independently each of the antigen binding domains, binds to a tumor antigen selected from among 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, the antigen binding domain contains at least a first antigen binding domain and a second antigen binding domain, wherein the first antigen binding domain and second antigen binding domain bind to the same TAA. In some embodiments, the first antigen binding domain and the second antigen binding domain binds a different epitope of the same TAA. In some embodiments, the first antigen binding domain and the second antigen binding domain binds the same epitope of the same TAA. In some embodiments, the antigen binding domain contains at least a first antigen binding domain and a second antigen binding domain wherein the first antigen binding domain and the second antigen binding domain bind a different TAA.

In some embodiments, the co-stimulatory receptor binding region (CRBR) contains at least a first CRBR and a second CRBR, wherein the first CRBR and second CRBR bind to the same co-stimulatory receptor. In some embodiments, the first co-stimulatory receptor binding region (CRBR) and the second CRBR binds a different epitope of the same co-stimulatory receptor. In some embodiments, the first co-stimulatory receptor binding region (CRBR) and the second CRBR binds the same epitope of the same co-stimulatory receptor. In some embodiments, the co-stimulatory receptor binding region (CRBR) contains at least a first CRBR and a second CRBR. In some embodiments, the first CRBR and the second CRBR bind a different co-stimulatory receptor.

In some embodiments, the at least one co-stimulatory receptor binding region (CRBR) binds a co-stimulatory receptor selected from among 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), and NKG2D. In some embodiments, the at least one co-stimulatory receptor binding region (CRBR) binds a co-stimulatory receptor selected from among 41BB (CD137), OX40 (CD134), and glucocorticoid-induced TNFR-related protein (GITR).

In some of any of the provided embodiments, the at least one inhibitory receptor binding region (IRBR) is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody. In some embodiments, the antibody or antigen-binding fragment thereof is a Fv, a scFv, a Fab, a single domain antibody (sdAb), a VNAR, or a VHH. In some embodiments, the antibody or antigen-binding fragment is an sdAb. In some embodiments, the sdAb is a human or humanized sdAb. In some embodiments, the sdAb is VHH, VNAR, an engineered VH domain or an engineered VK domain. In some embodiments, the antibody or antigen-binding fragment thereof is an scFv. In some embodiments, the antibody or antigen-binding fragment thereof is a Fab. In some of any of the provided embodiments herein involving a construct containing at least one inhibitory receptor binding domain, the inhibitory receptor is selected from among PD-1, CTLA-4, TIGIT, VISTA or TIM3, such as expressed on a T cell, for example a human T cell. In some embodiments, the T cell is an activated T cell. In some of any of the provided embodiments, the at least one inhibitory receptor binding region (IRBR) binds PD-1.

In some embodiments, the multispecific polypeptide construct contains a first linking peptide (LP1) between the first antigen binding domain and the Fc region. In some embodiments, the multispecific polypeptide construct contains a second linking peptide (LP2) between the CD3 binding region and the second antigen binding domain. In some embodiments, the multispecific polypeptide construct contains a first linking peptide (LP1) between the first co-stimulatory receptor binding region (CRBR) and the Fc region. In some embodiments, the multispecific polypeptide construct contains a second linking peptide (LP2) between the CD3 binding region and the second co-stimulatory receptor binding region (CRBR). In some embodiments, the multispecific polypeptide construct contains a first linking peptide (LP1) between the antigen binding domain or co-stimulatory receptor binding region and the Fc region and a second linking peptide (LP2) between the CD3 binding region and the antigen binding domain or CRBR, and wherein the multispecific polypeptide construct has the structural arrangement from N-terminus to C-terminus as follows: first antigen binding domain or CRBR-LP1-Fc region-linker-CD3 binding region-LP2-second antigen binding domain or CRBR.

In some embodiments, the linker is a cleavable linker. In some embodiments, the two linking peptides are not identical to each other. In some embodiments, LP1 or LP2 is independently a peptide of about 1 to 20 amino acids in length. In some embodiments, LP1 or LP2 independently contain a peptide that is or includes any Gly-Ser linker as set forth in SEQ ID NOs: 10-13, 119, 135, 147, 149 or GGS.

In some embodiments, the anti-CD3 antibody or antigen binding fragment is an Fv antibody fragment. In some embodiments, the Fv antibody fragment includes a disulfide stabilized anti-CD3 binding Fv fragment (dsFv). In some embodiments, the anti-CD3 antibody or antigen-binding fragment includes a VH CDR1 including the amino acid sequence TYAMN (SEQ ID NO: 16); a VH CD2 including the amino acid sequence RIRSKYNNYATYYADSVKD (SEQ ID NO: 17); a VH CDR3 including the amino acid sequence HGNFGNSYVSWFAY (SEQ ID NO: 18), a VL CDR1 including the amino acid sequence RSSTGAVTTSNYAN (SEQ ID NO: 19); a VL CDR2 including the amino acid sequence GTNKRAP (SEQ ID NO: 20); and a VL CDR3 including the amino acid sequence ALWYSNLWV (SEQ ID NO: 21).

In some examples, the anti-CD3 Fv includes a VH having the amino acid sequence of any of SEQ ID NOS: 14 and 32-62 or a sequence that exhibits at least 90%, 91%, 92%, 93%, 94%, 95%, 96%, 97%, 98% or 99% sequence identity to any of SEQ ID NOS: 14 and 32-62; and a VL having the amino acid sequence of any of SEQ ID NOS: 15 and 63-81 or a sequence that exhibits at least 90%, 91%, 92%, 93%, 94%, 95%, 96%, 97%, 98% or 99% sequence identity to any of SEQ ID NOS: 15 and 63-81.

In some embodiments, the anti-CD3 antibody or antigen-binding fragment is an Fv. In some embodiments, the anti-CD3 Fv comprises: a VH having the amino acid sequence of any of SEQ ID NOS: 14, 32-43, 45-47, 48, and 287 or a sequence that exhibits at least 90%, 91%, 92%, 93%, 94%, 95%, 96%, 97%, 98% or 99% sequence identity to any of SEQ ID NOS: 14, 32-43, 45-47, 48, and 287; and a VL having the amino acid sequence of any of SEQ ID NOS: 15, 63, 65-71, 73, 75, 77, and 288 or a sequence that exhibits at least 90%, 91%, 92%, 93%, 94%, 95%, 96%, 97%, 98% or 99% sequence identity to any of SEQ ID NOS: 15, 63, 65-71, 73, 75, 77, and 288. In some cases, the anti-CD3 Fv comprises the amino acid sequence of SEQ ID NO: 14 and the amino acid sequence of SEQ ID NO: 15. In other cases, the anti-CD3 Fv comprises the amino acid sequence of SEQ ID NO: 287 and the amino acid sequence of SEQ ID NO:288.

In some embodiments, the VH and VL chain regions of the CD3 binding domain each independently comprise at least one amino acid modification. In some embodiments, the at least one amino acid modification of the VH and VL chain regions of the CD3 binding domain increase the stability of the CD3 binding domain. In some embodiments, the at least one amino acid modification of the VH and VL chain regions of the CD3 binding domain increase the ability of the CD3 binding domain to bind CD3. In some embodiments, the at least one amino acid modification of the VH and VL chain regions of the CD3 binding domain increase the stability of the CD3 binding domain by creating a disulfide linkage between the VH and VL chain regions.

In some embodiments, the CD3 binding region has a disulfide stabilized linkage between the VH and VL regions. In some embodiments, the anti-CD3 antibody or antigen-binding fragment is disulfide stabilized Fv (dsFv). In some embodiments, the disulfide stabilized anti-CD3 Fv comprises an anti-CD3 VH with the mutation 44 to Cys and an anti-CD3 VL with the mutation 100 to Cys by Kabat numbering. In some embodiments, the disulfide stabilized anti-CD3 Fv comprises an anti-CD3 VH with the mutation G44C and an anti-CD3 VL with the mutation G100C by Kabat numbering. In some embodiments, the disulfide stabilized anti-CD3 Fv comprises an anti-CD3 VH with the mutation at position 105 to Cys and an anti-CD3 VL with the mutation position 43 to Cys by Kabat numbering. In some embodiments, the anti-CD3 dsFv comprises: a VH having the amino acid sequence of any of SEQ ID NOS: 44, 49-62, 290, and 311 or a sequence that exhibits at least 90%, 91%, 92%, 93%, 94%, 95%, 96%, 97%, 98% or 99% sequence identity to any of SEQ ID NOS: 44, 49-62, 290, and 311; and a VL having the amino acid sequence of any of SEQ ID NOS: 64, 72, 74, 76, 78-81, 241 and 289 or a sequence that exhibits at least 90%, 91%, 92%, 93%, 94%, 95%, 96%, 97%, 98% or 99% sequence identity to any of SEQ ID NOS: 64, 72, 74, 76, 78-81, 241 and 289. In some embodiments, the anti-CD3 dsFv includes the amino acid sequence of SEQ ID NO: 44 and the amino acid sequence of SEQ ID NO: 72. In some embodiments, the anti-CD3 dsFv includes the amino acid sequence of SEQ ID NO: 44 and the amino acid sequence of SEQ ID NO: 241. In some embodiments, the anti-CD3ε binding domain thereof includes a variable heavy chain (VH) comprising the amino acid sequence of SEQ ID NO: 290 and a variable light chain (VL) comprising the amino acid sequence of SEQ ID NO:289. In some embodiments, the anti-CD3ε binding domain thereof includes a variable heavy chain (VH) comprising the amino acid sequence of SEQ ID NO: 311 and a variable light chain (VL) comprising the amino acid sequence of SEQ ID NO:289.

In some of any such embodiments, the multispecific polypeptide construct is conjugated to an agent. In some embodiments, the agent is a therapeutic agent, an antineoplastic agent, a toxin or fragment thereof, a detectable moiety or a diagnostic agent. In some embodiments, the agent is conjugated to the multispecific polypeptide construct via a linker.

Provided herein are polynucleotide(s) encoding any of the provided multispecific polypeptide constructs. Provided herein are polynucleotides encoding any of the provided polypeptide chains of any of the provided multispecific polypeptide constructs. Provided herein are polynucleotides containing a first nucleic acid sequence encoding a first polypeptide of any of the provided multispecific constructs and a second nucleic acid sequence encoding any of the provided second polypeptides of the multispecific construct, wherein the first and second nucleic acid sequence are separated by an internal ribosome entry site (IRES), or a nucleic acid encoding a self-cleaving peptide or a peptide that causes ribosome skipping. In some embodiments, the first nucleic acid sequence and second nucleic acid sequence are operably linked to the same promoter. In some embodiments, the multispecific polypeptide construct contains a third polypeptide chain, and the polynucleotide further contains a third nucleic acid encoding the third polypeptide of the multispecific construct. In some embodiments, the third nucleic acid is separated from the first and/or second polypeptide by an internal ribosome entry site (IRES), or a nucleic acid encoding a self-cleaving peptide or a peptide that causes ribosome skipping and/or the third nucleic acid sequence is operably linked to the same promoter as the first and/or second nucleic acid sequence. In some embodiments, the nucleic acid encoding a self-cleaving peptide or a peptide that causes ribosome skipping is selected from a T2A, a P2A, a E2A or a F2A.

Provided herein are vectors containing any of the provided polynucleotides. In some embodiments, the vector is an expression vector. In some embodiments, the vector is a viral vector or a eukaryotic vector, optionally wherein the eukaryotic vector is a mammalian vector.

Provided herein are cells containing polynucleotides or any of the provided polynucleotides, vectors or any of the provided vectors. In some embodiments, the cell is recombinant or isolated. In some embodiments, the cell is a mammalian cell. In some embodiments, the cell is a HEK293 or CHO cell.

Provided herein are methods of producing a multispecific polypeptide construct including introducing into a cell a polynucleotide or any of the provided polynucleotides or a vector or any of the provided vectors and culturing the cell under conditions to produce the multispecific polypeptide construct.

Provided herein are methods of producing a multispecific polypeptide construct including culturing any of the provided cells under conditions in which the multispecific polypeptide is produced by the cell. In some embodiments, the cell is a mammalian cell. In some examples, the cell is a HEK293 or CHO cell. In some embodiments, the method further includes isolating or purifying the multispecific polypeptide construct from the cell. In some embodiments, the multispecific polypeptide construct is a heterodimer.

Provided herein are multispecific polypeptide constructs produced by any of the methods provided.

Provided herein are pharmaceutical compositions containing any of the provided multispecific polypeptide constructs and a pharmaceutically acceptable carrier. In some embodiments, the pharmaceutical composition is sterile.

Provided herein are methods of stimulating or inducing an immune response, the method including contacting a target cell and a T cell with any of the provided multispecific polypeptide constructs or pharmaceutical compositions, said target cell expressing a tumor associated antigen recognized by the multispecific polypeptide construct. In some embodiments, the target cell is a tumor cell expressing the tumor associated antigen (TAA). In some embodiments, the multispecific polypeptide construct includes a cleavage linker that functions as a substrate for a protease and the inducing or stimulating the immune response is increased in the presence of the protease. In some embodiments, the protease is produced by an immune effector cell, by a tumor, or by cells present in the tumor microenvironment. In some embodiments, the protease is produced by an immune effector cell and the immune effector cell is an activated T cell, a natural killer (NK) cell, or an NK T cell. In some embodiments, the immune effector cell is in proximity to cells that express the antigen. In some embodiments, the protease is produced by a tumor that is in proximity to cells that express the TAA in a tissue and/or produced by a tumor that is co-localized with TAA in a tissue, and wherein the protease cleaves the cleavable linker in the multispecific polypeptide construct when the multispecific polypeptide construct is exposed to the protease.

In some embodiments, the protease is selected from among matriptase, a matrix metalloprotease (MMP), granzyme B, and combinations thereof. In some embodiments, the protease is granzyme B. In some embodiments, the contacting is carried out ex vivo or in vitro. In some embodiments, the contacting is carried out in vivo in a subject.

Provided herein are methods of stimulating or inducing an immune response in a subject including administering, to a subject in need thereof, a therapeutically effective amount of any of the provided multispecific conjugates or pharmaceutical compositions. In some embodiments, the method increases cell-mediated immunity. In some embodiments, the method increases T-cell activity. In some embodiments, the method increases cytolytic T-cell (CTL) activity. In some embodiments, the immune response is increased against a tumor or cancer. In some embodiments, the method treats a disease or condition in the subject.

Provided herein are methods of treating a disease or condition in a subject, the method including administering, to a subject in need thereof, a therapeutically effective amount of any of the provided multispecific conjugates of or any of the provided pharmaceutical compositions. In some embodiments, the disease or condition is a tumor or a cancer. In some embodiments, said subject is a human.

One skilled in the art will appreciate that the antibodies of the disclosure have a variety of uses. For example, the proteins of the disclosure are used as therapeutic agents for a variety of disorders. The antibodies of the disclosure are also used as reagents in diagnostic kits or as diagnostic tools, or these antibodies can be used in competition assays to generate therapeutic reagents.

BRIEF DESCRIPTION OF DRAWINGS

FIG. 2A depicts representative B7H3-targeted constrained CD3 engagers without a 4-1BB binding domain as a CRBR (designated cx3095 or cx3834). cx3834 has the reverse knob and hole configuration in comparison to cx3095, such that the first polypeptide chain of cx3834 depicted in FIG. 2A contains the Fc hole polypeptide and the second polypeptide depicted has the Fc knob polypeptide. Representative B7H3-targeted constrained CD3 engager with a 41BB binding domain as a CRBR are depicted in FIG. 2B (designated cx3091), cx3091 has a 41BB-targeting sdAb positioned at the C-termini of the opposite chain of the heterodimer and thereby display monovalent binding to 41BB. Each of the representative constructs cx3095, cx3834 and cx3091 have a B7H3-targeting sdAb positioned at the N and C-termini of one chain of the heterodimer and thereby display bivalent binding to B7H3. FIG. 2C-2F depict representative B7H3-targeted constrained CD3 engagers with B7H3-targeting sdAb positioned at the N and C-termini of one chain of the heterodimer and a CRBR (e.g. OX40, GITR, ICOS, or CD28 sdAb) positioned at the C-termini of the opposite chain of the heterodimer.

FIG. 3 depicts representative 5T4-targeted constrained CD3 engagers without (top) and with a 41BB binding domain (bottom). cx3546 and cx3547 have the same 5T4-targeting sdAb (12E9) positioned at the N-termini of one chain of the heterodimer and distinct 5T4-targeting sdAbs (14B5 or 16G10, respectively) positioned at the C-termini of one chain of the heterodimer. cx3499 and cx3497 are identical to cx3546 and cx3547, respectively, but have a 41BB-targeting sdAb positioned at the C-termini of the opposite chain of the Fc heterodimer. Each of cx3546, cx3547, cx3499 and cx3497 contain a cleavable linker between the Fc region and the CD3 binding region. cx5185 and cx5951 are the same but the former includes a 4-1BB targeting sdAb positioned C-terminally to the CD3 binding region; both contain a non-cleavable linker between the Fc region and the CD3 binding region and contain humanized versions of the 5T4-targeting sdAbs, hz12E9v9 and hz16G10v11, positioned at the N- and C-termini of the Fc heterodimer. These representative 5T4-targeted constrained CD3 engagers display bivalent binding to 5T4 and in constructs containing a 41BB binding domain, display monovalent binding to 41BB.

FIG. 4B shows binding to A375 cells (a B7H3 positive melanoma cell line) of each of the assessed constructs. FIG. 4C and FIG. 4D depicts binding to T-cells and demonstrates binding only by the DART-Fc format B7H3×CD3 but lack of binding to T-cells by the constrained CD3 engagers containing a 41BB binding domain (cx3091) or lacking a 41BB binding domain (cx3095). FIG. 4A and FIG. 4C display histograms of the normalized cell counts vs fluorescence at 200 nM of each construct. The full titration of each construct on the various cell types are shown in FIG. 4B and FIG. 4D. In FIG. 4A and FIG. 4C, the secondary anti-human APC antibody only control is shown in the filled black trace, while the positive control anti-CD3 binding is shown in the open trace, and cx3091, cx3095 and DART-Fc B7H3×CD3 are shown in the gray shaded traces in FIG. 4A and FIG. 4C.

FIG. 5A and FIG. 5B show binding to Ovcar-5 cells (a 5T4 positive melanoma cell line). FIG. 5C and FIG. 5D depict binding to T cells and show the lack of binding to T-cells in isolation by the tested constructs. FIG. 5A and FIG. 5C display histograms of the normalized cell counts vs fluorescence at 200 nM of each construct. The full titration of each construct on the various cell types are shown in FIG. 5B and FIG. 5D. In FIGS. 5A and 5C, the secondary anti-human APC antibody only control is shown in the filled black trace, while the positive control anti-CD3 binding is shown in the open trace, and cx3497 and cx3547 are shown in the gray shaded traces in FIG. 5A and FIG. 5C.

In FIG. 6A, a representative B7H3-targeted constrained CD3 engaging construct that contains a 41BB binding domain, cx3091 compared to the similar construct lacking a 41BB binding domain, cx3095 was assessed against a Jurkat 41BB NFκB-Luciferase reporter cells to assess 41BB agonism in the presence of a B7H3 positive cell line, A375 and cognate A375 B7H3 knock-out cell line (A375 ΔB7H3). Notably, cx3091 was capable of potent and robust 41BB agonism. cx3095 induced a minor amount NFκB signaling likely mediated by TCR/CD3 signaling, independent of 41BB signaling. In FIGS. 6B and 6C, representative B7H3-targeted constrained CD3 enaging constructs containing a 41BB binding domain (cx3091), an OX40 binding domain (cx3723), or no CRBD (cx3834) were assessed against an OX40 reporter Jurkat cell line (FIG. 6B) or a 41BB reporter Jurkat cell line (FIG. 6C) in co-cultures with A375 target antigen-expressing cells.

FIG. 8A and FIG. 8B show T-cell mediated cytotoxicity as determined by total cell apoptosis by caspase activation (cells positive for caspase-3/7 substrate) among labeled target cells in the respective cell lines. FIGS. 8C and 8D depict depletion of the target cells resulting from T-cell mediated cytotoxicity.

FIG. 11A and FIG. 11B show CD4 T-cell activation, whereas FIGS. 11C and 11D show CD8 T-cell activation. T-cell activation as evidenced by CD71 upregulation was measured by flow cytometry.

FIGS. 14A and 14B demonstrates the capacity of constrained CD3 engaging constructs incorporating a co-stimulatory receptor binding domain to mediate specific agonism of the respective co-stimulatory signaling pathway. Herein a Jurkat OX40 (FIG. 14A) or Jurkat 41BB (FIG. 14B) NFκB-Luciferase reporter cell was used. Exemplary B7H3-targeting constrained CD3 engaging constructs incorporating either no co-stimulatory receptor binding domain (cx3834), an OX40 binding domain (cx3723) or a 41BB binding domain (cx3091) were used herein. cx3723 and cx3091 incorporating either OX40 or 41BB binding domain, respectively, were found to induce specific agonism of the co-stimulatory receptor targeted. Some induced NFκB signaling was observed with all constructs including the no co-stimulatory receptor binding region containing construct, suggesting that target dependent CD3 signaling mediates NFκB signaling in this system. The B7H3 positive cell line A375 was used.

FIG. 19A is a schematic of various B7H3-targeting constrained CD3 constructs composed of two polypeptides, Chain 1 and Chain 2. Chain 1 contains either a heterodimeric Fc "hole," linked via a non-cleavable linker to an anti-CD3 VL domain modified at G100C (top); a B7H3-targeting sdAb linked to a heterodimeric Fc "hole," linked via a non-cleavable linker to an anti-CD3 VL domain (middle); or an B7H3-targeting sdAb linked to a heterodimeric Fc "hole," linked via a non-cleavable linker to an anti-CD3 VL domain modified at G100C (bottom). Chain 2 contains either a B7H3-targeted sdAb, linked to a complementary heterodimeric Fc "knob," linked via the linker as above to an anti-CD3 VH domain modified at G44C linked to second B7H3 sdAb (top); a B7H3-targeted sdAb, linked to a complementary heterodimeric Fc "knob," linked via the linker as above to an anti-CD3 VH domain (middle); or a B7H3-targeted sdAb, linked to a complementary heterodimeric Fc "knob," linked via the linker as above to an anti-CD3 VH domain modified by G44C (bottom). When co-expressed the CD3 binding domain is properly assembled via the association of the VL:VH on the hole and knob, respectively. Where denoted the VH:VL interaction is stabilized by an engineered disulfide bond between the modified residues G44C in the VH domain and G100C in the VL domain.

FIG. 19C is a schematic of various B7H3-targeting constrained CD3 constructs composed of three polypeptides, Chain 1, Chain 2 and Chain 3, wherein the B7H3 targeting domain is a FAB. Chain 1 contains a BH73-targeting VH, an IgG Constant Heavy 1 (CH1) linked via a hinge to a first member of a heterodimeric Fc (Fc-Het-1), linked via the linker as above to an anti-CD3 VL domain that either lacks (top) or contains the modification of G100C (bottom). Chain 2 contains a BH73-targeting VH, an IgG Constant Heavy 1 (CH1) linked via a hinge to a second member of a heterodimeric Fc (Fc-Het-2), linked via the linker as above to an anti-CD3 VH domain that either lacks (top) or contains the modification of G44C (bottom). Chain 3 contains a complementary B7H3-targeting VL domain linked to human Ig Constant Light (CL) region. When co-expressed the CD3 binding domain is properly assembled via the association of the VL:VH on the complimentary heterodimeric Fc regions. Where denoted the VH:VL interaction is stabilized by an engineered disulfide bond between the modified residues G44C in the VH domain and G100C in the VL domain.

FIG. 20 is a schematic of three DLL3-targeting constrained CD3 constructs composed of two polypeptides, Chain 1 and Chain 2. Chain 1 contains a heterodimeric Fc "hole", linked via a non-cleavable linker to an anti-CD3 VL domain modified at G100C linked to a co-stimulatory receptor targeting sdAb. Chain 2 contains either a DLL3-targeted sdAb, linked to a complementary heterodimeric Fc "knob", linked via the linker as above to an anti-CD3 VH domain modified at G44C linked to second DLL3-targeted sdAb (top); a heterodimeric Fc "knob", linked via the linker as above to an anti-CD3 VH domain modified at G44C linked to a DLL3-targeted sdAb (middle); or a DLL3-targeted sdAb, linked to a complementary heterodimeric Fc "knob", linked via the linker as above to an anti-CD3 VH domain modified by G44C (bottom).

FIG. 21A shows binding to B7H3 positive A375 cells. FIG. 21B shows the lack of binding to B7H3 negative CCRF-CEM cells and isolated T-cells.

FIG. 21C shows that engaging B7H3 positive A375 cells with a molecule that is bivalent and bi-epitopic to B7H3 (cx5187) induced more potent CD3 signaling than constructs that are monovalent to B7H3 (cx5873 and cx5965). FIG. 21D shows the lack of activation of T-cells in the presence of B7H3 negative CCRF-CEM cells. A Jurkat CD3 NFAT-GFP reporter cell line was used to assess CD3 agonism.

FIG. 22A shows that targeting B7H3 positive A375 cells with a construct that is bivalent and bi-epitopic to B7H3 (cx5187) induced more potent T-cell mediated cytotoxicity than constructs that are monovalent to B7H3 (cx5873 and cx5965). FIG. 22B depicts the lack of T-cell mediated cytotoxicity against B7H3 negative CCRF-CEM cells.

FIG. 23A-D depict the ability of representative B7H3-targeting constrained CD3 engaging molecules to activate T-cells in the presence of B7H3 positive A375 cells, but not in the presence of B7H3 negative CCRF-CEM cells. FIGS. 23A and 23B show that targeting B7H3 positive A375 cells with a construct that is bivalent and bi-epitopic to B7H3 (cx5187), induced more potent CD25 expression on CD4+ and CD8+ T-cells, respectively, than constructs that are monovalent to B7H3 (cx5873 and cx5965). FIGS. 23C and 23D show the lack of CD25 expression on CD4+ and CD8+ T-cells, respectively, in the presence of B7H3 negative CCRF-CEM cells.

FIG. 31A depicts various representative B7H3-targeted constrained CD3 engagers with a 4-1BB binding domain as a CRBR. cx5841 and cx5187 have a B7H3-targeting sdAb positioned on the N and C-termini of one chain of the heterodimer, the Fc knob, and have 41BB-targeting sdAb positioned at the C-termini of the opposite chain of the heterodimer, the Fc hole, but have the VH and VL of the CD3 binding Fv positioned on opposite sides with respect to each other.

FIG. 31B and FIG. 31C depict mean fluorescence intensity (MFI) of the GFP reporter when the B7H3 positive cell line A375 or the B7H3 negative cell line CCRF-CEM, respectively, were co-cultured with Jurkat CD3 NFAT-GFP reporter cells. FIG. 31D and FIG. 31E depict relative luminescent units (RLU) of the luciferase reporter when the B7H3 positive cell line A375 or the B7H3 negative cell line CCRF-CEM, respectively, were co-cultured with Jurkat CD3 NFAT-Luciferase reporter cells.

DETAILED DESCRIPTION

The present disclosure provides constrained T-cell engaging fusion proteins in the form of multispecific polypeptide constructs that bind at least CD3, a second antigen, and a co-stimulatory receptor. Also provided in the present disclosure are T-cell engaging fusion proteins in the form of multispecific polypeptide constructs that bind at least CD3, a second antigen, and an inhibitory receptor. Also provided in the present disclosure are T-cell engaging fusion proteins in the form of multispecific polypeptide constructs that bind at least CD3, a second antigen, a co-stimulatory receptor and an inhibitory receptor.

In some embodiments, the multispecific polypeptide constructs provided herein include at least a first component that includes an immunoglobulin Fc region, a second component that includes one or more copies of at least a binding domain that binds CD3 (referred to herein as an anti-CD3 binding domain or a CD3 binding region, which are terms that are used interchangeably herein), and a linker, such as a polypeptide linker, that joins the first component and the second component. In the provided multispecific polypeptide constructs, one or both of the first and second components contain at least one antigen binding domain, which, when engaged upon binding to antigen, render the constrained CD3 binding region substantially able to bind CD3. In some embodiments, the antigen is a tumor associated antigen (TAA). In addition, in some aspects, one or both of the first and second components of the multispecific polypeptide constructs also comprise at least one co-stimulatory receptor binding region (CRBR) that binds to a co-stimulatory receptor. In other aspects, one or both of the first and second components of the multispecific polypeptide constructs also comprise at least one inhibitory receptor binding region (IRBR) that binds to an inhibitory receptor. In particular aspects of the provided disclosure, one of the first and second component of the multispecific polypeptide construct contains a CRBR and the other of the first and second component contains an IRBR. In some embodiments, the linker is a non-cleavable linker. In some embodiments, the linker is a cleavable linker.

Figure 1:
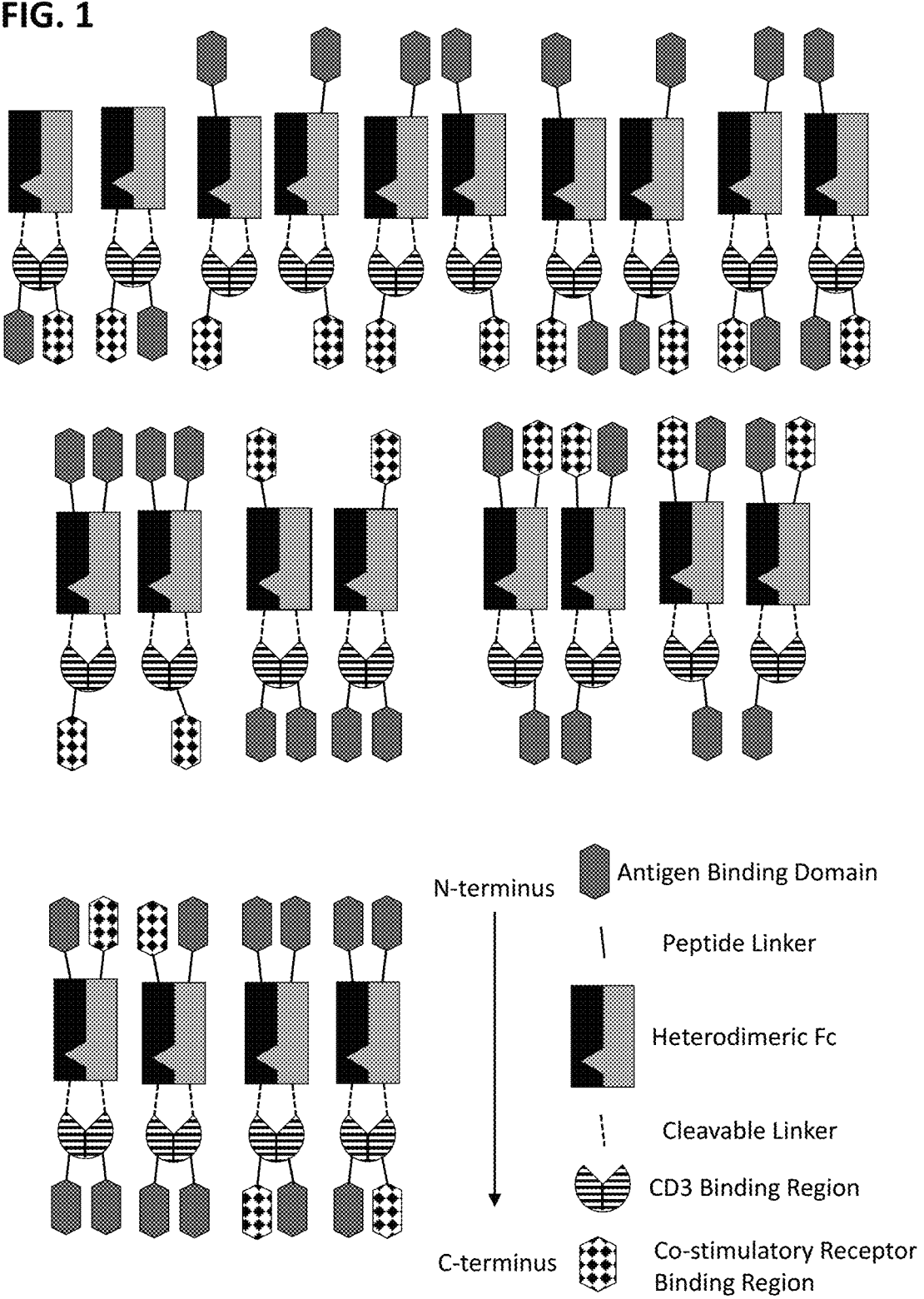
FIG. 1 is a schematic of the basic components of the multispecific polypeptide constructs of the present disclosure having constrained CD3 binding. The antigen binding domain(s) are positioned at the amino and/or carboxy termini. The Fc region, such as a heterodimeric Fc region, is positioned N-terminal to the CD3 binding region. This positioning of the Fc in close proximity to the CD3 binding region obstructs CD3 binding. The co-stimulatory receptor binding region (CRBR)(s) is positioned at the amino and/or carboxy termini. The exemplary multispecific constructs depicted can further contain a second CRBR if the multispecific molecule has one or two antigen binding domain(s).
Figure 2A:
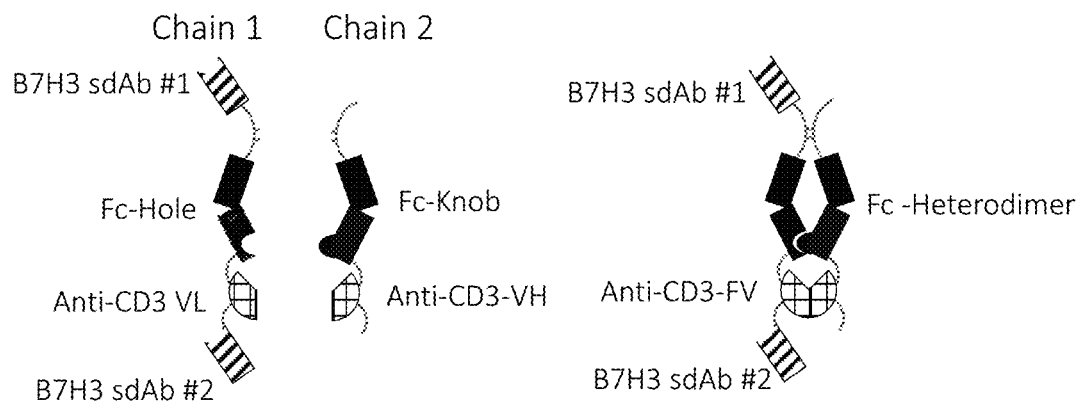
FIGS. 2A-2F depict various representative B7H3-targeted constrained CD3 engagers with or without a CRBR.
Figure 2B:
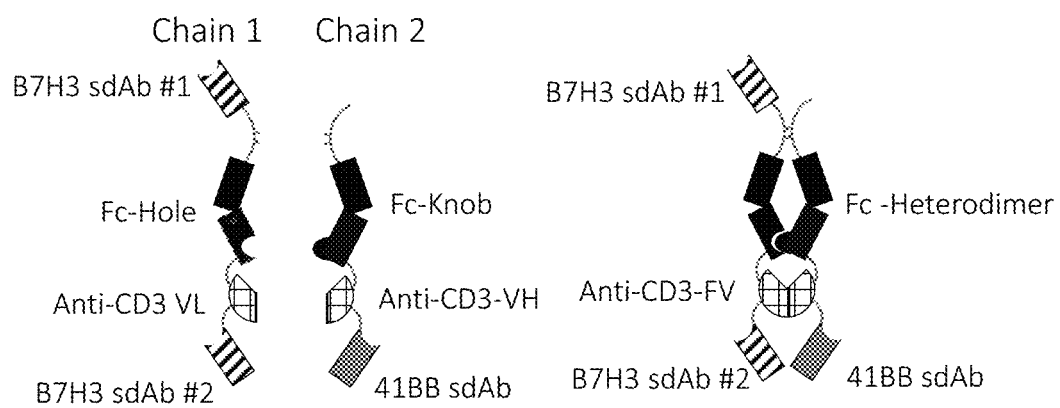
Figure 2C:
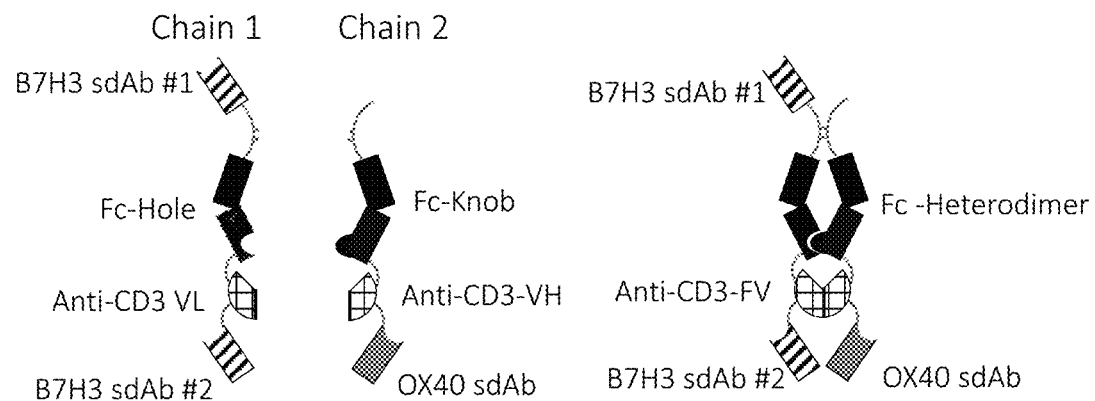
Figure 2D:
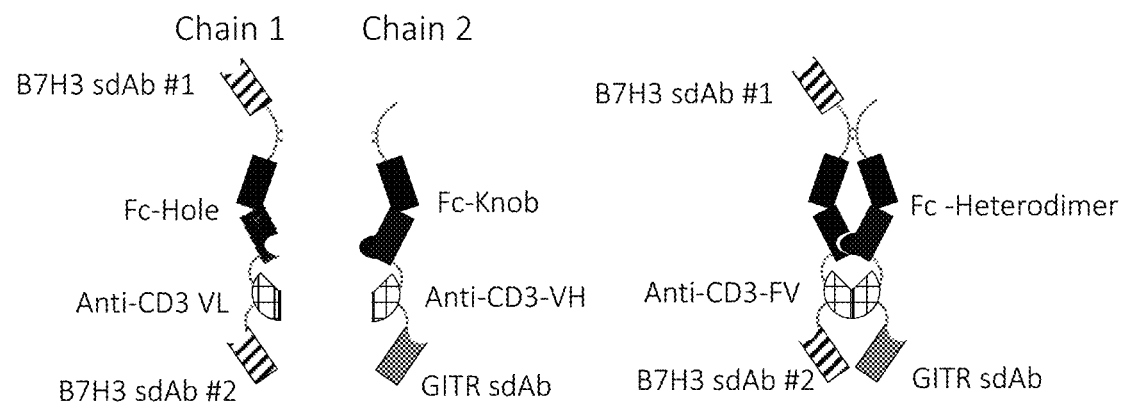
Figure 2E:
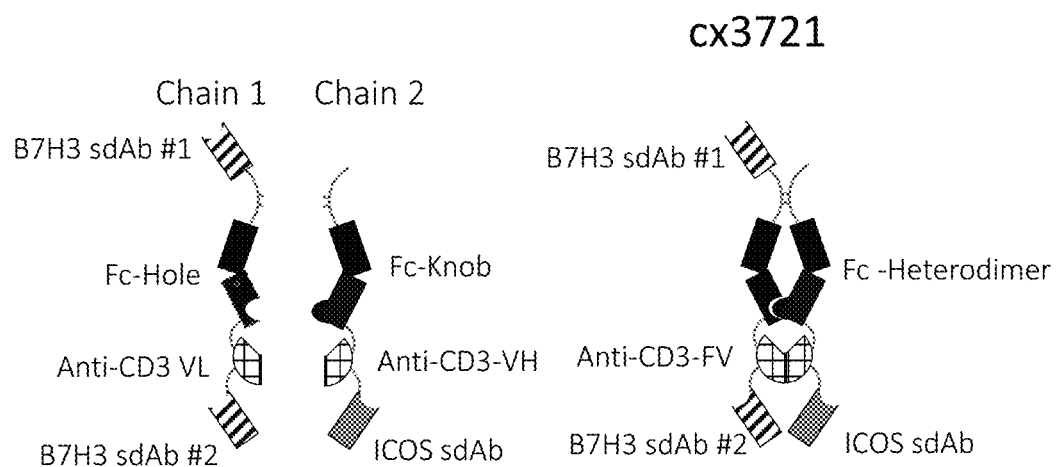
Figure 2F:
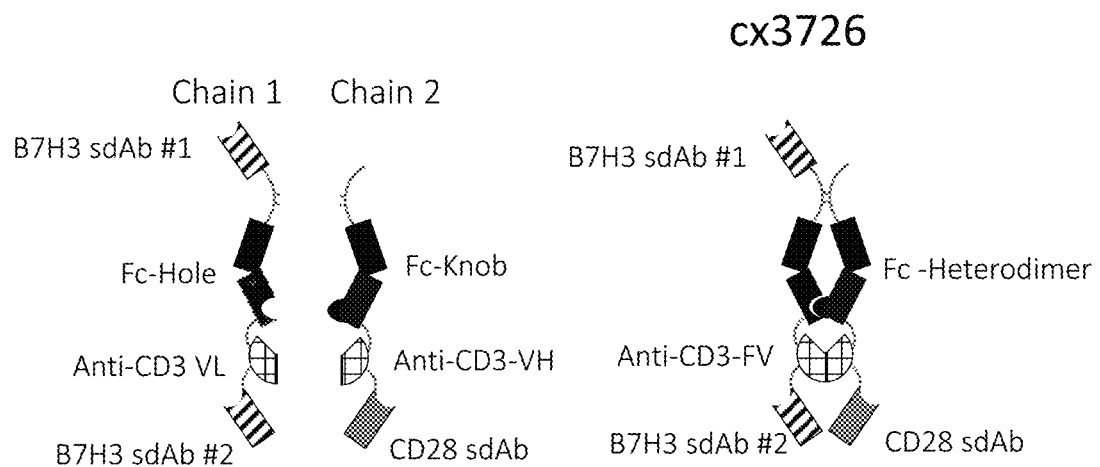

In some embodiments, the provided multispecific polypeptide constructs include a configuration in which the first component containing the Fc region is N-terminal to the second component containing the CD3 binding region. In such an embodiment, the first and second components are joined via a linker that is C-terminal to the end of the Fc region. In some embodiments, the antigen binding domain(s) and/or the CRBR(s) are positioned on the amino-terminal (N-term) region of the multispecific polypeptide construct. In some embodiments, the antigen binding domain(s) and/or the CRBR(s) are positioned on the carboxy-terminal (C-term) region of the multispecific polypeptide construct. In some embodiments, the antigen binding domain(s) and/or the CRBR(s) are positioned on both the N- and C-terminal regions of the multispecific polypeptide construct. Various configurations of a multispecific polypeptide construct as provided herein are shown in FIG. 1.

Figure 18A:
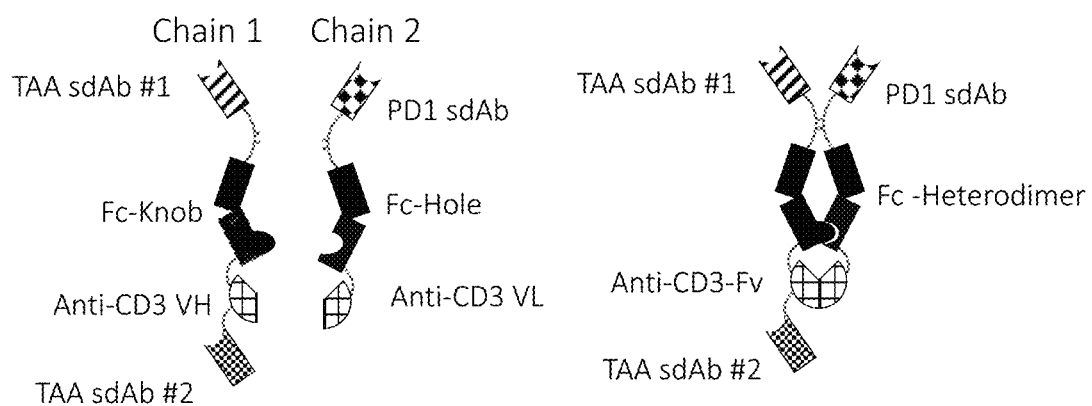
FIGS. 18A-18B depicts a series of schematics representing various TAA-targeted constrained CD3 engaging constructs containing an anti-PD1 binding domain. The basic components of the TAA-targeted constrained CD3 engaging constructs of the present disclosure have constrained CD3 binding. The antigen binding domain(s) are positioned at the amino and/or carboxy termini. The Fc region, such as a heterodimeric Fc region, is positioned N-terminal to the CD3 binding region. This positioning of the Fc in close proximity to the CD3 binding region obstructs CD3 binding. In an exemplary embodiments, the anti-PD1 binding domain is positioned N-terminal to the heterodimeric Fc, and may contain a 41BB costimulatory binding domain C-terminal to the anti-CD3 binding domain.

In some embodiments, the provided multispecific polypeptide constructs include a configuration in which the first component containing the Fc region is N-terminal to the second component containing the CD3 binding region. In such an embodiment, the first and second components are joined via a linker that is C-terminal to the end of the Fc region. In some embodiments, the antigen binding domain(s) and/or the IRBR(s) are positioned on the amino-terminal (N-term) region of the multispecific polypeptide construct. In some embodiments, the antigen binding domain(s) and/or the IRBR(s) are positioned on the carboxy-terminal (C-term) region of the multispecific polypeptide construct. In some embodiments, the antigen binding domain(s) and/or the IRBR(s) are positioned on both the N- and C-terminal regions of the multispecific polypeptide construct. Various configurations of a multispecific polypeptide construct as provided herein are shown in FIG. 18A.

Figure 18B:
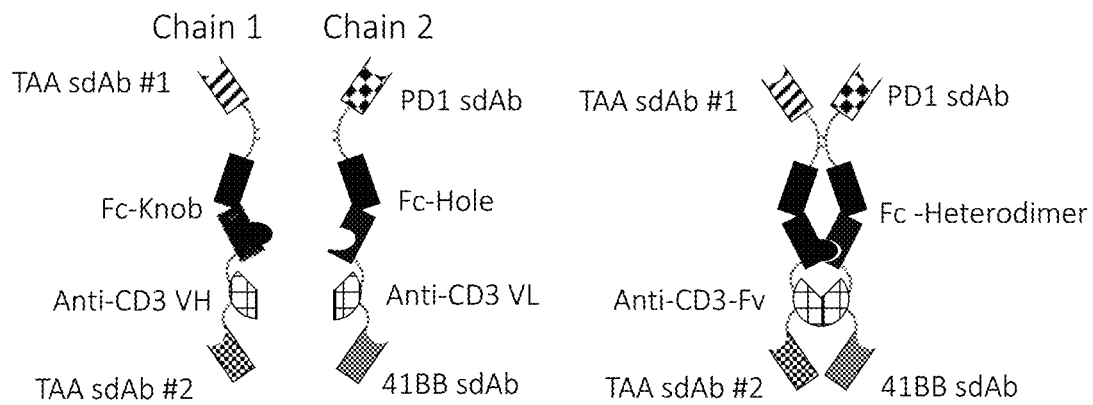

In some embodiments, the provided multispecific polypeptide constructs include a configuration in which the first component containing the Fc region is N-terminal to the second component containing the CD3 binding region. In such an embodiment, the first and second components are joined via a linker that is C-terminal to the end of the Fc region. In some embodiments, the antigen binding domain(s) and/or the CRBR(s) are positioned on the amino-terminal (N-term) region of the multispecific polypeptide construct and the antigen binding domain(s) and/or the IRBR(s) are positioned on the carboxy-terminal (C-term) region of the multispecific polypeptide construct. In some embodiments, the antigen binding domain(s) and/or the IRBR(s) are positioned on the amino-terminal (N-term) region of the multispecific polypeptide construct and the antigen binding domain(s) and/or the CRBR(s) are positioned on the carboxy-terminal (C-term) region of the multispecific polypeptide construct. Various configurations of a multispecific polypeptide construct as provided herein are shown in FIG. 18B.

The provided multispecific polypeptide constructs exhibit constrained T-cell engaging activity because such constructs only substantially bind to CD3 once an antigen is bound via the antigen-bind domain. This is exemplified in the Examples and Figures provided herein, which demonstrate the ability of constrained CD3 engaging proteins to efficiently bind TAA positive cells, while having little to no binding of T cells. This unique property allows constrained CD3 engaging proteins to distribute to sites where TAA is present without binding to peripheral T cells. This format is distinct from other CD3 engaging multispecific constructs, in that constitutive CD3 binding is disallowed or eliminated, providing a significant benefit by avoiding peripheral T-cell binding and permitting superior distribution to the site(s) where antigen is present as recognized by the antigen binding domain. For example, as shown in the Examples, the constrained CD3 engaging format enables similar potency to the DART-Fc format (e.g. published PCT Appl. No. WO2017/030926), however, binding to peripheral T-cell is significantly attenuated. Furthermore, other CD3 engaging constructs mediate antigen-dependent T-cell activation, however, the multispecific polypeptide constructs provided herein mediate both antigen dependent T-cell binding and activation.

The constrained T-cell engaging activity of the provided multispecific polypeptide constructs is due, in some aspects, to the positioning of the Fc region N-terminal to the CD3-binding region. In some embodiments, such positioning reduces, attenuates, dampens and/or prevents CD3 binding by the CD3 binding region. In the absence of antigen binding by the antigen binding domain, the multispecific polypeptide constructs provided herein demonstrate reduced or eliminated CD3 binding and T-cell activating capacity. In some embodiments, in the presence of an antigen binding event mediated by the antigen binding domain(s) of the multispecific polypeptide constructs, the capacity to bind CD3 by the CD3 binding region is greatly enhanced. In some embodiments, in the presence of an antigen binding event mediated by the antigen binding domains(s) of the multispecific polypeptide constructs the capacity to activate T-cells is greatly enhanced. Engagement of its cognate antigen by the antigen binding domain(s) within the multispecific polypeptide construct leads to subsequent T-cell engagement and mediates antigen-dependent T-cell activation, such as cytotoxicity, cytokine release, degranulation and proliferation. In some embodiments, the provided multispecific polypeptide constructs can be used to increase an immune response, such as to enhance T-cell activity, including cytolytic (or cytotoxic) T-cell activity. The modulation of the immune response can, in some aspects, treat a disease or condition in a subject.

In some embodiments, the multispecific polypeptide constructs of the disclosure exhibit specificity for CD3, one or more other antigen, and one or more co-stimulatory receptor. In some embodiments, the multispecific polypeptide constructs of the disclosure exhibit specificity for CD3, one or more other antigen, and one or more inhibitory receptor. In some embodiments, the multispecific polypeptide constructs of the disclosure exhibit specificity for CD3, one or more other antigen, one or more co-stimulatory receptor and one or more inhibitory receptor. In some embodiments, the multispecific polypeptide constructs can contain one or more antigen binding domain, such as 1, 2, or 3 antigen binding domains, able to bind one or more TAA, such as 2 or 3 antigen binding domains. In some embodiments, the multispecific polypeptide constructs can contain one or more co-stimulatory receptor binding regions (CRBRs), such as 1, 2, or 3 CRBRs, able to bind one or more co-stimulatory receptors, such as 2 or 3 co-stimulatory receptors. In some embodiments, the multispecific polypeptide constructs can contain one or more inhibitory receptor binding regions (IRBRs), such as 1, 2, or 3 IRBRs, able to bind one or more inhibitory receptors, such as 2 or 3 inhibitory receptors. Formats of exemplary constructs are shown in FIG. 1-3 and FIGS. 18A-B.

In some embodiments, the one or more CRBRs bind a co-stimulatory receptor expressed on the surface of a T cell. Non-limiting examples of costimulatory receptors to which a CRBR can be targeted include, for example, 41BB, OX40, CD27, GITR, CD28, ICOS, CD40L, BAFFR, BCMA, TACI, or NKG2d. In some embodiments, the one or more CRBR is or comprises a binding domain (e.g. sdAb, scFv, or Fab) that binds to the co-stimulatory receptor. As shown herein, the presence of a CRBR in the provided multispecific polypeptide constructs increases or potentiates T cell activity upon co-engagement of CD3 by the CD3 binding region.

In some cases, the one or more CRBRs bind a co-stimulatory receptor that is not constitutively expressed on a T cell. In some embodiments, the one or more CRBR binds a co-stimulatory receptor that is upregulated, induced, or expressed upon T cell activation. In some embodiments, the CRBR binds a co-stimulatory receptor that is a member of the tumor necrosis factor (TNF) receptor family, such as a TNFRSF member that is upregulated, induced, or expressed upon T cell activation. In some embodiments, the CRBR binds a co-stimulatory receptor that is a member of the B7 family, such as a B7 family member that is upregulated, induced, or expressed upon T cell activation. Among such costimulatory receptors whose expression is upregulated, or in which surface expression is induced, among activated T cells include, for example, 41BB, OX40 and GITR. In some aspects, the CD3-binding region of the provided multispecific polypeptide constructs induces or enhances T cell activation upon binding of the CD3 binding region to CD3, which in turn leads to increased or upregulated expression of such co-stimulatory receptors. In such examples, binding of a CRBR to the costimulatory receptor, e.g. 41BB, OX40 or GITR, is increased, or is made feasible, only following engagement of CD3 by the CD3 binding region of the multispecific polypeptide construct, thereby regulating costimulatory activity of the provided multispecific construct to target cells. In some cases, this addresses problems of other T cell engagers because it avoids an antigen "sink" effect due to binding to CD3 and/or costimulatory receptors expressed on peripheral T cells, such as resting T cells or non-desired cells, which otherwise may accelerate systemic clearance. In some embodiments, the provided multispecific polypeptide constructs exhibit an increased half-life and/or improved pharmacokinetic or pharmacodynamics properties, such as better tumor exposure, compared to other T cell engagers that are able to bind to peripheral cells, such as bispecific T cell engagers, for example DART-Fc.

In some embodiments, the one or more IRBRs bind an inhibitory receptor expressed on the surface of a T cell. In some aspects, the inhibitory receptor is one whose expression is upregulated or increased on an activated T cell. Non-limiting examples of inhibitory receptors to which an IRBR can be targeted include, for example, PD-1, CTLA-4, TIGIT, VISTA, TIM3 or LAG3. In some embodiments, the one or more IRBR is or comprises a binding domain (e.g. sdAb, scFv, or Fab) that binds to the inhibitory receptor.

In some embodiments, the one or more IRBRs bind an inhibitory receptor and block or inhibit the interaction with its ligand, thereby blocking inhibitory activity of the T cell. In some embodiments, the IRBR is a PD-1 binding polypeptide that binds to PD-1. In some cases, the provided PD-1 binding polypeptides directly block or inhibit the interaction between PD-L1/L2 and PD-1. In some aspects, inclusion of a IRBR on a multispecific polypeptide construct inhibits or reduce the interaction between an inhibitory receptor and its ligand, e.g. PD-L1 and/or PD-L2 and PD-1, to thereby modulate immune responses. While transmission of an inhibitory signal may lead to downmodulation in immune cell responses (and a resulting downmodulation in the overall immune response), blocking an inhibitory signal in immune cells leads to upmodulation of immune cell responses (and a resulting upmodulation of an immune response). In some cases, modulation by enhancement of an immune response can be used to treat certain disease or conditions in which the immune response is suppressed, such as cancers. Generally, the ability to block inhibitory interactions occurs at the immune synapse and/or in the tumor microenvironment upon binding of the CD3 binding region to CD3 on a T cells and/or binding of the antigen binding domain to a TAA. In particular embodiments, the provided multispecific polypeptide constructs reduce, inhibit or suppress the inhibitory signal mediated by the inhibitory receptor in a cell, such as a T cell.

In some embodiments, the one or more antigen binding domains bind an antigen on a tumor cell or a cell of the tumor microenvironment. In some aspects, the provided multispecific polypeptide constructs can be used to increase immune responses, such as T-cell activity, e.g. cytotoxicity activity, against a tumor or cancer. In some embodiments, the provided multispecific polypeptide constructs can be used to treat a tumor or cancer in the subject.

In some embodiments, the one or more antigen binding domains bind the same antigen. In some embodiments, the multispecific polypeptide constructs include more than one antigen binding domains that bind distinct epitopes on the same antigen. In some embodiments, the multispecific polypeptide constructs include more than one antigen binding domain that bind one or more distinct antigens. In some embodiments, the multispecific polypeptide constructs include more than one antigen binding domains that bind distinct epitopes on the same antigens as well as include additional antigen binding domains that bind to one or more distinct antigens. In some examples, the provided multispecific polypeptide constructs provide multivalent engagement of one or more TAA, such as through at least a first antigen-binding domain and a second antigen-binding domain. For example, in some embodiments, the polypeptide constructions include at least a first antigen-binding single domain antibody (sdAb) and a second antigen-binding sdAb. In some aspects, the first and second antigen-binding domain binds the same antigen.

Further, in some aspects, the multispecific polypeptide constructs of the disclosure ensure that there will be no or reduced binding of T-cells via CD3 in peripheral blood, as the CD3 binding region of these constructs is constrained or otherwise blocked and/or inhibited by the presence of the Fc region. Thus, the multispecific polypeptide constructs of the disclosure provide a number of advantages. In some aspects, these constructs limit the sink effect caused by binding all T-cells. In some aspects, these constructs reduce systemic toxicity.

In some embodiments, the provided multispecific polypeptide constructs of the disclosure allow for controlled biodistribution to a desired site in a subject, such as, for example, a site of tumor-associated antigen (TAA) expression. Sites of TAA expression include, for example, tumor and the surrounding tumor microenvironment.

In some embodiments, the multispecific polypeptide constructs provided herein exist in two states in terms of capacity to bind CD3 and subsequently activate T-cells: (1)

the "inactive" state occurs when there is no binding of any or all of the antigen binding domain(s), such that the CD3 binding is constrained and T-cell interaction is obviated or reduced, and (2) the "active" state occurs upon antigen binding by any or all of the antigen binding domain(s), such that the CD3 binding region is able to bind CD3 and the T-cell interaction is allowed.

In some embodiments, the Fc region is linked to the CD3 binding domain via a linker or linkers. In some embodiments, the Fc region is linked to the CD3 binding region via a non-cleavable linker or linkers. In some embodiments, the Fc region is linked to the CD3 binding region via a cleavable linker or an otherwise labile linker or linkers.

In some aspects, the multispecific polypeptide constructs of the disclosure allow for therapeutic efficacy in the absence of cleavage, such as in the absence of proteolysis. In some embodiments, the linker is a non-cleavable linker.

In some embodiments, the Fc region and the CD3 binding region are linked by a cleavable linker, such as linkers that can be specifically cleaved in the presence of a protease. In some aspects, enhanced CD3 binding occurs following cleavage of the cleavable linker. In some such aspects, the "active" state can be further amplified via several mechanisms, including via cleavage of the linker joining the CD3 binding region and the Fc region. In some embodiments, the cleavable linker is a linker that contains a substrate recognition site for a protease. In some embodiments, wherein the Fc region and the CD3 binding region are linked by a cleavable linker, enhanced CD3 binding may occur following cleavage within the linker(s).

In some embodiments, the Fc region is a homodimeric Fc region. In some embodiments, the Fc region is a heterodimeric Fc region. In some embodiments, the Fc region is a monomeric Fc region. In some embodiments, the Fc region of the multispecific polypeptide constructs are capable of interacting with FcγRs and mediating innate immune effector functions, for example, antibody dependent cellular toxicity (ADCC) and antibody dependent cellular phagocytosis (ADCP). In some embodiments, the Fc region of the multispecific polypeptide constructs are capable of interacting with complement proteins, namely C1q, and mediating complement dependent cytotoxicity. Thus, in some aspects, the multispecific polypeptide constructs of the disclosure allow for multiple immune effector mechanisms, including innate immune effectors and T-cells.

In some embodiments, the linker is a cleavable linker. In some embodiments, wherein the Fc region and the CD3 binding region are operably linked by a cleavable linker, cleavage of the linker(s) between the Fc region and the CD3 binding region may separate the multispecific polypeptide constructs into a first and second component. Depending on the composition of the multispecific polypeptide construct, the first and second component may have distinct functionalities. In some embodiments, the Fc region is a region that exhibits one or more effector functions, such as ADCC, CDC or ADCP functions. In such examples, the multispecific polypeptide constructs of the disclosure can be used to produce a self-amplifying system. For example, the multispecific constructs can be used as follows: ADCC mediated by NK cell following TAA targeting and CD16 binding of Fc region results in the release granzyme B that is capable of extracellular proteolysis and cleavage of linkers between the first and second components of the multispecific polypeptide constructs.

In some aspects, the multispecific polypeptide constructs provide a two-in-one therapeutic moiety having dual effector functions, wherein proteolytic activation of the multispecific polypeptide constructs, such as via the cleavable linker, produces two components that each have biological activity. The multispecific polypeptide constructs of the disclosure are capable of providing Fc-mediated effector functions, such as for example, ADCC (e.g., release of Granzyme B by NK cells), ADCP, and/or CDC.

It is contemplated that the constrained CD3 engaging constructs are amenable for use with any TAA-binding domain, allowing better therapeutic exposure within the tumor or tumor-microenvironment by avoiding interactions with peripheral T-cells and mediating potent TAA-dependent T-cell cytotoxicity. In some aspects, the incorporation of a protease cleavable linker between the Fc and the components of the CD3 binding domain enables for amplification of the T-cell activating capacity by allowing full exposure of the CD3 binding domain. Depending on the specific linker included, the amplification step can be mediated by tumor associated proteases or by granzymes released following antigen dependent-T-cell activation. If a tumor protease cleavable linker is included the amplification is mediated by the tumor or tumor-microenvironment. Whereas, if a granzyme B cleavable linker is included the amplification may be self-mediated by T-cells following antigen-dependent activation. Furthermore, in cases wherein an effector enabled Fc is included in the construct, amplification may be mediated by granzymes released from NK cell that occurs through an ADCC mechanism.

In some embodiments, the cleavable linker is cleaved by a protease that is produced in the tumor microenvironment and/or that is produced or secreted by T cells upon T cell activation, such as can be induced by initial binding of the CD3 binding region to CD3 in the tumor microenvironment via binding of the antigen binding domain(s) to a TAA. In some embodiments, the protease is granzyme B. In some aspects, the multispecific polypeptide constructs of the disclosure leverage the ability of a protease within the tumor microenvironment and/or granzyme B to cleave the linker within the multispecific polypeptide construct at a position below the Fc immunoglobulin polypeptide, thereby generating two therapeutically active proteins with, in some cases, distinct effector cell engagement. In some aspects, upon cleavage of the cleavable linker, the cleaved first portion or component retains Fc-effector functions and bivalent targeting of a first antigen, such as, e.g., a TAA, via a first antigen-binding domain, and the second portion or component retains the ability for T-cell engagement, as separation of the CD3 binding region from the Fc region allows for CD3 binding. The cleaved second portion or component also, in some cases, retains the ability for binding to a TAA, which can be a bivalent binding via a second antigen-binding domain.

The multispecific polypeptide constructs of the disclosure are designed to ensure that the protease that cleaves the cleavable linker does not need to be tumor-biased (e.g., does not need to be differently expressed only at a tumor site and/or in the tumor environment). Rather, these multispecific polypeptide constructs only require that the protease is present in the same location as the TAA. The valency of these constructs will drive biodistribution and retention within the tumor and/or tumor microenvironment.

In some embodiments, the second portion or component contains a CD3 binding region that is monovalent to CD3, such that there will be no activation of T-cell unless there is TAA present. In some aspects, where the multivalent polypeptide construct contains a cleavable linker, the cleaved second portion or component allows for TAA-dependent, T-cell-mediated cytotoxicity. In some cases, the cleaved second portion or component ensures there will be no FcRn interaction. Furthermore, the cleaved second portion or component will be sufficiently small in size, for example, only ~50 kDa, which will ensure rapid clearance if, for any reason, the cleaved second portion or component distributes outside tumor site after cleavage and/or if it is aberrantly cleaved outside of the tumor site.

In some embodiments, the multispecific polypeptide constructs of the disclosure allow for T-cell and NK cell mediated cytotoxicity to occur simultaneously. In some cases, such activity can occur in a multispecific polypeptide construct in which is contained a first antigen binding domain, e.g., a first anti-TAA antigen binding domain, and a second antigen binding domain, e.g., a second anti-TAA antigen binding domain, that can target distinct and/or non-competing epitopes on a given TAA.

In some aspects, the multispecific polypeptide constructs of the disclosure provide a number of advantages over current bispecific therapeutics. The multispecific polypeptide constructs of the disclosure are smaller than a conventional therapeutic antibody, e.g., 150 kDa vs. 125 kDa, which will allow for better target, e.g. tumor, penetration. First, the size of the entire multispecific polypeptide construct provides long half-life for the uncleaved construct, and upon cleavage of the construct, the cleaved second portion or component will be sufficiently small to ensure a short half-life. In some aspects, the multispecific polypeptide constructs of the disclosure exhibit reduced systemic toxicity or toxicity of any area outside the tumor and/or tumor microenvironment, since CD3 binding by the CD3 binding region depends on TAA engagement before CD3 engagement will occur. In some cases, the inclusion of a cleavable linker specific to a protease of the tumor environments reduces CD3 binding by the multispecific constructs until proteolytic activation and TAA engagement, thereby amplifying or enhancing the CD3 engagement. Further, the additional presence of the CRBR in the provided multispecific polypeptide constructs provide for antigen dependent specific co-stimulatory signaling to further increase or enhance T cell activity at a desired site or location, such as with a tumor and/or tumor microenvironment. Likewise, including of a IRBR in the provided multispecific polypeptide constructs also can enhance T cell activity by removing or blocking checkpoint inhibitory signals.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

I. DEFINITIONS

Unless otherwise defined, scientific and technical terms used in connection with the present disclosure shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and antigen-binding portions or fragments of immunoglobulin (Ig) molecules, i.e., molecules that contain an antigen binding site that specifically binds (immunoreacts with) an antigen. The term antibody encompasses not only intact polyclonal or monoclonal antibodies, but also fragments thereof, such as dAb, Fab, Fab', F(ab')$_2$, Fv), single chain (scFv) or single domain antibody (sdAb). Typically, an "antigen-binding fragment" contains at least one CDR of an immunoglobulin heavy and/or light chain that binds to at least one epitope of the antigen of interest. In this regard, an antigen-binding fragment may comprise 1, 2, 3, 4, 5, or all 6 CDRs of a variable heavy chain (VH) and variable light chain (VL) sequence from antibodies that bind the antigen, such as generally six CDRs for an antibody containing a VH and a VL ("CDR1," "CDR2" and "CDR3" for each of a heavy and light chain), or three CDRs for an antibody containing a single variable domain. Antigen binding fragments include single domain antibodies, such as those only containing a VH or only containing a VL, including, for example, $V_HH$, $V_{NAR}$, engineered $V_H$ or $V_K$ domains.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, IgG$_3$, IgG$_4$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

As used herein, the term "epitope" includes any specific portion of an antigen targeted by an antibody, antibody fragment or other binding domain. The term "epitope" includes any protein region to which specific binding is directed. The term "epitope" includes any protein determinant involved in specific binding with a binding molecule, such as an antibody or antigen-binding fragment Epitopic determinants usually consist of chemically active surface groupings of molecules such as amino acids or sugar side chains and usually have specific three dimensional structural characteristics, as well as specific charge characteristics. For example, antibodies may be raised against N-terminal, central, or C-terminal peptides of a polypeptide. In addition, antibodies may be raised against linear or discontinuous epitopes of a polypeptide.

As used herein, the terms "specific binding," or "specifically binds" is the ability of a binding molecule, such as an antibody or an antigen-binding fragment, to preferentially bind an antigen in a complex mixture of proteins and/or macromolecules. A binding molecule is said to exhibit "specific binding" or "preferential binding" if it reacts or associates more frequently, more rapidly, with greater duration and/or with greater affinity with a particular cell or target antigen than it does with alternative cells or target antigens. A binding molecule specifically binds or preferentially binds to a target if it binds with greater affinity, avidity, more readily, and/or with greater duration than it binds to other substances. In some aspects, specific binding can refer to the non-covalent interactions of the type that occur between an immunoglobulin molecule and an antigen for which the immunoglobulin is specific. It is understood that specific binding or preferential binding does not necessarily require (although it can include) exclusive binding. Various known methods can be used to quantify or assess binding. The strength, or affinity of binding interactions can be expressed in terms of the dissociation constant ($K_d$) of the interaction, wherein a smaller $K_d$ represents a greater affinity. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity and is equal to the dissociation constant $K_d$. (See, generally, Davies et al. (1990) Annual Rev Biochem 59:439-473). A binding molecule, such as an antibody or antigen binding fragment, is said to specifically bind, when the binding constant ($K_d$) is $\leq 1$ µM, for example, in some embodiments 100 nM, in some embodiments $\leq 10$ nM, and in some embodiments $\leq 100$ pM to about 1 pM, as measured by assays such as radioligand binding assays or similar assays known to those skilled in the art.

The terms "polypeptide" and "protein" are used interchangeably herein and refer to a molecular chain of two or more amino acids linked through peptide bonds. The terms include post-translational modifications of the polypeptide, for example, glycosylation, acetylation, phosphorylation and the like. The terms also include molecules in which one or more amino acid analogs or non-canonical or unnatural amino acids that can be synthesized, or expressed recombinantly using known protein engineering techniques. In addition, proteins can be derivatized. A protein can be a single polypeptide chain or a multimer (dimer) of at least two polypeptide chains covalently bonded to each other by, for example, interchain disulfide bonds. Thus, monomeric, dimeric, and higher order multimeric polypeptides are within the scope of the defined term. Multimeric polypeptides can be homomultimeric (of identical polypeptide chains) or heteromultimeric (of non-identical polypeptide chains).

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "polynucleotide" as referred to herein means nucleotides of at least 10 bases in length, either ribonucleotides or deoxynucleotides or a modified form of either type of nucleotide. The term includes single and double stranded forms of DNA. Polynucleotides in accordance with the disclosure include the nucleic acid molecules encoding polypeptides of the multispecific polypeptide constructs shown herein.

The term "isolated polynucleotide" as used herein shall mean a polynucleotide of genomic, cDNA, or synthetic origin or some combination thereof, which by virtue of its origin (1) is not associated with all or a portion of a polynucleotide found in nature, (2) is operably linked to a polynucleotide that it is not linked to in nature, or (3) does not occur in nature as part of a larger sequence.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

As applied to polypeptides, the term "substantial identity" means that two peptide sequences, when optimally aligned, such as by the programs GAP or BESTFIT using default gap weights, share at least 80 percent sequence identity, for example, in some embodiments, at least 90 percent sequence identity, in some embodiments, at least 95 percent sequence identity, and in some embodiments, at least 99 percent sequence identity. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y $^{99}$Tc, $^{111}$In, $^{125}$I, $^{131}$I), fluorescent labels (e.g., a fluorophore, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "tumor associated antigen" or "TAA" as used herein refers to a counter-structure that is present primarily on tumor cells of a mammalian subject but generally not found on normal cells of the mammalian subject. A tumor specific antigen need not be exclusive to tumor cells but the percentage of cells of a particular mammal that have the tumor associated antigen is sufficiently high or the levels of the tumor associated antigen on the surface of the tumor are sufficiently high such that it can be targeted by anti-tumor therapeutics, such as multispecific polypeptide constructs as provided, and provide prevention or treatment of the mammal from the effects of the tumor. In some embodiments, in a random statistical sample of cells from a mammal with a tumor, at least 50% of the cells displaying a TAA are cancerous. In other embodiments, at least 60%, 70%, 80%, 85%, 90%, 95%, or 99% of the cells displaying a TAA are cancerous.

As used herein, a composition refers to any mixture of two or more products, substances, or compounds, including cells. It may be a solution, a suspension, liquid, powder, a paste, aqueous, non-aqueous or any combination thereof.

The term "pharmaceutical composition" refers to a composition suitable for pharmaceutical use in a mammalian subject, often a human. A pharmaceutical composition typically comprises an effective amount of an active agent (e.g., multispecific polypeptide construct) and a carrier, excipient, or diluent. The carrier, excipient, or diluent is typically a pharmaceutically acceptable carrier, excipient or diluent, respectively.

The terms "treating," "treatment," or "therapy" of a disease or disorder as used herein mean slowing, stopping or reversing the disease or disorders progression, as evidenced by decreasing, cessation or elimination of either clinical or diagnostic symptoms, by administration of a pharmaceutical composition of the disclosure either alone or in combination with another compound as described herein. "Treating," "treatment," or "therapy" also means a decrease in the severity of symptoms in an acute or chronic disease or disorder or a decrease in the relapse rate. As used herein in the context of cancer, the terms "treatment" or, "inhibit," "inhibiting" or "inhibition" of cancer refers to at least one of: a statistically significant decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), or a statistically significant increase in progression free survival (PFS) or overall survival (OS). "Preventing," "prophylaxis," or "prevention" of a disease or disorder refers to administration of a pharmaceutical composition, either alone or in combination with another compound, to prevent the occurrence or onset of a disease or disorder or some or all of the symptoms of a disease or disorder or to lessen the likelihood of the onset of a disease or disorder.

The terms "effective amount" or "therapeutically effective amount" refer to a quantity and/or concentration of a composition that when administered into a patient either alone (i.e., as a monotherapy) or in combination with additional therapeutic agents, yields a statistically significant decrease in disease progression as, for example, by ameliorating or eliminating symptoms and/or the cause of the disease. An effective amount may be an amount that relieves, lessens, or alleviates at least one symptom or biological response or effect associated with a disease or disorder, prevents progression of the disease or disorder, or improves physical functioning of the patient.

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present. Generally, a substantially pure composition will comprise more than about 80 percent of all macromolecular species present in the composition, for example, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

As used herein, a "subject" is a mammal, such as a human or other animal, and typically is human. The subject, e.g. patient, includes those in need of a treatment for treating a disease or disorder. The term patient includes human and veterinary subjects. The subject can be male or female and can be any suitable age, including infant, juvenile, adolescent, adult, and geriatric subjects.

Other chemistry terms herein are used according to conventional usage in the art, as exemplified by The McGraw-Hill Dictionary of Chemical Terms (Parker, S., Ed., McGraw-Hill, San Francisco (1985)).

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

II. MULTISPECIFIC POLYPEPTIDE CONSTRUCTS

Provided herein is a multispecific polypeptide construct containing a first component containing an immunoglobulin Fc region and a second component comprising a CD3-binding region, wherein the first and second components are coupled by a linker, the Fc region is positioned N-terminal to the CD3-binding region; and one or both of the first and second components comprises (1) an antigen binding domain that binds a tumor associated antigen (TAA) and (2) a co-stimulatory receptor binding region (CRBR) that binds a co-stimulatory receptor. Also provided herein is a multispecific polypeptide construct containing a first component containing an immunoglobulin Fc region and a second component comprising a CD3-binding region, wherein the first and second components are coupled by a linker, the Fc region is positioned N-terminal to the CD3-binding region; and one or both of the first and second components comprises (1) an antigen binding domain that binds a tumor associated antigen (TAA) and (2) an inhibitory receptor binding region (IRBR) that binds an inhibitory receptor. In some embodiments, the multispecific polypeptide construct contains at least one antigen binding domain that binds a TAA. In some embodiments, the multispecific polypeptide construct contains at least a first antigen binding domain that binds a TAA and a second antigen binding domain that binds a TAA. In some embodiments, the multispecific polypeptide construct contains at least one CRBR that binds a co-stimulatory receptor and/or at least one IRBR that binds an inhibitory receptor. Exemplary formats of multispecific constructs provided herein are shown in FIG. 1-3 and FIGS. 18A and 18B.

In some embodiments, the multispecific polypeptide construct contains in order, from N-terminus to C-terminus: an immunoglobulin Fc region; a linker; a CD3 binding region that binds CD3 (CD3ε); and at least two binding domains where one is an antigen binding domain that binds a TAA and the other is a CRBR that binds a co-stimulatory receptor.

In some embodiments, the multispecific polypeptide construct contains in order, from N-terminus to C-terminus: at least two binding domains where one is an antigen binding domain that binds to a tumor-associated antigen (TAA) and the other is a CRBR that binds a costimulatory receptor; an immunoglobulin Fc region; a linker; and a CD3 binding region that binds CD3 (CD3ε).

In some embodiments, the multispecific polypeptide construct contains in order, from N-terminus to C-terminus: an immunoglobulin Fc region; a linker; a CD3 binding region that binds CD3 (CD3ε); and at least two binding domains where one is an antigen binding domain that binds a TAA and the other is a IRBR that binds an inhibitory receptor.

In some embodiments, the multispecific polypeptide construct contains in order, from N-terminus to C-terminus: an immunoglobulin Fc region; a linker; a CD3 binding region that binds CD3 (CD3ε); and at least two binding domains where one is an antigen binding domain that binds a TAA and the other is a IRBR that binds a inhibitory receptor.

In some embodiments, the multispecific polypeptide construct contains in order, from N-terminus to C-terminus: at least two binding domains where one is an antigen binding domain that binds to a tumor-associated antigen (TAA) and the other is a IRBR that binds a inhibitory receptor; an immunoglobulin Fc region; a linker; and a CD3 binding region that binds CD3 (CD3ε).

In some embodiments, the multispecific polypeptide construct contains, in order, from N-terminus to C-terminus: at least one antigen binding domain that binds to a tumor-associated antigen (TAA) or a CRBR that binds a co-stimulatory receptor; an immunoglobulin Fc region; a linker; a CD3 binding region that binds CD3 (CD3ε); and the other of the at least one antigen binding domain that binds to a TAA or the CRBR that binds a co-stimulatory receptor. In some embodiments, the N- or C-terminal portion of the multispecific polypeptide construct contains one antigen binding domains that bind to a TAA. In some embodiments, the N- or C-terminal portion of the multispecific polypeptide construct contains two antigen binding domains that bind to a TAA. In some embodiments, each of the antigen binding domains that bind a TAA is the same. In some embodiments, at least a first antigen binding domain and a second antigen binding domain bind to a different TAA or to a different epitope of the same TAA.

In some embodiments, the multispecific polypeptide construct contains, in order, from N-terminus to C-terminus: at least one antigen binding domain that binds to a tumor-associated antigen (TAA) or a IRBR that binds an inhibitory receptor; an immunoglobulin Fc region; a linker; a CD3 binding region that binds CD3 (CD3ε); and the other of the at least one antigen binding domain that binds to a TAA or the IRBR that binds a inhibitory receptor. In some embodiments, the N- or C-terminal portion of the multispecific polypeptide construct contains one antigen binding domains that bind to a TAA. In some embodiments, the N- or C-terminal portion of the multispecific polypeptide construct contains two antigen binding domains that bind to a TAA. In some embodiments, each of the antigen binding domains that bind a TAA is the same. In some embodiments, at least a first antigen binding domain and a second antigen binding domain bind to a different TAA or to a different epitope of the same TAA.

In some embodiments, the multispecific polypeptide construct contains, in order, from N-terminus to C-terminus: a CRBR that binds a co-stimulatory receptor; an immunoglobulin Fc region; a linker; a CD3 binding region that binds CD3 (CD3ε); and at least one antigen binding domains that binds to a TAA. In some embodiments, the C-terminal portion of the multispecific polypeptide construct contains one antigen binding domains that binds to a TAA. In some embodiments, the C-terminal portion of the multispecific polypeptide construct contains two antigen binding domains that bind to a TAA. In some embodiments, each of the antigen binding domains that bind a TAA is the same. In some embodiments, at least a first antigen binding domain and a second antigen binding domain bind to a different TAA or to a different epitope of the same TAA.

In some embodiments, the multispecific polypeptide construct contains, in order, from N-terminus to C-terminus: a IRBR that binds a inhibitory receptor; an immunoglobulin Fc region; a linker; a CD3 binding region that binds CD3 (CD3ε); and at least one antigen binding domains that binds to a TAA. In some embodiments, the C-terminal portion of the multispecific polypeptide construct contains one antigen binding domains that binds to a TAA. In some embodiments, the C-terminal portion of the multispecific polypeptide construct contains two antigen binding domains that bind to a TAA. In some embodiments, each of the antigen binding domains that bind a TAA is the same. In some embodiments, at least a first antigen binding domain and a second antigen binding domain bind to a different TAA or to a different epitope of the same TAA.

In some embodiments, the multispecific polypeptide construct contains, in order, from N-terminus to C-terminus: at least one antigen binding domains that binds to a TAA; an immunoglobulin Fc region; a linker; a CD3 binding region that binds CD3 (CD3ε); and a CRBR that binds a co-stimulatory receptor. In some embodiments, the N-terminal portion of the multispecific polypeptide construct contains one antigen binding domains that binds to a TAA. In some embodiments, the N-terminal portion of the multispecific polypeptide construct contains two antigen binding domains that bind to a TAA. In some embodiments, each of the antigen binding domains that bind a TAA is the same. In some embodiments, at least a first antigen binding domain and a second antigen binding domain bind to a different TAA or to a different epitope of the same TAA.

In some embodiments, the multispecific polypeptide construct contains, in order, from N-terminus to C-terminus: at least one antigen binding domains that binds to a TAA; an immunoglobulin Fc region; a linker; a CD3 binding region that binds CD3 (CD3ε); and a IRBR that binds an inhibitory receptor. In some embodiments, the N-terminal portion of the multispecific polypeptide construct contains one antigen binding domains that binds to a TAA. In some embodiments, the N-terminal portion of the multispecific polypeptide construct contains two antigen binding domains that bind to a TAA. In some embodiments, each of the antigen binding domains that bind a TAA is the same. In some embodiments, at least a first antigen binding domain and a second antigen binding domain bind to a different TAA or to a different epitope of the same TAA.

In some embodiments, the multispecific polypeptide construct contains in order, from N-terminus to C-terminus: at least one antigen binding domain that binds to a TAA; an immunoglobulin Fc region; a linker; a CD3 binding region that binds CD3 (CD3ε); and at least two binding domains where one is an antigen binding domain that binds a TAA and the other is a CRBR that binds a co-stimulatory receptor. In some embodiments, the C-terminal portion of the multispecific polypeptide construct contains two antigen binding domains that bind to a TAA. In some embodiments, each of the antigen binding domains that bind a TAA is the same. In some embodiments, at least a first antigen binding domain and a second antigen binding domain bind to a different TAA or to a different epitope of the same TAA.

In some embodiments, the multispecific polypeptide construct contains in order, from N-terminus to C-terminus: at least one antigen binding domain that binds to a TAA; an immunoglobulin Fc region; a linker; a CD3 binding region that binds CD3 (CD3ε); and at least two binding domains where one is an antigen binding domain that binds a TAA and the other is a IRBR that binds an inhibitory receptor. In some embodiments, the C-terminal portion of the multispecific polypeptide construct contains two antigen binding domains that bind to a TAA. In some embodiments, each of the antigen binding domains that bind a TAA is the same. In some embodiments, at least a first antigen binding domain and a second antigen binding domain bind to a different TAA or to a different epitope of the same TAA.

In some embodiments, the multispecific polypeptide construct contains in order, from N-terminus to C-terminus: at least two binding domains where one is an antigen binding domain that binds to a tumor-associated antigen (TAA) and the other is a CRBR that binds a co-stimulatory receptor; an immunoglobulin Fc region; a linker; a CD3 binding region that binds CD3 (CD3ε); and at least one antigen binding domain that binds to a TAA. In some embodiments, the N-terminal portion of the multispecific polypeptide construct contains two antigen binding domains that bind to a TAA. In some embodiments, each of the antigen binding domains that bind a TAA is the same. In some embodiments, at least a first antigen binding domain and a second antigen binding domain bind to a different TAA or to a different epitope of the same TAA.

In some embodiments, the multispecific polypeptide construct contains in order, from N-terminus to C-terminus: at least two binding domains where one is an antigen binding domain that binds to a tumor-associated antigen (TAA) and the other is a IRBR that binds an inhibitory receptor; an immunoglobulin Fc region; a linker; a CD3 binding region that binds CD3 (CD3ε); and at least one antigen binding domain that binds to a TAA. In some embodiments, the N-terminal portion of the multispecific polypeptide construct contains two antigen binding domains that bind to a TAA. In some embodiments, each of the antigen binding domains that bind a TAA is the same. In some embodiments, at least a first antigen binding domain and a second antigen binding domain bind to a different TAA or to a different epitope of the same TAA.

In some embodiments, the multispecific polypeptide construct contains in order, from N-terminus to C-terminus: at least two binding domains where one is an antigen binding domain that binds to a tumor-associated antigen (TAA) and the other is a CRBR that binds a co-stimulatory receptor; an immunoglobulin Fc region; a linker; a CD3 binding region that binds CD3 (CD3ε); and at least two binding domain where one is an antigen binding domain that binds to a TAA and the other is a IRBR that binds an inhibitory receptor. In some embodiments, each of the antigen binding domains that bind a TAA is the same. In some embodiments, at least a first antigen binding domain and a second antigen binding domain bind to a different TAA or to a different epitope of the same TAA.

In some embodiments, the multispecific polypeptide construct contains in order, from N-terminus to C-terminus: at least two binding domains where one is an antigen binding domain that binds to a tumor-associated antigen (TAA) and the other is a IRBR that binds an inhibitory receptor; an immunoglobulin Fc region; a linker; a CD3 binding region that binds CD3 (CD3ε); and at least two binding domain where one is an antigen binding domain that binds to a TAA and the other is a CRBR that binds a co-stimulatory receptor. In some embodiments, each of the antigen binding domains that bind a TAA is the same. In some embodiments, at least a first antigen binding domain and a second antigen binding domain bind to a different TAA or to a different epitope of the same TAA.

In some embodiments, the multispecific polypeptide construct is a dimer, in which dimerization is formed by covalent or non-covalent interactions between two polypeptide chains. In some embodiments, the two polypeptide chains are covalently bonded to each other by, for example, interchain disulfide bonds. In some embodiments, the Fc region mediates dimerization via interchain disulfide bonds. In some embodiments, the multispecific polypeptide construct contains a homodimeric Fc region in which, in some cases, both polypeptide chains of the multispecific polypeptide construct are identical (homodimer). In some embodiments, the multispecific polypeptide construct contains a heterodimeric Fc region in which, in some cases, the polypeptide chains of the multispecific polypeptide construct are different (heterodimer). In particular examples of a heterodimeric multispecific polypeptide construct, the CD3-binding region is a two chain polypeptide containing a VH and a VL chain, such as is an Fv antibody fragment containing the VH and VL. In some embodiments, the Fv antibody fragment includes a disulfide stabilized anti-CD3 binding Fv fragment (dsFv).

In some embodiments, the multispecific polypeptide construct is formed from or includes two polypeptides, including a first polypeptide comprising a first Fc polypeptide of a heterodimeric Fc region, a linker, a VH domain of an anti-CD3 antibody or antigen binding fragment (e.g. Fv); and a second polypeptide comprising a second Fc polypeptide of the heterodimeric Fc region, the linker, a VL domain of the anti-CD3 antibody or antigen binding fragment (e.g. Fv). In some embodiments, the first polypeptide contains one or two antigen-binding domain that binds to a TAA or a chain thereof. In some embodiments, the second polypeptide contains one or two antigen-binding domain that binds to a TAA or a chain thereof. In some embodiments, each antigen-binding domain that binds to a TAA is located N-terminally to the Fc polypeptide and/or C-terminally to the chain of the CD3-binding region. In some embodiments, the first polypeptide or second polypeptide or both the first and second polypeptide further includes a CRBR, such that the multispecific polypeptide construct contains at least one CRBR. In some embodiments, the multispecific polypeptide construct contains two CRBR. In some embodiments, the CRBR of the first and/or second polypeptide can be located N-terminally to the Fc polypeptide and/or C-terminally to the chain of the CD3-binding region. In some embodiments, the first polypeptide or second polypeptide or both the first and second polypeptide further includes a IRBR, such that the multispecific polypeptide construct contains at least one IRBR. In some embodiments, the multispecific polypeptide construct contains two IRBR. In some embodiments, the IRBR of the first and/or second polypeptide can be located N-terminally to the Fc polypeptide and/or C-terminally to the chain of the CD3-binding region. In some embodiments, the first polypeptide or second polypeptide or both the first and second polypeptide further includes a CRBR and the first polypeptide or second polypeptide or both the first and second polypeptide further includes a IRBR, such that the multispecific polypeptide construct contains at least one CRBR and at least one IRBR.

Various exemplary multispecific polypeptide constructs containing at least two polypeptide chains are described herein, including in FIGS. 1-3 and 18A-B. Any of such configurations of a multispecific polypeptide construct are contemplated.

In some embodiments, the multispecific polypeptide construct contains at least two antigen binding domains that bind a tumor-associated antigen (TAA) and at least one co-stimulatory receptor binding region (CRBR) that binds a co-stimulatory receptor. In some embodiments, the multispecific polypeptide construct contains (1) a first polypeptide comprising in order of N-terminus to C-terminus: a first antigen binding domain that binds a tumor-associated antigen (TAA), the first Fc polypeptide of a heterodimeric Fc region, a linker (e.g. a cleavable linker), a chain (e.g. VH or VL) of an anti-CD3 antibody or antigen binding fragment (e.g. Fv or dsFv), and a second antigen binding domain that binds a tumor-associated antigen (TAA); and a second polypeptide comprising in order of N-terminus to C-terminus; and (2) a second polypeptide comprising in order of N-terminus to C-terminus: the second Fc polypeptide of the heterodimeric Fc region, the same linker (e.g. same cleavable linker), the other chain (other of the VH or VL) of the anti-CD3 antibody or antigen binding fragment, and a co-stimulatory receptor binding region (CRBR) that binds a co-stimulatory receptor. In some embodiments, the multispecific polypeptide construct contains (1) a first polypeptide comprising in order of N-terminus to C-terminus: a first antigen binding domain that binds a tumor-associated antigen (TAA), the first Fc polypeptide of a heterodimeric Fc region, a linker (e.g. a cleavable linker), a chain (e.g. VH or VL) of an anti-CD3 antibody or antigen binding fragment (e.g. Fv or dsFv), and a second antigen binding domain that binds a tumor-associated antigen (TAA); and a second polypeptide comprising in order of N-terminus to C-terminus; and (2) a second polypeptide comprising in order of N-terminus to C-terminus: a co-stimulatory receptor binding region (CRBR) that binds a co-stimulatory receptor, the second Fc polypeptide of the heterodimeric Fc region, the same linker (e.g. same cleavable linker), and the other chain (other of the VH or VL) of the anti-CD3 antibody or antigen binding fragment.

In some embodiments, the multispecific polypeptide construct contains at least two antigen binding domains that bind a tumor-associated antigen (TAA) and at least one inhibitory receptor binding region (IRBR) that binds an inhibitory receptor. In some embodiments, the multispecific polypeptide construct contains (1) a first polypeptide comprising in order of N-terminus to C-terminus: a first antigen binding domain that binds a tumor-associated antigen (TAA), the first Fc polypeptide of a heterodimeric Fc region, a linker (e.g. a cleavable linker), a chain (e.g. VH or VL) of an anti-CD3 antibody or antigen binding fragment (e.g. Fv or dsFv), and a second antigen binding domain that binds a tumor-associated antigen (TAA); and a second polypeptide comprising in order of N-terminus to C-terminus; and (2) a second polypeptide comprising in order of N-terminus to C-terminus: the second Fc polypeptide of the heterodimeric Fc region, the same linker (e.g. same cleavable linker), the other chain (other of the VH or VL) of the anti-CD3 antibody or antigen binding fragment, and a inhibitory receptor binding region (IRBR) that binds an inhibitory receptor. In some embodiments, the multispecific polypeptide construct contains (1) a first polypeptide comprising in order of N-terminus to C-terminus: a first antigen binding domain that binds a tumor-associated antigen (TAA), the first Fc polypeptide of a heterodimeric Fc region, a linker (e.g. a cleavable linker), a chain (e.g. VH or VL) of an anti-CD3 antibody or antigen binding fragment (e.g. Fv or dsFv), and a second antigen binding domain that binds a tumor-associated antigen (TAA); and a second polypeptide comprising in order of N-terminus to C-terminus; and (2) an inhibitory receptor binding region (IRBR) that binds an inhibitory receptor, a second polypeptide comprising in order of N-terminus to C-terminus: the second Fc polypeptide of the heterodimeric Fc region, the same linker (e.g. same cleavable linker), and the other chain (other of the VH or VL) of the anti-CD3 antibody or antigen binding fragment.

In some embodiments, the multispecific polypeptide construct contains at least two antigen binding domains that bind a tumor-associated antigen (TAA), at least one costimulatory receptor binding region (CRBR) that binds a costimulatory receptor, and at least one inhibitory receptor binding region (IRBR) that binds an inhibitory receptor. In some embodiments, the multispecific polypeptide construct contains (1) a first polypeptide comprising in order of N-terminus to C-terminus: a first antigen binding domain that binds a tumor-associated antigen (TAA), the first Fc polypeptide of a heterodimeric Fc region, a linker (e.g. a cleavable linker), a chain (e.g. VH or VL) of an anti-CD3 antibody or antigen binding fragment (e.g. Fv or dsFv), and a second antigen binding domain that binds a tumor-associated antigen (TAA); and (2) a second polypeptide comprising in order of N-terminus to C-terminus: one of a CRBR or an IRBR, the second Fc polypeptide of the heterodimeric Fc region, the same linker (e.g. same cleavable linker), the other chain (other of the VH or VL) of the anti-CD3 antibody or antigen binding fragment, and the other of the CRBR or IRBR.

Each of the components of the multispecific polypeptide constructs of the disclosure is described in more detail below.

1. Anti-CD3 Binding Domains

The multispecific polypeptide constructs of the disclosure include one or more copies of an anti-CD3 binding domain. The anti-CD3 binding domains of the disclosure activate T cells via engagement of CD3ε on the T cells. The anti-CD3 binding domains of the disclosure agonize, stimulate, activate, and/or otherwise augment CD3-mediated T cell activation. Biological activities of CD3 include, for example, T cell activation and other signaling through interaction between CD3 and the antigen-binding subunits of the T-Cell Receptor (TCR). For example, the anti-CD3 binding domains of the disclosure completely or partially activate T cells via engagement of CD3ε on T cells by partially or completely modulating, e.g., agonizing, stimulating, activating or otherwise augmenting CD3-mediated T cell activation.

In preferred embodiments, the anti-CD3 binding domains of the disclosure specifically bind the epsilon chain of CD3, also known as CD3ε. The anti-CD3ε binding domains of the disclosure activate T cells via engagement of CD3ε on the T cells. The anti-CD3ε binding domains of the disclosure include monoclonal antibodies, such as, for example, mammalian monoclonal antibodies, primate monoclonal antibodies, fully human monoclonal antibodies, as well as humanized monoclonal antibodies and chimeric antibodies, as well as antigen-binding fragments thereof. In some embodiments, the anti-CD3ε binding domain includes one or more copies of an antibody or an antigen-binding fragment thereof.

In some embodiments, the anti-CD3ε binding domain includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the anti-CD3 binding domain includes an Fv antibody fragment that binds CD3ε (referred to herein as an anti-CD3F Fv fragment). In some embodiments, the anti-CD3ε Fv antibody fragment is a disulfide stabilized anti-CD3 binding Fv fragment (dsFv). In some embodiments, the anti-CD3 binding domain is monovalent for binding CD3.

In some embodiments, the CD3 binding region is not a single chain antibody. For example, in some aspects, the CD3 binding region is not a single chain variable fragment (scFv).

In some embodiments, the CD3 binding region is an Fv antibody fragment containing a variable heavy chain (Hv, also called VH) and variable light chain (Lv, also called VL), such as any as described. In aspects of such embodiments, the immunoglobulin Fc region is a heterodimeric Fc region containing two different Fc polypeptides capable of heterodimeric association between both polypeptides of the Fc heterodimer, such as any as described in Section II.2. In such embodiments, the variable heavy chain (Hv) and variable light chain (Lv) of the CD3 binding region are linked on opposite chains of the heterodimeric Fc.

In some embodiments, the anti-CD3ε binding domain includes a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes at least the amino acid sequence TYAMN (SEQ ID NO: 16); a VH CD2 sequence that includes at least the amino acid sequence RIRSKYNNYATYYADSVKD (SEQ ID NO: 17); and a VH CDR3 sequence that includes at least the amino acid sequence HGNFGNSYVSWFAY (SEQ ID NO: 18).

In some embodiments, the anti-CD3ε binding domain includes a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RSSTGAVTTSNYAN (SEQ ID NO: 19); a VL CDR2 sequence that includes at least the amino acid sequence GTNKRAP (SEQ ID NO: 20); and a VL CDR3 sequence that includes at least the amino acid sequence ALWYSNLWV (SEQ ID NO: 21).

In some embodiments, the anti-CD3ε binding domain includes a VH CDR1 sequence that includes at least the amino acid sequence TYAMN (SEQ ID NO: 16); a VH CD2 sequence that includes at least the amino acid sequence RIRSKYNNYATYYADSVKD (SEQ ID NO: 17); a VH CDR3 sequence that includes at least the amino acid sequence HGNFGNSYVSWFAY (SEQ ID NO: 18), a VL CDR1 sequence that includes at least the amino acid sequence RSSTGAVTTSNYAN (SEQ ID NO: 19); a VL CDR2 sequence that includes at least the amino acid sequence GTNKRAP (SEQ ID NO: 20); and a VL CDR3 sequence that includes at least the amino acid sequence ALWYSNLWV (SEQ ID NO: 21).

In some embodiments, the anti-CD3ε binding domain includes a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence TYAMN (SEQ ID NO: 16); a VH CD2 sequence that includes a sequence that is at least 90%, 91%, 92%, 93%, 94%, 95%, 96%, 97%, 98%, 99% or more identical to the amino acid sequence RIRSKYNNYATYYADSVKD (SEQ ID NO: 17); and a VH CDR3 sequence that includes a sequence that is at least 90%, 91%, 92%, 93%, 94%, 95%, 96%, 97%, 98%, 99% or more identical to the amino acid sequence HGNFGNSYVSWFAY (SEQ ID NO: 18).

In some embodiments, the anti-CD3ε binding domain includes a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RSSTGAVTTSNYAN (SEQ ID NO: 19); a VL CDR2 sequence that includes a sequence that is at least 90%, 91%, 92%, 93%, 94%, 95%, 96%, 97%, 98%, 99% or more identical to the amino acid sequence GTNKRAP (SEQ ID NO: 20); and a VL CDR3 sequence that includes a sequence that is at least 90%, 91%, 92%, 93%, 94%, 95%, 96%, 97%, 98%, 99% or more identical to the amino acid sequence ALWYSNLWV (SEQ ID NO: 21).

In some embodiments, the anti-CD3ε binding domain includes a VH CDR1 sequence that includes at least the amino acid sequence GFTFNTYAMN (SEQ ID NO: 312); a VH CDR2 sequence that includes at least the amino acid sequence RIRSKYNNYATY (SEQ ID NO: 318); a VH CDR3 sequence that includes at least the amino acid sequence HGNFGNSYVSWFAY (SEQ ID NO: 18), a VL CDR1 sequence that includes at least the amino acid sequence RSSTGAVTTSNYAN (SEQ ID NO: 19); a VL CDR2 sequence that includes at least the amino acid sequence GTNKRAP (SEQ ID NO: 20); and a VL CDR3 sequence that includes at least the amino acid sequence ALWYSNLWV (SEQ ID NO: 21).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence TYAMN (SEQ ID NO: 16); a VH CD2 sequence that is at least 90%, 91%, 92%, 93%, 94%, 95%, 96%, 97%, 98%, 99% or more identical to the amino acid sequence RIRSKYNNYATYYADSVKD (SEQ ID NO: 17); a VH CDR3 sequence that is at least 90%, 91%, 92%, 93%, 94%, 95%, 96%, 97%, 98%, 99% or more identical to the amino acid sequence HGNFGNSYVSWFAY (SEQ ID NO: 18), a VL CDR1 sequence that is at least 90%, 91%, 92%, 93%, 94%, 95%, 96%, 97%, 98%, 99% or more identical to the amino acid sequence RSSTGAVTTSNYAN (SEQ ID NO: 19); a VL CDR2 sequence that is at least 90%, 91%, 92%, 93%, 94%, 95%, 96%, 97%, 98%, 99% or more identical to the amino acid sequence GTNKRAP (SEQ ID NO: 20); and a VL CDR3 sequence that is at least 90%, 91%, 92%, 93%, 94%, 95%, 96%, 97%, 98%, 99% or more identical to the amino acid sequence ALWYSNLWV (SEQ ID NO: 21).

In some embodiments, the anti-CD3ε binding domain includes a VH CDR1 sequence that includes at least the amino acid sequence GFTFNTYAMN (SEQ ID NO: 312); a VH CDR2 sequence that includes at least the amino acid sequence RIRSKYNNYATY (SEQ ID NO: 318; a VH CDR3 sequence that includes at least the amino acid sequence HGNFGNSYVSWFAY (SEQ ID NO: 18), a VL CDR1 sequence that includes at least the amino acid sequence GSSTGAVTTSNYAN (SEQ ID NO: 319); a VL CDR2 sequence that includes at least the amino acid sequence GTNKRAP (SEQ ID NO: 320); and a VL CDR3 sequence that includes at least the amino acid sequence ALWYSNHWV (SEQ ID NO: 315).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFNTYAMN (SEQ ID NO: 312); a VH CDR2 sequence that is at least 90%, 91%, 92%, 93%, 94%, 95%, 96%, 97%, 98%, 99% or more identical to the amino acid sequence RIRSKYNNYATY (SEQ ID NO: 313); a VH CDR3 sequence that is at least 90%, 91%, 92%, 93%, 94%, 95%, 96%, 97%, 98%, 99% or more identical to the amino acid sequence HGNFGNSYVSWFAY (SEQ ID NO: 18), a VL CDR1 sequence that is at least 90%, 91%, 92%, 93%, 94%, 95%, 96%, 97%, 98%, 99% or more identical to the amino acid sequence GSSTGAVTTSNYAN (SEQ ID NO: 319); a VL CDR2 sequence that is at least 90%, 91%, 92%, 93%, 94%, 95%, 96%, 97%, 98%, 99% or more identical to the amino acid sequence GTNKRAP (SEQ ID NO: 320); and a VL CDR3 sequence that is at least 90%, 91%, 92%, 93%, 94%, 95%, 96%, 97%, 98%, 99% or more identical to the amino acid sequence ALWYSNHWV (SEQ ID NO: 315).

In some embodiments, the anti-CD3ε binding domain thereof is an Fv fragment that includes a combination of heavy chain variable amino acid sequence and a light chain variable amino acid sequence. In some embodiments, the anti-CD3ε binding domain thereof is an Fv fragment that includes a combination of heavy chain variable amino acid sequence and a light chain variable amino acid sequence comprising an amino acid sequence that is at least 90%, 91%, 92%, 93%, 94%, 95%, 96%, 97%, 98%, 99% or more identical to an amino acid sequence selected from the group consisting of SEQ ID NOs: 32-81 and 241. In some embodiments, the anti-CD3ε binding domain thereof is an Fv fragment that includes a combination of heavy chain variable amino acid sequence and a light chain variable amino acid sequence comprising an amino acid sequence selected from the group consisting of SEQ ID NOs: 32-81 and 241. In some embodiments, the anti-CD3ε binding domain thereof is an Fv fragment that includes a combination of a heavy chain variable amino acid sequence selected from the group of SEQ ID NO: 32-62 and a light chain variable amino acid sequence selected from the group consisting of SEQ ID NO: 63-81 and 241. In some embodiments, the anti-CD3ε binding domain thereof is an Fv fragment that includes a combination of a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 32-62 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 63-81 and 241 an amino acid sequence.

In some embodiments, the anti-CD3ε binding domain thereof includes a combination of a heavy chain variable region amino acid sequence and a light chain variable region amino acid sequence comprising an amino acid sequence selected from the group of SEQ ID NO: 32-81 and 241. In some embodiments, the anti-CD3ε binding domain thereof includes a combination of a heavy chain variable region amino acid sequence selected from the group of SEQ ID NO: 32-62 and a light chain variable region amino acid sequence comprising an amino acid sequence selected from the group of SEQ ID NO: 63-81 and 241.

In some embodiments, the anti-CD3ε Fv antibody fragment includes a combination of heavy chain variable amino acid sequence and a light chain variable amino acid sequence selected from the group of SEQ ID NO: 14, 15, 32-81, 241, 287-291 and 311. In some embodiments, the anti-CD3ε Fv antibody fragment includes a combination of heavy chain variable amino acid sequence and a light chain variable amino acid sequence that is at least 90%, 91%, 92%, 93%, 94%, 95%, 96%, 97%, 98%, 99% or more identical to an amino acid sequence selected from the group consisting of SEQ ID NO: 14, 15, 32-81, 241, 287-291, and 311. In some embodiments, the anti-CD3ε Fv antibody fragment includes a combination of a variable heavy chain amino acid sequence selected from the group of SEQ ID NO: 14, 32-62, and 287, 290, and 311 and a variable light chain amino acid sequence selected from the group consisting of SEQ ID NO: 15, 63-81, 241, 288 and 289. In some embodiments, the anti-CD3ε Fv antibody fragment includes a combination of a variable heavy chain amino acid sequence that is at least 90%, 91%, 92%, 93%, 94%, 95%, 96%, 97%, 98%, 99% or more identical to an amino acid sequence selected from the group consisting of SEQ ID NO: 14, 32-62, 287, 290 and 311, and a variable light chain amino acid sequence that is at least 90%, 91%, 92%, 93%, 94%, 95%, 96%, 97%, 98%, 99% or more identical to an amino acid sequence selected from the group consisting of SEQ ID NO: 15, 63-81, 241, 288 and 289.

In some embodiments, the anti-CD3ε binding domain thereof is an Fv fragment that includes a combination of heavy chain variable amino acid sequence and a light chain variable amino acid sequence. In some embodiments, the anti-CD3ε Fv antibody fragment includes a combination of a variable heavy chain amino acid sequence that is at least 90%, 91%, 92%, 93%, 94%, 95%, 96%, 97%, 98%, 99% or more identical to an amino acid sequence selected from the group consisting of SEQ ID NO: 14, 32-43, 45-47, 48 and 287 and a variable light chain amino acid sequence that is at least 90%, 91%, 92%, 93%, 94%, 95%, 96%, 97%, 98%, 99% or more identical to an amino acid sequence selected from the group consisting of SEQ ID NO: 15, 63, 65-71, 73, 75, 77, and 288. In some embodiments, the anti-CD3ε Fv antibody fragment includes a combination of a variable heavy chain amino acid sequence selected from the group of SEQ ID NO: 14, 32-43, 45-47, 48 and 287 and a variable light chain amino acid sequence selected from the group consisting of SEQ ID NO: 15, 63, 65-71, 73, 75, 77, and 288.

In some embodiments, the anti-CD3ε binding domain thereof includes a variable heavy chain (Hv) comprising an amino acid sequence that is at least 90%, 91%, 92%, 93%, 94%, 95%, 96%, 97%, 98%, 99% or more identical to the amino acid sequence of SEQ ID NO: 14. In some embodiments, the anti-CD3ε binding domain includes a variable light chain (Lv) comprising an amino acid sequence that is at least 90%, 91%, 92%, 93%, 94%, 95%, 96%, 97%, 98%, 99% or more identical to the amino acid sequence of SEQ ID NO: 15. In some embodiments, the anti-CD3ε binding domain thereof includes a variable heavy chain (Hv) comprising an amino acid sequence that is at least 90%, 91%, 92%, 93%, 94%, 95%, 96%, 97%, 98%, 99% or more identical to the amino acid sequence of SEQ ID NO: 14 and a variable light chain (Lv) comprising an amino acid sequence that is at least 90%, 91%, 92%, 93%, 94%, 95%, 96%, 97%, 98%, 99% or more identical to the amino acid sequence of SEQ ID NO: 15. In some embodiments, the anti-CD3ε binding domain thereof includes a variable heavy chain (Hv) comprising the amino acid sequence of SEQ ID NO: 14. In some embodiments, the anti-CD3ε binding domain includes a variable light chain (Lv) comprising the amino acid sequence of SEQ ID NO: 15. In some embodiments, the anti-CD3ε binding domain thereof includes a variable heavy chain (Hv) comprising the amino acid sequence of SEQ ID NO: 14 and a variable light chain (Lv) comprising the amino acid sequence of SEQ ID NO: 15.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 287. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 288. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 287 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 288. In some embodiments, the anti-CD3ε binding domain thereof includes a variable heavy chain (VH) comprising the amino acid sequence of SEQ ID NO: 287. In some embodiments, the anti-CD3ε binding domain includes a variable light chain (VL) comprising the amino acid sequence of SEQ ID NO: 288. In some embodiments, the anti-CD3ε binding domain thereof includes a variable heavy chain (VH) comprising the amino acid sequence of SEQ ID NO: 287 and a variable light chain (VL) comprising the amino acid sequence of SEQ ID NO: 288.

In particular embodiments, the Fv is a disulfide stabilized Fv fragment (dsFv) in which the the $V_H$-$V_L$ heterodimer is stabilized by an interchain disulfide bond. In some embodiments, the interchain disulfide bond is engineered by mutation of position in framework positions of the VH and/or VL chain. In some embodiments, the VH chain contains the mutation at position 44 with Cys and the VL chain contains the mutation at position 100 with Cys, each by kabat numbering. For example, in some embodiments, the VH chain contains the mutation G44C and the VL chain contains the mutation G100C, each by kabat numbering. In some embodiments, the disulfide stabilized anti-CD3 Fv comprises an anti-CD3 VH with the mutation at position 105 to Cys and an anti-CD3 VL with the mutation position 43 to Cys by Kabat numbering.

In some embodiments, the anti-CD3ε Fv antibody fragment includes a combination of a variable heavy chain amino acid sequence that is at least 90%, 91%, 92%, 93%, 94%, 95%, 96%, 97%, 98%, 99% or more identical to an amino acid sequence selected from the group consisting of SEQ ID NO: 44 and 49-62, 290, and 311, and a variable light chain amino acid sequence that is at least 90%, 91%, 92%, 93%, 94%, 95%, 96%, 97%, 98%, 99% or more identical to an amino acid sequence selected from the group consisting of SEQ ID NO: 64, 72, 74, 76, 78-81, 241, and 289. In some of any such embodiments, the anti-CD3 Fv is a dsFv that has a VH chain containing the mutation G44C and a VL chain containing the mutation G100C, each by kabat numbering. In some embodiments, the anti-CD3ε Fv antibody fragment includes a combination of a variable heavy chain amino acid sequence selected from the group of SEQ ID NO: 44 and 49-62, 290, and 311 and a variable light chain amino acid sequence selected from the group consisting of SEQ ID NO: 64, 72, 74, 76, 78-81, 241, and 289.

In some embodiments, the anti-CD3ε binding domain thereof includes a variable heavy chain (Hv) comprising an amino acid sequence that is at least 90%, 91%, 92%, 93%, 94%, 95%, 96%, 97%, 98%, 99% or more identical to the amino acid sequence of SEQ ID NO: 44. In some embodiments, the anti-CD3ε binding domain includes a variable light chain (Lv) comprising an amino acid sequence that is at least 90%, 91%, 92%, 93%, 94%, 95%, 96%, 97%, 98%, 99% or more identical to the amino acid sequence of SEQ ID NO: 72. In some embodiments, the anti-CD3ε binding domain thereof includes a variable heavy chain (Hv) comprising an amino acid sequence that is at least 90%, 91%, 92%, 93%, 94%, 95%, 96%, 97%, 98%, 99% or more identical to the amino acid sequence of SEQ ID NO: 44 and a variable light chain (Lv) comprising an amino acid sequence that is at least 90%, 91%, 92%, 93%, 94%, 95%, 96%, 97%, 98%, 99% or more identical to the amino acid sequence of SEQ ID NO: 72. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (Hv) comprising the amino acid sequence of SEQ ID NO: 44. In some embodiments, the anti-CD3ε binding domain includes a variable light chain (Lv) comprising the amino acid sequence of SEQ ID NO: 72. In some embodiments, the anti-CD3ε binding domain thereof includes a variable heavy chain (Hv) comprising the amino acid sequence of SEQ ID NO: 44 and a variable light chain (Lv) comprising the amino acid sequence of SEQ ID NO: 72.

In some embodiments, the anti-CD3ε binding domain thereof includes a variable heavy chain (Hv) comprising an amino acid sequence that is at least 90%, 91%, 92%, 93%, 94%, 95%, 96%, 97%, 98%, 99% or more identical to the amino acid sequence of SEQ ID NO: 44. In some embodiments, the anti-CD3ε binding domain includes a variable light chain (Lv) comprising an amino acid sequence that is at least 90%, 91%, 92%, 93%, 94%, 95%, 96%, 97%, 98%, 99% or more identical to the amino acid sequence of SEQ ID NO: 241. In some embodiments, the anti-CD3ε binding domain thereof includes a variable heavy chain (Hv) comprising an amino acid sequence that is at least 90%, 91%, 92%, 93%, 94%, 95%, 96%, 97%, 98%, 99% or more identical to the amino acid sequence of SEQ ID NO: 44 and a variable light chain (Lv) comprising an amino acid sequence that is at least 90%, 91%, 92%, 93%, 94%, 95%, 96%, 97%, 98%, 99% or more identical to the amino acid sequence of SEQ ID NO: 241. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (Hv) comprising the amino acid sequence of SEQ ID NO: 44. In some embodiments, the anti-CD3ε binding domain includes a variable light chain (Lv) comprising the amino acid sequence of SEQ ID NO: 241. In some embodiments, the anti-CD3ε binding domain thereof includes a variable heavy chain (Hv) comprising the amino acid sequence of SEQ ID NO: 44 and a variable light chain (Lv) comprising the amino acid sequence of SEQ ID NO: 241.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 290. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 289. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 290 and a variable light chain (VL) comprising an amino acid sequence that is at least 90%, 91%, 92%, 93%, 94%, 95%, 96%, 97%, 98%, 99% or more identical to the amino acid sequence of SEQ ID NO:289. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (VH) comprising the amino acid sequence of SEQ ID NO: 290. In some embodiments, the anti-CD3ε binding domain includes a variable light chain (VL) comprising the amino acid sequence of SEQ ID NO: 289. In some embodiments, the anti-CD3ε binding domain thereof includes a variable heavy chain (VH) comprising the amino acid sequence of SEQ ID NO: 290 and a variable light chain (VL) comprising the amino acid sequence of SEQ ID NO:289.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 311. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 289. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO:311 and a variable light chain (VL) comprising an amino acid sequence that is at least 90%, 91%, 92%, 93%, 94%, 95%, 96%, 97%, 98%, 99% or more identical to the amino acid sequence of SEQ ID NO:289. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (VH) comprising the amino acid sequence of SEQ ID NO: 311. In some embodiments, the anti-CD3ε binding domain includes a variable light chain (VL) comprising the amino acid sequence of SEQ ID NO: 289. In some embodiments, the anti-CD3ε binding domain thereof includes a variable heavy chain (VH) comprising the amino acid sequence of SEQ ID NO: 311 and a variable light chain (VL) comprising the amino acid sequence of SEQ ID NO:289.

2. Immunoglobulin Fc Polypeptides

The multispecific polypeptide constructs of the disclosure includes an immunoglobulin Fc region. In some embodiments, the immunoglobulin Fc region is an IgG isotype selected from the group consisting of IgG1 isotype, IgG2 isotype, IgG3 isotype, and IgG4 subclass. In some embodiments, the Fc region is a human Fc. In some embodiments, the immunoglobulin Fc region is a polypeptide comprising an amino acid sequence selected from the group consisting of SEQ ID NOs: 1-6. In some embodiments, the immunoglobulin Fc region contains an Fc chain that is an immunologically active fragment of any of SEQ ID Nos: 1-6. In some embodiments, the immunoglobulin Fc region contains an Fc polypeptide chain that is at least 50%, 60%, 65%, 70%, 75%, 80%, 85%, 90%, 91%, 92%, 93%, 94%, 95%, 96%, 97%, 98%, or 99% identical to the amino acid sequence of any of SEQ ID NOs: 1-6 or an immunologically active fragment thereof.

In some embodiments, the multispecific polypeptide construct is a dimer formed by polypeptides, each containing an Fc. In some specific embodiments, identical or substantially identical polypeptides will be dimerized to create a homodimer. In some embodiments, the dimer is a homodimer in which the two polypeptides of the multispecific polypeptide construct are the same. In other cases, the Fc region is formed by Fc domains that are mutated or modified to promote heterodimerization in which different polypeptides can be dimerized to yield a heterodimer. Thus, in some embodiments, the dimer is a heterodimer in which two polypeptide chains of the multispecific polypeptide construct are different. Exemplary modifications to promote heterodimerization are known, including any as described below.

In general, the Fc region is responsible for effector functions, such as complement-dependent cytotoxicity (CDC) and antibody-dependent cell cytotoxicity (ADCC), in addition to the antigen-binding capacity, which is the main function of immunoglobulins. Additionally, the FcRn sequence present in the Fc region plays the role of regulating the IgG level in serum by increasing the in vivo half-life by conjugation to an in vivo FcRn receptor. In some embodiments, such functions can be altered, such as reduced or enhanced, in an Fc for use with the provided multispecific polypeptide constructs.

In some embodiments, the Fc region of the provided multispecific polypeptide constructs exhibit one or more effector functions. In some cases, the Fc region is capable of providing Fc-mediated effector functions, such as for example, ADCC (e.g., release of granzyme B by NK cells), ADCP, and/or CDC. In some embodiments in which the multispecific polypeptide constructs contain a cleavable linker, cleavage of the linker can produce two components that each have biological activity: the CD3-binding region that is able to bind and engage CD3 on a T cell, which, in some aspects, also can contain the CRBR for inducing a costimulatory signal on the T cell; and the Fc region linked to the TAA-antigen binding domain that can exhibit target-specific effector function. In particular embodiments provided herein, the multispecific polypeptide constructs contain a non-cleavable linker and may, in some aspects, not exhibit an independent Fc-mediated effector function.

In some embodiments, the Fc region includes an Fc polypeptide that is mutated or modified to alter one or more effector functions. Various examples of mutations to Fc polypeptides to alter, such as reduce, effector function are known, including any as described below. In some embodiments, reference to amino acid substitutions in an Fc region is by EU numbering by Kabat (also called Kabat numbering) unless described with reference to a specific SEQ ID NO. EU numbering is known and is according to the most recently updated IMGT Scientific Chart (IMGT®, the international ImMunoGeneTics information System®, www.imgt.org/IMGTScientificChart/Numbering/Hu_IGHGnber.html (created: 17 May 2001, last updated: 10 Jan. 2013) and the EU index as reported in Kabat, E. A. et al. Sequences of Proteins of Immunological interest. 5th ed. US Department of Health and Human Services, NIH publication No. 91-3242 (1991).

In some embodiments, provided multispecific polypeptide constructs that contain an Fc region that exhibits reduced effector functions, may be a desirable candidate for applications in which constrained CD3 binding is desired yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the multispecific polypeptide constructs and/or cleaved components thereof lack FcγR binding (hence likely lacking ADCC activity), but retains FcRn binding ability. The primary cells for mediating ADCC, NK cells, express FcγRIII only, whereas monocytes express FcγRI, FcγRII and FcγRIII. Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the multispecific polypeptide construct or cleaved components thereof is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

In some embodiments, the immunoglobulin Fc region or immunologically active fragment thereof is an IgG isotype. For example, the immunoglobulin Fc region of the fusion protein is of human IgG1 isotype, having an amino acid sequence:

```
                                        (SEQ ID NO: 1)
PAPELLGGPS VFLFPPKPKD TLMISRTPEV TCVVVDVSHE

DPEVKFNWYV DGVEVHNAKT KPREEQYNST YRVVSVLTVL

HQDWLNGKEY KCKVSNKALP APIEKTISKA KGQPREPQVY

TLPPSRDELT KNQVSLTCLV KGFYPSDIAV EWESNGQPEN

NYKTTPPVLD SDGSFFLYSK LTVDKSRWQQ GNVFSCSVMH

EALHNHYTQK SLSLSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 1.

In some embodiments, an IgG1 Fc polypeptide or a variant thereof such as any described below can be made in a G1 m1 or G1 m3 allotype. In some embodiments, the Fc region can contain amino acids of the human G1 m1 allotype, such as residues containing Asp (D) and Leu (L) at positions 356 and 358, e.g. as set forth in SEQ ID NO:1. In some cases, an Fc polypeptide can contain amino acid substitutions E356D and M358L to reconstitute residues of allotype G1 m1. In other embodiments, the Fc region can contain amino acids of the human G1 m3 allotype, such as residues Glu (E) and Met (M) at positions 356 and 358 by EU numbering, e.g. as set forth in SEQ ID NOS: 194 and 195. In some cases, an Fc polypeptide can contain amino acid substitutions D356E and L358M to reconstitute residues of allotype G1 m3.

In some embodiments, the human IgG1 Fc region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11, the contents of each of which are hereby incorporated by reference in their entireties.

In some embodiments, the Fc region, such as the human IgG1 Fc region is modified to enhance ADCC activity or CDC activity. Examples of mutations that enhance ADCC include modification at Ser239 and Ile332, for example Ser239Asp and Ile332Glu (S239D, I332E). Examples of mutations that enhance CDC include modifications at Lys326 and Glu333. In some embodiments, the Fc region is modified at one or both of these positions, for example Lys326Ala and/or Glu333Ala (K326A and E333A) using the Kabat numbering system.

In some embodiments, the Fc region is altered to provide reduced Fc-mediated effector functions, such as via reduced Fc receptor binding, e.g. binding to FcγR binding but generally not FcRn binding. In some embodiments, the human IgG1 Fc region fusion proteins of the present disclosure lack or have reduced Fucose attached to the N-linked glycan-chain at N297. There are numerous ways to prevent fucosylation, including but not limited to production in a FUT8 deficient cell line; addition inhibitors to the mammalian cell culture media, for example Castanospermine; and metabolic engineering of the production cell line. In some embodiments, the human IgG1 Fc region is modified at amino acid Asn297 (Boxed, Kabat Numbering) to prevent glycosylation of the fusion protein, e.g., Asn297Ala (N297A) or Asn297Asp (N297D).

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In some embodiments, the Fc region of the fusion protein is modified at amino acid Leu235 (Boxed in SEQ ID NO:1 above, Kabat Numbering) to alter Fc receptor interactions, e.g., Leu235Glu (L235E) or Leu235Ala (L235A). In some embodiments, the Fc region of the fusion protein is modified at amino acid Leu234 (Boxed in SEQ ID NO:1 above, Kabat Numbering) to alter Fc receptor interactions, e.g., Leu234Ala (L234A). In some embodiments, the Fc region of the fusion protein is altered at both amino acid 234 and 235, e.g., Leu234Ala and Leu235Ala (L234A/L235A) or Leu234Val and Leu235Ala (L234V/L235A). In preferred embodiments, modifications within the Fc region reduce binding to Fc-receptor-gamma receptors while have minimal impact on binding to the neonatal Fc receptor (FcRn).

In some embodiments, the human IgG Fc region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et al 2006, *J. Biol Chem Vol.* 281(33) 23514-23524), Met428Leu and Asn434Ser (M428L, N434S) (Zalevsky et al 2010 *Nature Biotech*, Vol. 28(2) 157-159) (EU index of Kabat et al 1991 *Sequences of Proteins of Immunological Interest*). In some embodiments, the mutated or modified Fc polypeptide includes the following mutations: Met252Tyr and Met428Leu or Met252Tyr and Met428Val (M252Y, M428L, or M252Y, M428V) using the Kabat numbering system.

In some embodiments, the Fc region of the fusion protein is lacking an amino acid at one or more of the following positions to reduce Fc receptor binding: Glu233 (E233), Leu234 (L234), or Leu235 (L235). In these embodiments, Fc deletion of these three amino acids reduces the complement protein C1q binding.

```
                                            (SEQ ID NO: 2)
PAPGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSRDELTKNQ VSLTCLVKGF YPSDIAVEWE SNGQPENNYK

TTPPVLDSDG SFFLYSKLTV DKSRWQQGNV FSCSVMHEAL

HNHYTQKSLS LSPGK
```

In some embodiments, the Fc region is mutated in one or more of the following positions to reduce Fc receptor binding: Glu233 (E233), Leu234 (L234), or Leu235 (L235). The one or more mutations can include E233P, L234V and/or L235A.

In some embodiments, the Fc region of the fusion protein is altered at Gly236 (boxed in SEQ ID NO:1 above) to reduce Fc receptor binding. For example, wherein Gly236 is deleted from the fusion protein. In some embodiments, the human IgG1 Fc region is modified at amino acid Gly236 to enhance the interaction with CD32A, e.g., Gly236Ala (G236A).

In particular embodiments, the mutations of the Fc region to reduce Fc effector function, e.g. via reducing Fc receptor binding to FcγR, include mutations from among any of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G or E233P/L234V/L235A/G236del.

In some embodiments, the human IgG1 Fc region lacks Lys447 (EU index of Kabat et al 1991 *Sequences of Proteins of Immunological Interest*).

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 2.

In some embodiments, the immunoglobulin Fc region or immunologically active fragment of the fusion protein is of human IgG2 isotype, having an amino acid sequence:

(SEQ ID NO: 3)
PAPPVAGPSV FLFPPKPKDT LMISRTPEVT CVVVDVSHED

PEVQFNWYVD GVEVHNAKTK PREEQF[N]STF RVVSVLTVVH

QDWLNGKEYK CKVSNKGLPA PIEKTISKTK GQPREPQVYT

LPPSREEMTK NQVSLTCLVK GFYPSDISVE WESNGQPENN

YKTTPPMLDS DGSFFLYSKL TVDKSRWQQG NVFSCSVMHE

ALHNHYTQKS LSLSPGK

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 3.

In some embodiments, the human IgG2 Fc region is modified at amino acid Asn297 (Boxed, to prevent to glycosylation of the antibody, e.g., Asn297Ala (N297A) or Asn297Asp (N297D). In some embodiments, the human IgG2 Fc region lacks Lys447 (EU index of Kabat et al 1991 *Sequences of Proteins of Immunological Interest*).

In some embodiments, the immunoglobulin Fc region or immunologically active fragment of the fusion protein is of human IgG3 isotype, having an amino acid sequence:

(SEQ ID NO: 4)
PAPELLGGPS VFLFPPKPKD TLMISRTPEV TCVVVDVSHE

DPEVQFKWYV DGVEVHNAKT KPREEQY[N]ST FRVVSVLTVL

HQDWLNGKEY KCKVSNKALP APIEKTISKT KGQPREPQVY

TLPPSREEMT KNQVSLTCLV KGFYPSDIAV EWESSGQPEN

NYNTTPPMLD SDGSFFLYSK LTVDKSRWQQ GNIFSCSVMH

EALHN[R]FTQK SLSLSPGK

In some embodiments, the antibody or immunologically active fragment thereof comprises a human IgG3 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 4.

In some embodiments, the human IgG3 Fc region is modified at amino acid Asn297 (Boxed, Kabat Numbering) to prevent to glycosylation of the antibody, e.g., Asn297Ala (N297A) or Asn297Asp (N297D). In some embodiments, the human IgG3 Fc region is modified at amino acid 435 to extend the half-life, e.g., Arg435His (R435H). In some embodiments, the human IgG3 Fc region lacks Lys447 (EU index of Kabat et al 1991 *Sequences of Proteins of Immunological Interest*).

In some embodiments, the immunoglobulin Fc region or immunologically active fragment of the fusion protein is of human IgG4 isotype, having an amino acid sequence:

(SEQ ID NO: 5)
PAPE[FL]GGPS VFLFPPKPKD TLMISRTPEV TCVVVDVSQE

DPEVQFNWYV DGVEVHNAKT KPREEQF[N]ST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLGK

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 5.

In some embodiments, the immunoglobulin Fc region or immunologically active fragment of the fusion protein is of human IgG4 isotype, having an amino acid sequence:

(SEQ ID NO: 6)
PAPELLGGPS VFLFPPKPKD TLMISRTPEV TCVVVDVSQE

DPEVQFNWYV DGVEVHNAKT KPREEQF[N]ST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLGK

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 6.

In other embodiments, the human IgG4 Fc region is modified at amino acid 235 to alter Fc receptor interactions, e.g., Leu235Glu (L235E). In some embodiments, the human IgG4 Fc region is modified at amino acid Asn297 (Boxed, Kabat Numbering) to prevent to glycosylation of the antibody, e.g., Asn297Ala (N297A) or Asn297Asp (N297D). In some embodiments, the human IgG4 Fc region lacks Lys447 (EU index of Kabat et al 1991 *Sequences of Proteins of Immunological Interest*).

In some embodiments, the human IgG Fc region is modified to stabilize the homodimerization at the CH3:CH3 interface by introducing two disulfide bonds by changing Ser354 to Cys (S354C) and Tyr349 to Cys (Y349C) (S354C/Y349C).

In particular embodiments of multispecific polypeptide constructs provided herein, the human IgG Fc region is modified to induce heterodimerization. Various methods are known for promoting heterodimerization of complementary Fc polypeptides, see e.g. Ridgway et al, Protein Eng. 9:617-621 (1996); Merchant et al, Nat. Biotechnol. 16(7): 677-81 (1998); Moore et al. (2011) MAbs, 3:546-57; Von Kreudenstein et al. MAbs, (2013) 5:646-54; Gunasekaran et al. (2010) J. Biol. Chem., 285:19637-46; Leaver-Fay et al. (2016) Structure, 24:641-51; Ha et al. (2016) Frontiers in Immunology, 7:1; Davis et al. (2010) Protein Eng Des Sel, 23:195-202; published international PCT Appl. No. WO 1998/050431, WO 2009/089004, WO2011143545 WO 2014/067011, WO 2012/058768, WO2018027025; published U.S. patent Appl. No. US20140363426, US20150307628, US20180016354, US20150239991; and U.S. Pat. Nos. 5,731,168, 7,183,076, 9,701,759, 9,605,084, and 9,650,446. Methods to promote heterodimerization of Fc chains include mutagenesis of the Fc region, such as by including a set of "knob-into-hole" mutations or including mutations to effect electrostatic steering of the Fc to favor attractive interactions among different polypeptide chains. For example, in some embodiments, the Fc polypeptides of a heterodimer includes a mutation to alter charge polarity across the Fc dimer interface such that coexpression of electrostatically matched Fc chains support favorable attractive interactions thereby promoting desired Fc heterodimer formation, whereas unfavorable repulsive charge interactions suppress unwanted Fc homodimer formation (Guneskaran et al. (2010) JBC, 285: 19637-19646). When co-expressed in a cell, association between the chains is possible but the chains do not substantially self-associate due to charge repulsion. Other strategies for generating a heterodimeric Fc include mixing human IgG and IgA CH3 domain segments to create a complementary CH3 heterodimer, which is referred to as a SEED Fc.

Methods and variants for heterodimerization also include those described in published international PCT App. WO2014/145806, including "knobs and holes" mutations (also called "skew" variants), mutations that relate to "electrostatic steering" or "charge pairs," and pI variants. Heterodimeric variants also include any as described in U.S. published Appl. No. US2012/0149876 or US2018/011883.

In some embodiments, to promote heterodimerization both polypeptides of the Fc heterodimer contain paired or complementary amino acid modifications. Exemplary paired amino acid modification of polypeptides of an Fc fusion are set forth in Table 1.

TABLE 1

Paired amino acids of Heterodimeric Fc

| First Fc polypeptide | Second Fc Polypeptide |
| --- | --- |
| T366W | T366S/L368W/Y407V |
| T366W/S354C | T366S/L368A/Y407V/Y349C |
| S364H/F405A | Y349T/Y349F |
| T350V/L351Y/F405A/Y407V | T350V/T366L/K392L/T394W |
| K360D/D399M/Y407A | E345R/Q347R/T366V/K409V |
| K409D/K392D | D399K/E356K |
| K360E/K409W | Q347R/D399V/F405T |
| L360E/K409W/Y349C | Q347R/399V/F405T/S354C |
| K370E/K409W | E357N/D399V/F405T |

In some embodiments, modifications include introduction of a protuberance (knob) into a first Fc polypeptide and a cavity (hole) into a second Fc polypeptide such that the protuberance is positionable in the cavity to promote complexing of the first and second Fc-containing polypeptides. Amino acids targeted for replacement and/or modification to create protuberances or cavities in a polypeptide are typically interface amino acids that interact or contact with one or more amino acids in the interface of a second polypeptide.

In some embodiments, a first Fc polypeptide that is modified to contain protuberance (hole) amino acids include replacement of a native or original amino acid with an amino acid that has at least one side chain which projects from the interface of the first Fc polypeptide and is therefore positionable in a compensatory cavity (hole) in an adjacent interface of a second polypeptide. Most often, the replacement amino acid is one which has a larger side chain volume than the original amino acid residue. One of skill in the art knows how to determine and/or assess the properties of amino acid residues to identify those that are ideal replacement amino acids to create a protuberance. In some embodiments, the replacement residues for the formation of a protuberance are naturally occurring amino acid residues and include, for example, arginine (R), phenylalanine (F), tyrosine (Y), or tryptophan (W). In some examples, the original residue identified for replacement is an amino acid residue that has a small side chain such as, for example, alanine, asparagine, aspartic acid, glycine, serine, threonine, or valine.

In some embodiments, a second Fc polypeptide that is modified to contain a cavity (hole) is one that includes replacement of a native or original amino acid with an amino acid that has at least one side chain that is recessed from the interface of the second polypeptide and thus is able to accommodate a corresponding protuberance from the interface of a first polypeptide. Most often, the replacement amino acid is one which has a smaller side chain volume than the original amino acid residue. One of skill in the art knows how to determine and/or assess the properties of amino acid residues to identify those that are ideal replacement residues for the formation of a cavity. Generally, the replacement residues for the formation of a cavity are naturally occurring amino acids and include, for example, alanine (A), serine (S), threonine (T) and valine (V). In some examples, the original amino acid identified for replacement is an amino acid that has a large side chain such as, for example, tyrosine, arginine, phenylalanine, or tryptophan.

The CH3 interface of human IgG1, for example, involves sixteen residues on each domain located on four anti-parallel β-strands which buries 1090 A2 from each surface (see e.g., Deisenhofer et al. (1981) Biochemistry, 20:2361-2370; Miller et al., (1990) J Mol. Biol., 216, 965-973; Ridgway et al., (1996) Prot. Engin., 9: 617-621; U.S. Pat. No. 5,731,168). Modifications of a CH3 domain to create protuberances or cavities are described, for example, in U.S. Pat. No. 5,731,168; International Patent Applications WO98/50431 and WO 2005/063816; and Ridgway et al., (1996) Prot. Engin., 9: 617-621. In some examples, modifications of a CH3 domain to create protuberances or cavities are typically targeted to residues located on the two central anti-parallel β-strands. The aim is to minimize the risk that the protuberances which are created can be accommodated by protruding into the surrounding solvent rather than being accommodated by a compensatory cavity in the partner CH3 domain.

For example, in some embodiments the heterodimeric Fc includes a polypeptide having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Tyr349 to Cys (Y349C) on opposite CH3 domains (Reviewed in Carter, 2001 Journal of Immunological Methods, 248: 7-15).

In particular embodiments, a multispecific polypeptide construct contains a first and second Fc able to mediate Fc heterodimerization contains a first Fc polypeptide containing mutations T366W and S354C and a second Fc polypeptide containing mutations T366S, L368A, Y407V and Y349C. In some embodiments, the first Fc polypeptide is selected from an Fc polypeptide comprising the sequence set forth in SEQ ID NO: 291 or 297 and the second Fc polypeptide is selected from an Fc polypeptide comprising the sequence set forth in SEQ ID NO: 292, 295 or 299. In some embodiments, the first Fc polypeptide is or comprises the sequence of amino acids set forth in any of SEQ ID NOS: 82, 86, 94 or 96 and the second Fc polypeptide is or comprises the sequence of amino acids set forth in any of SEQ ID NOS: 83, 87, 90, 92, 98 or 100.

In some embodiments, the Fc polypeptide exhibits features providing Fc-mediated effector functions. In particular examples, the first Fc polypeptide is or comprises the sequence set forth in SEQ ID NOs:291 and a second Fc polypeptide that is or comprises SEQ ID NO: 292 or 295. In some embodiments, the first Fc polypeptide is or comprises the sequence set forth in SEQ ID NO: 82 and the second Fc polypeptide is or comprises the sequence set forth in SEQ ID NO: 83 or 90. In some embodiments, the first Fc polypeptide is or comprises the sequence set forth in SEQ ID NO: 86 and the second Fc polypeptide is or comprises the sequence set forth in SEQ ID NO: 87 or 92. The first and second Fc polypeptide can be formatted on either polypeptide chain of the construct.

In some embodiments, one or both of the first and second Fc polypeptides can further include one or more amino acid mutations to further reduce one or more Fc effector functions, such as reduced Fc receptor binding. Exemplary mutations to reduce Fc effector functions include any as described. In some embodiments, the modification can be a deletion of one or more positions Glu233 (E233), Leu234 (L234), or Leu235 (L235), such as a deletion of amino acids Glu233 (E233), Leu234 (L234), and Leu235 (L235). In some embodiments, the first Fc polypeptide is selected from an Fc polypeptide comprising the sequence set forth in SEQ ID NO: 293 or 298 and the second Fc polypeptide is selected from an Fc polypeptide comprising the sequence set forth in SEQ ID NO: 294, 296 or 300. In some embodiments, the first Fc polypeptide is or comprises the sequence of amino acids set forth in any of SEQ ID NOS: 84, 88, 95 or 97 and the second Fc polypeptide is or comprises the sequence of amino acids set forth in any of SEQ ID NOS: 85, 89, 91, 93, 99 or 101.

In particular examples, the first Fc polypeptide is or comprises the sequence set forth in SEQ ID NOs:293 and a second Fc polypeptide that is or comprises SEQ ID NO: 294 or 296. In some embodiments, the first Fc polypeptide is or comprises the sequence set forth in SEQ ID NO: 84 and the second Fc polypeptide is or comprises the sequence set forth in SEQ ID NO: 85 or 91. In some embodiments, the first Fc polypeptide is or comprises the sequence set forth in SEQ ID NO: 88 and the second Fc polypeptide is or comprises the sequence set forth in SEQ ID NO: 89 or 93. The first and second Fc polypeptide can be formatted on either polypeptide chain of the construct.

In some embodiments, the first Fc polypeptide or second Fc polypeptide further includes mutations M252Y and/or M428V. In particular examples, the first Fc polypeptide is or comprises the sequence set forth in SEQ ID NO:297 and the second Fc polypeptide is or comprises the sequence set forth in SEQ ID NO:299. In some embodiments, the first Fc polypeptide is or comprises the sequence set forth in SEQ ID NO:94 and the second Fc polypeptide is or comprises the sequence set forth in SEQ ID NO: 98. In some embodiments, the first Fc polypeptide is or comprises the sequence set forth in SEQ ID NO:96 and the second Fc polypeptide is or comprises the sequence set forth in SEQ ID NO: 100. In other examples, the first Fc polypeptide is or comprises the sequence set forth in SEQ ID NO:298 and the second Fc polypeptide is or comprises the sequence set forth in SEQ ID NO:300. In some embodiments, the first Fc polypeptide is or comprises the sequence set forth in SEQ ID NO:95 and the second Fc polypeptide is or comprises the sequence set forth in SEQ ID NO: 99. In some embodiments, the first Fc polypeptide is or comprises the sequence set forth in SEQ ID NO:97 and the second Fc polypeptide is or comprises the sequence set forth in SEQ ID NO: 101. The first and second Fc polypeptide can be formatted on either polypeptide chain of the construct.

Additional examples of variants that can facilitate the promotion of heterodimers are any combination or pair of steric variants (e.g. skew variants) of a first Fc polypeptide and a second Fc polypeptide from among: S364K/E357Q and L368D/K370S; L368D/K370S and S364K; L368E/K370S and S364K; T411T/E360E/Q362E and D401K; L368D/K370S and S364K/E357L, K370S and S364K/E357Q and T366S/L368A/Y407V and T366W or 366S/L368A/Y407V/Y349C and T366W/S354C), where each pair represents mutations in the first Fc polypeptide and second Fc polypeptide. In particular embodiments, a provided construct contains a first and second Fc polypeptide containing the pair of mutations L368D/K370S and S364K and E357Q.

An additional mechanism that can be used in the generation of heterodimers is sometimes referred to as "electrostatic steering" as described in Gunasekaran et al., J. Biol. Chem. 285(25):19637 (2010). This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". In one embodiments, a first Fc polypeptide can contain mutations D221E/P228E/L368E and a second Fc polypeptide can contain mutations D221R/P228R/K409R. In another embodiments, a first Fc polypeptide can contain mutations C220E/P228E/368E and a second Fc polypeptide can contain mutations C220R/E224R/P228R/K409R.

In some embodiments, heterodimerization can be facilitated by pI variants. In some aspects, a pI variant can include those that increase the pI of the protein (basic changes). In other aspects, the pI variant can include those that decrease the pI of the protein (acidic changes). In some cases, all combinations of these variants can be done, including combinations in which one Fc polypeptide may be wild type, or a variant that does not display a significantly different pI from wild-type, and the other Fc polypeptide can be either more basic or more acidic. Alternatively, each Fc polypeptide can be changed, one to more basic and one to more acidic. In some embodiments, at least one Fc polypeptide is a negative pI variant Fc containing mutations Q295E/N384D/Q418E/N421D.

In some embodiments, a combination of steric heterodimerization variants (e.g. knob and hole) and pI or charge pair variants can be used.

In particular embodiments, the provided constructs contains (a) a first Fc polypeptide comprising the skew variants S364K/E357Q; and b) a second Fc polypeptide containing skew variants L368D/K370S and the pI variants N208D/Q295E/N384D/Q418E/N421D. In some embodiments, one or both of the first and second polypeptide can contain further mutations to reduce Fc effector activity, such as the exemplary mutations E233P/L234V/L235A/G236del/S267K. An example of such a first Fc polypeptide and a second Fc polypeptide able to mediate Fc heterodimeriztion comprise the sequences set forth in SEQ ID NOs:285 and 286. The first and second Fc polypeptide can be formatted on either polypeptide chain of the construct.

The resulting multispecific polypeptide constructs can be purified by any suitable method such as, for example, by affinity chromatography over Protein A or Protein G columns. Where two nucleic acid molecules encoding different polypeptides are transformed into cells, formation of homo- and heterodimers will occur. Conditions for expression can be adjusted so that heterodimer formation is favored over homodimer formation.

Techniques for recovery of heterodimers from homodimers based on a differential affinity of the heterodimers for an affinity reagent are known. In some aspects, such techniques include designing a heterodimer so that one of the Fc polypeptide chains does not bind to the affinity reagent protein A. In some cases, one of the polypeptide chain can contain one or more amino acid substitution to abrogate or reduce affinity for the protein A reagent in one of the polypeptides of the Fc heterodimer, see e.g. WO2017134440, WO2010151792, Jendeberg et al. (Jendeberg et al., (1997) J. Immunol. Methods, 201(1): 25-34. In some of these embodiments, the Fc region may be modified at the protein-A binding site on one member of the heterodimer so as to prevent protein-A binding and thereby enable more efficient purification of the heterodimeric fusion protein. An exemplary modification within this binding site is Ile253, for example Ile253Arg (I253R). In some embodiments, the modification may be H435R or H435R/Y436F. In some embodiments, an Fc polypeptide of an Fc heterodimer can contain a modification so that it is capable of binding protein A but not protein G (pA+/pG−). Exemplary pA+/pG− amino acid modifications include an Fc containing serine at position 428, serine at position 434 and optionally histidine at position 436, with reference to human IgG1 or comprising these residues at the corresponding positions in human IgG 2, 3, or 4. In some aspects, such amino acid modifications in one IgG Fc polypeptide at positions 428, 434 and optionally 436 reduces or prevents the binding of protein G, enhancing the purification of the protein.

In some embodiments, any of such modifications to confer differential affinity to an affinity reagent can be combined with any one or more other amino acid modifications described above. For example, the I253R modification maybe combined with either the T366S/L368A/Y407V modifications or with the T366W modifications. The T366S/L368A/Y407V modified Fc is capable of forming homodimers as there is no steric occlusion of the dimerization interface as there is in the case of the T336W modified Fc. Therefore, in some embodiments, the I253R modification is combined with the T366S/L368A/Y407V modified Fc to disallow purification any homodimeric Fc that may have formed. Similar modifications can be employed by combining T366S/L368A/Y407V and H453R.

In some embodiments, the Fc regions of the heterodimeric molecule additionally can contain one or more other Fc mutation, such as any described above. In some embodiments, the heterodimer molecule contains an Fc region with a mutation that reduces effector function.

In some embodiments, one Fc polypeptide of a heterodimeric Fc comprises the sequence of amino acids set forth in any of SEQ ID NOS: 291 (e.g. SEQ ID NO:82 or 86), or 297 (e.g. SEQ ID NO:94 or 96), and the other Fc polypeptide of the heterodimeric Fc contains the sequence of amino acids set forth in any of SEQ ID NOS:201 (e.g. SEQ ID NO:83 or 87), 295 (e.g. SEQ ID NO:90 or 92), or 299 (e.g. SEQ ID NO:98 or 100). In some embodiments, one Fc polypeptide of a heterodimeric Fc comprises the sequence of amino acids set forth in any of SEQ ID NOS: 293 (e.g. SEQ ID NO:84 or 88), or 298 (e.g. SEQ ID NO:95 or 97) and the other Fc polypeptide of the heterodimeric Fc comprises the sequence of amino acids set forth in any of SEQ ID NOS: 294 (e.g. SEQ ID NO:85 or 89), 296 (e.g. SEQ ID NO:91 or 93), or 300 (e.g. SEQ ID NO:99 or 101).

In some embodiments, the human IgG Fc region is modified to prevent dimerization. In these embodiments, the fusion proteins of the present disclosure are monomeric. For example modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the fusion protein contains a polypeptide derived from an immunoglobulin hinge region. The hinge region can be selected from any of the human IgG subclasses. For example, the fusion protein may contain a modified IgG1 hinge having the sequence of EPKSSDKTH-TCPPC (SEQ ID NO: 7), where in the Cys220 that forms a disulfide with the C-terminal cysteine of the light chain is mutated to serine, e.g., Cys220Ser (C220S). In other embodiments, the fusion protein contains a truncated hinge having a sequence DKTHTCPPC (SEQ ID NO: 8).

In some embodiments, the fusion protein has a modified hinge from IgG4, which is modified to prevent or reduce strand exchange, e.g., Ser228Pro (S228P), having the sequence ESKYGPPCPPC (SEQ ID NO: 9). In some embodiments, the fusion protein contains linker polypeptides. In other embodiments, the fusion protein contains linker and hinge polypeptides.

3. Linkers

The provided multispecific polypeptide constructs contain a linker that joins or couples the first component containing the immunoglobulin Fc region and the second component containing the CD3 binding region. In some embodiments, the linker is positioned at the end of the C-terminal region of the Fc region, such that the Fc region is N-terminal to the CD3 binding region. Because the provided multispecific polypeptide constructs are multimers, such as dimers containing a first and second polypeptide that together form the first and second component, the provided constructs include a linker joining the Fc portion and the CD3 binding region of the first and a linker joining the Fc portion and the CD3 binding region of the second polypeptide. In some embodiments, the first polypeptide includes a first Fc polypeptide of a heterodimeric Fc region, a linker, and a first domain (e.g. VH) of a CD3 binding region, and the second polypeptide includes a second Fc polypeptide of the heterodimeric Fc region, a linker and second domain (e.g. VL) of the CD3 binding region. Typically, the linkers present in the first and second polypeptides of the multispecific polypeptide construct are the same. Thus, in some embodiments, each domain of the CD3 binding domain is linked via a linker, such as the same linker, to opposite polypeptides of the Fc, such as heterodimeric Fc.

Various polypeptide linkers for use in fusion proteins are known (see e.g. Chen et al. (2013) Adv. Drug. Deliv. 65:1357-1369; and International PCT publication No. WO 2014/099997, WO2000/24884; U.S. Pat. Nos. 5,258,498; 5,525,491; 5,525,491, 6,132,992).

In some embodiments, the linker is chosen so that, when the CD3 binding region is joined to the Fc region of the multispecific polypeptide conjugate, the CD3 binding region is constrained and not able to, or not substantially able to, bind or engage CD3 on the surface of a cell, e.g. T cell, upon contact of the multispecific polypeptide construct with the cell. Various assays can be employed to assess binding or engagement of CD3 by the multispecific polypeptide construct, including assays to assess T cell binding, NFAT activation using a reporter system, cytolytic T cell activity, cytokine production and/or expression of T cell activation markers. Exemplary assays are shown in the provided Examples. Typically, the linker also is one that ensures correct folding of the polypeptide construct, does not exhibit a charge that would be inconsistent with the activity or function of the linked polypeptides or form bonds or other interactions with amino acid residues in one or more of the domains that would impede or alter activity of the linked polypeptides. In some embodiments, the linker is a polypeptide linker. The polypeptide linker can be a flexible linker or a rigid linker or a combination of both.

In some aspects, the linker is a short, medium or long linker. In some embodiments, the linker is up to 40 amino acids in length. In some embodiments, the linker is up to 25 amino acids in length. In some embodiments, the linker is at least or is at least about 2 amino acids in length. In some aspects, a suitable length is, e.g., a length of at least one and typically fewer than about 40 amino acid residues, such as 2-25 amino acid residues, 5-20 amino acid residues, 5-15 amino acid residues, 8-12 amino acid. In some embodiments, the linker is from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids. In some embodiments, the linker is 2, 3, 4, 5, 6, 7, 8, 9, 10, 11, 12, 13, 14, 15, 16, 17, 18, 19 or 20 amino acids in length.

In certain aspects, the longer the linker length, the greater the CD3 binding when the multispecific polypeptide conjugate is bounds to its antigen, e.g. TAA. Thus, in some aspects, the linker is greater than 12 amino acids in length, such as greater than 13, 14, 15, 16, 17 or 18 amino acids in length. In some embodiments, the linker is 12 to 40 amino acids in length, 12 to 30 amino acids, 12 to 24 amino acids, 12 to 18 acids, 12 to 15 amino acids, 15 to 40 amino acids, 15 to 30 amino acids, 15 to 24 amino acids, 15 to 18 amino acids, 18 to 40 amino acids, 18 to 30 amino acids, 18 to 24 amino acids, 24 to 40 amino acids, 24 to 30 amino acids or 30 to 40 amino acids.

The linkers can be naturally-occurring, synthetic or a combination of both. Particularly suitable linker polypeptides predominantly include amino acid residues selected from Glycine (Gly), Serine (Ser), Alanine (Ala), and Threonine (Thr). For example, the linker may contain at least 75% (calculated on the basis of the total number of residues present in the peptide linker), such as at least 80%, at least 85%, or at least 90% of amino acid residues selected from Gly, Ser, Ala, and Thr. The linker may also consist of Gly, Ser, Ala and/or Thr residues only. In some embodiments, the linker contains 1-25 glycine residues, 5-20 glycine residues, 5-15 glycine residues, or 8-12 glycine residues. In some aspects, suitable peptide linkers typically contain at least 50% glycine residues, such as at least 75% glycine residues. In some embodiments, a peptide linker comprises glycine residues only. In some embodiments, a peptide linker comprises glycine and serine residues only.

In some embodiments, these linkers are composed predominately of the amino acids Glycine and Serine, denoted as GS-linkers herein. In some embodiments, the linker contains (GGS)n, wherein n is 1 to 10, such as 1 to 5, for example 1 to 3, such as GGS(GGS)n (SEQ ID NO:171), wherein n is 0 to 10. In particular embodiments, the linker contains the sequence (GGGGS)n (SEQ ID NO: 173), wherein n is 1 to 10 or n is 1 to 5, such as 1 to 3. In further embodiments, the linker contains (GGGGGS)n (SEQ ID NO:172), wherein n is 1 to 4, such as 1 to 3. The linker can include combinations of any of the above, such as repeats of 2, 3, 4, or 5 GS, GGS, GGGGS (SEQ ID NO: 149), and/or GGGGGS (SEQ ID NO:135) linkers may be combined. In some embodiments, such a linker is 2, 3, 4, 5, 6, 7, 8, 9, 10, 11, 12, 13, 14, 15, 16, 17, 18 or 19 amino acids in length.

In some embodiments, the linker is (in one-letter amino acid code): GGS, GGGGS (SEQ ID NO: 149), or GGGGGS (SEQ ID NO: 135). In some embodiments, the GS-linker comprises an amino acid sequence of GGSGGS, i.e., $(GGS)_2$ (SEQ ID NO: 10); GGSGGSGGS, i.e., $(GGS)_3$ (SEQ ID NO: 11); GGSGGSGGSGGS, i.e., $(GGS)_4$ (SEQ ID NO: 12); GGSGGSGGSGGSGGS, i.e., $(GGS)_5$ (SEQ ID NO: 13); GGGGGSGGGGGSGGGGGS, i.e., $(G5S)_3$ (SEQ ID NO: 119), GGSGGGGSGGGGSGGGGS (SEQ ID NO: 147) and GGGGSGGGGSGGGGS (SEQ ID NO:170). In some embodiments, the linker is GGGG (SEQ ID NO:103). In some embodiments, the linker is GGGGG (SEQ ID NO:250). In some of any of the above examples, serine can be replaced with alanine (e.g., (Gly4Ala) (SEQ ID NO: 326) or (Gly3Ala) (SEQ ID NO: 325)).

In some embodiments, the linker includes a peptide linker having the amino acid sequence $Gly_x$-Xaa-$Gly_y$-Xaa-$Gly_z$ (SEQ ID NO:174), wherein each Xaa is independently selected from Alanine (Ala), Valine (Val), Leucine (Leu), Isoleucine (Ile), Methionine (Met), Phenylalanine (Phe), Tryptophan (Trp), Proline (Pro), Glycine (Gly), Serine (Ser), Threonine (Thr), Cysteine (Cys), Tyrosine (Tyr), Asparagine (Asn), Glutamine (Gln), Lysine (Lys), Arginine (Arg), Histidine (His), Aspartate (Asp), and Glutamate (Glu), and wherein x, y, and z are each integers in the range from 1-5. In some embodiments, each Xaa is independently selected from the group consisting of Ser, Ala, and Thr. In a specific variation, each of x, y, and z is equal to 3 (thereby yielding a peptide linker having the amino acid sequence Gly-Gly-Gly-Xaa-Gly-Gly-Gly-Xaa-Gly-Gly-Gly (SEQ ID NO:175), wherein each Xaa is selected as above.

In some embodiments, the linker is serine-rich linkers based on the repetition of a (SSSSG) n (SEQ ID NO:185) motif where n is at least 1, though n can be 2, 3, 4, 5, 6, 7, 8 and 9.

In some cases, it may be desirable to provide some rigidity into the peptide linker. This may be accomplished by including proline residues in the amino acid sequence of the peptide linker. Thus, in some embodiments, a linker comprises at least one proline residue in the amino acid sequence of the peptide linker. For example, a peptide linker can have an amino acid sequence wherein at least 25% (e.g., at least 50% or at least 75%) of the amino acid residues are proline residues. In one particular embodiment, the peptide linker comprises proline residues only.

In some aspects, a peptide linker comprises at least one cysteine residue, such as one cysteine residue. For example, in some embodiments, a linker comprises at least one cysteine residue and amino acid residues selected from the group consisting of Gly, Ser, Ala, and Thr. In some such embodiments, a linker comprises glycine residues and cysteine residues, such as glycine residues and cysteine residues only. Typically, only one cysteine residue will be included per peptide linker. One example of a specific linker comprising a cysteine residue includes a peptide linker having the amino acid sequence $Gly_m$-Cys-$Gly_n$, wherein n and m are each integers from 1-12, e.g., from 3-9, from 4-8, or from 4-7. In a specific variation, such a peptide linker has the amino acid sequence GGGGG-C-GGGGG (SEQ ID NO:177).

In some embodiments, the linker of the fusion protein is a structured or constrained linker. In particular embodiments, the structured linker contains the sequence (AP)n or (EAAAK)n (SEQ ID NO:178), wherein n is 2 to 20, preferably 4 to 10, including but not limited to, AS-(AP)n-GT (SEQ ID NO:179) or AS-(EAAAK)n-GT (SEQ ID NO:180), wherein n is 2 to 20, such as 2, 3, 4, 5, 6, 7, 8, 9, 10, 11, 12, 13, 14 or 15. In other embodiments, the linker comprises the sequences (GGGGA)n (SEQ ID NO:181), (PGGGS)n (SEQ ID NO:182), (AGGGS)n (SEQ ID NO:183) or GGS-(EGKSSGSGSESKST)n-GGS (SEQ ID NO:184, wherein n is 2 to 20. In some embodiments, the linker is SSSASASSA (SEQ ID NO:186), GSPGSPG (SEQ ID NO:187), or ATTTGSSPGPT (SEQ ID NO:176). In some embodiments, such linkers, by virtue of their structure, may be more resistant to proteolytic degradation, thereby offering an advantage when injected in vivo.

In some embodiments, the linker is not a cleavable linker, also called non-cleavable linker. In some embodiments, the linker is not a cleavable by a protease. In some embodiments, a linker that is not a cleavable linker or that is not cleavable by a protease is one that is generally stable for in vivo delivery or recombinant production. In some aspects, a linker that is not cleavable by a protease includes those that do not contain at least one peptide bond which preferably lies within a cleavable peptide sequence or recognition site of a protease. In particular embodiments, a non-cleavable linker is not a target substrate for a protease, such that it is not preferentially or specifically cleaved by a protease compared to a linker that contains a substrate recognition site for the same protease.

In some embodiments, the linker does not contains a substrate recognition site or cleavage site for a particular protease, which is the sequence recognized by the active site of a protease that is cleaved by a protease. Typically, for example, for a serine protease, a cleavage sequence is made up of the P1-P4 and P1'-P4' amino acids in a substrate, where cleavage occurs after the P1 position. Typically, a cleavage sequence for a serine protease is six residues in length to match the extended substrate specificity of many proteases, but can be longer or shorter depending upon the protease. Typically, the linker does not include a P1-P1' scissile bond sequence that is recognized by a protease. In some aspects, a non-cleavable linker or a linker that does not contain a substrate recognition site that is specifically recognized for cleavage by a protease is one whose cleavage by a protease is substantially less than cleavage of a target substrate of the protease.

In some embodiments, the linker is a cleavable linker. In some aspects, a cleavable linker is a linker, such as any described above, that further includes a sequence that is a substrate for a protease due to the presence of at least one bond that can be broken under physiological conditions. In some cases, a cleavable linker is susceptible to or sensitive to cleavage under specific conditions that exist in vivo, such as following exposure to an extracellular protease, including those present in cellular environments in vivo. In some cases, the protease may be present in a particular physiological microenvironment, such as the tumor microenvironment, thereby restricting the sites at which cleavage may occur.

A protease typically exhibits specificity or preference for cleavage of a particular target substrate compared to another non-target substrate. Such a degree of specificity can be determined based on the rate constant of cleavage of a sequence, e.g. linker, which is a measure of preference of a protease for its substrate and the efficiency of the enzyme. Any method to determine the rate of increase of cleavage over time in the presence of various concentrations of substrate can be used to calculate the specificity constant. For example, a substrate is linked to a fluorogenic moiety, which is released upon cleavage by a protease. By determining the rate of cleavage at different protease concentrations the specificity constant for cleavage ($k_{cat}/K_m$) can be determined for a particular protease towards a particular linker. In some embodiments, a cleavable linker is a linker that is capable of being specifically cleaved by a protease at a rate of about at least $1\times10^4$ $M^{-1}S^{-1}$, or at least $5\times10^4$ $M^{-1}S$, at least $10\times10^4$ $M^{-1}S$. at least $10\times10^5$ $M^{-1}S$ or more.

In some embodiments, the multispecific polypeptide constructs of the disclosure include a cleavable linker that joins the first and second components. In some embodiments, the cleavable linker includes an amino acid sequence that can serve as a substrate for a protease, usually an extracellular protease. For example, the cleavable linker may include a cleavage sequence containing at least one peptide bond which preferably lies within a cleavable peptide sequence of a protease. Suitable proteases include, for example, matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. In particular embodiments, the protease is a protease that is produced by a tumor, an activated immune effector cell (e.g. a T cell or a NK cell), or a cell in a tumor microenvironment. In some embodiments, the protease is a granzyme B, a matriptase or an MMP, such as MMP-2.

The cleavable linker may be selected based on a protease that is produced by a tumor that is in proximity to cells that express the target and/or produced by a tumor that is co-localized in tissue with the desired target of the multispecific polypeptide constructs. There are reports in the literature of increased levels of proteases having known substrates in a number of cancers, e.g., solid tumors. See, e.g., La Rocca et al, (2004) British J. of Cancer 90(7): 1414-1421.

In some embodiments, the cleavable linker that joins the first and second component multispecific polypeptide construct is cleaved by a protease produced by an immune effector cell that is activated by one of the components. For example, multispecific polypeptide constructs that encompass an effector enabled or enhanced IgG Fc region are capable of eliciting ADCC when engaged with the target antigen. Central to ADCC is the release of granzyme B and perforin from the effector cells, namely NK cells and cytotoxic T-cells. Upon release granzyme B enters the target cell in a perforin dependent manner wherein it mediates apoptosis. Importantly, granzyme B is active within the extracellular synapse between the effector cell and the target cell. In some embodiments, the cleavable linker that joins the first and second component multispecific polypeptide construct is cleaved by granzyme B. Granzyme B is released during effector cell activation mediated by one of the components of the multispecific polypeptide construct. In some embodiments, granzyme B and other proteases can be produced by immune effector cells, including activated T cells or NK cells. In some embodiments, activation of T cells by CD3 engagement upon binding of a TAA by a multispecific polypeptide construct may release such proteases, which then can cleave a specific cleavable linker thereby potentiating or increasing activity of the CD3 binding molecule to engage CD3. In some embodiments, the cleavage can amplify or increase the activity achieved by the multispecific construct when bound to TAA in an uncleaved state.

Exemplary substrates include but are not limited to substrates cleavable by one or more of the following enzymes or proteases: ADAMS, ADAMTS, e.g. ADAM8; ADAM9; ADAM10; ADAM12; ADAM15; ADAM17/TACE; ADAMDEC1; ADAMTS1; ADAMTS4; ADAMTS5; aspartate proteases, e.g., BACE or Renin; aspartic cathepsins, e.g., Cathepsin D or Cathepsin E; Caspases, e.g., Caspase 1, Caspase 2, Caspase 3, Caspase 4, Caspase 5, Caspase 6, Caspase 7, Caspase 8, Caspase 9, Caspase 10, or Caspase 14; cysteine cathepsins, e.g., Cathepsin B, Cathepsin C, Cathepsin K, Cathepsin L, Cathepsin S, Cathepsin V/L2, Cathepsin X/Z/P; Cysteine proteinases, e.g., Cruzipain; Legumain; Otubain-2; KLKs, e.g., KLK4, KLK5, KLK6, KLK7, KLK8, KLK10, KLK11, KLK13, or KLK14; Metallo proteinases, e.g., Meprin; Neprilysin; PSMA; BMP-1; MMPs, e.g., MMP1, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, or MMP27, serine proteases, e.g., activated protein C, Cathepsin A, Cathepsin G, Chymase, coagulation factor proteases (e.g., FVIIa, FIXa, FXa, FXIa, FXIIa), Elastase, granzyme B, Guanidinobenzoatase, HtrA1, Human Neutrophil Elastase, Lactoferrin, Marapsin, NS3/4A, PACE4, Plasmin, PSA, tPA, Thrombin, Tryptase, uPA; Type II Transmembrane Serine Proteases (TTSPs), e.g., DESC1, DPP-4, FAP, Hepsin, Matriptase-2, Matriptase, TMPRSS2, TMPRSS3, or TMPRSS4; and any combination thereof.

In some embodiments, the cleavable linker is cleaved by multiple proteases, e.g., 2 or more proteases, 3 or more proteases, 4 or more proteases, and so on.

In some embodiments, the cleavable linker is selected for use with a specific protease, for example a protease that is known to be produced by a tumor that is in proximity to cells that express the target and/or produced by a tumor that is co-localized with the target of the multispecific polypeptide construct.

In some embodiments, the cleavable linker contains a substrate recognition site or cleavage site for a particular protease, which is the sequence recognized by the active site of a protease that is cleaved by a protease. Typically, for example, for a serine protease, a cleavage sequence is made up of the P1-P4 and P1'-P4' amino acids in a substrate, where cleavage occurs after the P1 position. Typically, a cleavage sequence for a serine protease is six residues in length to match the extended substrate specificity of many proteases, but can be longer or shorter depending upon the protease. Typically, the cleavable linker includes a P1-P1' scissile bond sequence that is recognized by a protease. In some aspects, the cleavable linker is engineered to introduce a peptide bond able to be cleaved by a specific protease, for example by introducing a substrate recognition site sequence or cleavage sequence of the protease.

In some embodiments, the cleavable linker includes a combination of two or more substrate sequences. In some embodiments, each substrate sequence is cleaved by the same protease. In some embodiments, at least two of the substrate sequences are cleaved by different proteases. In some embodiments, the cleavable linker comprises an amino acid that is a substrate for granzyme B. In some embodiments, a granzyme B cleavable linker contains an amino acid sequence having the general formula P4 P3 P2 P1↓P1' (SEQ ID NO: 150), wherein P4 is amino acid I, L, Y, M, F, V, or A; P3 is amino acid A, G, S, V, E, D, Q, N, or Y; P2 is amino acid H, P, A, V, G, S, or T; P1 is amino acid D or E; and P1' is amino acid I, L, Y, M, F, V, T, S, G or A. In some embodiments, a granzyme B cleavable linker contains an amino acid sequence having the general formula P4 P3 P2 P1↓P1' (SEQ ID NO: 151), wherein P4 is amino acid I or L; P3 is amino acid E; P2 is amino acid P or A; P1 is amino acid D; and P1' is amino acid I, V, T, S, or G.

In some embodiments, the substrate for granzyme B comprises the amino acid sequence LEAD (SEQ ID NO: 22), LEPG (SEQ ID NO: 142), or LEAE (SEQ ID NO:143). In some embodiments, the cleavable linker contains the amino acid sequence the cleavable linker comprises the amino acid sequence IEPDI (SEQ ID NO:136), LEPDG (SEQ ID NO:152, LEADT (SEQ ID NO:137), IEPDG (SEQ ID NO:138), IEPDV (SEQ ID NO:139), IEPDS (SEQ ID NO:140), IEPDT (SEQ ID NO:141), IEPDP (SEQ ID NO:144), LEPDG (SEQ ID NO:152) or LEADG (SEQ ID NO:153).

In some embodiments, the cleavable linker comprises an amino acid that is a substrate for matriptase. In some embodiments, the cleavable linker comprises the sequence P4QAR↓(A/V) (SEQ ID NO: 154), wherein P4 is any amino acid. In some embodiments, the cleavable linker comprises the sequence RQAR(A/V) (SEQ ID NO: 155). In some embodiments, the substrate for matriptase comprises the amino acid sequence RQAR (SEQ ID NO: 23). In some embodiments, the cleavable linker comprises the amino acid sequence RQARV (SEQ ID NO: 156).

In some embodiments, the cleavable linker comprises an amino acid that is a substrate for one or more matrix metalloproteases (MMPs). In some embodiments, the MMP is MMP-2. In some embodiments, the cleavable linker contains. the general formula P3 P2 P1↓P1' (SEQ ID NO: 157), wherein P3 is P, V or A; P2 is Q or D; P1 is A or N; and P1' is L, I or M. In some embodiments, the cleavable linker contains the general formula P3 P2 P1↓P1' (SEQ ID NO: 158), wherein P3 is P; P2 is Q or D; P1 is A or N; and P1' is L or I. In some embodiments, the substrate for MMP comprises the amino acid sequence PAGL (SEQ ID NO: 24).

In some embodiments, the cleavable linker comprises a combination of an amino acid sequence that is a substrate for granzyme B and an amino acid sequence that is a substrate for matriptase. In some embodiments, the cleavable linker comprises a combination of the amino acid sequence LEAD (SEQ ID NO: 22) and the amino acid sequence RQAR (SEQ ID NO: 23).

In some embodiments, the cleavable linker comprises a combination of an amino acid sequence that is a substrate for granzyme B and an amino acid sequence that is a substrate for MMP. In some embodiments, the cleavable linker comprises a combination of the amino acid sequence LEAD (SEQ ID NO: 22) and the amino acid sequence PAGL (SEQ ID NO: 24).

In some embodiments, the cleavable linker comprises a combination of an amino acid sequence that is a substrate for matriptase and an amino acid sequence that is a substrate for MMP. In some embodiments, the cleavable linker comprises a combination of the amino acid sequence RQAR (SEQ ID NO: 23) and the amino acid sequence PAGL (SEQ ID NO: 24).

In some embodiments, the cleavable linker comprises a combination of an amino acid sequence that is a substrate for granzyme B, an amino acid sequence that is a substrate for matriptase, and an amino acid sequence that is a substrate for MMP. In some embodiments, the cleavable linker comprises a combination of an amino acid sequence that is a substrate for granzyme B and an amino acid sequence that is a substrate for MMP. In some embodiments, the cleavable linker comprises a combination of the amino acid sequence LEAD (SEQ ID NO: 22), the amino acid sequence RQAR (SEQ ID NO: 23), and the amino acid sequence PAGL (SEQ ID NO: 24).

The cleavable linker can include any known linkers. Examples of cleavable linkers are described in Be'liveau et al. (2009) FEBS Journal, 276; U.S. published application Nos. US20160194399; US20150079088; US20170204139; US20160289324; US20160122425; US20150087810; US20170081397; U.S. Pat. No. 9,644,016.

In some embodiments, the cleavable linker comprises an amino acid sequence selected from the group consisting of TGLEADGSPAGLGRQARVG (SEQ ID NO: 25); TGLEADGSRQARVGPAGLG (SEQ ID NO: 26); TGSPAGLEADGSRQARVGS (SEQ ID NO: 27); TGPAGLGLEADGSRQARVG (SEQ ID NO: 28); TGRQARVGLEADGSPAGLG (SEQ ID NO: 29); TGSRQARVGPAGLEADGS (SEQ ID NO: 30); and TGPAGLGSRQARVGLEADGS (SEQ ID NO: 31); GPAGLGLEPDGSRQARVG (SEQ ID NO: 104); GGSGGGGIEPDIGGSGGS (SEQ ID NO: 105); GGSGGGGLEADTGGSGGS (SEQ ID NO: 106); GSIEPDIGS (SEQ ID NO: 107); GSLEADTGS (SEQ ID NO: 108); GGSGGGGIEPDGGGSGGS (SEQ ID NO: 109); GGSGGGGIEPDVGGSGGS (SEQ ID NO: 110); GGSGGGGIEPDSGGSGGS (SEQ ID NO: 111); GGSGGGGIEPDTGGSGGS (SEQ ID NO: 112); GGGSLEPDGSGS (SEQ ID NO: 113); and GPAGLGLEADGSRQARVG (SEQ ID NO: 114), GGEGGGGSGGSGGGS (SEQ ID NO: 115); GSSAGSEAGGSGQAGVGS (SEQ ID NO: 116); GGSGGGGLEAEGSGGGGS (SEQ ID NO: 117); GGSGGGGIEPDPGGSGGS(SEQ ID NO: 118); TGGSGGGGIEPDIGGSGGS (SEQ ID NO: 148).

4. Antigen Binding Domains

The multispecific polypeptide constructs of the present disclosure include at least one antigen binding domain, such as at least a first antigen binding domain and a second antigen binding domain. In some aspects, the antigen binding domain, or independently each of the antigen binding domains, is selected from an antibody or antigen binding fragment, a natural (or native) cognate binding partner, an Anticalin (engineered lipocalin), a Darpin, a Fynomer, a Centyrin (engineered fibronectin III domain), a cystine-knot domain, an Affilin, an Affibody, or an engineered CH3 domain. In some embodiments, the natural cognate binding partner comprises an extracellular domain or binding fragment thereof of the native cognate binding partner of the TAA, or a variant thereof that exhibits binding activity to the TAA.

In some embodiments, the antigen binding domain, or independently each of the antigen binding domains, such as the first antigen-binding domain and the second antigen binding domains, includes one or more copies of an antibody or an antigen-binding fragment thereof. In some embodiments, the antigen binding domain or independently each of the antigen binding domains, such as the first antigen-binding domain and the second antigen binding domains, includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the antigen binding domain, or independently each of the antigen binding domains, such as the first antigen-binding domain and the second antigen binding domains, is a single chain antibody. In some examples, the single chain is an scFv, a scAb, a single domain heavy chain antibody, or a single domain light chain antibody.

In some embodiments, the antigen binding domain, or independently each of the antigen binding domains, such as the first antigen-binding domain and the second antigen binding domains, is a single chain antibody. In some examples, the single chain is an scFv, a scAb, a single domain heavy chain antibody, or a single domain light chain antibody.

In some embodiments, the antigen binding domain or independently each of the antigen binding domains, such as the first antigen-binding domain and the second antigen binding domains, includes one or more single domain antibody (sdAb) fragments, for example $V_H$H, VNAR, engineered $V_H$ or $V_K$ domains. $V_H$Hs can be generated from natural camelid heavy chain only antibodies, genetically modified rodents that produce heavy chain only antibodies, or naïve/synthetic camelid or humanized camelid single domain antibody libraries. $V_{NAR}$s can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the antigen binding domain or independently each of the antigen binding domains, such as the first antigen-binding domain and/or the second antigen binding domains, of the multispecific polypeptide constructs contains at least one sdAb or an scFv that binds a TAA. In some embodiments, the at least one scFv or sdAb that binds a TAA is positioned amino-terminally relative to the Fc region and/or carboxy-terminally relative to the CD3 binding region of the multispecific polypeptide construct. In some embodiments, the multispecific polypeptide construct contains only one scFv or sdAb that binds to a TAA, which can be positioned either amino-terminally relative to the Fc region and/or carboxy-terminally relative to the CD3 binding region. In some embodiments, the multispecific polypeptide construct contains two scFvs or sdAbs that bind to a TAA, positioned amino-terminally relative to the Fc region and/or carboxy-terminally relative to the CD3 binding region. In some embodiments, the multispecific polypeptide construct contains three scFv or sdAb, in which two are positioned amino-terminally relative to the Fc region or carboxy-terminally relative to the CD3 binding region, and the third is positioned at the other end of the multispecific polypeptide construct.

In some embodiments, the multispecific polypeptide construct is formed from or includes two polypeptides, including a first polypeptide comprising a first Fc polypeptide of a heterodimeric Fc region, a linker, a VH domain of an anti-CD3 antibody or antigen binding fragment (e.g. Fv), and an scFv or sdAb that binds to a tumor-associated antigen; and a second polypeptide comprising a second Fc polypeptide of the heterodimeric Fc region, the linker, a VL domain of the anti-CD3 antibody or antigen binding fragment (e.g. Fv) and, optionally, the same or different scFv or sdAb that binds to a tumor-associated antigen. The scFv or sdAb that binds to a TAA can be positioned amino terminally relative to an Fc polypeptide of the heterodimeric Fc and/or carboxy-terminally relative to a VH or VL chain of the CD3 binding region. At least one of the first and/or second polypeptide of the multispecific polypeptide construct also includes a CRBR that binds a costimulatory receptor or a chain thereof as described in Section II.5. In some embodiments, the CRBR that binds a costimulatory receptor is a scFv or sdAb and is included as part of the first and/or second polypeptide of the multispecific polypeptide construct. In some embodiments, the CRBR that binds a costimulatory receptor is a Fab, and the multispecific polypeptide construct is additionally formed from a third polypeptide where at least the first and second polypeptide include a chain of the Fab that binds a costimulatory receptor (e.g. VH-CH1 or VL-CL of a Fab) and the third polypeptide contains the other chain of the Fab that binds the costimulatory receptor (e.g. the other of VH-CH1 or VL-CL of a Fab).

In some embodiments, the antigen binding domain or independently each of the antigen binding domains, such as the first antigen-binding domain and/or the second antigen binding domains, of the multispecific polypeptide constructs contains binding domains as single domain antibodies (sd-Abs).

In some embodiments, the antigen binding domain or independently each of the antigen binding domains, such as the first antigen-binding domain and the second antigen binding domains, contains more than one chain. In some embodiments, the antigen binding domain or independently each of the antigen binding domains, such as the first antigen-binding domain and/or the second antigen binding domains, of the multispecific polypeptide constructs contains VH and VL sequences assembled as FABs.

In some embodiments, the antigen binding domain or independently each of the antigen binding domains, such as the first antigen-binding domain and/or the second antigen binding domains, of the multispecific polypeptide constructs contains a VH-CH1 (Fd) and a VL-CL of a Fab antibody that binds a TAA. In some embodiments, the Fab antibody containing a VH-CH1 (Fd) and a VL-CL is positioned amino-terminally relative to the Fc region and/or carboxy-terminally relative to the CD3 binding region of the multispecific polypeptide construct. In some embodiments, the multispecific polypeptide construct contains only one Fab antibody, containing a VH-CH1 (Fd) and VL-CL, that binds to a TAA, which can be positioned either amino-terminally relative to the Fc region and/or carboxy-terminally relative to the CD3 binding region. In some embodiments, the multispecific polypeptide construct contains two Fab antibody fragments, each containing a VH-CH1 (Fd) and VL-CL, that binds to a TAA, in which one is positioned amino-terminally relative to the Fc region and the other is positioned carboxy-terminally relative to the CD3 binding region.

In some embodiments, the multispecific polypeptide construct is formed from or includes three or more polypeptides, including a first polypeptide comprising a first Fc polypeptide of a heterodimeric Fc region, a linker and a VH-CH1 (Fd) or VL-CL of a Fab antibody fragment that binds to a tumor-associated antigen; a second polypeptide comprising a second Fc polypeptide of the heterodimeric Fc region, the linker and, optionally, the same VH-CH1 (Fd) or VL-CL of the Fab antibody fragment that binds to a tumor-associated antigen, and a third polypeptide comprising the other of the VH-CH1 (Fd) or VL-CL of the Fab antibody fragment that binds to the TAA. The first, second and/or third polypeptide of the multispecific polypeptide construct also can include a CRBR that binds a costimulatory receptor or a chain thereof (e.g. VH-CH1 or VL-CL of a Fab) as described in Section II.5. In some embodiments, the CRBR that binds a costimulatory receptor is a scFv or sdAb and is included as part of the first and/or second polypeptide of the multispecific polypeptide construct. In some embodiments, the CRBR that binds a costimulatory receptor is a Fab, and the multispecific polypeptide construct is additionally formed from a fourth polypeptide where at least a first and second polypeptide include a chain of the Fab that binds the costimulatory receptor (e.g. VH-CH1 or VL-CL of a Fab) and the fourth polypeptide contains the other chain of the Fab that binds the costimulatory receptor (e.g. the other of VH-CH1 or VL-CL of a Fab).

In some embodiments, the antigen binding domain, or independently each of the antigen binding domains, is or includes an extracellular domain or binding fragment thereof of the natural (or native) cognate binding partner of the TAA, or a variant thereof that exhibits binding activity to the TAA.

In some embodiments, the antigen binding domain or independently each of the antigen binding domains, such as the first antigen-binding domain and the second antigen binding domains, bind the same antigen. In some embodiments, there are more than one antigen binding domain that binds a TAA and each of the antigen binding domains, such as the first antigen-binding domain and the second antigen binding domains, bind a different antigen. In some embodiments, each of the antigen binding domains, such as the first antigen-binding domain and the second antigen binding domains, bind the same tumor associated antigen (TAA). In some embodiments, each of the antigen binding domains, such as the first antigen-binding domain and the second antigen binding domains bind a different TAA. In some embodiments, the each of the antigen binding domains, such as the first antigen-binding domain and the second antigen binding domains bind a different epitope on the same TAA. In some embodiments, each of the antigen binding domains, such as the first antigen-binding domain and the second antigen binding domains, bind the same epitope on the same TAA.

In some embodiments, the antigen binding domain, or independently each of the antigen binding domains that binds TAA results in monovalent, bivalent, trivalent, or tetravalent binding to the TAA. In some embodiments, bivalent binding to the TAA comprises two antigen binding domains that bind the same epitope of the same antigen (e.g. mono-epitopic). In some embodiments, bivalent binding to the TAA comprises two antigen binding domains that bind different epitopes of the same antigen (e.g. bi-epitopic). In some embodiments, monovalent binding to the TAA comprises one antigen binding domain that binds one epitope of the antigen (e.g. mono-epitopic).

In some embodiments, the TAA is selected from the group consisting of 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, at least one antigen binding domain, or independently each antigen binding domain, binds the tumor associated antigen (TAA) folate receptor alpha (FRα). For example, the antigen binding domain contains the binding domain as an sdAb that binds FRα. Exemplary FRα-binding sdAbs are set forth in SEQ ID NOS: 120, 121, and 122. The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any the foregoing SEQ ID No and bind FRα.

In some embodiments, at least one antigen binding domain, or independently each antigen binding domain, binds the tumor associated antigen (TAA) cMET. For example, the antigen binding domain contains the binding domain as a sdAb that binds cMET. An exemplary cMET-binding sdAb is set forth in SEQ ID NO: 123 (U.S. Pat. No. 9,346,884). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to a the foregoing SEQ ID No and bind cMET.

In some embodiments, at least one antigen binding domain, or independently each antigen binding domain, binds the tumor associated antigen (TAA) B7H3. For example, the antigen binding domain contains the binding domain as an scFv that binds B7H3. An exemplary B7H3-binding scFv is set forth in SEQ ID NO: 124. In some embodiments, the antigen binding domain is a sdAb, such as a VHH. Exemplary B7H3-binding sdAbs are set forth in any of SEQ ID NOS: 301-305. In some embodiments, the antigen binding domain is or contains a Fab antibody fragment comprising a VH-CH1 (Fd) and LC. An exemplary B7H3 Fd is set forth in SEQ ID NO: 127 and an exemplary B7H3 LC is set forth in SEQ ID NO: 128 (PCT Publication No, WO2017/030926). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to a any of the foregoing SEQ ID Nos and bind B7H3.

In some embodiments, at least one antigen binding domain, or independently each antigen binding domain, binds the tumor associated antigen (TAA) CD20. In some embodiments, such an antigen-binding domain contains a VH set forth in SEQ ID NO: 189 and a VL set forth in SEQ ID NO: 190 or a sequence that exhibits at least at or about 85%, 90%, 95%, 96%, 97%, 98%, 98%, or 99% sequence identity to SEQ ID NO: 189 or SEQ ID NO:190. For example, the antigen binding domain contains the binding domain as an scFv that binds CD20. Exemplary CD20-binding scFvs are set forth in SEQ ID NO: 125 (U.S. Pub. No. US 2005/0123546). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind CD20.

In some embodiments, at least one antigen binding domain, or independently each antigen binding domain, binds the tumor associated antigen (TAA) DLL3. For example, the antigen binding domain contains the binding domain as an scFv that binds DLL3. Exemplary DLL3-binding scFv is set forth in SEQ ID NO: 126 and 188 (U.S. Pub. No. US 2017/0037130). In some embodiments, the antigen binding domain is a sdAb, such as a VHH. Exemplary DLL3-binding sdAbs are set forth in any of SEQ ID NO: 306 or SEQ ID NO:307. In some embodiments, the antigen binding domain is or contains a Fab antibody fragment comprising a Fd and LC that binds DLL3. An exemplary DLL3 Fd is set forth in SEQ ID NO: 133 and an exemplary DLL3 LC is set forth in SEQ ID NO: 134 (U.S. Pat. No. 8,044,178). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind DLL3.

In some embodiments, at least one antigen binding domain, or independently each antigen binding domain, binds the tumor associated antigen (TAA) 5T4. In some embodiments, the antigen binding domain is a sdAb, such as a VHH. Exemplary 5T4-binding sdAbs are set forth in any of SEQ ID NO: 322 or SEQ ID NO:323. In some embodiments, the antigen binding domain is or contains a Fab antibody fragment comprising a Fd and LC that binds 5T4.

An exemplary 5T4 Fd is set forth in SEQ ID NO: 129 and an exemplary 5T4 LC is set forth in SEQ ID NO: 130. In some embodiments, the antibody binding domain comprises a VH-CH1 (Fd) or VL-CL as set forth in SEQ ID NOS: 167 and 168 (U.S. Pat. No. 8,044,178). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind 5T4.

In some embodiments, at least one antigen binding domain, or independently each antigen binding domain, binds the tumor associated antigen (TAA) gpNMB. In some embodiments, the antigen binding domain is or contains a Fab fragment comprising a Fd and LC chain. An exemplary gpNMB Fd is set forth in SEQ ID NO: 131 and an exemplary gpNMB LC is set forth in SEQ ID NO: 132. The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind gpNMB.

In some embodiments, the antigen binding domain is linked, directly or indirectly via a linker, to the Fc region and/or to the CD3 binding region. In some embodiments, linkage is via a linker. In some embodiments, the linker is a linking peptide (LP), which can include any flexible or rigid linker as described in Section II.3, although generally peptides linking the antigen binding domain or domains is not a cleavable liker.

In some embodiments, the multispecific polypeptide construct comprises a first linking peptide (LP1) between the first antigen binding domain and the Fc region. In some embodiments, the multispecific polypeptide construct comprises a second linking peptide (LP2) between the CD3 binding region and the second antigen binding domain. In some embodiments, the multispecific polypeptide construct comprises a first linking peptide (LP1) between the first antigen binding domain and the Fc region and a second linking peptide (LP2) between the CD3 binding region and the second antigen binding domain. In some aspects, the multispecific polypeptide construct has the structural arrangement from N-terminus to C-terminus as follows: first antigen binding domain-LP1-Fc region-linker-CD3 binding region-LP2-second antigen binding domain. In some embodiments, the two linking peptides are not identical to each other.

In some embodiments, the LP1 or LP2 is independently a peptide of about 1 to 20 amino acids in length. In some embodiments, the LP1 or LP2 is independently a peptide that is or comprises any Gly-Ser linker as set forth in SEQ ID NOs: 10-13, 119, 135, 147, 149 or GGS.

5. Co-Stimulatory Receptor Binding Regions (CRBR)

The multispecific polypeptide constructs of the present disclosure include one or more co-stimulatory receptor binding region (CRBR) that binds a co-stimulatory receptor. In some embodiments, the one or more CRBR of the provided multispecific polypeptide constructs bind a co-stimulatory receptor expressed on T cells. In some embodiments, the co-stimulatory receptor is upregulated, induced, or expressed on the surface of an activated T cell. In some aspects, the CRBR binds a co-stimulatory receptor and stimulates the co-stimulatory receptor. In some embodiments, agonistic binding of the co-stimulatory receptor to the CRBR of the multispecific polypeptide induces downstream signaling in the T cell to potentiate or enhance T cell activation or functionalities following engagement of CD3. In some embodiments, the CRBR, or independently each of the CRBRs, is an antibody or antigen binding fragment, a natural cognate binding partner of the co-stimulatory receptor, an Anticalin (engineered lipocalin), a Darpin, a Fynomer, a Centyrin (engineered fibroneticin III domain), a cystine-knot domain, an Affilin, an Affibody, or an engineered CH3 domain.

In some embodiments, the CRBR, or independently each of the CRBRs, such as the first CRBR and the second CRBR, includes one or more copies of an antibody or an antigen-binding fragment thereof. In some embodiments, the CRBR or independently each of the CRBRs, such as the first CRBR and the second CRBR, includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody.

In some embodiments, the CRBR, or independently each of the CRBRs, such as the first CRBR and the second CRBR, is a single chain antibody. In some examples, the single chain is an scFv, a scAb, a single domain heavy chain antibody, or a single domain light chain antibody.

In some embodiments, the CRBR, or independently each of the CRBRs, such as the first CRBR and the second CRBR, includes one or more single domain antibody (sdAb) fragments, for example $V_H$H, $V_{NAR}$, engineered $V_H$ or $V_K$ domains. $V_H$Hs can be generated from natural camelid heavy chain only antibodies, genetically modified rodents that produce heavy chain only antibodies, or naïve/synthetic camelid or humanized camelid single domain antibody libraries. $V_{NAR}$s can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the CRBR, or independently each of the CRBRs such as the first CRBR and/or the second CRBR, of the multispecific polypeptide constructs contains at least one sdAb or an scFv that binds a co-stimulatory receptor. In some embodiments, the at least one scFv or sdAb that binds a co-stimulatory receptor is positioned amino-terminally relative to the Fc region and/or carboxy-terminally relative to the CD3 binding region of the multispecific polypeptide construct. In some embodiments, the multispecific polypeptide construct contains only one scFv or sdAb that binds to a co-stimulatory receptor, which can be positioned either amino-terminally relative to the Fc region and/or carboxy-terminally relative to the CD3 binding region. In some embodiments, the multispecific polypeptide construct contains two scFv or sdAb that bind to a co-stimulatory receptor, positioned amino-terminally relative to the Fc region and/or carboxy-terminally relative to the CD3 binding region.

In some embodiments, the multispecific polypeptide construct is formed from or includes two polypeptides, including a first polypeptide comprising a first Fc polypeptide of a heterodimeric Fc region, a linker, a VH domain of an anti-CD3 antibody or antigen binding fragment (e.g. Fv), and an scFv or sdAb that binds to a co-stimulatory receptor; and a second polypeptide comprising a second Fc polypeptide of the heterodimeric Fc region, the linker, a VL domain of the anti-CD3 antibody or antigen binding fragment (e.g. Fv) and, optionally, another, the same or different, scFv or sdAb that binds to a co-stimulatory receptor. The scFv or sdAb that binds the co-stimulatory receptor can be positioned amino terminally relative to an Fc polypeptide of the heterodimeric Fc and/or carboxy-terminally relative to a VH or VL chain of the CD3 binding region. At least one of the first and/or second polypeptide of the multispecific polypeptide construct also includes an antigen binding domain that binds a TAA or a chain thereof as described in Section II.4. In some embodiments, the antigen binding domain that binds a TAA is a scFv or sdAb and is included as part of the first and/or second polypeptide of the multispecific polypeptide construct. In some embodiments, the antigen binding domain that binds a TAA is a Fab, and the multispecific polypeptide construct is additionally formed from a third polypeptide where at least the first and second polypeptide include a chain of the Fab that binds TAA (e.g. VH-CH1 or VL-CL of a Fab) and the third polypeptide contains the other chain of the Fab that binds TAA (e.g. the other of VH-CH1 or VL-CL of a Fab).

In some embodiments, the multispecific polypeptide construct is formed from or includes two polypeptides, including a first polypeptide comprising in order: a first antigen binding domain specific for a TAA, a first Fc polypeptide of a heterodimeric Fc region, a linker, a VH domain of an anti-CD3 antibody or antigen binding fragment (e.g. Fv), and a second antigen binding domain specific for a TAA; and a second polypeptide containing the CRBR and comprising in order: a second Fc polypeptide of the heterodimeric Fc region, the linker, a VL domain of the anti-CD3 antibody or antigen binding fragment (e.g. Fv), wherein the CRBR is positioned amino terminally to the Fc region and/or C-terminally to the CD3 binding region. In some embodiments, the CRBR is positioned on the second polypeptide carboxy-terminally to the CD3 binding region. In some embodiments, the CRBR is positioned on the second polypeptide amino-terminally to the Fc region. In some embodiments, the CRBR is positioned amino terminally to the Fc region and C-terminally to the CD3 binding region. In some embodiments, the first and second antigen binding domain specific to a TAA are the same. In some embodiments, the first and second antigen binding domain specific to a TAA are different. In some embodiments, the first antigen binding domain and the second antigen binding domain bind a different TAA. In some embodiments, the first antigen binding domain and the second antigen binding domain bind a distinct or non-overlapping epitope of the same TAA and/or compete for binding to the same TAA.

In some embodiments, the CRBR or independently each of the CRBRs, such as the first CRBR and/or the second CRBR, contains more than one chain. In some embodiments, the CRBR or independently each of the CRBRs, such as the first CRBR and/or the second CRBR, of the multispecific polypeptide constructs contains VH and VL sequences assembled as FABs.

In some embodiments, the CRBR or independently each of the CRBRs, such as the first CRBR and/or the second CRBR, of the multispecific polypeptide constructs contains a VH-CH1 (Fd) and a VL-CL of a Fab antibody that binds a co-stimulatory receptor. In some embodiments, the Fab antibody containing a VH-CH1 (Fd) and a VL-CL is positioned amino-terminally relative to the Fc region and/or carboxy-terminally relative to the CD3 binding region of the multispecific polypeptide construct. In some embodiments, the multispecific polypeptide construct contains only one Fab antibody, containing a VH-CH1 (Fd) or VL-CL, that binds to a co-stimulatory receptor, which can be positioned either amino-terminally relative to the Fc region and/or carboxy-terminally relative to the CD3 binding region. In some embodiments, the multispecific polypeptide construct contains two Fab antibody fragments, each containing a VH-CH1 (Fd) and VL-CL, that binds to a co-stimulatory receptor, in which one is positioned amino-terminally relative to the Fc region and the other is positioned carboxy-terminally relative to the CD3 binding region.

In some embodiments, the multispecific polypeptide construct is formed from or includes three or more polypeptides, including a first polypeptide comprising a first Fc polypeptide of a heterodimeric Fc region, a linker and a VH-CH1 (Fd) or VL-CL of a Fab antibody fragment that binds to a co-stimulatory receptor; a second polypeptide comprising a second Fc polypeptide of the heterodimeric Fc region, the linker and, optionally, the same VH-CH1 (Fd) or VL-CL of the Fab antibody fragment that binds to a co-stimulatory receptor, and a third polypeptide comprising the other of the VH-CH1 (Fd) or VL-CL of the Fab antibody fragment that binds to the co-stimulatory receptor. The first, second and/or third polypeptide of the multispecific polypeptide construct also can include an antigen binding domain that binds a TAA or a chain thereof as described in Section II.4. In some embodiments, the antigen binding domain that binds a TAA is a scFv or sdAb and is included as part of the first and/or second polypeptide of the multispecific polypeptide construct. In some embodiments, the antigen binding domain that binds a TAA is a Fab, and the multispecific polypeptide construct is additionally formed from a fourth polypeptide where at least a first and second polypeptide include a chain of the Fab that binds TAA (e.g. VH-CH1 or VL-CL of a Fab) and the fourth polypeptide contains the other chain of the Fab that binds TAA (e.g. the other of VH-CH1 or VL-CL of a Fab).

In some embodiments, the CRBR, or independently each of the CRBRs, is or includes a natural (native) cognate binding partner of the co-stimulatory receptor (e.g. a natural ligand), or a variant thereof that exhibits binding activity to the co-stimulatory receptor.

In some embodiments, the one or more CRBR of the provided multispecific polypeptide constructs bind a co-stimulatory receptor expressed on T cells. In some embodiments, there are more than one CRBR that binds to a costimulatory receptor and each of the CRBRs, such as the first CRBR and the second CRBR, bind the same co-stimulatory receptor. In some embodiments, each of the CRBRs, such as the first CRBR and the CRBR, bind a different co-stimulatory receptor. In some embodiments, each of the CRBRs, such as the first CRBR and the second CRBR bind a different epitope on the same co-stimulatory receptor. In some embodiments, each of the CRBRs, such as the CRBR and the CRBR, bind the same epitope on the same co-stimulatory receptor.

In some embodiments, the CRBR, or independently each of the CRBRs that binds a co-stimulatory receptor results in monovalent, bivalent, trivalent, or tetravalent binding to the co-stimulatory receptor.

In some embodiments, the co-stimulatory receptor is expressed on T cells, such as primary T cells of a subject. In some embodiments, the co-stimulatory receptor is expressed on human T cells, such as primary human T cells of a human subject.

In some embodiments, the co-stimulatory receptor is a member of the tumor necrosis factor (TNF) receptor family. In some embodiments, the costimulatory receptor is a member of the immunoglobulin superfamily (IgSF). In some embodiments, the costimulatory receptor is a member of the B7 family of receptors.

In some embodiments, the co-stimulatory receptor is a 41BB (CD137), a OX40 (CD134), a CD27, a glucocorticoid-induced TNFR-related protein (GITR), a CD28, an ICOS, a CD40, a B-cell activating factor receptor (BAFF-R), a B-cell maturation antigen (BCMA), a Transmembrane activator and CAML interactor (TACI), and a NKG2D. In some embodiments, the co-stimulatory receptor is selected from 41BB, OX40, GITR, ICOS, or CD28. In some embodiments, the co-stimulatory receptor is selected from 41BB, OX40, or GITR.

In some embodiments, the costimulatory receptor is 41BB. In some embodiments, the costimulatory receptor is OX40. In some embodiments, the costimulatory receptor is GITR. In some embodiments, the costimulatory receptor is ICOS. In some embodiments, the costimulatory receptor is CD28.

In some embodiments, the CRBR of the multispecific polypeptide is or comprises an agonistic binding molecule to the co-stimulatory receptor. The CRBR can bind to the co-stimulatory receptor and initiate, induce, or stimulate a reaction or activity that is similar to or the same as that initiated, induced, or stimulated by the receptor's natural ligand. In some aspects, the binding of the CRBR to the co-stimulatory receptor induces or stimulates a downstream signal that is more than 5%, more than 10%, more than 20%, more than 30%, more than 40%, more than 50%, more than 60%, more than 70%, more than 80%, more than 90%, or more than 100% of the signal that is initiated, induced, or stimulated by the receptor's natural ligand.

In some embodiments, the one or more CRBR is an antibody or fragment thereof that binds to the co-stimulatory receptor 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA). In some embodiments, the one or more CRBR is an antibody or fragment thereof that binds to the co-stimulatory receptor 41BB, OX40, GITR, ICOS, or CD28. In some embodiments, the one or more CRBR is an antibody or fragment thereof that binds to the co-stimulatory receptor 41BB, OX40, or GITR. In particular embodiments, the co-stimulatory binding region is a single chain fragment, such as a single domain antibody or an scFv. Exemplary polypeptides for binding 41BB, OX40 and GITR are described in PCT publication. No. WO2017123650, WO2017123673, and WO2017015623, respectively. In some embodiments, the one or more CRBR is a single domain antibody (sdAb) that binds the co-stimulatory receptor, such as those described in PCT publication. No. WO2017123650, WO2017123673, and WO2017015623.

In some examples, the co-stimulatory receptor binding region (CRBR) binds or comprises a natural cognate binding partner of 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), NKG2D. In some embodiments, the natural cognate binding partner is selected from 41BB ligand (41BBL), OX40L (CD252), CD70, GITR Ligand/TNFSF18, CD80 (B7-1), CD86 (B7-2), ICOS Ligand (ICOSL), CD154 (CD40L), B-cell activating factor (BAFF), A proliferation-inducing ligand (APRIL), NKG2D ligands, or a functional fragment thereof.

In some embodiments, the co-stimulatory receptor binding region (CRBR) is an antibody or antigen binding fragment that binds 41BB. In particular examples, the CRBR that binds 4-1BB is a single domain antibody. In some embodiments, the sdAb contains a CDR1 GFSFSINAMG (set forth in SEQ ID NO:308), a CDR2 AIESGRNTV (set forth in SEQ ID NO:309) and a CDR3 LKGNRVVSPSVAY (set forth in SEQ ID NO: 310). Examples of sdAb that target 41BB are described in PCT publication. No. WO2017123650.

Exemplary sequences of CRBRs are set forth in Table 2.

In some embodiments, at least one CRBR, or independently each CRBR, binds the co-stimulatory receptor 41BB. In some examples, the CRBR is or contains an antibody or antigen binding fragment specific to or that binds 41BB, such as a sdAb or fragments containing a VH and VL (e.g. scFv). In some embodiments, at least on CRBR, or independently each CRBR, is a natural ligand of 41BB or is a functional binding fragment thereof. In some embodiments, at least one CRBR, or independently each CRBR, is an anticalin. Exemplary 41BB-binding CRBRs are set forth in any of SEQ ID NOS: 191-215 and 321. In some embodiments, a 4-1BB binding CRBR is a functional fragment of 41BB ligand (41BBL) containing the extracellular domain or a truncated portion thereof, such as corresponding to amino acids 50-254 of UniProt No. P41273, e.g. as set forth in SEQ ID NO:191, or a truncated portion or fragment thereof set forth in any one of SEQ ID NOS: 207-214. In some embodiments, a 4-1BB binding CRBR is an anticalin set forth in any one of SEQ ID NOs: 198-206. In some embodiments, the 4-1BB-binding CRBR is a sdAb, such as a VHH. In some embodiments, a sdAb, such as a VHH, contains a CDR1, a CDR2 and a CDR3 having a sequence set forth in SEQ ID No: 308, 309 and 310, respectively. A 41BB-binding CRBR, such as a sdAb, can include the sequence set forth in SEQ ID NO:215. A 41BB-binding CRBR, such as a sdAb, can include the sequence set forth in SEQ ID NO:321. In some embodiments, the 4-1BB-binding domain contains an antigen binding antibody fragment containing a VH and a VL, such as a single chain fragment in which the VH and VL are separated by a linker, for example an scFv. In some embodiments, the 41BB binding CRBR contains a VH set forth in any of SEQ ID NOS: 192, 194 and 196 and a VL set forth in any of SEQ ID NO: 193, 195 or 197. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind 41BB.

In some embodiments, at least one CRBR, or independently each CRBR, binds the co-stimulatory receptor OX40. In some examples, the CRBR is or contains an antibody or antigen binding fragment specific to or that binds OX40, such as a sdAb or fragments containing a VH and VL (e.g. scFv). In some embodiments, at least on CRBR, or independently each CRBR, is a natural ligand of OX40 or is a functional binding fragment thereof. Exemplary of such OX40-binding CRBRs are set forth in any of SEQ ID NOS: 216-225. In some embodiments, the OX40-binding CRBR contains an VH set forth in any of SEQ ID NOS: 221 and 223 and a VL set forth in any of SEQ ID NO: 222 and 224. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind OX40.

In some embodiments, at least one CRBR, or independently each CRBR, binds the co-stimulatory receptor GITR. In some examples, the CRBR is or contains an antibody or antigen binding fragment specific to or that binds GITR, such as a sdAb or fragments containing a VH and VL (e.g. scFv). In some embodiments, at least one CRBR, or independently each CRBR, is a natural ligand of GITR or is a functional binding fragment thereof. Exemplary of such GITR-binding CRBRs are set forth in any of SEQ ID NOS: 226-235. In some embodiments, the GITR binding CRBR contains a VH set forth in any of SEQ ID NOS: 227, 229, 233 and a VL set forth in any of SEQ ID NO: 228, 230 and 234. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind GITR.

In some embodiments, at least one CRBR, or independently each CRBR, binds the co-stimulatory receptor CD27. In some examples, the CRBR is or contains an antibody or antigen binding fragment specific to or that binds CD27, such as a sdAb or fragments containing a VH and VL (e.g. scFv). In some embodiments, at least one CRBR, or independently each CRBR, is a natural ligand of CD27 or is a functional binding fragment thereof. Exemplary of such CD27-binding CRBRs are set forth in any of SEQ ID NOS: 236-238. In some embodiments, the CD27 binding CRBR contains a VH set forth SEQ ID NO: 237 and a VL set forth in SEQ ID NO: 238. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind CD27.

In some embodiments, at least one CRBR, or independently each CRBR, binds the co-stimulatory receptor ICOS. In some examples, the CRBR is or contains an antibody or antigen binding fragment specific to or that binds ICOS, such as a sdAb or fragments containing a VH and VL (e.g. scFv). In some embodiments, at least one CRBR, or independently each CRBR, is a natural ligand of ICOS or is a functional binding fragment thereof. An exemplary ICOS-binding CRBR sequence is set forth in SEQ ID NO: 239.

In some embodiments, at least one CRBR, or independently each CRBR, binds the co-stimulatory receptor CD28. In some examples, the CRBR is or contains an antibody or antigen binding fragment specific to or that binds CD28, such as a sdAb or fragments containing a VH and VL (e.g. scFv). In some embodiments, at least one CRBR, or independently each CRBR, is a natural ligand of CD28 or is a functional binding fragment thereof. An exemplary CD28-binding CRBR sequence is set forth in SEQ ID NO: 240.

TABLE 2

Exemplary CRBR Sequences

| CRBR | Format | Reference | SEQ ID NO |
| --- | --- | --- | --- |
| 41BB binding CRBR Sequences | | | |
| 41BBL | Natural Ligand | UniProt accession no. P41273 | 191 |
| PF-05082566 | VH | US 2012/0237498 (SEQ ID NO: 43) | 192 |
|  | VL | US 2012/0237498 (SEQ ID NO: 45) | 193 |
| BMS663513 | VH | WO 2005/035584 (SEQ ID NO: 9) | 194 |
|  | VL | WO 2005/035584 (SEQ ID NO: 6) | 195 |
| MSB7 | VH | US 2017/0226215 (SEQ ID NO: 138) | 196 |
|  | VL | US 2017/0226215 (SEQ ID NO: 28) | 197 |
| 41BB Anticalin | Anticalin | WO 2016/177762 (SEQ ID NO: 12) | 198 |
| 41BB Anticalin | Anticalin | WO 2016/177762 (SEQ ID NO: 13) | 199 |
| 41BB Anticalin | Anticalin | WO 2016/177762 (SEQ I D NO: 14) | 200 |
| 41BB Anticalin | Anticalin | WO 2016/177762 (SEQ ID NO: 15) | 201 |
| 41BB Anticalin | Anticalin | WO 2016/177762 (SEQ ID NO: 16) | 202 |
| 41BB Anticalin | Anticalin | WO 2016/177762 (SEQ ID NO: 17) | 203 |
| 41BB Anticalin | Anticalin | WO 2016/177762 (SEQ ID NO: 18) | 204 |
| 41BB Anticalin | Anticalin | WO 2016/177762 SEQ ID NO: 19) | 205 |
| 41BB Anticalin | Anticalin | WO 2016/177762 (SEQ ID NO: 20) | 206 |
| 71-254 of human 41BBL | 41BB ligand | WO 2017/167672 (SEQ ID NO: 3) | 207 |
| 85-254 of human 41BBL | 41BB ligand | WO 2017/167672 (SEQ ID NO: 4) | 208 |
| 80-254 of human 41BBL | 41BB ligand | WO 2017/167672 (SEQ ID NO: 5) | 209 |
| 52-254 of human 41BBL | 41BB ligand | WO 2017/167672 (SEQ ID NO: 6) | 210 |
| 71-248 of human 41BBL | 41BB ligand | WO 2017/167672 (SEQ ID NO: 7) | 211 |
| 85-248 of human 41BBL | 41BB ligand | WO 2017/167672 (SEQ ID NO: 8 | 212 |
| 80-248 of human 41BBL | 41BB ligand | WO 2017/167672 (SEQ ID NO: 9) | 213 |
| 52-248 of human 41BBL | 41BB ligand | WO 2017/167672 (SEQ ID NO: 10) | 214 |
| 41BB sdAb | sdAb | US 2017/0198050 | 215 |
| 41BB sdAb | sdAb |  | 321 |
| OX40-binding CRBR Sequences | | | |
| OX40 ligand | Natural Ligand | UniProt accession no. P23510 | 216 |
| OX40 ligand | Natural Ligand | U.S. Pat. No. 7,959,925 (SEQ ID NO: 2) | 217 |
| human OX40L: 51-183 | Natural Ligand | WO 2017/167672 (SEQ ID NO: 11) | 218 |
| Human Ox40L: 51-183 N90D | Natural Ligand | WO 2017/167672 (SEQ ID NO: 12) | 219 |

TABLE 2-continued

Exemplary CRBR Sequences

| CRBR | Format | Reference | SEQ ID NO |
|---|---|---|---|
| Human OX40L: 52-183 | Natural Ligand | WO 2017/167672 (SEQ ID NO: 13) | 220 |
| 1A07 | VH | US 2015/0307617 (SEQ ID NO: 56) | 221 |
| | VL | US 2015/0307617 (SEQ ID NO: 59) | 222 |
| 1949 | VH | WO 2016/179517 (SEQ ID NO: 16) | 223 |
| | VL | WO 2016/179517 | 224 |
| 1D10v1 | sdAb | U.S. Pat. No. 9,006,399 | 225 |
| GITR-binding CRBR Sequences | | | |
| GITR ligand | Natural Ligand | UniProt no. Q9UNG2 | 226 |
| 36E5 | VH | US 2014/0348841 (SEQ ID NO: 104) | 227 |
| | VL | US 2014/0348841 (SEQ ID NO: 105) | 228 |
| TRX-518 | VH | US 2013/0183321 (SEQ ID NO: 54) | 229 |
| | VL | US 2013/0183321 (SEQ ID NO: 44) | 230 |
| 5H7v2 | VH | US 2015/0064204 (SEQ ID NO: 282) | 231 |
| | VL | US 2015/0064204 (SEQ ID NO: 134) | 232 |
| 41G5v2 | VH | US 2015/0064204 (SEQ ID NO: 312) | 233 |
| | VL | US 2015/0064204 (SEQ ID NO: 124) | 234 |
| C06v3 | sdAb | US 2017/0022284 (SEQ ID NO: 59) | 235 |
| CD27-binding CRBR Sequences | | | |
| CD70-ECD | Natural Ligand | UniProt no. P32970; ECD set forth as residues 39-193 | 236 |
| 1F5 | VH | US 2011/0274685 | 237 |
| | VL | US 2011/0274685 | 238 |
| CD28-binding CRBR Sequences | | | |
| CD28 sdAb | sdAb | | 239 |
| ICOS-binding CRBR Sequences | | | |
| ICOS sdAb | sdAb | | 240 |

In some embodiments, the one or more CRBR is linked, directly or indirectly via a linker, to the Fc region and/or to the CD3 binding region. In some embodiments, linkage is via a linker. In some embodiments, the linker is a linking peptide (LP), which can include any flexible or rigid linker as described in Section II.3, although generally the peptide linking the CRBR or regions is not a cleavable liker.

In some embodiments, the multispecific polypeptide construct comprises a linking peptide (LP) between the CRBR and the Fc region. In some embodiments, the multispecific polypeptide construct comprises a linking peptide (LP) between the CD3 binding region and the CRBR.

In some embodiments, the multispecific polypeptide construct comprises more than one CRBRs. In some embodiments, the multispecific polypeptide construct comprises a first linking peptide (LP1) between the first CRBR and the Fc region. In some embodiments, the multispecific polypeptide construct comprises a second linking peptide (LP2) between the CD3 binding region and the second CRBR. In some embodiments, the multispecific polypeptide construct comprises a first linking peptide (LP1) between the first CRBR and the Fc region and a second linking peptide (LP2) between the CD3 binding region and the second CRBR. In some aspects, the multispecific polypeptide construct has the structural arrangement from N-terminus to C-terminus as follows: CRBR and/or antigen binding domain-LP1-Fc region-linker-CD3 binding region-LP2-CRBR and/or antigen binding domain. In some embodiments, the two linking peptides are not identical to each other.

In some embodiments, the LP (e.g., LP1 or LP2) is independently a peptide of about 1 to 20 amino acids in length. In some embodiments, the LP1 or LP2 is independently a peptide that is or comprises any Gly-Ser linker as set forth in SEQ ID NOs: 10-13, 119, 135, 147, 149 or GGS.

6. Inhibitory Receptor Binding Regions (IRBR)

The multispecific polypeptide constructs of the present disclosure include one or more inhibitor receptor binding region (IRBR) that binds an inhibitory receptor. In some embodiments, the one or more IRBR of the provided multispecific polypeptide constructs bind an inhibitory receptor expressed on T cells. In some embodiments, the inhibitory receptor is upregulated, induced, or expressed on the surface of an activated T cell. In some aspects, the IRBR blocks an interaction between the inhibitory receptor and its ligand, thereby reducing, suppressing or decreasing an inhibitory signal in the cell to which the IRBR binds, e.g. T cell. In some embodiments, the IRBR, or independently each of the IRBRs, is an antibody or antigen binding fragment, a natural cognate binding partner of the co-stimulatory receptor, an Anticalin (engineered lipocalin), a Darpin, a Fynomer, a Centyrin (engineered fibroneticin III domain), a cystine-knot domain, an Affilin, an Affibody, or an engineered CH3 domain.

In some embodiments, the IRBR, or independently each of the IRBRs, such as the first IRBR and the second IRBR, includes one or more copies of an antibody or an antigen-binding fragment thereof. In some embodiments, the IRBR or independently each of the IRBRs, such as the first IRBR and the second IRBR, includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody.

In some embodiments, the IRBR, or independently each of the IRBRs, such as the first IRBR and the second IRBR, is a single chain antibody. In some examples, the single chain is an scFv, a scAb, a single domain heavy chain antibody, or a single domain light chain antibody.

In some embodiments, the IRBR, or independently each of the IRBRs, such as the first IRBR and the second IRBR, includes one or more single domain antibody (sdAb) fragments, for example $V_HH$, $V_{NAR}$, engineered $V_H$ or $V_K$ domains. $V_HHs$ can be generated from natural camelid heavy chain only antibodies, genetically modified rodents that produce heavy chain only antibodies, or naïve/synthetic camelid or humanized camelid single domain antibody libraries. $V_{NAR}s$ can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the IRBR, or independently each of the IRBRs such as the first IRBR and/or the second IRBR, of the multispecific polypeptide constructs contains at least one sdAb or an scFv that binds an inhibitory receptor. In some embodiments, the at least one scFv or sdAb that binds an inhibitory receptor is positioned amino-terminally relative to the Fc region and/or carboxy-terminally relative to the CD3 binding region of the multispecific polypeptide construct. In some embodiments, the multispecific polypeptide construct contains only one scFv or sdAb that binds to an inhibitory receptor, which can be positioned either amino-terminally relative to the Fc region and/or carboxy-terminally relative to the CD3 binding region. In some embodiments, the multispecific polypeptide construct contains two scFv or sdAb that bind to an inhibitory receptor, positioned amino-terminally relative to the Fc region and/or carboxy-terminally relative to the CD3 binding region.

In some embodiments, the multispecific polypeptide construct is formed from or includes two polypeptides, including a first polypeptide comprising a first Fc polypeptide of a heterodimeric Fc region, a linker, a VH domain of an anti-CD3 antibody or antigen binding fragment (e.g. Fv), and an scFv or sdAb that binds to an inhibitory receptor; and a second polypeptide comprising a second Fc polypeptide of the heterodimeric Fc region, the linker, a VL domain of the anti-CD3 antibody or antigen binding fragment (e.g. Fv) and, optionally, another, the same or different, scFv or sdAb that binds to an inhibitory receptor. The scFv or sdAb that binds the inhibitory receptor can be positioned amino terminally relative to an Fc polypeptide of the heterodimeric Fc and/or carboxy-terminally relative to a VH or VL chain of the CD3 binding region. At least one of the first and/or second polypeptide of the multispecific polypeptide construct also includes an antigen binding domain that binds a TAA or a chain thereof as described in Section II.4. In some embodiments, the antigen binding domain that binds a TAA is a scFv or sdAb and is included as part of the first and/or second polypeptide of the multispecific polypeptide construct. In some embodiments, the antigen binding domain that binds a TAA is a Fab, and the multispecific polypeptide construct is additionally formed from a third polypeptide where at least the first and second polypeptide include a chain of the Fab that binds TAA (e.g. VH-CH1 or VL-CL of a Fab) and the third polypeptide contains the other chain of the Fab that binds TAA (e.g. the other of VH-CH1 or VL-CL of a Fab).

In some embodiments, the multispecific polypeptide construct is formed from or includes two polypeptides, including a first polypeptide comprising in order: a first antigen binding domain specific for a TAA, a first Fc polypeptide of a heterodimeric Fc region, a linker, a VH domain of an anti-CD3 antibody or antigen binding fragment (e.g. Fv), and a second antigen binding domain specific for a TAA; and a second polypeptide containing the IRBR and comprising in order: a second Fc polypeptide of the heterodimeric Fc region, the linker, a VL domain of the anti-CD3 antibody or antigen binding fragment (e.g. Fv), wherein the IRBR is positioned amino terminally to the Fc region and/or C-terminally to the CD3 binding region. In some embodiments, the IRBR is positioned on the second polypeptide carboxy-terminally to the CD3 binding region. In some embodiments, the IRBR is positioned on the second polypeptide amino-terminally to the Fc region. In some embodiments, the IRBR is positioned amino terminally to the Fc region and C-terminally to the CD3 binding region. In some embodiments, the first and second antigen binding domain is specific to a TAA are the same. In some embodiments, the first and second antigen binding domain is specific to a TAA are different. In some embodiments, the first antigen binding domain and the second antigen binding domain bind a different TAA. In some embodiments, the first antigen binding domain and the second antigen binding domain bind a distinct or non-overlapping epitope of the same TAA and/or compete for binding to the same TAA.

In some embodiments, the IRBR or independently each of the IRBRs, such as the first IRBR and/or the second IRBR, contains more than one chain. In some embodiments, the IRBR or independently each of the IRBRs, such as the first IRBR and/or the second IRBR, of the multispecific polypeptide constructs contains VH and VL sequences assembled as FABs.

In some embodiments, the antigen binding domain or independently each of the antigen binding domains, such as the first antigen-binding domain and/or the second antigen binding domains, of the multispecific polypeptide constructs contains a VH-CH1 (Fd) and a VL-CL of a Fab antibody that binds an inhibitory receptor. In some embodiments, the Fab antibody containing a VH-CH1 (Fd) and a VL-CL is positioned amino-terminally relative to the Fc region and/or carboxy-terminally relative to the CD3 binding region of the multispecific polypeptide construct. In some embodiments, the multispecific polypeptide construct contains only one Fab antibody, containing a VH-CH1 (Fd) or VL-CL, that binds to an inhibitory receptor, which can be positioned either amino-terminally relative to the Fc region and/or carboxy-terminally relative to the CD3 binding region. In some embodiments, the multispecific polypeptide construct contains two Fab antibody fragments, each containing a VH-CH1 (Fd) and VL-CL, that binds to an inhibitory receptor, in which one is positioned amino-terminally relative to the Fc region and the other is positioned carboxy-terminally relative to the CD3 binding region.

In some embodiments, the multispecific polypeptide construct is formed from or includes three or more polypeptides, including a first polypeptide comprising a first Fc polypeptide of a heterodimeric Fc region, a linker and a VH-CH1 (Fd) or VL-CL of a Fab antibody fragment that binds to an inhibitory receptor; a second polypeptide comprising a second Fc polypeptide of the heterodimeric Fc region, the linker and, optionally, the same VH-CH1 (Fd) or VL-CL of the Fab antibody fragment that binds to a inhibitory receptor, and a third polypeptide comprising the other of the VH-CH1 (Fd) or VL-CL of the Fab antibody fragment that binds to the inhibitory receptor. The first, second and/or third polypeptide of the multispecific polypeptide construct also can include an antigen binding domain that binds a TAA or a chain thereof as described in Section II.4. In some embodiments, the antigen binding domain that binds a TAA is a scFv or sdAb and is included as part of the first and/or second polypeptide of the multispecific polypeptide construct. In some embodiments, the antigen binding domain that binds a TAA is a Fab, and the multispecific polypeptide construct is additionally formed from a fourth polypeptide where at least a first and second polypeptide includes a chain of the Fab that binds TAA (e.g. VH-CH1 or VL-CL of a Fab) and the fourth polypeptide contains the other chain of the Fab that binds TAA (e.g. the other of VH-CH1 or VL-CL of a Fab).

In some embodiments, the IRBR, or independently each of the IRBRs, is or includes a natural (native) cognate binding partner of the inhibitor receptor (e.g. a natural ligand), or a variant thereof that exhibits binding activity to the inhibitory receptor.

In some embodiments, the one or more IRBR of the provided multispecific polypeptide constructs bind a inhibitory receptor expressed on T cells. In some embodiments, there are more than one IRBR that binds to an inhibitory receptor and each of the IRBRs, such as the first IRBR and the second IRBR, bind the same co-stimulatory receptor. In some embodiments, each of the IRBRs, such as the first IRBR and the second IRBR, bind a different inhibitory receptor. In some embodiments, each of the IRBRs, such as the first IRBR and the second IRBR bind a different epitope on the same inhibitory receptor. In some embodiments, each of the IRBRs, such as the first IRBR and the second IRBR, bind the same epitope on the same inhibitory receptor.

In some embodiments, the IRBR, or independently each of the IRBRs that binds a inhibitory receptor results in monovalent, bivalent, trivalent, or tetravalent binding to the inhibitory receptor.

In some embodiments, the inhibitory receptor is expressed on T cells, such as primary T cells of a subject. In some embodiments, the inhibitory receptor is expressed on human T cells, such as primary human T cells of a human subject.

In some embodiments, the inhibitory receptor is a member of the tumor necrosis factor (TNF) receptor family. In some embodiments, the inhibitory receptor is a member of the immunoglobulin superfamily (IgSF).

In some embodiments, the inhibitory receptor is Programmed cell death protein 1 (PD-1), cytotoxic T-lymphocyte associated protein 4 (CTLA-4), T cell immunoreceptor with Ig and ITIM domains (TIGIT), V-domain immunoglobulin suppressor of T cell activation (VISTA), T cell immunoglobulin and mucin-domain containing-3 (TIM3), or lymphocyte activation gene 3 (LAG3). In some embodiments, the one or more IRBR is an antibody or fragment thereof that binds to the inhibitor receptor PD-1, CTLA-4, TIGIT, VISTA, TIM3 or LAG3. In particular embodiments, the antibody or antigen-binding fragment is humanized or is human.

In some examples, the co-stimulatory receptor binding region (CRBR) binds or comprises a natural cognate binding partner of PD-1, CTLA-4, TIGIT, VISTA, or TIM3. In some embodiments, the natural cognate binding partner is selected from PD-L1, PD-L2, CD80, CD86, CD155, CD112, or VSIG-3/IGSF11, or a functional fragment thereof.

In some examples, the IRBR contains an antibody fragment, such as an scFv, that contains a variable light (VL) chain and a variable heavy (VH) chain of an antibody that that binds an inhibitory receptor, such as PD-1, CTLA-4, TIGIT, VISTA, or TIM3. In some examples, the IRBR contains a single domain antibody or a VHH domain that specifically binds an inhibitory receptor, such as a PD-1, CTLA-4, TIGIT, VISTA, or TIM3, see e.g. described in PCT publication No. WO2018068695 or WO2018068201.

In some embodiments, the inhibitory receptor is PD-1. In come embodiments, the one or more IRBR is an antibody fragment that binds to PD-1.

In some embodiments, the IRBR is or contains a VHH domain that binds PD-1 comprising a CDR1, CDR2 and CDR3 contained in a VHH amino acid sequences selected from any of SEQ ID NO: 243 or 251-256, or an amino acid sequence that has at least 90%, 91%, 92%, 93%, 94%, 95%, 96%, 97%, 98%, or 99% sequence identity to the VHH region amino acid selected from any one of SEQ ID NOs: 243 or 251-256 and binds PD-1.

In some embodiments, the IRBR is or contains a VHH domain that contains a CDR1, CDR2, CDR3 contained in a VHH domain set forth in SEQ ID NO:243, or an amino acid sequence that has at least 90%, 91%, 92%, 93%, 94%, 95%, 96%, 97%, 98%, or 99% sequence identity to the VHH region amino acid selected set forth in SEQ ID NO: 243 and that binds PD-1. In some embodiments, the IRBR is or contains a VHH domain that has the amino acid sequence set forth in SEQ ID NO: 243 or an amino acid sequence that has at least 90%, 91%, 92%, 93%, 94%, 95%, 96%, 97%, 98%, or 99% sequence identity to the amino acid selected set forth in SEQ ID NO: 243 and that binds PD-1. In some embodiments, IRBR is or contains a VHH domain that is a humanized variant of the amino acid sequence set forth in SEQ ID NO: 243.

In some embodiments, an IRBR that binds PD-1 has a VHH domain that comprises a CDR1 set forth in any one of SEQ ID NOS: 268, 272 or 273, a CDR2 set forth in SEQ ID NO: 278 and a CDR3 set forth in SEQ ID NO: 283.

In some embodiments, an IRBR that binds PD-1 has a VHH domain that contains a CDR1, CDR2, and CDR3 set forth in SEQ ID NOs: 272, 278, and 283, respectively. In some embodiments, an IRBR that binds PD-1 has a VHH domain that contains a CDR1, CDR2 and CDR3 set forth in SEQ ID NOs: 268, 278, and 283, respectively. In some embodiments, the an IRBR that binds PD-1 has a VHH domain that contains a CDR1, CDR2 and CDR3 set forth in SEQ ID NOs: 273, 278, and 283, respectively.

In some aspects, the IRBR is or contains a VHH domain that contains a CDR1, CDR2 and CDR3 contained in a VHH amino acid sequence selected from any of SEQ ID NO:251-267, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 251-267 and that binds PD-1.

In some cases, the IRBR contains a VHH domain that is a humanized variant that has the amino acid sequence set forth in any of SEQ ID NOS: 251-267 or an amino acid sequence that has at least 90%, 91%, 92%, 93%, 94%, 95%, 96%, 97%, 98%, or 99% sequence identity to the VHH region amino acid selected from any one of SEQ ID NOs: 251-267 and that binds PD-1. In some embodiments, the IRBR is or contains a VHH domain sequence that is a humanized VHH domain having the sequence of amino acids set forth in any one of SEQ ID NOS: 251-267.

In some embodiments, the one or more IRBR is linked, directly or indirectly via a linker, to the Fc region and/or to the CD3 binding region. In some embodiments, linkage is via a linker. In some embodiments, the linker is a linking peptide (LP), which can include any flexible or rigid linker as described, such as in Section II.3, although generally the peptide linking the IRBR or regions is not a cleavable liker.

In some embodiments, the multispecific polypeptide construct comprises a linking peptide (LP) between the IRBR and the Fc region. In some embodiments, the multispecific polypeptide construct comprises a linking peptide (LP) between the CD3 binding region and the IRBR.

In some embodiments, the multispecific polypeptide construct comprises more than one IRBR. In some embodiments, the multispecific polypeptide construct comprises a first linking peptide (LP1) between the first IRBR and the Fc region. In some embodiments, the multispecific polypeptide construct comprises a second linking peptide (LP2) between the CD3 binding region and the second IRBR. In some embodiments, the multispecific polypeptide construct comprises a first linking peptide (LP1) between the first IRBR and the Fc region and a second linking peptide (LP2) between the CD3 binding region and the second CRBR. In some aspects, the multispecific polypeptide construct has the structural arrangement from N-terminus to C-terminus as follows: IRBR and/or antigen binding domain-LP1-Fc region-linker-CD3 binding region-LP2-IRBR and/or antigen binding domain. In some embodiments, the two linking peptides are not identical to each other.

In some embodiments, the LP (e.g., LP1 or LP2) is independently a peptide of about 1 to 20 amino acids in length. In some embodiments, the LP1 or LP2 is independently a peptide that is or comprises any Gly-Ser linker as set forth in SEQ ID NOs: 10-13, 119, 135, 147, 149 or GGS.

In some embodiments, the multispecific polypeptide construct contains both a CRBR and an IRBR. In some embodiments, one of the CRBR or IRBR is positioned amino-terminally relative to the Fc region and the other of the CRBR or IRBR is positioned carboxy-terminally relative to the CD3 binding region of the multispecific polypeptide construct. In some embodiments, the CRBR and IRBR are present on different polypeptide of a heterodimeric multispecific polypeptide construct, in which at least one of the polypeptides also contains the at least one antigen binding domain specific to a TAA. In some embodiments, the CRBR and IRBR are present on the same polypeptide (first polypeptide) of a heterodimeric multispecific polypeptide construct and the at least one antigen binding domain specific to a TAA is on the other (or second) polypeptide of the heterodimeric multispecific polypeptide construct.

In some embodiments, the multispecific polypeptide construct is formed from or includes two polypeptides. In some aspects, the first polypeptide comprises in order: a first antigen binding domain specific for a TAA, a first Fc polypeptide of a heterodimeric Fc region, a linker, a VH domain of an anti-CD3 antibody or antigen binding fragment (e.g. Fv), and a second antigen binding domain specific for a TAA; and a second polypeptide comprising in order: one of the IRBR or CRBR, a second Fc polypeptide of the heterodimeric Fc region, the linker, a VL domain of the anti-CD3 antibody or antigen binding fragment (e.g. Fv), and the other of the IRBR or CRBR. In some embodiments, the IRBR is positioned on the second polypeptide carboxy-terminally to the CD3 binding region and the CRBR is positioned on the second polypeptide amino-terminally to the Fc region. In some embodiments, the IRBR is positioned on the second polypeptide amino-terminally to the Fc region and the CRBR is positioned on the second polypeptide carboxy-terminally to the CD3 binding region. In some embodiments, the first and second antigen binding domain is specific to a TAA are the same. In some embodiments, the first and second antigen binding domain is specific to a TAA are different. In some embodiments, the first antigen binding domain and the second antigen binding domain bind a different TAA. In some embodiments, the first antigen binding domain and the second antigen binding domain bind a distinct or non-overlapping epitope of the same TAA and/or compete for binding to the same TAA.

Exemplary formats of a multispecific polypeptide construct containing an IRBR are set forth in FIGS. 18A and 18B.

III. PHARMACEUTICAL COMPOSITION

Provided herein are compositions of any of the provided multispecific polypeptide constructs. It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed., Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203 (1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In some embodiments, the multispecific polypeptide constructs, conjugated multispecific polypeptide constructs, and compositions thereof—referred to collectively herein as the Therapeutic(s) and derivatives, fragments, analogs and homologs thereof, can be incorporated into pharmaceutical compositions suitable for administration. Principles and considerations involved in preparing such compositions, as well as guidance in the choice of components are provided, for example, in Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the multispecific polypeptide construct or a conjugated thereof and a pharmaceutically acceptable carrier. Where a multispecific polypeptide construct includes a fragment of an antibody, the smallest fragment of the antibody that specifically binds to the target protein can be used. For example, based upon the variable-region sequences of an antibody, peptide molecules can be designed that retain the ability of the antibody to bind the target protein sequence. Such peptides can be synthesized chemically and/or produced by recombinant DNA technology. (See, e.g., Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be suitable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

In some embodiments, the pharmaceutical composition is administered to a subject through any route, including orally, transdermally, by inhalation, intravenously, intra-arterially, intramuscularly, direct application to a wound site, application to a surgical site, intraperitoneally, by suppository, subcutaneously, intradermally, transcutaneously, by nebulization, intrapleurally, intraventricularly, intra-articularly, intraocularly, or intraspinally.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the multispecific polypeptide construct are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the therapeutics are prepared with carriers that will protect the compound against rapid elimination from the body, such as sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the therapeutics can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

In some embodiments, the pharmaceutical composition comprises a pharmaceutically-acceptable excipient, for example a filler, binder, coating, preservative, lubricant, flavoring agent, sweetening agent, coloring agent, a solvent, a buffering agent, a chelating agent, or stabilizer. Examples of pharmaceutically-acceptable fillers include cellulose, dibasic calcium phosphate, calcium carbonate, microcrystalline cellulose, sucrose, lactose, glucose, mannitol, sorbitol, maltol, pregelatinized starch, corn starch, or potato starch. Examples of pharmaceutically-acceptable binders include polyvinylpyrrolidone, starch, lactose, xylitol, sorbitol, maltitol, gelatin, sucrose, polyethylene glycol, methyl cellulose, or cellulose. Examples of pharmaceutically-acceptable coatings include hydroxypropyl methylcellulose (HPMC), shellac, corn protein zein, or gelatin. Examples of pharmaceutically-acceptable disintegrants include polyvinylpyrrolidone, carboxymethyl cellulose, or sodium starch glycolate. Examples of pharmaceutically-acceptable lubricants include polyethylene glycol, magnesium stearate, or stearic acid. Examples of pharmaceutically-acceptable preservatives include methyl parabens, ethyl parabens, propyl paraben, benzoic acid, or sorbic acid. Examples of pharmaceutically-acceptable sweetening agents include sucrose, saccharine, aspartame, or sorbitol. Examples of pharmaceutically-acceptable buffering agents include carbonates, citrates, gluconates, acetates, phosphates, or tartrates.

Sustained-release preparations can be prepared. Suitable examples of sustained-release preparations include semipermeable matrices of solid hydrophobic polymers containing the antibody, which matrices are in the form of shaped articles, e.g., films, or microcapsules. In some embodiments, the pharmaceutical composition further comprises an agent for the controlled or sustained release of the product, such as injectable microspheres, bio-erodible particles, polymeric compounds (polylactic acid, polyglycolic acid), beads, or liposomes. Examples of sustained-release matrices include polyesters, hydrogels (for example, poly(2-hydroxyethylmethacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

Further provided are kits comprising the pharmaceutical compositions (or articles of manufacture) described herein. The pharmaceutical compositions can be included in a container, pack, or dispenser together with instructions for administration. The kits described herein may also include other materials desirable from a commercial and user standpoint, including other buffers, diluents, filters, needles, syringes, and package inserts with instructions for performing any methods described herein.

The formulation can also contain more than one multispecific polypeptide construct as necessary for the particular indication being treated, for example, those with complementary activities that do not adversely affect each other. In some embodiments, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In some embodiments, the dosage of the pharmaceutical composition is a single dose or a repeated dose. In some embodiments, the doses are given to a subject once per day, twice per day, three times per day, or four or more times per day. In some embodiments, about 1 or more (such as about 2 or more, about 3 or more, about 4 or more, about 5 or more, about 6 or more, or about 7 or more) doses are given in a week. In some embodiments, multiple doses are given over the course of days, weeks, months, or years. In some embodiments, a course of treatment is about 1 or more doses (such as about 2 or more does, about 3 or more doses, about 4 or more doses, about 5 or more doses, about 7 or more doses, about 10 or more doses, about 15 or more doses, about 25 or more doses, about 40 or more doses, about 50 or more doses, or about 100 or more doses).

In some embodiments, the pharmaceutical composition is administered to a subject. Generally, dosages and routes of administration of the pharmaceutical composition are determined according to the size and condition of the subject, according to standard pharmaceutical practice. For example, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans. The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. The optimal dosage and treatment regime for a particular patient can readily be determined by one skilled in the art of medicine by monitoring the patient for signs of disease and adjusting the treatment accordingly.

IV. METHODS OF USE AND THERAPEUTIC ADMINISTRATION

Also provided are methods for using and uses of the multispecific polypeptide constructs. Such methods and uses include therapeutic methods and uses, for example, involving administration of the molecules or compositions containing the same, to a subject having a disease, condition, or disorder, such as a tumor or cancer. In some embodiments, the molecule and/or composition is administered in an effective amount to effect treatment of the disease or disorder. Uses include uses of the multispecific polypeptide constructs in such methods and treatments, and in the preparation of a medicament in order to carry out such therapeutic methods. In some embodiments, the methods are carried out by administering the multispecific polypeptide constructs, or compositions comprising the same, to the subject having or suspected of having the disease or condition. In some embodiments, the methods thereby treat the disease or condition or disorder in the subject.

In one embodiment, a multispecific polypeptide construct of the disclosure may be used as therapeutic agents. Such agents will generally be employed to diagnose, prognose, monitor, treat, alleviate, and/or prevent a disease or pathology in a subject. A therapeutic regimen is carried out by identifying a subject, e.g., a human patient or other mammal suffering from (or at risk of developing) a disorder using standard methods. A multispecific polypeptide construct is administered to the subject. A multispecific polypeptide construct is administered to the subject and will generally have an effect due to its binding with the target(s).

In some embodiments, provided herein is a method of modulating an immune response in a subject by administering a therapeutically effective amount of any of the provided multispecific conjugates or pharmaceutical compositions. In some embodiments, the method of modulating an immune response increases or enhances an immune response in a subject. For example, the increase or enhanced response may be an increase in cell-mediated immunity. In some examples, the method increases T-cell activity, such as cytolytic T-cell (CTL) activity. In some embodiments, the modulated (e.g., increased) immune response is against a tumor or cancer.

Administration of the multispecific polypeptide construct may activate innate immune cells via engagement of FcγRs through the Fc-region of the multispecific polypeptide construct. Administration of the multispecific polypeptide construct may agonize, stimulate, activate, and/or augment innate immune cell effector functions, including ADCC, cytokine release, degranulation and/or ADCP. Administration of the multispecific polypeptide construct may activate T-cell once the linker(s) joining the first and second component is cleaved by a protease thereby allowing the anti-CD3 binding portion to bind CD3ε on the T cells. Administration of the multispecific polypeptide construct may agonize, stimulate, activate, and/or augment CD3-mediated T cell activation, cytotoxicity, cytokine release and/or proliferation.

In some embodiments, the provided methods are for treating a disease or condition in a subject by administering a therapeutically effective amount of any of the provided multispecific conjugates or pharmaceutical compositions. In some embodiments, the disease or condition is a tumor or a cancer. Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this disclosure can be used to prevent the onset or reoccurrence of the disease or disorder in a subject, e.g., a human or other mammal, such as a non-human primate, companion animal (e.g., cat, dog, horse), farm animal, work animal, or zoo animal. The terms subject and patient are used interchangeably herein.

In some embodiments, the pharmaceutical composition can be used to inhibit growth of mammalian cancer cells (such as human cancer cells). A method of treating cancer can include administering an effective amount of any of the pharmaceutical compositions described herein to a subject with cancer. The effective amount of the pharmaceutical composition can be administered to inhibit, halt, or reverse progression of cancers. Human cancer cells can be treated in vivo, or ex vivo. In ex vivo treatment of a human patient, tissue or fluids containing cancer cells are treated outside the body and then the tissue or fluids are reintroduced back into the patient. In some embodiments, the cancer is treated in a human patient in vivo by administration of the therapeutic composition into the patient.

Non-liming examples of disease include: all types of cancers (breast, lung, colorectal, prostate, melanomas, head and neck, pancreatic, etc.), rheumatoid arthritis, Crohn's disuse, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic, and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; endometrial cancer; gastric cancer; glioblastoma; head and neck cancer, such as esophageal cancer; lung cancer, such as by way of non-limiting example, non-small cell lung cancer; multiple myeloma ovarian cancer; pancreatic cancer; prostate cancer; sarcoma, such as osteosarcoma; renal cancer, such as by way of nonlimiting example, renal cell carcinoma; and/or skin cancer, such as by way of nonlimiting example, squamous cell cancer, basal cell carcinoma, or melanoma. In some embodiments, the cancer is a squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

A therapeutically effective amount of a multispecific polypeptide construct of the disclosure relates generally to the amount needed to achieve a therapeutic objective. As noted above, this may be a binding interaction between the multispecific polypeptide construct and its target antigen(s) that, in certain cases, agonize, stimulate, activate, and/or augment FcγR-mediated innate immune cell activation or CD3-mediated T cell activation. The amount required to be administered will furthermore depend on the binding affinity of the multispecific polypeptide construct for its specific antigen(s), and will also depend on the rate at which an administered multispecific polypeptide construct is depleted from the free volume other subject to which it is administered. Common ranges for therapeutically effective dosing of a multispecific polypeptide construct may be, by way of nonlimiting example, from about 0.01 μg/kg body weight to about 10 mg/kg body weight. In some embodiments, the therapeutically effective dosing of a multispecific polypeptide construct of the disclosure may be, by way of nonlimiting example, from about 0.01 mg/kg body weight to about 5-10 mg/kg body weight. Common dosing frequencies may range, for example, from twice daily to once a week.

Efficaciousness of treatment is determined in association with any known method for diagnosing or treating the particular disorder. Methods for the screening of multispecific polypeptide construct that possess the desired specificity include, but are not limited to, enzyme linked immunosorbent assay (ELISA) and other immunologically mediated techniques known within the art. A variety of means are known for determining if administration of the provided multispecific polypeptide constructs sufficiently modulates immunological activity by eliminating, sequestering, or inactivating immune cells mediating or capable of mediating an undesired immune response; inducing, generating, or turning on immune cells that mediate or are capable of mediating a protective immune response; changing the physical or functional properties of immune cells; or a combination of these effects. Examples of measurements of the modulation of immunological activity include, but are not limited to, examination of the presence or absence of immune cell populations (using flow cytometry, immunohistochemistry, histology, electron microscopy, polymerase chain reaction (PCR)); measurement of the functional capacity of immune cells including ability or resistance to proliferate or divide in response to a signal (such as using T-cell proliferation assays and pepscan analysis based on 3H-thymidine incorporation following stimulation with anti-CD3 antibody, anti-T-cell receptor antibody, anti-CD28 antibody, calcium ionophores, PMA (phorbol 12-myristate 13-acetate) antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (e.g., by flow cytometry, enzyme-linked immunosorbent assays, Western blot analysis, protein microarray analysis, immunoprecipitation analysis); measurement of biochemical markers of activation of immune cells or signaling pathways within immune cells (e.g., Western blot and immunoprecipitation analysis of tyrosine, serine or threonine phosphorylation, polypeptide cleavage, and formation or dissociation of protein complexes; protein array analysis; DNA transcriptional, profiling using DNA arrays or subtractive hybridization); measurements of cell death by apoptosis, necrosis, or other mechanisms (e.g., annexin V staining, TUNEL assays, gel electrophoresis to measure DNA laddering, histology; fluorogenic caspase assays, Western blot analysis of caspase substrates); measurement of the genes, proteins, and other molecules produced by immune cells (e.g., Northern blot analysis, polymerase chain reaction, DNA microarrays, protein microarrays, 2-dimensional gel electrophoresis, Western blot analysis, enzyme linked immunosorbent assays, flow cytometry); and measurement of clinical symptoms or outcomes such as improvement of autoimmune, neurodegenerative, and other diseases involving self-proteins or self-polypeptides (clinical scores, requirements for use of additional therapies, functional status, imaging studies) for example, by measuring relapse rate or disease severity.

The multispecific polypeptide construct are also useful in a variety of diagnostic and prophylactic formulations. In one embodiment, a multispecific polypeptide construct is administered to patients that are at risk of developing one or more of the aforementioned disorders. A patient's or organ's predisposition to one or more of the disorders can be determined using genotypic, serological or biochemical markers.

In another embodiment of the disclosure, a multispecific polypeptide construct is administered to human individuals diagnosed with a clinical indication associated with one or more of the aforementioned disorders. Upon diagnosis, a multispecific polypeptide construct is administered to mitigate or reverse the effects of the clinical indication.

Combination Therapies

In some embodiments, the multispecific polypeptide constructs, conjugated multispecific polypeptide constructs, and compositions thereof—referred to collectively herein as the Therapeutic(s)—are administered in conjunction with one or more additional agents, or a combination of additional agents. Suitable additional agents include current pharmaceutical and/or surgical therapies for an intended application. For example, the Therapeutic(s) can be used in conjunction with an additional chemotherapeutic or antineoplastic agent. For example, the Therapeutic(s) and additional agent are formulated into a single therapeutic composition, and the Therapeutic(s) and additional agent are administered simultaneously. In some embodiments, the Therapeutic(s) and additional agent are separate from each other, e.g., each is formulated into a separate therapeutic composition, and the Therapeutic(s) and the additional agent are administered simultaneously, or the Therapeutic(s) and the additional agent are administered at different times during a treatment regimen. For example, the Therapeutic(s) is administered prior to the administration of the additional agent, the Therapeutic(s) is administered subsequent to the administration of the additional agent, or the Therapeutic(s) and the additional agent are administered in an alternating fashion. As described herein, the Therapeutic(s) and additional agent are administered in single doses or in multiple doses. In some embodiments, the additional agent is coupled or otherwise attached to the Therapeutic(s). Suitable additional agents are selected according to the purpose of the intended application (i.e., killing, prevention of cell proliferation, hormone therapy or gene therapy). Such agents may include but is not limited to, for example, pharmaceutical agents, toxins, fragments of toxins, alkylating agents, enzymes, antibiotics, antimetabolites, antiproliferative agents, hormones, neurotransmitters, DNA, RNA, siRNA, oligonucleotides, antisense RNA, aptamers, diagnostics, radiopaque dyes, radioactive isotopes, fluorogenic compounds, magnetic labels, nanoparticles, marker compounds, lectins, compounds that alter cell membrane permeability, photochemical compounds, small molecules, liposomes, micelles, gene therapy vectors, viral vectors, and the like. Finally, combinations of agents or combinations of different classes of agents may be used.

In one embodiment, the multispecific polypeptide constructs are administered in combination therapy, i.e., combined with other agents, e.g., therapeutic agents, that are useful for treating pathological conditions or disorders, such as autoimmune disorders and inflammatory diseases. The term "in combination" in this context means that the agents are given substantially contemporaneously, either simultaneously or sequentially. If given sequentially, at the onset of administration of the second compound, the first of the two compounds is still detectable at effective concentrations at the site of treatment.

For example, the combination therapy can include one or more multispecific polypeptide constructs of the disclosure co-formulated with, and/or co-administered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more multispecific polypeptide constructs described herein may be used in combination with two or more of the therapeutic agents described herein. Such combination therapies may advantageously utilize lower dosages of the administered therapeutic agents, thus avoiding possible toxicities or complications associated with the various monotherapies.

In other embodiments, one or more multispecific polypeptide constructs of the disclosure can be co-formulated with, and/or co-administered with, one or more anti-inflammatory drugs, immunosuppressants, or metabolic or enzymatic inhibitors. Nonlimiting examples of the drugs or inhibitors that can be used in combination with the antibodies described herein, include, but are not limited to, one or more of: nonsteroidal anti-inflammatory drug(s) (NSAIDs), e.g., ibuprofen, tenidap, naproxen, meloxicam, piroxicam, diclofenac, and indomethacin; sulfasalazine; corticosteroids such as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diamino-6-pteridinyl) methyl] methylamino] benzoyl]-L-glutamic acid); and inhibitors of pyrimidine biosynthesis, e.g., dihydroorotate dehydrogenase (DHODH) inhibitors. Suitable therapeutic agents for use in combination with the antibodies of the disclosure include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppressants, e.g., cyclosporin, tacrolimus (FK-506); and mTOR inhibitors, e.g., sirolimus (rapamycin—RAPAMUNE™ or rapamycin derivatives, e.g., soluble rapamycin derivatives (e.g., ester rapamycin derivatives, e.g., CCI-779); agents that interfere with signaling by proinflammatory cytokines such as TNFα or IL-1 (e.g. IRAK, NIK, IKK, p38 or MAP kinase inhibitors); COX2 inhibitors, e.g., celecoxib, rofecoxib, and variants thereof; phosphodiesterase inhibitors, e.g., R973401 (phosphodiesterase Type IV inhibitor); phospholipase inhibitors, e.g., inhibitors of cytosolic phospholipase 2 (cPLA2) (e.g., trifluoromethyl ketone analogs); inhibitors of vascular endothelial cell growth factor or growth factor receptor, e.g., VEGF inhibitor and/or VEGF-R inhibitor; and inhibitors of angiogenesis. Suitable therapeutic agents for use in combination with the antibodies of the disclosure are immunosuppressants, e.g., cyclosporin, tacrolimus (FK-506); mTOR inhibitors, e.g., sirolimus (rapamycin) or rapamycin derivatives, e.g., soluble rapamycin derivatives (e.g., ester rapamycin derivatives, e.g., CCI-779); COX2 inhibitors, e.g., celecoxib and variants thereof; and phospholipase inhibitors, e.g., inhibitors of cytosolic phospholipase 2 (cPLA2), e.g., trifluoromethyl ketone analogs. Additional examples of therapeutic agents that can be combined with a multispecific polypeptide construct include one or more of: 6-mercaptopurines (6-MP); azathioprine sulphasalazine; mesalazine; olsalazine; chloroquine/hydroxychloroquine (PLAQUENIL®); pencillamine; aurothiornalate (intramuscular and oral); azathioprine; coichicine; beta-2 adrenoreceptor agonists (salbutamol, terbutaline, salmeteral); xanthines (theophylline, aminophylline); cromoglycate; nedocromil; ketotifen; ipratropium and oxitropium; mycophenolate mofetil; adenosine agonists; antithrombotic agents; complement inhibitors; and adrenergic agents.

V. EXEMPLARY EMBODIMENTS

Among the provided embodiments are:

1. A multispecific polypeptide construct, the multispecific polypeptide construct comprising a first component comprising an immunoglobulin Fc region and a second component comprising a CD3-binding region, wherein:

the first and second components are coupled by a linker, wherein the Fc region is positioned N-terminal to the CD3-binding region; one or both of the first and second components comprises at least one antigen binding domain that binds a tumor associated antigen (TAA); and one or both of the first and second components comprises at least one co-stimulatory receptor binding region (CRBR) that binds a co-stimulatory receptor.

2. A multispecific polypeptide construct, the multispecific polypeptide construct comprising a first component comprising an immunoglobulin Fc region and a second component comprising a CD3-binding region, wherein:

the first and second components are coupled by a linker, wherein the Fc region is positioned N-terminal to the CD3-binding region;

one or both of the first and second components comprises at least one antigen binding domain that binds a tumor associated antigen (TAA); and one or both of the first and second components comprises at least one inhibitory receptor binding region (IRBR) that binds an inhibitory receptor.

3. A multispecific polypeptide construct, the multispecific polypeptide construct comprising a first component comprising an immunoglobulin Fc region and a second component comprising a CD3-binding region, wherein:
the first and second components are coupled by a linker, wherein the Fc region is positioned N-terminal to the CD3-binding region;
one or both of the first and second components comprises at least one antigen binding domain that binds a tumor associated antigen (TAA);
one or both of the first and second components comprises at least one co-stimulatory receptor binding region (CRBR) that binds a co-stimulatory receptor; and
one or both of the first and second components comprises at least one inhibitory receptor binding region (IRBR) that binds an inhibitory receptor.

4. The multispecific polypeptide construct of embodiment any of embodiments 1-3, wherein the CD3-binding region binds CD3 (CD3ε).

5. The multispecific polypeptide construct of embodiment embodiment any of embodiments 1-4, wherein the at least one antigen binding domain is positioned amino-terminally relative to the Fc region and/or carboxy-terminally relative to the CD3 binding region of the multispecific polypeptide construct.

6. The multispecific polypeptide construct of any of embodiments 1 and 3-5, wherein the at least one co-stimulatory receptor binding region (CRBR) is positioned amino-terminally relative to the Fc region and/or carboxy-terminally relative to the CD3 binding region of the multispecific polypeptide construct.

7. The multispecific polypeptide construct of any of embodiments 2-5, wherein the at least one inhibitory receptor binding region (IRBR) is positioned amino-terminally relative to the Fc region and/or carboxy-terminally relative to the CD3 binding region of the multispecific polypeptide construct.

8. The multispecific polypeptide construct of any of embodiments 1-7, wherein the first component comprises a first antigen binding domain and the second component comprises a second antigen binding domain, wherein each of the antigen binding domains bind a tumor associated antigen (TAA).

9. The multispecific polypeptide construct of embodiment 8, wherein the first antigen binding domain is positioned amino-terminally relative to the Fc region of the multispecific construct and the second antigen binding domain is positioned carboxy-terminally relative to the CD3 binding region of the multispecific construct.

10. The multispecific polypeptide construct of embodiment 8 or embodiment 9, wherein the first or the second component further comprises the co-stimulatory receptor binding region (CRBR).

11. The multispecific polypeptide construct of embodiment 8 or embodiment 9, wherein the first or the second component further comprises the inhibitory receptor binding region (IRBR).

12. A multispecific polypeptide construct, wherein the multispecific construct comprises in order, from N-terminus to C-terminus:
a co-stimulatory receptor binding region (CRBR) that binds a co-stimulatory receptor and/or an antigen binding domain that binds a tumor-associated antigen (TAA);
an immunoglobulin Fc region;
a linker;
a CD3 binding region that binds CD3 (CD3ε); and
a co-stimulatory receptor binding region (CRBR) that binds a co-stimulatory receptor and/or an antigen binding domain that binds to a tumor-associated antigen (TAA);
wherein the multispecific polypeptide construct comprises at least one CRBR and at least one antigen binding domain.

13. The multispecific polypeptide construct of embodiment 12, wherein the multispecific polypeptide construct comprises only one co-stimulatory receptor binding region (CRBR).

14. A multispecific polypeptide construct, wherein the multispecific construct comprises in order, from N-terminus to C-terminus:
an inhibitory receptor binding region (IRBR) that binds a inhibitory receptor and/or an antigen binding domain that binds a tumor-associated antigen (TAA);
an immunoglobulin Fc region;
a linker;
a CD3 binding region that binds CD3 (CD3ε); and
a inhibitory receptor binding region (IRBR) that binds a inhibitory receptor and/or an antigen binding domain that binds to a tumor-associated antigen (TAA);
wherein the multispecific polypeptide construct comprises at least one IRBR and at least one antigen binding domain.

15. The multispecific polypeptide construct of embodiment 14, wherein the multispecific polypeptide construct comprises only one inhibitory receptor binding region (IRBR).

16. A multispecific polypeptide construct, wherein the multispecific construct comprises in order, from N-terminus to C-terminus:
one of an inhibitory receptor binding region (IRBR) that binds a inhibitory receptor or a co-stimulatory receptor binding region (CRBR) that binds a costimulatory receptor, and/or an antigen binding domain that binds a tumor-associated antigen (TAA);
an immunoglobulin Fc region;
a linker;
a CD3 binding region that binds CD3 (CD3ε); and
the other of the IRBR or the CRBR, and/or an antigen binding domain that binds to a tumor-associated antigen (TAA);
wherein the multispecific polypeptide construct comprises at least one IRBR, at least one CRBR, and at least one antigen binding domain.

17. The multispecific polypeptide construct of embodiment embodiment any of embodiments 12-16, wherein the multispecific polypeptide construct comprises two antigen binding domains that binds to a TAA.

18. The multispecific polypeptide construct of embodiment 17, wherein the antigen binding domains bind to the same tumor-associated antigen (TAA).

19. The multispecific polypeptide construct of embodiment 17 or embodiment 18, wherein one antigen binding domain is positioned amino-terminally relative to the Fc region and one antigen binding domain is positioned carboxy-terminally relative to the CD3 binding region.

20. A multispecific polypeptide construct, wherein the multispecific construct comprises in order, from N-terminus to C-terminus:
an immunoglobulin Fc region;
a linker;

a CD3 binding region that binds CD3 (CD3ε); and
an antigen binding domain that binds a tumor-associated antigen (TAA) and a co-stimulatory receptor binding region (CRBR) that binds a co-stimulatory receptor.

21. A multispecific polypeptide construct, wherein the multispecific construct comprises in order, from N-terminus to C-terminus:
an antigen binding domain that binds a tumor-associated antigen (TAA) and a co-stimulatory receptor binding region (CRBR) that binds a co-stimulatory receptor;
an immunoglobulin Fc region;
a linker; and
a CD3 binding region that binds CD3 (CD3ε).

22. A multispecific polypeptide construct, wherein the multispecific construct comprises in order, from N-terminus to C-terminus:
an immunoglobulin Fc region;
a linker;
a CD3 binding region that binds CD3 (CD3ε); and
an antigen binding domain that binds a tumor-associated antigen (TAA) and an inhibitory receptor binding region (IRBR) that binds an inhibitory receptor.

23. A multispecific polypeptide construct, wherein the multispecific construct comprises in order, from N-terminus to C-terminus: an antigen binding domain that binds a tumor-associated antigen (TAA) and an inhibitory receptor binding region (IRBR) that binds a inhibitory receptor;
an immunoglobulin Fc region;
a linker; and
a CD3 binding region that binds CD3 (CD3ε).

24. The multispecific polypeptide construct of any of embodiments 1-23, wherein the Fc region is a homodimeric Fc region.

25. The multispecific polypeptide construct of any of embodiments 1-24, wherein the Fc region is an Fc region of a human IgG1, a human IgG2, a human IgG3, or a human IgG4, or is an immunologically active fragment thereof.

26. The multispecific polypeptide construct of any of embodiments 1-25, wherein the Fc region comprises a polypeptide comprises the amino acid sequence set forth in SEQ ID NO: 1 or a sequence of amino acids that has at least 90%, 91%, 92%, 93%, 94%, 95%, 96%, 97%, 98%, 99% sequence identity to SEQ ID NO:1.

27. The multispecific polypeptide construct of any of embodiments 1-25, wherein the Fc region comprises a polypeptide comprises the amino acid sequence set forth in SEQ ID NO: 2 or a sequence of amino acids that has at least 90%, 91%, 92%, 93%, 94%, 95%, 96%, 97%, 98%, 99% sequence identity to SEQ ID NO:2;
the Fc region comprises a polypeptide comprises the amino acid sequence set forth in SEQ ID NO: 4 or a sequence of amino acids that has at least 90%, 91%, 92%, 93%, 94%, 95%, 96%, 97%, 98%, 99% sequence identity to SEQ ID NO:4; or
the Fc region comprises a polypeptide comprises the amino acid sequence set forth in SEQ ID NO: 5 or a sequence of amino acids that has at least 90%, 91%, 92%, 93%, 94%, 95%, 96%, 97%, 98%, 99% sequence identity to SEQ ID NO:5.

28. The multispecific polypeptide construct of any of embodiments 1-19, 25-27, wherein the Fc region is a heterodimeric Fc region.

29. The multispecific polypeptide construct of embodiment 28, wherein one or both Fc polypeptides of the heterodimeric Fc region comprises at least one modification to induce heterodimerization compared to a polypeptide of a homodimeric Fc region, optionally compared to the Fc polypeptide set forth in SEQ ID NO:1 or an immunologically active fragment thereof.

30. The multispecific polypeptide construct of embodiment 29, wherein each of the Fc polypeptides of the heterodimeric Fc independently comprise at least one amino acid modification.

31. The multispecific polypeptide construct of embodiment 30, wherein each of the Fc polypeptides of the heterodimeric Fc comprise a knob-into-hole modification or comprise a charge mutation to increase electrostatic complementarity of the polypeptides.

32. The multispecific polypeptide construct of embodiment 31, wherein the amino acid modification is a knob-into-hole modification.

33. The multispecific polypeptide of any of embodiments 28-32, wherein the first Fc polypeptide of the heterodimeric Fc comprises the modification selected from among Thr366Ser, Leu368Ala, Tyr407Val, and combinations thereof and the second Fc polypeptide of the heterodimeric Fc comprises the modification Thr366Trp.

34. The multispecific polypeptide of embodiment 33, wherein the first and second Fc polypeptides further comprises a modification of a non-cysteine residue to a cysteine residue, wherein the modification of the first polypeptide is at one of the position Ser354 and Tyr349 and the modification of the second Fc polypeptide is at the other of the position Ser354 and Tyr349.

35. The multispecific polypeptide construct of embodiment 31, wherein the amino acid modification is a charge mutation to increase electrostatic complementarity of the polypeptides.

36. The multispecific polypeptide construct of any of embodiments 28-31 and 35, wherein the first and/or second Fc polypeptides or each of the first and second Fc polypeptide comprise a modification in complementary positions, wherein the modification is replacement with an amino acid having an opposite charge to the complementary amino acid of the other polypeptide.

37. The multispecific polypeptide construct of any of embodiments 29-36, wherein one of the first or second Fc polypeptide of the heterodimeric Fc further comprises a modification at residue Ile253.

38. The multispecific polypeptide construct of embodiment 37, wherein the modification is Ile253Arg.

39. The multispecific polypeptide construct of any of embodiments 29-38, wherein one of the first or second Fc polypeptide of the heterodimeric Fc further comprises a modification at residue His435.

40. The multispecific polypeptide construct of embodiment 39, wherein the modification is His435Arg.

41. The multispecific polypeptide construct of any of embodiments 1-40, wherein the Fc region comprises a polypeptide that lacks Lys447.

42. The multispecific polypeptide construct of any of embodiments 1-41, wherein the Fc region comprises a polypeptide comprising at least one modification to enhance FcRn binding.

43. The multispecific polypeptide construct of embodiment 42, wherein the modification is at a position selected from the group consisting of Met252, Ser254, Thr256, Met428, Asn434, and combinations thereof.

44. The multispecific polypeptide construct of embodiment 43, wherein the modification is at a position selected from the group consisting of Met252Y, Ser254T, Thr256E, Met428L, Met428V, Asn434S, and combinations thereof.

45. The multispecific polypeptide construct of embodiment 43, wherein the modification is at position Met252 and at position Met428.

46. The multispecific polypeptide construct of embodiment 45, wherein the modification is Met252Y and Met428L.

47. The multispecific polypeptide construct of embodiment 45, wherein the modification is Met252Y and Met428V.

48. The multispecific polypeptide construct of any of embodiments 28-47, wherein the first polypeptide of the heterodimeric Fc comprises the sequence of amino acids set forth in any of SEQ ID NOS:82, 86, 94 or 96, and the second polypeptide of the heterodimeric Fc comprises the sequence of amino acids set forth in any of SEQ ID NOS:83, 87, 90, 92, 98 or 100.

49. The multispecific polypeptide construct of any of embodiments 1-48, wherein the Fc region comprises a polypeptide comprising at least one amino acid modification that reduces effector function and/or reduces binding to an effector molecule selected from an Fc gamma receptor or C1q.

50. The multispecific polypeptide construct of embodiment 49, wherein the one or more amino acid modification is deletion of one or more of Glu233, Leu234 or Leu235.

51. The multispecific polypeptide construct of any of embodiments 28-48, 49 and 50, wherein the first polypeptide of the heterodimeric Fc comprises the sequence of amino acids set forth in any of SEQ ID NOS: 84, 88, 95 or 97 and the second polypeptide of the heterodimeric Fc comprises the sequence of amino acids set forth in any of SEQ ID NOS: 85, 89, 91, 93, 99 or 101.

52. The multispecific polypeptide construct of any of embodiments 1-48, wherein the Fc region comprises a polypeptide comprising at least one modification to enhance FcγR binding.

53. The multispecific polypeptide construct of embodiment 52, wherein the modification is modification at Ser239 or Ile332.

54. The multispecific polypeptide construct of any of embodiments 1-48 and 52, wherein the glycosylation of the Fc region is modified to enhance FcγR binding as compared to an unmodified Fc region.

55. The multispecific polypeptide construct of embodiment 54, wherein the Fc region lacks or has reduced fucose content.

56. The multispecific polypeptide construct of any of embodiments 1-55, wherein the CD3 binding region is an anti-CD3 antibody or antigen-binding fragment.

57. The multispecific polypeptide construct of embodiment 56, wherein the anti-CD3 antibody or antigen binding fragment comprises a variable heavy chain region (VH) and a variable light chain region (VL).

58. The multispecific polypeptide construct of any of embodiments 1-57, wherein the CD3 binding region is monovalent.

59. The multispecific polypeptide construct of any of embodiments 1-58, wherein the CD3 binding region is an variable fragment (Fv) comprising a variable heavy chain region (VH) and a variable light chain region (VL).

60. The multispecific polypeptide construct of any of embodiments 56-58, wherein the anti-CD3 antibody or antigen binding fragment is not a single chain antibody, optionally is not a single chain variable fragment (scFv).

61. The multispecific polypeptide construct of any of embodiments 57-60, wherein the Fc is a heterodimeric Fc and the VH and VL that comprise the anti-CD3 antibody or antigen binding fragment are linked to opposite polypeptides of the heterodimeric Fc.

62. The multispecific polypeptide construct of any of embodiments 1-61, wherein the CD3 binding region is not able to, or is not substantially able to, bind or engage CD3 unless at least one of the antigen binding domain is bound to its TAA.

63. The multispecific polypeptide construct of any of embodiments 1-62, wherein the CD3 binding region is not able to, or is not substantially able, to bind or engage CD3 unless at least two of the antigen binding domain is bound to its TAA.

64. The multispecific polypeptide construct of any of embodiments 1-63, wherein the linker is a polypeptide linker.

65. The multispecific polypeptide construct of embodiment 64, wherein the linker is a polypeptide of up to 25 amino acids in length.

66. The multispecific polypeptide construct of embodiment 64 or embodiment 65, wherein the linker is a polypeptide of from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids.

67. The multispecific polypeptide construct of any of embodiments 64-66, wherein the linker is a polypeptide that is 3, 4, 5, 6, 7, 8, 9, 10, 11, 12, 13, 14, 15, 16, 17, 18, 19 or 20 amino acids in length.

68. The multispecific polypeptide construct of any of embodiments 64-67, wherein the linker is a polypeptide that is 3 to 18 amino acids in length.

69. The multispecific polypeptide construct of any of embodiments 64-67, wherein the linker is a polypeptide that is 12 to 18 amino acids in length.

70. The multispecific polypeptide construction of any of embodiments 64-67, wherein the linker is a polypeptide that is 15 to 18 amino acids in length.

71. The multispecific polypeptide construct of any of embodiments 1-70, wherein the linker is a non-cleavable linker.

72. The multispecific polypeptide construct of embodiment 71, wherein the non-cleavable linker does not contain a substrate recognition site that is specifically recognized for cleavage by a protease.

73. The multispecific polypeptide construct of embodiment 71 or embodiment 72, wherein the non-cleavable linker comprises GS, GGS, GGGGS (SEQ ID NO:149), GGGGGS (SEQ ID NO:135) and combinations thereof.

74. The multispecific polypeptide construct of any of embodiments 71-73, wherein the non-cleavable linker comprises (GGS)n, wherein n is 1 to 10.

75. The multispecific polypeptide construct of any of embodiments 71-74, wherein the non-cleavable linker comprises (GGGGS)n (SEQ ID NO: 173), wherein n is 1 to 10.

76. The multispecific polypeptide construct of any of embodiments 71-75, wherein the non-cleavable linker comprises (GGGGGS)n (SEQ ID NO:172), wherein n is 1 to 4.

77. The multispecific polypeptide construct of any of embodiments 71-76, wherein the non-cleavable linker comprises GGS.

78. The multispecific polypeptide construct of any of embodiments 71-76, wherein the non-cleavable linker comprises GGGGS (SEQ ID NO: 149).

79. The multispecific polypeptide construct of any of embodiments 71-76, wherein the non-cleavable linker comprises GGGGGS (SEQ ID NO: 135).

80. The multispecific polypeptide construct of any of embodiments 71-76, wherein the non-cleavable linker comprises (GGS)$_2$ (SEQ ID NO: 10).

81. The multispecific polypeptide construct of any of embodiments 71-76, wherein the non-cleavable linker comprises GGSGGSGGS (SEQ ID NO: 11).

82. The multispecific polypeptide construct of any of embodiments 71-76, wherein the non-cleavable linker comprises GGSGGSGGSGGS (SEQ ID NO: 12).

83. The multispecific polypeptide construct of any of embodiments 71-76, wherein the non-cleavable linker comprises GGSGGSGGSGGSGGS (SEQ ID NO: 13).

84. The multispecific polypeptide construct of any of embodiments 71-76, wherein the non-cleavable linker comprises GGGGGSGGGGGSGGGGGS (SEQ ID NO: 119).

85. The multispecific polypeptide construct of any of embodiments 71-76, wherein the non-cleavable linker comprises GGSGGGGSGGGGSGGGGS (SEQ ID NO: 147).

86. The multispecific polypeptide construct of any of embodiments 71-76, wherein the non-cleavable linker comprises and GGGGSGGGGSGGGGS (SEQ ID NO:170).

87. The multispecific polypeptide construct of any of embodiments 1-70, wherein the linker is a cleavable linker.

88. A multispecific polypeptide construct, the multispecific polypeptide construct comprising a first component comprising a heterodimeric Fc region and a second component comprising an anti-CD3 antibody or antigen-binding fragment comprising a variable heavy chain region (VH) and a variable light chain region (VL), wherein:
the VH and VL that comprise the anti-CD3 antibody or antigen binding fragment are linked to opposite polypeptides of the heterodimeric Fc;
the first and second components are coupled by a cleavable linker, wherein the heterodimeric Fc region is positioned N-terminal to the anti-CD3 antibody;
one or both of the first and second components comprises at least one antigen binding domain that binds a tumor associated antigen (TAA); and
one or both of the first and second components comprises at least one co-stimulatory receptor binding region (CRBR) that binds a co-stimulatory receptor.

89. The multispecific polypeptide construct of embodiment 88, wherein one or both of the first and second component further comprises at least one inhibitory receptor binding region (IRBR) that binds an inhibitory receptor.

90. A multispecific polypeptide construct, the multispecific polypeptide construct comprising a first component comprising a heterodimeric Fc region and a second component comprising an anti-CD3 antibody or antigen-binding fragment comprising a variable heavy chain region (VH) and a variable light chain region (VL), wherein:
the VH and VL that comprise the anti-CD3 antibody or antigen binding fragment are linked to opposite polypeptides of the heterodimeric Fc;
the first and second components are coupled by a cleavable linker, wherein the heterodimeric Fc region is positioned N-terminal to the anti-CD3 antibody;
one or both of the first and second components comprises at least one antigen binding domain that binds a tumor associated antigen (TAA); and
one or both of the first and second components comprises at least one inhibitory receptor binding region (IRBR) that binds a inhibitory receptor.

91. The multispecific polypeptide construct of embodiment 90, wherein one or both of the first and second component further comprises at least one costimulatory receptor binding region (CRBR) that binds a co-stimulatory receptor.

92. The multispecific polypeptide construct of embodiment any of embodiments 88-91, wherein binding of the CD3-binding region to CD3 is substantially reduced when the multispecific polypeptide construct is in an uncleaved state compared to a cleaved state.

93. The multispecific polypeptide of embodiment embodiment any of embodiments 88-92, wherein in a cleaved state the first and second components are not linked.

94. The multispecific polypeptide construct of any of embodiments 88-93, wherein the cleavable linker is a polypeptide that functions as a substrate for a protease.

95. The multispecific polypeptide construct of embodiment 94, wherein the protease is produced by an immune effector cell, by a tumor, or by cells present in the tumor microenvironment.

96. The multispecific polypeptide construct of embodiment 95, wherein the protease is produced by an immune effector cell and the immune effector cell is an activated T cell, a natural killer (NK) cell, or an NK T cell.

97. The multispecific polypeptide construct of any of embodiments 94-96, wherein the protease is selected from among matriptase, a matrix metalloprotease (MMP), granzyme B, and combinations thereof.

98. The multispecific polypeptide construct of embodiment 97, wherein the protease is granzyme B.

99. The multispecific polypeptide construct of any of embodiments 88-98, wherein the cleavable linker comprises an amino acid sequence of the general formula P4 P3 P2 P1↓P1' (SEQ ID NO: 150), wherein P4 is amino acid I, L, Y, M, F, V, or A; P3 is amino acid A, G, S, V, E, D, Q, N, or Y; P2 is amino acid H, P, A, V, G, S, or T; P1 is amino acid D or E; and P1' is amino acid I, L, Y, M, F, V, T, S, G or A.

100. The multispecific polypeptide construct of any of embodiments 88-99, wherein the cleavable linker comprises an amino acid sequence of the general formula P4 P3 P2 P1↓P1' (SEQ ID NO: 151), wherein P4 is amino acid I or L; P3 is amino acid E; P2 is amino acid P or A; P1 is amino acid D; and P1' is amino acid I, V, T, S, or G.

101. The multispecific polypeptide construct of any of embodiments 88-100, wherein the cleavable linker comprises the amino acid sequence IEPDI (SEQ ID NO:136), LEPDG (SEQ ID NO:152, LEADT (SEQ ID NO:137), IEPDG (SEQ ID NO:138), IEPDV (SEQ ID NO:139), IEPDS (SEQ ID NO:140), IEPDT (SEQ ID NO:141) or LEADG (SEQ ID NO:153).

102. The multispecific polypeptide construct of any of embodiments 88-101, wherein the cleavable linker comprises an amino acid sequence selected from the group consisting of SEQ ID NOs: 22, 105-112, 136-141, 148, 150-153.

103. The multispecific polypeptide construct of any of embodiments 88=102, wherein the cleavable linker comprises the amino acid sequence set forth in SEQ ID NO:105.

104. The multispecific polypeptide construct of embodiment 103, wherein the protease is matriptase.

105. The multispecific polypeptide construct of any of embodiments 88-105, wherein:
the cleavable linker comprises the sequence P1QAR↓(A/V) (SEQ ID NO: 154), wherein P1 is any amino acid; or
the cleavable linker comprises the sequence RQAR(A/V) (SEQ ID NO: 155).

106. The multispecific polypeptide construction of any of embodiments 88-105, wherein the cleavable linker comprises the sequence RQARV (SEQ ID NO: 156).

107. The multispecific polypeptide construct of any of embodiments 88-106, wherein the cleavable linker comprises an amino acid sequence selected from the group consisting of SEQ ID NOs: 23, 154-156.

108. The multispecific polypeptide construct of embodiment 97, wherein the protease is an MMP.

109. The multispecific polypeptide construct of embodiment 108, wherein the MMP is MMP-2.

110. The multispecific polypeptide construct of any of embodiments 88-109, wherein the cleavable linker comprises the general formula P3 P2 P1↓P1' (SEQ ID NO: 157), wherein P3 is P, V or A; P2 is Q or D; P1 is A or N; and P1' is L, I or M.

111. The multispecific polypeptide construct of any of embodiments 88-110, wherein the cleavable linker comprises the general formula P3 P2 P1↓P1' (SEQ ID NO: 158), wherein P3 is P; P2 is Q or D; P1 is A or N; and P1' is L or I.

112. The multispecific polypeptide construct of any of embodiments 88-111, wherein the cleavable linker comprises the sequence PAGL (SEQ ID NO:24).

113. The multispecific polypeptide construct of any of embodiments 88-112, wherein the cleavable linker comprises an amino acid sequence selected from the group consisting of SEQ ID NOs:22-31, 104-114, 117-118, 136-144, 148, 150-158.

114. The multispecific polypeptide construct of any of embodiments 61-113, wherein the multispecific polypeptide construct comprises at least (i) a first polypeptide comprising the first Fc polypeptide of the heterodimeric Fc region, the linker and the VH or VL domain of the anti-CD3 antibody or antigen binding fragment; and (ii) a second polypeptide comprising the second Fc polypeptide of the heterodimeric Fc region, the linker, optionally the same linker as present in the first polypeptide, and the other of the VH or VL domain of the anti-CD3 antibody or antigen binding fragment,
wherein one or both of the first and second polypeptide comprise at least one antigen-binding domain that binds to a tumor associated antigen (TAA) and one or both of the first and second components comprises at least one co-stimulatory receptor binding region (CRBR) that binds a co-stimulatory receptor,
wherein the multispecific polypeptide construct comprises at least one CRBR and at least one antigen binding domain.

115. The multispecific polypeptide construct of any of embodiments 1-114, wherein one or more antigen binding domain that binds TAA results in monovalent, bivalent, trivalent, or tetravalent binding to the TAA.

116. The multispecific polypeptide construct of embodiment 114 or embodiment 115, wherein only one of the first or second polypeptide comprises the at least one antigen-binding domain that binds a TAA.

117. The multispecific polypeptide construct of any of embodiments 114-116, wherein the at least one antigen binding domain is positioned amino-terminally relative to the Fc region and/or is positioned carboxy-terminally relative to the CD3 binding region of one of the first or second polypeptide of the multispecific polypeptide construct.

118. The multispecific polypeptide construct of embodiment embodiment any of embodiments 114-116, wherein the at least one antigen binding domain is positioned amino-terminally relative to the Fc region of the multispecific construct and the second antigen binding domain is positioned carboxy-terminally relative to the CD3 binding region of the multispecific construct.

119. The multispecific polypeptide construct of any of embodiments 114-118, wherein only one of the first or second polypeptide comprises the at least one co-stimulatory receptor binding region (CRBR) that binds a co-stimulatory receptor.

120. The multispecific polypeptide construct of any of embodiments 114-119, wherein the co-stimulatory receptor binding region (CRBR) is positioned amino-terminally relative to the Fc region or is positioned carboxy-terminally relative to the CD3 binding region of one of the first or second polypeptide of the multispecific polypeptide construct.

121. The multispecific polypeptide construct of any of embodiments 1114-120, wherein:
the first polypeptide comprises in order of N-terminus to C-terminus: a first antigen binding domain that binds a tumor-associated antigen (TAA), the first Fc polypeptide of the heterodimeric Fc region, the linker, the VL or VH of the anti-CD3 antibody or antigen binding fragment, and a second antigen binding domain that binds a tumor-associated antigen (TAA); and
the second polypeptide comprises in order of N-terminus to C-terminus: the second Fc polypeptide of the heterodimeric Fc region, the linker, optionally the same linker as present in the first polypeptide, the other of the VH or VL of the anti-CD3 antibody or antigen binding fragment, and the co-stimulatory receptor binding region (CRBR) that binds a co-stimulatory receptor.

122. The multispecific polypeptide construct of any of embodiments 1-121, wherein the antigen binding domain, or independently each of the antigen binding domains, comprises an extracellular domain or binding fragment thereof of the native cognate binding partner of the TAA, or a variant thereof that exhibits binding activity to the TAA.

123. The multispecific polypeptide construct of any of embodiments 1-121, wherein the antigen binding domain, or independently each of the antigen binding domains, is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

124. The multispecific polypeptide construct of any of embodiments 1-123, wherein the at least one co-stimulatory receptor binding region (CRBR) is or comprises the extracellular domain or binding fragment thereof of the native cognate binding partner of the co-stimulatory receptor, or a variant thereof that exhibits binding activity to the co-stimulatory receptor.

125. The multispecific polypeptide construct of any of embodiments 1-123, wherein the at least one co-stimulatory receptor binding region (CRBR) is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

126. The multispecific polypeptide construct of embodiment 123 or embodiment 125, wherein the antibody or antigen-binding fragment thereof is a Fv, a scFv, a Fab, a single domain antibody (sdAb), a VNAR, or a VHH.

127. The multispecific polypeptide construct of embodiment 123, embodiment 125, or embodiment 114, wherein the antibody or antigen-binding fragment is an sdAb.

128. The multispecific polypeptide construct of embodiment 127, wherein the sdAb is a human or humanized sdAb.

129. The multispecific polypeptide construct of embodiment 127 or embodiment 128, wherein the sdAb is VHH, VNAR, an engineered VH domain or an engineered VK domain.

130. The multispecific polypeptide construct of embodiment 123, embodiment 125, or embodiment 126, wherein the antibody or antigen-binding fragment thereof is an scFv.

131. The multispecific polypeptide construct of embodiment 123, embodiment 125, or embodiment 126, wherein the antibody or antigen-binding fragment thereof is a Fab.

132. The multispecific polypeptide construct of any of embodiments 1-123 and 125-131, wherein the multispecific polypeptide construct comprises:
(i) a first polypeptide comprising the first Fc polypeptide of the heterodimeric Fc region, the linker and the VH domain of the anti-CD3 antibody or antigen binding fragment;
(ii) a second polypeptide comprising the second Fc polypeptide of the heterodimeric Fc region, the linker and the VL domain of the anti-CD3 antibody or antigen binding fragment;
(iii) a third polypeptide comprising a VH-CH1 (Fd) or VL-CL of a Fab antibody fragment that binds to a tumor-associated antigen,
(iv) a fourth polypeptide comprising a VH-CH1 (Fd) or VL-CL of a Fab antibody fragment that binds to a co-stimulatory receptor,
wherein the first and/or second polypeptide further comprises (1) the other of the VH-CH1 (Fd) or VL-CL of the Fab antibody fragment that binds to the tumor-associated antigen and the (2) other of the VH-CH1 (Fd) or VL-CL of the Fab antibody fragment that binds to the co-stimulatory receptor.

133. The multispecific polypeptide construct of any of embodiments 1-123 and 125-131, wherein the multispecific polypeptide construct comprises:
(i) a first polypeptide comprising the first Fc polypeptide of the heterodimeric Fc region, the linker and the VH domain of the anti-CD3 antibody or antigen binding fragment;
(ii) a second polypeptide comprising the second Fc polypeptide of the heterodimeric Fc region, the linker and the VL domain of the anti-CD3 antibody or antigen binding fragment; and
(iii) a third polypeptide comprising a VH-CH1 (Fd) or VL-CL of a Fab antibody fragment that binds to a co-stimulatory receptor,
wherein the first and/or second polypeptide further comprises the other of the VH-CH1 (Fd) or VL-CL of the Fab antibody fragment that binds to the co-stimulatory receptor, and
the first and/or second polypeptide further comprises at least one antigen binding domain that binds a tumor associated antigen (TAA).

134. The multispecific polypeptide construct of any of embodiments 1-123 and 1125-131, wherein the multispecific polypeptide construct comprises:
(i) a first polypeptide comprising the first Fc polypeptide of the heterodimeric Fc region, the linker and the VH domain of the anti-CD3 antibody or antigen binding fragment;
(ii) a second polypeptide comprising the second Fc polypeptide of the heterodimeric Fc region, the linker and the VL domain of the anti-CD3 antibody or antigen binding fragment; and
(iii) a third polypeptide comprising a VH-CH1 (Fd) or VL-CL of a Fab antibody fragment that binds to a tumor-associated antigen,
wherein the first and/or second polypeptide further comprises the other of the VH-CH1 (Fd) or VL-CL of the Fab antibody fragment that binds to the tumor-associated antigen, and
the first and/or second polypeptide further comprises at least one co-stimulatory receptor binding region (CRBR) that binds a co-stimulatory receptor.

135. The multispecific polypeptide construct of embodiment 133 or embodiment 134, wherein only one of the first or second polypeptide comprises the other of the VH-CH1 (Fd) or VL-CL of the Fab antibody fragment.

136. The multispecific polypeptide construct of embodiment 133 or embodiment 134, wherein both the first or second polypeptide comprises the other of the VH-CH1 (Fd) or VL-CL of the Fab antibody fragment.

137. The multispecific polypeptide construct of embodiment 135 or embodiment 136, wherein the other of the VH-CH1 (Fd) or VL-CL of the Fab antibody fragment is positioned amino-terminally relative to the Fc region and/or at the carboxy-terminally relative to the CD3 binding region of one of the first or second polypeptide of the multispecific polypeptide construct.

138. The multispecific polypeptide construct of any of embodiments 135-137, wherein the other of the VH-CH1 (Fd) or VL-CL of the Fab antibody fragment is positioned amino-terminally relative to the Fc region of the first polypeptide or second polypeptide and at the carboxy-terminally relative to the CD3 binding region of the other of the first or second polypeptide.

139. The multispecific polypeptide construct of any of embodiments 1-138, wherein the antigen binding domain, or independently each of the antigen binding domains, binds to a tumor antigen selected from among 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

140. The multispecific polypeptide construct of any of embodiments 1-139, wherein the antigen binding domain comprises at least a first antigen binding domain and a second antigen binding domain, wherein the first antigen binding domain and second antigen binding domain bind to the same TAA.

141. The multispecific polypeptide construct of embodiment 140, wherein the first antigen binding domain and the second antigen binding domain binds a different epitope of the same TAA.

142. The multispecific polypeptide construct of embodiment 140, wherein the first antigen binding domain and the second antigen binding domain binds the same epitope of the same TAA.

143. The multispecific polypeptide construct of any of embodiments 1-142, wherein the antigen binding domain comprises at least a first antigen binding domain and a second antigen binding domain wherein the first antigen binding domain and the second antigen binding domain bind a different TAA.

144. The multispecific polypeptide construct of any of embodiments 1-143, wherein the co-stimulatory receptor binding region (CRBR) comprises at least a first CRBR and a second CRBR, wherein the first CRBR and second CRBR bind to the same co-stimulatory receptor.

145. The multispecific polypeptide construct of embodiment 144, wherein the first co-stimulatory receptor binding region (CRBR) and the second CRBR binds a different epitope of the same co-stimulatory receptor.

146. The multispecific polypeptide construct of embodiment 144, wherein the first co-stimulatory receptor binding region (CRBR) and the second CRBR binds the same epitope of the same co-stimulatory receptor.

147. The multispecific polypeptide construct of any of embodiments 1-146, wherein the co-stimulatory receptor binding region (CRBR) comprises at least a first CRBR and a second CRBR.

148. The multispecific polypeptide construct of any of embodiments 1-147, wherein the first CRBR and the second CRBR bind a different co-stimulatory receptor.

149. The multispecific polypeptide construct of any of embodiments 1-148, wherein the at least one co-stimulatory receptor binding region (CRBR) binds a co-stimulatory receptor selected from among 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), and NKG2D.

150. The multispecific polypeptide construct of any of embodiments 1-149, wherein the at least one co-stimulatory receptor binding region (CRBR) binds a co-stimulatory receptor selected from among 41BB (CD137), OX40 (CD134), and glucocorticoid-induced TNFR-related protein (GITR).

151. The multispecific polypeptide construct of any of embodiments 1-150, wherein the at least one inhibitory receptor binding region (IRBR) is or comprises the extracellular domain or binding fragment thereof of the native cognate binding partner of the co-stimulatory receptor, or a variant thereof that exhibits binding activity to the co-stimulatory receptor.

152. The multispecific polypeptide construct of any of embodiments 1-150, wherein the at least one inhibitory receptor binding region (IRBR) is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

153. The multispecific polypeptide construct of embodiment embodiment 152, wherein the antibody or antigen-binding fragment thereof is a Fv, a scFv, a Fab, a single domain antibody (sdAb), a VNAR, or a VHH.

154. The multispecific polypeptide construct of embodiment embodiment 152, or embodiment 114, wherein the antibody or antigen-binding fragment is an sdAb.

155. The multispecific polypeptide construct of embodiment 154, wherein the sdAb is a human or humanized sdAb.

156. The multispecific polypeptide construct of embodiment 154 or embodiment 155, wherein the sdAb is VHH, VNAR, an engineered VH domain or an engineered VK domain.

157. The multispecific polypeptide construct of embodiment 152, embodiment or embodiment 153, wherein the antibody or antigen-binding fragment thereof is an scFv.

158. The multispecific polypeptide construct of embodiment embodiment embodiment 152 or embodiment 153, wherein the antibody or antigen-binding fragment thereof is a Fab.

159. The multispecific polypeptide construct of any of embodiments 1-158, wherein the inhibitory receptor binding region (IRBR) comprises at least a first IRBR and a second IRBR, wherein the first IRBR and second IRBR bind to the same inhibitory receptor.

160. The multispecific polypeptide construct of embodiment 159, wherein the first inhibitory receptor binding region (IRBR) and the second CRBR binds a different epitope of the same inhibitory receptor.

161. The multispecific polypeptide construct of embodiment 159, wherein the first inhibitory receptor binding region (IRBR) and the second IRBR binds the same epitope of the same inhibitory receptor.

162. The multispecific polypeptide construct of any of embodiments 1-161, wherein the inhibitory receptor binding region (IRBR) comprises at least a first IRBR and a second IRBR.

163. The multispecific polypeptide construct of any of embodiments 1-162, wherein the first IRBR and the second IRBR bind a different inhibitory receptor.

164. The multispecific polypeptide construct of any of embodiments 1-163, wherein the at least one receptor binding region (IRBR) binds a cinhibitory receptor selected from among PD-1, CTLA-4, TIGIT, VISTA or TIM3.

165. The multispecific polypeptide construct of any of embodiments 1-164, wherein the at least one inhibitory receptor binding region (IRBR) binds PD-1.

166. The multispecific polypeptide construct of any of embodiments 1-165, wherein the multispecific polypeptide construct comprises a first linking peptide (LP1) between the first antigen binding domain and the Fc region.

167. The multispecific polypeptide construct of any of embodiments 1-166, wherein the multispecific polypeptide construct comprises a second linking peptide (LP2) between the CD3 binding region and the second antigen binding domain.

168. The multispecific polypeptide construct of any of embodiments 1-166, wherein the multispecific polypeptide construct comprises a first linking peptide (LP1) between the first co-stimulatory receptor binding region (CRBR) and the Fc region.

169. The multispecific polypeptide construct of any of embodiments 1-168, wherein the multispecific polypeptide construct comprises a second linking peptide (LP2) between the CD3 binding region and the second co-stimulatory receptor binding region (CRBR).

170. The multispecific polypeptide construct of any of embodiments 1-169, wherein the multispecific polypeptide construct comprises a first linking peptide (LP1) between the antigen binding domain or co-stimulatory receptor binding region and the Fc region and a second linking peptide (LP2) between the CD3 binding region and the antigen binding domain or CRBR, and wherein the multispecific polypeptide construct has the structural arrangement from N-terminus to C-terminus as follows: first antigen binding domain or CRBR-LP1-Fc region-linker-CD3 binding region-LP2-second antigen binding domain or CRBR.

171. The multispecific polypeptide construct of embodiment 170, wherein the linker is a cleavable linker.

172. The multispecific polypeptide construct of embodiment 170 and embodiment 171, wherein the two linking peptides are not identical to each other.

173. The multispecific polypeptide construct of any of embodiments 166-172, wherein LP1 or LP2 is independently a peptide of about 1 to 20 amino acids in length.

174. The multispecific polypeptide of embodiment 173, wherein LP1 or LP2 independently comprise a peptide that is or comprises any Gly-Ser linker as set forth in SEQ ID NOs: 10-13, 119, 135, 147, 149 or GGS.

175. The multispecific polypeptide construct of any of embodiments 1-174, wherein the anti-CD3 antibody or antigen binding fragment is an Fv antibody fragment.

176. The multispecific polypeptide construct of embodiment 175, wherein the Fv antibody fragment comprises a disulfide stabilized anti-CD3 binding Fv fragment (dsFv).

177. The multispecific polypeptide construct of any of embodiments 1-176, wherein the anti-CD3 antibody or antigen-binding fragment comprises a VH CDR1 comprising the amino acid sequence TYAMN (SEQ ID NO: 16); a VH CD2 comprising the amino acid sequence RIRSKYNNYATYYADSVKD (SEQ ID NO: 17); a VH CDR3 comprising the amino acid sequence HGNFGNSYVSWFAY (SEQ ID NO: 18), a VL CDR1 comprising the amino acid sequence RSSTGAVTTSNYAN (SEQ ID NO: 19); a VL CDR2 comprising the amino acid sequence GTNKRAP (SEQ ID NO: 20); and a VL CDR3 comprising the amino acid sequence ALWYSNLWV (SEQ ID NO: 21).

178. The multispecific polypeptide construct of embodiment 149 or embodiment 150, wherein the anti-CD3 dsFv comprises:
a VH having the amino acid sequence of any of SEQ ID NOS: 14 and 32-62 or a sequence that exhibits at least 90%, 91%, 92%, 93%, 94%, 95%, 96%, 97%, 98% or 99% sequence identity to any of SEQ ID NOS: 14 and 32-62; and
a VL having the amino acid sequence of any of SEQ ID NOS: 15 and 63-81 or a sequence that exhibits at least 90%, 91%, 92%, 93%, 94%, 95%, 96%, 97%, 98% or 99% sequence identity to any of SEQ ID NOS: 15, 63-81 and 241.

179. The multispecific polypeptide construct of any of embodiments 175-178, wherein the anti-CD3 dsFv comprises the amino acid sequence of SEQ ID NO: 14 and the amino acid sequence of SEQ ID NO: 15.

180. The multispecific polypeptide construct of any of embodiments 175-179, wherein the anti-CD3 dsFv comprises the amino acid sequence of SEQ ID NO: 44 and the amino acid sequence of SEQ ID NO: 72 or the anti-CD3 dsFv comprises the amino acid sequence of SEQ ID NO: 44 and the amino acid sequence of SEQ ID NO: 241.

181. The multispecific polypeptide construct of any of embodiments 1-181, wherein the multispecific polypeptide construct is conjugated to an agent.

182. The multispecific polypeptide construct of embodiment 181, wherein the agent is a therapeutic agent, an antineoplastic agent, a toxin or fragment thereof, a detectable moiety or a diagnostic agent.

183. The multispecific polypeptide construct of embodiment 182, wherein the agent is conjugated to the multispecific polypeptide construct via a linker.

184. A polynucleotide(s) encoding the multispecific polypeptide constructs of any of embodiments 1-183.

185. A polynucleotide encoding a polypeptide chain of any of the multispecific polypeptide constructs of any of embodiments 1-183.

186. A polynucleotide, comprising a first nucleic acid sequence encoding a first polypeptide of a multispecific construct of any of embodiments 1-183 and a second nucleic acid sequence encoding a second polypeptide of the multispecific construct, wherein the first and second nucleic acid sequence are separated by an internal ribosome entry site (IRES), or a nucleic acid encoding a self-cleaving peptide or a peptide that causes ribosome skipping.

187. The polynucleotide of embodiment 186, wherein the first nucleic acid sequence and second nucleic acid sequence are operably linked to the same promoter.

188. The polynucleotide of embodiment 186 or embodiment 187, wherein the multispecific polypeptide construct comprises a third polypeptide chain, and the polynucleotide further comprises a third nucleic acid encoding the third polypeptide of the multispecific construct.

189. The polynucleotide of embodiment 188, wherein the third nucleic acid is separated from the first and/or second polypeptide by an internal ribosome entry site (IRES), or a nucleic acid encoding a self-cleaving peptide or a peptide that causes ribosome skipping and/or the third nucleic acid sequence is operably linked to the same promoter as the first and/or second nucleic acid sequence.

190. The polynucleotide of any of embodiments 186-189, wherein the nucleic acid encoding a self-cleaving peptide or a peptide that causes ribosome skipping is selected from a T2A, a P2A, a E2A or a F2A.

191. A vector, comprising the polynucleotide of any of embodiments 184-190.

192. The vector of embodiment 191 that is an expression vector.

193. The vector of embodiment 191 or embodiment 192 that is a viral vector or a eukaryotic vector, optionally wherein the eukaryotic vector is a mammalian vector.

194. A cell, comprising polynucleotide or polynucleotides of any of embodiments 184-190, or a vector or vectors of any of embodiments 191-193.

195. The cell of embodiment 194, wherein the cell is recombinant or isolated.

196. The cell of embodiment 195, wherein the cell is a mammalian cell.

197. The cell of embodiment 196, wherein the cell is a HEK293 or CHO cell.

198. A method of producing a multispecific polypeptide construct, the method comprising introducing into a cell a polynucleotide or polynucleotides of any of embodiments 184-190 or a vector or vectors of any of embodiments 191-193 and culturing the cell under conditions to produce the multispecific polypeptide construct.

199. A method of producing a multispecific polypeptide construct, the method comprising culturing the cell of any of embodiments 194-198 under conditions in which the multispecific polypeptide is produced by the cell.

200. The cell of embodiment 198 or embodiment 199, wherein the cell is a mammalian cell.

201. The cell of embodiment 200, wherein the cell is a HEK293 or CHO cell.

202. The method of embodiment 198 or embodiment 199, further comprising isolating or purifying the multispecific polypeptide construct from the cell.

203. The method of any of embodiments 198-202, wherein the multispecific polypeptide construct is a heterodimer.

204. A multispecific polypeptide construct produced by the method of any of embodiments 198-203.

205. A pharmaceutical composition comprising the multispecific polypeptide construct of any of embodiments 1-183 or embodiment 204 and a pharmaceutically acceptable carrier.

206. The pharmaceutical composition of embodiment 205 that is sterile.

207. A method of stimulating or inducing an immune response, the method comprising contacting a target cell and a T cell with the multispecific polypeptide construct of any of embodiments 1-183 or embodiment 204 or the pharmaceutical composition of embodiments 205 or embodiment 206, said target cell expressing a tumor associated antigen recognized by the multispecific polypeptide construct.

208. The method of embodiment 207, wherein the target cell is a tumor cell expressing the tumor associated antigen (TAA).

209. The method of embodiment 207 or embodiment 208, wherein the multispecific polypeptide construct comprises a cleavage linker that functions as a substrate for a protease and the inducing or stimulating the immune response is increased in the presence of the protease.

210. The method of embodiment 209, wherein the protease is produced by an immune effector cell, by a tumor, or by cells present in the tumor microenvironment.

211. The method of embodiment 209 or embodiment 210, wherein the protease is produced by an immune effector cell and the immune effector cell is an activated T cell, a natural killer (NK) cell, or an NK T cell.

212. The method of embodiment 211, wherein the immune effector cell is in proximity to cells that express the antigen.

213. The method of any of embodiments 207-212, wherein the protease is produced by a tumor that is in proximity to cells that express the TAA in a tissue and/or produced by a tumor that is co-localized with TAA in a tissue, and wherein the protease cleaves the cleavable linker in the multispecific polypeptide construct when the multispecific polypeptide construct is exposed to the protease.

214. The method of any of embodiments 207-213, wherein the protease is selected from among matriptase, a matrix metalloprotease (MMP), granzyme B, and combinations thereof.

215. The method of embodiment 214, wherein the protease is granzyme B.

216. The method of any of embodiments 207-215, wherein the contacting is carried out ex vivo or in vitro.

217. The method of any of embodiments 207-216, wherein the contacting is carried out in vivo in a subject.

218. A method of stimulating or inducing an immune response in a subject, the method comprising administering, to a subject in need thereof, a therapeutically effective amount of the multispecific conjugate of any of embodiments 1-183 or embodiment 204 or the pharmaceutical composition of embodiments 205 or embodiment 206.

219. The method of any of embodiments 207-218, which increases cell-mediated immunity.

220. The method of any of embodiments 207-219, which increases T-cell activity.

221. The method of any of embodiments 207-220, which increases cytolytic T-cell (CTL) activity.

222. The method of any of embodiments 207-221, wherein the immune response is increased against a tumor or cancer.

223. The method of any of embodiments 207-222, wherein the method treats a disease or condition in the subject.

224. A method of treating a disease or condition in a subject, the method comprising administering, to a subject in need thereof, a therapeutically effective amount of the multispecific conjugate of any of embodiments 1-183 or the pharmaceutical composition of embodiments 205 or embodiment 206.

225. The method of embodiment 223 or embodiment 224, wherein the disease or condition is a tumor or a cancer.

226. The method of any of embodiments 207-225, wherein said subject is a human.

VI. EXAMPLES

The following examples are included for illustrative purposes only and are not intended to limit the scope of the invention.

Example 1: Generation of Multispecific Polypeptide Constructs Containing a Constrained CD3 Binding Region and a Co-Stimulatory Receptor Binding Domain Example 1 describes the generation and expression of multispecific polypeptide constructs containing a CD3 binding region that exhibits constrained CD3 binding, a binding domain that binds a co-stimulatory receptor, and one or more antigen binding domains that binds a cell surface antigen, such as a tumor associated antigen (TAA). The multispecific constructs were generated in various configurations, as shown in FIG. 1, and exemplified further in FIGS. 2A-2F and FIG. 3, to contain a heterodimeric Fc region of an immunoglobulin coupled by a linker (e.g. a cleavable linker or non-cleavable) to the CD3 binding region, the one or more antigen binding domain that binds a tumor associated antigen (TAA) positioned amino-terminally relative to the Fc region and/or carboxy-terminally relative to the CD3 binding region, and at least one co-stimulatory receptor binding region (CRBR) positioned amino-terminally relative to the Fc region and/or carboxy-terminally relative to the CD3 binding region.

Exemplary representative constructs with different TAA antigen binding domains, costimulatory receptor binding regions and linkers were generated. Similar constructs can be generated using other heterodimeric Fc configurations, including other knob-into-hole configurations, such as any as described; other linkers, including non-cleavable linkers or other cleavable linkers, particularly polypeptide linkers that include a substrate recognition site for a protease, such as granzyme B, matriptase and/or an MMP; other CD3-binding regions, including other anti-CD3 antibodies, including dsFv or other monovalent fragments; other TAA antigen-binding fragments, such as scFv, sdAb or Fab formats; or other costimulatory receptor binding regions, such as scFv, sdAb or Fab formats.

In the exemplary constructs, polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, an Fc hole polypeptide (e.g. set forth in SEQ ID NO:83 or 292); a cleavable linker, such as one containing one or more substrate recognition sites for a protease; and a variable light (VL) domain of a dsFv anti-CD3 antibody (e.g. set forth in SEQ ID NO:72). The second polypeptide chain generally included in order, from the N-terminus to C-terminus, an Fc knob polypeptide (e.g. set forth in SEQ ID NO: 82 or 291); the same cleavable linker as the first polypeptide chain; and a variable heavy domain of a dsFv anti-CD3 antibody (e.g. set forth in SEQ ID NO:44). The exemplary cleavable linker, GGSGGG-GIEPDIGGSGGS (SEQ ID NO:105) containing a substrate recognition site for granzyme B was used in exemplary constructs.

One or both of the polypeptide chains additionally encoded one or more TAA antigen binding domain amino terminal to the Fc domain and/or carboxy terminal to the CD3 binding region, and a co-stimulatory receptor binding domain amino terminal to the Fc domain and/or carboxy terminal to the CD3 binding region, in various configurations. Exemplary generated proteins incorporated TAA and co-stimulatory receptor binding domains as single domain antibodies (sdAbs).

In the exemplary constructs, the TAA antigen binding domain (e.g. sdAb) was linked at the N-terminus to one or both polypeptide chains of the Fc heterodimer (e.g. hole and/or knob) by a peptide linker, e.g. PGGGG (SEQ ID NO:102) and/or was linked at the C-terminus to one or both domains (e.g. VH and/or VL) of the CD3 binding region by a peptide linker, e.g. GGGG (SEQ ID NO:103). Other similar peptide linkers can be employed. Any antigen binding domain that binds to a TAA can be employed in the provided multispecific polypeptide constructs. Exemplary generated proteins contained an antigen binding domain that binds one of the following tumor associated antigens: B7H3 and 5T4. In some cases, the TAA antigen binding domains were the same. In some cases, the TAA antigen binding domains were different, such that the generated multispecific polypeptide constructs exhibited specificity for at least two different TAAs, to different epitopes of the same TAA or the same epitopes of the same TAA.

In the exemplary constructs, the costimulatory binding region (e.g. sdAb) was linked at the C-terminus to a polypeptide chain of the Fc heterodimer (e.g. hole and/or knob) by a peptide linker, e.g. GGGG (SEQ ID NO:103). Generally, the costimulatory binding region (e.g. sdAb) was carboxy-terminal relative to the CD3 binding region. Other similar peptide linkers can be employed. Any costimulatory binding region that binds to a costimulatory receptor can be employed in the provided multispecific polypeptide constructs. Exemplary generated proteins contained a costimulatory binding region that binds one of the following costimulatory receptors: 41BB, OX40, GITR, ICOS, CD28, or CD27.

Exemplary multispecific polypeptide constructs were generated containing two TAA antigen binding domains specific for the same epitope of B7H3, and further containing an additional co-stimulatory receptor binding region targeting 41BB (cx3091), an additional co-stimulatory receptor binding region targeting OX40 (cx3723), an additional co-stimulatory receptor binding region targeting GITR (cx3724), an additional co-stimulatory receptor binding region targeting ICOS (cx3721), or an additional co-stimulatory receptor binding region targeting CD28 (cx3726)(FIG. 2A-2F). For comparison, multispecific polypeptide constructs were generated containing two TAA antigen binding domains specific for the same epitope of B7H3 without a CRBR (cx3095 or 3834) (FIG. 2A). cx3834 has the reverse knob and hole configuration in comparison to cx3095, such that the first polypeptide chain of cx3834 depicted in FIG. 2A contains the Fc hole polypeptide and the second polypeptide depicted has the Fc knob polypeptide.

Exemplary multispecific polypeptide constructs were generated containing TAA antigen binding domains specific for 5T4 with an additional CRBR targeting 4-1BB. Some exemplary constructs generated contained a sdAb (containing a CDR1, a CDR2 and a CDR3 set forth in SEQ ID Nos: 308, 309, and 310, respectively; e.g. ser forth in SEQ ID NO:215) targeting a 4-1BB co-stimulatory receptor. The generated constructs included (cx3497 and cx3499), each with a different antigen binding domain targeting 5T4. Control constructs for cx3497 and cx3499 without the CRBR also were generated designated cx3547 and cx3546, respectively. (FIG. 3)

The CRBRs used in the exemplary multispecific polypeptide constructs are set forth in Table E1.

TABLE E1

CRBRs in Exemplary multispecific polypeptide constructs

| Exemplary Generated Molecules | CRBR | SEQ ID NO |
|---|---|---|
| cx3091, cx3497, cx3499 | 41BB sdAb RH3v5-1 | 215 |
| cx3723 | OX40 sdAb 1D10v1 | 225 |
| cx3724 | GITR sdAb C06v3 | 235 |
| cx3721 | ICOS sdAb | 239 |
| cx3726 | CD28 sdAb | 240 |

Polynucleotides were generated to encode polypeptide chains of exemplary multispecific polypeptide constructs designated cx3095, cx3834, cx3723, cx3724, cx3721, cx3726 and cx3091 (each targeting B7H3); cx3546, cx3547, cx3497 and cx3499 (each targeting 5T4). The constructs were generated to contain a cleavable or non-cleavable linker.

Separate plasmids encoding each chain of the heterodimeric constrained CD3 binding protein were transiently transfected at an equimolar ratio into mammalian cells (either HEK293 or CHO) using polyethylenimine. Recombinant protein secreted into the supernatant was collected after 3-7 days, and purified by protein A chromatography, followed by either preparative size exclusion chromatography (SEC) or flow-through hydrophobic interaction chromatography (HIC). Heterodimeric protein was selectively purified owing to a mutation designed into one chain of the heterodimeric Fc at position I253R or H435R (usually the hole-Fc) such that it did not bind protein A. The second chromatography step on SEC (AKTA with Superdex-200 resin) or FT-HIC (AKTA with butyl/phenyl sepharose) was used to remove undesired cross-paired species containing two heterodimeric Fcs that were more hydrophobic and twice the expected molecular weight.

The method favored production of heterodimeric multispecific polypeptide constructs, containing properly paired species of heterodimeric Fc and the disulfide stabilized anti-CD3 Fv as described (anti-CD3 VH with the mutation G44C as set forth in SEQ ID NO: 44 and VL with the mutation G100C as set forth in SEQ ID NO: 72). Purified heterodimeric constrained CD3 binding protein was stable and did not accumulate cross-paired species upon prolonged incubation at 4° C. or increased protein concentration.

Example 2: Binding to Cancer Cells and Primary T Cells by Flow Cytometry

This Example describes studies assessing binding of exemplary constructs to T cells or to cancer cells. These studies were carried out in single cultures containing either only the T cells or only the cancer cells in isolation from each other.

Binding of an exemplary multispecific polypeptide construct of the disclosure, referred to herein as cx3091 and cx3095 (with and without a co-stimulatory receptor binding region, respectively), to CD3 on the surface of primary T cells and to B7H3 expressing cells (A375) was assessed. As described in Example 1, cx3091 and cx3095 contained a B7H3 binding domains that are single domain antibodies. Additionally, cx3091 contains a 41BB binding domain that is a single domain antibody. The tumor antigen binding domains of the tested constructs bind the B7H3, which is not expressed on the primary T cells. For comparison purposes the DART-Fc format was produced using a similar method incorporating polypeptide sequences as set forth in SEQ ID NO: 169, 145, or 146. Primary T cells were negatively enriched from PBMCs isolated from healthy human donor leukopaks. Bound constructs were detected with fluorophore-conjugated secondary antibodies specific for either human and binding was measured by flow cytometry. Cells incubated with secondary antibody only served as negative controls.

Figure 4A:
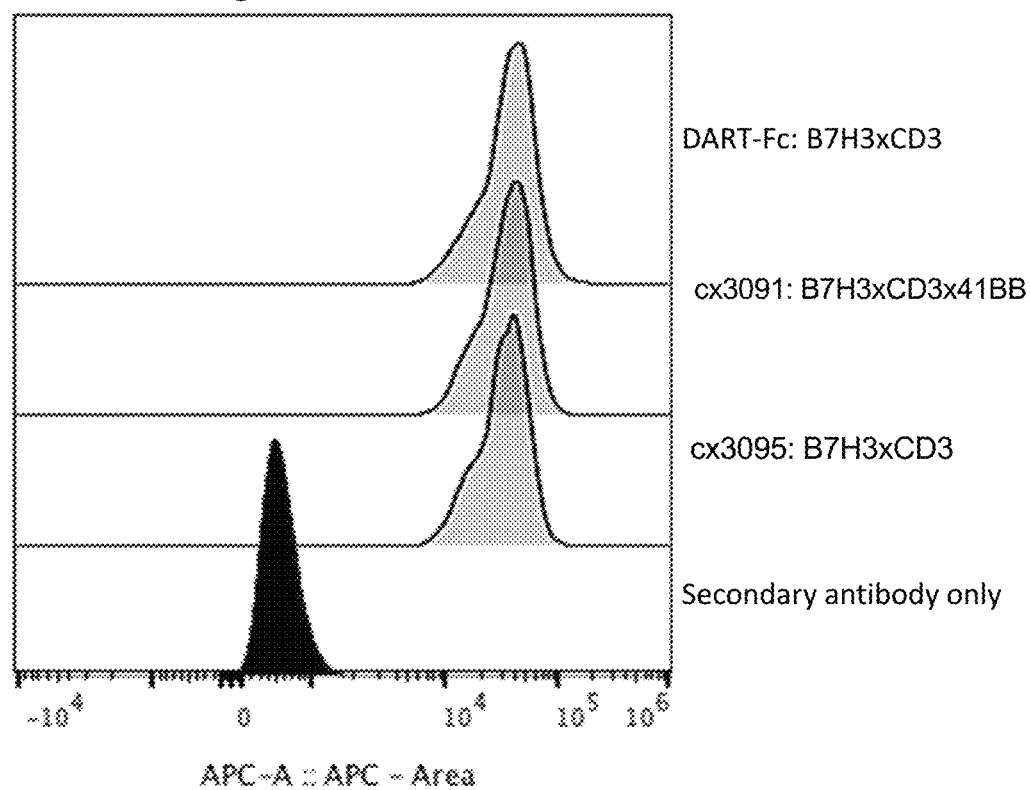
FIG. 4A-4D depicts cellular binding by representative B7H3-targeting constrained CD3 engaging constructs, cx3091 (with a 41BB binding domain) and cx3095 (without a 41BB binding domain), compared to the DART-Fc format B7H3×CD3 FIG. 4A
Figure 4B:
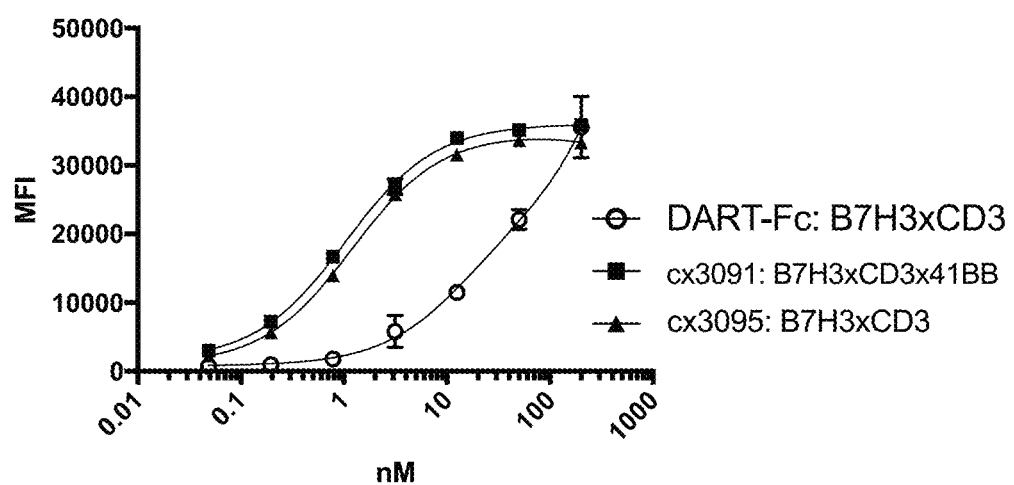
Figure 4C:
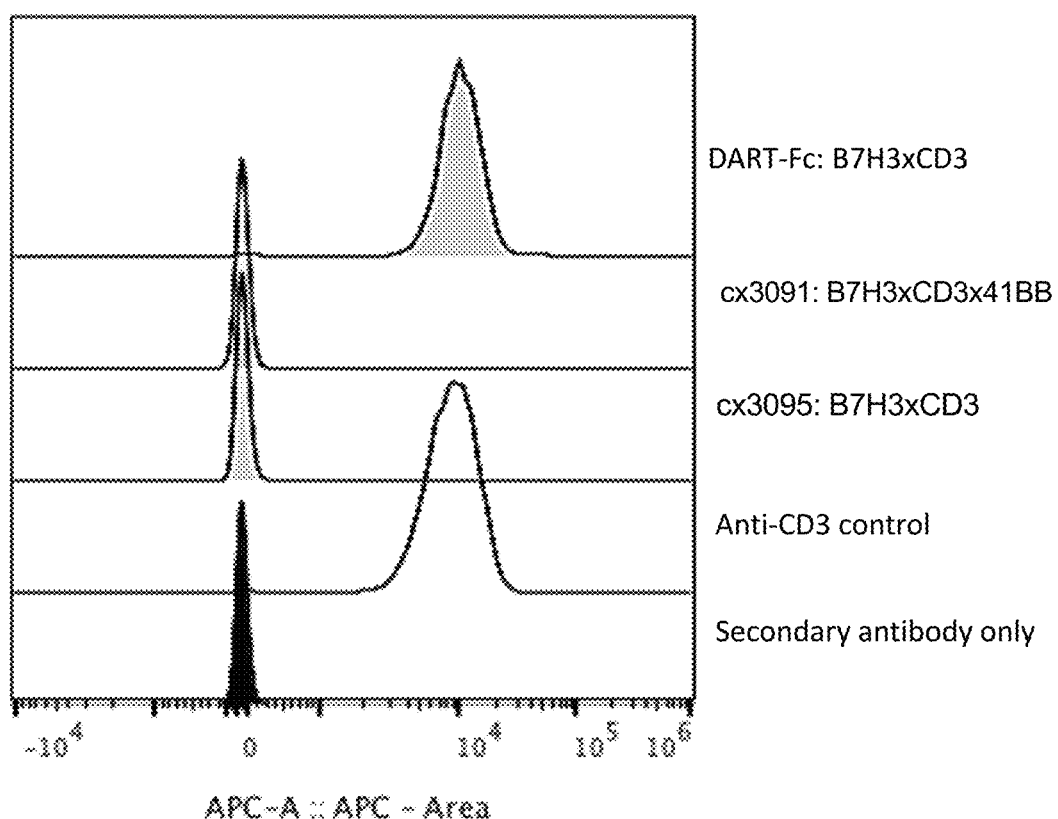
Figure 4D:
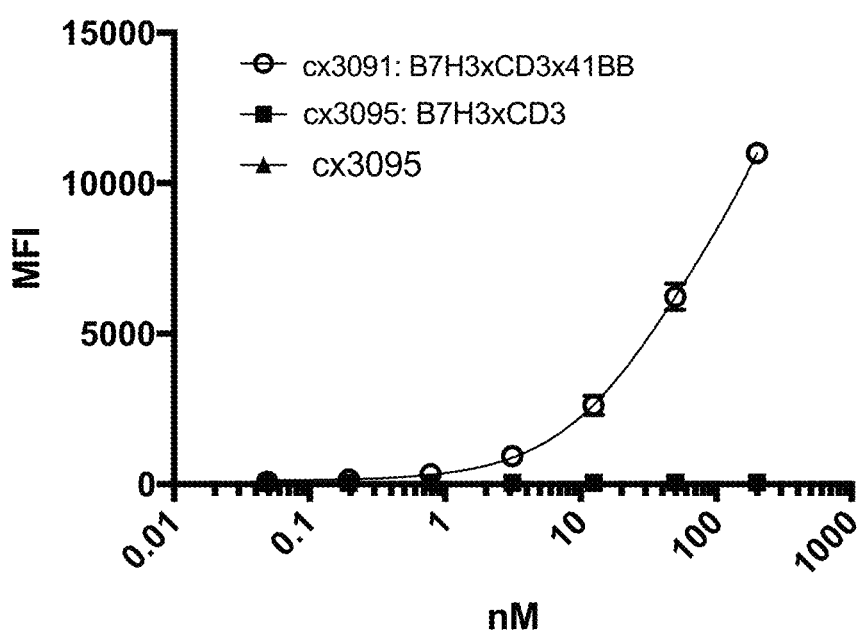

For the studies, a titration of 48 pM to 200 nM of each construct, cx3091, cx3095, or the B7H3×CD3 DART-Fc was used. The representative B7H3-targeting constrained CD3 engaging constructs were found to bind B7H3 expressing cells (A375) (FIGS. 4A and 4B), but lacked the capacity to bind T-cells (FIGS. 4C and 4D). Notably only the DART-Fc format was observed to allow for T-cell binding in the absence of B7H3 engagement. Importantly, it was observed that the addition of a 41BB binding domain did not mediate T-cell binding, consistent with requirement for T-cell activation for 41BB expression.

Figure 5A:
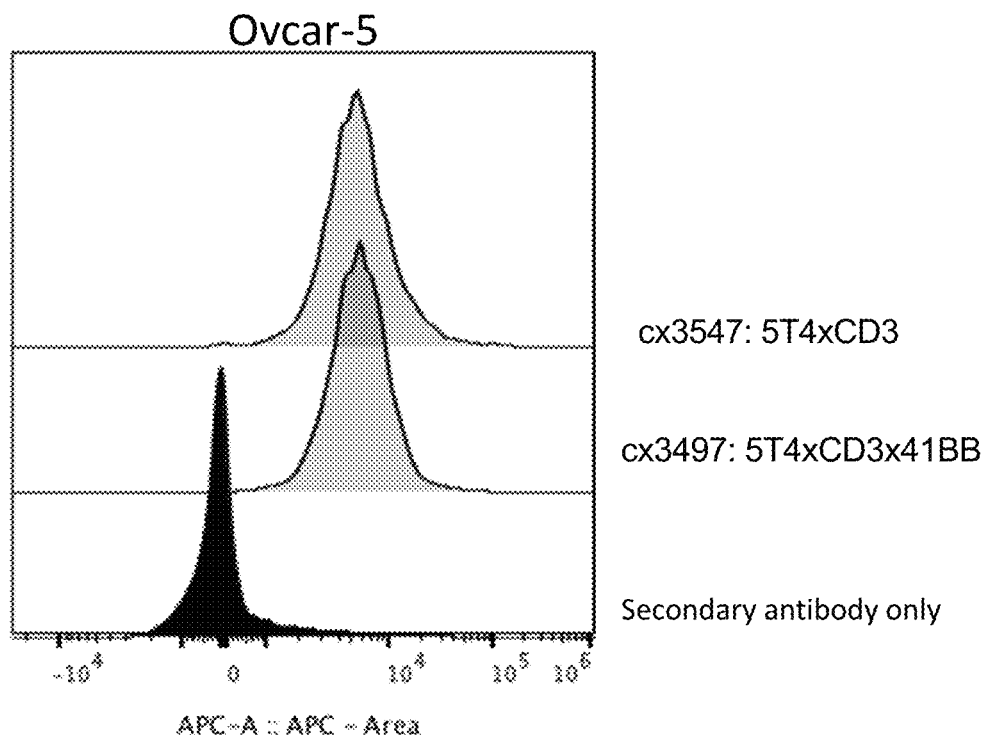
FIG. 5A-5D depicts cellular binding by representative 5T4-targeting constrained CD3 engaging constructs, cx3497 (with a 41BB binding domain) and cx3547 (without a 41BB binding domain).
Figure 5B:
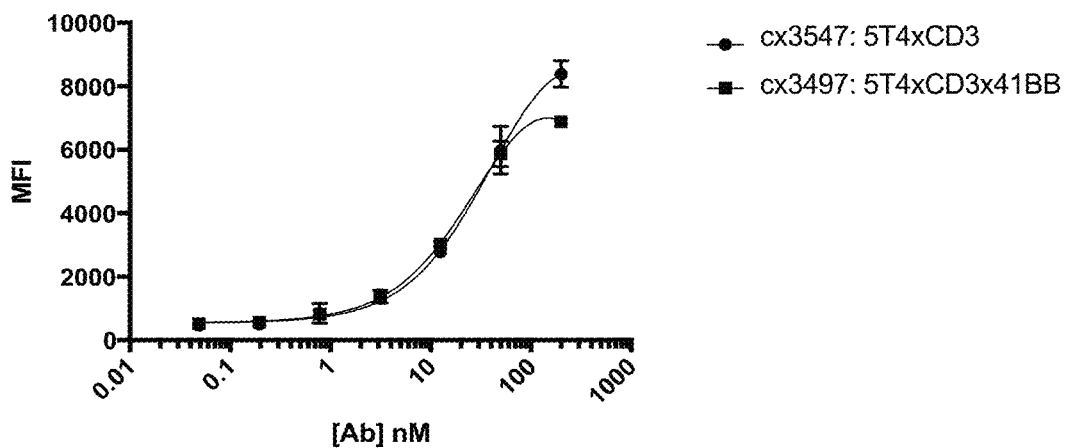
Figure 5C:
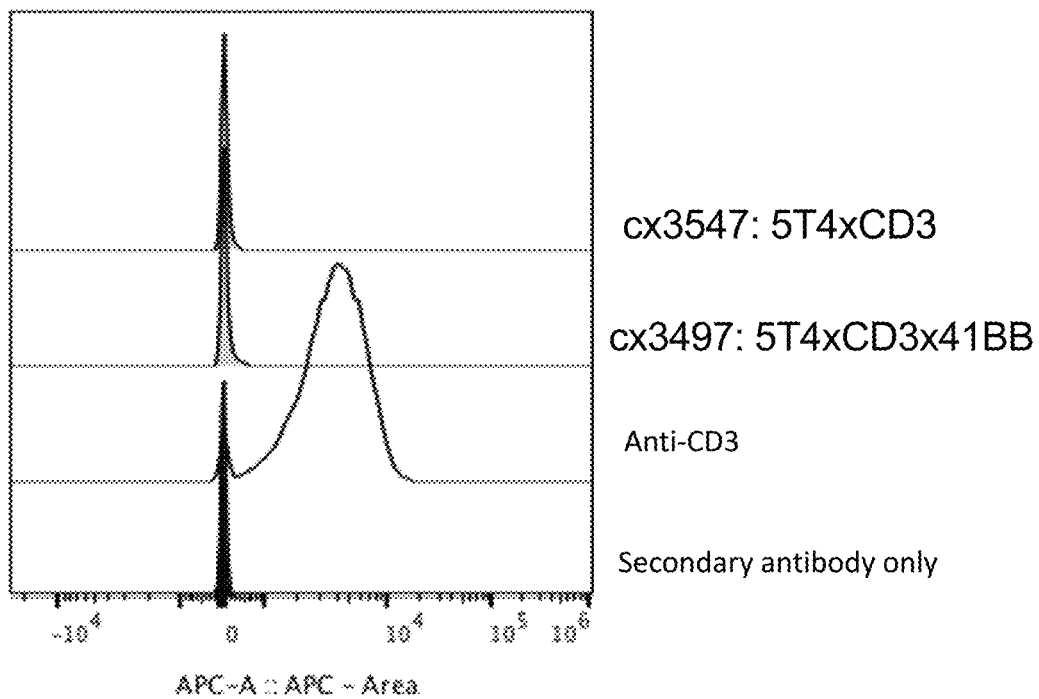
Figure 5D:
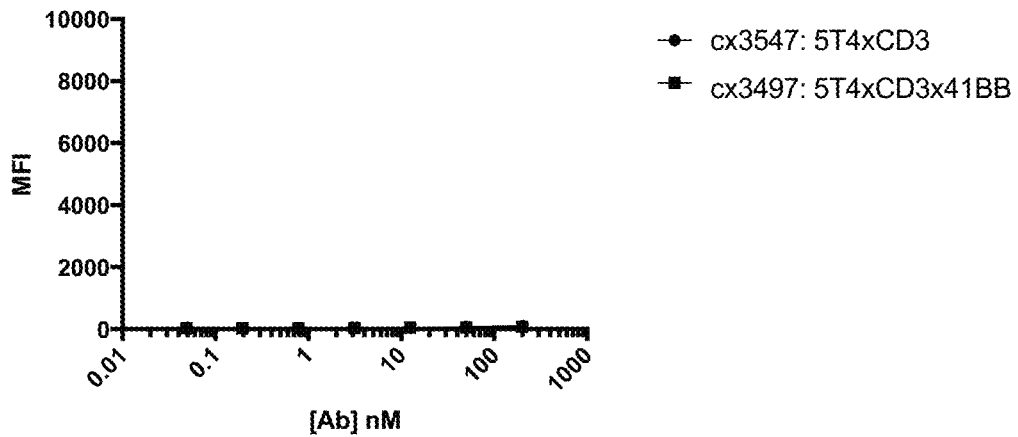

In a further study, similar constrained binding was observed for representative 5T4-targeting constrained CD3 engaging constructs generated as substantially described in Example 1; cx3497 incorporates an additional 41BB binding domain, whereas cx3547 did not incorporate a co-stimulatory receptor binding region. Single domain antibodies were incorporated as the 5T4 binding domains of both constructs as well as the 41BB binding domain of cx3497. As shown in FIGS. 5A and 5B, both constructs displayed binding to a 5T4 expressing cell, Ovcar-5. The constructs, however, were unable to bind T-cells in isolation (FIGS. 5C and 5D).

Example 3: Assessment of Co-Stimulatory Receptor Signaling Using a Reporter Assay This example describes assessment of the ability of various constructs to activate either a 41BB or OX40 reporter Jurkat cell line in co-cultures with target antigen-expressing cells. Antigen targeting constrained CD3 engaging constructs were titrated onto co-cultures of target cells and engineered Jurkat cells that express cell surface 41BB or OX40 and NFκB-driven Luciferase. Engagement of 41BB or OX40 results in NFκB signaling and production of Luciferase. For reporter assays utilizing adherent target cells, target cells were seeded, allowed to settle at room temperature for uniform distribution, and incubated for several hours at 37° C. to permit adherence prior to addition of reporter cells and antigen targeting constrained CD3 engaging constructs. After 6 hours of co-incubation of the reporter cells, target cells (antigen positive or negative cells) and constrained CD3 engaging construct, the BioGlo reagent (Promega) was added and luminescence was measured on a SpectraMaxL.

In this exemplary assay, the multispecifc construct that were tested included a B7H3-targeted constrained CD3 with a 41BB-binding costimulatory receptor binding region (cx3091) or an OX40 binding region (cx3723). As a control, corresponding B7H3-targeted constrained CD3 constructs without the costimulatory receptor binding region also were tested (either cx3095 or cx3834). The target cells were A375 cells expressing B7H3 (A375) or A375 that were knocked-down (deleted) for B7H3 (A375(A)B7H3)).

Figure 6A:
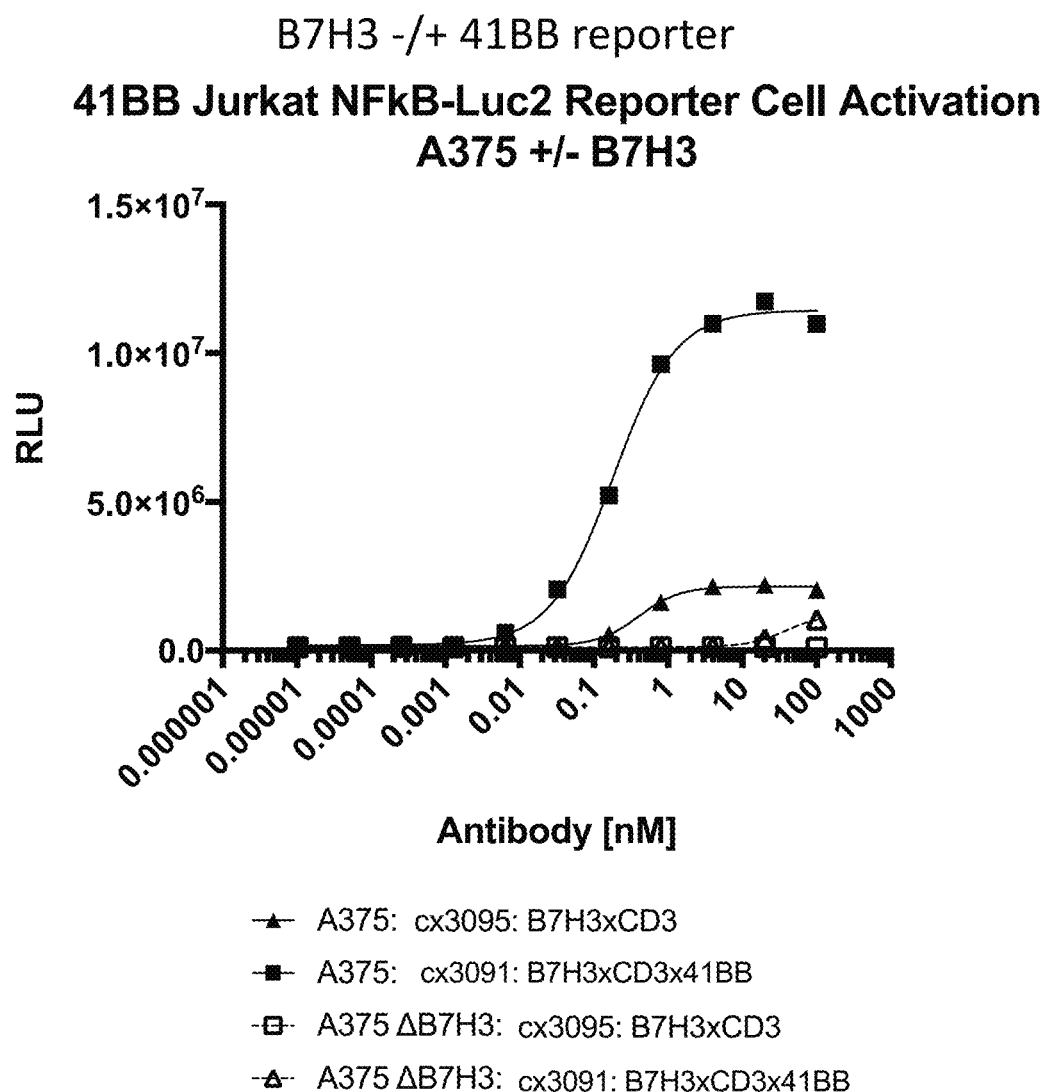
FIG. 6A-6C depicts the capacity to mediate target antigen specific agonism of a costimulatory receptor (41BB or OX40) by representative B7H3-targeted constrained CD3 engaging constructs.

As shown in FIG. 6A, an exemplary B7H3-targeted constrained CD3 engaging construct that contains a 41BB binding domain (cx3091) was shown to mediate target antigen specific 41BB agonism as indicated by an increase in reporter signal compared to co-cultures incubated in the presence of the corresponding construct not containing the costimulatory binding region (cx3095). Similarly, no 41BB agonism was observed in T cells that were co-cultured with target cells that did not express the B7H3 target antigen consistent with an observation that the B7H3-targeted constrained CD3 construct with a costimulatory binding region exhibited capacity to mediate T-cell co-stimulatory signaling solely in a target antigen-dependent manner.

Figure 6B:
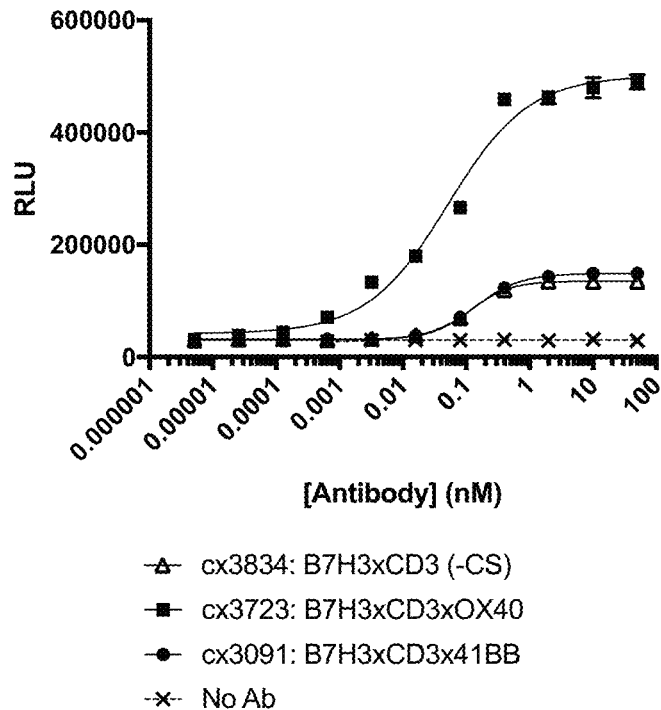
Figure 6C:
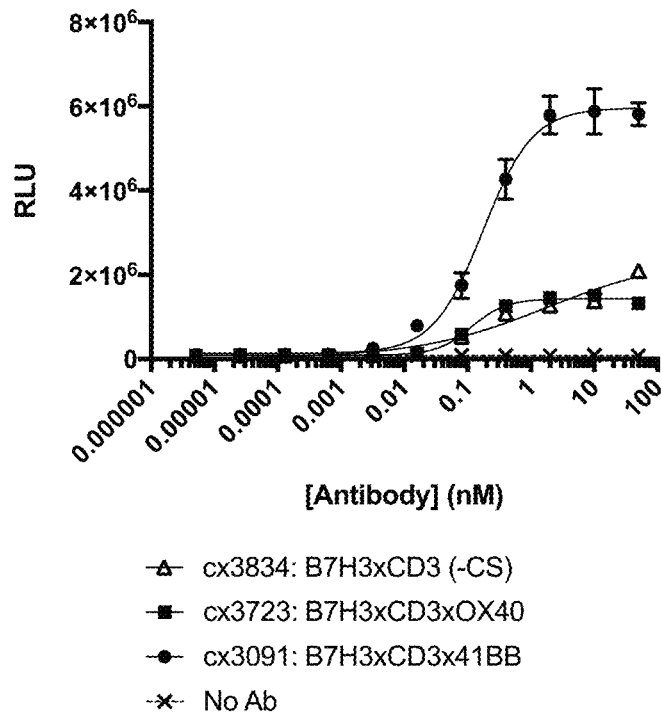

As shown in FIGS. 6B and 6C, similar results were observed for a B7H3-targeted constrained CD3 engaging construct that contains an OX40-binding domain (cx3723). Notably, the B7H3-targeted constrained CD3 engaging construct that contained an OX40 binding domain did not enhance NFκB signaling in the 41BB expressing reporter cells (FIG. 6C), while the B7H3-targeted constrained CD3 engaging construct that contained an 41BB binding domain did not enhance NFκB signaling in the OX40 expressing reporter cells (FIG. 6B) above the level observed for the B7H3-targeted constrained CD3 engaging construct lacking a co-stimulatory binding domain.

These results demonstrate an additional functional property of the antigen-targeted constrained CD3 engaging constructs that incorporate a co-stimulatory receptor binding region to mediate antigen dependent specific co-stimulatory signaling.

Example 4: Assessment of CD3 Reporter T Cell Activation Using a Reporter Assay

This example describes assessment of the ability of various constructs to activate a CD3 NFAT reporter Jurkat cell line in co-cultures with target antigen-expressing cells. Antigen targeting constrained CD3 engaging constructs were titrated onto co-cultures of target cells (expressing B7H3 or that were knocked down for B7H3, B7H3−/−) and engineered Jurkat cells that express NFAT-driven green fluorescence protein (GFP). Engagement of CD3 results in NFAT signaling and production of green fluorescence. For reporter assays utilizing adherent target cells, target cells were seeded, allowed to settle at room temperature for uniform distribution, and incubated for several hours at 37° C. to permit adherence prior to addition of reporter cells and antigen targeting constrained CD3 engaging constructs. Assay plates were serially imaged using an IncuCyte ZOOM system and CD3 reporter cell activation was determined by measuring total green object integrated intensity.

In this exemplary assay, the multispecific construct that were tested included a B7H3-targeted constrained CD3 with a 41BB-binding costimulatory receptor binding region (cx3091). As a control, a corresponding B7H3-targeted constrained CD3 without the costimulatory receptor binding region also was tested (either cx3095). The target cells were A375 cells expressing B7H3 (A375).

Figure 7A:
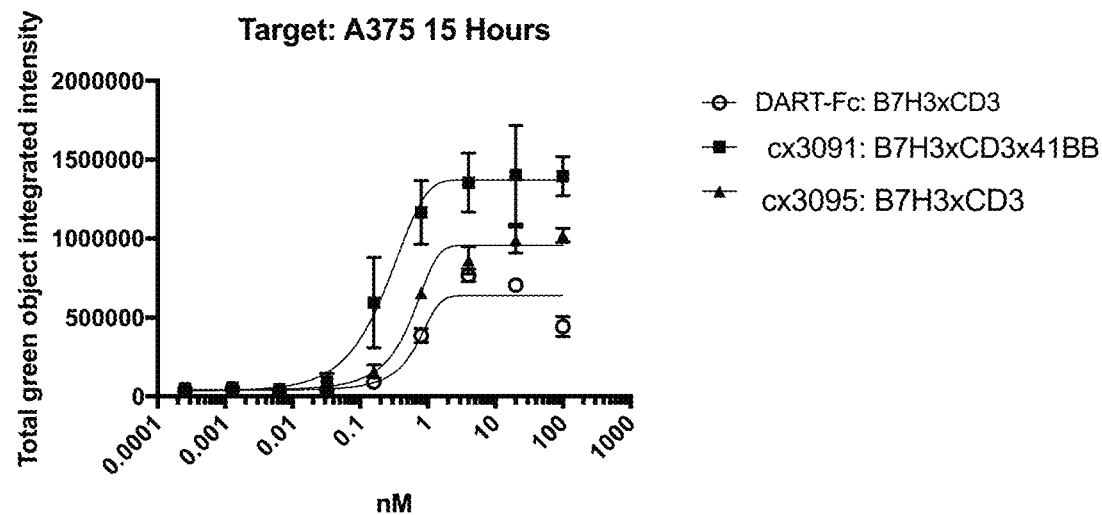
FIG. 7A-7B depicts the capacity to mediate target antigen specific T-cell activation by a representative B7H3-targeted constrained CD3 engaging constructs, cx3095 and cx3091, and an alternative DART-Fc format targeting B7H3 and CD3. Jurkat CD3 NFAT-GFP reporter cells were used to assess T-cell activation in the presence of a B7H3 positive cell line, A375 (FIG. 7A) and A375 B7H3 knock-out cell line, A375 ΔB7H3) (FIG. 7B). Notably, the 41BB containing construct, cx3091 displayed enhanced NFAT signaling, likely due increased Jurkat cell viability and/or reduced exhaustion following TCR/CD3 signaling.
Figure 7B:
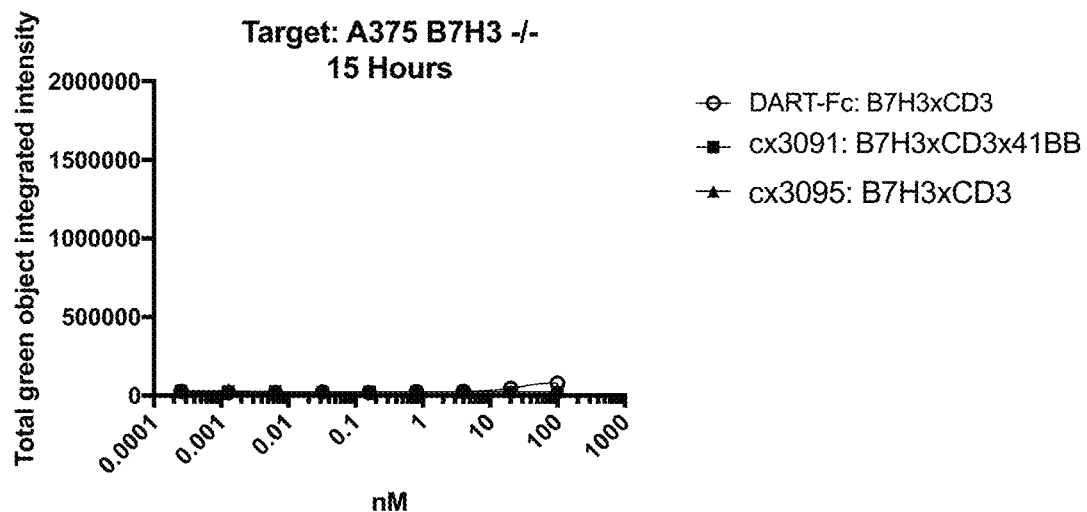

As shown in FIG. 7A, an exemplary B7H3-targeted constrained CD3 engaging construct exhibited capacity to mediate target antigen specific T-cell activation when incubated in reporter T cell co-cultures in the presence of B7H3-expressing target cells. Reporter activity, however, was not observed in co-cultures that did not include B7H3 target cells (FIG. 7B). Similarly T cell activation as measured by reporter activity also was observed for the exemplary DART-Fc, which also binds to B7H3, in the presence of antigen-expressing A375 cells but not B7H3-negative cells. Notably, the 41BB containing construct, cx3091 displayed enhanced NFAT signaling compared to constructs that did not contain a CRBR, which may be due to increased Jurkat cell viability and/or reduced exhaustion following TCR/CD3 signaling.

These results demonstrate that while T-cell binding via the CD3-binding domain is restricted or inhibited on isolated T-cells (as shown in Example 2), once the multispecific polypeptides provided herein are bound to a cognate antigen, they are capable of engaging T-cells and mediating T-cell activation.

Example 5: Assessment of Functional Activity

Figure 8A:
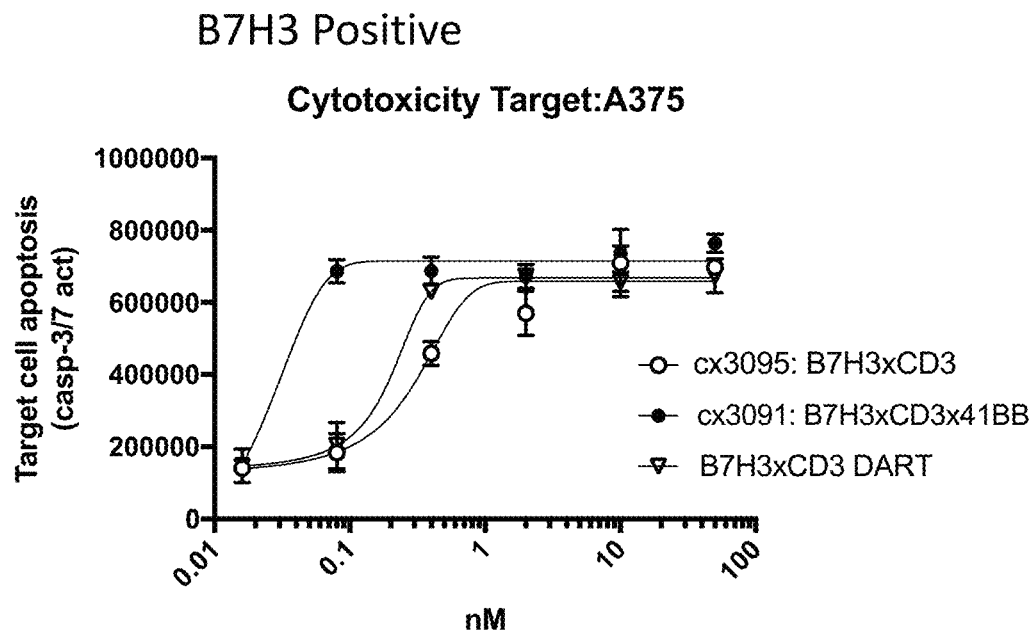
FIG. 8A-8D depicts the potency of T-cell-mediated cytotoxicity driven by representative B7H3-targeted constrained CD3 engaging constructs with a 41BB binding domain, cx3091, and without a 41BB binding domain, cx3095, compared to an alternative DART-Fc format targeting B7H3 and CD3. A titration range of 50 nM to 80 pM of the CD3 engaging constructs on the B7H3 positive A375 cell line are shown in FIGS. 8A and 8C and a B7H3 knock-out A549 are shown in FIGS. 8B and 8D.
Figure 8B:
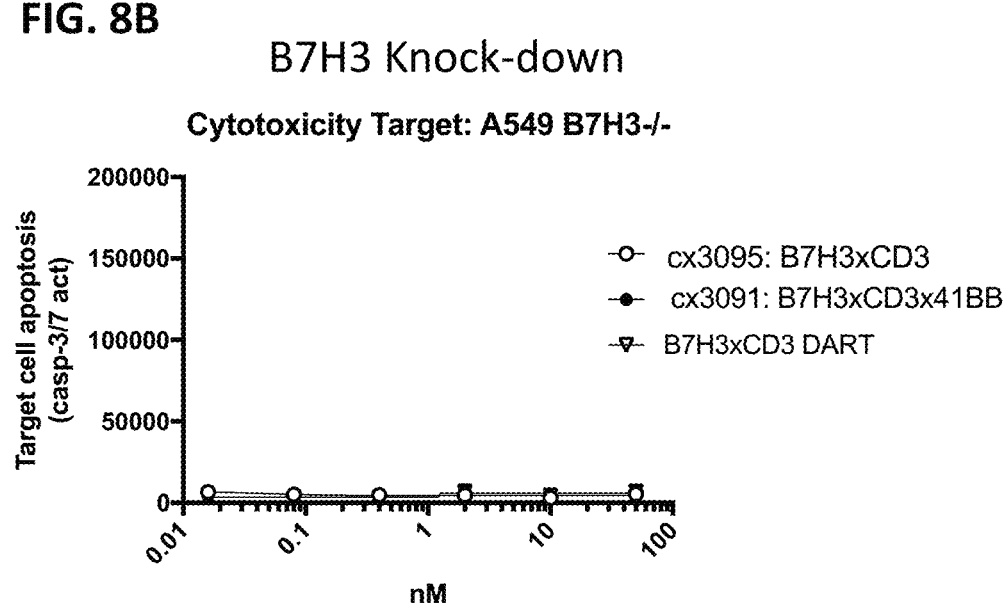
Figure 8C:
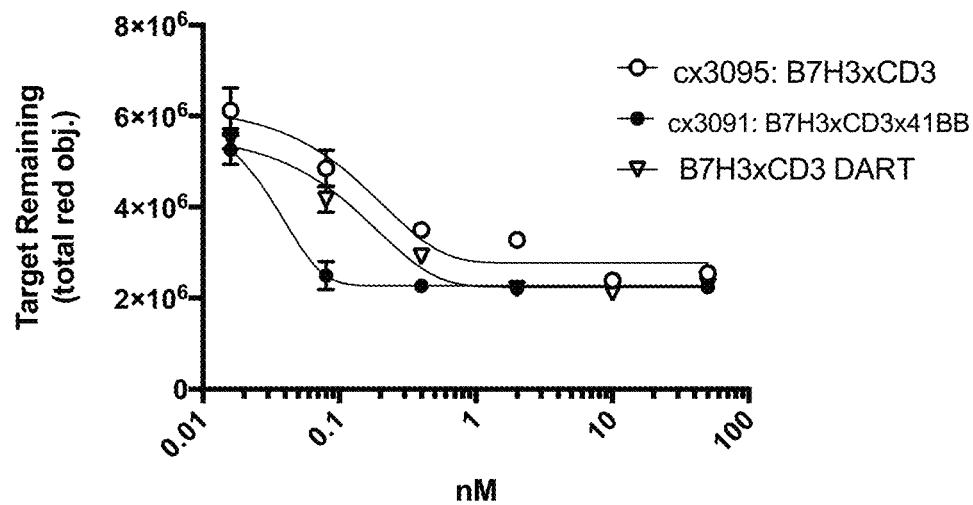
Figure 8D:
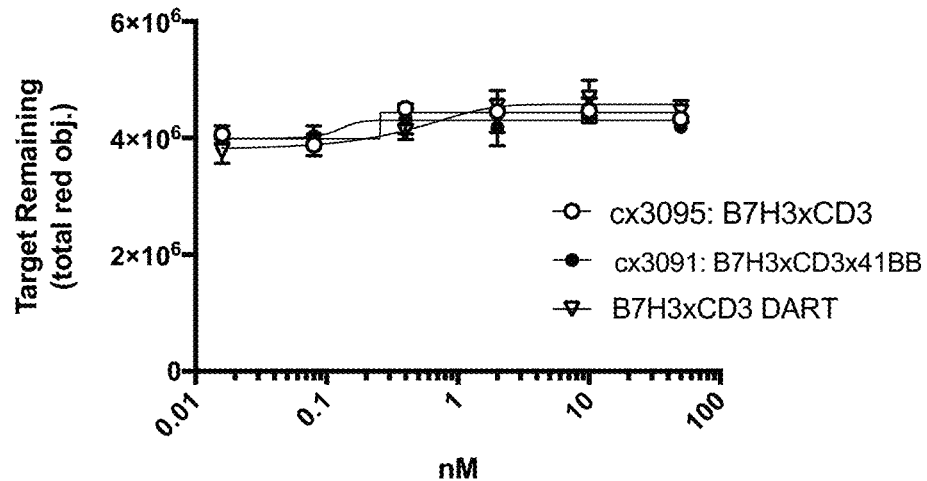

This Example describes the assessment and characterization of the tested constrained CD3 engaging constructs in human primary T cell in vitro assays.
1. T Cell-Mediated Cytotoxicity Target cells were fluorescently labeled with CytoID red. For cytotoxicity assays utilizing adherent target cells, target cells were seeded, allowed to settle at room temperature for uniform distribution, and incubated for several hours at 37° C. to permit adherence prior to addition of other assay components. Primary T cells were negatively enriched from PBMCs isolated from healthy human donor leukopaks and added at a 10:1-40:1 T cell-to-target cell ratio. Green caspase-3/7 reagent was added, which fluorescently labeled nuclear DNA of cells undergoing apoptosis. Antibodies were titrated onto the co-culture and assay plates were serially imaged using an IncuCyte ZOOM system. Target cell death was determined by measuring total red/green overlap object area (as shown in FIGS. 8A, 8B, 9A-9E, 10A, 10B). Herein target cells are labeled as red with the CytoID red, while apoptosis was monitored with the green fluorescent caspase-3/7 substrate, thus apoptotic target cells are those that are dual labeled red and green. Target cell depletion was determined by measuring total red object remaining at the end of the assay as shown in FIGS. 8C and 8D.

In an exemplary assay shown in FIGS. 8A-8D, a multispecifc construct was tested that included a B7H3-targeted constrained CD3 with a 41BB-binding costimulatory receptor binding region (cx3091). As a control, a corresponding B7H3-targeted constrained CD3 without the costimulatory receptor binding region also was tested (cx3095) or the DART-Fc that also binds to B7H3. The target cells were A375 expressing B7H3 or A549 cells that were knocked down for B7H3. The exemplary B7H3-targeted constrained CD3 engaging construct cx3095 induced potent T-cell-mediated cytotoxicity of antigen positive cell lines (FIGS. 8A and 8C) but not antigen negative cell lines (FIGS. 8B and 8D), consistent with the capacity to potently induce antigen-dependent T-cell activation. The control construct cx3095 not containing a costimulatory binding region and the DART-Fc also exhibited cytotoxic activity, although to levels less than observed for cx3091, particularly at the lowest concentrations tested. cx3095 displayed similar potency to an alternative format, DART-Fc B7H3×CD3, which also lacks a 41BB-binding domain.

Figure 9A:
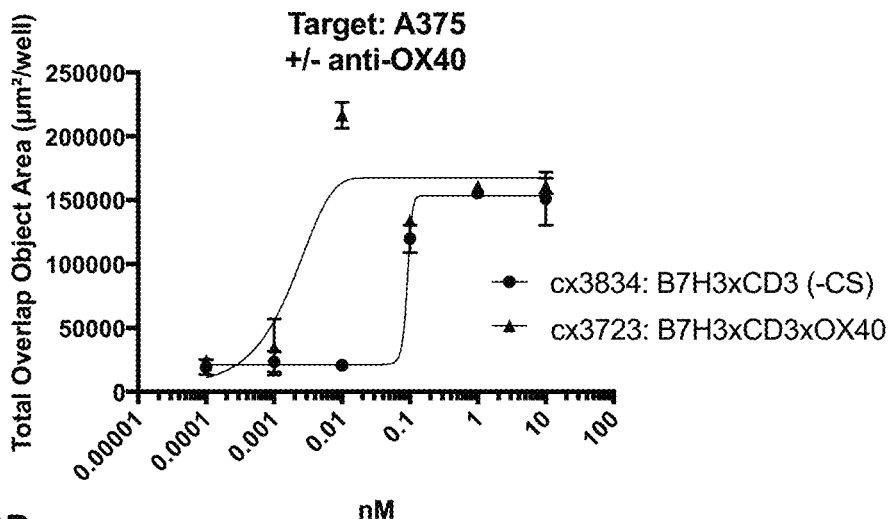
FIG. 9A-9E is a series of graphs that depict the potency of target-dependent T-cell mediated cytotoxicity induced by B7H3-targeted constrained CD3 engaging constructs incorporating various co-stimulatory receptor binding region toward A375 cells. Exemplary B7H3-targeting constrained CD3 engaging constructs incorporating either no co-stimulatory receptor binding domain (cx3834), an OX40 binding domain (FIG. 9A cx3723), a 41BB binding domain (FIG. 9B cx3091), a GITR binding domain (FIG. 9C cx3724), an ICOS binding domain (FIG. 9D cx3721) or an CD28 binding domain (FIG. 9E cx3726) were used herein. Cytotoxicity is shown by total overlap area to represent target cell apoptosis as measured by quantitating the double positive fluorescence of labeled target cells (A375) and the caspase-3/7 substrate.
Figure 9B:
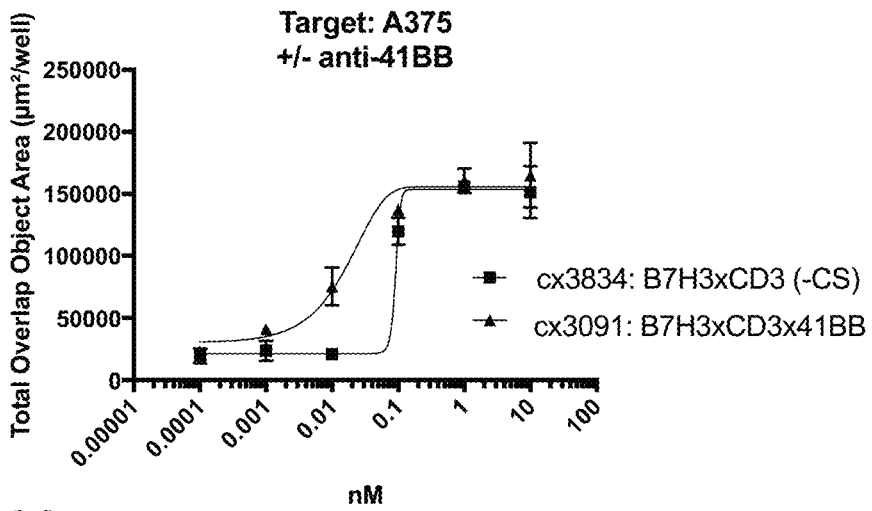
Figure 9C:
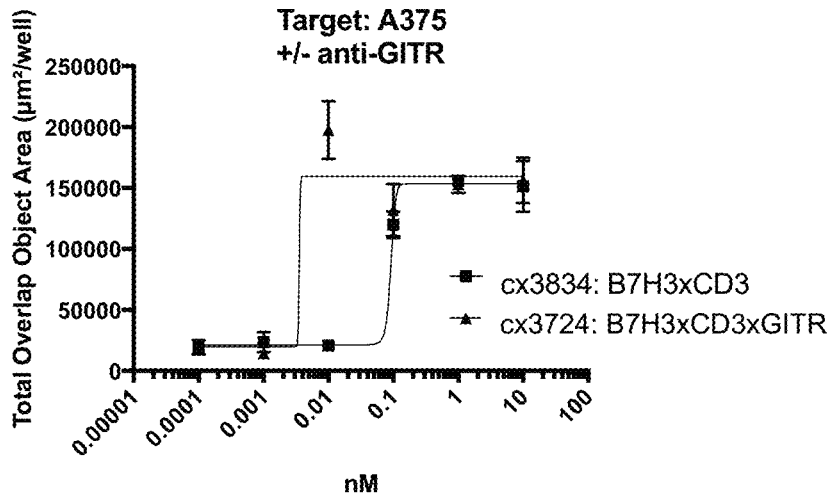
Figure 9D:
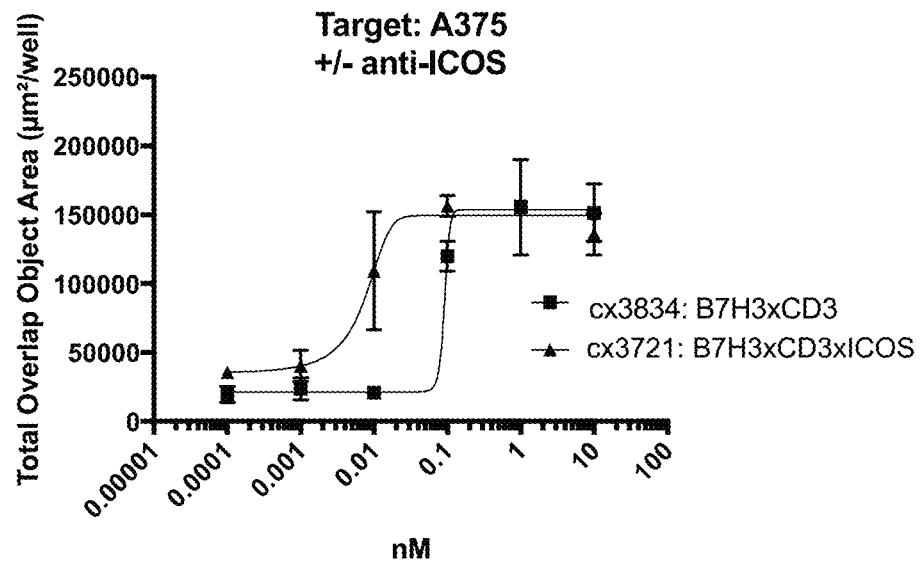
Figure 9E:
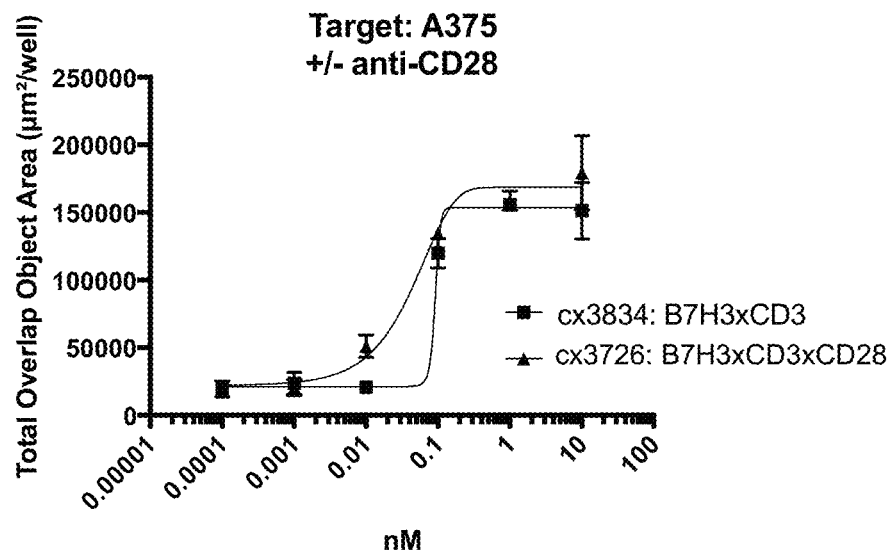

In similar assays, similar results were observed by other B7H3-targeted constrained multispecific polypeptide constructs that incorporated costimulatory binding regions binding other costimulatory receptors. Multispecific polypeptide constructs that incorporated a co-stimulatory receptor binding region targeting OX40 (cx3723; FIG. 9A), 41BB (cx3091; FIG. 9B), GITR (cx3724; FIG. 9C), ICOS (cx3721; FIG. 9D), or CD28 (cx3726; FIG. 9E) each enabled superior T-cell mediated cytotoxicity of B7H3-positive cells, A375, compared to a similar construct lacking the co-stimulatory receptor binding region (cx3834).

Figure 10A:
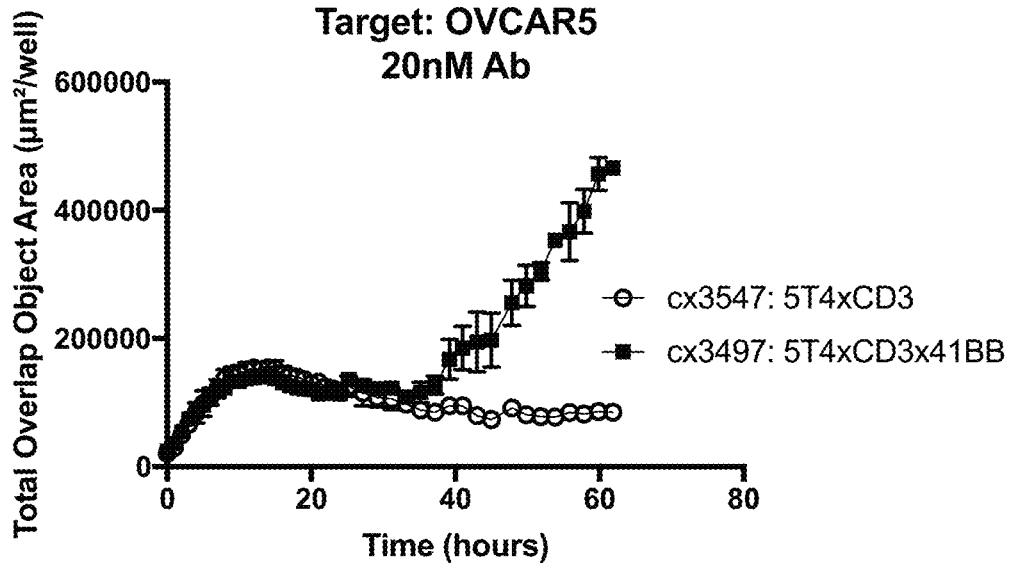
FIGS. 10A and 10B depicts the kinetics of T-cell cytotoxicity mediated by representative 5T4-targeting constrained CD3 engaging constructs, cx3497 (with a 41BB binding domain) and cx3547 (without a 41BB binding domain) toward a 5T4 positive cell line, Ovcar-5 (FIG. 10A), and a 5T4 negative cell line, CCRF-CEM (FIG. 10B). Total overlap area is representative of double positive: cleaved caspase-3/7 substrate in fluorescently labeled target cells. The initial cytotoxicity observed on the antigen negative cell line is likely mediated by MHC-mismatch between the target cells and the T-cells. Notably only cx3497 containing a 41BB binding domain was capable of inducing cytotoxicity and the kinetics are consistent with that of 41BB upregulation following TCR-signaling.
Figure 10B:
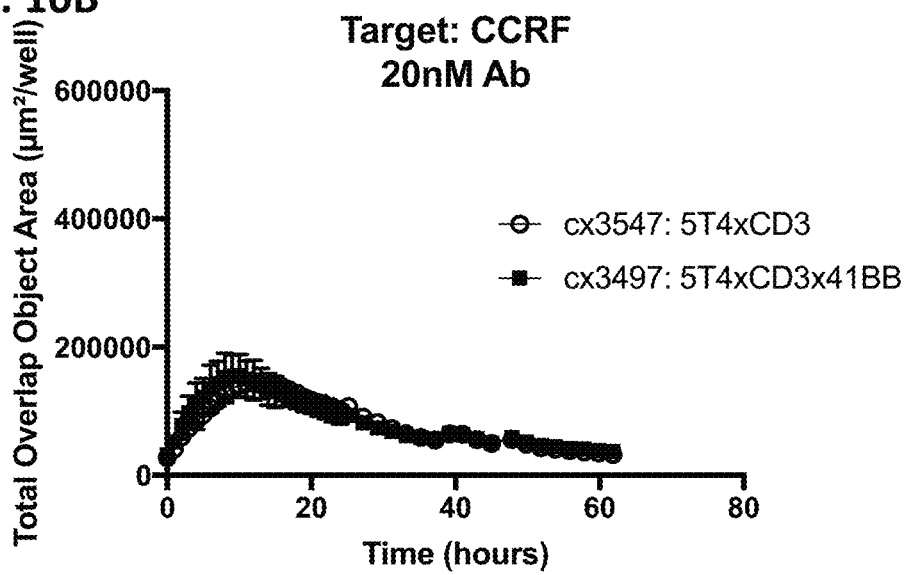

A similar assay was carried out with 5T4-targeted constrained CD3 constructs with a 41BB-binding costimulatory receptor binding region (cx3497). As a control, a corresponding 5T4-targeted constrained CD3 without the costimulatory receptor binding region also was tested (cx3547). The target cells were Ovcar-5 cells expressing 5T4 or CCRF-CEM cells that do not substantially express 5T4. As shown in FIG. 10A-10B, a representative 5T4-targeted constrained CD3 engaging construct, cx3547, lacked the capacity to mediate antigen specific cytotoxicity, whereas the addition of a 41BB binding domain induced specific T-cell cytotoxicity toward a 5T4 expressing cell line, Ovcar-5, but not toward a 5T4 negative cell line, CCRF-CEM. Notably, T-cell mediated cytotoxicity mediated by cx3497 was not observed until approximately 40 hours, which is consistent with the kinetics of 41BB upregulation following TCR signaling.

These results show that the addition of the co-stimulatory receptor binding region targeting a costimulatory receptor, such as 41BB, enhanced the potency of T-cell mediated cytotoxicity over the constructs that lack a costimulatory receptor binding region. These observations support that the antigen-targeted constrained CD3 format with additional co-stimulatory receptor binding capacity provided herein exhibit improved activity compared to other CD3 engaging formats, including the ability to display enhanced potency for mediating cytotoxicity, without substantially binding T-cells absent antigen engagement.

2. T Cell Activation

To assess T cell activation, suspension cells from T cell-mediated cytotoxicity assays above were collected and stained with a live/dead stain and fluorophore-conjugated anti-CD4, anti-CD8, anti-CD25, and/or anti-CD71 antibodies. Cells were analyzed using a SONY SA3800 spectral analyzer and CD4+ or CD8+ T cell activation was determined by measuring expression levels of CD25 or CD71. T-cell activation was monitored by flow cytometric analysis of the expression level of CD71 on CD4 and CD8 populations.

Figure 11A:
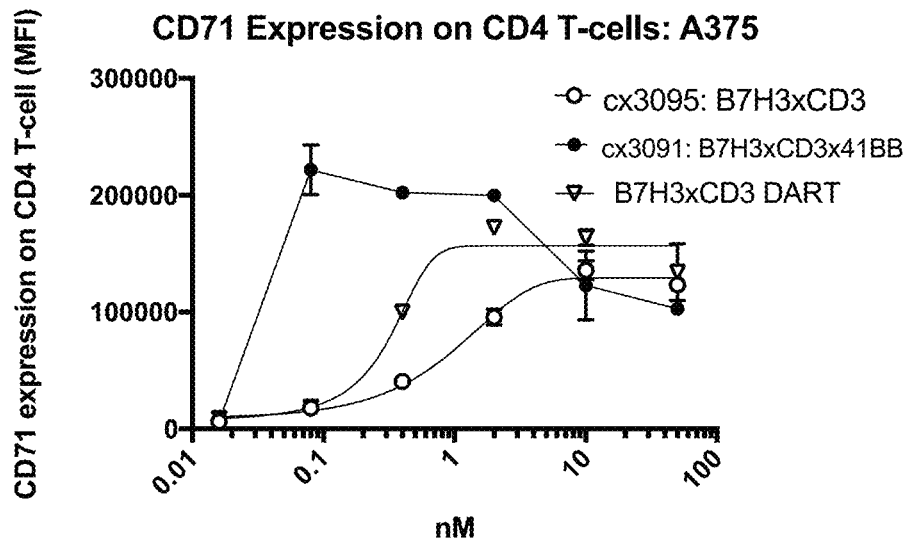
FIG. 11A-11D depicts the potency of T-cell activation driven by representative B7H3-targeted constrained CD3 engaging constructs with a 41BB binding domain, cx3091, and without a 41BB binding domain, cx3095, compared to an alternative DART-Fc format targeting B7H3 and CD3. A titration range of 50 nM to 80 pM of the CD3 engaging constructs on the B7H3 positive A375 cell line are shown in FIGS. 11A and 11C and a B7H3 knock-out A549 cell line are shown in FIGS. 11B and 11D.
Figure 11B:
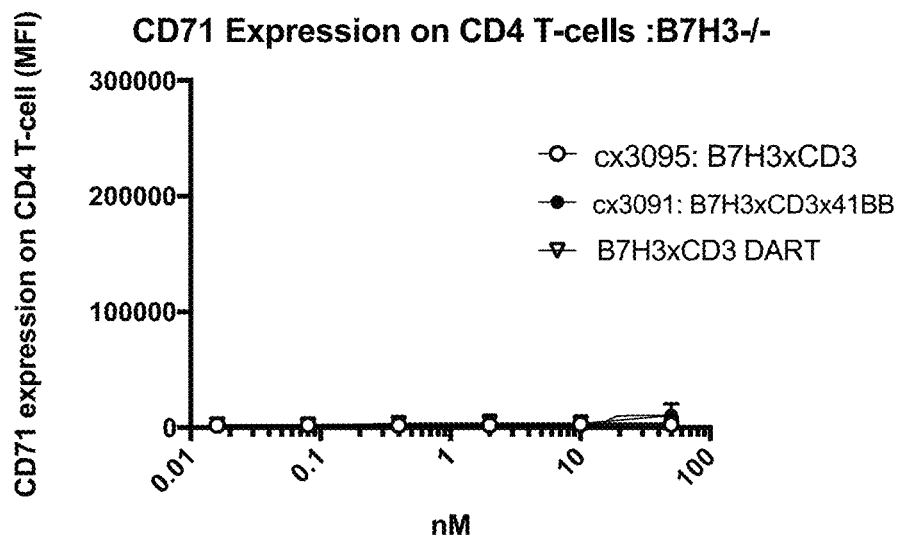
Figure 11C:
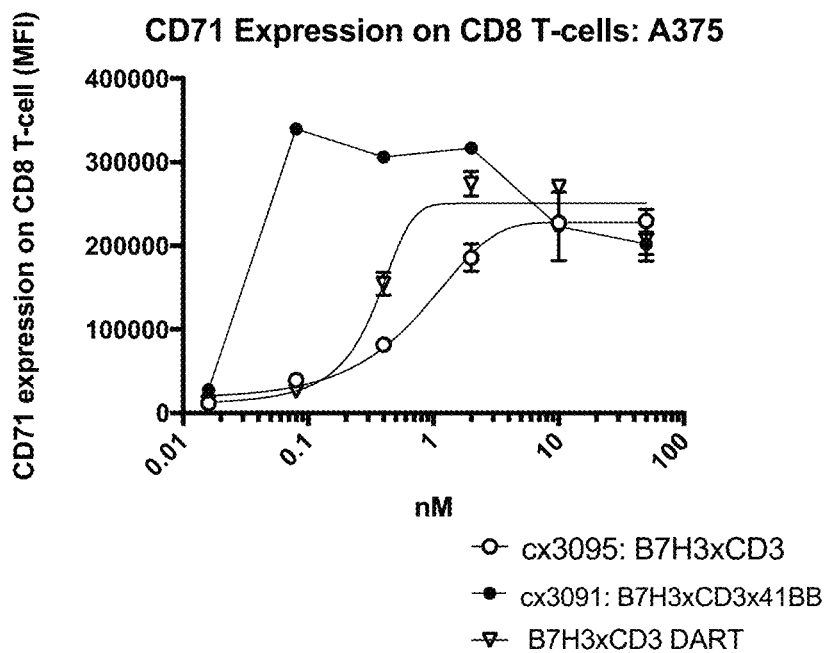
Figure 11D:
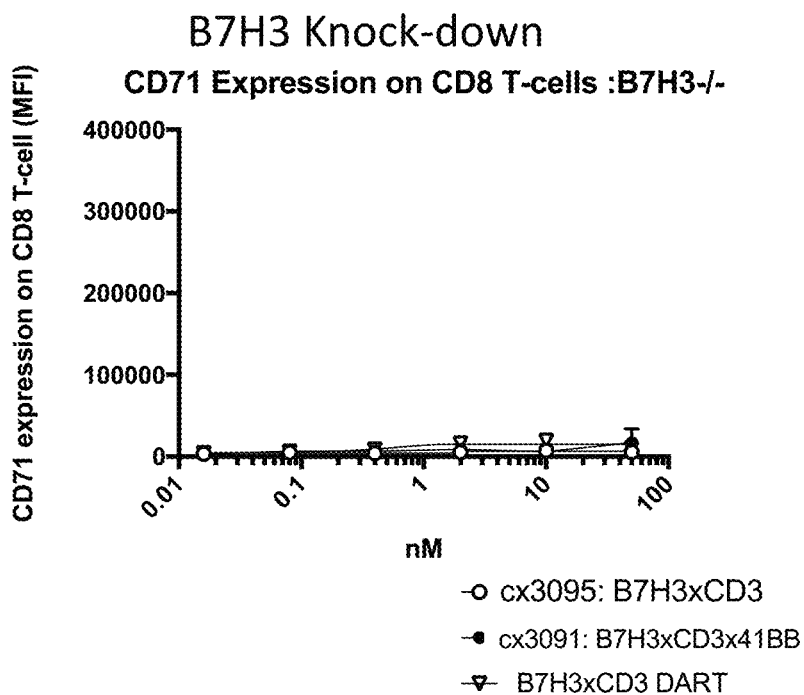

To assess T cell activation cx3091, cx3095 or the DART-Fc B7H3×CD3 were incubated for 20 hours in a co-culture of T-cells and target cells, either B7H3 positive A375 cells or A549 cells in which B7H3 has been knocked-out. T-cell activation was monitored by flow cytometric analysis of the expression level of CD71 on CD4 and CD8 populations. T cell activation, as measured by induction of CD71, was evident in CD4 (FIG. 11A) and CD8 T cells (FIG. 11C) that had been incubated with B7H3-expressing target cells in the presence of all tested constructs. However, as shown, the B7H3-targeted constrained CD3 engaging construct incorporating a 41BB binding domain, cx3091, was superior to both the similar construct, cx3095, that lacks the 41BB binding domain and the DART-Fc in the degree of T cell activation observed. As shown in FIG. 11B and FIG. 11D, no T cell activation as measured by CD71 expression was observed in CD4+ or CD8+ T cells, respectively, in the assay in the absence of B7H3 antigen.

3. T Cell Cytokine Production

To assess cytokine production, FluoroSpot membranes were coated with IFNγ capture antibodies overnight at 4° C. Membranes were washed with PBS and antibody titrations, target cells and T cells negatively enriched from PBMCs were added. Target cell:T cell co-culture cells were seeded at a 1:10 ratio. Assay plates were incubated for ~24 h at 37° C. and membranes were prepared according to the manufacturer's instructions. Membranes were imaged using a CTL-ImmunoSpot S6 Universal Analyzer. Cytokine spot count was measured using uniform exposure time and intensity settings among assay wells.

Figure 12A:
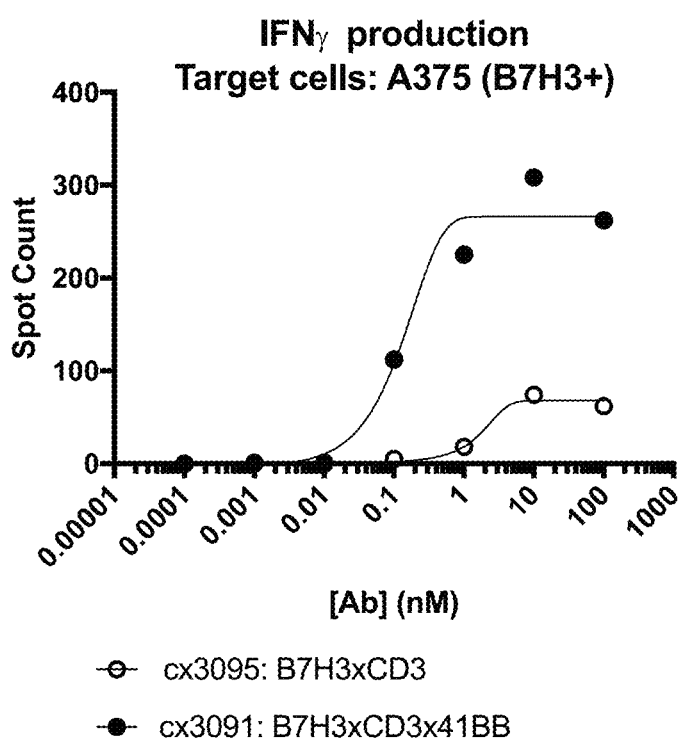
FIGS. 12A and 12B shows a comparison of IFNγ production by T-cells treated with representative B7H3-targeted constrained CD3 engaging constructs with a 41BB binding domain, cx3091, and without a 41BB binding domain, cx3095 in the presence of B7H3 positive, A375 (FIG. 12A), and B7H3 negative, CCRF-CEM (FIG. 12B) target cells. Cytokine production was monitored by flourospot assay.
Figure 12B:
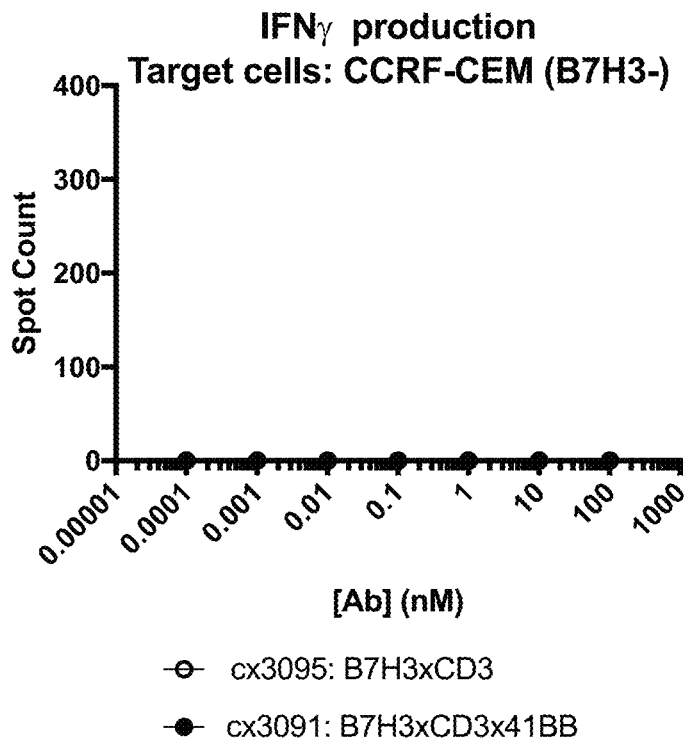

In an exemplary assay, the multispecific construct that was tested included a B7H3-targeted constrained CD3 with a 41BB-binding costimulatory receptor binding region (cx3091). As a control, a corresponding B7H3-targeted constrained CD3 without the costimulatory receptor binding region also was tested (cx3095). The target cells were A375 expressing B7H3 or CCRF-CEM cells that do not express B7H3. The antigen-targeted constrained CD3 engaging construct elicited cytokine production from T-cells in a B7H3-dependent manner, as shown by production of IFN-gamma only in co-cultures containing B7H3-expressing target cells (FIG. 12A) but not in co-cultures with B7H3-negative (B7H3-) target cells (FIG. 12B). The degree of cytokine production was substantially greater in the presence of the cx3091 construct containing the 41BB-binding domain, consistent with the ability of the incorporation of the 41BB binding domain to enhance specific T-cell activation.

4. T Cell Cytokine Production (ELISA)

Supernatants from T cell-mediated cytotoxicity assays, described in part 1 above with 5T4-targeted constrained CD3 constructs, were analyzed for IFNγ content by sandwich ELISA (BioLegend, USA). Additionally, the construct cx3499 containing a 41BB binding domain and cx3546 without a 41BB binding domain (see e.g. Example 1 and FIG. 3) also were assessed in the assay. The manufacturer's instructions were followed and a standard curve was generated from which cytokine concentration values of supernatant samples were interpolated. Samples that had absorbance values below the lower limit of detection were assigned a cytokine concentration equal to half that of the lowest standard concentration.

Figure 13:
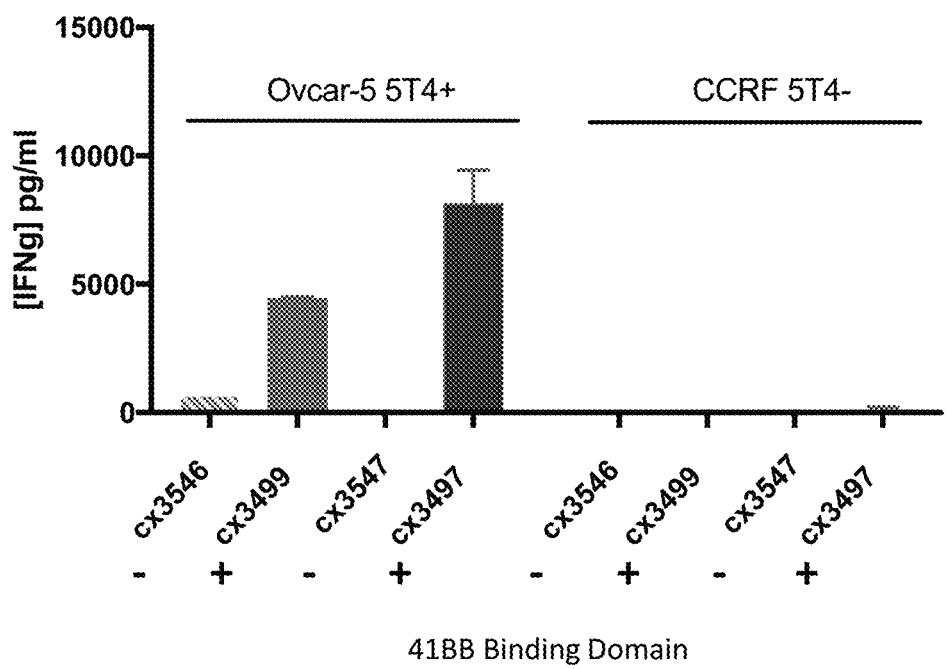
FIG. 13 shows a comparison of IFNγ production by T-cell treated with representative 5T4-targeted constrained CD3 engaging constructs with a 41BB binding domain, cx3499 and cx3497, and without a 41BB binding domain, cx3546 and cx3547 in the presence of 5T4 positive, Ovcar-5 cells, and 5T4 negative, CCRF-CEM cells. Cytokine production was monitored by ELISA. cx3546 and cx3499 contain the same 5T4-targeting sdAbs, and 3547 and 3497 contain the same 5T4-targeting sdAbs. Thus, the only difference between these sets of constructs is the addition of the 41BB binding domain. 5T4-targeted constrained CD3 engaging constructs incorporating a 41BB binding domain, display enhanced capacity to induce IFNγ production from T-cells in an antigen-dependent manner.

FIG. 13 shows that representative 5T4-targeted constrained CD3 engaging constructs were observed to elicit enhanced IFNγ production by T-cells in an antigen dependent manner when a 41BB binding domain was incorporated into the constructs (cx3499 and cx3497) but was not observed in similar constructs that did not contain a 41BB binding domain (cx3546 and cx3547).

5. NFκB-Luciferase Reporter

The capacity of constrained CD3 engaging constructs containing a co-stimulatory receptor binding domain to mediate specific agonism of the respective co-stimulatory signaling pathway was also assessed. A Jurkat OX40 (FIG. 14A) or 41BB (FIG. 14B) NFκB-Luciferase reporter cell was used to test exemplary B7H3-targeting constrained CD3 engaging constructs containing either no co-stimulatory receptor binding domain (cx3834), an OX40 binding domain (cx3723) or a 41BB binding domain (cx3091). As shown in FIG. 14A and FIG. 14B, cx3723 and cx3091 incorporating either OX40 or 41BB binding domain, respectively, were found to induce specific agonism of the targeted co-stimulatory receptor. Some induced NFκB signaling was observed with all constructs including the no co-stimulatory receptor binding region containing construct, suggesting that target dependent CD3 signaling mediates some NFκB signaling in this system. The B7H3 positive cell line A375 was used.

Example 6: Generation of PD-1 sdAb

Single domain antibodies targeting human PD-1 were generated via immunization of llamas and alpaca. Llamas and alpacas were immunized with a recombinant version of the human PD-1 extracellular domain (ECD; amino acids 25-167 of human PD-1 set forth in SEQ ID NO:242, e.g. UniProt No. Q15116) set forth as follows:

```
                      (residues 25-167 of SEQ ID NO: 242)
LDSPDRPWNPPTFSPALLVVTEGDNATFTCSFSNTSESFVLNWYRMSPSN
QTDKLAAFPEDRSQPGQDCRFRVTQLPNGRDFHMSVVRARRNDSGTYLCG
AISLAPKAQIKESLRAELRVTERRAEVPTAHPSPSPRSAGQFQ
```

Following the development of specific anti-PD1 antibody titers, llama/alpaca peripheral blood mononuclear cells (PBMCs) were isolated from 500 mL of blood from the immunized animal and total mRNA was isolated using the Qiagen RNeasy Maxi Kit and subsequently converted to first strand cDNA using Thermo Superscript IV Reverse Transcriptase and oligo-dT priming. Single domain antibody (sdAb; also called VHH) sequences were specifically amplified via PCR using the cDNA as template and cloned into a yeast surface display vector as sdAb-Fc-AGA2 fusion proteins. The Fc was a human IgG1 Fc (set forth in SEQ ID NO:1).

Yeast libraries displaying these sdAbs were enriched using recombinant forms of the PD-1 ECD via magnetic bead isolation followed by fluorescence activated cell sorting (FACS). Sorted yeast were plated out and isolated colonies were picked into 96-well blocks and grown in media that switched the expression from surface displayed sdAb-Fc to secretion into the media. Exemplary identified sdAbs sare set forth in Table E2.

TABLE E2

PD-1 sdAbs

| Clone name | CDR1 | SEQ ID NO | CDR2 | SEQ ID NO | CDR3 | SEQ ID NO | VHH SEQ ID NO |
|---|---|---|---|---|---|---|---|
| 18H10 | GSVTGANTMG | 272 | LIGNYVTH | 278 | YTDNLGTS | 283 | 243 |

Example 7: Humanization of Camelid Derived PD-1 sdAb

The exemplary camelid derived PD-1 sdAb, 18N10, was humanized using the human VH3-23 germline as scaffold. Camelid residues that contribute to solubility, specificity, stability and/or affinity remained unmodified. In addition all humanized variants contained the modification of Leu11Glu (L11E) and the carboxy-terminal modifications of Ser112Lys (S112K) and Ser113Pro (S113P) as these are known prevent or reduce the recognition of pre-existing ADA directed toward sdAbs (as described in US2060207981).

Table E3 sets forth exemplary PD-1 sdAbs humanized variants.

Example 8: Binding of sdAb to PD-1 Expressing Cells by Flow Cytometry

Specificity and relative affinity were assessed for purified sdAb-Fcs on PD-1-expressing cells. For transient transfection of 293 cells, freeStyle 293 cells were resuspended at $1 \times 10^6$ cells per mL in fresh FreeStyle 293 expression medium. Cells were seeded into 50 mL per transfection and incubated on a shaker at 37° C. while transfection reagents were prepared. 50 μg of each transfection plasmid were diluted into 500 μL of OptiMEM. In a separate tube for each transfection, 150 μg of polyethylenimine (PEI; 75 μL of a 2 mg/mL solution) were added to 500 μL of OptiMEM and then mixed 1:1 with the DNA:OptiMEM solution. DNA and PEI were complexed for 15 minutes at room temperature. DNA:PEI complexes were then added drop-wise to a prepared flask of FreeStyle 293 cells and mixed by swirling. Transfected cells were incubated overnight in a 37° C. shaker to allow time for protein expression. Transfection

TABLE E3

PD-1 sdAbs Humanized Variants

| Clone name | CDR1 | SEQ ID NO | CDR2 | SEQ ID NO | CDR3 | SEQ ID NO | VHH SEQ ID NO |
|---|---|---|---|---|---|---|---|
| 18H10 Humanized Variants | | | | | | | |
| hz18H10v1 | GSMTGANTMG | 268 | LIGNYVTH | 278 | YTDNLGTS | 283 | 251 |
| hz18H10v2 | GSMTGANTMG | 268 | LIGNYVTH | 278 | YTDNLGTS | 283 | 252 |
| hz18H10v3 | GSMTGANTMG | 268 | LIGNYVTH | 278 | YTDNLGTS | 283 | 253 |
| hz18H10v4 | GSMTGANTMG | 268 | LIGNYVTH | 278 | YTDNLGTS | 283 | 254 |
| hz18H10v5 | GSMTGANTMG | 268 | LIGNYVTH | 278 | YTDNLGTS | 283 | 255 |
| hz18H10v6 | GSVTGANTMG | 272 | LIGNYVTH | 278 | YTDNLGTS | 283 | 256 |
| hz18H10v7 | GSITGANTMG | 273 | LIGNYVTH | 278 | YTDNLGTS | 283 | 257 |
| hz18H10v8 | GSVTGANTMG | 272 | LIGNYVTH | 278 | YTDNLGTS | 283 | 258 |
| hz18H10v9 | GSVTGANTMG | 272 | LIGNYVTH | 278 | YTDNLGTS | 283 | 259 |
| hz18H10v10 | GSMTGANTMG | 268 | LIGNYVTH | 278 | YTDNLGTS | 283 | 260 |
| hz18H10v11 | GSVTGANTMG | 272 | LIGNYVTH | 278 | YTDNLGTS | 283 | 261 |
| hz18H10v12 | GSVTGANTMG | 272 | LIGNYVTH | 278 | YTDNLGTS | 283 | 262 |
| hz18H10v13 | GSMTGANTMG | 268 | LIGNYVTH | 278 | YTDNLGTS | 283 | 263 |
| hz18H10v14 | GSVTGANTMG | 272 | LIGNYVTH | 278 | YTDNLGTS | 283 | 264 |
| hz18H10v15 | GSITGANTMG | 273 | LIGNYVTH | 278 | YTDNLGTS | 283 | 265 |
| hz18H10v16 | GSITGANTMG | 273 | LIGNYVTH | 278 | YTDNLGTS | 283 | 266 |
| hz18H10v17 | GSITGANTMG | 273 | LIGNYVTH | 278 | YTDNLGTS | 283 | 267 | plasmids used encoded citrine-tagged full-length PD1 proteins of human (hu), cynomolgus (cy) and murine (mu) origin.

Binding of exemplary PD-1-sdAb-Fc fusion proteins described in Examples 6 and 7 were assessed by flow cytometry using the transiently transfected PD-1-expressing cells. Untransfected FreeStyle 293 cells (UT 293) or transiently transfected FreeStyle 293 cells (huPD1-FL 293, cyPD1-FL 293 or muPD1-FL 293) were diluted to 0.5×10× $10^6$ cells/mL in FACS Buffer (1×TBS, 0.01% FBS, 0.002% Sodium Azide) and plated at 100 µL/well in a 96-well round bottom assay plate. The assay plates were centrifuged at about 750 rpm for 5 minutes, then the supernatants were removed and primary antibody dilutions were added as follows. A three-fold, 9-point serial dilution of 18H10 or hz18H10v7 in FACS buffer was prepared, ranging from 111 nM to 0.0169 nM and 50 µL/well of diluted antibody was added to the assay plates containing 293 cells. Cells were incubated in the antibody dilutions for 30 minutes at 4° C. After the 30-minute incubation, the assay plates were centrifuged at about 750 rpm for 5 minutes, washed with 150 µL FACS Buffer, and centrifuged again at about 750 rpm for 5 minutes. The wash was removed and 50 µL/well of Alexa Fluor 647 conjugated donkey-Anti-Human IgG diluted 1:1000 in FACS buffer was added and incubated for 20 minutes at 4° C. Assay plates were then centrifuged at 750 rpm for 5 minutes, washed with 150 µL FACS Buffer, and centrifuged again at 750 rpm for 5 minutes. The wash was removed and the cells were resuspended in 30 µL/well of FACS Buffer for analysis by flow cytometry (iQue Intellicyte).

Figure 15A:
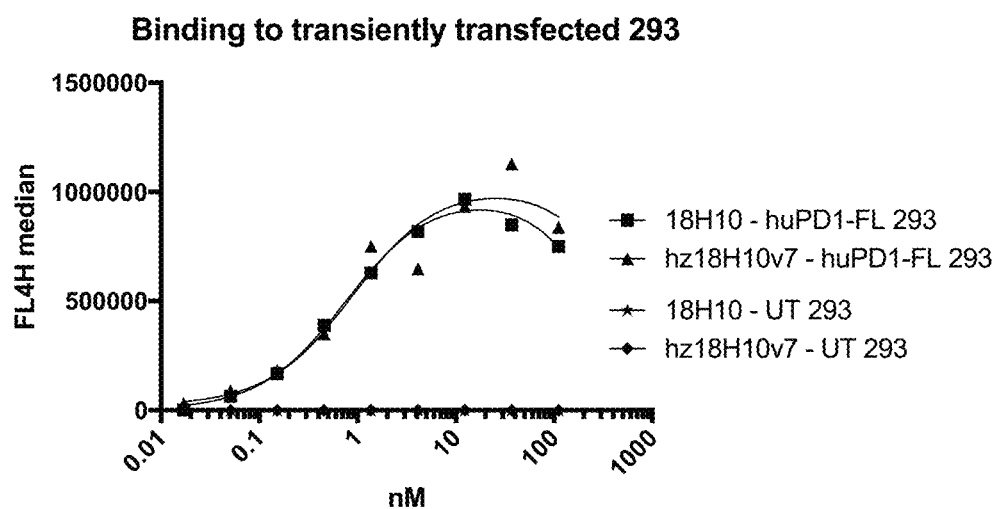
FIG. 15A-15C depict the binding of 18H10 and its humanized variant hz18H10v7 to FreeStyle 293 cells expressing human PD-1 (FIG. 15A), cynomolgus PD-1 (FIG. 15B) or mouse PD-1 (FIG. 15C). Binding to untransfected (293) cells also was assessed and is shown.
Figure 15B:
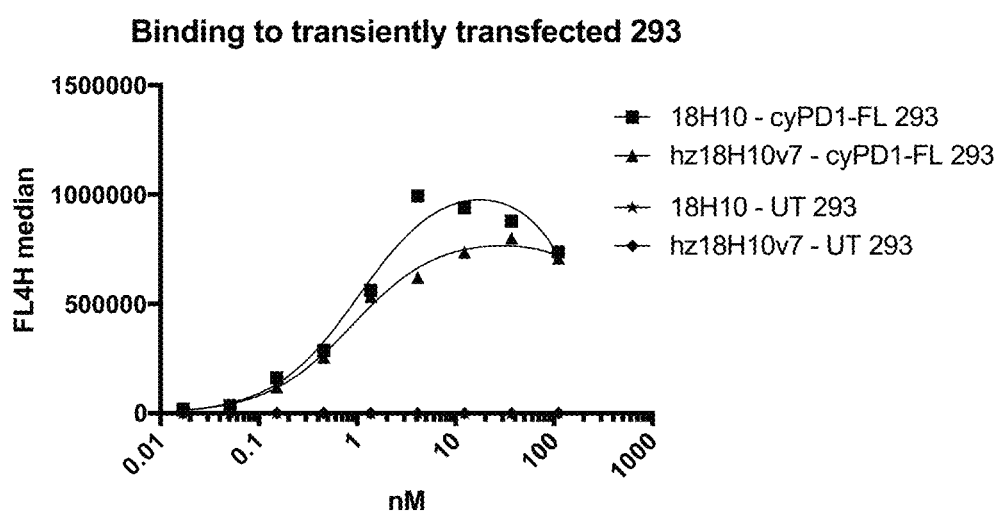
Figure 15C:
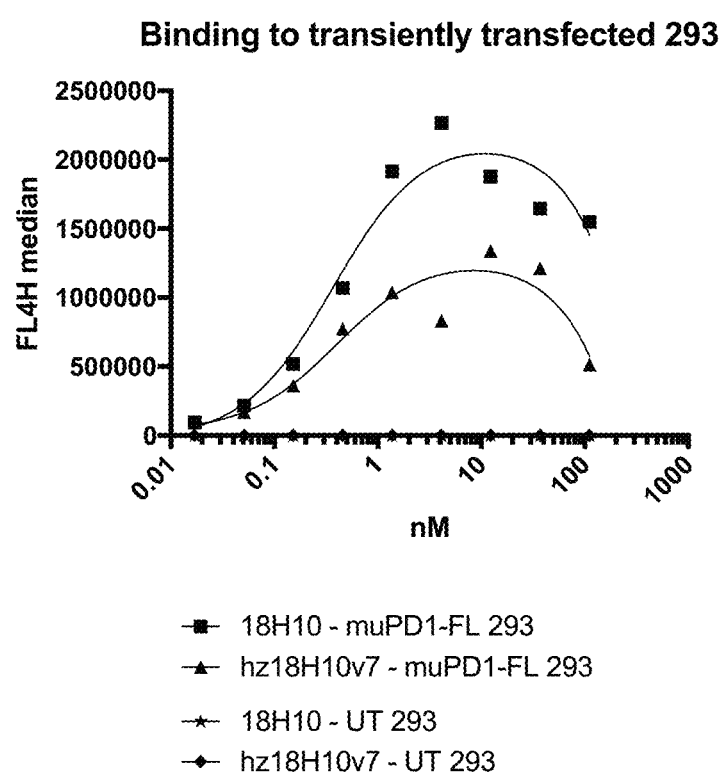

Exemplary results are set forth in FIGS. 15A-15C for 18H10 (parental derived from llama; SEQ ID NO:243) or 18H10hzv7 (SEQ ID NO:257) for binding human PD-1 expressing cells (huPD1-FL 293, FIG. 15A), cynomolgus PD-1 expressing cells (cynoPD1-FL 293, FIG. 15B), or mouse PD-1 expressing cells (muPD1-FL 293, FIG. 15C), each compared to non-expressing (UT 293) cells.

Example 9: Assessment of Binding of PD-1 sdAb to Activated Human T Cells by Flow Cytometry Binding of PD-1-sdAb-Fc fusion proteins to activated human T cells was assessed by flow cytometry.

For enrichment and activation of human T cells, Peripheral blood mononuclear cells (PBMCs) were isolated from human donor blood using density gradient centrifugation. Blood samples were diluted with PBS/2% FBS (1:2) and 30 mL of diluted blood was layered onto 15 mL of Lymphoprep density gradient medium. After centrifugation, the PBMC layer at the interphase of plasma and Lymphoprep was removed and remaining red blood cells were lysed using red blood cell lysis buffer for 5 minutes at room temperature. Non-T cell populations were labeled with biotinylated anti-lineage marker antibodies against CD14, CD16, CD19, CD20, CD36, CD56, CD123, TCR γ/δ (20 minutes, room temperature) and depleted using magnetic streptavidin particles. The unbound cell supernatant containing the T cell fraction was retained. Enriched human T cells were activated for 3 days by plating them at a density of about 2×$10^6$ cells per mL media in tissue culture plates coated with 1 µg/mL mouse anti-human CD3 (OKT3). Activated T cells were washed once in PBS before further use in binding assays.

Figure 16:
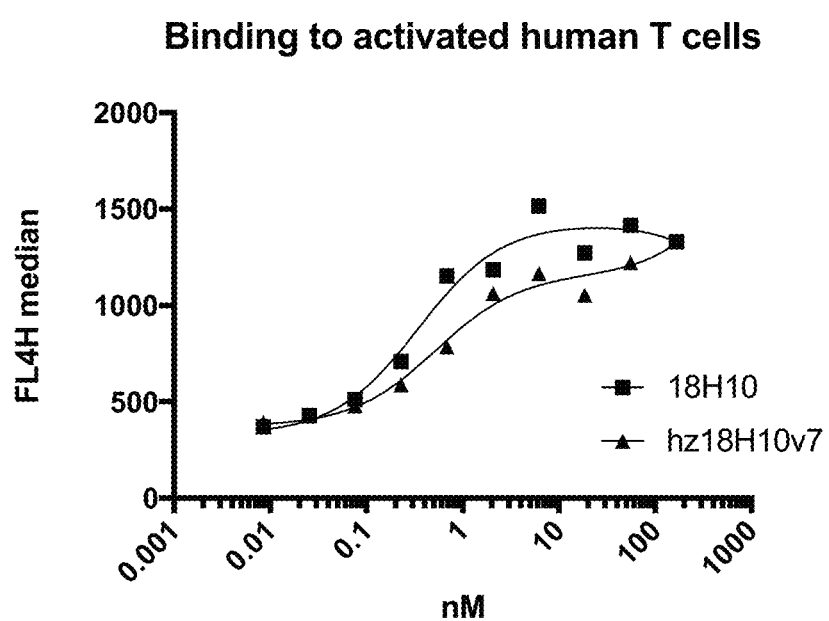
FIG. 16 is a graph depicting the binding of 18H10 and its humanized variant hz18H10v7 to activated human T cells. Test article binding to activated T cells was quantified by flow cytometry.

Binding was assessed and quantified by flow cytometry substantially as described in Example 8, except for binding to activated human T cells, a four-fold, 10-point serial dilution of 18H10 (SEQ ID NO: 243) or humanized 18H10 (hzv7; SEQ ID NO: 257) ranging from 167 nM to 0.00847 nM was used for incubation, As shown in FIG. 16, the tested exemplary PD-1-targeting construct and the humanized variant were found to bind the enriched and activated human T cells.

Example 10: Assessment of PD-1/PD-L1 Blockade Using a Reporter Assay

A PD-1-expressing Jurkat effector reporter cell line, in which TCR engagement leads to the transcription of a luciferase reporter gene, was used to assess the ability of exemplary sdAbs targeting PD-1 to block the interaction of PD-1 and PD-L1. In the assay, PD-L1-expressing aAPC/CHOK1 cells were co-cultured with the Jurkat reporter cells to provide a TCR-specific activation signal, while simultaneously suppressing this signal through the engagement of PD-1 on the effector cell. The ability of PD-1 sdAb to block the suppressed signal, and enhance TCR engagement, was monitored.

PD-L1 expressing aAPC/CHOK1 cells were plated in 100 µl Ham's F12 supplemented with 10% FBS one day before the assay. On the day of the assay, all media was discarded and replaced with 40 µL of assay media (RPMI 1640, supplemented with 1% FBS) containing titrations of the test proteins containing 18H10 (SEQ ID NO: 243) or humanized 18H10 (hzv7; SEQ ID NO: 257) (starting concentration: 50 nM, titrated 1:4). Jurkat PD-1 reporter cells were then added to the plates (40 µL) and the plate was incubated for 6 h (37° C., 5% CO2 in a humidified atmosphere). After the incubation, an equal volume of BioGlo Luciferase Assay Substrate was added to the wells and incubated for 10 minutes at room temperature and luminescence was assessed and analyzed.

Figure 17:
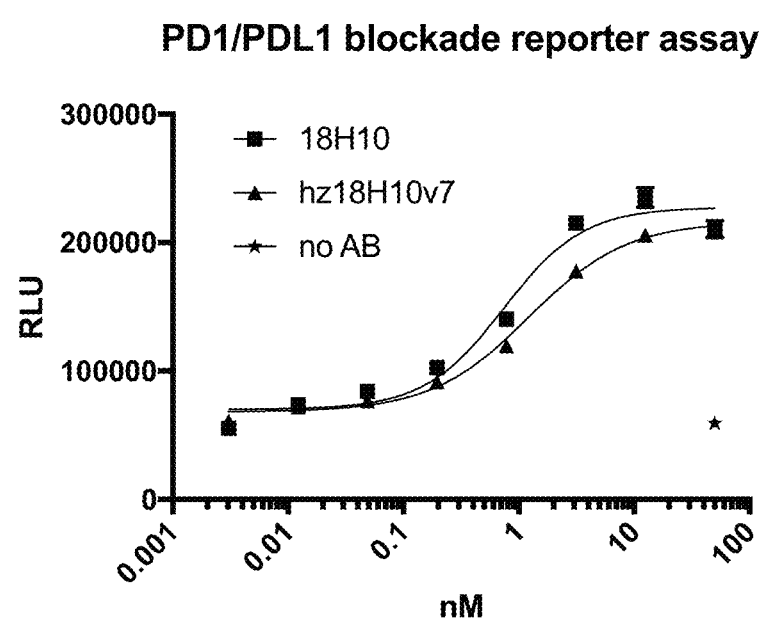
FIG. 17 is a graph depicting the ability of 18H10 and its humanized variant hz18H10v7 to block PD1/PDL1-mediated suppression of T cell receptor (TCR) signaling in a Jurkat reporter luciferase assay system.

As shown in FIG. 17, blockade of PD-1/PD-L1 by the exemplary tested proteins 18H10 (SEQ ID NO: 243) or humanized 18H10 (hzv7; SEQ ID NO: 257) was observed as indicated by the presence of TCR engagement and luciferase transcription.

Example 11: Method of Producing TAA-Targeted Constrained CD3 Binding Proteins with Anti-PD1 sdAbs Multispecific polypeptide constructs were generated containing a disulfide stabilized anti-CD3 Fv binding region that exhibits constrained CD3 binding, a heterodimeric Fc domain, one or more TAA antigen binding domains positioned amino-terminally relative to the Fc region and/or carboxy-terminally relative to the CD3 binding region, and an inhibitory receptor binding region (IRBR) containing a single domain antibody (sdAb) against PD-1, which was positioned amino-terminally relative to the Fc region and/or carboxy-terminally relative to the CD3 binding region. In some cases, the multispecific polypeptide constructs were generated to contain at least one co-stimulatory receptor binding region (CRBR), e.g. against 41BB, which was positioned amino-terminally relative to the Fc region and/or carboxy-terminally relative to the CD3 binding region. The multispecific constructs were generated in various configurations, as shown in FIG. 18A-18B.

In the exemplary constructs, polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, an Fc hole polypeptide (e.g. set forth in SEQ ID NO: 91, or in some cases SEQ ID NO:93); a cleavable or a non-cleavable linker, such as one containing one or more substrate recognition sites for a protease; and a variable light (VL) domain of a dsFv anti-CD3 antibody (e.g. set forth in SEQ ID NO:241). The second polypeptide chain generally included in order, from the N-terminus to C-terminus, an Fc knob polypeptide (e.g. set forth in SEQ ID NO: 84, or in some cases SEQ ID NO:88); the same cleavable linker or the same non-cleavable linker as the first polypeptide chain; and a variable heavy domain of a dsFv anti-CD3 antibody (e.g. set forth in SEQ ID NO:44). The constructs were generated with the exemplary non-cleavable linker, GGGGGSGGGGGSGGGGGS (SEQ ID NO:119), or the exemplary cleavable linker, GGSGGGGIEPDIGGSGGS (SEQ ID NO:105) containing a substrate recognition site for granzyme B. One or both of the polypeptide chains additionally encoded PD-1 sdAb (e.g. SEQ ID NO:243 or SEQ ID NO: 257) as an inhibitory receptor binding region amino terminal to the Fc domain and/or carboxy terminal to the CD3 binding region, and/or a 4-1BB sdAb (e.g. SEQ ID NO:215) as a co-stimulatory receptor binding domain amino terminal to the Fc domain and/or carboxy terminal to the CD3 binding region, in various configurations.

Separate plasmids encoding each chain of a heterodimeric constrained CD3 binding protein were transiently transfected at an equimolar ratio into mammalian cells (either HEK293 or CHO) using polyethylenimine. Recombinant protein secreted into the supernatant was collected after 3-7 days, and secreted recombinant protein was purified by protein A chromatography, followed by either preparative size exclusion chromatography (SEC) or flow-through hydrophobic interaction chromatography (HIC). Heterodimeric protein was selectively purified owing to a mutation designed into one chain of the heterodimeric Fc at position I253R or H435R (usually the hole-Fc) such that it did not bind protein A. The second chromatography step on SEC (AKTA with Superdex-200 resin) or FT-HIC (AKTA with butyl/phenyl sepharose) was used to remove undesired cross-paired species containing two heterodimeric Fcs that were more hydrophobic and twice the expected molecular weight.

The method favored production of heterodimeric multi-specific polypeptide constructs, containing properly paired species of heterodimeric Fc and the disulfide stabilized anti-CD3 Fv as described (e.g. anti-CD3 VH with the mutation G44C as set forth in SEQ ID NO: 44 and VL with the mutation G100C as set forth in SEQ ID NO: 241). Purified heterodimeric constrained CD3 binding protein was stable and did not accumulate cross-paired species upon prolonged incubation at 4° C. or increased protein concentration.

Example 12: Generation of Constructs with Constrained CD3 Binding

Example 12 describes the generation and expression of multispecific polypeptide constructs containing a CD3 binding region that exhibits constrained CD3 binding. The multispecific constructs were generated in various configurations, as shown in FIGS. 1, 19A-C and FIG. 20, to contain a heterodimeric Fc region of an immunoglobulin coupled by a linker (e.g. a non-cleavable linker) to the CD3 binding region, and one or more antigen binding domains that binds a tumor associated antigen (TAA) positioned amino-terminally relative to the Fc region and/or carboxy-terminally relative to the CD3 binding region of the multispecific polypeptide construct.

A. Design and Generation of Constructs

Polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, a first Fc polypeptide (e.g. an Fc hole polypeptide); a non-cleavable linker; and a variable light (VL) domain of an anti-CD3 antibody. The second polypeptide chain generally included in order, from the N-terminus to C-terminus, a second Fc polypeptide (e.g. an Fc knob polypeptide); the same non-cleavable linker as the first polypeptide chain; and a variable heavy (VH) domain of an anti-CD3 antibody. The anti-CD3 antibody included either a disulfide-stabilized (dsFv) antibody (anti-CD3 VH with the mutation G44C and VL with the mutation G100C) or contained a non-disulfide stabilized Fv antibody, as set forth in Table E4. Various exemplary Fc polypeptide pairs to facilitate heterodimerization of the polypeptide chains were used as set forth in Tables E12. One or both of the polypeptide chains additionally encoded one or more TAA antigen binding domain amino-terminal to the Fc domain and/or carboxy-terminal to the CD3 binding region, in various configurations. Similar constructs can be generated using other heterodimeric Fc configurations, including other knob-into-hole configurations, such as any as described; other CD3-binding regions, including other anti-CD3 antibodies, including dsFv or other monovalent fragments; or other TAA antigen-binding fragments, such as scFv, sdAb or Fab formats can also be used.

Among generated constructs, the non-cleavable linker included linkers ranging from 3-18 amino acids in size. Examples of non-cleavable linkers used in exemplary generated molecules were GGS, GGSGGS (SEQ ID NO:10), GGSGGSGGS (SEQ ID NO:11), GGSGGSGGSGGS (SEQ ID NO:12), GGSGGSGGSGGSGGS (SEQ ID NO:13), and GGGGGSGGGGGSGGGGGS (SEQ ID NO:119, contained in exemplary construct cx5823 and cx5952) or GGSGGGGSGGGGSGGGGS (SEQ ID NO:147).

Any antigen binding domain that binds to a TAA can be employed in the provided multispecific polypeptide constructs. Exemplary generated proteins contained an antigen binding domain that binds B7H3 (CD276) or Delta-like 3 (DLL3). The antigen-binding domain can include single chain fragments (e.g. sdAb or scFv) or two chain antigen-binding fragments (Fabs). When the TAA was provided as a single chain fragment, e.g. sdAb or scFv, the TAA antigen binding domain was linked at the N-terminus to one or both polypeptide chains of the Fc heterodimer (e.g. hole and/or knob) by a peptide linker, e.g. PGGGG (SEQ ID NO:102) and/or was linked at the C-terminus to one or both domains (e.g. VH and/or VL) of the CD3 binding region by a peptide linker, e.g. GGGG (SEQ ID NO:103). Other similar peptide linkers can be employed. When the TAA was provided as a Fab antigen-binding fragment the construct was composed of a VH and CH1 linked directly to one or both Fc polypeptides without a linker, as well as a light chain composed of a VL and CL. These TAA binding Fabs can be located on the amino- or carboxy-terminus of the heterodimeric Fc.

Multispecific polypeptide constructs were generated containing 1, 2, 3 or 4 TAA antigen binding domain, such as to provide for monovalent, bivalent, trivalent, or tetravalent binding, respectively. In some cases, the TAA antigen binding domains were the same (mono-epitopic). In some cases, the TAA antigen binding domains were different, such that the generated multispecific polypeptide constructs exhibited specificity for at least two different TAAs, to different epitopes of the same TAA (bi-epitopic) or the same epitopes of the same TAA (mono-epitopic).

Figure 19B:
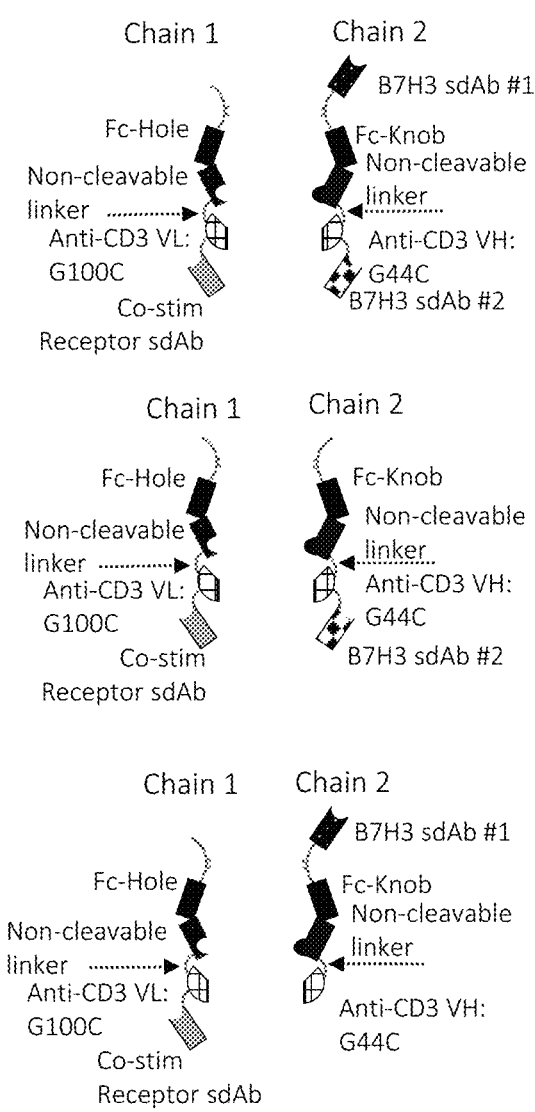
FIG. 19B is a schematic of various B7H3-targeting constrained CD3 constructs composed of two polypeptides, Chain 1 and Chain 2. Chain 1 contains a heterodimeric Fc "hole," linked via a non-cleavable linker to an anti-CD3 VL domain modified at G100C linked to a co-stimulatory receptor targeting sdAb. Chain 2 contains either a B7H3-targeted sdAb, linked to a complementary heterodimeric Fc "knob," linked via the linker as above to an anti-CD3 VH domain modified at G44C linked to second B7H3-targeted sdAb (top); a heterodimeric Fc "knob," linked via the linker as above to an anti-CD3 VH domain modified at G44C linked to a B7H3-targeted sdAb (middle); or a B7H3-targeted sdAb, linked to a complementary heterodimeric Fc "knob," linked via the linker as above to an anti-CD3 VH domain modified by G44C (bottom). When co-expressed the CD3 binding domain is properly assembled via the association of the VL:VH on the hole and knob, respectively. VH:VL interaction is stabilized by an engineered disulfide bond between the modified residues G44C in the VH domain and G100C in the VL domain. The resulting constructs are engage B7H3 either in bivalent (top) or monovalent (middle and bottom) manner. All the constructs herein express contain a co-stimulatory receptor targeting sdAb.

Among the generated proteins were constructs in which the TAA antigen binding domains were composed as single domain antibodies (sdAbs) of antigen-binding fragments (Fabs). Polynucleotides were generated to encode polypeptide chains of exemplary multispecific polypeptide constructs containing non-cleavable linkers. These included sdAb-containing constructs designated cx3072, cx5952, cx6079, cx6080, cx6081, cx5823, cx5873, and cx5965, targeting B7H3 as depicted in FIGS. 19A and 19B; Fab-containing constructs designated cx5067, cx6083, and cx6084, targeting B7H3 as depicted in FIG. 19C; and sdAb-containing cx5352, cx5800, and cx5801 targeting DLL3 as depicted in FIG. 20. Some constructs were generated wherein the VH domain of the dsFv anti-CD3 antibody and the sdAb were both linked to the same side (e.g. hole or knob side) of the Fc heterodimer (e.g. cx3072 and cx5952, shown in FIG. 19A). Constructs were engineered without a disulfide stabilized Fv or were engineered with a disulfide linkage stabilizing the VH and VL domains of the anti-CD3 antibody. Notably, some of the exemplary constructs generated additionally contained a sdAb (containing a CDR1, a CDR2 and a CDR3 set forth in SEQ ID Nos: 308, 309 and 310, respectively; e.g. set forth in SEQ ID NO:215) targeting a 4-1BB co-stimulatory receptor (e.g. cx5823, cx5873, cx5965, cx5352, cx5801, cx5800). A list of exemplary constrained CD3 binding constructs having sdAb and Fab TAA domains is given below in

TABLE E4

Exemplary Constrained CD3 engaging constructs

| Construct ID | Chain | N-term sdAb (Target) | Fc | Linker | CD3 Binding Domain | C-term sdAb (Target) | Disulfide Stabilized |
|---|---|---|---|---|---|---|---|
| cx5823 | 1 | B7H3 sdAb 4 (SEQ ID NO: 301) | xELL-Knob (SEQ ID NO: 88) | GGGGGSGGGGSG GGGGS (SEQ ID NO: 119) | VH13 (SEQ ID NO: 44) | B7H3 sdAb 5 (SEQ ID NO: 303) | yes |
|  | 2 | None | xELL-Hole (SEQ ID NO: 93) | GGGGGSGGGGSG GGGGS (SEQ ID NO: 119) | VL10 (SEQ ID NO: 72) | Co-stim Receptor sdAb |  |
| cx5952 | 1 | B7H3 sdAb 4 (SEQ ID NO: 301) | xELL-Knob (SEQ ID NO: 88) | GGGGGSGGGGSG GGGGS (SEQ ID NO: 119) | VH13 (SEQ ID NO: 44) | B7H3 sdAb 5 (SEQ ID NO: 303) | yes |
|  | 2 | None | xELL-Hole (SEQ ID NO: 93) | GGGGGSGGGGSG GGGGS (SEQ ID NO: 119) | VL10 (SEQ ID NO: 72) | None |  |
| cx6079 | 1 | B7H3 sdAb 4 (SEQ ID NO: 301) | Fc-Het-1 (SEQ ID NO: 285) | GGGGSGGGGSGG GS (SEQ ID NO: 170) | VH32 (SEQ ID NO: 287) | None | no |
|  | 2 | B7H3 sdAb 4 (SEQ ID NO: 301) | Fc-Het-2 (SEQ ID NO: 286) | GGGGSGGGGSGG GS (SEQ ID NO: 170) | VL20 (SEQ ID NO: 288) | None |  |
| cx6080 | 1 | B7H3 sdAb 4 (SEQ ID NO: 301) | Fc-Het-1 (SEQ ID NO: 285) | GGGGSGGGGSGG GS (SEQ ID NO: 170) | VH33 (SEQ ID NO: 311) | None | yes |
|  | 2 | B7H3 sdAb 4 (SEQ ID NO: 301) | Fc-Het-2 (SEQ ID NO: 286) | GGGGSGGGGSGG GS (SEQ ID NO: 170) | VL21 (SEQ ID NO: 289) | None |  |
| cx6081 | 1 | B7H3 sdAb 4 (SEQ ID NO: 301) | Fc-Het-1 (SEQ ID NO: 285) | GGGGSGGGGSGG GS (SEQ ID NO: 170) | VH13 (SEQ ID NO: 44) | None | yes |
|  | 2 | B7H3 sdAb 4 (SEQ ID NO: 301) | Fc-Het-2 (SEQ ID NO: 286) | GGGGSGGGGSGG GS (SEQ ID NO: 170) | VL10 (SEQ ID NO: 72) | None |  |
| cx3072 | 1 | B7H3 sdAb 2 (SEQ ID NO: 302) | IgG1-Knob (SEQ ID NO: 82, 86 or 291) | GGGGGSGGGGSG GGGGS (SEQ ID NO: 119) | VH13 (SEQ ID NO: 44) | B7H3 sdAb 1 (SEQ ID NO: 305) | yes |
|  | 2 | None | IgG1-Knob (SEQ ID NO: 83, 87 or 292) | GGGGGSGGGGSG GGGGS (SEQ ID NO: 119) | VL10 (SEQ ID NO: 72) | None |  |

TABLE E4-continued

Exemplary Constrained CD3 engaging constructs

| Construct ID | Chain | N-term sdAb (Target) | Fc | Linker | CD3 Binding Domain | C-term sdAb (Target) | Disulfide Stabilized |
|---|---|---|---|---|---|---|---|
| cx5873 | 1 | None | xELL-Knob (SEQ ID NO: 84, 88 or 293) | GGGGSGGGGGSG GGGS (SEQ ID NO: 119) | VH13 (SEQ ID NO: 44) | B7H sdAb 3 (SEQ ID NO: 304) | yes |
|  | 2 | None | xELL-Hole (SEQ ID NO: 91, 93 or 296) | GGGGGSGGGGSG GGGS (SEQ ID NO: 119) | VL10 (SEQ ID NO: 72) | Co-stim Receptor sdAb |  |
| cx5965 | 1 | B7H3 sdAb 4 (SEQ ID NO: 301) | xELL-Knob (SEQ ID NO: 84, 88 or 293) | GGGGGSGGGGGSG GGGS (SEQ ID NO: 119) | VH13 (SEQ ID NO: 44) | none | yes |
|  | 2 | None | xELL-Hole (SEQ ID NO: 91, 93 or 296) | GGGGGSGGGGGSG GGGS (SEQ ID NO: 119) | VL10 (SEQ ID NO: 72) | Co-stim Receptor sdAb |  |
| cx5352 | 1 | DLL3 sdAb 1 (SEQ ID NO: 306) | xELL-Knob (SEQ ID NO: 84, 88 or 293) | GGGGGSGGGGGSG GGGS (SEQ ID NO: 119) | VH13 (SEQ ID NO: 44) | DLL3 sdAb2 (SEQ ID NO: 307) | yes |
|  | 2 | None | xELL-Hole (SEQ ID NO: 91, 93 or 296) | GGGGGSGGGGGSG GGGS (SEQ ID NO: 119) | VL10 (SEQ ID NO: 72) | Co-stim Receptor sdAb |  |
| cx5800 | 1 | DLL3 sdAb 1 (SEQ ID NO: 306) | xELL-Knob (SEQ ID NO: 84, 88 or 293) | GGGGGSGGGGGSG GGGS (SEQ ID NO: 119) | VH13 (SEQ ID NO: 44) | None | yes |
|  | 2 | None | xELL-Hole (SEQ ID NO: 91, 93 or 296) | GGGGGSGGGGGSG GGGS (SEQ ID NO: 119) | VL10 (SEQ ID NO: 72) | Co-stim Receptor sdAb |  |
| cx5801 | 1 | None | xELL-Knob (SEQ ID NO: 84, 88 or or 293) | GGGGGSGGGGGSG GGGS (SEQ ID NO: 119) | VH13 (SEQ ID NO: 44) | DLL3 sdAb 2 (SEQ ID NO: 307) | yes |
|  | 2 | None | xELL-Hole (SEQ ID NO: 91, 93 or 296) | GGGGGSGGGGGSG GGGS (SEQ ID NO: 119) | VL10 (SEQ ID NO: 72) | Co-stim Receptor sdAb |  |
| cx5187 | 1 | B7H3 sdAb 4 (SEQ ID NO: 301) | xELL-Knob (SEQ ID NO: 84, 88 or 293) | GGGGGSGGGGGSG GGGS (SEQ ID NO: 119) | VH13 (SEQ ID NO: 44) | B7H3 sdAb 3 (SEQ ID NO: 304) | yes |
|  | 2 | None | xELL-Hole (SEQ ID NO: 91, 93 or 296) | GGGGGSGGGGGSG GGGS (SEQ ID NO: 119) | VL10 (SEQ ID NO: 72) | Co-stim Receptor sdAb |  |
| cx5067 | 1 | B7H3-Fab (SEQ ID NOs: 127, 128) | Fc-Het-1 (SEQ ID NO: 285) | GGGGSGGGGSGGG GS (SEQ ID NO: 170) | VH32 (SEQ ID NO: 287) | None | no |
|  | 2 | B7H3-Fab (SEQ ID NOs: 127, 128) | Fc-Het-2 (SEQ ID NO: 286) | GGGGSGGGGSGGG GS (SEQ ID NO: 170) | VL20 (SEQ ID NO: 288) | None |  |
| cx6083 | 1 | B7H3-Fab (SEQ ID NOs: 127, 128) | Fc-Het-1 (SEQ ID NO: 285) | GGGGSGGGGSGGG GS (SEQ ID NO: 170) | VH33 (SEQ ID NO: 311) | None | yes |
|  | 2 | B7H3-Fab (SEQ ID NOs: 127, 128) | Fc-Het-2 (SEQ ID NO: 286) | GGGGSGGGGSGGG GS (SEQ ID NO: 170) | VL21 (SEQ ID NO: 289) | None |  |

TABLE E4-continued

Exemplary Constrained CD3 engaging constructs

| Construct ID | Chain | N-term sdAb (Target) | Fc | Linker | CD3 Binding Domain | C-term sdAb (Target) | Disulfide Stabilized |
|---|---|---|---|---|---|---|---|
| cx6084 | 1 | B7H3-Fab (SEQ ID NOs: 127, 128) | Fc-Het-1 (SEQ ID NO: 285) | GGGGSGGGGSGGG GS (SEQ ID NO: 170) | VH13 (SEQ ID NO: 44) | None | yes |
|  | 2 | B7H3-Fab (SEQ ID NOs: 127, 128) | Fc-Het-2 (SEQ ID NO: 286) | GGGGSGGGGSGGG GS (SEQ ID NO: 170) | VL10 (SEQ ID NO: 72) | None |  |

B. Expression and Purification of Generated Constructs

Separate plasmids encoding each chain of the heterodimeric constrained CD3 binding protein were transiently transfected at an equimolar ratio into mammalian cells (either HEK293 or CHO) using polyethylenimine. Recombinant protein secreted into the supernatant was collected after 3-14 days, and purified by protein A chromatography, followed by either preparative size exclusion chromatography (SEC) or flow-through hydrophobic interaction chromatography (HIC). In some cases, heterodimeric protein was enriched for during purification due to a mutation designed into one chain of the heterodimeric Fc at position I253R or H435R (e.g. in the hole-Fc) such that it did not bind protein A, and thus homodimers of I253R or H435R were not purified. The second chromatography step by SEC (AKTA with Superdex-200 resin) or FT-HIC (AKTA with butyl/phenyl sepharose) was used to remove undesired cross-paired species containing two heterodimeric Fcs that were more hydrophobic and twice the expected molecular weight.

The method favored production of heterodimeric multispecific polypeptide constructs, containing properly paired species of heterodimeric Fc and the anti-CD3 Fv (e.g. disulfide stabilized anti-CD3 Fv). Purified heterodimeric constrained CD3 binding protein was stable and did not accumulate cross-paired species upon prolonged incubation at 4° C. or increased protein concentration.

Example 13: Assessment of CD3-Constrained Multispecific Constructs Containing Single or Multiple B7H3-Binding Targeting Domains Activity of constructs containing a monovalent sdAb antigen-binding domain (positioned at either the N or C-terminus) was compared to activity of dual binding constructs that contained antigen-targeting sdAbs positioned at both the N and C-termini. Each of the constructs tested contained a CRBR positioned C-terminally to the CD3 binding domain.

A. Binding

Figure 21A:
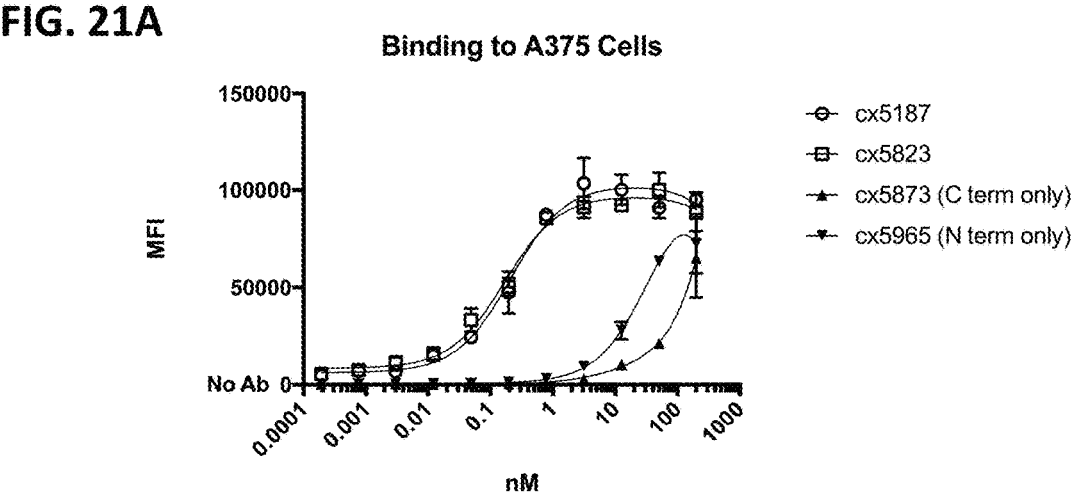
FIGS. 21A and 21B depict cellular binding of representative B7H3-targeting constrained CD3 engaging constructs. cx5187 and cx5823 each contain two B7H3 binding domains while complex cx5873 and cx5965 each contain one B7H3 binding domain.
Figure 21B:
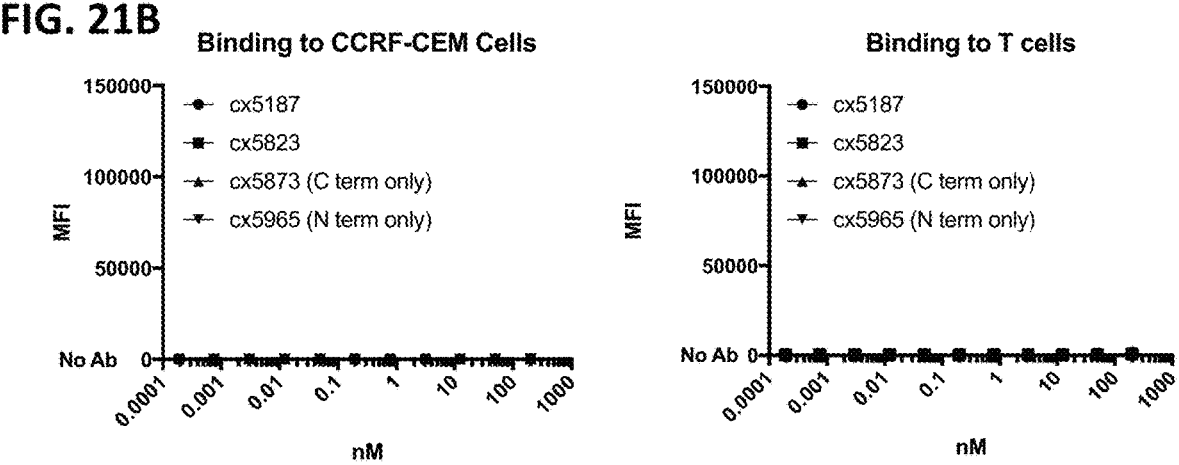

Binding of exemplary multispecific constructs containing an antigen-binding domain directed against B7H3 were assessed for binding to B7H3 positive A375 tumor cells, B7H3 negative CCRF-CEM cells or primary T-cells. As shown in FIG. 21A the bivalent B7H3-targeting constrained CD3 engaging constructs, cx5187 and cx5823, displayed higher affinity binding to B7H3 positive A375 cells, compared to the monovalent versions, cx5873 and cx5965. None of these constructs displayed any detectable binding to B7H3 negative CCRF-CEM cells or isolated T-cells (FIG. 21B).

B. T Cell Reporter Activity

B7H3 Antigen-dependent CD3 agonistic capacities of antigen-targeted constrained CD3 engaging constructs that engage the antigen in a monovalent or bivalent manner were assessed using CD3-NFAT Jurkat reporter cells. The Jurkat cells express NFAT-driven green fluorescence protein (GFP). Agonism of CD3 results in NFAT signaling and production of green fluorescence. In this assay, target cells included either A375 (B7H3 positive) or CCRF-CEM (B7H3 negative) cells. For reporter assays utilizing adherent antigen expressing target cells, target cells were seeded, allowed to settle at room temperature for uniform distribution, and incubated for several hours at 37° C. to permit adherence prior to addition of reporter cells and antigen targeting constrained CD3 engaging constructs. Assay plates were serially imaged using an IncuCyte ZOOM system and CD3 reporter cell activation was determined by measuring total green object integrated.

Figure 21C:
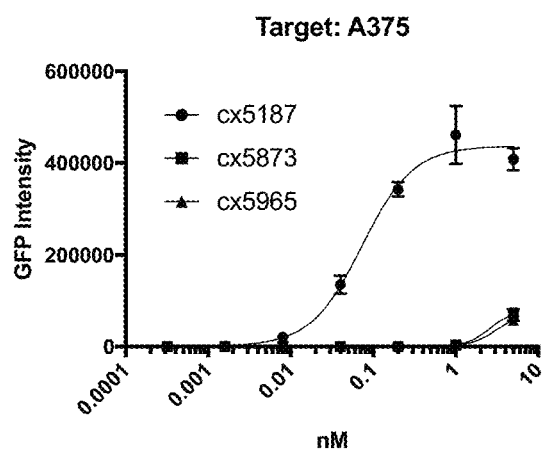
FIG. 21C and FIG. 21D depict the ability of representative B7H3-targeting constrained CD3 engaging constructs to agonize CD3 in a target dependent manner.
Figure 21D:
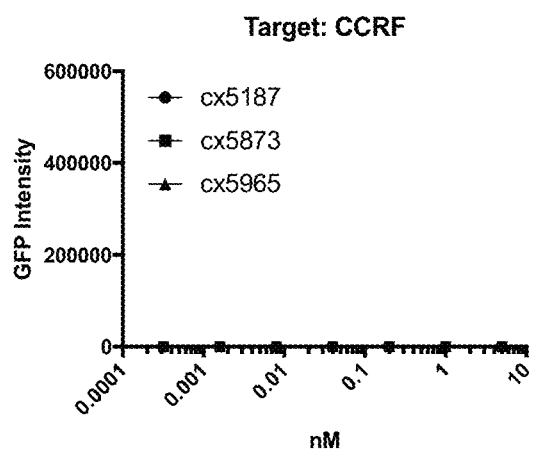

As shown in FIG. 21C, substantially increased fluorescence reporter activity was observed in the presence of the exemplary bivalent B7H3-targeted construct cx5187 compared to reporter activity for the exemplary monovalent constructs cx5873 and cx5965. No reporter activity was observed when constructs were incubated with Jurkat reporter cells co-cultured with B7H3-negative CCRF target cells (FIG. 21D).

C. Cytotoxic Activity

Cytotoxicity of B7H3-targeted CD3 constrained binding constructs was assessed against a melanoma cell line, A375, and a T-cell acute lymphoblastic leukemia cell line, CCRF-CEM, which were used as B7H3 positive and negative cell lines, respectively. To assess cytotoxicity, target cells were seeded at $1.0 \times 10^4$ cells per well, allowed to settle at room temperature for uniform distribution, and incubated for several hours at 37° C. Primary T cells were negatively enriched from PBMCs isolated from healthy human donor leukopaks and added at a 10:1 T cell-to-target cell ratio. Green caspase-3/7 reagent was added, which fluorescently labels nuclear DNA of cells undergoing apoptosis was added. Multispecific constructs with constrained CD3 engaging activity were titrated onto the co-culture and assay plates were serially imaged using an IncuCyte ZOOM system. Target cell death was determined by measuring total red/green overlap object area.

Figure 22A:
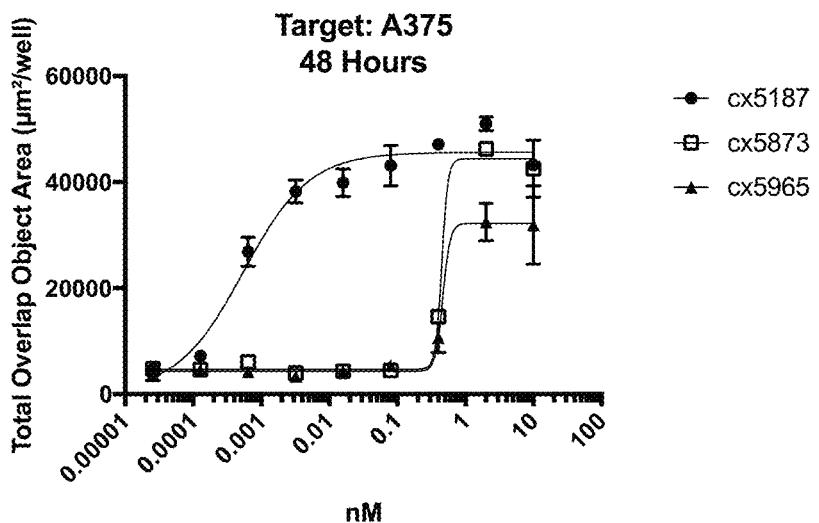
FIGS. 22A and 22B depict the ability of representative B7H3-targeting constrained CD3 engaging constructs to induce T-cell mediated cytotoxicity in a target dependent manner.
Figure 22B:
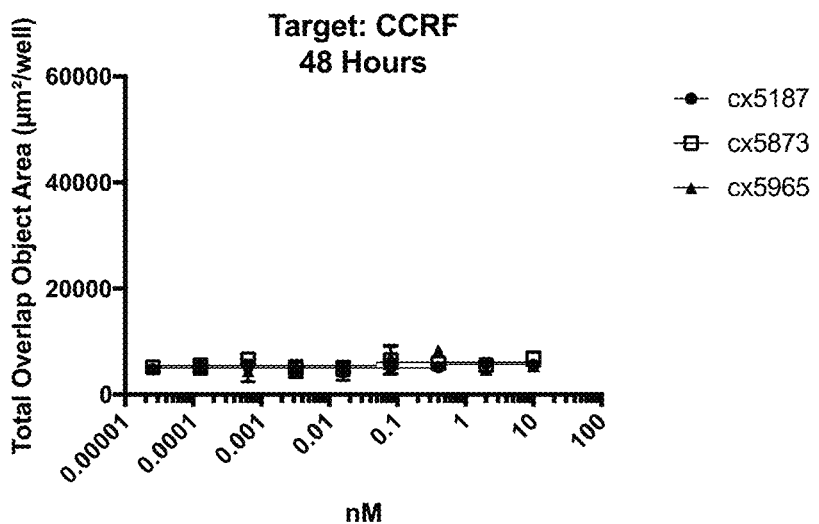

As shown in FIG. 22A an exemplary bivalent B7H3-targeted constrained CD3 engaging construct, cx5187, displayed enhanced target-dependent T-cell mediated cytotoxicity compared to the monovalent versions of the constructs, cx5873 and cx5965. In these assays, no cytotoxicity was observed in the absence of B7H3 expression of the target cells, as shown in FIG. 22B wherein the CCRF-CEM cells were used as target cells.

D. T Cell Modulation

T cell modulation was assessed by monitoring T cell activation by expression of CD25 in suspension cells from T cell cytotoxicity assays above, involving culture of T cells with B7H3 positive (A375) or B7H3 negative cell lines (CCRF-CEM) in the presence of cx5187, cx5873 or cx5965. To assess T cell activation, suspension cells from T cell cytotoxicity assays above, involving culture of T cells with B7H3 positive (A375) or B7H3 negative cell lines (CCRF-CEM) in the presence of an exemplary B7H3-targeted constrained CD3 engaging construct were collected. Cells were stained with a live/dead stain and fluorophore-conjugated anti-CD4, anti-CD8 and anti-CD25 antibodies. Cells were analyzed using a SONY SA3800 spectral analyzer and CD4+ or CD8+ T cell activation was determined by measuring expression levels of CD25 or percent CD25 positive cells.

As shown in FIGS. 23A and 23B, an exemplary bivalent B7H3-targeted constrained CD3 engaging construct, cx5187, displayed enhanced target-dependent T-cell mediated activation compared to the monovalent versions of the constructs, cx5873 and cx5965, as evidenced by enhanced potency of CD25 upregulation on CD4 and CD8 T-cells. In these assays, no T-cell activation was observed in the absence of B7H3 expression of the target cells, as shown in FIGS. 23C and 23D, wherein the CCRF-CEM cells were used as target cells. These results demonstrated that the B7H3-targeting constrained CD3 engaging constructs induced potent antigen-dependent activation of both CD4 and CD8 T-cells.

D. Summary

Together, these results demonstrate that constructs containing either monovalent or divalent sdAb antigen-binding domains and a CRBR are capable of antigen-dependent CD3 binding and activation of activation of T cells. Notably, the bivalent antigen-targeted constrained CD3 engaging constructs displayed superior antigen-dependent CD3 binding and activity than the monovalent antigen-targeted constrained CD3 engaging constructs. These results are consistent with a finding that constructs containing dual antigen-binding domains positioned at both the N and C-termini have superior binding and T cell activity than monovalent constructs containing only a single monovalent antigen-binding domain. Furthermore, without wishing to be bound by theory, positioning one of the sdAbs C-terminal to the CD3 binding domain may form a more optimal immune synapse compared to constructs wherein the sdAbs are only positioned N-terminal to the Fc as the latter may increase the immune synapse distance.

Example 14: Assessment of CD3-Constrained Multispecific Constructs Containing Single or Multiple Antigen-Binding DLL3-Targeting Domains This example describes the assessment and characterization of exemplary generated DLL3-targeted constrained CD3 engaging constructs in human primary T cell in vitro assays.

Constructs containing DLL3-targeted sdAb were assessed for T-cell activating activity in a T cell reporter assay. Activity of DLL3-targeted constrained CD3 engaging constructs that were formatted with an anti-DLL3 sdAb (e.g. cx5352, cx5800, and cx5801) as the antigen-binding domain(s) were assessed (see FIG. 20, see also Table E4 and E7). All tested constructs contained a disulfide-stabilized anti-CD3 Fv (dsFv) containing an interchain disulfide bond created by the modification of anti-CD3 VH G44C paired with VL G100C. Further, each DLL3-targeted construct was engineered to contain a co-stimulatory receptor sdAb C-terminal to the CD3 dsFv.

A. Binding

Figure 24A:
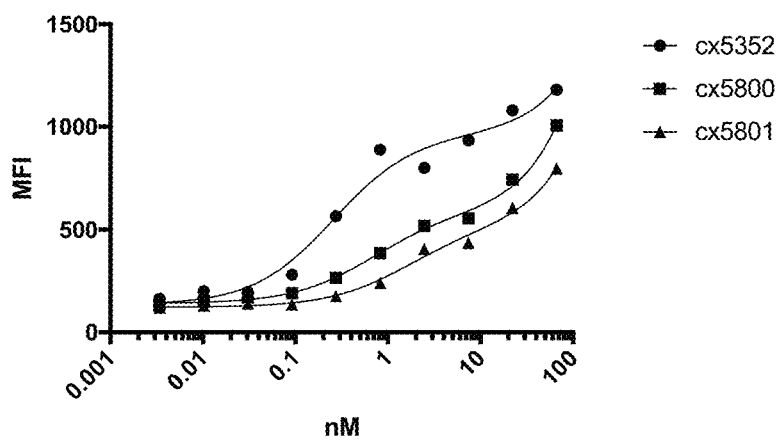
FIGS. 24A and 24B demonstrate that the monovalent and bivalent DLL3-targeting constrained CD3 engaging constructs bound to a DLL3 expressing cell line, SHP-77 (FIG. 24A), but not to isolated T-cells (FIG. 24B). Binding was assessed by flow cytometry.
Figure 24B:
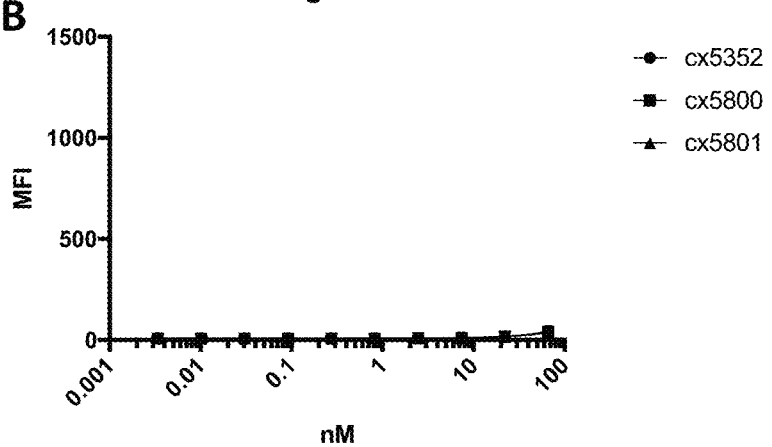

Binding of exemplary multispecific constructs containing an antigen-binding domain directed against DLL3 were assessed for binding to DLL3 positive SHP-77 tumor cells or primary T-cells. As shown in FIG. 24A the bivalent DLL3-targeting constrained CD3 engaging constructs, cx5352 displayed higher affinity binding to DLL3 positive, SHP-77 cells compared to the monovalent versions, cx5800 and cx5801. None of the constructs tested displayed binding to DLL3-negative primary T cells, as depicted in FIG. 24B. These binding assays were conducted by flow cytometry, wherein bound constructs were detected using a fluorophore-conjugated anti-human IgG Fc secondary antibody.

B. T Cell Reporter Activity

Figure 24C:
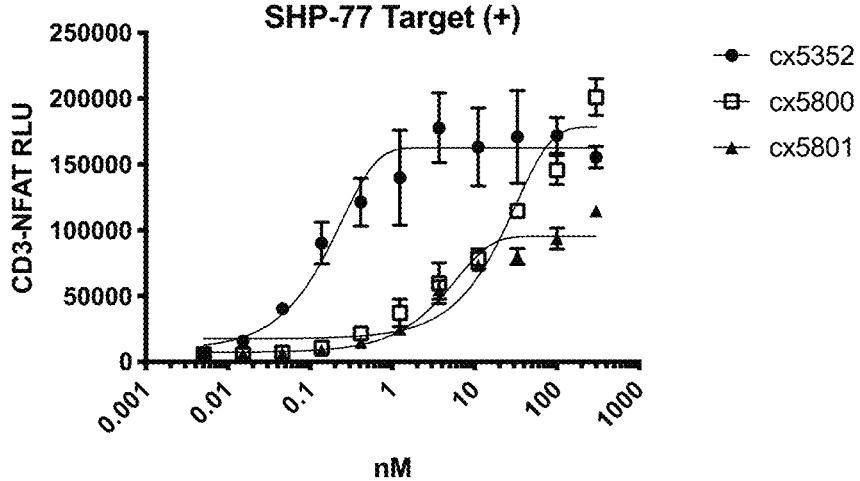
FIG. 24C depicts the ability of representative DLL3-targeting constrained CD3 engaging constructs to agonize CD3 signaling in the presence of DLL3 positive SHP-77 cells. Engaging DLL3 positive cells with a construct that is bivalent and bi-epitopic to DLL3 (cx5352) induced more potent T-cell activation than constructs that are monovalent to DLL3 (cx5800 and cx5801). A Jurkat CD3 NFAT-Luciferase reporter cell line was used to assess CD3 signaling.

T cell activity was assessed in a reporter assay substantially as described in Example 13, except that Jurkat cells expressing NFAT-driven Luciferase were used and luciferase activity was monitored. NFAT-driven Luciferase CD3 Jurkat reporter cells were co-cultured with SHP-77 (DLL3-positive) target cells in the presence of monovalent and bivalent constructs containing antigen-binding domains against the DLL3 antigen (see FIG. 20). Specifically, as shown in FIG. 24C, the exemplary bivalent construct cx5352 induced substantially greater luciferase activity in this assay compared to the exemplary monovalent constructs cx5800 and cx5801. These results are consistent with results observed with B7H3-targeted constructs, thereby indicating that the activity of the constructs is not specific to a particular target antigen.

C. Summary

Together, these results demonstrate that constrained anti-CD3 constructs formatted with anti-DLL3 sdAb binding domains and CRBRs are capable of binding to a DLL3-expressing cell line, SHP-77, and eliciting antigen-dependent T-cell activation. This suggests that the constrained anti-CD3 constructs described herein are not specific to a target antigen, but are effective at binding various antigens to elicit T-cell cytotoxicity and activation against target-expressing cells.

Example 15: Generation and Assessment of CD3-Constrained Multispecific Constructs Containing Antigen-Binding 5T4-Targeting Domain with or without a Costimulatory Binding Region Multispecific constructs were generated to contain a heterodimeric Fc region of an immunoglobulin coupled by a linker (e.g. a non-cleavable linker) to the CD3 binding region, and antigen binding domains that binds the 5T4 tumor associated antigen (TAA) positioned amino-terminally relative to the Fc region and carboxy-terminally relative to the CD3 binding region of the multispecific polypeptide construct. Constructs were generated with or without a 4-1BB targeting sdAb as a CRBR and T cell activity was compared in various assays.

A. Design and Generation of Constructs

Exemplary multispecific constructs were generated with formats as depicted in FIG. 3. Polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, a first Fc polypeptide (e.g. an Fc hole polypeptide); a non-cleavable linker; and a variable light (VL) domain of an anti-CD3 antibody. The second polypeptide chain generally included in order, from the N-terminus to C-terminus, a second Fc polypeptide (e.g. an Fc knob polypeptide); the same non-cleavable linker as the first polypeptide chain; and a variable heavy (VH) domain of an anti-CD3 antibody. The anti-CD3 antibody included a disulfide-stabilized (dsFv) antibody (anti-CD3 VH with the mutation G44C and VL with the mutation G100C), as set forth in Table E5. One of the polypeptide chains additionally encoded two 5T4 antigen binding domains, one amino-terminal to the Fc domain and one carboxy-terminal to the CD3 binding region. The exemplary construct cx5951 was generated without a CRBR, whereas the construct cx5185 contained a 4-1BB antigen binding domain (e.g. sdAb) as a CRBR positioned carboxy-terminally relative to the CD3 binding region, e.g. a sdAb containing a CDR1, a CDR2 and a CDR3 set forth in SEQ ID NO: 308, 309, and 310, respectively; e.g. set forth in SEQ ID NO:215).

Components of the exemplary constrained CD3 binding constructs having 5T4-targeting sdAb domains is given below in Table E5. The constructs were expressed and purified substantially as described in Example 12.

Figure 25A:
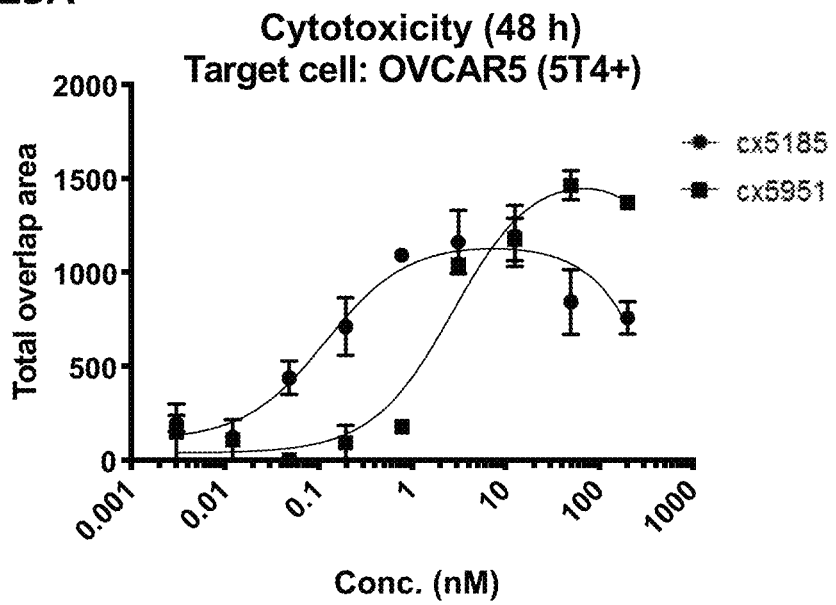
FIGS. 25A and 25B depicts the potency of T-cell-mediated cytotoxicity driven by exemplary 5T4-targeted constrained CD3 engaging constructs with a 41BB binding domain, cx5185, and without a 41BB binding domain, cx5951. A titration range of 200 nM to 3.1 pM of the CD3 engaging constructs on the 5T4-positive Ovcar5 cell line is shown in FIG. 25A and the 5T4-negative CCRF-CEM cell line shown in FIG. 25B.
Figure 25B:
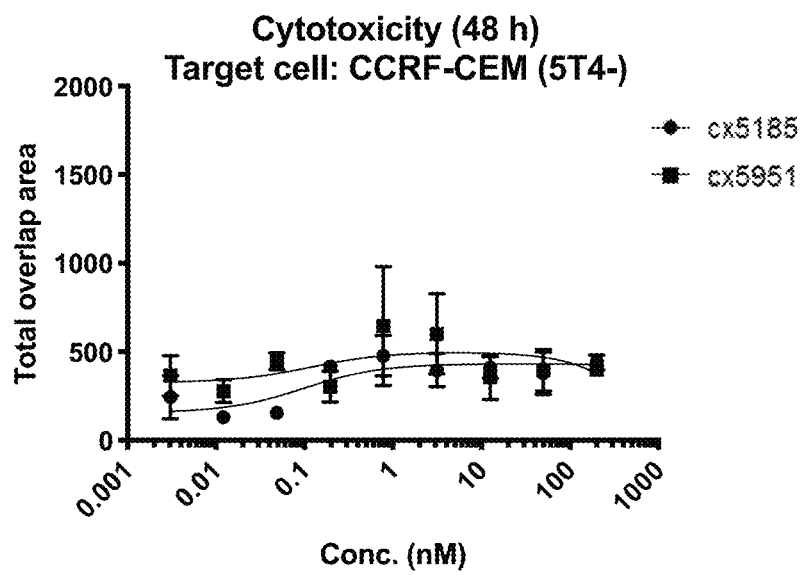
Figure 26A:
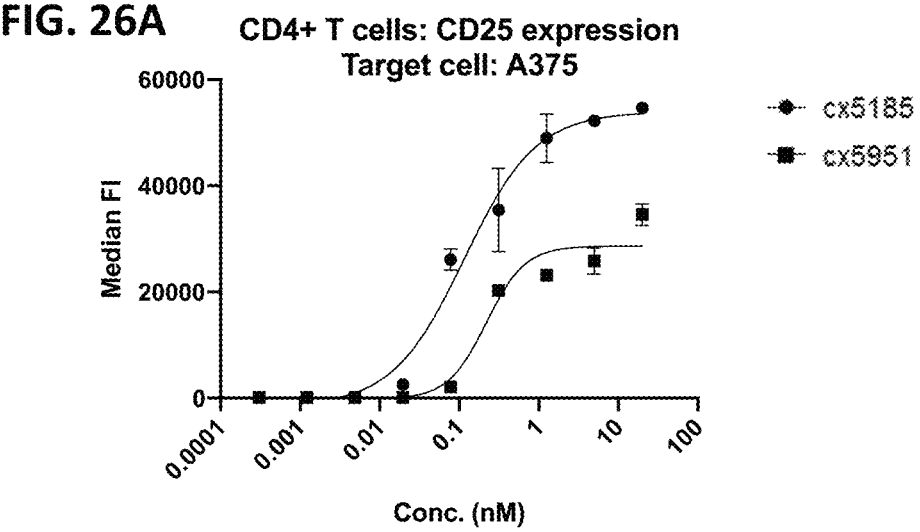
FIGS. 26A-F depict T cell activation as assessed by CD25 expression on CD4 (FIG. 26A-C) and CD8 (FIG. 29D-F) cells following incubation with representative 5T4-targeted constrained CD3 engaging constructs with a 41BB binding domain, cx5185, and without a 41BB binding domain, cx5951, in the presence of various 5T4 positive cells, A375 (FIGS. 26A and 26D), Ovcar-5 (FIGS. 26B and 26E), SHP-77 (FIGS. 26C and 26F). T-cell activation was assessed by flow cytometery monitoring cell surface expression of CD25.
Figure 26B:
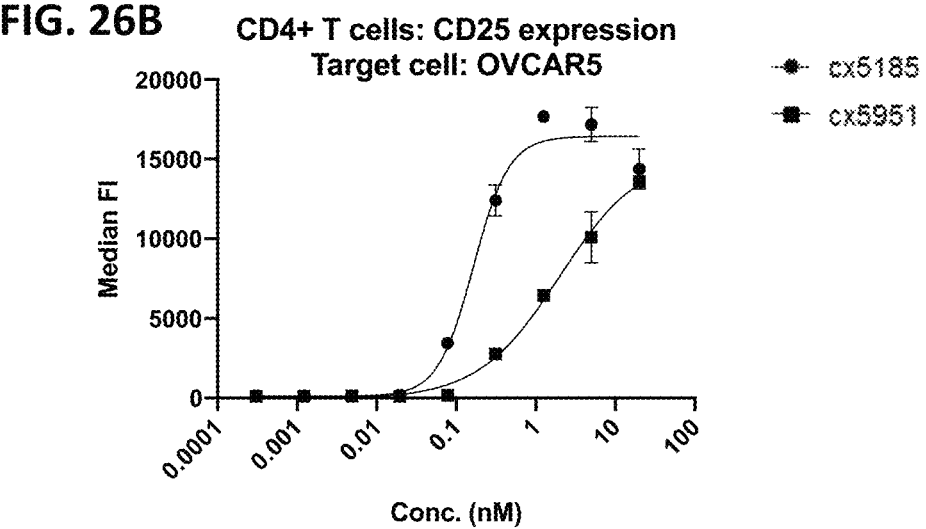
Figure 26C:
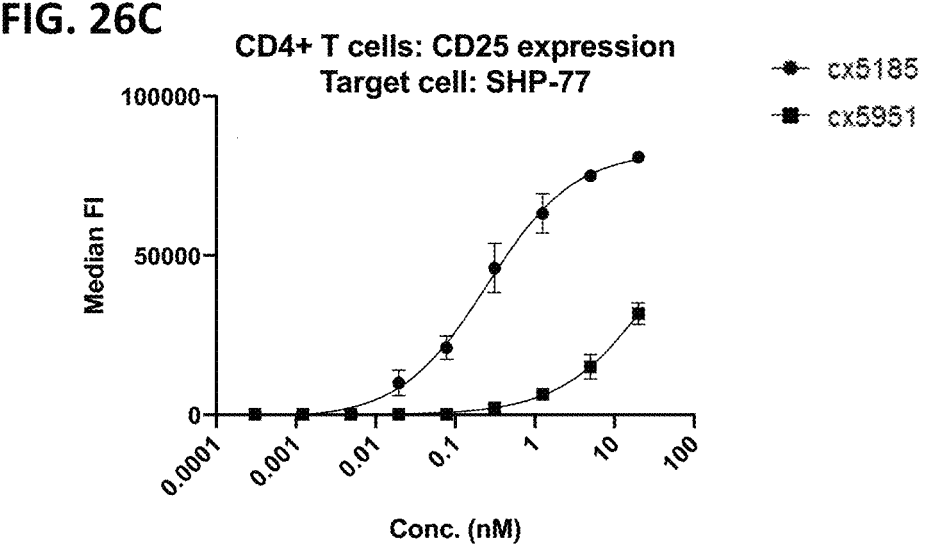
Figure 26D:
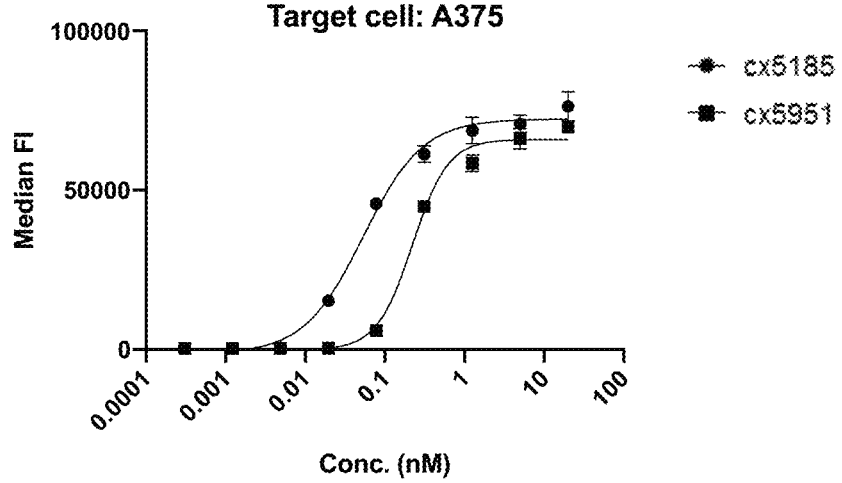
Figure 26E:
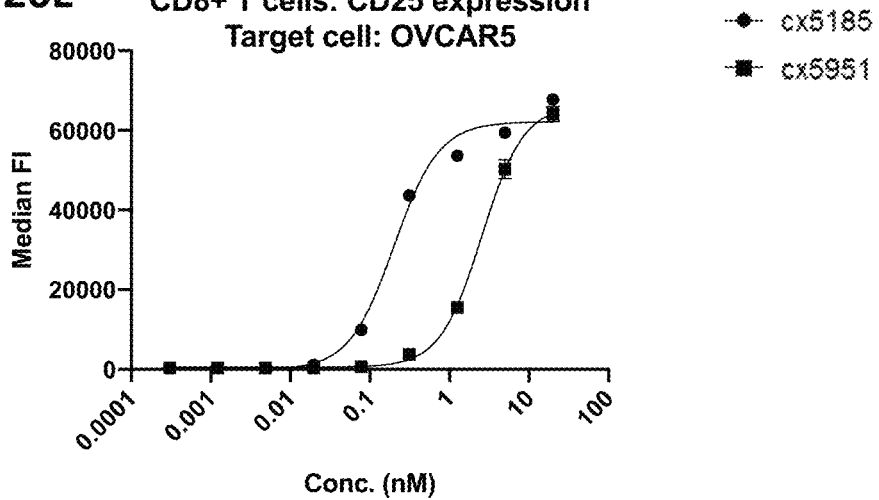
Figure 26F:
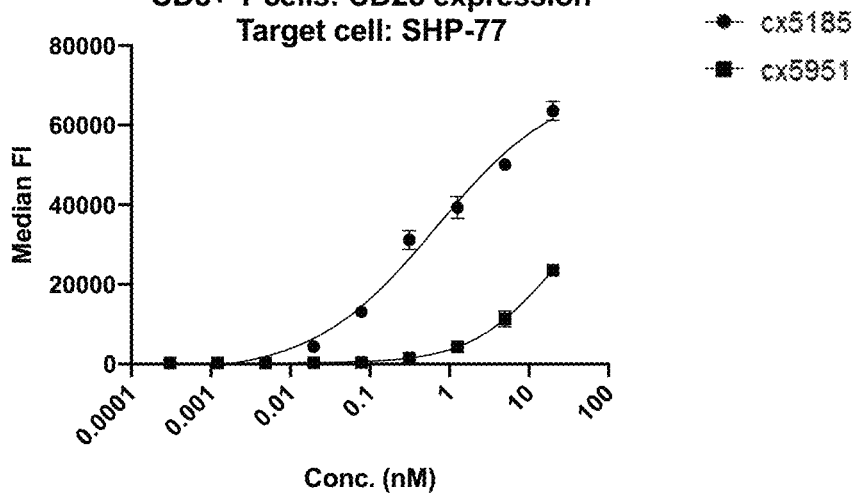

As shown in FIG. 25A after 48 hours a marked difference in potency of T-cell mediated target cell cytotoxicity against 5T4-expressing target cells was observed with the 5T4-targeted constrained CD3 engaging construct with a 41BB-binding costimulatory receptor binding region, cx5185, compared to a the same construct lacking the 41BB-binding costimulatory receptor binding region, cx5951. Cytotoxic activity against non-target cells was not observed (FIG. 25B).

These observations support that the antigen-dependent constrained CD3 format with the additional co-stimulatory capacity provided herein, display enhanced potency of mediated cytotoxicity compared to other CD3 engaging formats.

2. T Cell Activation

To assess T cell activation mediated by exemplary 5T4-targeted constrained CD3 engaging constructs, cx5185 and cx5951 were incubated in a co-culture of T-cells and 5T4-expressing target cells, either A375 cells, Ovcar-5 cells, or SHP-77 cells. To assess T cell activation, cells were collected and stained with a live/dead stain and fluorophore-conjugated anti-CD4, anti-CD8, and/or anti-CD25 antibodies. Cells were analyzed using a SONY SA3800 spectral analyzer and CD4+ or CD8+ T cell activation was deter-

TABLE E5

Exemplary constrained CD3 engaging constructs containing 5T4-targeting domain

| Construct ID | Chain | N-term sdAb (Target) | Fc | Linker | CD3 Binding Domain | C-term sdAb (Target) | Disulfide Stabilized |
|---|---|---|---|---|---|---|---|
| cx5951 | 1 | 5T4 sdAb hz12E9v9 (SEQ ID NO: 322) | xELL-Knob (SEQ ID NO: 84) | GGGGGSGGGGGSG GGGGS (SEQ ID NO: 119) | VH13 (SEQ ID NO: 44) | 5T4 sdAb hz16G10v11 (SEQ ID NO: 323) | yes |
|  | 2 | None | xELL-Hole (SEQ ID NO: 85) | GGGGGSGGGGGSG GGGGS (SEQ ID NO: 119) | VL10 (SEQ ID NO: 72) | None |  |
| cx5185 | 1 | 5T4 sdAb hz12E9v9 (SEQ ID NO: 322) | xELL-Knob (SEQ ID NO: 84) | GGGGGSGGGGGSG GGGGS (SEQ ID NO: 119) | VH13 (SEQ ID NO: 44) | 5T4 sdAb hz16G10v11 (SEQ ID NO: 323) | yes |
|  | 2 | None | xELL-Hole (SEQ ID NO: 91) | GGGGGSGGGGGSG GGGGS (SEQ ID NO: 119) | VL10 (SEQ ID NO: 72) | 41BB sdAb (e.g. SEQ ID NO: 215) |  |

B. T Cell Activity

Activity of the constructs described above to engage CD3 in various assays was compared.

1. Cytotoxic Activity

Cytotoxic activity towards target cells was assessed in the presence of exemplary 5T4-targeted contructs with a 41BB-binding costimulatory receptor binding region (cx5185) or without the CRBR (cx5951). For cytotoxicity assays, Ovcar-5 cells expressing 5T4 or control CCRF-CEM cells that do not express 5T4 were used as target cells and were seeded, allowed to settle at room temperature for uniform distribution, and incubated for several hours at 37° C. to permit adherence prior to addition of other assay components. Primary T cells were negatively enriched from PBMCs isolated from healthy human donor leukopaks and added at a 10:1-40:1 T cell-to-target cell ratio. Herein target cells were labeled as red with the CytoID red, while apoptosis was monitored with the green fluorescent caspase-3/7 substrate; thus apoptotic target cells are those that are dual labeled red and green. Assay plates were serially imaged using an IncuCyte ZOOM system. Target cell death was determined by measuring total red/green overlap object area.

mined by measuring expression levels of CD25. T-cell activation was assessed by CD25 expression on CD4 and CD8 populations. T cell activation, as measured by expression of CD25, was evident in CD4 (FIGS. 26A-C) and CD8 (FIGS. 26D-F) T cells that had been incubated with 5T4-expressing target cells in the presence of the exemplary constructs. As shown in FIGS. 26A-F, the 5T4-targeted constrained CD3 engaging construct incorporating the 41BB binding domain (cx5185) displayed enhanced activating capacity toward both CD4 and CD8 T-cells compared to the similar construct lacking the 41BB binding domain, cx5951.

3. T Cell Cytokine Production

Figure 27A:
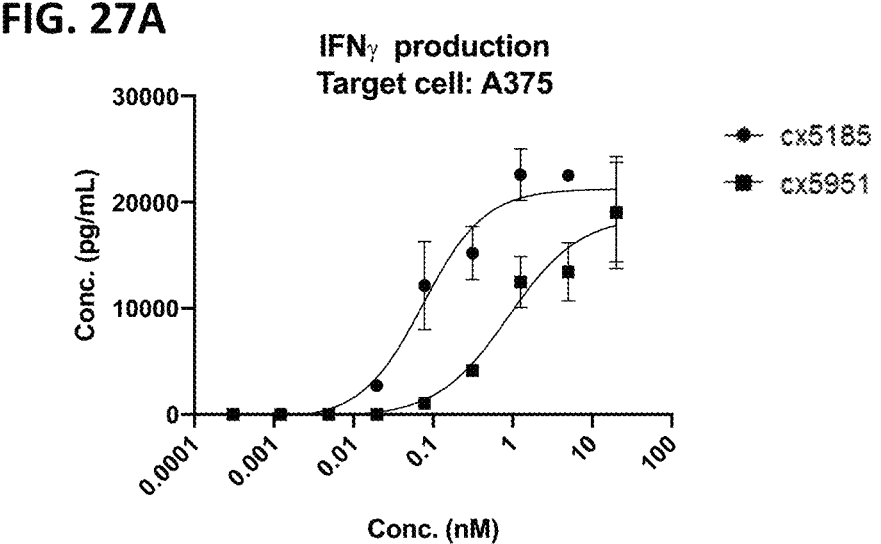
FIGS. 27A-C shows a comparison of IFNγ production by T-cells treated with a titration of representative 5T4-targeted constrained CD3 engaging constructs with a 41BB binding domain, cx5185, and without a 41BB binding domain, cx5951, in the presence of 5T4 positive cell lines, A375 (FIG. 27A), SHP-77 (FIG. 27B), and Ovcar5 (FIG. 27C).
Figure 27B:
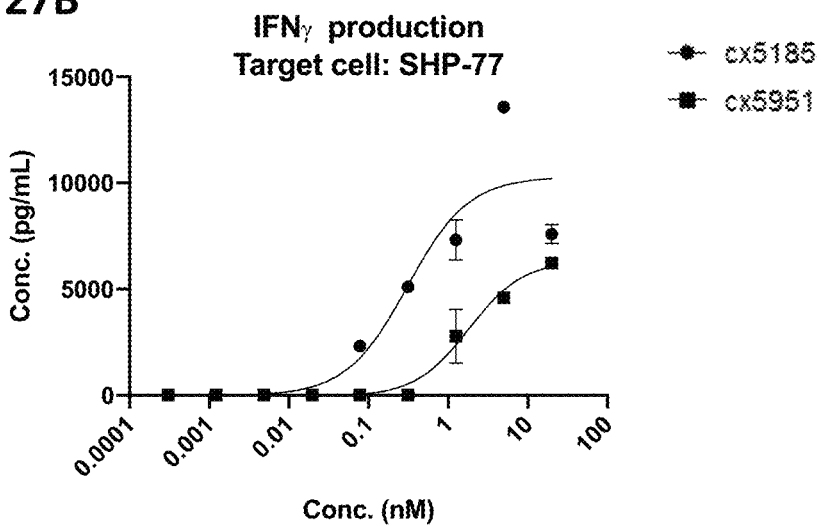
Figure 27C:
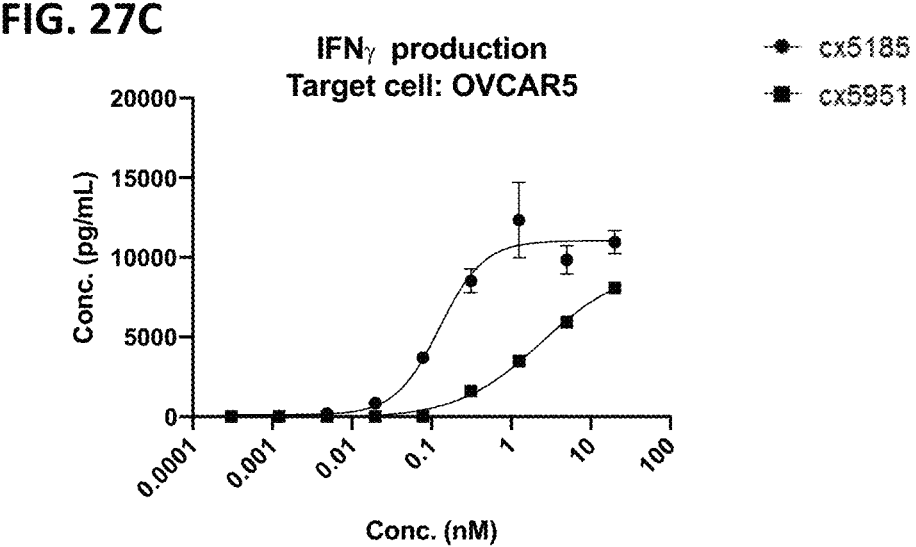

The impact of the incorporation of the 41BB binding domain into an exemplary 5T4-targeted constrained CD3 engaging construct on T-cell mediated IFNγ production was assessed using various 5T4-expressing cell lines, A375 (FIG. 27A), SHP-77 (FIG. 27B) or Ovcar5 (FIG. 27C). After co-culture of T cells and 5T4-expressing target cells, supernatants were analyzed for IFNγ content by sandwich ELISA (BioLegend, USA). The manufacturer's instructions were followed and a standard curve was generated from which cytokine concentration values of supernatant samples were interpolated. Samples that had absorbance values below the lower limit of detection were assigned a cytokine concentration equal to half that of the lowest standard concentration. As shown in FIGS. 27A-27C, the 5T4-targeted constrained CD3 engaging construct incorporating the 41BB binding domain, cx5185, displayed enhanced IFNγ production compared to the similar construct lacking the 41BB binding domain, cx5951.

4. T Cell Proliferation

Figure 28A:
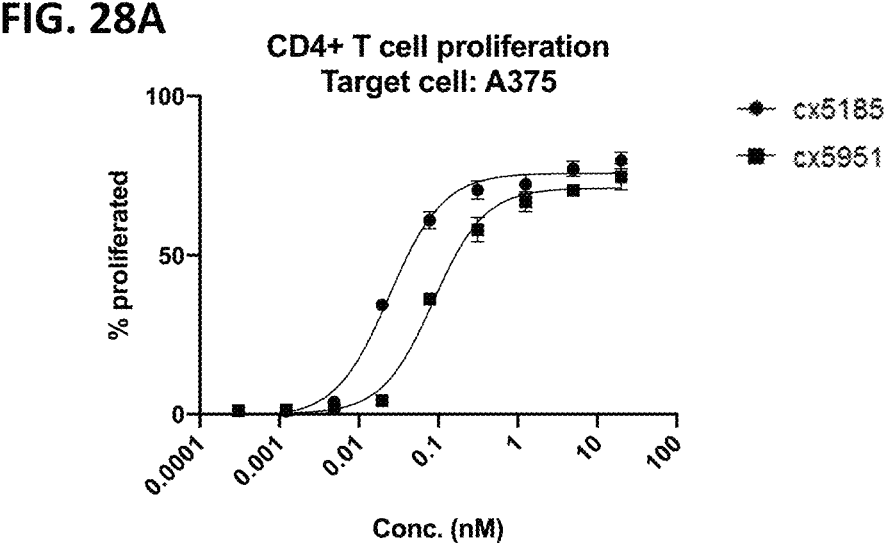
FIG. 28A-F depict T cell proliferation on CD4 (FIG. 28A-C) and CD8 (FIG. 28D-F) T cells following incubation with representative 5T4-targeted constrained CD3 engaging constructs with a 41BB binding domain, cx5185, and without a 41BB binding domain, cx5951, in the presence of various 5T4 positive cell lines, A375 (FIGS. 28A and 28D), Ovcar-5 (FIGS. 28B and 28E), SHP-77 (FIGS. 28C and 28F). T-cell proliferation was monitored via dilution of CellTrace™ dye. The results depict the percent of proliferating cells as monitored by dilution of CellTrace™ Violet dye.
Figure 28B:
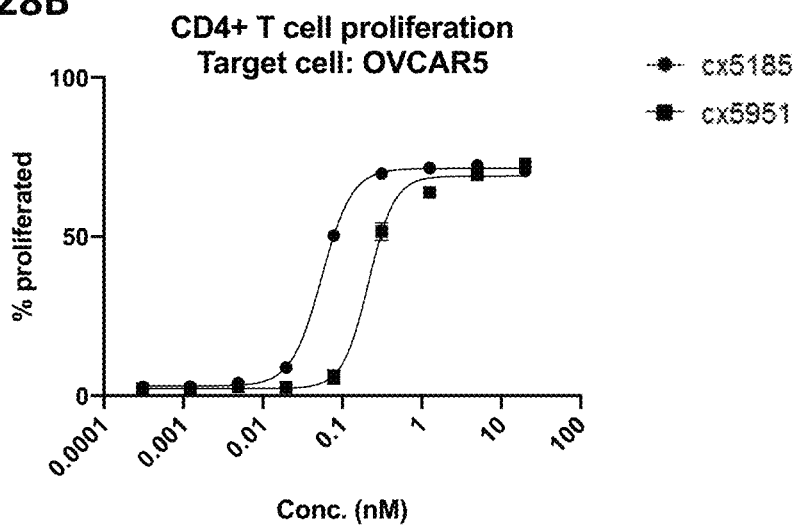
Figure 28C:
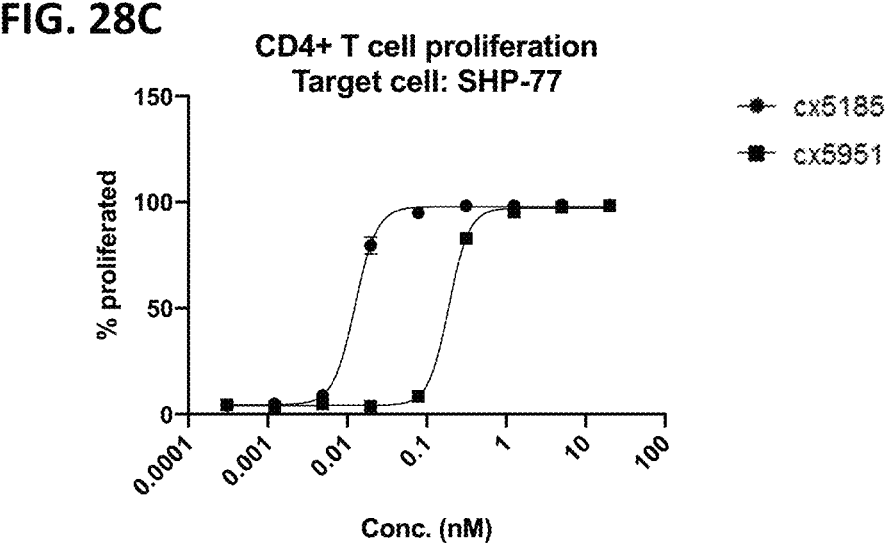
Figure 28D:
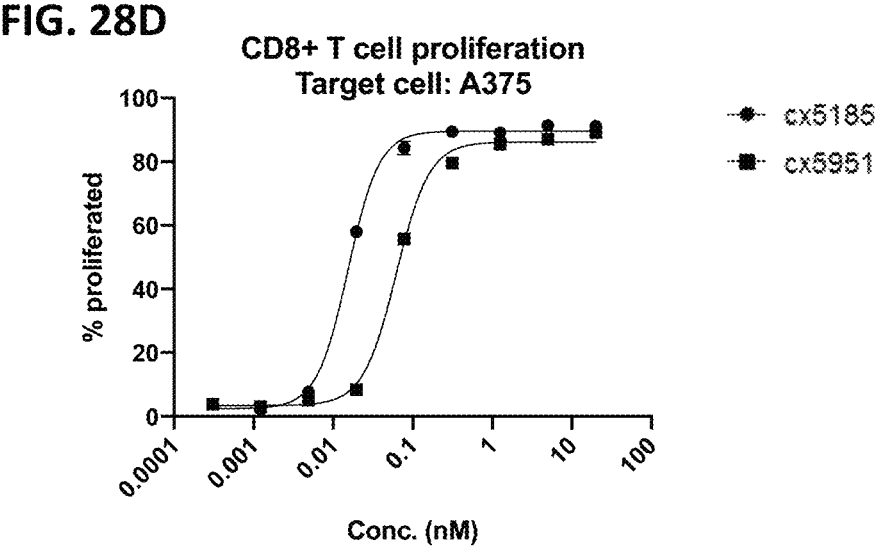
Figure 28E:
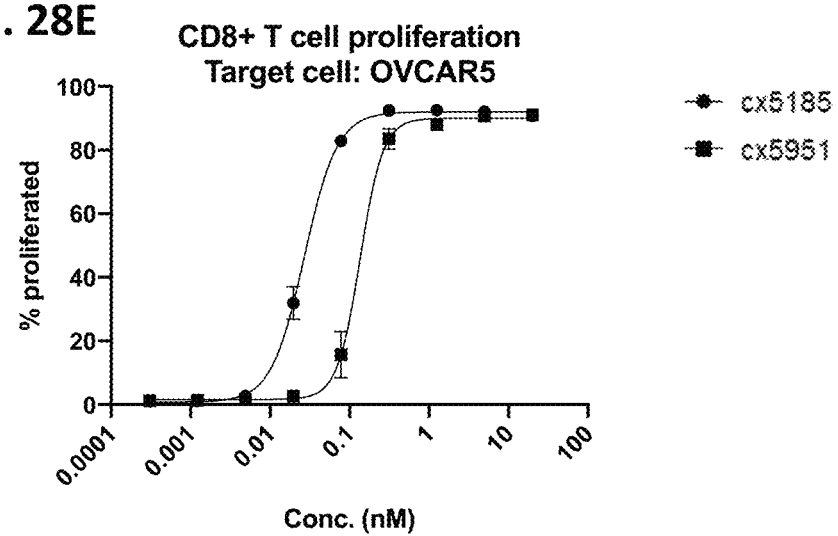
Figure 28F:
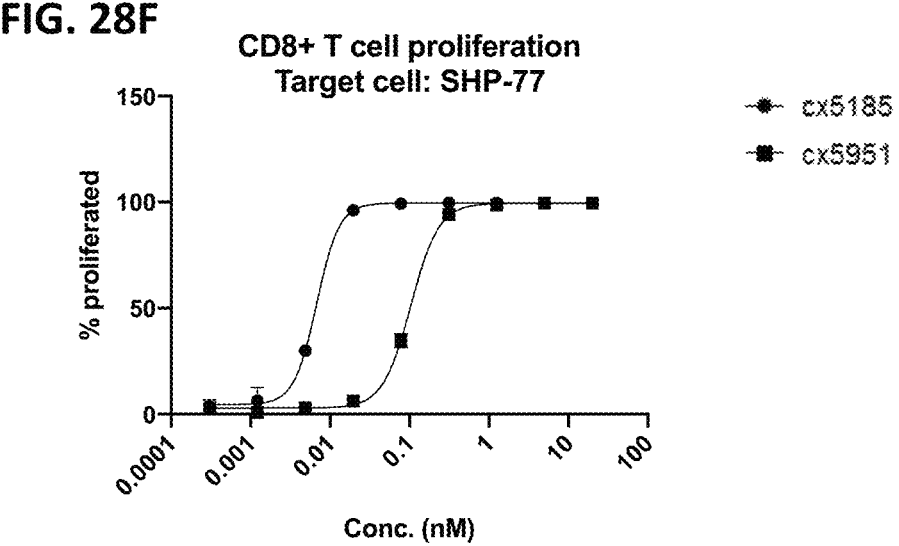

T-cell proliferation was assessed by measuring the dilution of CellTrace™ Violet dye (Thermo Fisher Scientific) in labeled CD4+ or CD8+ T cells by flow cytometry. T cells were negatively enriched from PBMCs and labeled with CellTrace™ Violet according to the manufacturer's protocol. 5T4-targeted constrained CD3 engaging constructs were titrated onto co-cultures of labeled T cells and 5T4-expressing cells A375 (FIGS. 28A and 28D), Ovcar-5 (FIGS. 28B and 28D), or SHP-77 (FIGS. 28C and 28F) and assay plates were incubated at 37 degrees C. for five days. Cells were stained with the viability dye propidium iodide as well as fluorophore-conjugated anti-CD4 and anti-CD8 antibodies and analyzed using a SONY SA3800 spectral analyzer. Percent proliferated CD4+ or CD8+ T cells was determined by gating on the appropriate viable T cell subpopulation and measuring the percentage of cells with CellTrace™ Violet intensities lower than that of T cells from untreated co-cultures.

The 5T4-targeted constrained CD3 engaging construct incorporating the 41BB binding domain, cx5185, enhanced the proliferation of both CD4 (FIGS. 28A-C) and CD8 (FIGS. 28D-F) T-cells compared to the similar construct lacking the 41BB binding domain, cx5951.

5. T Cell Mitochondrial Assessment

Figure 29A:
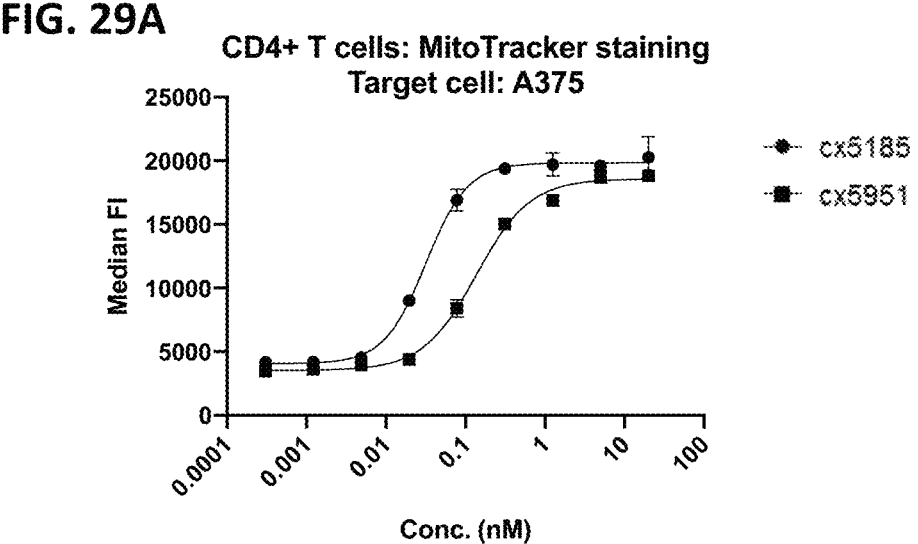
FIG. 29A-F depicts assessment of mitochondrial function in CD4 (FIG. 29A-C) and CD8 (FIG. 29D-F) T-cells following incubation with representative 5T4-targeted constrained CD3 engaging constructs with a 41BB binding domain, cx5185, and without a 41BB binding domain, cx5951, in the presence of various 5T4 positive cells, A375 (FIGS. 29A and 29D), Ovcar-5 (FIGS. 29B and 29E), SHP-77 (FIGS. 29C and 29F). Mitochondrial function was assessed by flow cytometery using MitoTracker Green, a fluorescent mitochondria-selective probe that accumulates in active mitochondria.
Figure 29B:
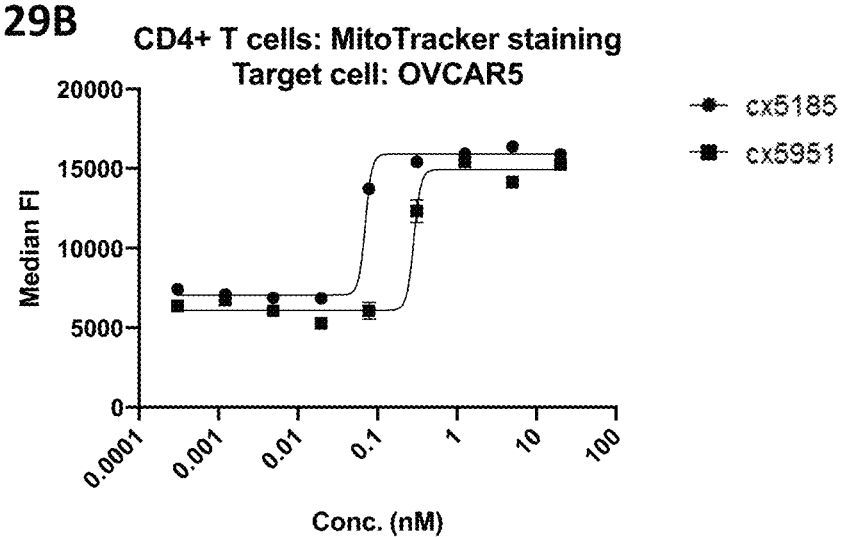
Figure 29C:
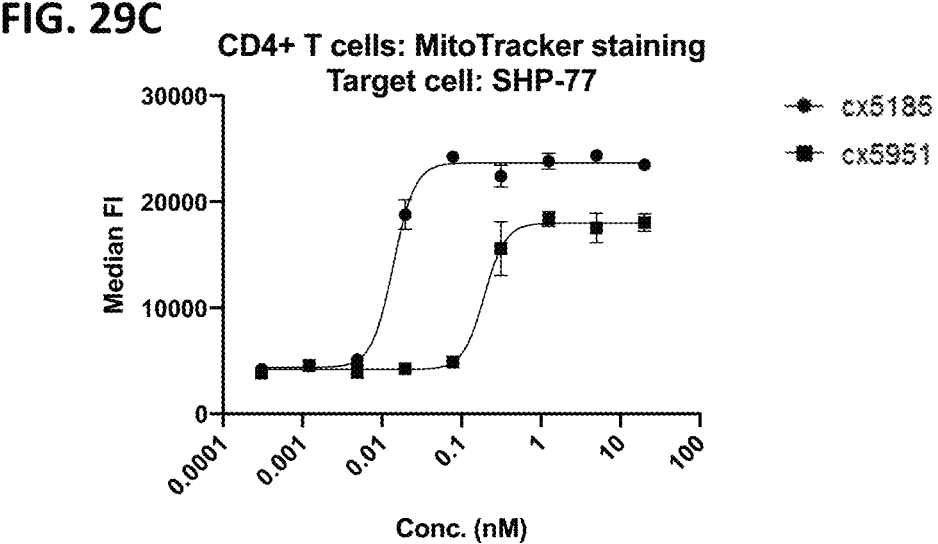
Figure 29D:
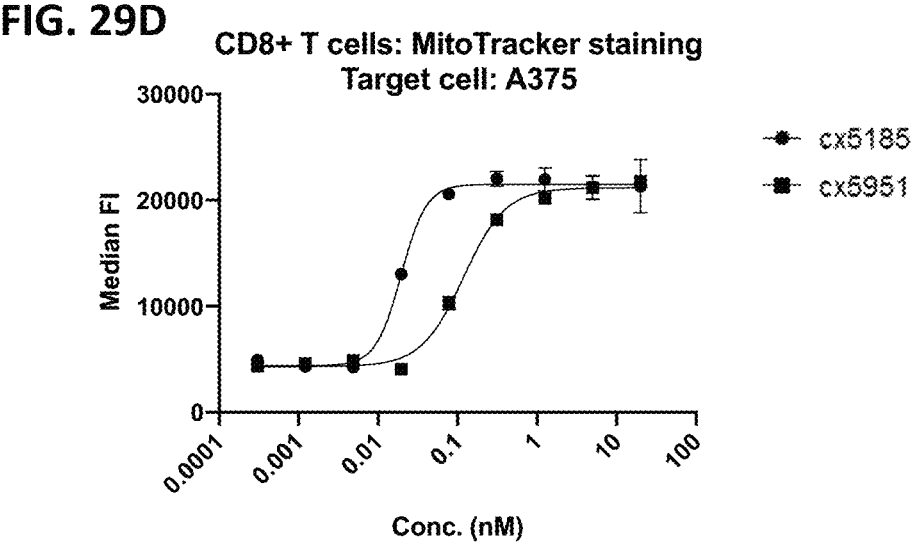
Figure 29E:
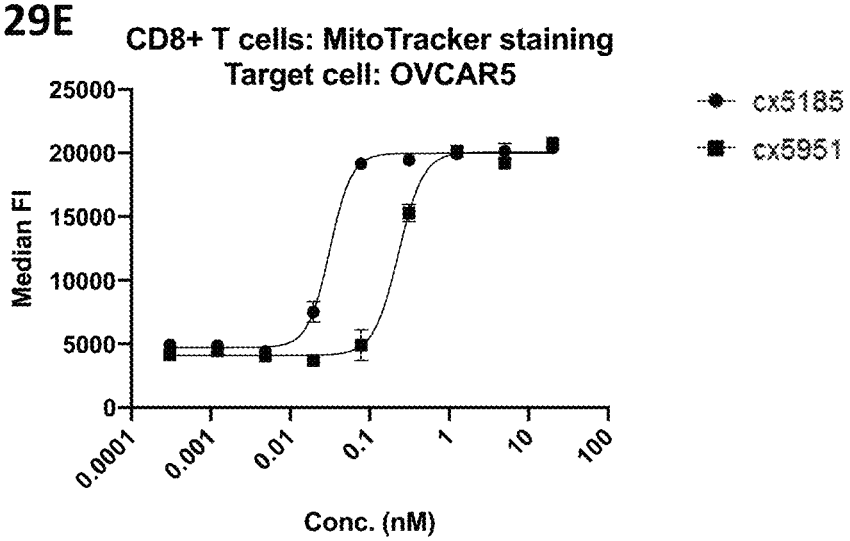
Figure 29F:
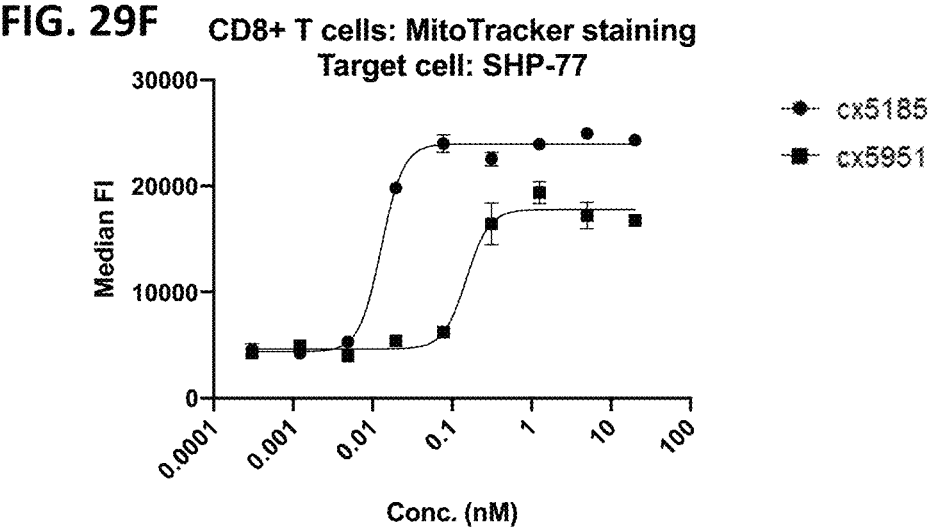

41BB signaling has been suggested to enhance mitochondrial function. Mitochodrial function can be monitored using the mitochondrial-selective fluorescent probe MitoTracker Green (Thermo Fisher Scientific), which accumulates in active mitochondria. To assess mitochondrial function of T cells, T cells were co-cultured for five days with 5T4-expressing cell lines A375 (FIGS. 29A and 29D), Ovcar-5 (FIGS. 29B and 29E), or SHP-77 (FIGS. 29C and 29F) in the presence of exemplary 5T4-targeted constrained CD3 engaging constructs. MitoTracker Green was added at a final cell staining concentration of 100 nM as well as the viability dye propidium iodide and fluorophore-conjugated anti-CD4 and anti-CD8 antibodies, and cells were analyzed using a SONY SA3800 spectral analyzer. Median MitoTracker Green fluorescent intensity of CD4+ or CD8+ T cells was determined by gating on the appropriate viable T cell subpopulation. The 5T4-targeted constrained CD3 engaging construct incorporating the 41BB binding domain, cx5185, enhanced mitochondrial function of both CD4 (FIGS. 29A-C) and CD8 (FIGS. 29D-F) T-cells compared to the similar construct lacking the 41BB binding domain, cx5951.

6. T Cell Reporter Assay

Figure 30:
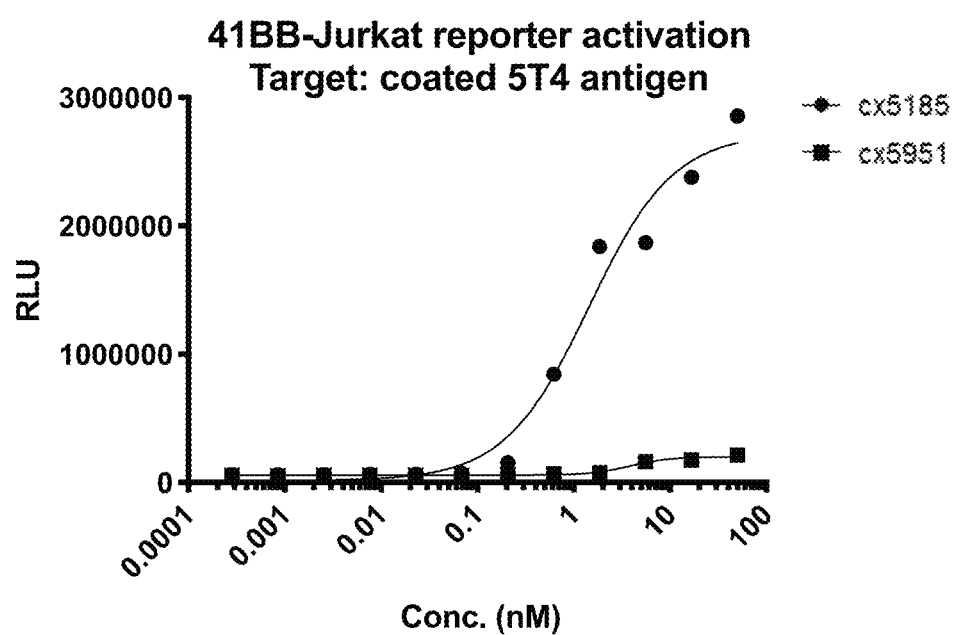
FIG. 30 shows the ability of the 5T4-targeted constrained CD3 engaging construct with a 41BB binding domain, cx5185, but not the same construct lacking a 41BB binding domain, cx5951 to mediate 41BB signaling. 41BB signaling was monitored using a Jurkat 41BB NFkB-luciferase reporter cell and recombinant plate bound 5T4 as the source of the antigen.

The capacity of constrained CD3 engaging constructs containing 5T4-targeted sdAbs to mediate specific agonism of the 41BB co-stimulatory signaling pathway was also assessed. A Jurkat 41BB NFκB-Luciferase reporter cell (see e.g. Example 3) was used to test exemplary 5T4-targeting constrained CD3 engaging constructs with either no co-stimulatory receptor binding domain (cx5951) or a 41BB binding domain (cx5185). Recombinant plate bound 5T4 was used as the source of the antigen As shown in FIG. 30, cx5185 incorporating the 41BB binding domain was found to induce specific agonism of the targeted co-stimulatory receptor.

C. Summary

Together, these results demonstrate that CD3 engaging constructs containing 5T4-targeting sdAb domains, with and without a CRBR, are capable of antigen-dependent activation of T cells. Notably, the 5T4-targeted constrained CD3 engaging construct incorporating a 41BB binding domain displayed superior antigen-dependent and activity than the 5T4-targeted constrained CD3 engaging construct without a 41BB binding domain.

Example 16: Comparison of Orientation of CD3 Binding Region in CD3-Constrained Multispecific Constructs Containing B7H3-Targeting Domains Additional B7H3-targeting multispecific polypeptide constructs were generated containing an Fv as a CD3 binding region in which the VH or VL of the anti-CD3 Fv in the constructs was positioned C-terminally to either the Fc-knob or Fc-hole of the heterodimeric Fc region. The generated CD3-constrained multispecific polypeptide constructs were assessed for the ability to activate T cells via CD3 engagement in a T cell reporter assay.

A. Design and Generation of Constructs

The multispecific constructs were generated as shown in FIG. 31A, to contain a heterodimeric Fc region of an immunoglobulin coupled by a linker (e.g. a non-cleavable linker) to the CD3 binding region, a 4-1BB antigen binding domain (e.g. sdAb) as a CRBR positioned carboxy-terminally relative to the CD3 binding region, and dual antigen binding domains that bind the B7H3 tumor associated antigen (TAA) positioned amino-terminally relative to the Fc region and carboxy-terminally relative to the CD3 binding region of the multispecific polypeptide construct.

Polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, a first Fc polypeptide (e.g. an Fc hole polypeptide); a non-cleavable linker; a variable light (VL; e.g. cx5187)) or variable heavy (VH; e.g. cx5841) domain of an anti-CD3 antibody; and a 4-1BB binding domain (e.g. sdAb, containing a CDR1, a CDR2 and a CDR3 set forth in SEQ ID Nos: 308, 309 and 310, respectively; e.g. set forth in SEQ ID NO:215) as a CRBR. The second polypeptide chain generally included in order, from the N-terminus to C-terminus, a first B7H3 antigen binding domain (e.g. B7H3 sdAb #1), a second Fc polypeptide (e.g. an Fc knob polypeptide); the same linker as the first polypeptide chain; the other of the variable heavy (VH) or variable light (VL) domain of an anti-CD3 antibody; and a second B7H3 antigen binding domain (e.g. B7H3 sdAb #2). The anti-CD3 antibody included a disulfide-stabilized (dsFv) antibody (anti-CD3 VH with the mutation G44C and VL with the mutation G100C).

Notably, as shown in FIG. 31A, the orientation of the anti-CD3 VH and anti-CD3 VL of the CD3 Fv were positioned differently relative to the Fc knob or Fc hole of the heterodimeric Fc region. As shown in the top of FIG. 31A, cx5841 was generated in which the first polypeptide of the heterodimeric construct had the VL of CD3 Fv positioned C-terminal to the Fc knob and B7H3 binding domain on the extreme N and C-termini and the second polypeptide of the heterodimeric construct had the VH of CD3 Fv positioned C-terminal to the Fc Hole and a 41BB binding on the extreme C-termini. In contrast, the bottom of FIG. 31A depicts the exemplary construct cx5187 in which the first polypeptide of the heterodimeric construct had the VH of CD3 Fv positioned C-terminal to the Fc knob and B7H3 binding domain on the extreme N and C-termini and the second polypeptide of the heterodimeric construct had the VL of CD3 Fv positioned C-terminal to the Fc Hole and a 41BB binding on the extreme C-termini.

Components of the exemplary generated constrained CD3 binding constructs are shown in Table E6. The constructs were expressed and purified substantially as described in Example 12.

TABLE E6

Exemplary constrained CD3 engaging constructs containing B7H3-targeting domain

| Construct ID | Chain | N-term sdAb (Target) | Fc | Linker | CD3 Binding Domain | C-term sdAb (Target) | Disulfide Stabilized |
|---|---|---|---|---|---|---|---|
| cx5841 | 1 | B7H3 sdAb 4 hz1A5v51 (SEQ ID NO: 301) | xELL-Knob (SEQ ID NO: 84, 88) | GGGGGSGGGGGSG GGGGS (SEQ ID NO: 119) | VL10 (SEQ ID NO: 72) | B7H3 sdAb 3 hz58E05v48 (SEQ ID NO: 304) | yes |
|  | 2 | None | xELL-Hole (SEQ ID NO: 91, 93) | GGGGGSGGGGGSG GGGGS (SEQ ID NO: 119) | VH13 (SEQ ID NO: 44) | 41BB sdAb (e.g. SEQ ID NO: 215) |  |
| cx5187 | 1 | B7H3 sdAb 4 hz1A5v51 (SEQ ID NO: 301) | xELL-Knob (SEQ ID NO: 84, 88) | GGGGGSGGGGGSG GGGGS (SEQ ID NO: 119) | VH13 (SEQ ID NO: 44) | B7H3 sdAb 3 hz58E05v48 (SEQ ID NO: 304) | yes |
|  | 2 | None | xELL-Hole (SEQ ID NO: 91, 93) | GGGGGSGGGGGSG GGGGS (SEQ ID NO: 119) | VL10 (SEQ ID NO: 72) | 41BB sdAb (SEQ ID NO: e.g. 215) |  |

B. T Cell Reporter Activity

To compare CD3 engagement, the exemplary constructs were tested in an antigen-dependent CD3 reporter assay by assessing their ability to activate a CD3 NFAT reporter Jurkat cell line in a co-culture with target antigen-expressing cells. Activation was assessed by monitoring either green fluorescent or luciferase reporter signal in Jurkat reporter cells.

Antigen targeting constrained CD3 engaging constructs were titrated onto co-cultures of either A375 cells expressing B7H3 or control CCRF-CEM cells not expressing B7H3, and engineered Jurkat cells that express NFAT-driven green fluorescence protein (GFP). Engagement of CD3 results in NFAT signaling and production of green fluorescence. For reporter assays utilizing adherent target cells, target cells were seeded, allowed to settle at room temperature for uniform distribution, and incubated for several hours at 37° C. to permit adherence prior to addition of reporter cells and antigen targeting constrained CD3 engaging constructs. Assay plates were serially imaged using an IncuCyte ZOOM system and CD3 reporter cell activation was determined by measuring total green object integrated intensity.

Figure 31B:
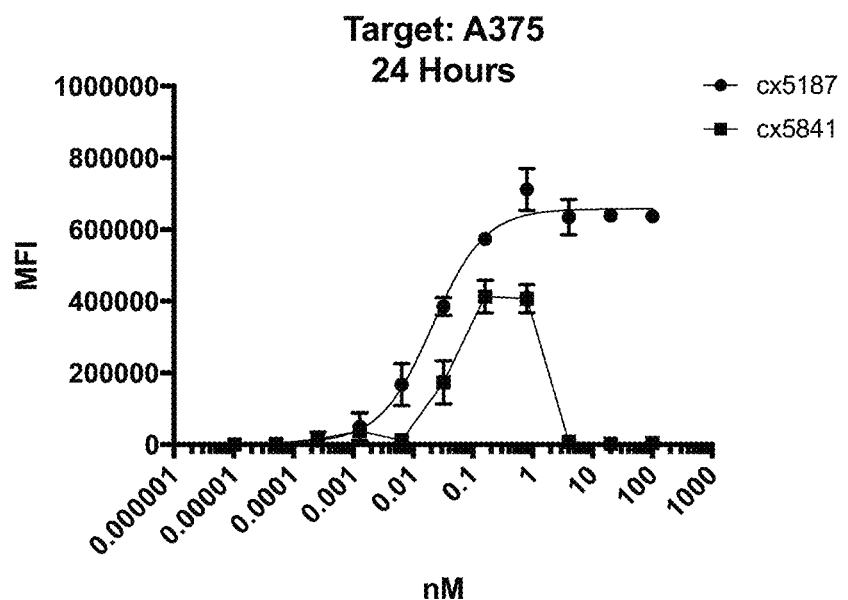
FIGS. 31B-E depict results of a T cell reporter assay for exemplary constructs described in FIG. 31A.
Figure 31C:
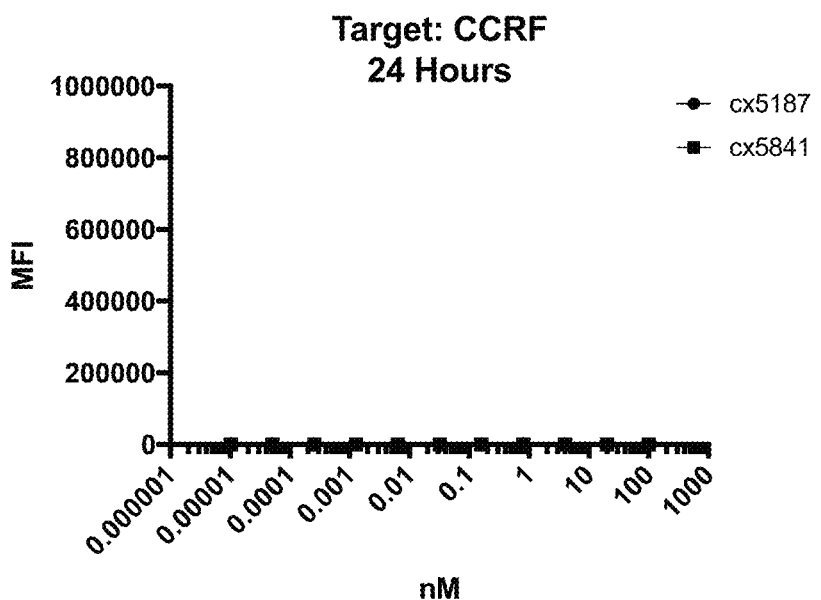

As shown in FIG. 31B, the exemplary B7H3-targeted constrained CD3 engaging constructs exhibited capacity to mediate target antigen specific T-cell activation when incubated in reporter T cell co-cultures in the presence of B7H3-expressing target cells. Reporter activity, however, was not observed in co-cultures with cells not expressing B7H3 (FIG. 31C). Notably, cx5187 with the Knob-VH; Hole-VL format displayed enhanced T cell activation compared to cx5841 with the Knob-VL; Hole-VH format.

Figure 31D:
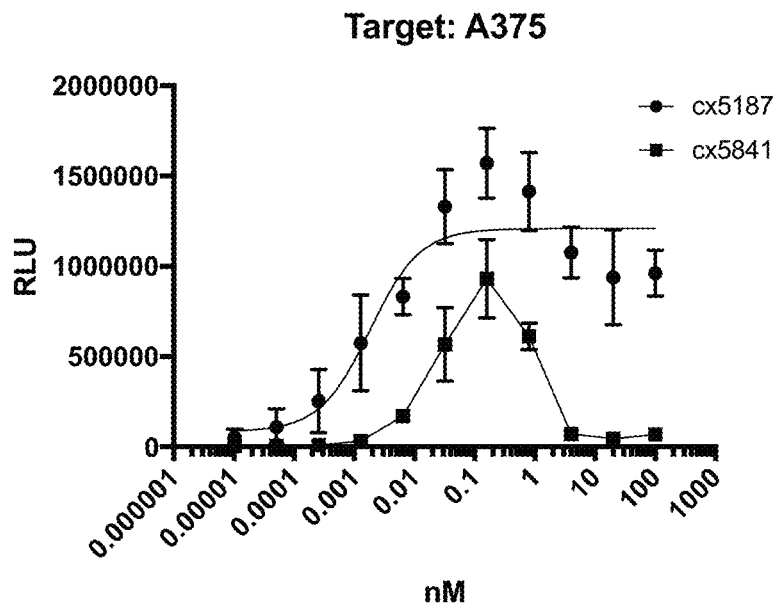
Figure 31E:
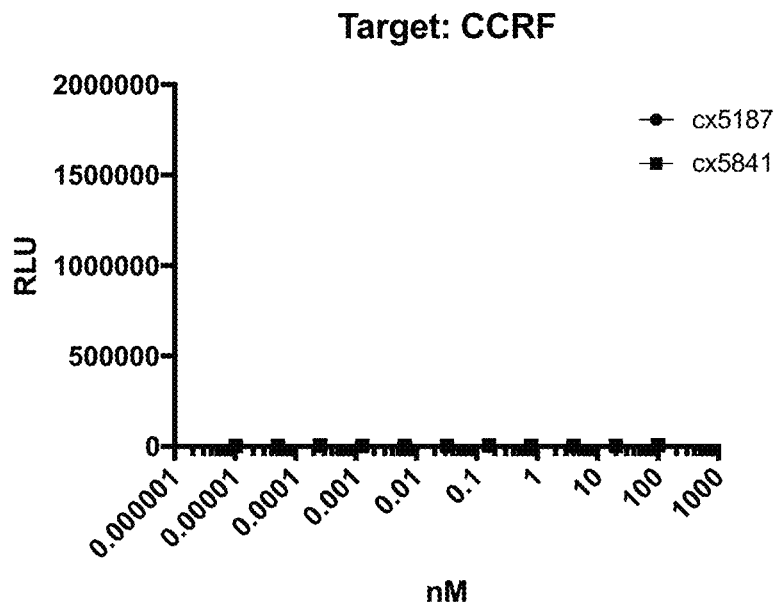

In a similar assay, the same antigen targeting constrained CD3 engaging constructs were titrated onto co-cultures of either A375 cells expressing B7H3 or control CCRF-CEM cells not expressing B7H3, and engineered Jurkat cells that express NFAT-driven luciferase. As shown in FIG. 31D, the exemplary B7H3-targeted constrained CD3 engaging constructs exhibited capacity to mediate target antigen specific T-cell activation when incubated in reporter T cell co-cultures in the presence of B7H3-expressing target cells. Again, reporter activity, was not observed in co-cultures with cells not expressing B7H3 (FIG. 31E). As in the GFP reporter assay, the construct with the Knob-VH; Hole-VL format (cx5187) displayed enhanced T cell activation compared to the construct with the Knob-VL; Hole-VH format (cx5841).

These results are consistent with an observation that enhanced CD3 engagement and activity is observed when the components of the CD3 Fv are oriented so that the VH and VL are positioned C-terminally to the Fc Knob and Fc Hole regions, respectively.

Example 17: Effect of Costimulatory Receptor Binding Region in CD3-Constrained Multispecific Constructs Containing DLL3-Targeting Domains Additional DLL3-targeting multispecific polypeptide constructs were generated with or without a costimulatory receptor binding region targeting 4-1BB. The generated CD3-constrained multispecific polypeptide constructs were assessed for the ability to activate T cells via CD3 engagement in a T cell reporter assay

A. Design and Generation of Constructs

Figure 32A:
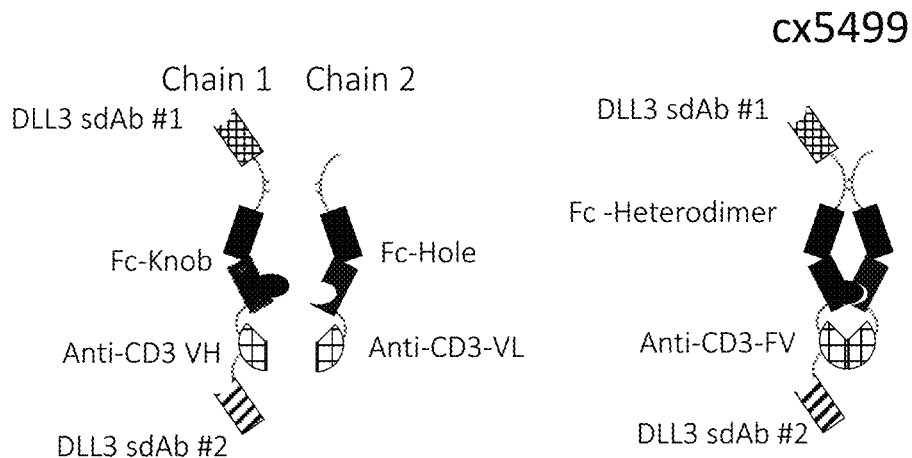
FIG. 32 depicts representative DLL3-targeted constrained CD3 engagers without a 41BB binding domain, cx5499 (FIG. 32A), and with a 41BB binding domain, cx5352 (FIG. 32B). cx5499 and cx5352 have a DLL3-targeting sdAb positioned at the N-terminus of one chain of the heterodimer and at the C-terminus of the same chain of the heterodimer. cx5352 and cx5499 are identical to each other with the exception that cx5352 has a 41BB-targeting sdAb positioned at the C-terminus of the opposite chain of the heterodimer, whereas cx5499 does not. These representative DLL3-targeted constrained CD3 engagers display bivalent binding to DLL3 and in constructs containing a 41BB binding domain, display monovalent binding 41BB.
Figure 32B:
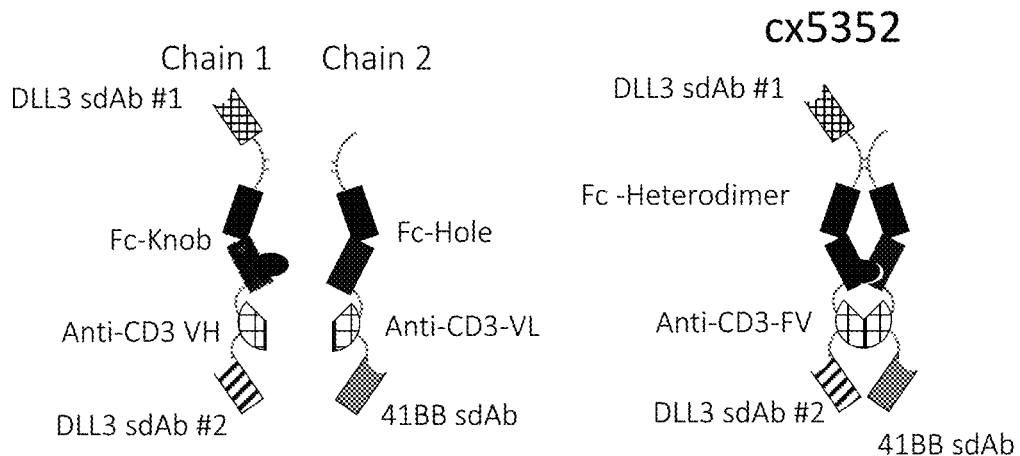

The multispecific constructs were generated as shown in FIG. 32A-B, to contain a heterodimeric Fc region of an immunoglobulin coupled by a linker (e.g. a non-cleavable linker) to the CD3 binding region, and dual antigen binding domains that bind the DLL3 tumor associated antigen (TAA) positioned amino-terminally relative to the Fc region and carboxy-terminally relative to the CD3 binding region of the multispecific polypeptide construct. In some cases, constructs also contained a 4-1BB antigen binding domain (e.g. sdAb containing a CDR1, a CDR2 and a CDR3 set forth in SEQ ID NO: 308, 309, and 310, respectively; e.g. set forth in SEQ ID NO:215) as a CRBR positioned carboxy-terminally relative to the CD3 binding region.

Polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, a first Fc polypeptide (e.g. an Fc hole polypeptide); a non-cleavable linker; and a variable light (VL) domain of an anti-CD3 antibody. In one construct, the first polypeptide additionally includes a 4-1BB binding domain (e.g. sdAb) as a CRBR carboxy-terminal to the VL domain of the CD3 Fv. The second polypeptide chain generally included in order, from the N-terminus to C-terminus, a second Fc polypeptide (e.g. an Fc knob polypeptide); the same linker as the first polypeptide chain; and a variable heavy (VH) domain of an anti-CD3 antibody. The anti-CD3 antibody included a disulfide-stabilized (dsFv) antibody (anti-CD3 VH with the mutation G44C and VL with the mutation G100C). The second polypeptide chain additionally encoded two DLL3 antigen binding domains, one amino-terminal to the Fc domain and one carboxy-terminal to the CD3 binding region. Notably, one of the exemplary constructs generated additionally contained a sdAb targeting a 4-1BB co-stimulatory receptor (e.g. cx5352).

Figure 33:
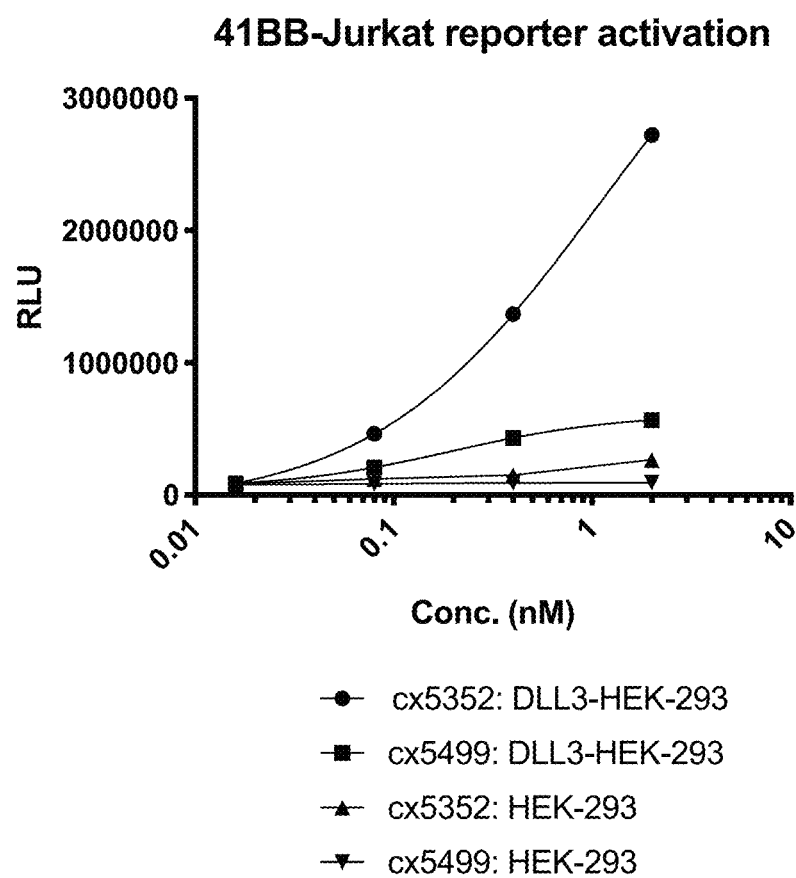
FIG. 33 shows the ability of the DLL3-targeted constrained CD3 engaging construct with a 41BB binding domain, cx5352, but not the same construct lacking a 41BB binding domain, cx5499, to mediate 41BB signaling. DLL3 dependent 41BB signaling was monitored using Jurkat 41BB NFkB-luciferase reporter cells co-cultured with either parental HEK-293 cells or HEK-293 transiently expressing a truncated version of DLL3, and activity is shown as relative luciferase units (RLU).

The exemplary constrained CD3 binding constructs having DLL3-targeting sdAb domains is given below in Table E7. The constructs were expressed and purified substantially as described in Example 12.

constrained CD3 engaging constructs with either no co-stimulatory receptor binding domain (cx5499) or a 41BB binding domain (cx5352). The reporter cells were co-cultured with either a DLL3 negative cell line, HEK-293, or HEK-293 cells transfected to transiently express a truncated version of DLL3 (e.g. 276-618 of SEQ ID NO:324). As shown in FIG. 33, cx5352 displayed DLL3-dependent 41BB agonism in which robust luciferase activity was only observed in the presence of DLL3-expressing cells. A low level of DLL3-dependent NFkB activation was observed with cx5499, indicating that CD3 signaling in this assay may lead to some NFkB activation.

2. Cytotoxic Activity

Figure 34A:
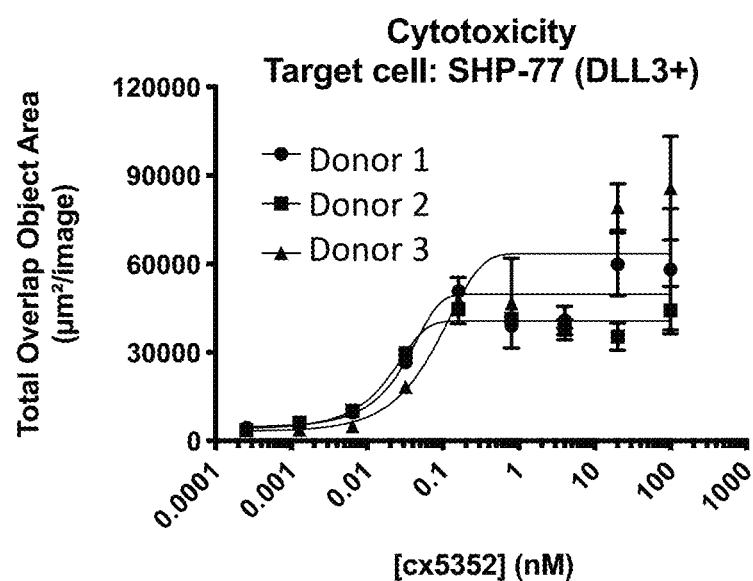
FIG. 34A-B depicts the potency of T-cell-mediated cytotoxicity driven by an exemplary DLL3-targeted constrained CD3 engaging construct with a 41BB binding domain, cx5352, toward a DLL3 positive cell line, SHP-77 (FIG. 34A) or a DLL3 negative cell line, HEK-293FS (FIG. 34B). Three distinct T-cell donors were used as the source of effector cells in this assay
Figure 34B:
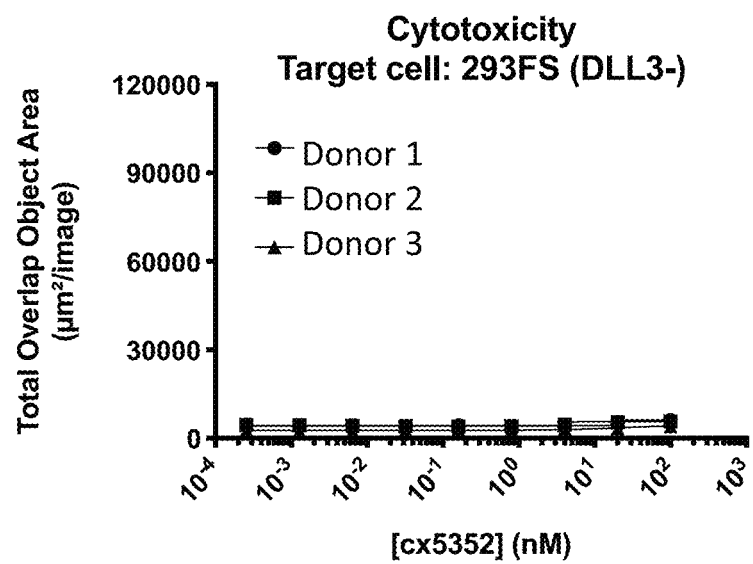

Primary human T cells were negatively enriched from PBMCs isolated from three different healthy human donor leukopaks and added at a 10:1-40:1 T cell-to-target cell ratio. Herein target cells were labeled as red with the CytoID red, while apoptosis was monitored with the green fluorescent caspase-3/7 substrate, thus apoptotic target cells those that are dual labeled red and green. Assay plates were serially imaged using an IncuCyte ZOOM system. Target cell death was determined by measuring total red/green overlap object area (as shown in FIGS. 34A-B).

In an exemplary assay, the CD3 engaging construct that was tested included DLL3-targeted sdAbs with a 41BB-binding CRBR (cx5352). The target cells were DLL3-expressing SHP-77 cells or 293FS cells that did not express DLL3. As shown in FIG. 34A, cx5352 was capable of eliciting T-cell mediated antigen specific cytotoxicity. No cytotoxicity was observed in the absence of the antigen as shown by no red/green overlap object area in co-cultures

TABLE E7

Exemplary constrained CD3 engaging constructs containing B7H3-targeting domain

| Construct ID | Chain | N-term sdAb (Target) | Fc | Linker | CD3 Binding Domain | C-term sdAb (Target) | Disulfide Stabilized |
|---|---|---|---|---|---|---|---|
| cx5499 | 1 | DLL3 sdAb 1 (SEQ ID NO: 306) | xELL-Knob (SEQ ID NO: 84, 88 or 293) | GGGGGSGGGGSG GGGGS (SEQ ID NO: 119) | VH13 (SEQ ID NO: 44) | DLL3 sdAb2 (SEQ ID NO: 307) | yes |
|  | 2 | None | xELL-Hole (SEQ ID NO: 91, 93 or 296) | GGGGGSGGGGSG GGGGS (SEQ ID NO: 119) | VL10 (SEQ ID NO: 72) | None |  |
| cx5352 | 1 | DLL3 sdAb 1 (SEQ ID NO: 306) | xELL-Knob (SEQ ID NO: 84, 88 or 293) | GGGGGSGGGGSG GGGGS (SEQ ID NO: 119) | VH13 (SEQ ID NO: 44) | DLL3 sdAb2 (SEQ ID NO: 307) | yes |
|  | 2 | None | xELL-Hole (SEQ ID NO: 91, 93 or 296) | GGGGGSGGGGSG GGGGS (SEQ ID NO: 119) | VL10 (SEQ ID NO: 72) | Co-stim Receptor sdAb (e.g. SEQ ID NO: 215) |  |

B. T Cell Activity

To compare activity of a DLL3-targeted construct that contained a CRBR positioned C-terminally at the CD3 binding domain to a construct that did not contain a CRBR, the exemplary constructs were tested in various assays to assess their effect on T cell activity.

1. T Cell Reporter Assay

The capacity of constrained CD3 engaging constructs containing a co-stimulatory receptor binding domain to mediate specific agonism of the co-stimulatory signaling pathway was assessed. A Jurkat 41BB NFkB-Luciferase reporter cell was used to test exemplary DLL3-targeting containing DLL3-netative cells (FIG. 34B). This data demonstrates the capacity of an exemplary DLL3-targeted constrained CD3 engaging construct with a 41BB binding domain to elicit T-cell mediated antigen specific cytotoxicity.

Figure 35A:
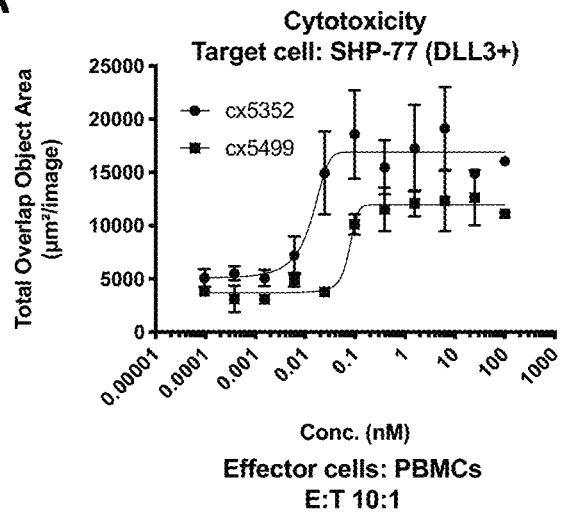
FIGS. 35A-C shows differences in potency of T-cell-mediated cytotoxicity driven by exemplary DLL3-targeted constrained CD3 engaging constructs with a 41BB binding domain, cx5352, and without a 41BB binding domain, cx5499. Herein various effector (T-cells) to target cells (SHP-77) ratio (effector:target cell ratio) were compared as follows: 10:1 (FIG. 35A), 5:1 (FIG. 35B) or 1.25:1 (FIG. 35C). Human PBMCs were used as the source of T-cells.
Figure 35B:
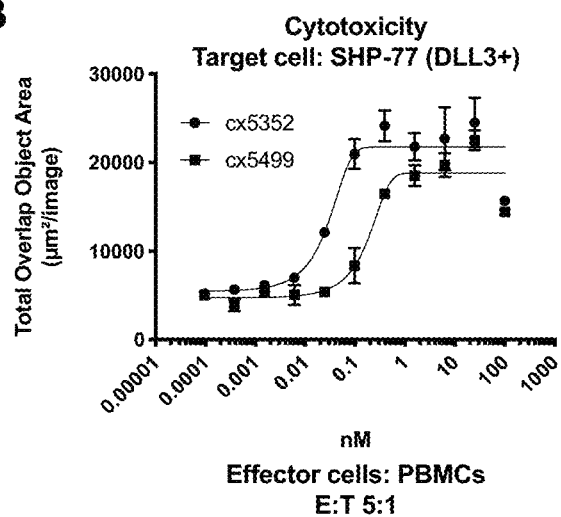
Figure 35C:
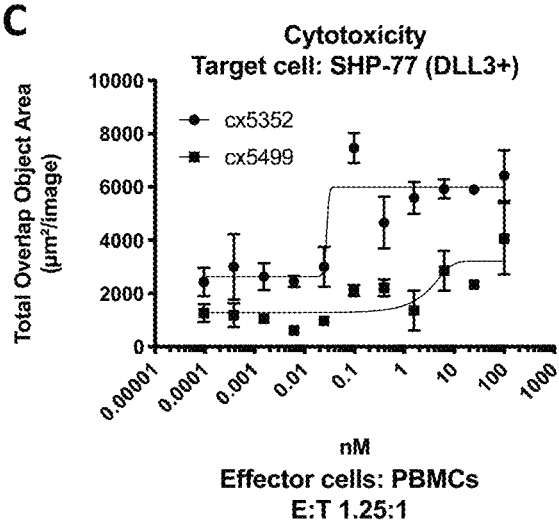

In a similar assay, primary human PBMCs isolated from healthy human donor leukopaks were added at a 10:1, 5:1, or 1.25:1 ratio of effector to target (E:T) cells. The PBMCs were co-cultured with DLL3-expressing SHP-77 target cells and incubated in the presence of increasing concentrations of exemplary constructs containing DLL3-targeted sdAbs with a CRBR (cx53532) and without a CRBR (cx5499). As shown in FIGS. 35A-C, cx5352 displayed enhanced cytotoxicity against target cells at all three E:T ratios analyzed.

3. T Cell Cytokine Expression

Supernatants from a T cell-mediated cytotoxicity assay, carried out substantially as described above with SHP-77 cells as target cells, were analyzed for IFNγ content by sandwich ELISA (BioLegend, USA). The manufacturer's instructions were followed and a standard curve was generated from which cytokine concentration values of supernatant samples were interpolated. Samples that had absorbance values below the lower limit of detection were assigned a cytokine concentration equal to half that of the lowest standard concentration.

Figure 36:
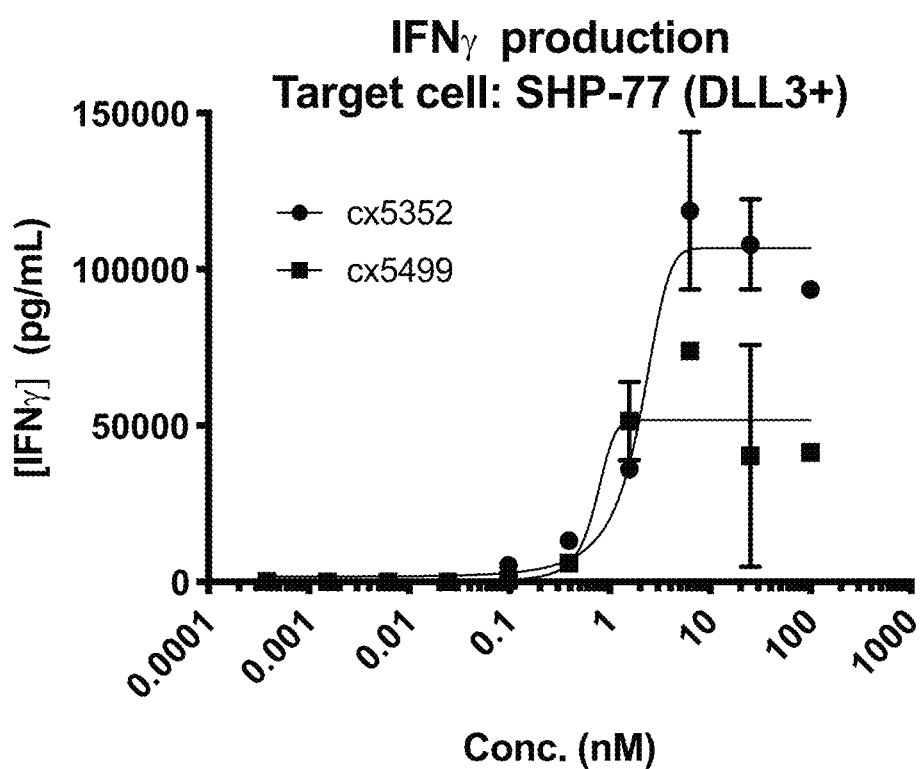
FIG. 36. shows a comparison of IFNγ production by T-cells treated with a titration of representative DLL3-targeted constrained CD3 engaging constructs with a 41BB binding domain, cx5352, and without a 41BB binding domain, cx5499, in the presence of the DLL3 positive cell line SHP-77.

As shown in FIG. 36, the DLL3-targeted constrained CD3 engaging construct incorporating the 41BB binding domain, cx5352, resulted in enhanced IFNγ production by T cells compared to the similar construct lacking the 41BB binding domain, cx5499.

Other Embodiments

While the invention has been described in conjunction with the detailed description thereof, the foregoing description is intended to illustrate and not limit the scope of the disclosure, which is defined by the scope of the appended claims. Other aspects, advantages, and modifications are within the scope of the following claims.

SEQUENCE TABLE

| SEQ ID NO | SEQUENCE | DESCRIPTION |
|---|---|---|
| 1 | PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK | IgG1 Fc |
| 2 | PAPGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVM HEAL HNHYTQKSLS LSPGK | xELL Fc |
| 3 | PAPPVAGPSV FLFPPKPKDT LMISRTPEVT CVVVDVSHED PEVQFNWYVD GVEVHNAKTK PREEQFNSTF RVVSVLTVVH QDWLNGKEYK CKVSNKGLPA PIEKTISKTK GQPREPQVYT LPPSREEMTK NQVSLTCLVK GFYPSDISVE WESNGQPENN YKTTPPMLDS DGSFFLYSKL TVDKSRWQQG NVFSCSVMHE ALHNHYTQKS LSLSPGK | IgG2 Fc |
| 4 | PAPELLGGPS VFLFPPKPKD TLMISRTPEV TCVVVDVSHE DPEVQFKWYV DGVEVHNAKT KPREEQYNST FRVVSVLTVL HQDWLNGKEY KCKVSNKALP APIEKTISKT KGQPREPQVY TLPPSREEMT KNQVSLTCLV KGFYPSDIAV EWESSGQPEN NYNTTPPMLD SDGSFFLYSK LTVDKSRWQQ GNIFSCSVMH EALHNRFTQK SLSLSPGK | IgG3 Fc |
| 5 | PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | IgG4 Fc |
| 6 | PAPELLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | IgG4 Fc |
| 7 | EPKSSDKTHTCPPC | Hinge |
| 8 | DKTHTCPPC | Hinge |
| 9 | ESKYGPPCPPC | Hinge |
| 10 | GGSGGS | (GGS)2 |
| 11 | GGSGGSGGS | (GGS)3 |
| 12 | GGSGGSGGSGGS | (GGS)4 |
| 13 | GGSGGSGGSGGSGGS | (GGS)5 |
| 14 | EVQLVESGGGLVQPKGSLKLSCAASGFTFNTYAMNWVRQAPGKGLEWVA RIRSKYNNYATYYADSVKDRFTISRDDSQSILYLQMNNLKTEDTAMYYCVR HGNFGNSYVSWFAYWGQGTLVTVSA | anti-CD3 Hv |
| 15 | QAVVTQESALTTSPGETVTLTCRSSTGAVTTSNYANWVQEKPDHLFTGLIG GTNKRAPGVPARFSGSLIGDKAALTITGAQTEDEAIYFCALWYSNLWVFGG GTKLTVL | anti-CD3 Lv |

SEQUENCE TABLE

| SEQ ID NO | SEQUENCE | DESCRIPTION |
|---|---|---|
| 16 | TYAMN | anti-CD3 VH CDR1 |
| 17 | RIRSKYNNYATYYADSVKD | anti-CD3 VH CDR2 |
| 18 | HGNFGNSYVSWFAY | anti-CD3 VH CDR3 |
| 19 | RSSTGAVTTSNYAN | anti-CD3 VL CDR1 |
| 20 | GTNKRAP | anti-CD3 VL CDR2 |
| 21 | ALWYSNLWV | anti-CD3 VL CDR3 |
| 22 | LEAD | Granzyme B substrate |
| 23 | RQAR | Granzyme B substrate |
| 24 | PAGL | MMP substrate |
| 25 | TGLEADGSPAGLGRQARVG | Linker |
| 26 | TGLEADGSRQARVGPAGLG | Linker |
| 27 | TGSPAGLEADGSRQARVGS | Linker |
| 28 | TGPAGLGLEADGSRQARVG | Linker |
| 29 | TGRQARVGLEADGSPAGLG | Linker |
| 30 | TGSRQARVGPAGLEADGS | Linker |
| 31 | TGPAGLGSRQARVGLEADGS | Linker |
| 32 | EVQLVESGGGLVQPGGSLRLSCAASGFTFSTYAMNWVRQAPGKGLEWVGRIRSKYNNYATYYADSVKDRFTISRDDSKNSLYLQMNSLKTEDTAVYYCVRHGNFGNSYVSWFAYWGQGTLVTVSS | anti-CD3 VH1 |
| 33 | EVKLVESGGGLVQPGGSLRLSCAASGFTFNTYAMNWVRQAPGKGLEWVARIRSKYNNYATYYADSVKDRFTISRDDSKSSLYLQMNNLKTEDTAMYYCVRHGNFGNSYVSWFAYWGQGTLVTVSS | anti-CD3 VH2 |
| 34 | EVKLVESGGGLVKPGRSLRLSCAASGFTFNTYAMNWVRQAPGKGLEWVARIRSKYNNYATYYADSVKDRFTISRDDSKSILYLQMNNLKTEDTAMYYCVRHGNFGNSYVSWFAYWGQGTLVTVSS | anti-CD3 VH3 |
| 35 | EVKLVESGGGLVKPGRSLRLSCAASGFTFNTYAMNWVRQAPGKGLEWVARIRSKYNNYATYYADSVKDRFTISRDDSKSILYLQMNSLKTEDTAMYYCVRHGNFGNSYVSWFAYWGQGTLVTVSS | anti-CD3 VH4 |
| 36 | EVKLVESGGGLVKPGRSLRLSCAASGFTFNTYAMNWVRQAPGKGLEWVARIRSKYNNYATYYADSVKDRFTISRDDSKSILYLQMNSLKTEDTAMYYCVRHGNFGNSYVSWFAYWGQGTLVTVSS | anti-CD3 VH5 |
| 37 | EVQLLESGGGLVQPGGSLRLSCAASGFTFSTYAMNWVRQAPGKGLEWVSRIRSKYNNYATYYADSVKGRFTISRDDSKNTLYLQMNSLRAEDTAVYYCVRHGNFGNSYVSWFAYWGQGTLVTVSS | anti-CD3 VH6 |
| 38 | EVQLVESGGGLVQPGGSLRLSCAASGFTFSTYAMSWVRQAPGKGLEWVGRIRSKYNNYATYYADSVKGRFTISRDDSKNTLYLQMNSLRAEDTAVYYCVRHGNFGDSYVSWFAYWGQGTLVTVSS | anti-CD3 VH7 |
| 39 | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVS | anti-CD3 VH8 |

-continued

| SEQ ID NO | SEQUENCE | DESCRIPTION |
|---|---|---|
| 40 | EVQLVESGGGLVQPGGSLRLSCAASGFTFNTYAMNWVRQAPGKGLEWVA RIRSKYNNYATYYADSVKGRFTISRDDSKNTLYLQMNSLRAEDTAVYYCVR HGNFGNSYVSWFAYWGQGTTVTVSS | anti-CD3 VH9 |
| 41 | EVQLVESGGGLVQPGGSLRLSCAASGFTFNTYAMNWVRQAPGKGLEWVA RIRSKYNNYATYYADSVKGRFTISRDDSKNTLYLQMNSLRAEDTAVYYCVR HGNFGNSYVSYFAYWGQGTTVTVSS | anti-CD3 VH10 |
| 42 | EVQLVESGGGLVQPKGSLKLSCAASGFTFNTYAMNWVRQAPGKGLEWVA RIRSKYNNYATYYADSVKDRFTISRDDSQSILYLQMNNLKTEDTAMYYCVR HGNFGNSYVSWFAYWGQGTLVTVSS | anti-CD3 VH11 |
| 43 | EVQLVESGGGLVQPGGSLRLSCAASGFTFNTYAMNWVRQAPGKGLEWVA RIRSKYNNYATYYADSVKGRFTISRDDAKNTLYLQMSSLRAEDTAVYYCVR HGNFGNSYVSWFAYWGQGTLVTVKP | anti-CD3 VH12 |
| 44 | EVQLVESGGGLVQPGGSLRLSCAASGFTFNTYAMNWVRQAPGKCLEWVAR IRSKYNNYATYYADSVKGRFTISRDDAKNTLYLQMSSLRAEDTAVYYCVRH GNFGNSYVSWFAYWGQGTLVTVKP | anti-CD3 VH13 |
| 45 | EVQLVESGGGLVQPGGSLRLSCAASGFTFNTYAMNWVRQAPGKGLEWVA RIRSKYNNYATYYADSVKGRFTISRDDAKNTLYLQMSSLRAEDTAVYYCVR HGNFGNSYVSWFAYWGCGTLVTVKP | anti-CD3 VH14 |
| 46 | EVQLVESGGGLVQPGGSLRLSCAASGFTFSTYAMNWVRQAPGKGLEWVAR IRSKYNNYATYYADSVKGRFTISRDDAKNTLYLQMSSLRAEDTAVYYCVRH GNFGNSYVSWFAYWGQGTLVTVSS | anti-CD3 VH15 |
| 47 | EVQLVESGGGLVQPGGSLRLSCAASGFTFNTYAMNWVRQAPGKGLEWVSR IRSKYNNYATYYADSVKGRFTISRDDAKNTLYLQMSSLRAEDTAVYYCVRH GNFGNSYVSWFAYWGQGTLVTVSS | anti-CD3 VH16 |
| 48 | EVQLVESGGGLVQPGGSLRLSCAASGFTFSTYAMNWVRQAPGKGLEWVSR IRSKYNNYATYYADSVKGRFTISRDDAKNTLYLQMSSLRAEDTAVYYCVRH GNFGNSYVSWFAYWGQGTLVTVSS | anti-CD3 VH17 |
| 49 | EVQLVESGGGLVQPGGSLRLSCAASGFTFSTYAMNWVRQAPGKCLEWVAR IRSKYNNYATYYADSVKGRFTISRDDAKNTLYLQMSSLRAEDTAVYYCVRH GNFGNSYVSWFAYWGQGTLVTVSS | anti-CD3 VH18 |
| 50 | EVQLVESGGGLVQPGGSLRLSCAASGFTFNTYAMNWVRQAPGKCLEWVSR IRSKYNNYATYYADSVKGRFTISRDDAKNTLYLQMSSLRAEDTAVYYCVRH GNFGNSYVSWFAYWGQGTLVTVSS | anti-CD3 VH19 |
| 51 | EVQLVESGGGLVQPGGSLRLSCAASGFTFSTYAMNWVRQAPGKCLEWVSRI RSKYNNYATYYADSVKGRFTISRDDAKNTLYLQMSSLRAEDTAVYYCVRH GNFGNSYVSWFAYWGQGTLVTVSS | anti-CD3 VH20 |
| 52 | EVQLVESGGGLVQPGGSLRLSCAASGFTFSTYAMNWVRQAPGKCLEWVGR IRSKYNNYATYYADSVKDRFTISRDDSKNSLYLQMNSLKTEDTAVYYCVRH GNFGNSYVSWFAYWGQGTLVTVSS | anti-CD3 VH21 |
| 53 | EVKLVESGGGLVQPGGSLRLSCAASGFTFNTYAMNWVRQAPGKCLEWVAR IRSKYNNYATYYADSVKDRFTISRDDSKSSLYLQMNNLKTEDTAMYYCVR HGNFGNSYVSWFAYWGQGTLVTVSS | anti-CD3 VH22 |
| 54 | EVKLVESGGGLVKPGRSLRLSCAASGFTFNTYAMNWVRQAPGKCLEWVAR IRSKYNNYATYYADSVKDRFTISRDDSKSILYLQMNNLKTEDTAMYYCVRH GNFGNSYVSWFAYWGQGTLVTVSS | anti-CD3 VH23 |
| 55 | EVKLVESGGGLVKPGRSLRLSCAASGFTFNTYAMNWVRQAPGKCLEWVAR IRSKYNNYATYYADSVKDRFTISRDDSKSILYLQMNSLKTEDTAMYYCVRH GNFGNSYVSWFAYWGQGTLVTVSS | anti-CD3 VH24 |
| 56 | EVKLVESGGGLVKPGRSLRLSCAASGFTFNTYAMNWVRQAPGKCLEWVAR IRSKYNNYATYYADSVKDRFTISRDDSKSILYLQMNSLKTEDTAMYYCVRH GNFGNSYVSWFAYWGQGTLVTVSS | anti-CD3 VH25 |
| 57 | EVQLLESGGGLVQPGGSLRLSCAASGFTFSTYAMNWVRQAPGKCLEWVSRI RSKYNNYATYYADSVKGRFTISRDDSKNTLYLQMNSLRAEDTAVYYCVRH GNFGNSYVSWFAYWGQGTLVTVSS | anti-CD3 VH26 |

| SEQ ID NO | SEQUENCE | DESCRIPTION |
|---|---|---|
| 58 | EVQLVESGGGLVQPGGSLRLSCAASGFTFSTYAMSWVRQAPGKCLEWVGRIRSKYNNYATYYADSVKGRFTISRDDSKNTLYLQMNSLRAEDTAVYYCVRHGNFGDSYVSWFAYWGQGTLVTVSS | anti-CD3 VH27 |
| 59 | EVQLVESGGGLVQPGGSLKLSCAASGFTFNKYAMNWVRQAPGKCLEWVARIRSKYNNYATYYADSVKDRFTISRDDSKNTAYLQMNNLKTEDTAVYYCVRHGNFGNSYISYWAYWGQGTLVTVS | anti-CD3 VH28 |
| 60 | EVQLVESGGGLVQPGGSLRLSCAASGFTFNTYAMNWVRQAPGKCLEWVARIRSKYNNYATYYADSVKGRFTISRDDSKNTLYLQMNSLRAEDTAVYYCVRHGNFGNSYVSWFAYWGQGTTVTVSS | anti-CD3 VH29 |
| 61 | EVQLVESGGGLVQPGGSLRLSCAASGFTFNTYAMNWVRQAPGKCLEWVARIRSKYNNYATYYADSVKGRFTISRDDSKNTLYLQMNSLRAEDTAVYYCVRHGNFGNSYVSYFAYWGQGTTVTVSS | anti-CD3 VH30 |
| 62 | EVQLVESGGGLVQPKGSLKLSCAASGFTFNTYAMNWVRQAPGKCLEWVARIRSKYNNYATYYADSVKDRFTISRDDSQSILYLQMNNLKTEDTAMYYCVRHGNFGNSYVSWFAYWGQGTLVTVSS | anti-CD3 VH31 |
| 63 | QAVVTQESALTTSPGETVTLTCRSSTGAVTTSNYANWVQEKPDHLFTGLIGGTNKRAPGVPARFSGSLIGDKAALTITGAQTEDEAIYFCALWYSNLWVFGGGTKLTVL | anti-CD3 VL1 |
| 64 | QAVVTQEPSLTVSPGGTVTLTCGSSTGAVTTSNYANWVQQKPGKSPRGLIGGTNKRAPGVPARFSGSLLGGKAALTISGAQPEDEADYYCALWYSNHWVFGCGTKLEIK | anti-CD3 VL2 |
| 65 | QAVVTQEPSLTVSPGGTVTLTCRSSTGAVTTSNYANWVQQKPGQAPRGLIGGTNKRAPWTPARFSGSLLGGKAALTITGAQAEDEADYYCALWYSNLWVFGGGTKLTVL | anti-CD3 VL3 |
| 66 | QAVVTQEPSFSVSPGGTVTLTCRSSTGAVTTSNYANWVQQTPGQAFRGLIGGTNKRAPGVPARFSGSLIGDKAALTITGAQADDESIYFCALWYSNLWVFGGGTKLTVL | anti-CD3 VL4 |
| 67 | QAVVTQEPSFSVSPGGTVTLTCRSSTGAVTTSNYANWVQQTPGQAFRGLIGGTNKRAPGVPARFSGSILGNKAALTITGAQADDESIYFCALWYSNLWVFGGGTKLTVL | anti-CD3 VL5 |
| 68 | QAVVTQEPSFSVSPGGTVTLTCRSSTGAVTTSNYANWVQQTPGQAFRGLIGGTNKRAPGVPARFSGSILGNKAALTITGAQADDESDYYCALWYSNLWVFGGGTKLTVL | anti-CD3 VL6 |
| 69 | QAVVTQEPSLTVSPGGTVTLTCGSSTGAVTTSNYANWVQEKPGQAFRGLIGGTNKRAPGTPARFSGSLLGGKAALTLSGAQPEDEAEYYCALWYSNLWVFGGGTKLTVL | anti-CD3 VL7 |
| 70 | QTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL | anti-CD3 VL8 |
| 71 | QAVVTQEPSLTVSPGGTVTLTCGSSTGAVTTSNYANWVQQKPGQAFRGLIGGTNKRAPGVPARFSGSLLGGKAALTISGAQPEDEADYYCALWYSNHWVFGGGTKLEIK | anti-CD3 VL9 |
| 72 | QAVVTQEPSLTVSPGGTVTLTCGSSTGAVTTSNYANWVQQKPGQAFRGLIGGTNKRAPGVPARFSGSLLGGKAALTISGAQPEDEADYYCALWYSNHWVFGCGTKLEIK | anti-CD3 VL10 |
| 73 | QAVVTQEPSLTVSPGGTVTLTCGSSTGAVTTSNYANWVQQKPGQCFRGLIGGTNKRAPGVPARFSGSLLGGKAALTISGAQPEDEADYYCALWYSNHWVFGEGTKLEIK | anti-CD3 VL11 |
| 74 | QAVVTQESALTTSPGETVTLTCRSSTGAVTTSNYANWVQEKPDHLFTGLIGGTNKRAPGVPARFSGSLIGDKAALTITGAQTEDEAIYFCALWYSNLWVFGCGTKLTVL | anti-CD3 VL12 |
| 75 | QAVVTQEPSLTVSPGGTVTLTCGSSTGAVTTSNYANWVQQKPGKSPRGLIGGTNKRAPGVPARFSGSLLGGKAALTISGAQPEDEADYYCALWYSNHWVFGGGTKLEIK | anti-CD3 VL13 |

-continued

| SEQ ID NO | SEQUENCE | DESCRIPTION |
|---|---|---|
| 76 | QAVVTQEPSLTVSPGGTVTLTCRSSTGAVTTSNYANWVQQKPGQAPRGLIG GTNKRAPWTPARFSGSLLGGKAALTITGAQAEDEADYYCALWYSNLWVFG CGTKLTVL | anti-CD3 VL14 |
| 77 | QAVVTQEPSFSVSPGGTVTLTCRSSTGAVTTSNYANWVQQTPGQAFRGLIG GTNKRAPGVPARFSGSLIGDKAALTITGAQADDESIYFCALWYSNLWVFGG GTKLTVL | anti-CD3 VL15 |
| 78 | QAVVTQEPSFSVSPGGTVTLTCRSSTGAVTTSNYANWVQQTPGQAFRGLIG GTNKRAPGVPARFSGSILGNKAALTITGAQADDESIYFCALWYSNLWVFGC GTKLTVL | anti-CD3 VL16 |
| 79 | QAVVTQEPSFSVSPGGTVTLTCRSSTGAVTTSNYANWVQQTPGQAFRGLIG GTNKRAPGVPARFSGSILGNKAALTITGAQADDESDYYCALWYSNLWVFG CGTKLTVL | anti-CD3 VL17 |
| 80 | QAVVTQEPSLTVSPGGTVTLTCGSSTGAVTTSNYANWVEKPGQAFRGLIG GTNKRAPGTPARFSGSLLGGKAALTLSGAQPEDEAEYYCALWYSNLWVFG CGTKLTVL | anti-CD3 VL18 |
| 81 | QTVVTQEPSLTVSPGGTVTLTCGSSTGAVTSGNYPNWVQQKPGQAPRGLIG GTKFLAPGTPARFSGSLLGGKAALTLSGVQPEDEAEYYCVLWYSNRWVFG CGTKLTVL | anti-CD3 VL19 |
| 82 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVYTLPPCRDELTKNQVSLWCLVKGFYP SDIAVEWESNGQPENNYKTTPPVLDSDGSFFLYSKLTVDKSRWQQGNVFSC SVMHEALHNHYTQKSLSLSPT | Knob Fc |
| 83 | DKTHTCPPCPAPELLGGPSVFLFPPKPKDTLMRSRTPEVTCVVVDVSHEDPE VKFNWYVDGVEVHNAKTKPREEQYNSTYRVVSVLTVLHQDWLNGKEYKC KVSNKALPAPIEKTISKAKGQPREPQVCTLPPSRDELTKNQVSLSCAVKGFYP SDIAVEWESNGQPENNYKTTPPVLDSDGSFFLVSKLTVDKSRWQQGNVFSC SVMHEALHNHYTQKSLSLSPT | Hole Fc |
| 84 | DKTHTCPPCPAPGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVYTLPPCRDELTKNQVSLWCLVKGFYPSD IAVEWESNGQPENNYKTTPPVLDSDGSFFLYSKLTVDKSRWQQGNVFSCSV MHEALHNHYTQKSLSLSPT | Knob Fc |
| 85 | DKTHTCPPCPAPGGPSVFLFPPKPKDTLMRSRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVCTLPPSRDELTKNQVSLSCAVKGFYPSDI AVEWESNGQPENNYKTTPPVLDSDGSFFLVSKLTVDKSRWQQGNVFSCSV MHEALHNHYTQKSLSLSPT | Hole Fc |
| 86 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVYTLPPCRDELTKNQVSLWCLVKGFYP SDIAVEWESNGQPENNYKTTPPVLDSDGSFFLYSKLTVDKSRWQQGNVFSC SVMHEALHNHYTQKSLSLSPG | Knob Fc |
| 87 | DKTHTCPPCPAPELLGGPSVFLFPPKPKDTLMRSRTPEVTCVVVDVSHEDPE VKFNWYVDGVEVHNAKTKPREEQYNSTYRVVSVLTVLHQDWLNGKEYKC KVSNKALPAPIEKTISKAKGQPREPQVCTLPPSRDELTKNQVSLSCAVKGFYP SDIAVEWESNGQPENNYKTTPPVLDSDGSFFLVSKLTVDKSRWQQGNVFSC SVMHEALHNHYTQKSLSLSPG | Hole Fc |
| 88 | DKTHTCPPCPAPGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVYTLPPCRDELTKNQVSLWCLVKGFYPSD IAVEWESNGQPENNYKTTPPVLDSDGSFFLYSKLTVDKSRWQQGNVFSCSV MHEALHNHYTQKSLSLSPG | Knob Fc |
| 89 | DKTHTCPPCPAPGGPSVFLFPPKPKDTLMRSRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVCTLPPSRDELTKNQVSLSCAVKGFYPSDI AVEWESNGQPENNYKTTPPVLDSDGSFFLVSKLTVDKSRWQQGNVFSCSV MHEALHNHYTQKSLSLSPG | Hole Fc |

| SEQ ID NO | SEQUENCE | DESCRIPTION |
|---|---|---|
| 90 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCS VMHEALHNRYTQKSLSLSPT | Hole Fc |
| 91 | DKTHTCPPCPAPGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVCTLPPSRDELTKNQVSLSCAVKGFYPSDI AVEWESNGQPENNYKTTPPVLDSDGSFFLVSKLTVDKSRWQQGNVFSCSV MHEALHNRYTQKSLSLSPT | Hole Fc |
| 92 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCS VMHEALHNRYTQKSLSLSPG | Hole Fc |
| 93 | DKTHTCPPCPAPGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVCTLPPSRDELTKNQVSLSCAVKGFYPSDI AVEWESNGQPENNYKTTPPVLDSDGSFFLVSKLTVDKSRWQQGNVFSCSV MHEALHNRYTQKSLSLSPG | Hole Fc |
| 94 | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVYTLPPCRDELTKNQVSLWCLVKGFYP SDIAVEWESNGQPENNYKTTPPVLDSDGSFFLYSKLTVDKSRWQQGNVFSC SVVHEALHNHYTQKSLSLSPT | Knob Fc |
| 95 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVYTLPPCRDELTKNQVSLWCLVKGFYPSDI AVEWESNGQPENNYKTTPPVLDSDGSFFLYSKLTVDKSRWQQGNVFSCSVV HEALHNHYTQKSLSLSPT | Knob Fc |
| 96 | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVYTLPPCRDELTKNQVSLWCLVKGFYP SDIAVEWESNGQPENNYKTTPPVLDSDGSFFLYSKLTVDKSRWQQGNVFSC SVVHEALHNHYTQKSLSLSPG | Knob Fc |
| 97 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVYTLPPCRDELTKNQVSLWCLVKGFYPSDI AVEWESNGQPENNYKTTPPVLDSDGSFFLYSKLTVDKSRWQQGNVFSCSVV HEALHNHYTQKSLSLSPG | Knob Fc |
| 98 | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCS VVHEALHNRYTQKSLSLSPT | Hole Fc |
| 99 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVCTLPPSRDELTKNQVSLSCAVKGFYPSDIA VEWESNGQPENNYKTTPPVLDSDGSFFLVSKLTVDKSRWQQGNVFSCSVVH EALHNRYTQKSLSLSPT | Hole Fc |
| 100 | DKTHTCPPCPAPELLGGPSVFLFPPKPKDTLYISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCS VVHEALHNRYTQKSLSLSPG | Hole Fc |
| 101 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVCTLPPSRDELTKNQVSLSCAVKGFYPSDIA VEWESNGQPENNYKTTPPVLDSDGSFFLVSKLTVDKSRWQQGNVFSCSVVH EALHNRYTQKSLSLSPG | Hole Fc |

| SEQ ID NO | SEQUENCE | DESCRIPTION |
|---|---|---|
| 102 | PGGGG | Peptide Linker |
| 103 | GGGG | Peptide Linker |
| 104 | GPAGLGLEPDGSRQARVG | Linker |
| 105 | GGSGGGGIEPDIGGSGGS | Linker |
| 106 | GGSGGGGLEADTGGSGGS | Linker |
| 107 | GSIEPDIGS | Linker |
| 108 | GSLEADTGS | Linker |
| 109 | GGSGGGGIEPDGGGSGGS | Linker |
| 110 | GGSGGGGIEPDVGGSGGS | Linker |
| 111 | GGSGGGGIEPDSGGSGGS | Linker |
| 112 | GGSGGGGIEPDTGGSGGS | Linker |
| 113 | GGGSLEPDGSGS | Linker |
| 114 | GPAGLGLEADGSRQARVG | Linker |
| 115 | GGEGGGGSGGSGGGS | Linker |
| 116 | GSSAGSEAGGSGQAGVGS | Linker |
| 117 | GGSGGGGLEAEGSGGGGS | Linker |
| 118 | GGSGGGGIEPDPGGSGGS | Linker |
| 119 | GGGGGSGGGGSGGGGS | Linker |
| 120 | QLQLQESGGGLVQPGGSLRLSCAASGFTLDNYAIGWFRQAPGKEREGVSCIS SSDGSTYYADSVKGRFTISRNNAKGTVYLLMNSLKPEDTAVYYCATELVPA CTYSNGRGPLDGMDYWGKGTQVTVKP | FR alpha sdAb |
| 121 | EVQLLESGGGEVQPGGSLRLSCAASGSIFSIDATAWYRQAPGKQRELVAIITS SGSTNYPESVKGRFTISRDNAKNTVYLQMSSLRAEDTAVYYCNAITRYGGS TYDFWGQGTLVTVKP | FR alpha sdAb |
| 122 | EVQPGGSLRLSCAASETFGVVFTLGWYRQAPGKGREFVARVTGTDTVDYA ESVKGRFTISSDFARNTVYLQMNSLRAEDTAVYYCNTGAYWGQGTLVTVK P | FR alpha sdAb |
| 123 | EVQLVESGGGLVQPGGSLRLSCAASGFILDYYAIGWFRQAPGKEREGVLCID ASDDITYYADSVKGRFTISRDNAKNTVYLQMNSLKPEDTGVYYCATPIGLSS SCLLEYDYDYWGQGTLVTVKP | cMET sdAb |
| 124 | EVQLVESGGGLVQPGGSLRLSCAASGFTFSSFGMHWVRQAPGKGLEWVAY ISSDSSAIYYADTVKGRFTISRDNAKNSLYLQMNSLRDEDTAVYYCGRGREN IYYGSRLDYWGQGTTVTVSSGGGGSGGGGSGGGGSDIQLTQSPSFLSASVG DRVTITCKASQNVDTNVAWYQQKPGKAPKALIYSASYRYSGVPSRFSGSGS GTDFTLTISSLQPEDFATYYCQQYNNYPFTFGQGTKLEIK | B7H3 scFv |
| 125 | QVQLVQSGAEVKKPGSSVKVSCKASGYAFSYSWINWVRQAPGQGLEWMG RIFPGDGDTDYNGKFKGRVTITADKSTSTAYMELSSLRSEDTAVYYCARNV FDGYWLVYWGQGTLVTVSGSGGGGSGGGGTGGGGSDIVMTQTPLSLPVTP GEPASISCRSSKSLLHSNGITYLYWYLQKPGQSPQLLIYQMSNLVSGVPDRFS GSGSGTDFTLKISRVEAEDVGVYYCAQNLELPYTFGGGTKVEIK | CD20 scFv |
| 126 | QVQLQESGPGLVKPSETLSLTCTVSGGSISSYYWSWIRQPPGKGLEWIGYVY YSGTTNYNPSLKSRVTISVDTSKNQFSLKLSSVTAADTAVYYCASIAVTGFY FDYWGQGTLVTVSSGGGGSGGGGSGGGGSEIVLTQSPGTLSLSPGERVTLSC RASQRVNNNYLAWYQQRPGQAPRLLIYGASSRATGIPDRFSGSGSGTDFTLT ISRLEPEDFAVYYCQQYDRSPLTFGGGTKLEIK | DLL3 scFv |

-continued

SEQUENCE TABLE

| SEQ ID NO | SEQUENCE | DESCRIPTION |
|---|---|---|
| 127 | EVQLVESGGGLVQPGGSLRLSCAASGFTFSSFGMHWVRQAPGKGLEWVAYISSDSSAIYYADTVKGRFTISRDNAKNSLYLQMNSLRDEDTAVYYCGRGRENIYYGSRLDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | B7H3 Fd |
| 128 | DIQLTQSPSFLSASVGDRVTITCKASQNVDTNVAWYQQKPGKAPKALIYSASYRYSGVPSRFSGSGSGTDFTLTISSLQPEDFATYYCQQYNNYPFTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | B7H3 LC |
| 129 | EVQLVESGGGLVQPKGSLKLSCAASGFTFNTYAMNWVRQAPGKGLEWVARIRSKSNNYATYYADSVKDRFTISRDDSQSMLYLQMNNLKTEDTAMYYCVRQWDYDVRAMNYWGQGTSVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 5T4 Fd |
| 130 | DIVMTQSHIFMSTSVGDRVSITCKASQDVDTAVAWYQQKPGQSPKWYWASTRLTGVPDRFTGSGSGTDFTLTISNVQSEDLADYFCQQYSSYPYTFGGGIKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 5T4 LC |
| 131 | QVQLQESGPGLVKPSQTLSLTCTVSGGSISSFNYYWSWIRHHPGKGLEWIGYIYYSGSTYSNPSLKSRVTISVDTSKNQFSLTLSSVTAADTAVYYCARGYNWNYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | gpNMB Fd |
| 132 | EIVMTQSPATLSVSPGERATLSCRASQSVDNNLVWYQQKPGQAPRLLIYGASTRATGIPARFSGSGSGTEFTLTISSLQSEDFAVYYCQQYNNWPPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | gpNMB LC |
| 133 | QIQLVQSGPELKKPGETVKISCKASGYTFTNYGMNWVKQAPGKGLKWMAWINTYTGEPTYADDFKGRFAFSLETSASTASLQIINLKNEDTATYFCARIGDSSPSDYWGQGTTLTVSSSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | DLL3 Fd |
| 134 | SIVMTQTPKFLLVSAGDRVTITCKASQSVSNDVVWYQQKPGQSPKLLIYYASNRYTGVPDRFAGSGYGTDFSFTISTVQAEDLAVYFCQQDYTSPWTFGGGIKLEIRRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | DLL3 LC |
| 135 | GGGGGS | Peptide Linker |
| 136 | IEPDI | Linker |
| 137 | LEADT | Linker |
| 138 | IEPDG | Linker |
| 139 | IEPDV | Linker |
| 140 | IEPDS | Linker |
| 141 | IEPDT | Linker |
| 142 | LEPD | Linker |
| 143 | LEAF | Linker |
| 144 | IEPDP | Linker |
| 145 | QAVVTQEPSLTVSPGGTVTLTCRSSTGAVTTSNYANWVQQKPGQAPRGLIGGTNKRAPWTPARFSGSLLGGKAALTITGAQAEDEADYYCALWYSNLWVFGGGTKLTVLGGGGSGGGGEVQLVESGGGLVQPGGSLRLSCAASGFTFSSFGMHWVRQAPGKGLEWVAYISSDSSAIYYADTVKGRFTISRDNAKNSLYLQMNS | Second Polypeptide Chain of B7-H3 x |

SEQUENCE TABLE

| SEQ ID NO | SEQUENCE | DESCRIPTION |
|---|---|---|
|  | LRDEDTAVYYCGRGRENIYYGSRLDYWGQGTTVTVSSGGCGGGKVAALKE KVAALKEKVAALKEKVAALKE | CD3 Bispecific DART-A Diabody |
| 146 | DKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKC KVSNKALPAPIEKTISKAKGQPREPQVYTLPPSREEMTKNQVSLSCAVKGFY PSDIAVEWESNGQPENNYKTTPPVLDSDGSFFLVSKLTVDKSRWQQGNVFS CSVMHEALHNRYTQKSLSLSPGK | Third Polypeptide Chain of B7-H3 x CD3 Bispecific DART-A Diabody |
| 147 | GGSGGGGSGGGGSGGGGS | Linker |
| 148 | TGGSGGGGIEPDIGGSGGS | Linker |
| 149 | GGGGS | Linker |
| 150 | $X_1 X_2 X_3 X_4 X_5$ (P4 P3 P2 P1 ↓ P1')<br>X1 = I, L, Y, M, F, V, or A;<br>(P4 = I, L, Y, M, F, V, or A)<br>X2 = A, G, S, V, E, D, Q, N, or Y;<br>(P3 = A, G, S, V, E, D, Q, N, or Y)<br>X3 = H, P, A, V, G, S, or T;<br>(P2 = H, P, A, V, G, S, or T)<br>X4 = D or E; (P1 = D or E)<br>X5 = I, L, Y, M, F, V, T, S, G or A<br>(P1' = I, L, Y, M, F, V, T, S, G or A) | Linker consensus |
| 151 | X1 E X3 D X5 (P4 P3 P2 P1 ↓ P1')<br>X1 = I or L; (P4 =I or L)<br>(P3 = E)<br>X3 = P or A; (P2 = P or A)<br>X5 = I, V, T, S, or G (P1' = I, V, T, S, or G) | Linker consensus |
| 152 | LEPDG | Linker |
| 153 | LEADG | Linker |
| 154 | $X_1 QARX_5$ (P1QAR↓(A/V))<br>X1 = any amino acid; (P1 is any amino acid)<br>X5 = A or V | Linker consensus |
| 155 | $RQARX_5$ (RQAR(A/V))<br>X5 = A or V | Linker consensus |
| 156 | RQARV | Linker |
| 157 | X1X2 X3 X4 (P3 P2 P1 ↓ P1')<br>X1 = P, V or A; (P3 = P, V or A)<br>X2 = Q or D; (P2 = Q or D)<br>X3 = A or N; (P1 = A or N)<br>X4 = L, I or M (P1' = L, I or M) | Linker consensus |
| 158 | PX2X3X4 (P3 P2 P1 ↓ P1')<br>(P3 = P)<br>X2 = Q or D; (P2 = Q or D)<br>X3 = A or N; (P1 is A or N)<br>X4 = L or I (P1' is L or I) | Linker consensus |
| 159 | GSGATNFSLLKQAGDVEENPGP | P2A |
| 160 | ATNFSLLKQAGDVEENPGP | P2A |
| 161 | QCTNYALLKLAGDVESNPGP | E2A |
| 162 | VKQTLNFDLLKLAGDVESNPGP | F2A |
| 163 | EGRGSLLTCGDVEENPGP | T2A |
| 164 | LEGGGEGRGSLLTCGDVEENPGPR | T2A |

| SEQ ID NO | SEQUENCE | DESCRIPTION |
|---|---|---|
| 165 | GGATCTGGAGCAACAAACTTCTCACTACTCAAACAAGCAGGTGACGTGG AGGAGAATCCCGGACCC | P2A DNA |
| 166 | GSPAGLEADGSRQARVGS | Linker |
| 167 | EVQLVESGGGL VQPKGSLKLS CAASGFTFNT YAMNWVRQAP GKGLEWVARI RSKSNNYATY YADSVKDRFT ISRDDSQSML YLQMNNLKTE DTAMYXCVRQ WDYDVRAMNY WGQGTSVTVS S | anti-5T4 VH |
| 168 | DIVMTQSHIF MSTSVGDRVS ITCKASQDVD TAVAWYQQKP GQSPKLLIYW ASTRLTGVPD RFTGSGSGTD FTLTISNVQS EDLADYFCQQ YSSYPYTFGG GTKLEIK | anti-5T4 VL |
| 169 | DIQLTQSPSF LSASVGDRVT ITCKASQNVD TNVAWYQQKP GKAPKALIYS ASYRYSGVPS RFSGSGSGTD FTLTISSLQP EDFATYYCQQ YNNYPFTFGQ GTKLEIKGGG SGGGGEVQLV ESGGGLVQPG GSLRLSCAAS GFTFSTYAMN WVRQAPGKGL EWVGRIRSKY NNYATYYADS VKDRFTISRD DSKNSLYLQM NSLKTEDTAV YYCVRHGNFG NSYVSWFAYW GQGTLVTVSS GGCGGGEVAA LEKEVAALEK EVAALEKEVA ALEKGGGDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SREEMTKNQV SLWCLVKGFY PSDIAVEWES NGQPENNYKT TPPVLDSDGS FFLYSKLTVD KSRWQQGNVF SCSVMHEALH NHYTQKSLSL SPGK | First Polypeptide Chain of B7-H3 x CD3 Bispecific DART-A Diabody |
| 170 | GGGGSGGGGSGGGGS | Linker |
| 171 | GGS(GGS)n wherein n is 0 to 10 | Linker |
| 172 | (GGGGGS)n wherein n is 1 to 4 | Linker |
| 173 | (GGGGS)n wherein n is 1 to 5 | Linker |
| 174 | Gly$_x$Xaa-Gly$_y$-Xaa-Gly$_z$ Xaa is independently selected from A, V, L, I, M, F, W, P, G, S, T, C, Y, N,Q, K, R, H, D, or E x, y, and z are each integers in the range from 1-5 | Linker |
| 175 | Gly-Gly-Gly-Xaa-Gly-Gly-Gly-Xaa-Gly-Gly-Gly Xaa is independently selected from A, V, L, I, M, F, W, P, G, S, T, C, Y, N,Q, K, R, H, D, or E | Linker |
| 176 | ATTTGSSPGPT | Linker |
| 177 | GGGGG-C-GGGGG | Linker |
| 178 | (EAAAK)n n = 2-20 | Linker |
| 179 | AS-(AP)n-GT n = 2-20 | Linker |
| 180 | AS-(EAAAK)n-GT n = 2-20 | Linker |
| 181 | (GGGGA)n n = 2-20 | Linker |
| 182 | (PGGGS)n n = 2-20 | Linker |
| 183 | (AGGGS)n n = 2-20 | Linker |
| 184 | GGS-(EGKSSGSGSESKST)n-GGS n = 2-20 | Linker |

SEQUENCE TABLE

| SEQ ID NO | SEQUENCE | DESCRIPTION |
|---|---|---|
| 185 | (SSSSG)n<br>n = 1-9 | Linker |
| 186 | SSSASASSA | Linker |
| 187 | GSPGSPG | Linker |
| 188 | QVQLQESGPG LVKPSETLSL TCTVSGGSIS SYYWSWIRQP PGKGLEWIGY<br>VYYSGTTNYN PSLKSRVTIS VDTSKNQFSL KLSSVTAADT AVYYCASIAV<br>TGFYFDYWGQ GTLVTVSSGG GGSGGGGSGG GGSEIVLTQS PGTLSLSPGE<br>RVTLSCRASQ RVNNNYLAWY QQRPGQAPRL LIYGASSRAT GIPDRFSGSG<br>SGTDFTLTIS RLEPEDFAVY YCQQYDRSPL TFGGGTKLEI K | DLL3 scFv |
| 189 | QVQLVQSGAE VKKPGSSVKV SCKASGYAFS YSWINWVRQA<br>PGQGLEWMGR IFPGDGDTDY NGKFKGRVTI TADKSTSTAY MELSSLRSED<br>TAVYYCARNV FDGYWLVYWG QGTLVTVSS | CD20 VH |
| 190 | DIVMTQTPLS LPVTPGEPAS ISCRSSKSLL HSNGITYLYW YLQKPGQSPQ<br>LLIYQMSNLV SGVPDRFSGS GSGTDFTLKI SRVEAEDVGV YYCAQNLELP<br>YTFGGGTKVE IKRTV | CD20 VL |
| 191 | ACPWAVSGARASPGSAASPRLREGPELSPDDPAGLLDLRQGMFAQLVAQN<br>VLLIDGPLSWYSDPGLAGVSLTGGLSYKEDTKELVVAKAGVYYVFFQLELR<br>RVVAGEGSGSVSLALHLQPLRSAAGAAALALTVDLPPASSEANSAFGFQGR<br>LLHLSAGQRLGVHLHTEARARHAWQLTQGATVLGLFRVTPEIPAGLPSPRSE | 41BBL |
| 192 | EVQLVQSGAEVKKPGESLRISCKGSGYSFSTYWISWVRQMPGKGLEWMGKI<br>YPGDSYTNYSPSFQGQVTISADKSISTAYLQWSSLKASDTAMYYCARGYGIF<br>DYWGQGTLVTVSS | 41BB VH |
| 193 | SYELTQPPSVSVSPGQTASITCSGDNIGDQYAHWYQQKPGQSPVLVIYQDKN<br>RPSGIPERFSGSNSGNTATLTISGTQAMDEADYYCATYTGFGSLAVFGGGIK<br>LTVL | 41BB VL |
| 194 | QVQLQQWGAGLLKPSETLSLTCAVYGGSFSGYYWSWIRQSPEKGLEWIGEI<br>NHGGYVTYNPSLESRVTISVDTSKNQFSLKLSSVTAADTAVYYCARDYGPG<br>NYDWYFDLWGRGTLVTVSS | 41BB VH |
| 195 | EIVLTQSPATLSLSPGERATLSCRASQSVSSYLAWYQQKPGQAPRLLIYDASN<br>RATGIPARFSGSGSGTDFTLTISSLEPEDFAVYYCQQRSNWPPALTFGGGTKV<br>EIK | 41BB VL |
| 196 | QMQLVQSGAEVKKPGASVKVSCKASGYSFSGYYMHWVRQAPGQGLEWM<br>GWVNPMSGGTNYAQKFQGRVTITRDTSASTAYMELSSLRSEDTAVYYCAR<br>EGMAMRLELDKWGQGTLVTVSS | 41BB VH |
| 197 | SYELTQPPSVSVAPGKTARITCGGNNIGSKSVHWYQQKPGQAPVLVIYYDSD<br>RPSGIPERFSGSNSGNTATLTISRVEAGDEADYYCQVWDSSSVVFGGGTQLT | 41BB VL<br>VL |
| 198 | QDSTSDLIPAPPLSKVPLQQNFQDNQFHGKWYVVGQAGNIKLREDKDPNK<br>MMATIYELKEDKSYNVTGVTFDDKKCTYAISTFVPGSQPGEFTLGKIKSFPG<br>HTSSLVRVVSTNYNQHAMVFFKFVFQNREEFYITLYGRTKELTSELKENFIR<br>FSKSLGLPENHIVFPVPIDQCIDG | 41BB<br>Anticalin |
| 199 | QDSTSDLIPAPPLSKVPLQQNFQDNQFHGKWYVVGQAGNIRLREDKDPIKM<br>MATIYELKEDKSYDVTMVKFDDKKCMYDIWTFVPGSQPGEFTLGKIKSFPG<br>HTSSLVRVVSTNYNQHAMVFFKFVFQNREEFYITLYGRTKELTSELKENFIR<br>FSKSLGLPENHIVFPVPIDQCIDG | 41BB<br>Anticalin |
| 200 | QDSTSDLIPAPPLSKVPLQQNFQDNQFHGKWYVVGQAGNIRLREDKDPNKM<br>MATIYELKEDKSYDVTAVAFDDKKCTYDIWTFVPGSQPGEFTLGKIKSFPGH<br>TSSLVRVVSTNYNQHAMVFFKFVFQNREEFYITLYGRTKELTSELKENFIRFS<br>KSLGLPENHIVFPVPIDQCIDG | 41BB<br>Anticalin |
| 201 | QDSTSDLIPAPPLSKVPLQQNFQDNQFHGKWYVVGQAGNIKLREDKDPNK<br>MMATIYELKEDKSYDVTAVAFDDKKCTYDIWTFVPGSQPGEFTLGKIKSFP<br>GHTSSLVRVVSTNYNQHAMVFFKFVFQNREEFYITLYGRTKELTSELKENFI<br>RFSKSLGLPENHIVFPVPIDQCIDG | 41BB<br>Anticalin |
| 202 | QDSTSDLIPA PPLSKVPLQQ NFQDNQFHGK WYVVGQAGNI<br>KLREDKSMMA TIYELKEDKS YDVTGVSFDD KKCTYAIMTF VPGSQPGEFT<br>LGKIKSFPGH TSSLVRVVST NYNQHAMVFF KFVFQNREEF YITLYGRTKE<br>LTSELKENFI RFSKSLGLPE NHIVFPVPID QCIDG | 41BB<br>Anticalin |

SEQUENCE TABLE

| SEQ ID NO | SEQUENCE | DESCRIPTION |
|---|---|---|
| 203 | QDSTSDLIPA PPLSKVPLQQ NFQDNQFHGK WYVVGQAGNI KLREDKDPVK MMATIYELKE DKSYDVTGVT FDDKKCRYDI STFVPGSQPG EFTFGKIKSF PGHTSSLVRV VSTNYNQHAM VFFKFVFQNR EEFYITLYGR TKELTSELKE NFIRFSKSLG LPENHIVFPV PIDQCIDG | 41BB Anticalin |
| 204 | QDSTSDLIPAPPLSKVPLQQNFQDNQFHGKWYVVGQAGNIRLREDKDPHKM MATIYELKEDKSYDVTGVTFDDKKCTYAISTFVPGSQPGEFTLGKIKSFPGH TSSLVRVVSTNYNQHAMVFFKFVFQNREEFYITLYGRTKELTSELKENFIRFS KSLGLPENHIVFPVPIDQCIDG | 41BB Anticalin |
| 205 | QDSTSDLIPAPPLSKVPLQQNFQDNQFHGKWYVVGQAGNIKLREDKDPNK MMATIYELKEDKSYDVTGVTFDDKKCTYAISTLVPGSQPGEFTFGKIKSFPG HTSSLVRVVSTNYNQHAMVFFKFVFQNREEFYITLYGRTKELTSELKENFIR FSKSLGLPENHIVFPVPIDQCIDG | 41BB Anticalin |
| 206 | QDSTSDLIPAPPLSKVPLQQNFQDNQFHGKWYVVGQAGNIRLREDKDPSKM MATIYELKEDKSYDVTAVTFDDKKCNYAISTFVPGSQPGEFTLGKIKSPGH TSSLVRVVSTNYNQHAMVFFKFVFQNREEFYITLYGRTKELTSELKENFIRFS KSLGLPENHIVFPVPIDQCIDG | 41BB Anticalin |
| 207 | REGPELSPDDPAGLLDLRQGMFAQLVAQNVLLIDGPLSWYSDPGLAGVSLT GGLSYKEDTKELVVAKAGVYYVFFQLELRRVVAGEGSGSVSLALHLQPLRS AAGAAAALALTVDLPPASSEARNSAFGFQGRLLHLSAGQRLGVHLHTEARAR HAWQLTQGATVLGLFRVTPEIPAGLPSPRSE | 71-254 of human 41BBL |
| 208 | LDLRQGMFAQLVAQNVLLIDGPLSWYSDPGLAGVSLTGGLSYKEDTKELV VAKAGVYYVFFQLELRRVVAGEGSGSVSLALHLQPLRSAAGAAAALALTVD LPPASSEARNSAFGFQGRLLHLSAGQRLGVHLHTEARARHAWQLTQGATVL GLFRVTPEIPAGLPSPRSE | 85-254 of human 41BBL |
| 209 | DPAGLLDLRQGMFAQLVAQNVLLIDGPLSWYSDPGLAGVSLTGGLSYKEDT KELVVAKAGVYYVFFQLELRRVVAGEGSGSVSLALHLQPLRSAAGAAAALA LTVDLPPASSEARNSAFGFQGRLLHLSAGQRLGVHLHTEARARHAWQLTQG ATVLGLFRVTPEIPAGLPSPRSE | 80-254 of human 41BBL |
| 210 | PWAVSGARASPGSAASPRLREGPELSPDDPAGLLDLRQGMFAQLVAQNVLL IDGPLSWYSDPGLAGVSLTGGLSYKEDTKELVVAKAGVYYVFFQLELRRVV AGEGSGSVSLALHLQPLRSAAGAAAALALTVDLPPASSEARNSAFGFQGRLL HLSAGQRLGVHLHTEARARHAWQLTQGATVLGLFRVTPEIPAGLPSPRSE | 52-254 of human 4-1BBL |
| 211 | REGPELSPDDPAGLLDLRQGMFAQLVAQNVLLIDGPLSWYSDPGLAGVSLT GGLSYKEDTKELVVAKAGVYYVFFQLELRRVVAGEGSGSVSLALHLQPLRS AAGAAAALALTVDLPPASSEARNSAFGFQGRLLHLSAGQRLGVHLHTEARAR HAWQLTQGATVLGLFRVTPEIPAGL | 71-248 of human 41BBL |
| 212 | LDLRQGMFAQLVAQNVLLIDGPLSWYSDPGLAGVSLTGGLSYKEDTKELV VAKAGVYYVFFQLELRRVVAGEGSGSVSLALHLQPLRSAAGAAAALALTVD LPPASSEARNSAFGFQGRLLHLSAGQRLGVHLHTEARARHAWQLTQGATVL GLFRVTPEIPAGL | 85-248 of human 41BBL |
| 213 | DPAGLLDLRQGMFAQLVAQNVLLIDGPLSWYSDPGLAGVSLTGGLSYKEDT KELVVAKAGVYYVFFQLELRRVVAGEGSGSVSLALHLQPLRSAAGAAAALA LTVDLPPASSEARNSAFGFQGRLLHLSAGQRLGVHLHTEARARHAWQLTQG ATVLGLFRVTPEIPAGL | 80-248 of human 41BBL |
| 214 | PWAVSGARASPGSAASPRLREGPELSPDDPAGLLDLRQGMFAQLVAQNVLL IDGPLSWYSDPGLAGVSLTGGLSYKEDTKELVVAKAGVYYVFFQLELRRVV AGEGSGSVSLALHLQPLRSAAGAAAALALTVDLPPASSEARNSAFGFQGRLL HLSAGQRLGVHLHTEARARHAWQLTQGATVLGLFRVTPEIPAGL | 52-248 of human 41BBL |
| 215 | EVQLLESGGGEVQPGGSLRLSCAASGFSFSINAMGWYRQAPGKRREFVAAI ESGRNTVYAESVKGRFTISRDNAKNTVYLQMSSLRAEDTAVYYCGLLKGN RVVSPSVAYWGQGTLVTVKP | 41BB sdAb |
| 216 | QVSHRYPRIQSIKVQFTEYKKEKGFILTSQKEDEIMKVQNNSVIINCDGFYLIS LKGYFSQEVNISLHYQKDEEPLFQLKKVRSVNSLMVASLTYKDKVYLNVTT DNTSLDDFHVNGGELILIHQNPGEFCVL | OX40 ligand |
| 217 | QVSHRYPRFQSIKVQFTEYKKEKGFILTSQKEDEIMKVQNNSVIINCDGF YLISLKGYFSQEVNISLHYQKDEEPLFQLKKVRSVNSLMVASLTYKDKVY LNVTTDNTSLDDFHVNGGELILIHQNPGEFCVL | OX40 ligand |

SEQUENCE TABLE

| SEQ ID NO | SEQUENCE | DESCRIPTION |
|---|---|---|
| 218 | QVSHRYPRIQSIKVQFTEYKKEKGFILTSQKEDEIMKVQNNSVIINCDGFYLIS LKGYFSQEVNISLHYQKDEEPLFQLKKVRSVNSLMVASLTYKDKVYLNVTT DNTSLDDFHVNGGELILIHQNPGEFCVL | OX40 ligand |
| 219 | QVSHRYPRIQSIKVQFTEYKKEKGFILTSQKEDEIMKVQNNSVIINCDGF YLISLKGYFSQEVNISLHYQKDEEPLFQLKKVRSVNSLMVASLTYKDKVY LNVTTDNTSLDDFHVNGGELILIHQNPGEFCVL | OX40 ligand |
| 220 | VSHRYPRIQSIKVQFTEYKKEKGFILTSQKEDEIMKVQNNSVIINCDGFYLISL KGYFSQEVNISLHYQKDEEPLFQLKKVRSVNSLMVASLTYKDKVYLNVTTD NTSLDDFHVNGGELILIHQNPGEFCVL | OX40 ligand |
| 221 | EVQLVQSGAEVKKPGASVKVSCKASGYTFTDSYMSWVRQAPGQGLEWIGD MYPDNGDSSYNQKFRERVTITRDTSTSTAYLELSSLRSEDTAVYYCVLAPR WYFSVWGQGTLVTVSS | OX40 VH |
| 222 | DIQMTQSPSSLSASVGDRVTITCRASQDISNYLNWYQQKPGKAPKLLIYYTS RLRSGVPSRFSGSGSGTDFTLTISSLQPEDFATYYCQQGHTLPPTFGQGTKVE IKRT | OX40 VL |
| 223 | EVQLVESGGGLVQPGGSLKLSCAASGFTFSGSAMHWVRQASGKGLEWVGR IRSKANSYATAYAASVKGRFTISRDDSKNTAYLQMNSLKTEDTAVYYCTSGI YDSSGYDYWGQGTLVTVSS | OX40 VH |
| 224 | DIVMTQSPLSLPVTPGEPASISCRSSQSLLHSNGYNYLDWYLQKPGQSPQLLI YLGSNRASGVPDRFSGSGSGTDFTLKISRVEAEDVGVYYCMQALQTPLTFG GGTKVEIK | OX40 VL |
| 225 | EVQLLESGGGEVQPGGSLRLSCAASGFTFSDAFMYWVRQAPGKGLEWVSSI SNRGLKTAYAESVKGRFTISRDNAKNTLYLQMSSLRAEDTAVYYCSRDVDG DFRGQGTLVTVKP | OX40 sdAb |
| 226 | QLETAKEPCMAKFGPLPSKWQMASSEPPCVNKVSDWKLEILQNGLYLIYGQ VAPNANYNDVAPFEVRLYKNKDMIQTLTNKSKIQNVGGTYELHVGDTIDLI FNSEHQVLKNNTYWGIILLANPQFIS | GITR ligand |
| 227 | QVQLVESGGGVVQPGRSLRLSCAASGFTFSSYAMSWVRQAPGKGLEWVAS ISSGGTTYYPDSVKGRFTISRDNSKNTLYLQMNSLRAEDTAVYYCARVGGY YDSMDYWGQGTLVTVSS | GITR VH |
| 228 | EIVLTQSPGTLSLSPGERATLSCRASESVDNYGVSFMNWYQQKPGQAPRLLI YAASNQGSGIPDRFSGSGSGTDFTLTISRLEPEDFAVYYCQQTKEVTWTFGQ GTKVEIK | GITR VL |
| 229 | QVTLRESGPALVKPTQTLTLTCTFSGFSLSTSGMGVGWIRQPPGKALEWLAH IWWDDDKYYQPSLKSRLTISKDTSKNQVVLTMTNMDPVDTATYYCARTRR YFPFAYWGQGTLVTVSS | GITR VH |
| 230 | EIVMTQSPATLSVSPGERATLSCKASQNVGTNVAWYQQKPGQAPRLLIYSA SYRYSGIPARFSGSGSGTEFTLTISSLQSEDFAVYYCQQYNTDPLTFGGGTKV EIK | GITR VL |
| 231 | QVQLQESGPGLVKPSETLSLTCTVSGGSISSGGYFWSWIRQPPGKGLEWIGYI YYSGTTYYNPSLKSRVTISIDTSKNQFSLKLSSVTAADTAVYYCARDLFYYD TSGPRGFDPWGQGTLVTVSS | GITR VH |
| 232 | EIVLTQSPGTLSLSPGERATLSCRASQTVSSNYLAWYQQKPGQAPRLLIYGSS TRATGIPDRFSGSGSGTDFTLTISRLEPEDFAVYYCQQYDSSPWTFGQGTKVE IK | GITR VL |
| 233 | QVQLVESGGGVVQPGRSLRLSCAASGFTFSSYGMHWVRQAPGKGLEWVA VIWYPGSNKYYAESVKGRFTISRDNSKNTLYLQMNSLRAEDTAVYYCARG GELGRYYYYGMDVWGQGTTVTVSS | GITR VH |
| 234 | DIQMTQSPSSLSASVGDRVTVTCRASQGIRNDLGWYQQKPGKAPKRLIYAA SSLQSGVPSRFSGSGSGTEFTLTISSLQPEDFATYYCLQHNNYPWTFGQGTKV DIK | GITR VL |
| 235 | EVQLLESGGGEVQPGGSLRLSCAASGSVFSIDAMGWYRQAPGKQRELVAVL SGISSAKYAASAPGRFTISRDNAKNTVYLQMSSLRAEDTAVYYCYADVSTG WGRDAHGYWGQGTLVTV | GITR sdAb |

-continued

SEQUENCE TABLE

| SEQ ID NO | SEQUENCE | DESCRIPTION |
|---|---|---|
| 236 | MPEEGSGCSVRRRPYGCVLRAALVPLVAGLVICLVVCIQRFAQAQQQLPLES LGWDVAELQLNHTGPQQDPRLYWQGGPALGRSFLHGPELDKGQLRIHRDG IYMVHIQVTLAICSSTTASRHHPTTLAVGICSPASRSISLLRLSFHQGCTIASQR LTPLARGDTLCTNLTGTLLPSRNTDETFFGVQWVRP | UniProt No. P32970, CD70-ECD residues 39-193 (underline) |
| 237 | QVQLVESGGGVVQPGRSLRLSCAASGFTFSSYDMHWVRQAPGKGLEWVA VIWYDGSNKYYADSVKGRFTISRDNSKNTLYLQMNSLRAEDTAVYYCARG SGNWGFFDYWGQGTLVTVSS | CD70 VH |
| 238 | DIQMTQSPSSLSASVGDRVTITCRASQGISRWLAWYQQKPEKAPKSLIYAAS SLQSGVPSRFSGSGSGTDFTLTISSLQPEDFATYYCQQYNTYPRTFGQGTKVE IK | CD70 VL |
| 239 | QVQLQQSGGGLVQPGGSLRLSCAASGSIFSINGMGWYRQAPGKERELVAGL TSGGSVTNYADSVKGRFTISRDNAKNTVYLQMNSLKPEDTAVYYCRAEIFT RTGENYYGMDYWGKGTQVTVKP | ICOS sdAb |
| 240 | EVQLVESGGGEVQPGGSLRLSCAASGRMFSNYAMGWFRQAPGKEREFVAA INYRRDAADYAESVKGRFTISRDNAKNTVYLQMNSLRAEDTAVYYCGFTY AGWASSRRDDYNYWGQGTLVTVKP | CD28 sdAb |
| 241 | QAVVTQEPSLTVSPGGTVTLTCGSSTGAVTTSNYANWVQQKPGQAFRGLIG GTNKRAPGVPARFSGSLLGGKAALTISGAQPEDEADYYCALWYSNHWVFG CGTKLTVL | anti-CD3 VL (CON) |
| 242 | MQIPQAPWPVVWAVLQLGWRPGWFLDSPDRPWNPPTFSPALLVVTEGDNA TFTCSFSNTSESFVLNWYRMSPSNQTDKLAAFPEDRSQPGQDCRFRVTQLPN GRDFHMSVVRARRNDSGTYLCGAISLAPKAQIKESLRAELRVTERRAEVPT AHPSPSPRPAGQFQTLVVGVVGGLLGSLVLLVWVLAVICSRAARGTIGARR TGQPLKEDPSAVPVFSVDYGELDFQWREKTPEPPVPCVPEQTEYATIVFPSG MGTSSPARRGSADGPRSAQPLRPEDGHCSWPL | PD-1 |
| 243 | QVQLVQSGGGLVQPGGSLRLSCVASGSMTGANTMGWYRQAPGKQRDLVA LIGNYHYADSVKGRFTISRENAKNTVILQMNSLNPEDTAVYYCYLYTDNLG TSWGQGTLVTVKPGG | 18H10 |
| 244 | GGSGGS | (GGS)2 linker |
| 245 | GGSGGS | (GGS)2 linker |
| 246 | GGSGGSGGS | (GGS)3 linker |
| 247 | GGSGGSGGSGGS | (GGS)4 linker |
| 248 | GGSGGSGGSGGSGGS | (GGS)5 linker |
| 249 | GGGG | glycine linker |
| 250 | GGGGG | glycine linker |
| 251 | EVQLVESGGGEVQPGGSLRLSCAASGSMTGANTMGWYRQAPGKGRDLVSL IGNYVTHYAESVKGRFTISRDNAKNTLYLQMSSLRAEDTAVYYCYLYTDNL GTSWGQGTLVTVKPGG | hz18H10v1 |
| 252 | EVQLVESGGGEVQPGGSLRLSCAASGSMTGANTMGWYRQAPGKQRDLVSL IGNYVTHYAESVKGRFTISRDNAKNTLYLQMSSLRAEDTAVYYCYLYTDNL GTSWGQGTLVTVKPGG | hz18H10v2 |
| 253 | EVQLVESGGGEVQPGGSLRLSCAASGSMTGANTMGWYRQAPGKQRDLVSL IGNYVTHYAESVKGRFTISRDNAKNTVYLQMSSLRAEDTAVYYCYLYTDNL GTSWGQGTLVTVKPGG | hz18H10v3 |

-continued

| SEQ ID NO | SEQUENCE | DESCRIPTION |
|---|---|---|
| 254 | EVQLVESGGGEVQPGGSLRLSCAASGSMTGANTMGWYRQAPGKQRDLVA LIGNYVTHYAESVKGRFTISRDNAKNTVYLQMSSLRAEDTAVYYCYLYTDN LGTSWGQGTLVTVKPGG | hz18H10v4 |
| 255 | EVQLVESGGGEVQPGGSLRLSCAASGSMTGANTMGWYRQAPGKQRDLVA LIGNYVTHYAESVKGRFTISRENAKNTVYLQMSSLRAEDTAVYYCYLYTDN LGTSWGQGTLVTVKPGG | hz18H10v5 |
| 256 | EVQLVESGGGEVQPGGSLRLSCAASGSVTGANTMGWYRQAPGKQRDLVAL IGNYVTHYAESVKGRFTISRDNAKNTVYLQMSSLRAEDTAVYYCYLYTDNL GTSWGQGTLVTVKPGG | hz18H10v6 |
| 257 | EVQLVESGGGEVQPGGSLRLSCAASGSITGANTMGWYRQAPGKQRDLVALI GNYVTHYAESVKGRFTISRDNAKNTVYLQMSSLRAEDTAVYYCYLYTDNL GTSWGQGTLVTVKPGG | hz18H10v7 |
| 258 | EVQLVESGGGEVQPGGSLRLSCAASGSVTGANTMGWYRQAPGKQRDLVSL IGNYVTHYAESVKGRFTISRDNAKNTLYLQMSSLRAEDTAVYYCYLYTDNL GTSWGQGTLVTVKPGG | hz18H10v8 |
| 259 | EVQLVESGGGEVQPGGSLRLSCAASGSVTGANTMGWYRQAPGKQRDLVSL IGNYVTHYAESVKGRFTISRDNAKNTVYLQMSSLRAEDTAVYYCYLYTDNL GTSWGQGTLVTVKPGG | hz18H10v9 |
| 260 | EVQLVESGGGEVQPGGSLRLSCAASGSMTGANTMGWYRQAPGKQRDLVSL IGNYVTHYAESVKGRFTISRENAKNTVYLQMSSLRAEDTAVYYCYLYTDNL GTSWGQGTLVTVKPGG | hz18H10v10 |
| 261 | EVQLVESGGGEVQPGGSLRLSCAASGSVTGANTMGWYRQAPGKQRDLVSL IGNYVTHYAESVKGRFTISRENAKNTVYLQMSSLRAEDTAVYYCYLYTDNL GTSWGQGTLVTVKPGG | hz18H10v11 |
| 262 | EVQLVESGGGEVQPGGSLRLSCAASGSVTGANTMGWYRQAPGKQRDLVAL IGNYVTHYAESVKGRFTISRENAKNTVYLQMSSLRAEDTAVYYCYLYTDNL GTSWGQGTLVTVKPGG | hz18H10v12 |
| 263 | EVQLVESGGGEVQPGGSLRLSCAASGSMTGANTMGWYRQAPGKQRELVA LIGNYVTHYAESVKGRFTISRENAKNTVYLQMSSLRAEDTAVYYCYLYTDN LGTSWGQGTLVTVKPGG | hz18H10v13 |
| 264 | EVQLVESGGGEVQPGGSLRLSCAASGSVTGANTMGWYRQAPGKQRDLVAL IGNYVTHYAESVKGRFTISRDNAKNTLYLQMSSLRAEDTAVYYCYLYTDNL GTSWGQGTLVTVKPGG | hz18H10v14 |
| 265 | EVQLVESGGGEVQPGGSLRLSCAASGSITGANTMGWYRQAPGKQRDLVALI GNYVTHYAESVKGRFTISRDNAKNTLYLQMSSLRAEDTAVYYCYLYTDNL GTSWGQGTLVTVKPGG | hz18H10v15 |
| 266 | EVQLVESGGGEVQPGGSLRLSCAASGSITGANTMGWYRQAPGKQRDLVALI GNYVTHYAESVKGRFTISRENAKNTVYLQMSSLRAEDTAVYYCYLYTDNL GTSWGQGTLVTVKPGG | hz18H10v16 |
| 267 | EVQLVESGGGEVQPGGSLRLSCAASGSITGANTMGWYRQAPGKQRDLVALI GNYVTHYAESVKGRFTISRDNAKNTVYLQMNSLRAEDTAVYYCYLYTDNL GTSWGQGTLVTVKPGG | hz18H10v17 |
| 268 | GSMTGANTMG | CDR1 |
| 269 | GGSGGSGGS | (GGS)3 linker |
| 270 | GGSGGSGGSGGS | (GGS)4 linker |
| 271 | GGSGGSGGSGGSGGS | (GGS)5 linker |
| 272 | GSVTGANTMG | CDR1 |
| 273 | GSITGANTMG | CDR1 |
| 274 | GGSGGS | (GGS)2 linker |

| SEQ ID NO | SEQUENCE | DESCRIPTION |
|---|---|---|
| 275 | GGSGGSGGS | (GGS)3 linker |
| 276 | GGSGGSGGSGGS | (GGS)4 linker |
| 277 | GGSGGSGGSGGSGGS | (GGS)5 linker |
| 278 | LIGNYVTH | CDR2 |
| 279 | GGSGGS | (GGS)2 linker |
| 280 | GGSGGSGGS | (GGS)3 linker |
| 281 | GGSGGSGGSGGS | (GGS)4 linker |
| 282 | GGSGGSGGSGGSGGS | (GGS)5 linker |
| 283 | YTDNLGTS | CDR3 |
| 284 | PAPGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK | Fc xELL |
| 285 | DKTHTCPPCPAPPVAGPSVFLFPPKPKDTLMISRTPEVTCVVVDVKHEDPEVKFNWY VDGVEVHNAKTKPREEEYNSTYRVVSVLTVLHQDWLNGKEYKCKVSNKALPAPIEK TISKAKGQPREPQVYTLPPSREEMTKNQVSLTCDVSGFYPSDIAVEWESDGQPENNY KTTPPVLDSDGSFFLYSKLTVDKSRWEQGDVFSCSVMHEALHNHYTQKSLSLSPGK | Fc-Het-1 |
| 286 | DKTHTCPPCPAPPVAGPSVFLFPPKPKDTLMISRTPEVTCVVVDVKHEDPEVKFNWY VDGVEVHNAKTKPREEQYNSTYRVVSVLTVLHQDWLNGKEYKCKVSNKALPAPIEK TISKAKGQPREPQVYTLPPSREQMTKNQVKLTCLVKGFYPSDIAVEWESNGQPENNY KTTPPVLDSDGSFFLYSKLTVDKSRWQQGNVFSCSVMHEALHNHYTQKSLSLSPGK | Fc-Het-2 |
| 287 | EVQLVESGGGLVQPGGSLRLSCAASGFTFSTYAMNWVRQAPGKGLEWVGRIRSKYN NYATYYADSVKGRFTISRDDSKNTLYLQMNSLRAEDTAVYYCVRHGNFGDSYVSWF AYWGQGTLVTVSS | CD3-VH32 |
| 288 | QAVVTQEPSLTVSPGGTVTLTCGSSTGAVTTSNYANWVQQKPGKSPRGLIGGTNKRA PGVPARFSGSLLGGKAALTISGAQPEDEADYYCALWYSNHWVFGGGTKLTVL | CD3-VL20 |
| 289 | QAVVTQEPSLTVSPGGTVTLTCGSSTGAVTTSNYANWVQQKPGKSPRGLIGGTNKRA PGVPARFSGSLLGGKAALTISGAQPEDEADYYCALWYSNHWVFGCGTKLTVL | CD3-VL21 |
| 290 | EVQLVESGGGLVQPGGSLRLSCAASGFTFSTYAMNWVRQAPGKCLEWVARIRSKYN NYATYYADTVKGRFTISRDDAKNTLYLQMSSLRAEDTAVYYCVRHGNFGDSYVSW FAYWGQGTLVTV | CD3-VH34 |
| 291 | DKTHTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIEK TISKAKGQPREPQVYTLPPCRDELTKNQVSLWCLVKGFYPSDIAVEWESNGQPENNY KTTPPVLDSDGSFFLYSKLTVDKSRWQQGNVFSCSVMHEALHNHYTQKSLSLSP | Knob Fc |
| 292 | DKTHTCPPCPAPELLGGPSVFLFPPKPKDTLMRSRTPEVTCVVVDVSHEDPEVKFNW YVDGVEVHNAKTKPREEQYNSTYRVVSVLTVLHQDWLNGKEYKCKVSNKALPAPIE KTISKAKGQPREPQVCTLPPSRDELTKNQVSLSCAVKGFYPSDIAVEWESNGQPENNY KTTPPVLDSDGSFFLVSKLTVDKSRWQQGNVFSCSVMHEALHNHYTQKSLSLSP | Hole Fc |
| 293 | DKTHTCPPCPAPGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKTI SKAKGQPREPQVYTLPPCRDELTKNQVSLWCLVKGFYPSDIAVEWESNGQPENNYK TTPPVLDSDGSFFLYSKLTVDKSRWQQGNVFSCSVMHEALHNHYTQKSLSLSP | Knob Fc |

-continued

| SEQ ID NO | SEQUENCE | DESCRIPTION |
|---|---|---|
| 294 | DKTHTCPPCPAPGGPSVFLFPPKPKDTLMRSRTPEVTCVVVDVSHEDPEVKFNWYVD GVEVHNAKTKPREEQYNSTYRVVSVLTVLHQDWLNGKEYKCKVSNKALPAPIEKTI SKAKGQPREPQVCTLPPSRDELTKNQVSLSCAVKGFYPSDIAVEWESNGQPENNYK TTPPVLDSDGSFFLVSKLTVDKSRWQQGNVFSCSVMHEALHNHYTQKSLSLSP | Hole Fc |
| 295 | DKTHTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIEK TISKAKGQPREPQVCTLPPSRDELTKNQVSLSCAVKGFYPSDIAVEWESNGQPENNYK TTPPVLDSDGSFFLVSKLTVDKSRWQQGNVFSCSVMHEALHNRYTQKSLSLSP | Hole Fc |
| 296 | DKTHTCPPCPAPGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKTI SKAKGQPREPQVCTLPPSRDELTKNQVSLSCAVKGFYPSDIAVEWESNGQPENNYKT TPPVLDSDGSFFLVSKLTVDKSRWQQGNVFSCSVMHEALHNRYTQKSLSLSP | Hole Fc |
| 297 | DKTHTCPPCPAPELLGGPSVFLFPPKPKDTLYISRTPEVTCVVVDVSHEDPEVKFNWY VDGVEVHNAKTKPREEQYNSTYRVVSVLTVLHQDWLNGKEYKCKVSNKALPAPIEK TISKAKGQPREPQVYTLPPCRDELTKNQVSLWCLVKGFYPSDIAVEWESNGQPENNY KTTPPVLDSDGSFFLYSKLTVDKSRWQQGNVFSCSVVHEALHNHYTQKSLSLSP | Knob Fc |
| 298 | DKTHTCPPCPAPGGPSVFLFPPKPKDTLYISRTPEVTCVVVDVSHEDPEVKFNWYVDG VEVHNAKTKPREEQYNSTYRVVSVLTVLHQDWLNGKEYKCKVSNKALPAPIEKTIS KAKGQPREPQVYTLPPCRDELTKNQVSLWCLVKGFYPSDIAVEWESNGQPENNYKT TPPVLDSDGSFFLYSKLTVDKSRWQQGNVFSCSVVHEALHNHYTQKSLSLSP | Knob Fc |
| 299 | DKTHTCPPCPAPELLGGPSVFLFPPKPKDTLYISRTPEVTCVVVDVSHEDPEVKFNWY VDGVEVHNAKTKPREEQYNSTYRVVSVLTVLHQDWLNGKEYKCKVSNKALPAPIEK TISKAKGQPREPQVCTLPPSRDELTKNQVSLSCAVKGFYPSDIAVEWESNGQPENNYK TTPPVLDSDGSFFLVSKLTVDKSRWQQGNVFSCSVVHEALHNRYTQKSLSLSP | Hole Fc |
| 300 | DKTHTCPPCPAPGGPSVFLFPPKPKDTLYISRTPEVTCVVVDVSHEDPEVKFNWYVDG VEVHNAKTKPREEQYNSTYRVVSVLTVLHQDWLNGKEYKCKVSNKALPAPIEKTIS KAKGQPREPQVCTLPPSRDELTKNQVSLSCAVKGFYPSDIAVEWESNGQPENNYKTT PPVLDSDGSFFLVSKLTVDKSRWQQGNVFSCSVVHEALHNRYTQKSLSLSP | Hole Fc |
| 301 | EVQLVESGGGEVQPGGSLRLSCAASGFSFSSNVMMWVRQAPGKGLEWVST IYSSGTGTFYAESVKGRFTISRDNAKNTLYLQMSSLRPEDTAVYYCATSGPV RGWGPRSQGTLVTVKP | B7H3 sdAb B7h3 hz1A5v51 |
| 302 | EVQLVESGGGEVQPGGSLRLSCAASGSTFSSYHMSWFRQAPGKQREPVATS HHGGTTNYAGSVKGRFTISRDNAKNTVYLQMNTLRAEDTAVYYCKADHG YQGRGMGQGTLVTVKP | sdAb B7H3 hz58E05v27 |
| 303 | EVQLVESGGGEVQPGGSLRLSCAASGFTFSSYHMSWFRQAPGKQRELVATS HHGGTTNYAGSVKGRFTISRDNAKNTVYLQMNTLRAEDTAVYYCKADHG YQGRGMGQGTLVTVKP | sdAb B7H3 hz58E05v55 |
| 304 | EVQLVESGGGEVQPGGSLRLSCAASGFTFSSYHMSWFRQAPGKQREPVATS HHGGTTNYAGSVKGRFTISRDNAKNTVYLQMNTLRAEDTAVYYCKADHG YQGRGMGQGTLVTVKP | sdAb B7H3 hz58E05v48 |
| 305 | EVQLVESGGGEVQPGGSLRLSCAPSERTFSTYTMGWFRQAPGKEREFVAVV NWGGGSKYYAESVKGRFTISRDNAKNTVYLQMSSLRAEDTAVYYCAAGG AYSGPYYDTRQYTYWGQGTLVTVKPGG | sdAb B7H3 hz57B04v24 |
| 306 | EVQLVESGGGEVQPGGSLRLSCAASGSIFSINAMGWYRQAPGKQRELVAGF TGDTNTIYAESVKGRFTISRDNAKNTVYLQMSSLRAEDTAVYYCAADVQLF SRDYEFWGQGTLVTVKP | sdAb DLL3 hz10D9v7 |
| 307 | EVQLVESGGGEVQPGGSLRLSCGPSEIITSDKSMGWVRQAPGKQRNLVAGIS NVGSTNYAQSVKGRFTISRDNAKNTVYLQMSSLRAEDTAVYYCYARDFEN EMGQGTLVTVKP | sdAb DLL3 hz8E7v16 |
| 308 | GFSFSINAMG | 41BB CDR1 |
| 309 | AIESGRNTV | 41BB CDR2 |
| 310 | LKGNRVVSPSVAY | 41BB CDR3 |

| SEQ ID NO | SEQUENCE | DESCRIPTION |
|---|---|---|
| 311 | EVQLVESGGGLVQPGGSLRLSCAASGFTFSTYAMNWVRQAPGKCLEWVGR IRSKYNNYATYYADSVKGRFTISRDDSKNTLYLQMNSLRAEDTAVYYCVRH GNFGDSYVSWFAMGQGTLVTVSS | CD3-VH33 |
| 312 | GFTFNTYAMN | anti-CD3 VH CDR1 |
| 313 | RIRSKYNNYATY | anti-CD3 VH CDR2 |
| 314 | HGNFGDSYVSWFAY | CD3-VH7, VH33 CDR3 |
| 315 | ALWYSNHWV | CD3-VL2, VL21 CDR3 |
| 316 | VLWYSNRWV | CD3-VL8 CDR3 |
| 317 | GFTFSTYAMN | CD3 VH33 CDR1 |
| 318 | RIRSKYNNYATY | CD3 VH33 CDR1 |
| 319 | GSSTGAVTTSNYAN | CD3 VL21 CDR1 |
| 320 | GTNKRAP | CD3 VL21 CDR2 |
| 321 | EVQLVESGGGEVQPGGSLRLSCAASGFSFSINAMGWYRQAPGKRREFVAAI ESGRNTVYAESVKGRFTISRDNAKNTVYLQMSSLRAEDTAVYYCGLLKGN RVVSPSVAYWGQGTLVTVKP | sdAb 41BB |
| 322 | EVQLVESGGGEVQPGGSLRLSCAASGRPFSSKTMAWFRQAPGKEREFVAAV RWIGGATRYTESVKGRFTISRDNAKNTVYLQMSSLRAEDTAVYYCAAGQA WGTKFTDYSDWGQGTLVTVKP | sdAb 5T4 hz12E9v9 |
| 323 | EVQLVESGGGEVQPGGSLRLSCAASGRPFSSYAMGWFRQAPGKERETVAA VSRNAGSSYYAESVKGRFTISRDNAKNTVYLQMSSLRAEDTAVYYCAARSA AYSRSSETYTEKHDYTYWGQGTLVTVKP | sdAb 5T4 hz16G10v11 |
| 324 | MVSPRMSGLLSQTVILALIFLPQTRPAGVFELQIHSFGPGPGPGAPRSPCSARL PCRLFFRVCLKPGLSEEAAESPCALGAALSARGPVYTEQPGAPAPDLPLPDG LLQVPFRDAWPGTFSFIIETWREELGDQIGGPAWSLLARV AGRRRLAAGGPWARDIQRAGAWELRFSYRARCEPPAVGTACTRLCRPRSAP SRCGPGLRPCAPLEDECEAPLVCRAGCSPEHGFCEQPGECRCLEGWTGPLCT VPVSTSSCLSPRGPSSATTGCLVPGPGPCDGNPCANGGS CSETPRSFECTCPRGFYGLRCEVSGVTCADGPCFNGGLCVGGADPDSAYICH CPPGFQGSNCEKRVDRCSLQPCRNGGLCLDLGHALRCRCRAGFAGPRCEHD LDDCAGRACANGGTCVEGGGAHRCSCALG FGGRDCRERADPCAARPCAHGGRCYAHFSGLVCACAPGYMGARCEFPVHP DGASALPAAPPGLRPGDPQRYLLPPALGLLVAAGVAGAALLLVHVRRRGHS QDAGSRLLAGTPEPSVHALPDALNNLRTQEG SGDGPSSSVDWNRPEDVDPQGIYVISAPSIYAREVATPLFPPLHTGRAGQRQ HLLFPYPSSILSVK | Human DLL3 |
| 325 | GGGA | Linker |
| 326 | GGGGA | Linker |

What is claimed:
1. A multispecific polypeptide construct, the multispecific polypeptide construct comprising a first component comprising an immunoglobulin Fc region and a second component comprising a CD3-binding region, wherein:
- the CD3-binding region is an anti-CD3 disulfide-stabilized Fv antibody fragment (anti-CD3 dsFv) comprising a variable heavy chain region (VH) and a variable light chain region (VL);
- the Fc is a heterodimeric Fc comprising a first Fc polypeptide and a second Fc polypeptide, wherein the VH and VL of the anti-CD3 dsFv are linked to opposite polypeptides of the heterodimeric Fc;
- the first and second components are coupled by a first polypeptide linker, wherein the first linker is 3-18 amino acids in length, wherein the Fc region is positioned amino-terminally relative to the CD3-binding region;
- one or both of the first and second components comprises at least one antigen binding domain that binds a tumor associated antigen (TAA), wherein each of the at least one antigen binding domain(s) is a camelid $V_HH$ or a humanized camelid $V_HH$, wherein the at least one antigen binding domain(s) is coupled to the construct by a second polypeptide linker that is 2-6 amino acids in length; and
- one or both of the first and second components comprises at least one co-stimulatory receptor binding region (CRBR) that binds a co-stimulatory receptor, wherein each of the at least one CRBR(s) is a camelid $V_HH$ or a humanized camelid $V_HH$, wherein the at least one CRBR(s) is coupled to the construct by a third polypeptide linker that is 2-6 amino acids in length;
- wherein each linker is independently composed of at least 50% glycine residues; and
- wherein the CD3-binding region is not able to bind cell surface CD3 as determined by flow cytometry, unless at least one of the antigen binding domain is bound to its TAA.

2. The multispecific polypeptide construct of claim 1, wherein the first component comprises the at least one antigen binding domain that binds a TAA, wherein the at least one antigen binding domain comprises a first antigen binding domain and a second antigen binding domain, wherein each of the antigen binding domains binds a TAA.

3. The multispecific polypeptide construct of claim 1, wherein the at least one antigen binding domain comprises a first antigen binding domain and a second antigen binding domain, wherein the first antigen binding domain is positioned amino-terminally relative to the Fc region of the multispecific polypeptide construct and the second antigen binding domain is positioned carboxy-terminally relative to the CD3-binding region of the multispecific polypeptide construct.

4. The multispecific polypeptide construct of claim 1, wherein the at least one CRBR is positioned carboxy-terminally relative to the CD3-binding region of the multispecific polypeptide construct.

5. A multispecific polypeptide construct, comprising in order from N-terminus to C-terminus:
(a) a co-stimulatory receptor binding region (CRBR) that binds a co-stimulatory receptor and/or an antigen binding domain that binds a tumor associated antigen (TAA);
(b) an immunoglobulin Fc region that is a heterodimeric Fc comprising a first Fc polypeptide and a second Fc polypeptide, wherein the CRBR and/or antigen binding domain of (a) are coupled to the immunoglobulin Fc region by a polypeptide linker that is 2-6 amino acids in length;
(c) a polypeptide linker that is 3-18 amino acids in length;
(d) a CD3-binding region that is an anti-CD3 disulfide-stabilized Fv antibody fragment (anti-CD3 dsFv) comprising a variable heavy chain region (VH) and a variable light chain region (VL), wherein the VH and VL of the anti-CD3 dsFv are linked to opposite polypeptides of the heterodimeric Fc; and
(e) a CRBR that binds a co-stimulatory receptor and/or an antigen binding domain that binds to a TAA, wherein the CRBR and/or antigen binding domain are coupled to the CD3-binding region by a polypeptide linker that is 2-6 amino acids in length,
wherein:
each linker is independently composed of at least 50% glycine residues;
wherein the multispecific polypeptide construct comprises (i) at least one CRBR, and the at least one CRBR is a camelid $V_HH$ or a humanized camelid $V_HH$ and (ii) at least one antigen binding domain that binds a TAA, and the at least one antigen binding domain is a camelid $V_HH$ or a humanized camelid $V_HH$; and
wherein the CD3-binding region is not able to bind cell surface CD3 as determined by flow cytometry, unless at least one of the antigen binding domain is bound to its TAA.

6. A multispecific polypeptide construct, wherein the multispecific polypeptide construct comprises in order, from N-terminus to C-terminus:
(1) (a) an immunoglobulin Fc region that is a heterodimeric Fc comprising a first Fc polypeptide and a second Fc polypeptide;
(b) a polypeptide linker that is 3-18 amino acids in length;
(c) a CD3-binding region that is an anti-CD3 disulfide-stabilized Fv antibody fragment (anti-CD3 dsFv) comprising a variable heavy chain region (VH) and a variable light chain region (VL), wherein the VH and VL of the anti-CD3 dsFv are linked to opposite polypeptides of the heterodimeric Fc; and
(d) an antigen binding domain that binds a tumor associated antigen (TAA) and a co-stimulatory receptor binding region (CRBR) that binds a co-stimulatory receptor, wherein the antigen binding domain and CRBR are coupled to the CD3-binding region by a polypeptide linker that is 2-6 amino acids in length; or
(2) (a) an antigen binding domain that binds a TAA and a CRBR that binds a co-stimulatory receptor;
(b) an immunoglobulin Fc region that is a heterodimeric Fc comprising a first Fc polypeptide and a second Fc polypeptide, wherein the antigen binding domain and CRBR of (2)(a) are coupled to the immunoglobulin Fc region by a polypeptide linker that is 2-6 amino acids in length;
(c) a polypeptide linker that is 3-18 amino acids in length; and
(d) a CD3-binding region that is an anti-CD3 disulfide-stabilized Fv antibody fragment (anti-CD3 dsFv) comprising a variable heavy chain region (VH) and a variable light chain region (VL), wherein the VH and VL of the anti-CD3 dsFv are linked to opposite polypeptides of the heterodimeric Fc; wherein
each linker is independently composed of at least 50% glycine residues wherein:

(i) the CD3-binding region is not able to bind cell surface CD3 as determined by flow cytometry, unless the antigen binding domain is bound to its TAA; and
(ii) each of the CRBR and the antigen binding domain is a camelid $V_HH$ or a humanized camelid $V_HH$.

7. The multispecific polypeptide construct of claim 1, wherein one or both Fc polypeptides of the heterodimeric Fc region comprises (a) a knob-into-hole modification or (b) a charge mutation to increase electrostatic complementarity of the polypeptides.

8. The multispecific polypeptide construct of claim 1, wherein the first polypeptide linker is a cleavable polypeptide linker.

9. The multispecific polypeptide construct of claim 1, wherein the first polypeptide linker is a non-cleavable polypeptide linker.

10. The multispecific polypeptide construct of claim 9, wherein the non-cleavable polypeptide linker comprises (GGS)n, wherein n is 1 to 10; (GGGGS)n (SEQ ID NO: 173), wherein n is 1 to 10; or (GGGGGS)n (SEQ ID NO:172), wherein n is 1 to 4.

11. The multispecific polypeptide construct of claim 1, wherein the at least one antigen binding domain comprises:
   a first antigen binding domain and a second antigen binding domain, wherein the first antigen binding domain and the second antigen binding domain bind to the same TAA;
   a first antigen binding domain and a second antigen binding domain, wherein the first antigen binding domain and the second antigen binding domain bind different epitopes of the same TAA;
   a first antigen binding domain and a second antigen binding domain, wherein the first antigen binding domain and the second antigen binding domain bind the same epitope of the same TAA; or
   a first antigen binding domain and a second antigen binding domain wherein the first antigen binding domain and the second antigen binding domain bind different TAAs.

12. The multispecific polypeptide construct of claim 1, wherein the at least one CRBR binds a co-stimulatory receptor selected from the group consisting of: 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), and NKG2D.

13. The multispecific polypeptide construct of claim 1, wherein the at least one CRBR binds to 41BB (CD137).

14. The multispecific polypeptide construct of claim 1, wherein the anti-CD3 dsFv comprises:
   a VH CDR1 comprising the amino acid sequence TYAMN (SEQ ID NO:16); a VH CDR2 comprising the amino acid sequence RIRSKYNNYATYYADSVKD (SEQ ID NO: 17); a VH CDR3 comprising the amino acid sequence HGNFGNSYVSWFAY (SEQ ID NO: 18), a VL CDR1 comprising the amino acid sequence RSSTGAVTTSNYAN (SEQ ID NO: 19); a VL CDR2 comprising the amino acid sequence GTNKRAP (SEQ ID NO: 20); and a VL CDR3 comprising the amino acid sequence ALWYSNLWV (SEQ ID NO: 21);
   a VH CDR1 comprising the amino acid sequence GFTFNTYAMN (SEQ ID NO: 312); a VH CDR2 comprising the amino acid sequence RIRSKYNNYATY (SEQ ID NO: 318); a VH CDR3 comprising the amino acid sequence HGNFGNSYVSWFAY (SEQ ID NO: 18), a VL CDR1 comprising the amino acid sequence RSSTGAVTTSNYAN (SEQ ID NO: 19); a VL CDR2 comprising the amino acid sequence GTNKRAP (SEQ ID NO: 20); and a VL CDR3 comprising the amino acid sequence ALWYSNLWV (SEQ ID NO: 21); or
   a VH CDR1 comprising the amino acid sequence GFTFNTYAMN (SEQ ID NO: 312); a VH CDR2 comprising the amino acid sequence RIRSKYNNYATY (SEQ ID NO: 318); a VH CDR3 comprising the amino acid sequence HGNFGNSYVSWFAY (SEQ ID NO: 18), a VL CDR1 comprising the amino acid sequence GSSTGAVTTSNYAN (SEQ ID NO: 319); a VL CDR2 comprising the amino acid sequence GTNKRAP (SEQ ID NO: 320); and a VL CDR3 comprising the amino acid sequence ALWYSNHWV (SEQ ID NO: 315).

15. The multispecific polypeptide construct of claim 1, wherein the multispecific polypeptide construct is conjugated to an agent selected from the group consisting of: a therapeutic agent, an antineoplastic agent, a toxin or fragment thereof, a detectable moiety, and a diagnostic agent.

16. A pharmaceutical composition comprising the multispecific polypeptide construct of claim 1 and a pharmaceutically acceptable carrier.

17. The multispecific polypeptide construct of claim 1, wherein the multispecific polypeptide construct comprises only one CRBR.

18. The multispecific polypeptide construct of claim 4, wherein the multispecific polypeptide construct comprises only one CRBR.

19. The multispecific polypeptide construct of claim 18, wherein the CRBR binds to 41BB.

20. The multispecific polypeptide construct of claim 9, wherein the non-cleavable polypeptide linker comprises the amino acid sequence set forth in any one of SEQ ID NO:10, SEQ ID NO:119, and SEQ ID NO:170.

21. The multispecific polypeptide construct of claim 1, wherein the anti-CD3 dsFv comprises:
   a VH having the amino acid sequence of any of SEQ ID NOS: 44, 49-62, 290, and 311; and
   a VL having the amino acid sequence of any of SEQ ID NOS: 64, 72, 74, 76, 78-81, 241 and 289.

22. The multispecific polypeptide construct of claim 1, wherein the anti-CD3 dsFv comprises a VH having the amino acid sequence of SEQ ID NO: 44; and a VL having the amino acid sequence of SEQ ID NO: 72.

23. The multispecific polypeptide construct of claim 1, wherein the anti-CD3 dsFv comprises a VH CDR1 sequence that includes at least the amino acid sequence GFTFNTYAMN (SEQ ID NO: 312); a VH CDR2 sequence that includes at least the amino acid sequence RIRSKYNNYATY (SEQ ID NO: 313); a VH CDR3 sequence that includes at least the amino acid sequence HGNFGNSYVSWFAY (SEQ ID NO: 18), a VL CDR1 sequence that includes at least the amino acid sequence GSSTGAVTTSNYAN (SEQ ID NO: 319); a VL CDR2 sequence that includes at least the amino acid sequence GTNKRAP (SEQ ID NO: 320); and a VL CDR3 sequence that includes at least the amino acid sequence ALWYSNHWV (SEQ ID NO: 315).

24. The multispecific polypeptide construct of claim 1, wherein the second component comprises the at least one co-stimulatory receptor binding region (CRBR).

25. The multispecific polypeptide construct of claim 2, wherein the second component comprises the at least one co-stimulatory receptor binding region (CRBR).

26. The multispecific polypeptide construct of claim 23, wherein the anti-CD3 dsFv comprises a VH having a sequence that exhibits at least 90% sequence identity to SEQ ID NO: 44; and a VL having a sequence that exhibits at least 90% sequence identity to SEQ ID NO: 72.

27. The multispecific polypeptide construct of claim 2, wherein the at least one CRBR is positioned carboxy-terminally relative to the CD3-binding region of the multispecific polypeptide construct.

\* \* \* \* \*